(12) United States Patent
Li et al.

(10) Patent No.: US 12,168,661 B2
(45) Date of Patent: Dec. 17, 2024

(54) FUNCTIONAL MATERIALS BASED ON STABLE CHEMICAL STRUCTURE

(71) Applicant: ARIZONA BOARD OF REGENTS, Scottsdale, AZ (US)

(72) Inventors: Jian Li, Tempe, AZ (US); Xinqiang Tan, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 394 days.

(21) Appl. No.: 17/178,901

(22) Filed: Feb. 18, 2021

(65) Prior Publication Data

US 2021/0323963 A1    Oct. 21, 2021

Related U.S. Application Data

(60) Provisional application No. 63/044,434, filed on Jun. 26, 2020, provisional application No. 62/979,596, filed on Feb. 21, 2020.

(51) Int. Cl.
| | |
|---|---|
| *C07D 471/22* | (2006.01) |
| *H10K 50/11* | (2023.01) |
| *H10K 85/60* | (2023.01) |

(52) U.S. Cl.
CPC ......... *C07D 471/22* (2013.01); *H10K 85/657* (2023.02); *H10K 85/6572* (2023.02); *H10K 50/11* (2023.02)

(58) Field of Classification Search
CPC ............... C07D 471/22; H10K 85/657; H10K 85/6572; H10K 2101/20; H01L 51/0071; H01L 51/0072
See application file for complete search history.

(56) References Cited

U.S. PATENT DOCUMENTS

| | | | |
|---|---|---|---|
| 4,769,292 A | 9/1988 | Tang |
| 5,707,745 A | 1/1998 | Forrest |
| 5,844,363 A | 12/1998 | Gu |
| 6,303,238 B1 | 10/2001 | Thompson |
| 7,279,704 B2 | 10/2007 | Walters |
| 8,106,199 B2 | 1/2012 | Jabbour |
| 8,389,725 B2 | 3/2013 | Li |
| 8,669,364 B2 | 3/2014 | Li |
| 8,816,080 B2 | 8/2014 | Li |
| 8,846,940 B2 | 9/2014 | Li |
| 8,927,713 B2 | 1/2015 | Li |

(Continued)

FOREIGN PATENT DOCUMENTS

| | | |
|---|---|---|
| CN | 108148088 A | 6/2018 |
| CN | 108794539 A | 11/2018 |

(Continued)

OTHER PUBLICATIONS

Machine Translation of KR20160067034A (Year: 2016).*

(Continued)

*Primary Examiner* — Jenna N Chandhok
(74) *Attorney, Agent, or Firm* — Riverside Law LLP

(57) ABSTRACT

A series of novel donor-acceptor type TADF luminogens have been designed with the aim of developing stable OLEDs with enhanced operational stability and improved color purity. These materials can be utilized in full color displays and lighting applications.

20 Claims, 1 Drawing Sheet

(56) References Cited

U.S. PATENT DOCUMENTS

| | | |
|---|---|---|
| 8,946,417 B2 | 2/2015 | Jian |
| 9,012,599 B2 | 4/2015 | Stoessel |
| 9,076,974 B2 | 7/2015 | Li |
| 9,082,989 B2 | 7/2015 | Li |
| 9,203,039 B2 | 12/2015 | Li |
| 9,221,857 B2 | 12/2015 | Li |
| 9,224,963 B2 | 12/2015 | Li |
| 9,238,668 B2 | 1/2016 | Li |
| 9,312,502 B2 | 4/2016 | Li |
| 9,318,725 B2 | 4/2016 | Li |
| 9,324,957 B2 | 4/2016 | Li |
| 9,382,273 B2 | 7/2016 | Li |
| 9,385,329 B2 | 7/2016 | Li |
| 9,425,415 B2 | 8/2016 | Li |
| 9,502,671 B2 | 11/2016 | Jian |
| 9,550,801 B2 | 1/2017 | Li |
| 9,598,449 B2 | 3/2017 | Li |
| 9,617,291 B2 | 4/2017 | Li |
| 9,673,409 B2 | 6/2017 | Li |
| 9,698,359 B2 | 7/2017 | Li |
| 9,711,739 B2 | 7/2017 | Li |
| 9,711,741 B2 | 7/2017 | Li |
| 9,711,742 B2 | 7/2017 | Li |
| 9,755,163 B2 | 9/2017 | Li |
| 9,818,959 B2 | 11/2017 | Li |
| 9,865,825 B2 | 1/2018 | Li |
| 9,879,039 B2 | 1/2018 | Li |
| 9,882,150 B2 | 1/2018 | Li |
| 9,899,614 B2 | 2/2018 | Li |
| 9,920,242 B2 | 3/2018 | Li |
| 9,923,155 B2 | 3/2018 | Li |
| 9,941,479 B2 | 4/2018 | Li |
| 9,947,881 B2 | 4/2018 | Li |
| 9,985,224 B2 | 5/2018 | Li |
| 10,020,455 B2 | 7/2018 | Li |
| 10,033,003 B2 | 7/2018 | Li |
| 10,056,564 B2 | 8/2018 | Li |
| 10,056,567 B2 | 8/2018 | Li |
| 10,158,091 B2 | 12/2018 | Li |
| 10,177,323 B2 | 1/2019 | Li |
| 10,211,411 B2 | 2/2019 | Li |
| 10,211,414 B2 | 2/2019 | Li |
| 10,263,197 B2 | 4/2019 | Li |
| 10,294,417 B2 | 5/2019 | Li |
| 10,392,387 B2 | 8/2019 | Li |
| 10,411,202 B2 | 9/2019 | Li |
| 10,414,785 B2 | 9/2019 | Li |
| 10,516,117 B2 | 12/2019 | Li |
| 10,566,553 B2 | 2/2020 | Li |
| 10,566,554 B2 | 2/2020 | Li |
| 10,615,349 B2 | 4/2020 | Li |
| 10,622,571 B2 | 4/2020 | Li |
| 10,727,422 B2 | 7/2020 | Li |
| 10,745,615 B2 | 8/2020 | Li |
| 10,790,457 B2 | 9/2020 | Li |
| 10,793,546 B2 | 10/2020 | Li |
| 10,804,476 B2 | 10/2020 | Li |
| 10,822,363 B2 | 11/2020 | Li |
| 10,836,785 B2 | 11/2020 | Li |
| 10,851,106 B2 | 12/2020 | Li |
| 10,886,478 B2 | 1/2021 | Li |
| 10,930,865 B2 | 2/2021 | Li |
| 10,937,976 B2 | 3/2021 | Li |
| 10,944,064 B2 | 3/2021 | Li |
| 10,964,897 B2 | 3/2021 | Li |
| 10,991,897 B2 | 4/2021 | Li |
| 10,995,108 B2 | 5/2021 | Li |
| 11,011,712 B2 | 5/2021 | Li |
| 11,063,228 B2 | 7/2021 | Li |
| 11,101,435 B2 | 8/2021 | Li |
| 11,114,626 B2 | 9/2021 | Li |
| 11,121,328 B2 | 9/2021 | Li |
| 11,145,830 B2 | 10/2021 | Li |
| 2005/0139810 A1 | 6/2005 | Kuehl |
| 2007/0160905 A1 | 7/2007 | Morishita |
| 2007/0252140 A1 | 11/2007 | Limmert |
| 2008/0269491 A1 | 10/2008 | Jabbour |
| 2009/0136779 A1 | 5/2009 | Cheng |
| 2009/0167167 A1 | 7/2009 | Aoyama |
| 2010/0288362 A1 | 11/2010 | Hatwar |
| 2011/0028723 A1 | 2/2011 | Li |
| 2011/0066763 A1 | 3/2011 | Minot |
| 2011/0301351 A1 | 12/2011 | Li |
| 2012/0095232 A1 | 4/2012 | Li |
| 2012/0108806 A1 | 5/2012 | Li |
| 2012/0146012 A1 | 6/2012 | Limmert |
| 2012/0202997 A1 | 8/2012 | Parham |
| 2012/0215001 A1 | 8/2012 | Li |
| 2012/0264938 A1 | 10/2012 | Li |
| 2012/0302753 A1 | 11/2012 | Li |
| 2013/0137870 A1 | 5/2013 | Li |
| 2013/0203996 A1 | 8/2013 | Li |
| 2013/0237706 A1 | 9/2013 | Li |
| 2014/0066628 A1 | 3/2014 | Li |
| 2014/0073798 A1 | 3/2014 | Li |
| 2014/0114072 A1 | 4/2014 | Li |
| 2014/0147996 A1 | 5/2014 | Vogt |
| 2014/0148594 A1 | 5/2014 | Li |
| 2014/0249310 A1 | 9/2014 | Li |
| 2014/0330019 A1 | 11/2014 | Li |
| 2014/0364605 A1 | 12/2014 | Li |
| 2015/0008419 A1 | 1/2015 | Li |
| 2015/0018558 A1 | 1/2015 | Li |
| 2015/0060804 A1 | 3/2015 | Kanitz |
| 2015/0105556 A1 | 4/2015 | Li |
| 2015/0123047 A1 | 5/2015 | Maltenberger |
| 2015/0162552 A1 | 6/2015 | Li |
| 2015/0194616 A1 | 7/2015 | Li |
| 2015/0207086 A1 | 7/2015 | Li |
| 2015/0228914 A1 | 8/2015 | Li |
| 2015/0274762 A1 | 10/2015 | Li |
| 2015/0287938 A1 | 10/2015 | Li |
| 2015/0311456 A1 | 10/2015 | Li |
| 2015/0318500 A1 | 11/2015 | Li |
| 2015/0349279 A1 | 12/2015 | Li |
| 2016/0028028 A1 | 1/2016 | Li |
| 2016/0028029 A1 | 1/2016 | Li |
| 2016/0043331 A1 | 2/2016 | Li |
| 2016/0133861 A1 | 5/2016 | Li |
| 2016/0133862 A1 | 5/2016 | Li |
| 2016/0190473 A1 | 6/2016 | Kim |
| 2016/0190474 A1 | 6/2016 | Kim |
| 2016/0194344 A1 | 7/2016 | Li |
| 2016/0197291 A1 | 7/2016 | Li |
| 2016/0285015 A1 | 9/2016 | Li |
| 2016/0359120 A1 | 12/2016 | Li |
| 2016/0359125 A1 | 12/2016 | Li |
| 2017/0005278 A1 | 1/2017 | Li |
| 2017/0012224 A1 | 1/2017 | Li |
| 2017/0040555 A1 | 2/2017 | Li |
| 2017/0047533 A1 | 2/2017 | Li |
| 2017/0066792 A1 | 3/2017 | Li |
| 2017/0069855 A1 | 3/2017 | Li |
| 2017/0077420 A1 | 3/2017 | Li |
| 2017/0125708 A1 | 5/2017 | Li |
| 2017/0267923 A1 | 9/2017 | Li |
| 2017/0271611 A1 | 9/2017 | Li |
| 2017/0301871 A1 | 10/2017 | Li |
| 2017/0305881 A1 | 10/2017 | Li |
| 2017/0331056 A1 | 11/2017 | Li |
| 2017/0342098 A1 | 11/2017 | Li |
| 2017/0373260 A1 | 12/2017 | Li |
| 2018/0006246 A1 | 1/2018 | Li |
| 2018/0053904 A1 | 2/2018 | Li |
| 2018/0130960 A1 | 5/2018 | Li |
| 2018/0138428 A1 | 5/2018 | Li |
| 2018/0148464 A1 | 5/2018 | Li |
| 2018/0159051 A1 | 6/2018 | Li |
| 2018/0166655 A1 | 6/2018 | Li |
| 2018/0175329 A1 | 6/2018 | Li |
| 2018/0194790 A1 | 7/2018 | Li |
| 2018/0219161 A1 | 8/2018 | Li |
| 2018/0226592 A1 | 8/2018 | Li |
| 2018/0226593 A1 | 8/2018 | Li |

(56) References Cited

U.S. PATENT DOCUMENTS

| | | |
|---|---|---|
| 2018/0277777 A1 | 9/2018 | Li |
| 2018/0301641 A1 | 10/2018 | Li |
| 2018/0312750 A1 | 11/2018 | Li |
| 2018/0331307 A1 | 11/2018 | Li |
| 2018/0334459 A1 | 11/2018 | Li |
| 2018/0337345 A1 | 11/2018 | Li |
| 2018/0337349 A1 | 11/2018 | Li |
| 2018/0337350 A1 | 11/2018 | Li |
| 2019/0013485 A1 | 1/2019 | Li |
| 2019/0067602 A1 | 2/2019 | Li |
| 2019/0109288 A1 | 4/2019 | Li |
| 2019/0194536 A1 | 6/2019 | Li |
| 2019/0259963 A1 | 8/2019 | Jian |
| 2019/0276485 A1 | 9/2019 | Li |
| 2019/0312217 A1 | 10/2019 | Li |
| 2019/0367546 A1 | 12/2019 | Li |
| 2019/0389893 A1 | 12/2019 | Li |
| 2020/0006678 A1 | 1/2020 | Li |
| 2020/0071330 A1 | 3/2020 | Li |
| 2020/0075868 A1 | 3/2020 | Li |
| 2020/0119288 A1 | 4/2020 | Li |
| 2020/0152891 A1 | 5/2020 | Li |
| 2020/0227656 A1 | 7/2020 | Li |
| 2020/0227660 A1 | 7/2020 | Li |
| 2020/0239505 A1 | 7/2020 | Li |
| 2020/0243776 A1 | 7/2020 | Li |
| 2020/0287153 A1 | 9/2020 | Li |
| 2020/0332185 A1 | 10/2020 | Li |
| 2020/0373505 A1 | 11/2020 | Li |
| 2020/0403167 A1 | 12/2020 | Li |
| 2021/0024526 A1 | 1/2021 | Li |
| 2021/0024559 A1 | 1/2021 | Li |
| 2021/0047296 A1 | 2/2021 | Li |
| 2021/0091316 A1 | 3/2021 | Li |
| 2021/0104687 A1 | 4/2021 | Li |
| 2021/0111355 A1 | 4/2021 | Jian |
| 2021/0126208 A1 | 4/2021 | Li |
| 2021/0193936 A1 | 6/2021 | Li |
| 2021/0193947 A1 | 6/2021 | Li |
| 2021/0217973 A1 | 7/2021 | Li |
| 2021/0230198 A1 | 7/2021 | Li |
| 2021/0261589 A1 | 8/2021 | Li |
| 2021/0273182 A1 | 9/2021 | Li |

FOREIGN PATENT DOCUMENTS

| | | |
|---|---|---|
| CN | 108948044 A | 12/2018 |
| CN | 110713482 A | 1/2020 |
| EP | 1617493 | 1/2006 |
| EP | 1968131 | 9/2008 |
| EP | 2020694 | 2/2009 |
| EP | 2684932 | 1/2014 |
| KR | 20110066763 | 6/2011 |
| KR | 20130043460 A | 4/2013 |
| KR | 20140027030 | 3/2014 |
| KR | 20140065357 A | 5/2014 |
| KR | 20160067034 A * | 6/2016 |
| WO | 2000070655 | 11/2000 |
| WO | 2006081780 | 8/2006 |
| WO | 2009003455 | 1/2009 |
| WO | 2009008277 | 1/2009 |
| WO | 2009011327 | 1/2009 |
| WO | 2009086209 | 7/2009 |
| WO | 2009111299 | 9/2009 |
| WO | 2010050778 | 5/2010 |
| WO | 2010105141 | 9/2010 |
| WO | 2010118026 A2 | 10/2010 |
| WO | 2011137429 A2 | 11/2011 |
| WO | 2011137431 A2 | 11/2011 |
| WO | 2012074909 | 6/2012 |
| WO | 2012112853 A1 | 8/2012 |
| WO | 2012142387 | 10/2012 |
| WO | 2012162488 A1 | 11/2012 |
| WO | 2013130483 A1 | 9/2013 |
| WO | 2014009310 | 1/2014 |
| WO | 2014031977 | 2/2014 |
| WO | 2014047616 A1 | 3/2014 |
| WO | 2014109814 | 7/2014 |
| WO | 2015027060 A1 | 2/2015 |
| WO | 2015099507 | 7/2015 |
| WO | 2015131158 | 9/2015 |
| WO | 2016025921 | 2/2016 |
| WO | 2016029137 | 2/2016 |
| WO | 2016029186 | 2/2016 |
| WO | 2016197019 | 12/2016 |
| WO | 2018071697 | 4/2018 |
| WO | 2018140765 | 8/2018 |
| WO | 2019079505 | 4/2019 |
| WO | 2019079508 | 4/2019 |
| WO | 2019079509 | 4/2019 |
| WO | 2019236541 | 12/2019 |
| WO | 2020018476 | 1/2020 |

OTHER PUBLICATIONS

Baldo et al., "Highly Efficient Phosphorescent Emission from Organic Electroluminescent Devices," Nature, vol. 395, Sep. 10, 1998, pp. 151-154.

Baldo et al., "Very high-efficiency green organic light-emitting devices based on electrophosphorescence," Applied Physics Letters, vol. 75, No. 1, Jul. 5, 1999, pp. 4-6.

Uoyama et al., "Highly efficient organic light-emitting diodes from delayed fluorescence" Nature, 492:234-238, (2012).

Yan, et al., "Palladium-catalyzed tandem N—H/C—H arylation: regioselective synthesis of N-heterocycle-fused phenanthridines as versatile blue-emitting luminophores," Organic & Biomolecular Chemistry, 11(45), 2013, 7966-7977.

Su "Pyridine-Containing Bipolar Host Materials for Highly Efficient Blue Phosphorescent OLEDs" Chem. Mater. 2008, 20, 1691-1693 1691.

Bunz "Large N-Heteroacenes: New Tricks for Very Old Dogs?" Angew. Chem. Int. Ed. 2013, 52, 3810-3821.

Kader Azaindolo[3,2, 1-jk]carbazoles New Building Blocks for Functional Organic Materials Chem. Eur. J. 2019, 25, 4412-4425.

Kotwica "Azaacenes Based Electroactive Materials: Preparation, Structure, Electrochemistry, Spectroscopy and Applications—A Critical Review" Materials 2021, 14, 5155.

Miao "Ten Years of N-Heteropentacenes as Semiconductors for Organic Thin-Film Transistors" Adv. Mater. 2014, 26, 5541-5549.

Richards "Putting the 'N' in ACENE: Pyrazinacenes and their structural relatives" Org. Biomol. Chem., Sep. 2011, 5005.

Bachowska, B. Monatshefte fuer Chemie, 126(2), 1995, 227-231.

* cited by examiner

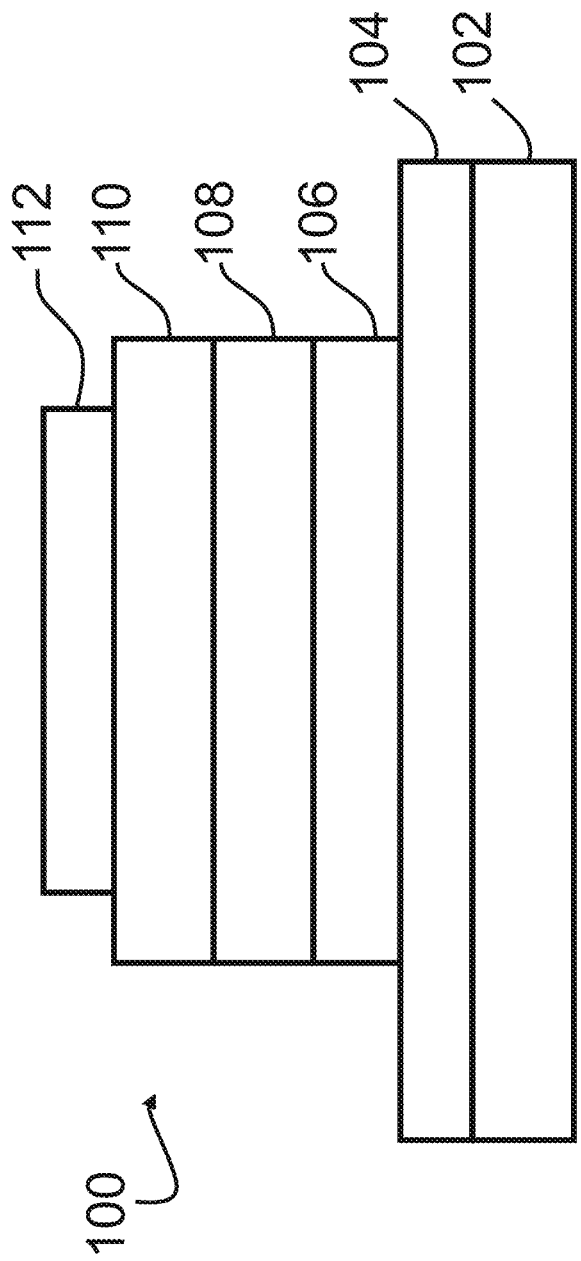

FUNCTIONAL MATERIALS BASED ON STABLE CHEMICAL STRUCTURE

CROSS-REFERENCE TO RELATED APPLICATIONS

The present application claims priority to U.S. Provisional Application No. 62/979,596, filed Feb. 21, 2020 and to U.S. Provisional Application No. 63/044,434, filed Jun. 26, 2020, both of which are incorporated by reference herein in their entirety.

STATEMENT REGARDING FEDERALLY SPONSORED RESEARCH OR DEVELOPMENT

This invention was made with government support under DE-EE0005075 and DE-EE0008721 awarded by the Department of Energy. The government has certain rights in the invention.

BACKGROUND OF THE INVENTION

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

In recent years, organic light emitting diodes (OLEDs) have attracted great attention from both academic and industrial areas due to their outstanding merits, like high color quality, wide-viewing angle, low cost fabrication, low power consumption, fast respond speed and high electron to photon conversion efficiency. Most of the organic light emitting diodes (OLEDs) are phosphorescent OLEDs using Iridium (Ir), palladium (Pd) and platinum (Pt) complexes, as these metal complexes have strong Spin-Orbital Coupling, they can efficiently emit light from their triplet exited state and reach nearly 100% internal efficiency. Thermally activated delayed fluorescence (TADF) OLEDs have the potential ability to become the cheaper alternatives to metal-based OLEDs owing to their lack of noble metals and their operational stability.

SUMMARY OF THE INVENTION

A compound is provided that has the structure of General Formula I:

General Formula I

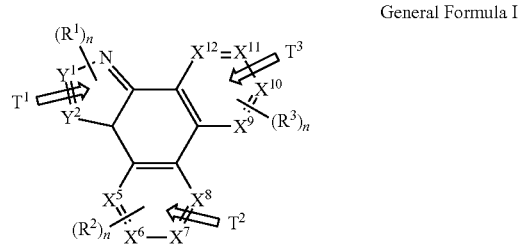

wherein:
$T^2$ and $T^3$ represent a Donor or an Acceptor; $T^1$ optionally represents a Donor;
$Y^1$ and $Y^2$ each independently represent C, N, Si, B, or P;
wherein when $Y^1$ and $Y^2$ both represent C, then two groups $R^1$ may optionally together form a fused aryl or heteroaryl ring having the following structure:

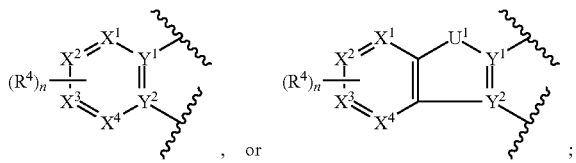

, or ;

wherein for any two adjacent $X^a$ and $X^b$ representing $X^5$-$X^8$ where a and b are integers from 5-8, then two groups $R^2$ may optionally together form a fused aryl or heteroaryl ring having the following structure:

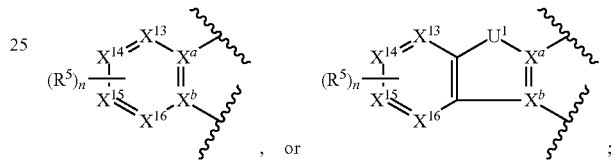

, or ;

wherein for any two adjacent $X^c$ and $X^d$ representing $X^9$-$X^{12}$ where c and d are integers from 9-12, then two groups $R^3$ may optionally together form a fused aryl or heteroaryl ring having the following structure:

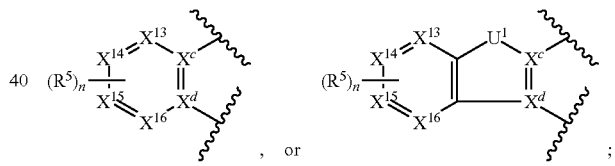

, or ;

$X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, and $X^{16}$ each independently represents C, N, Si, B, or P;
$U^1$ represents O, S, Se, $NR^{21}$, P=O, As=O, Bi=O, $CR^{21}R^{22}$, C=O, $SiR^{21}R^{22}$, $GeR^{21}R^{22}$, $NR^{21}$, $PR^{21}$, $PR^{21}R^{22}$, $R^{21}P$=O, $AsR^{21}$, $R^{21}As$=O, S=O, $SO_2$, Se=O, $SeO_2$, $BR^{21}$, $BR^{21}R^{22}$, $AlR^{21}$, $AlR^{21}R^{22}$, $R^{21}Bi$=O, or $BiR^{21}$;
each n is independently an integer, valency permitting; and
each of $R^1$, $R^2$, $R^3$, $R^4$, $R^5$, $R^{21}$ and $R^{22}$ independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, wherein two adjacent groups $R^1$, $R^2$, $R^3$, $R^4$, $R^5$, $R^{21}$, $R^{22}$, or a combination thereof may optionally together form a fused ring.

According to another aspect, an organic light emitting diode (OLED) including a compound of General Formula I is provided. According to another aspect, a light emitting device comprising the light emitting diode is provided.

BRIEF DESCRIPTION OF THE DRAWINGS

The following detailed description of preferred embodiments will be better understood when read in conjunction with the appended drawings. For the purpose of illustration, there are shown in the drawings embodiments which are presently preferred. It should be understood, however, that the disclosure is not limited to the precise arrangements and instrumentalities of the embodiments shown in the drawings.

The FIGURE is a schematic diagram of an organic light emitting device.

DETAILED DESCRIPTION

The present disclosure relates in part to the unexpected discovery that donor-acceptor type potential functional materials have good operational stability.

Definitions

It is to be understood that the figures and descriptions of the present disclosure have been simplified to illustrate elements that are relevant for a clear understanding of the present disclosure, while eliminating, for the purpose of clarity, many other elements found in the art related to phosphorescent organic light emitting devices and the like. Those of ordinary skill in the art may recognize that other elements and/or steps are desirable and/or required in implementing the compositions and devices disclosed. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods, materials and components similar or equivalent to those described herein can be used in the practice or testing of the present invention, the preferred methods, and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of 20%, ±10%, ±5%, +1%, or ±0.1% from the specified value, as such variations are appropriate.

Throughout this disclosure, various aspects can be presented in a range format. It should be understood that the description in range format is merely for convenience and brevity and should not be construed as an inflexible limitation on the scope of any composition or device. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

Headings are provided for convenience only and are not to be construed to limit the invention in any manner. Embodiments illustrated under any heading or in any portion of the disclosure may be combined with embodiments illustrated under the same or any other heading or other portion of the disclosure.

Disclosed are the components to be used to prepare the compositions of the disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions disclosed herein. Thus, if there are a variety of additional steps that can be performed it is understood that each of these additional steps can be performed with any specific embodiment or combination of embodiments of the methods.

The invention illustratively disclosed herein suitably may be practiced in the absence of any element which is not specifically disclosed herein.

As referred to herein, a linking atom or a linking group can connect two groups such as, for example, an N and C group. The linking atom can optionally, if valency permits, have other chemical moieties attached. For example, in one aspect, an oxygen would not have any other chemical groups attached as the valency is satisfied once it is bonded to two groups (e.g., N and/or C groups). In another aspect, when carbon is the linking atom, two additional chemical moieties can be attached to the carbon. Suitable chemical moieties include, but are not limited to, hydrogen, hydroxyl, alkyl, alkoxy, =O, halogen, nitro, amine, amide, thiol, aryl, heteroaryl, cycloalkyl, and heterocyclyl.

The term "cyclic structure" or the like terms used herein refer to any cyclic chemical structure which includes, but is not limited to, aryl, heteroaryl, cycloalkyl, cycloalkenyl, and heterocyclyl.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA$-$OA^2$ or —$OA$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bond, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triplebond. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is as described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O), or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is used as the term to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$-, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocyclyl," as used herein refers to single and multi-cyclic non-aromatic ring systems and "heteroaryl" as used herein refers to single and multi-cyclic aromatic ring systems: in which at least one of the ring members is other than carbon. The term "heterocyclyl" includes azetidine, dioxane, furan, imidazole, isothiazole, isoxazole, morpholine, oxazole, oxadiazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula A$^1$C(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —N$_3$.

The term "nitro" as used herein is represented by the formula —NO$_2$.

The term "nitrile" as used herein is represented by the formula —CN.

The term "ureido" as used herein refers to a urea group of the formula —NHC(O)NH$_2$ or —NHC(O)NH—.

The term "phosphoramide" as used herein refers to a group of the formula —P(O)(NA$^1$A$^2$)$_2$, where A$^1$ and A$^2$ can be, independently, hydrogen or an alkyl, cycloalkyl, alkoxy, alkenyl, cycloalkenyl, alkynyl, cycloalkynyl, aryl, or heteroaryl group as described herein.

The term "carbamoyl" as used herein refers to an amide group of the formula —CONA$^1$A$^2$, where A$^1$ and A$^2$ can be, independently, hydrogen or an alkyl, cycloalkyl, alkoxy, alkenyl, cycloalkenyl, alkynyl, cycloalkynyl, aryl, or heteroaryl group as described herein.

The term "sulfamoyl" as used herein refers to a group of the formula —S(O)$_2$NA$^1$A$^2$, where A$^1$ and A$^2$ can be, independently, hydrogen or an alkyl, cycloalkyl, alkoxy, alkenyl, cycloalkenyl, alkynyl, cycloalkynyl, aryl, or heteroaryl group as described herein.

The term "silyl" as used herein is represented by the formula —SiA$^1$A$^2$A$^3$, where A$^1$, A$^2$, and A$^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas S(O)A$^1$, S(O)$_2$A$^1$, OS(O)$_2$A$^1$, or OS(O)$_2$OA$^1$, where A$^1$ is hydrogen or an alkyl, cycloalkyl, alkenyl, cycloalkenyl, alkynyl, cycloalkynyl, aryl, or heteroaryl group as described herein. Throughout this specification "S(O)" is a short hand notation for S═O. The term "sulfonyl" is used herein to refer to the sulfo-oxo group represented by the formula —S(O)$_2$A$^1$, where A$^1$ is hydrogen or an alkyl, cycloalkyl, alkenyl, cycloalkenyl, alkynyl, cycloalkynyl, aryl, or heteroaryl group as described herein. The term "sulfone" as used herein is represented by the formula A'S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A'S(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R," "R$^1$," "R$^2$," "R$^3$," "R$^n$," where n is an integer, as used herein can, independently, include hydrogen or one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within a second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. It is also contemplated that, in certain aspects, unless expressly indicated to the contrary, individual substituents can be further optionally substituted (i.e., further substituted or unsubstituted).

In some aspects, a structure of a compound can be represented by a formula:

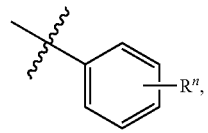

which is understood to be equivalent to a formula:

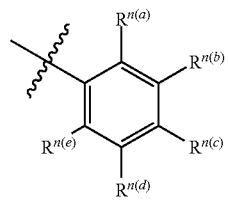

wherein n is typically an integer. That is, R$^n$ is understood to represent five independent substituents, R$^{n(a)}$, R$^{n(b)}$, R$^{n(c)}$, R$^{n(d)}$, R$^{n(e)}$. By "independent substituents," it is meant that each R substituent can be independently defined. For example, if in one instance R$^{n(a)}$ is halogen, then R$^{n(b)}$ is not necessarily halogen in that instance.

Several references to R, R$^1$, R$^2$, R$^3$, R$^4$, R$^5$, R$^6$, etc. are made in chemical structures and moieties disclosed and described herein. Any description of R, R$^1$, R$^2$, R$^3$, R$^4$, R$^5$, R$^6$, etc. in the specification is applicable to any structure or moiety reciting R, R$^1$, R$^2$, R$^3$, R$^4$, R$^5$, R$^6$, etc. respectively.

Compounds

The compounds disclosed herein are suited for use in a wide variety of optical and electro-optical devices, including, but not limited to, photo-absorbing devices such as solar- and photo-sensitive devices, organic light emitting devices (OLEDs), photo-emitting devices, or devices capable of both photo-absorption and emission and as markers for bio-applications.

The compounds disclosed herein are useful in a variety of applications. As light emitting materials, the compounds can be useful in organic light emitting devices (OLEDs), luminescent devices and displays, and other light emitting devices.

In another aspect, the compounds can provide improved efficiency, improved operational lifetimes, or both in light-ing devices, such as, for example, organic light emitting devices, as compared to conventional materials.

The compounds of the disclosure can be made using a variety of methods, including, but not limited to those recited in the examples provided herein.

Compounds of the Invention

In one aspect, the present disclosure relates to compounds of General Formula I:

General Formula I

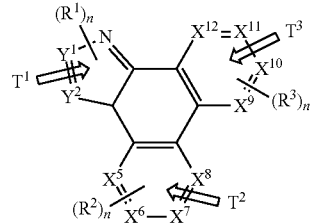

wherein:

T$^2$ and T$^3$ represent a Donor or an Acceptor; T$^1$ optionally represents a Donor;

$Y^1$ and $Y^2$ each independently represent C, N, Si, B, or P;

wherein when $Y^1$ and $Y^2$ both represent C, then two groups R may optionally together form a fused aryl or heteroaryl ring having the following structure:

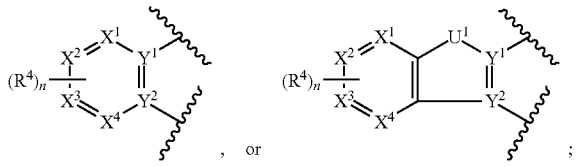

, or ;

wherein for any two adjacent $X^a$ and $X^b$ representing $X^5$-$X^8$ where a and b are integers from 5-8, then two groups $R^2$ may optionally together form a fused aryl or heteroaryl ring having the following structure:

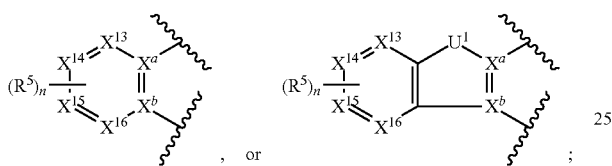

, or ;

wherein for any two adjacent $X^c$ and $X^d$ representing $X^9$-$X^{12}$ where c and d are integers from 9-12, then two groups $R^3$ may optionally together form a fused aryl or heteroaryl ring having the following structure:

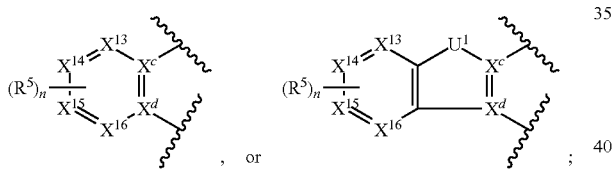

, or ;

wherein:

$X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, and $X^{16}$ each independently represents C, N, Si, B, or P;

$U^1$ represents O, S, Se, $NR^{21}$, P=O, As=O, Bi=O, $CR^{21}R^{22}$, C=O, $SiR^{21}R^{22}$, $GeR^{21}R^{22}$, $NR^{21}$, $PR^{21}$, $PR^{21}R^{22}$, $R^{21}$P=O, $AsR^{21}$, $R^{21}$As=O, S=O, $SO_2$, Se=O, $SeO_2$, $BR^{21}$, $BR^{21}R^{22}$, $AlR^{21}$, $AlR^{21}R^{22}$, $R^{21}$Bi=O, or $BiR^{21}$;

each n is independently an integer, valency permitting; and each of $R^1$, $R^2$, $R^3$, $R^4$, $R^5$, $R^{21}$ and $R^{22}$ independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, wherein two adjacent groups $R^1$, $R^2$, $R^3$, $R^4$, $R^5$, $R^{21}$, $R^{22}$, or a combination thereof may optionally together form a fused ring.

In one embodiment, the present disclosure relates to the compound, wherein one or more of the following conditions is true:

(i) $Y^1$ and $Y^2$ are each C, and two groups R are represented by one of the following structures, where dashed lines indicate bonds to $Y^1$ and $Y^2$ in General Formula I:

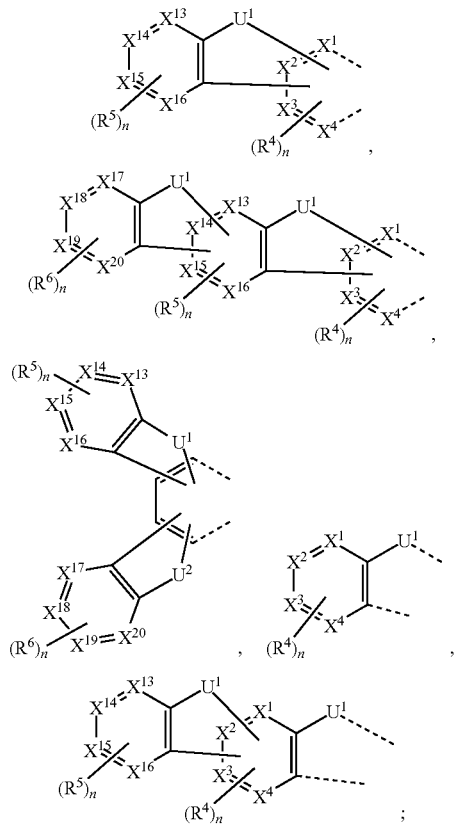

(ii) for two adjacent $X^a$ and $X^b$, two groups $R^2$ are represented by one of the following structures, where dashed lines indicate bonds to $X^a$ and $X^b$ in General Formula I:

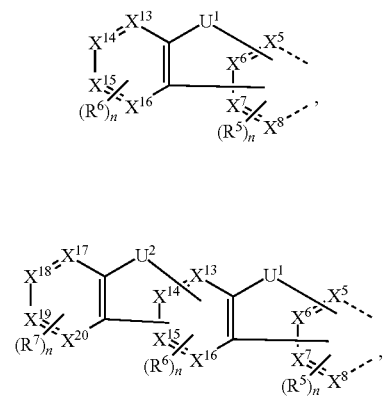

-continued

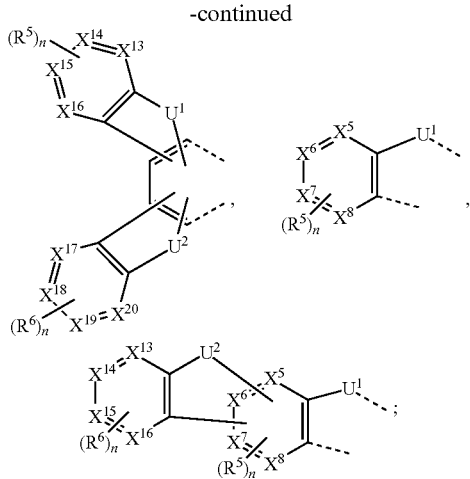

(iii) for two adjacent $X^c$ and $X^d$, two groups $R^3$ are represented by one of the following structures, where dashed lines indicate bonds to $X^c$ and $X^d$ in General Formula L

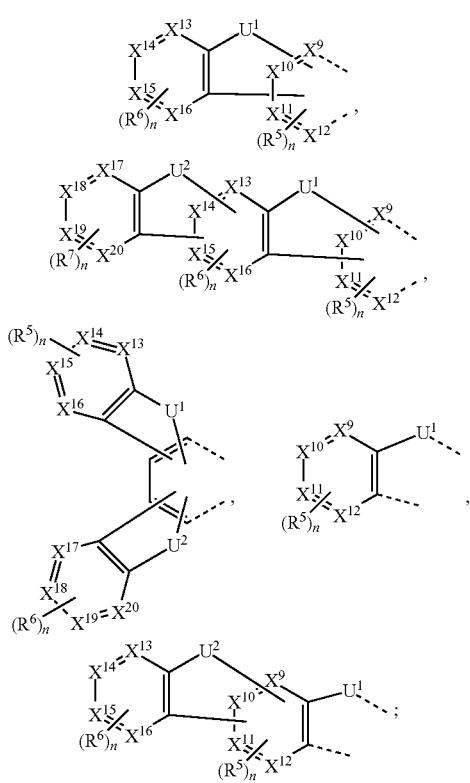

wherein:
$X^{13}$, $X^{14}$, $X^{15}$, $X^{16}$, $X^{17}$, $X^{18}$, $X^{19}$, and $X^{20}$ each independently represents C, N, Si, B, or P;
each $U^1$ and $U^2$ represents O, S, Se, P=O, As=O, Bi=O, $CR^{21}R^{22}$, C=O, $SiR^{21}R^{22}$, $GeR^{21}R^{22}$, $NR^{21}$, $PR^{21}$, $PR^{21}R^{22}$, $R^{21}P$=O, $AsR^{21}$, $R^{21}As$=O, S=O, $SO_2$, Se=O, $SeO_2$, $BR^{21}$, $BR^{21}R^{22}$, $AlR^{21}$, $AlR^{21}R^{22}$, $R^{21}Bi$=O, or $BiR^{21}$;
each $R^4$, $R^5$, $R^6$, and $R^7$ is independently absent or present as a single substituent or multiple substituents, valency permitting, and each occurrence of $R^4$, $R^5$, $R^6$, $R^{21}$ and $R^{22}$ independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof,
any two adjacent $R^4$, $R^5$, $R^6$, $R^7$, or a combination thereof may optionally together form a fused ring; and each occurrence of n is independently an integer, valency permitting.

In one embodiment, the present disclosure relates to the compound, wherein one or more of the following conditions are true:
(i) at least one of $Y^1$ and $Y^2$ represents C, and at least one $R^1$ is represented by the following structure:

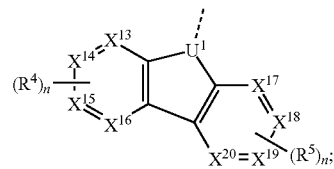

(ii) at least one $R^2$ is represented by the following structure:

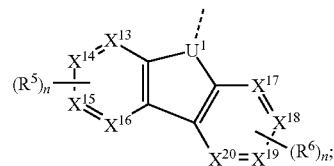

(iii) at least one $R^3$ is represented by the following structure:

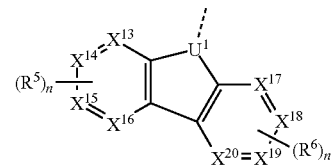

wherein:
dashed lines indicate the bond to General Formula I;
$X^{13}$, $X^{14}$, $X^{15}$, $X^{16}$, $X^{17}$, $X^{18}$, $X^{19}$, and $X^{20}$, each independently represents C, N, Si, B, or P;
$U^1$ represents N, P, As, B, Al, or Bi, $CR^{21}$, $SiR^{21}$, $GeR^{21}$, P=O, As=O, B, Bi=O, $PR^{21}R^{22}$, $R^{21}P$=O, $AsR^{21}$, $R^{21}As$=O, S=O, $SO_2$, Se=O, $SeO_2$, $R^{21}Bi$=O, or $BiR^{21}$;
each $R^4$, $R^5$ and $R^6$ is independently absent or present as a single substituent or multiple substituents, valency permitting, and each occurrence of $R^4$, $R^5$, $R^6$, $R^{21}$ and $R^{22}$ independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, any two adjacent $R^4$, $R^5$, $R^6$, or a combination thereof may optionally join to form a fused ring; and each occurrence of n is independently an integer, valency permitting.

In one embodiment, at least one of $X^5$, $X^6$, $X^7$, $X^8$, $X^9$, $X^{10}$, $X^{11}$, and $X^{12}$ represents N.

In one embodiment, at least two of $X^5$, $X^6$, $X^7$, $X^8$, $X^9$, $X^{10}$, $X^{11}$, and $X^{12}$ represents N.

In one embodiment, at least one of $X^5$, $X^6$, $X^7$, and $X^8$ represents N, and at least one of $X^9$, $X^{10}$, $X^{11}$, and $X^{12}$ represents N.

In one embodiment, the compound is represented by General Formula II, General Formula III, General Formula VI, General Formula V, or General Formula VI:

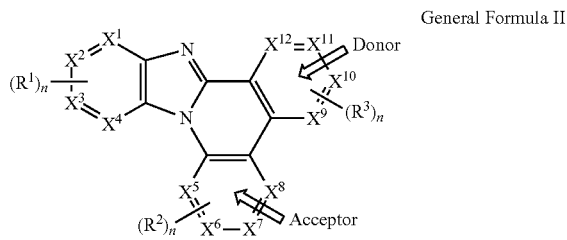

General Formula II

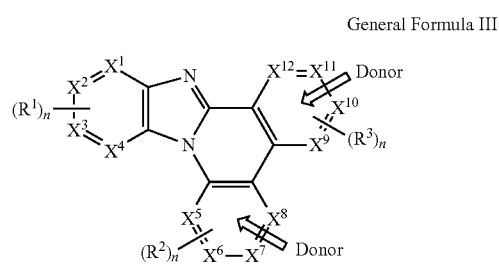

General Formula III

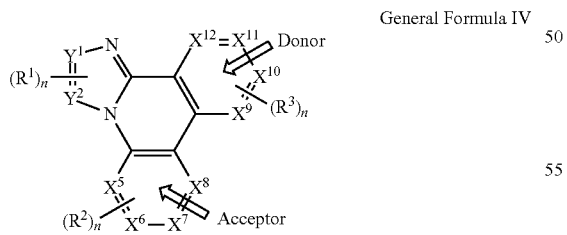

General Formula IV

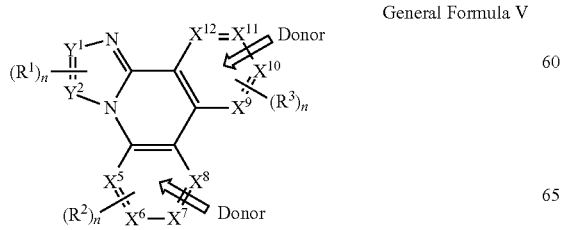

General Formula V

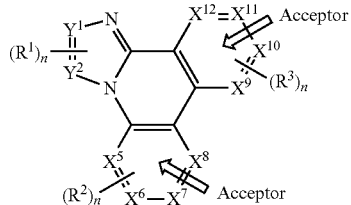

General Formula VI wherein:

$X^1$, $X^2$, $X^3$, $X^4$, $X^5$, $X^6$, $X^7$, $X^8$, $X^9$, $X^{10}$, $X^{11}$, and $X^{12}$ each independently represents C, N, Si, B, or P;

$Y^1$ and $Y^2$ each independently represent C, N, Si, B, or P;

each occurrence of n is independently an integer, valency permitting; and each occurrence of $R^1$, $R^2$, and $R^3$ independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and any two adjacent $R^1$, $R^2$, $R^3$, or a combination thereof may optionally together form a fused ring.

In one embodiment, the compound is represented by one of the following structures:

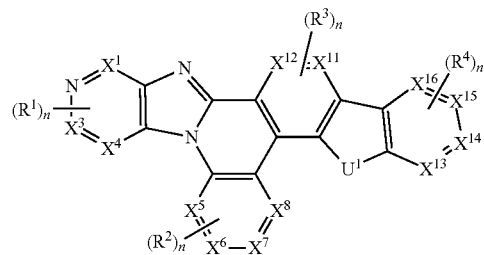

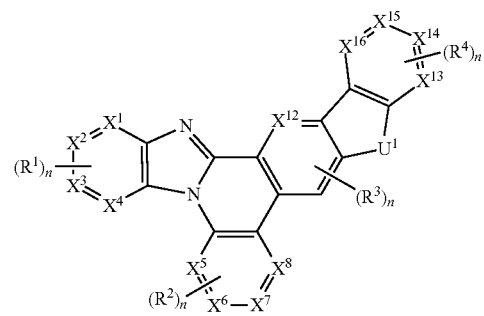

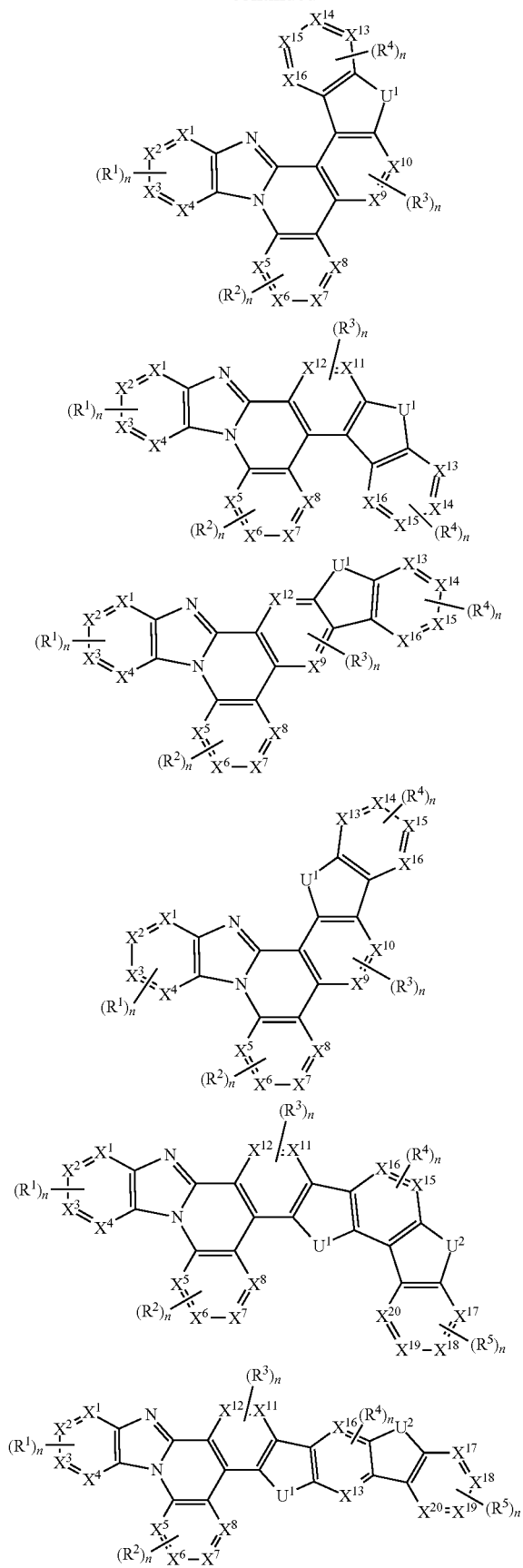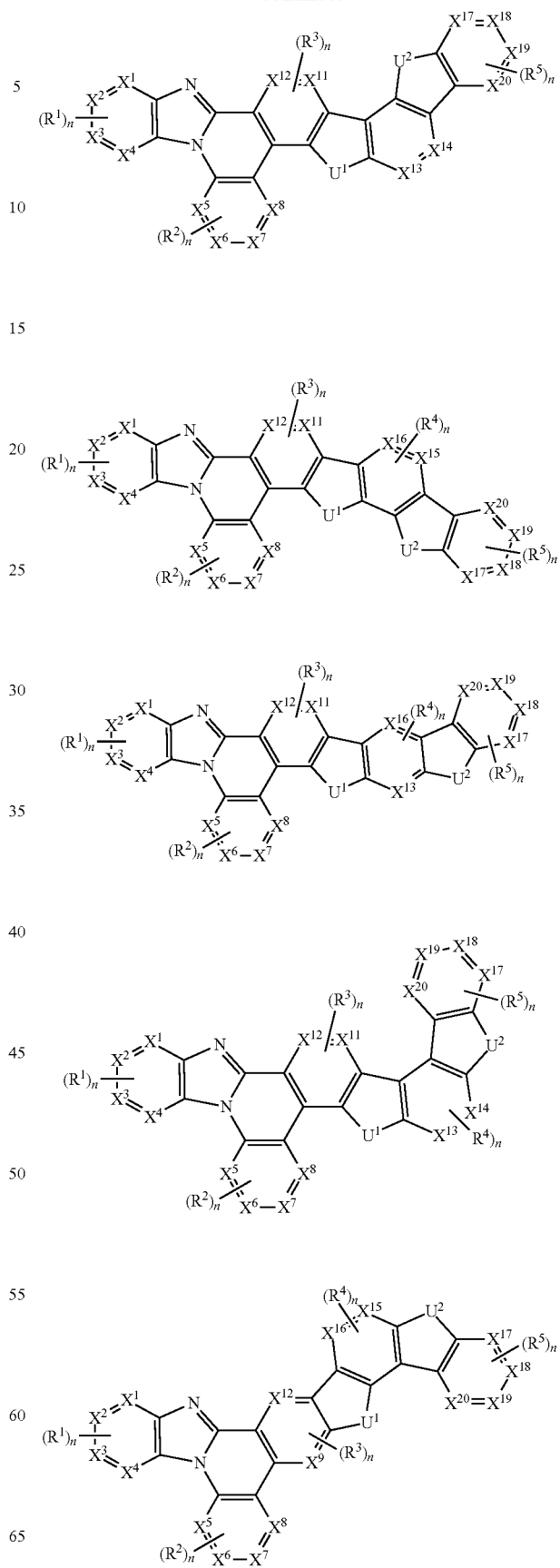

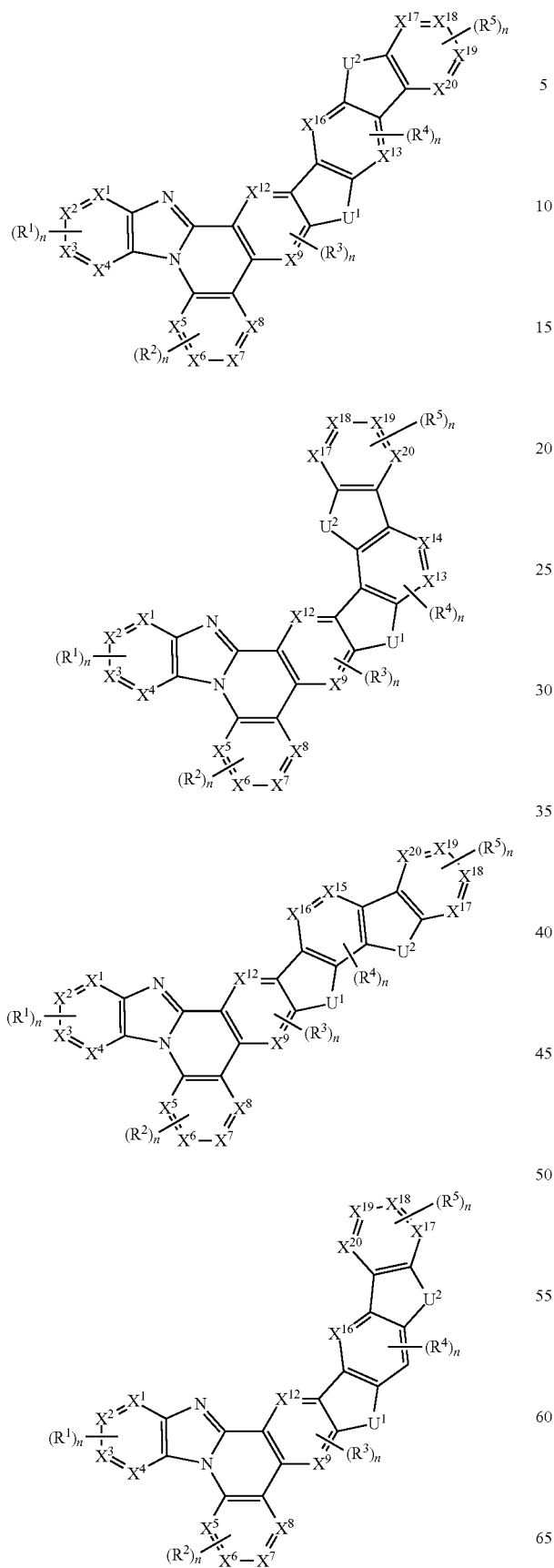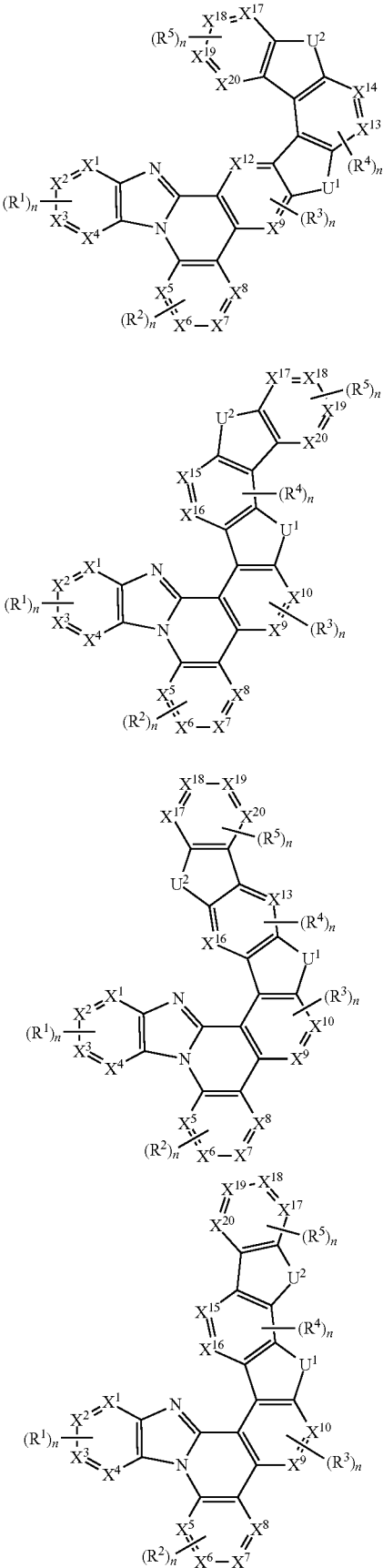

-continued
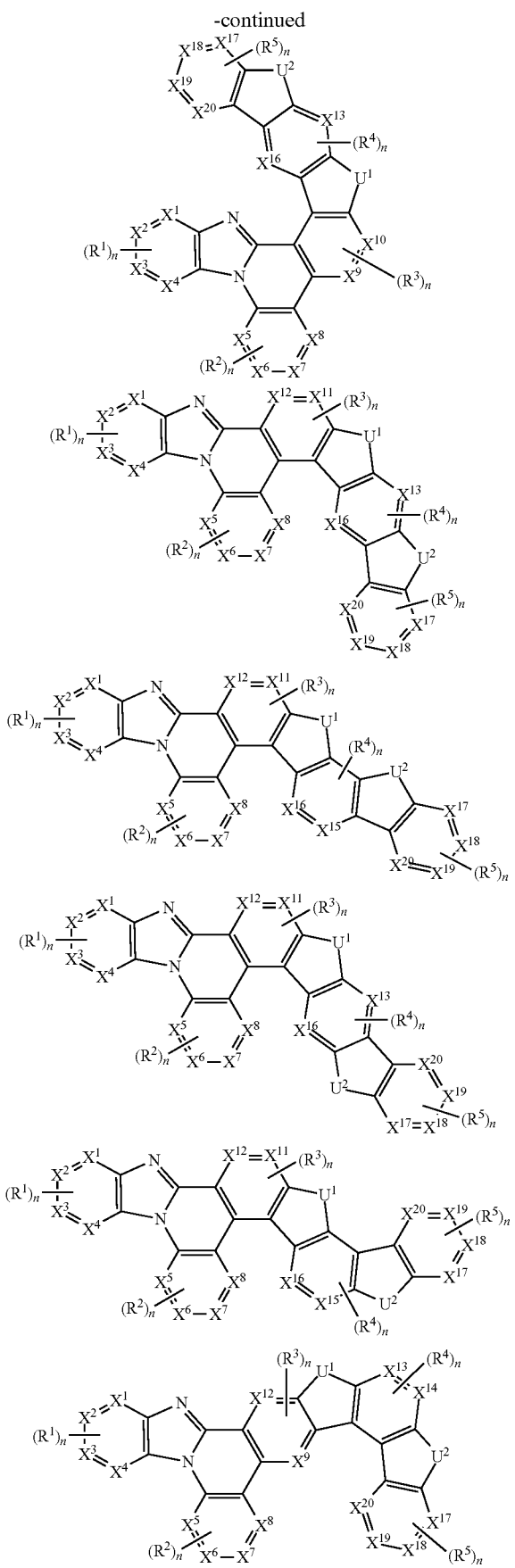
-continued
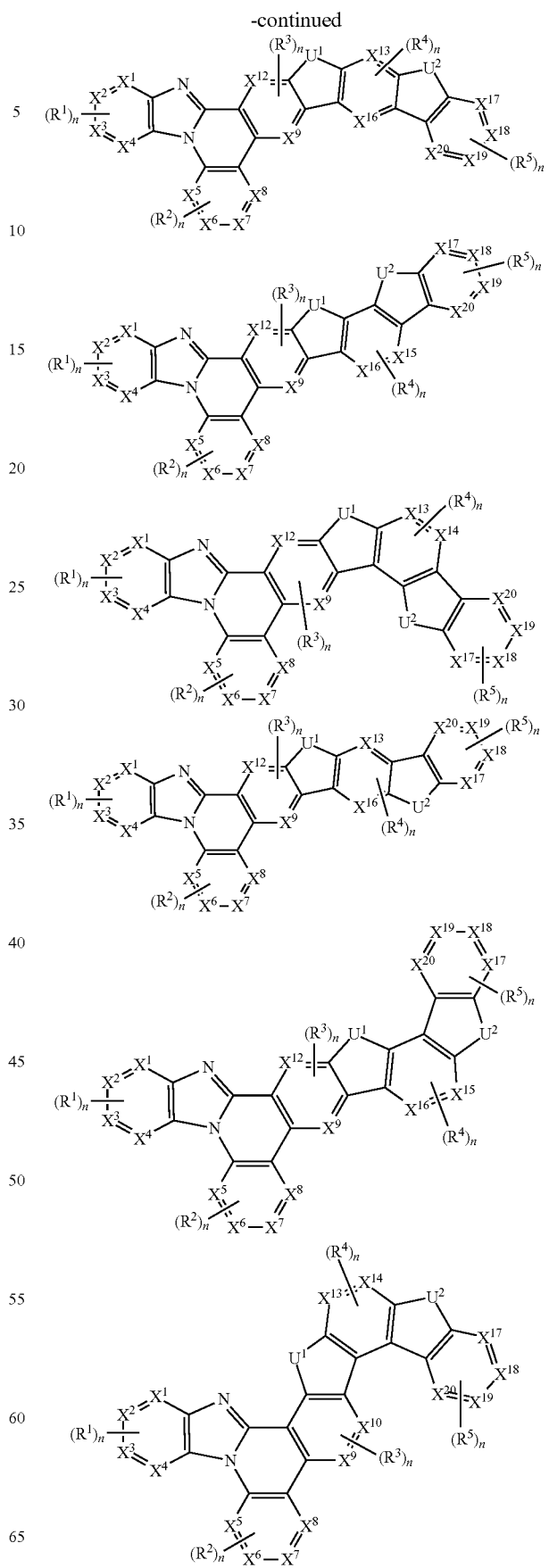

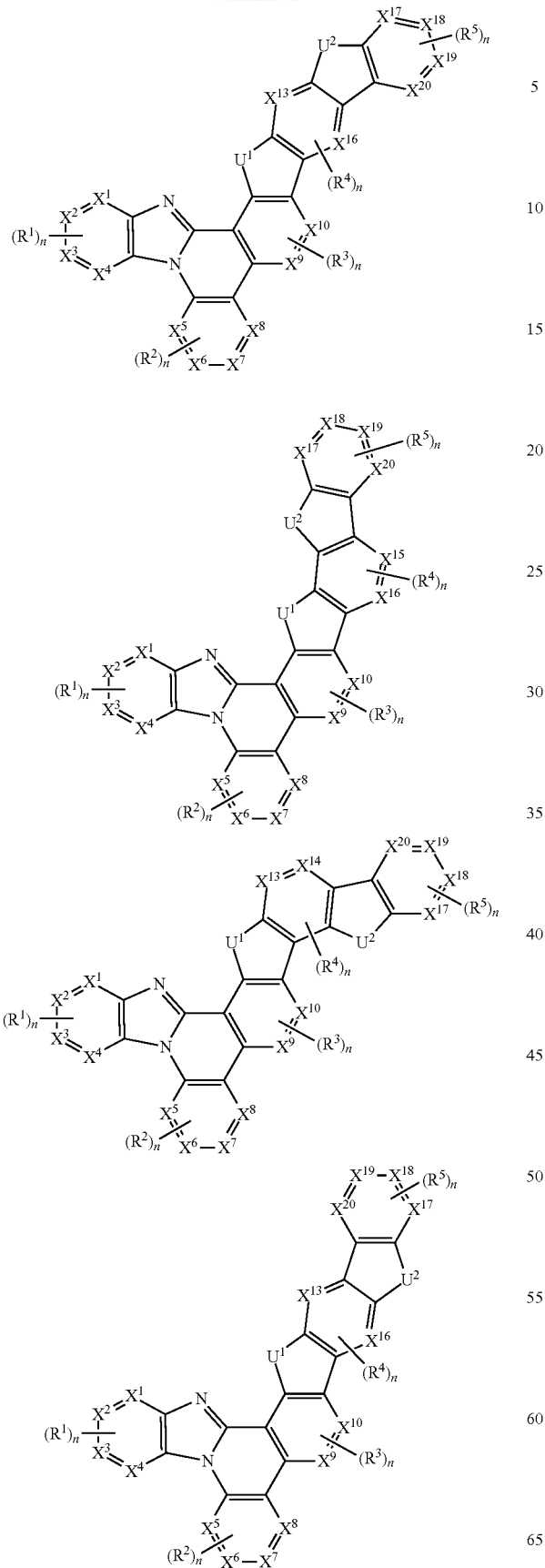
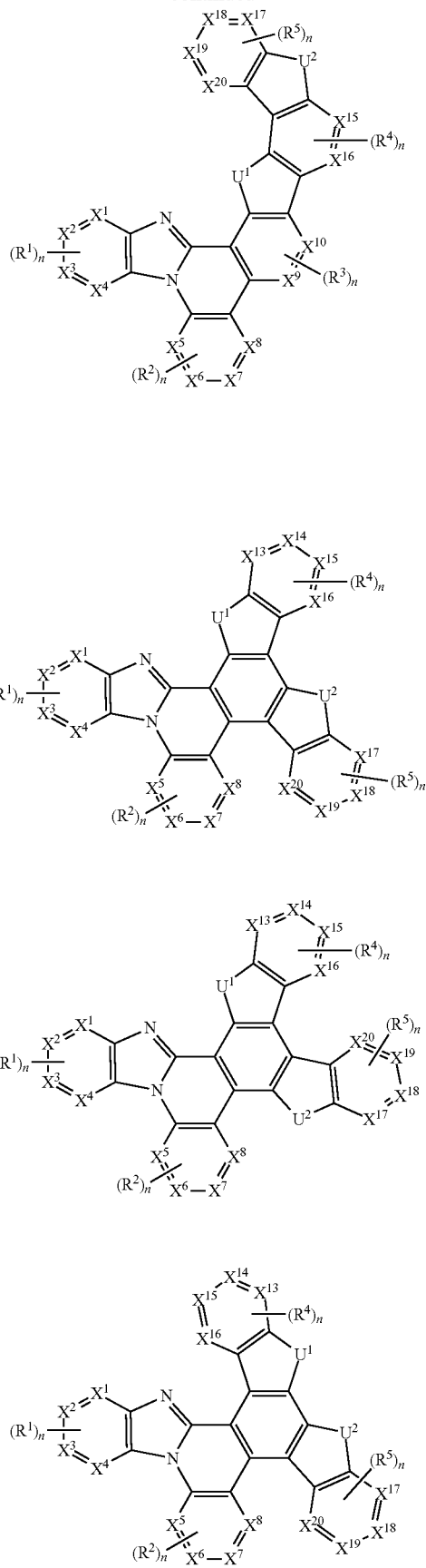

-continued

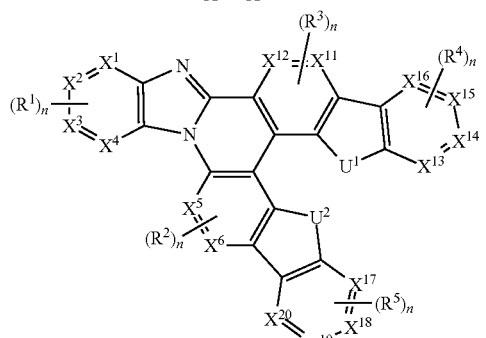
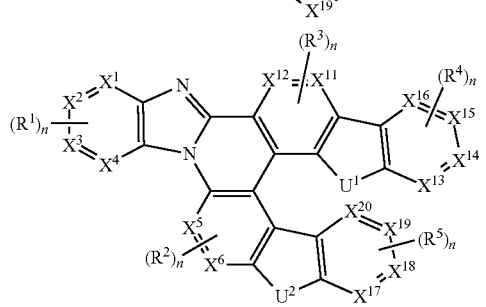
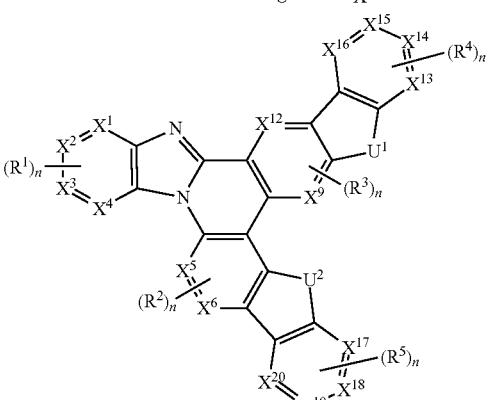
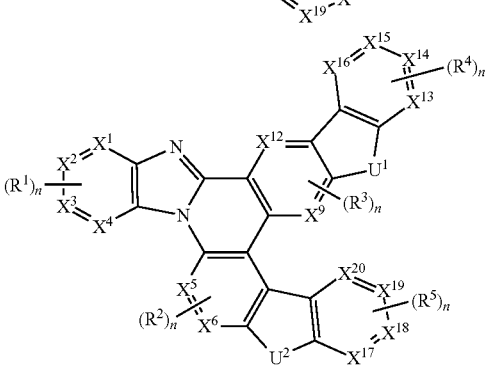
-continued
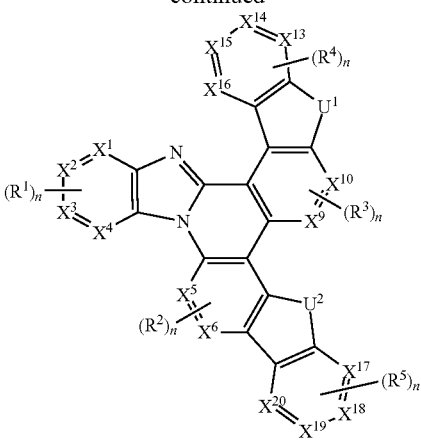
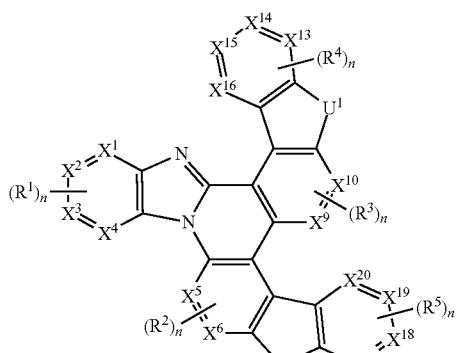
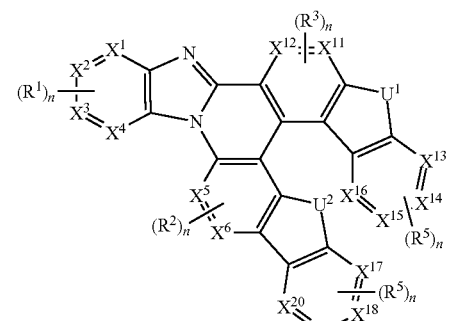
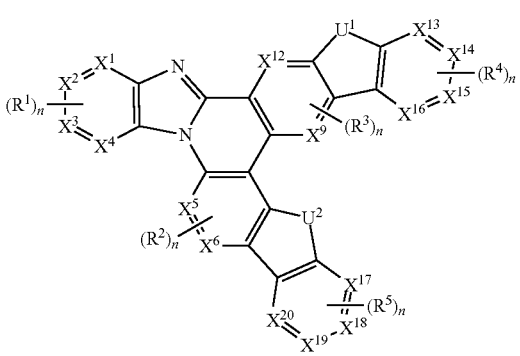

-continued
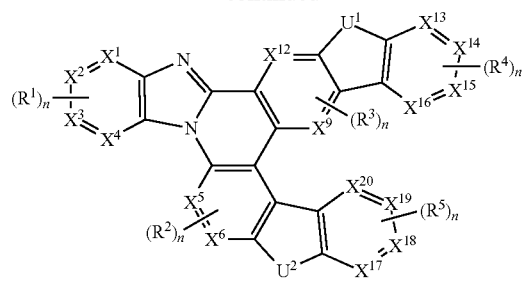
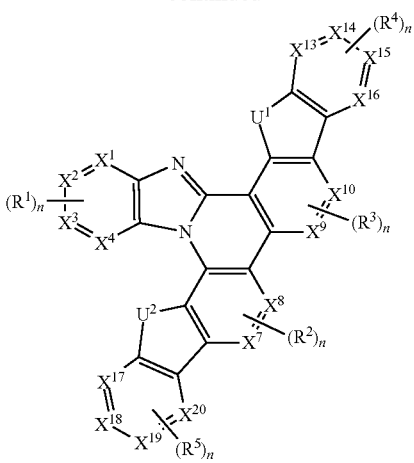
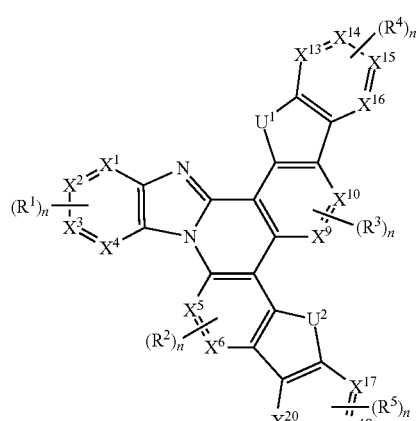
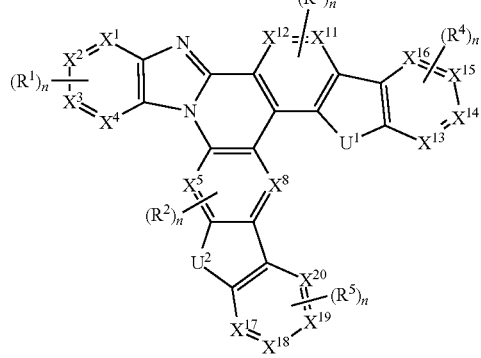
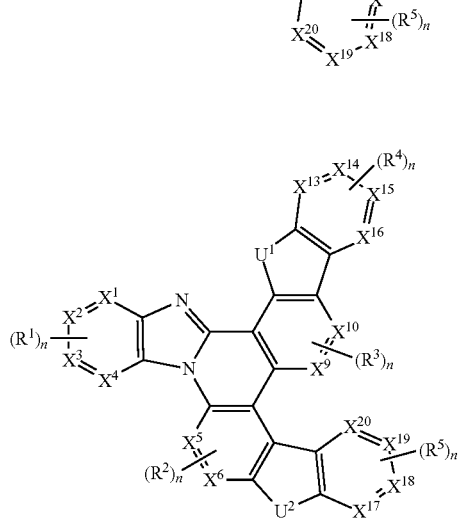
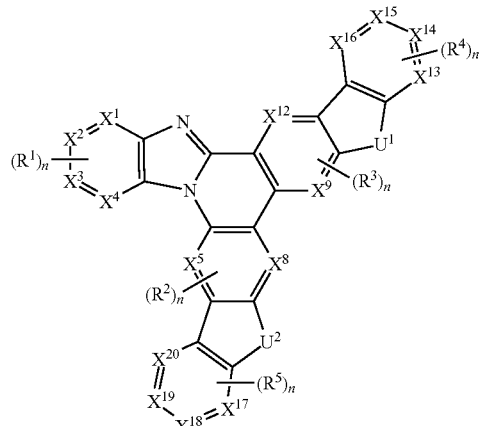
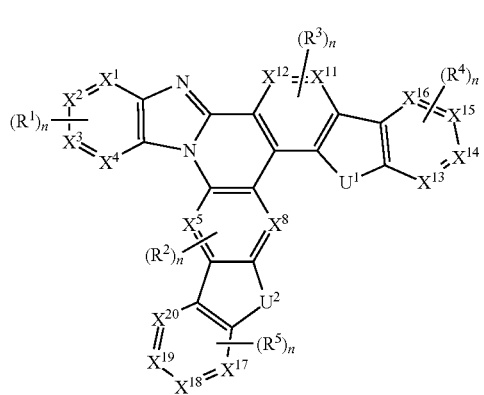
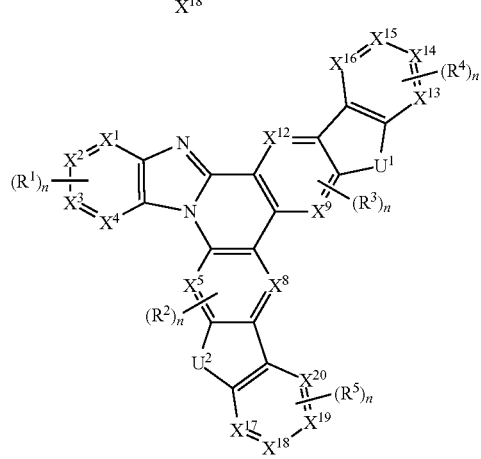

-continued

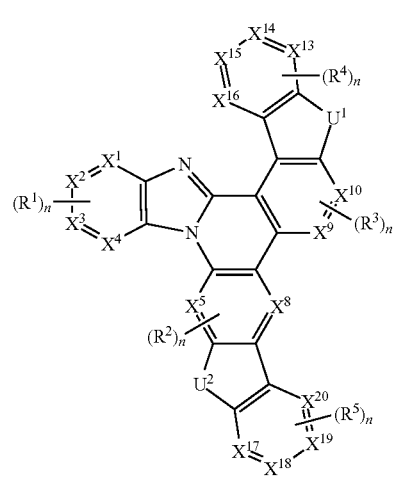
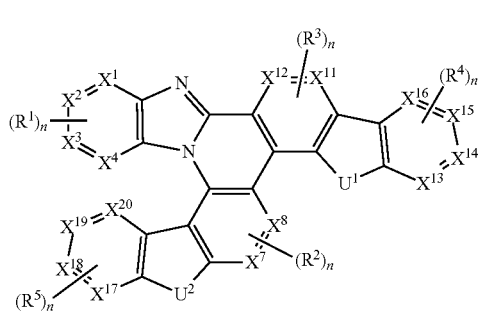
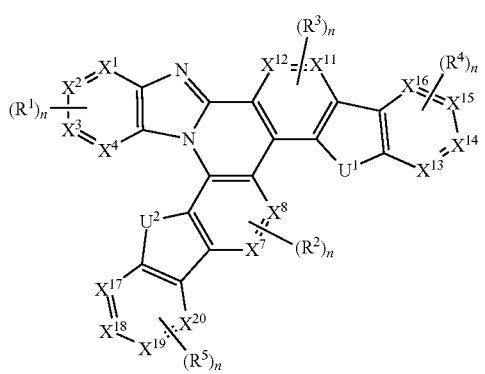
-continued
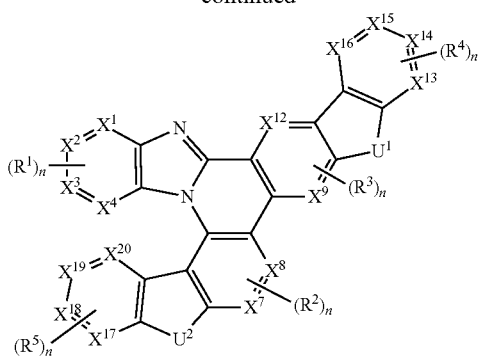
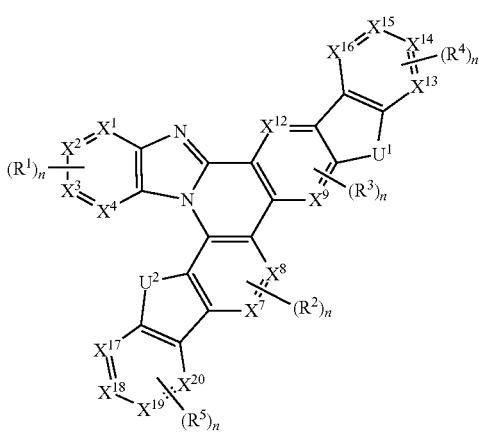
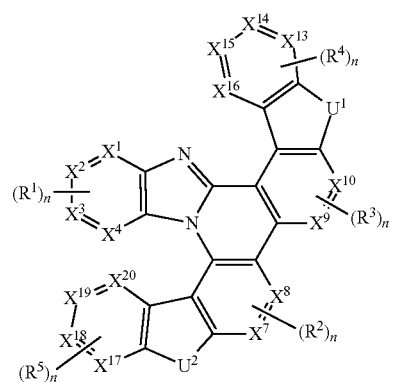
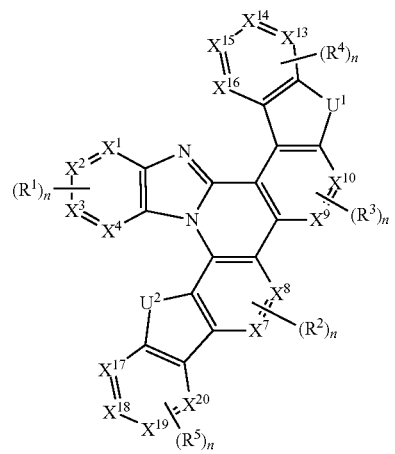

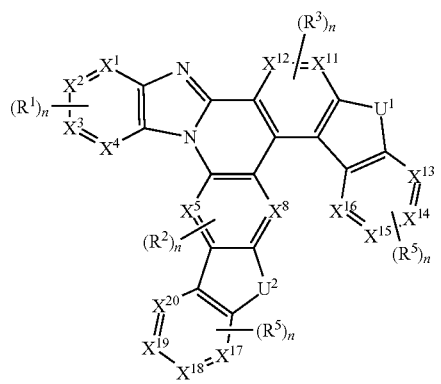
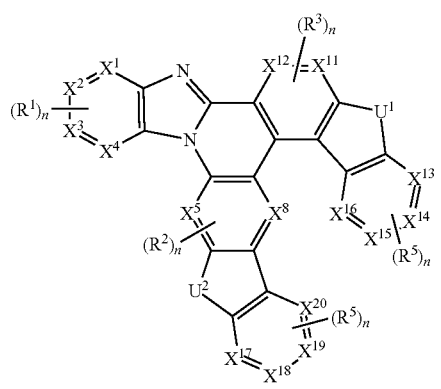
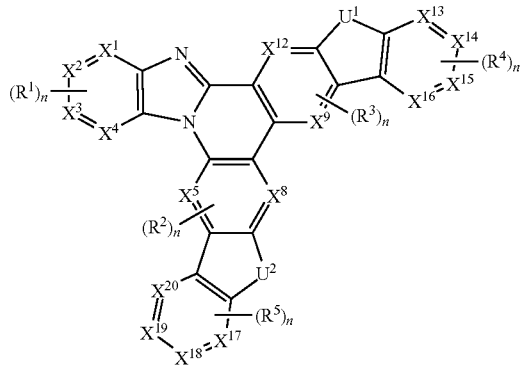
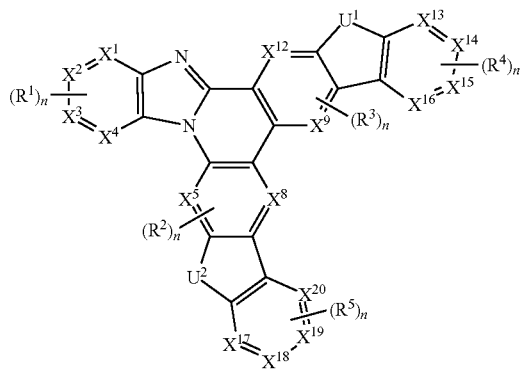
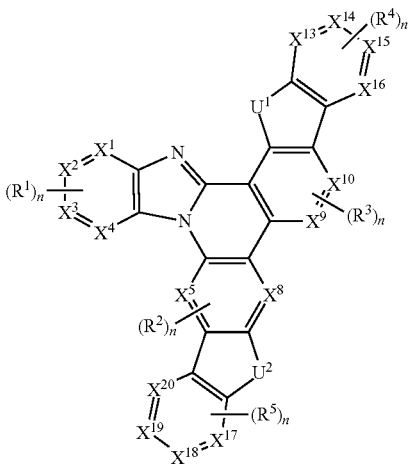
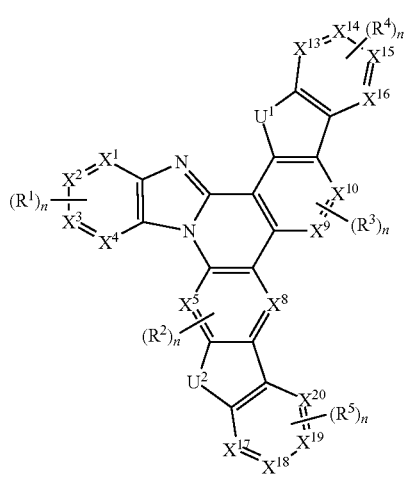
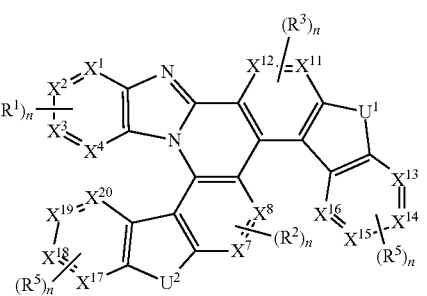
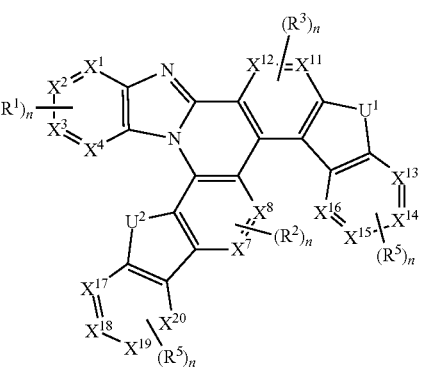

-continued
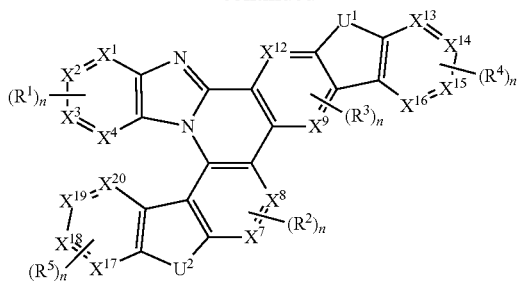
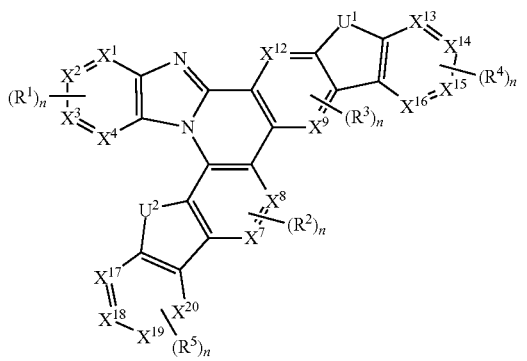
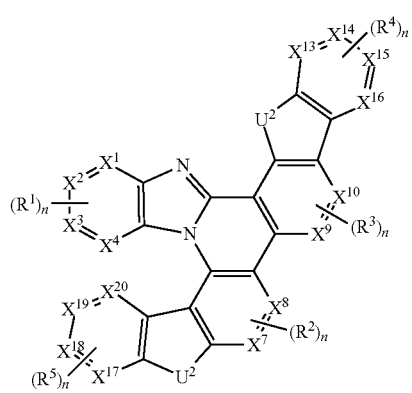
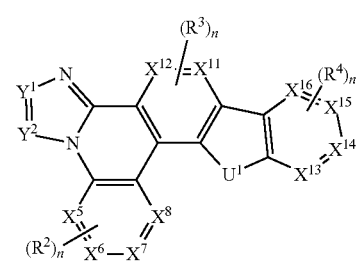
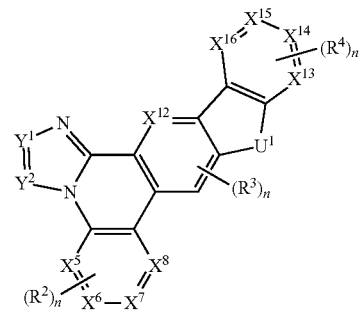
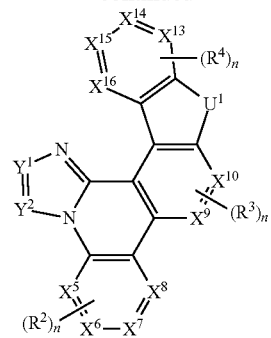
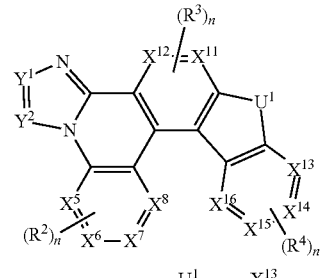
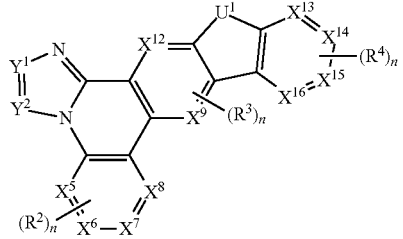
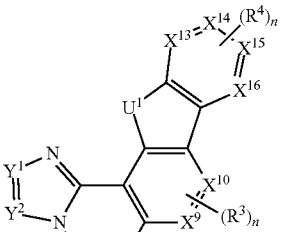
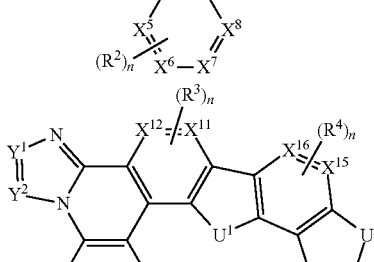
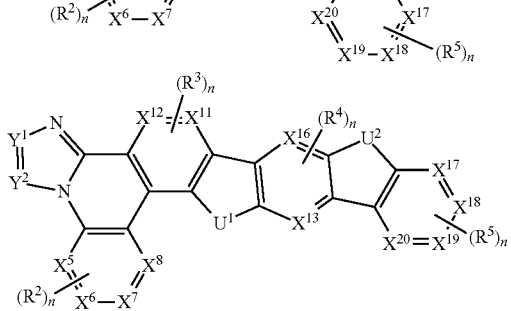

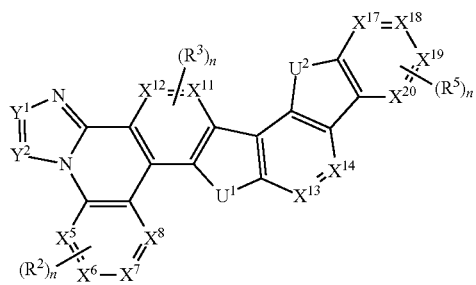
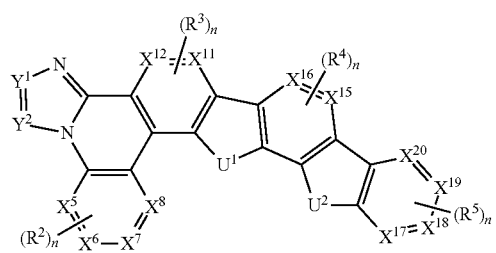
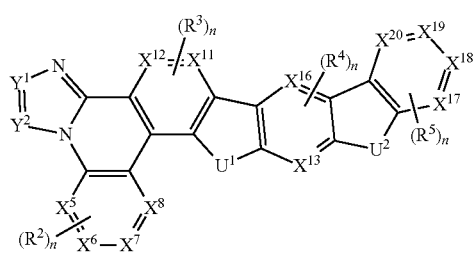
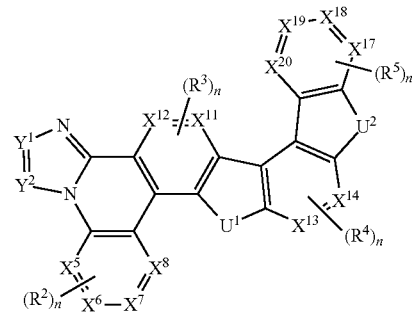
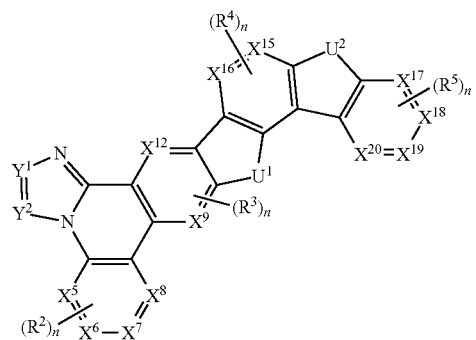
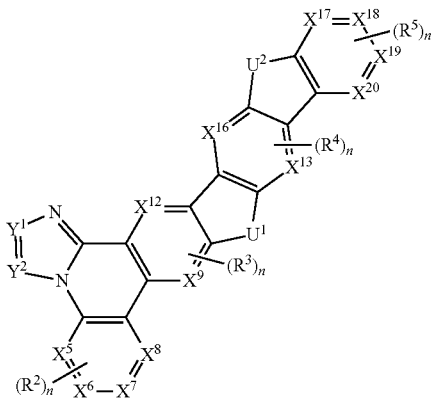
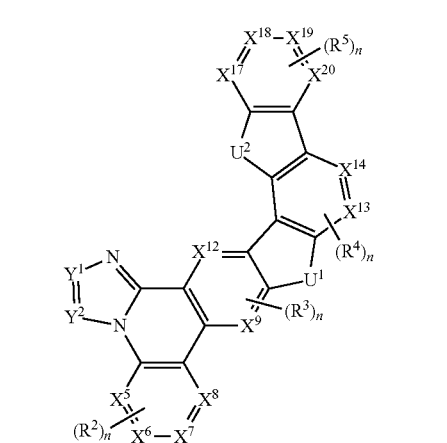
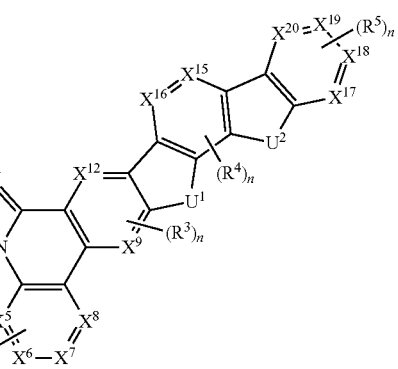
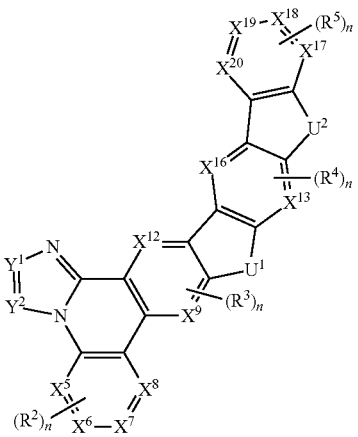

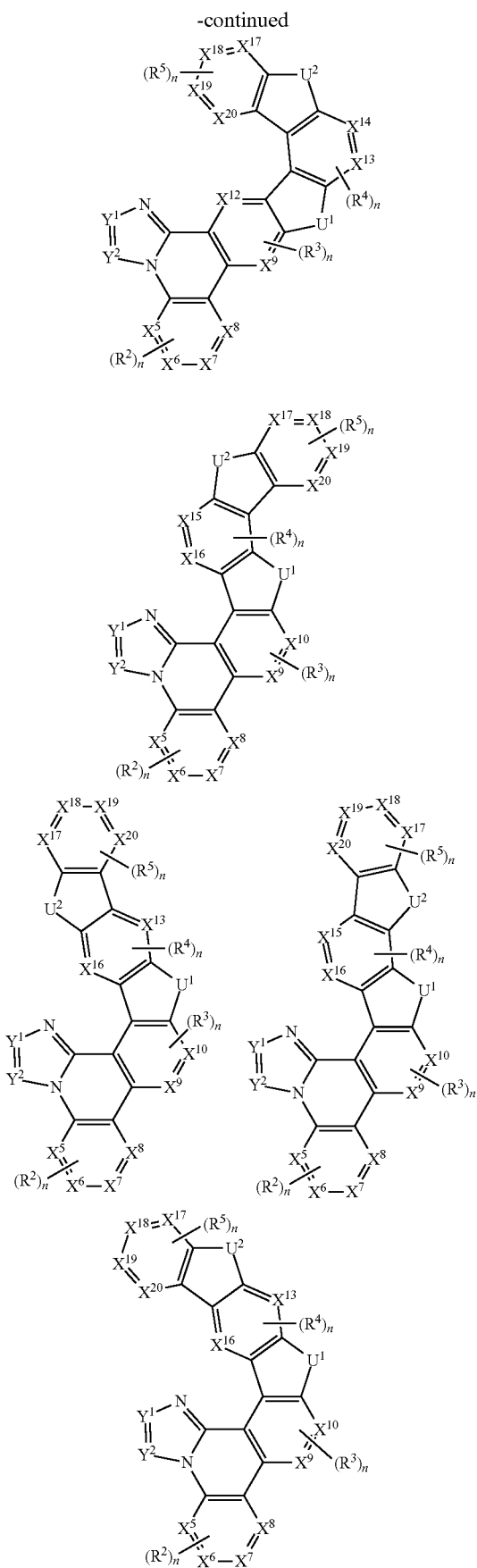
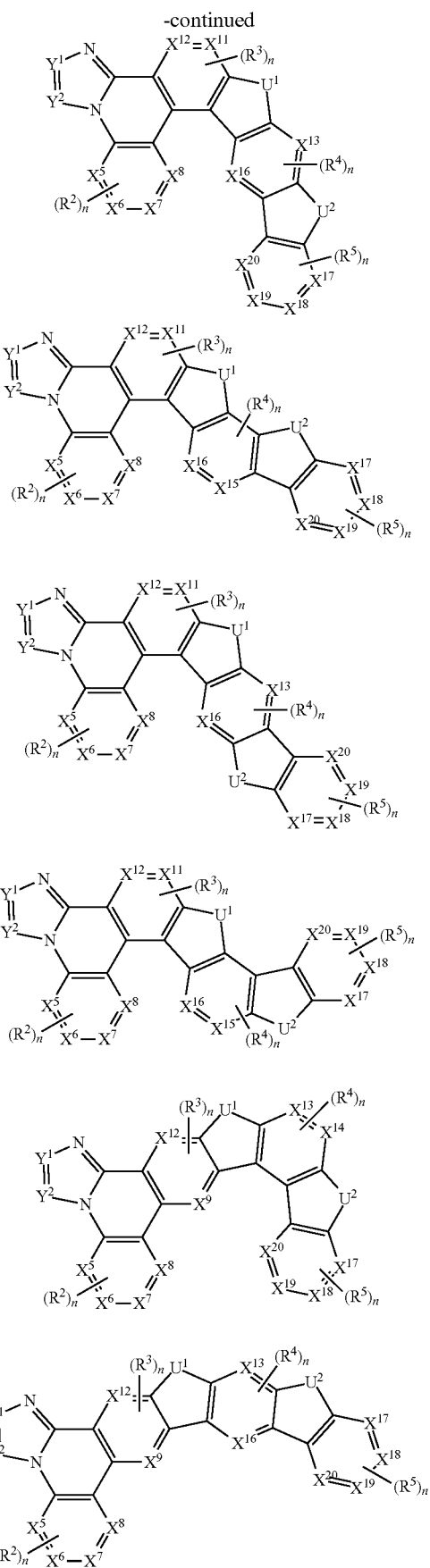

-continued
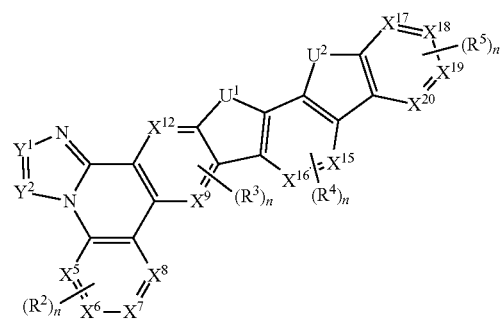
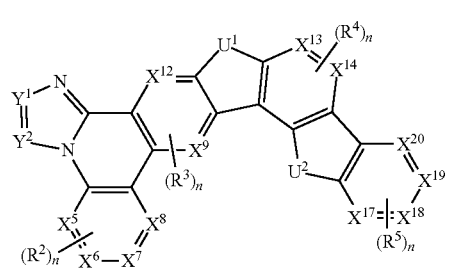
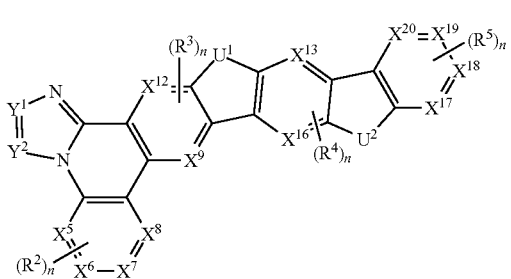
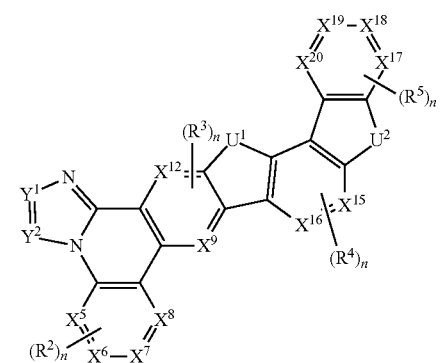
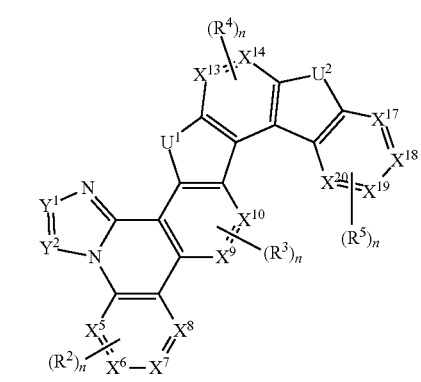
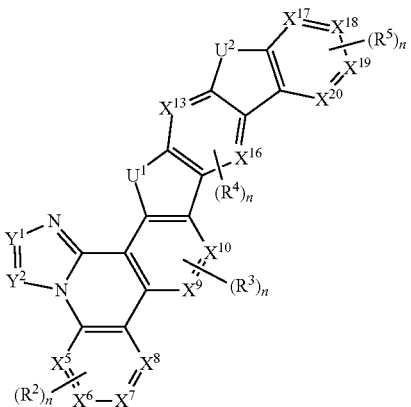
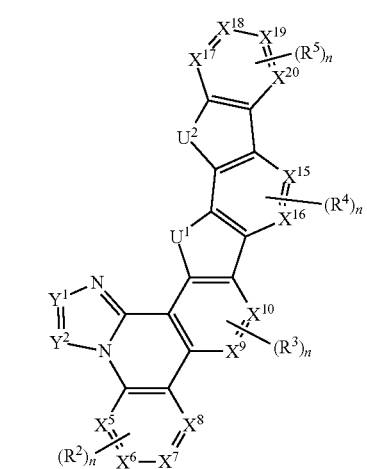
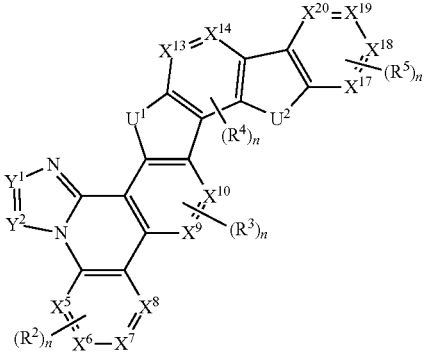
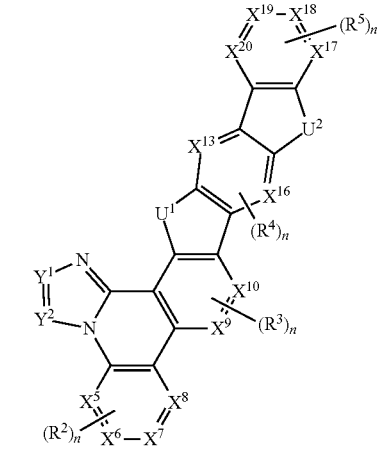

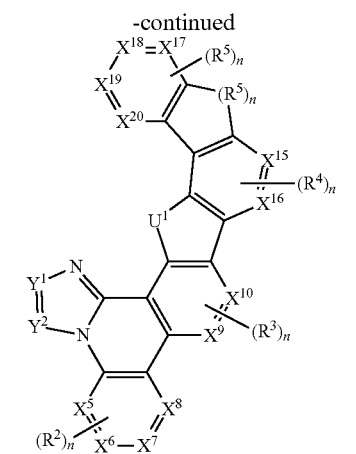
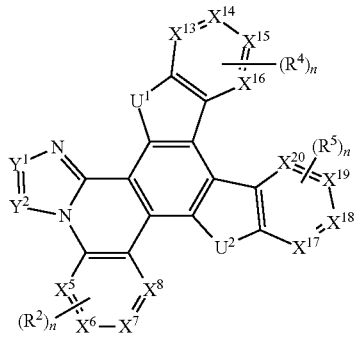
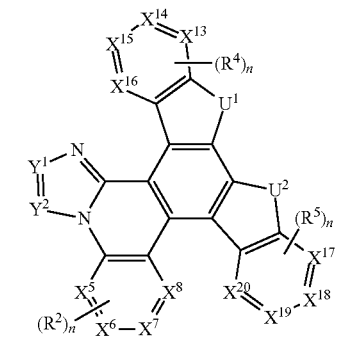
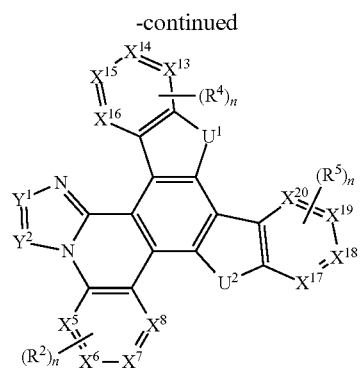
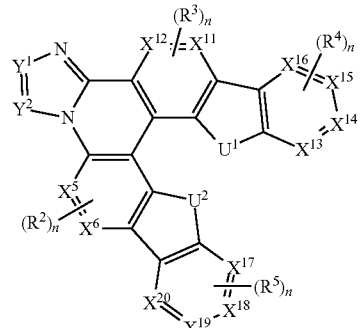
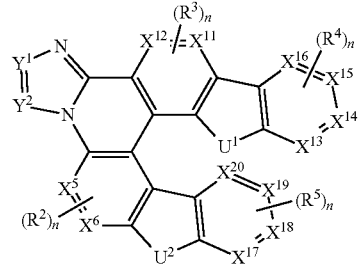
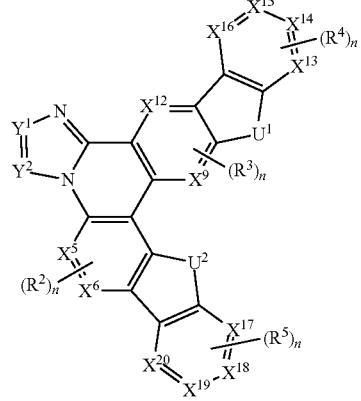
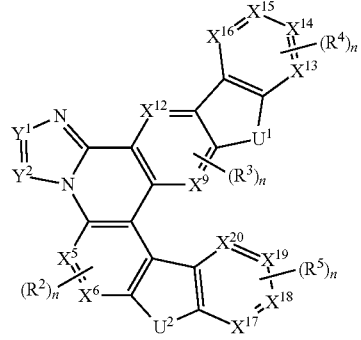

-continued
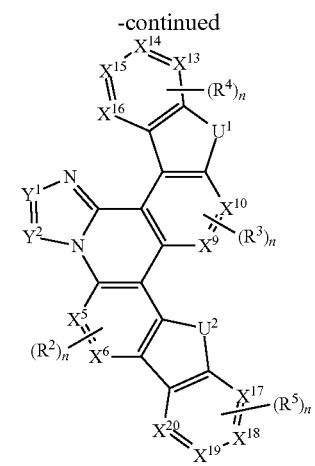
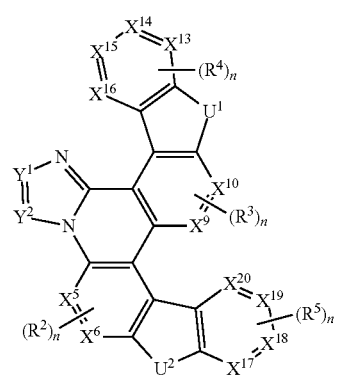
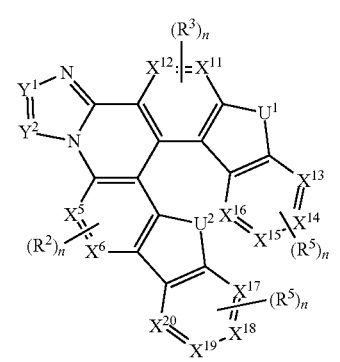
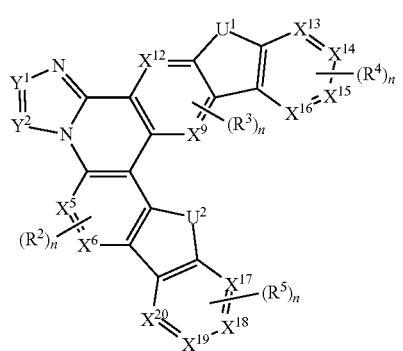
-continued
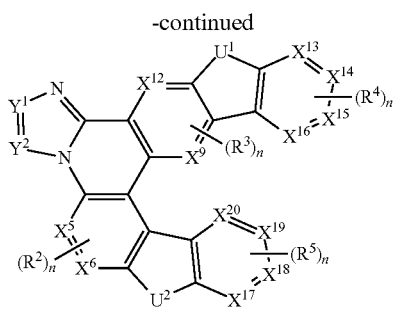
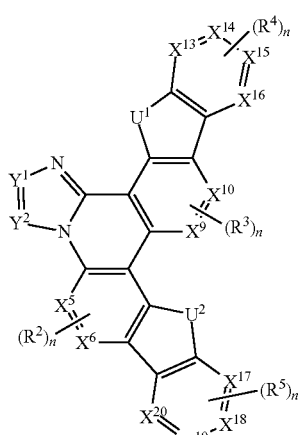
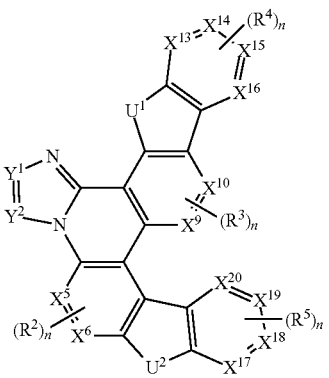
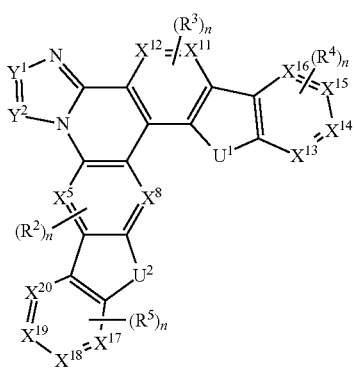

-continued
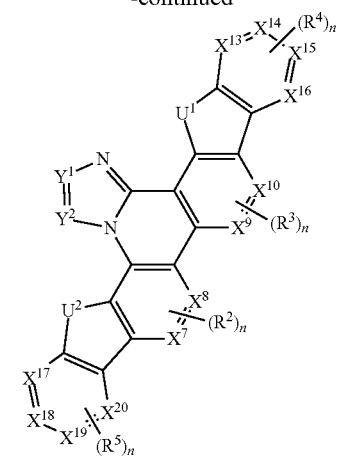
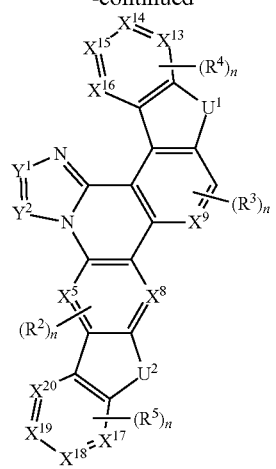
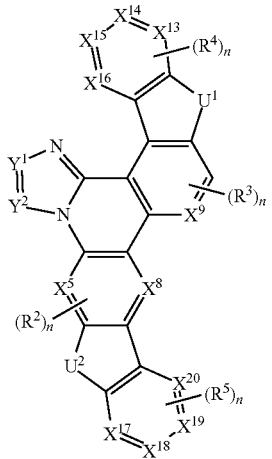
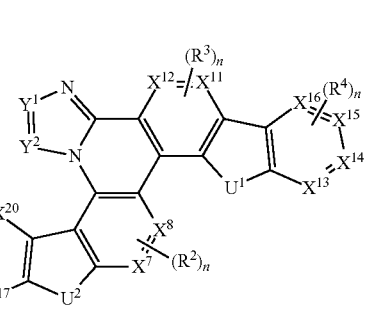
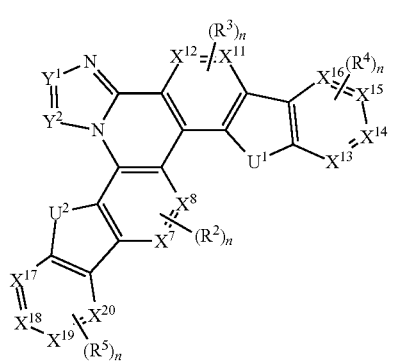

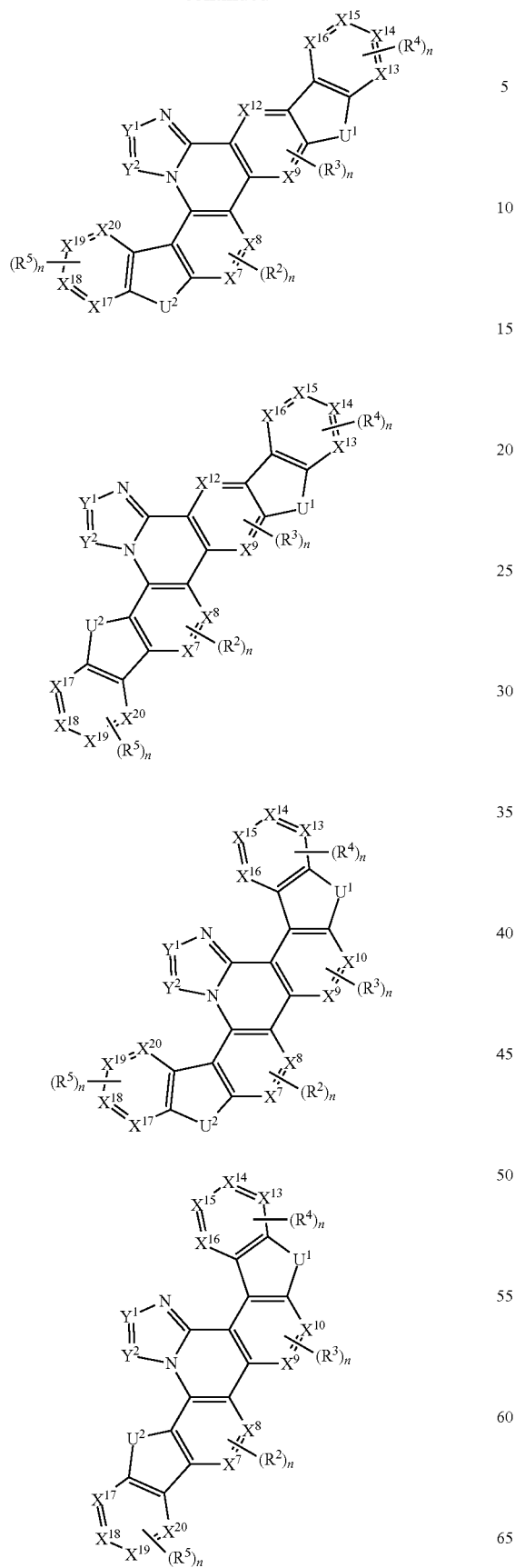
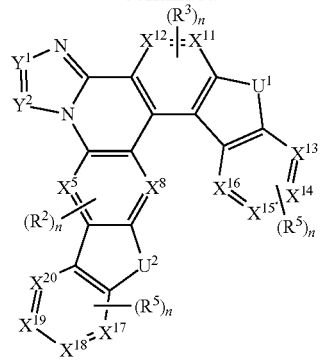
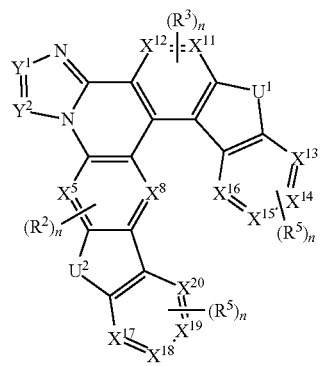
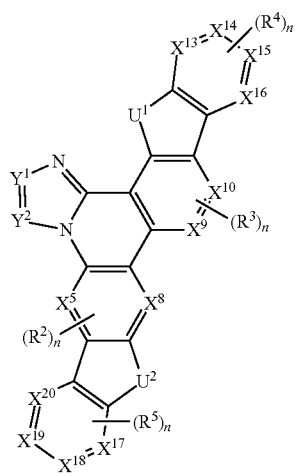
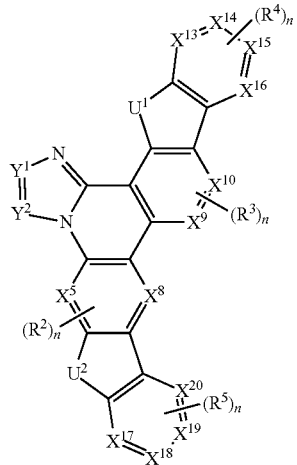

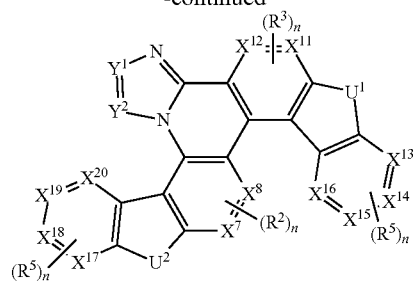
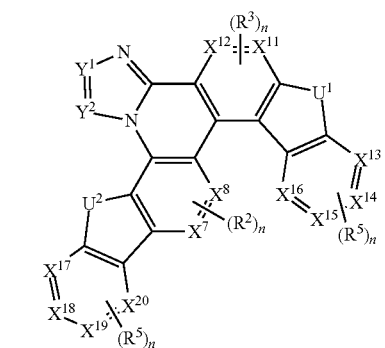
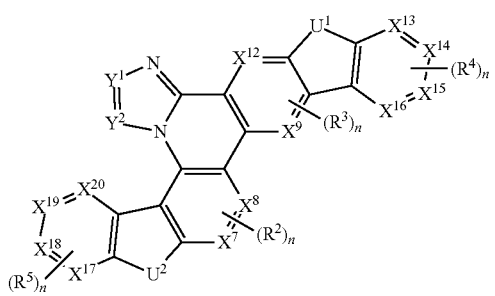
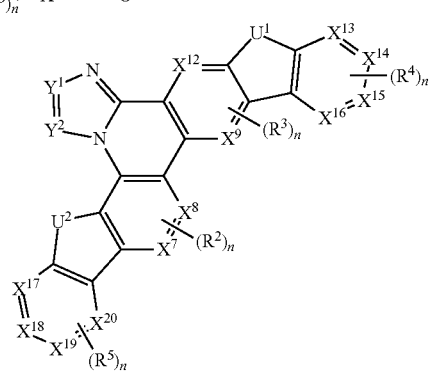
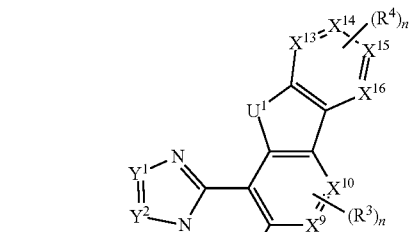
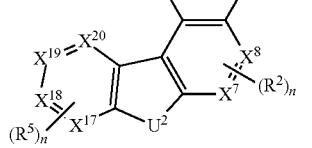
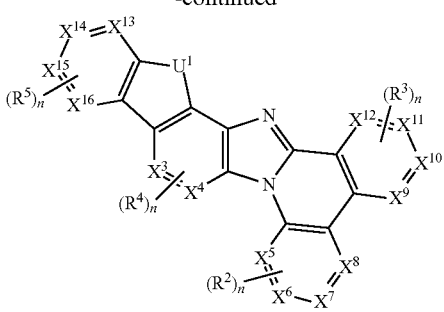
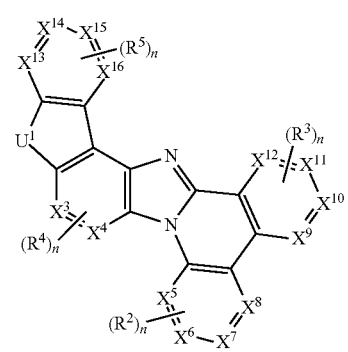
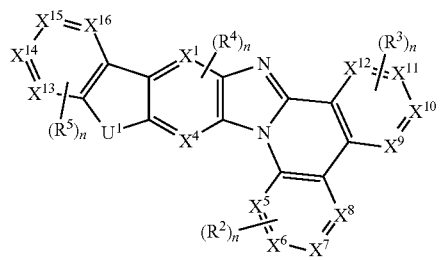
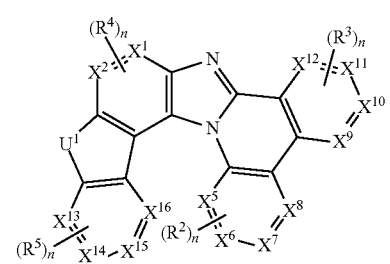
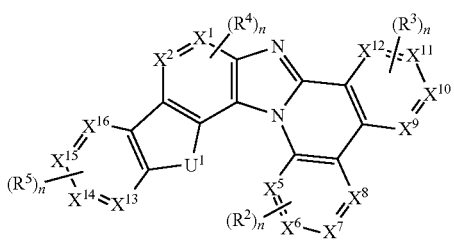

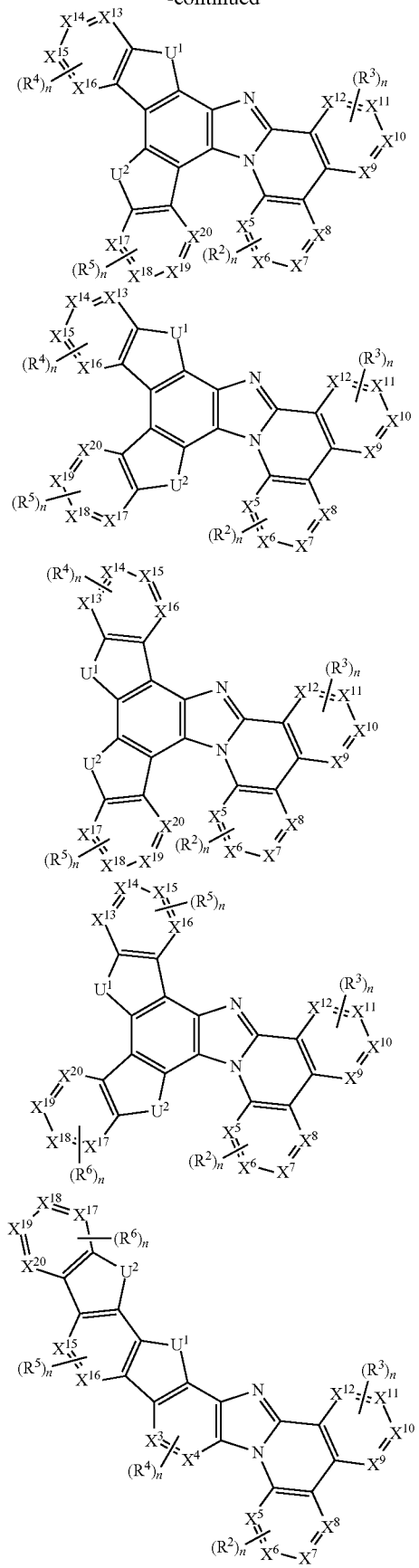
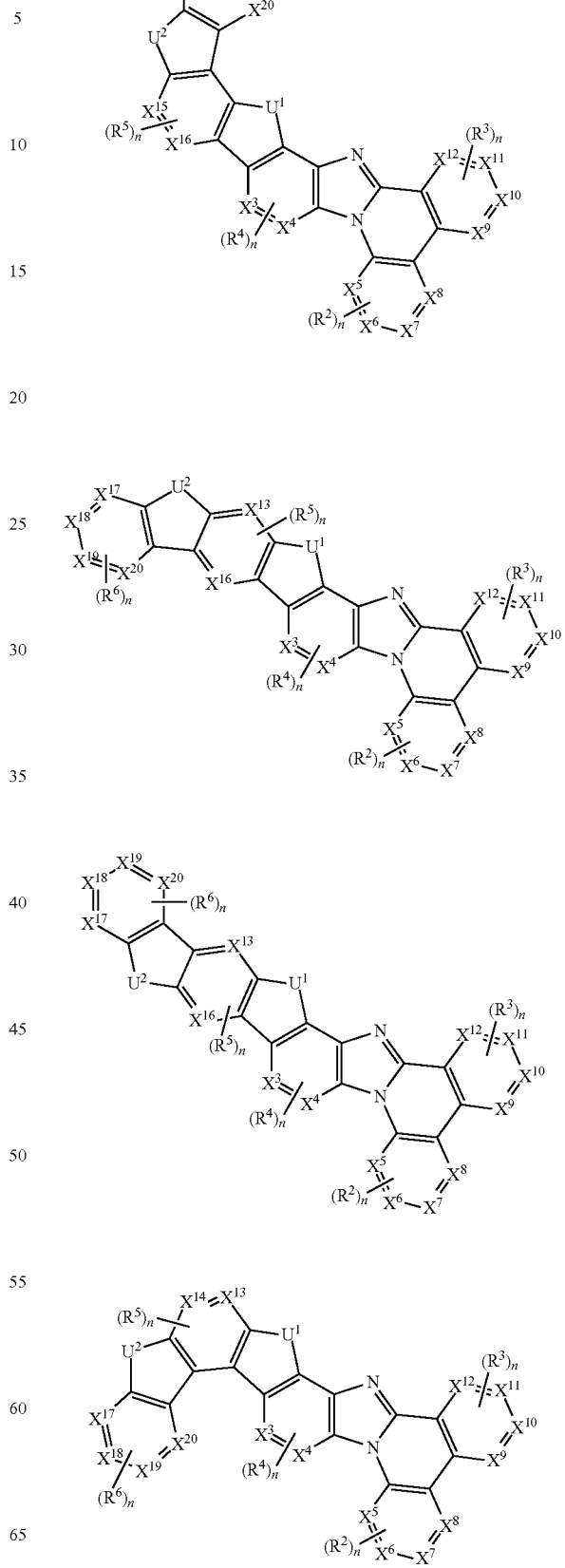

-continued
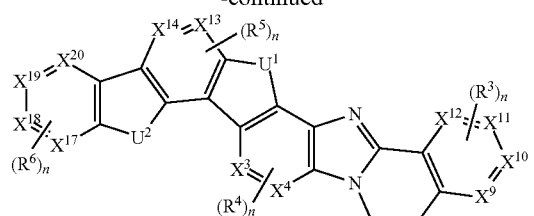
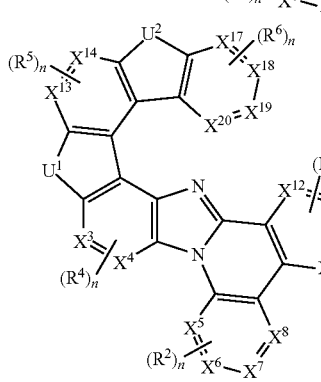
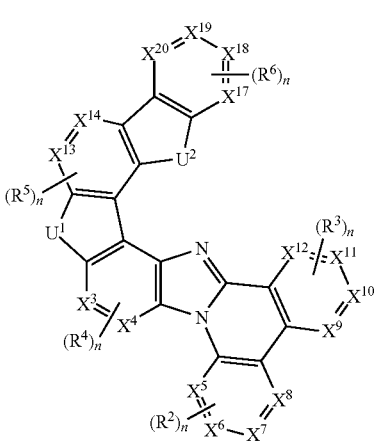
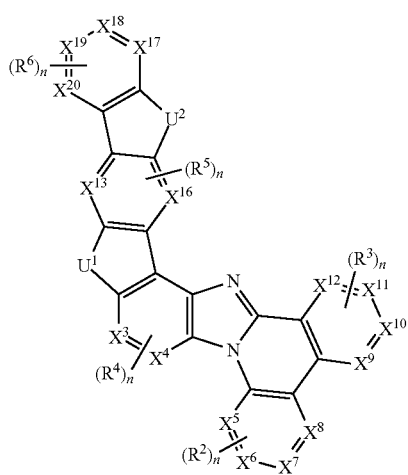
-continued
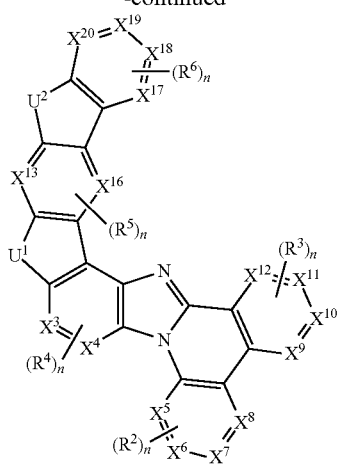
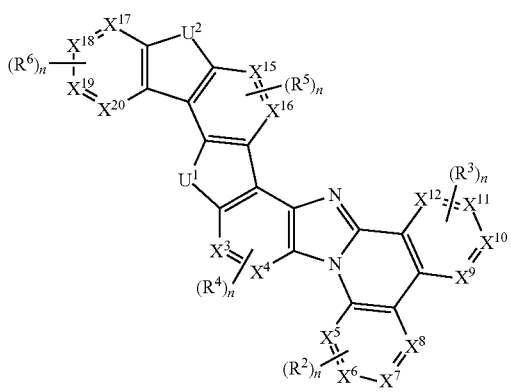
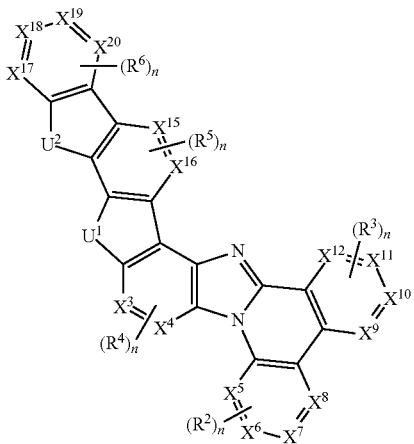
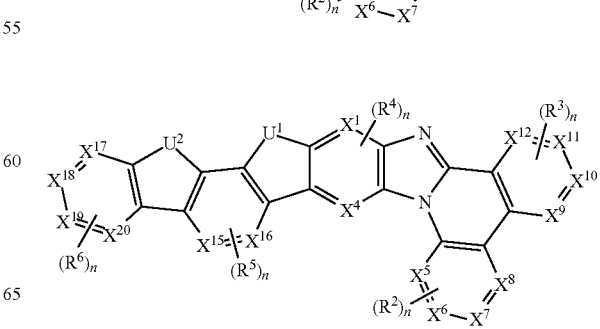

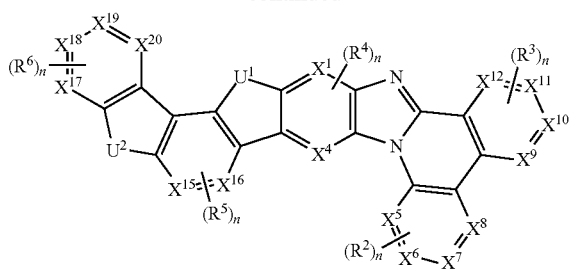
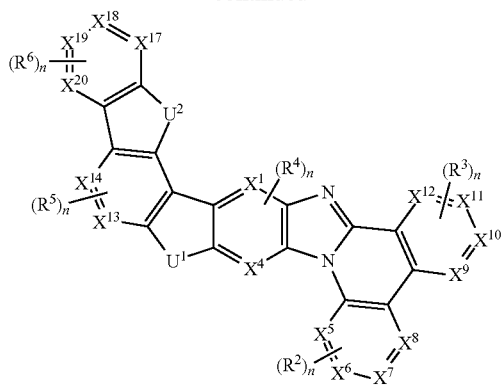
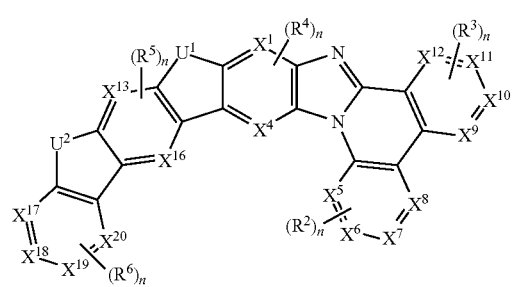
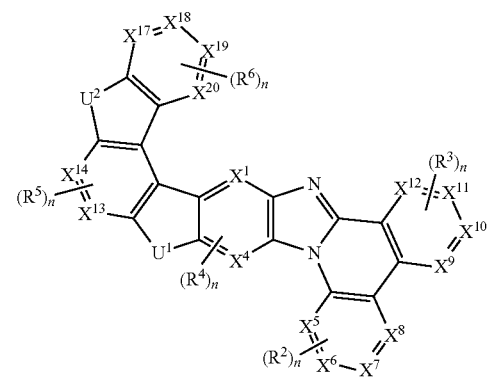
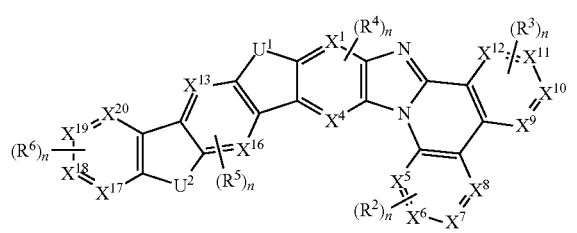
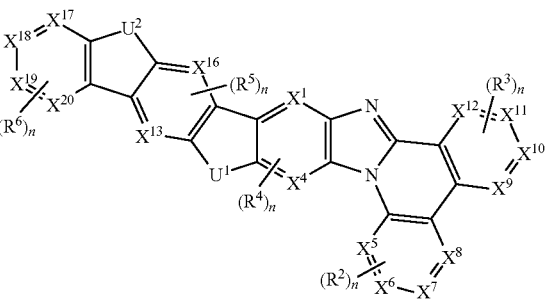
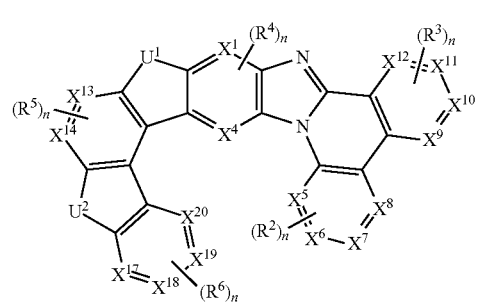
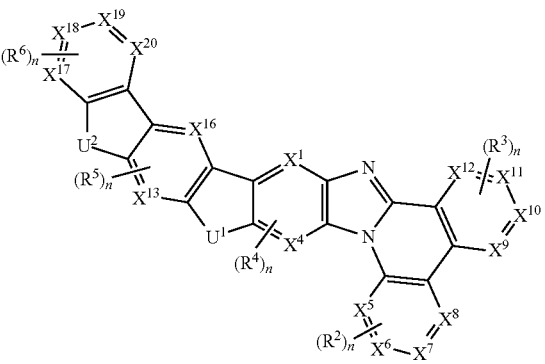
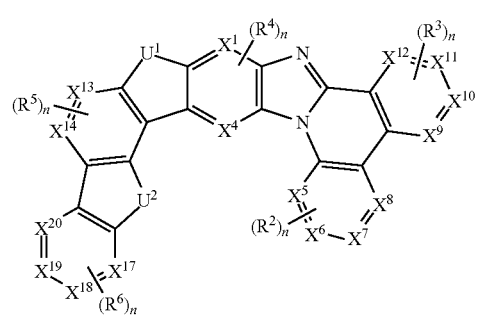
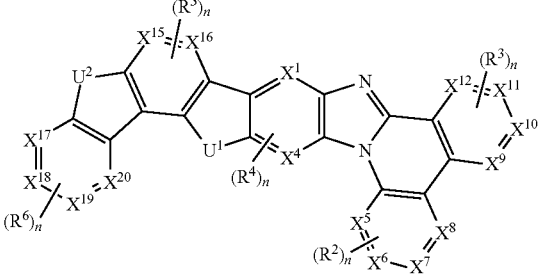

-continued
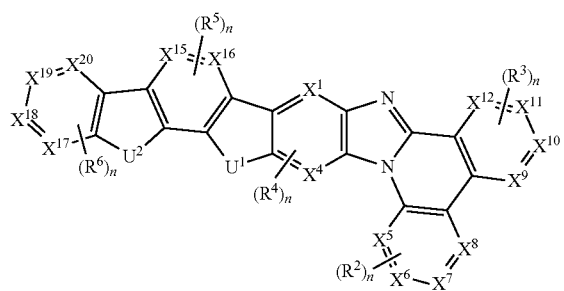
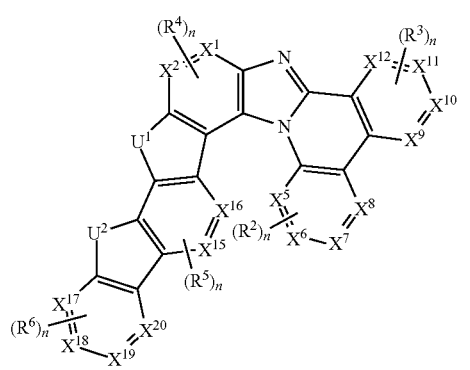
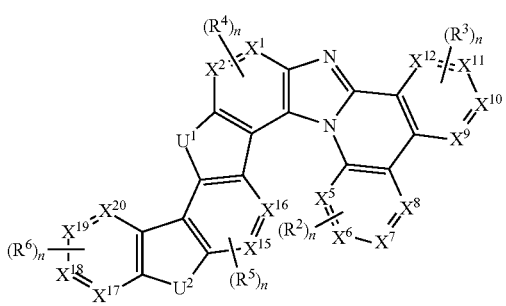
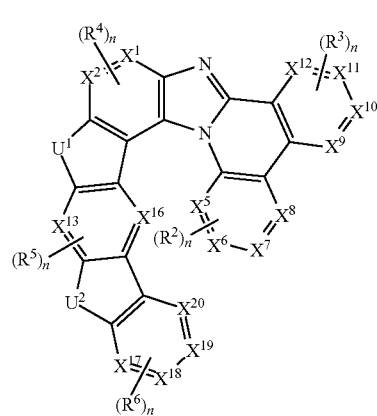
-continued
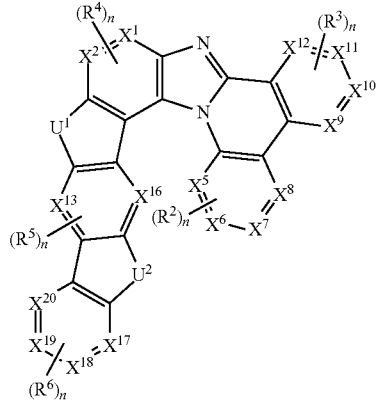
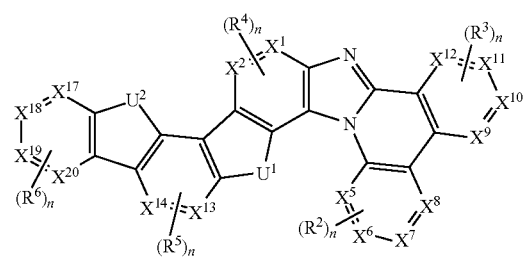
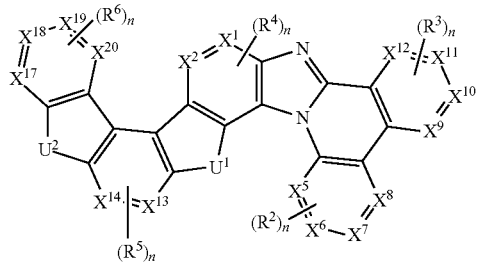
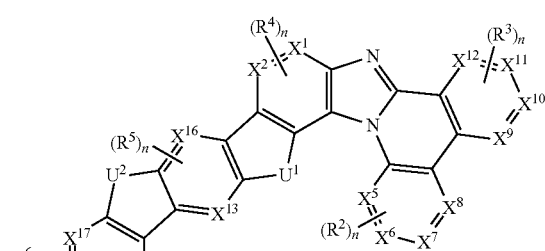
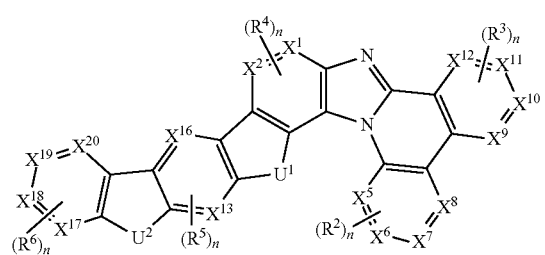

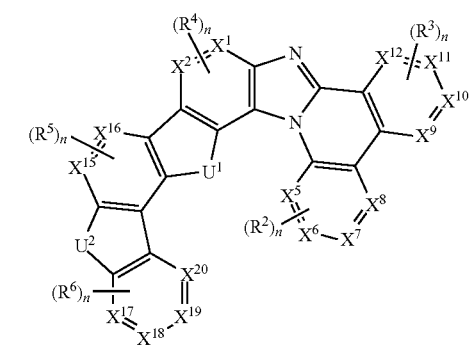
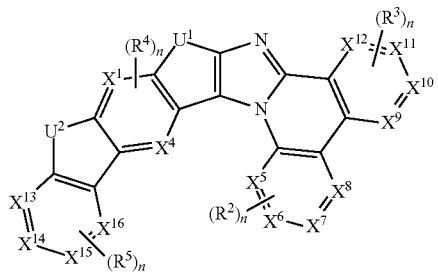
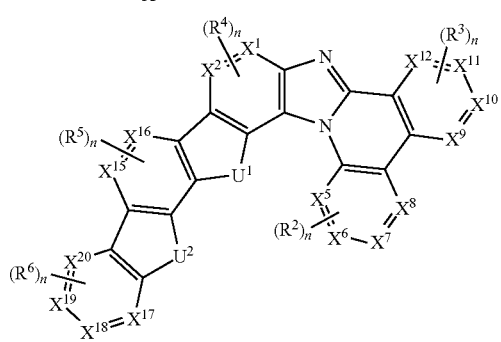
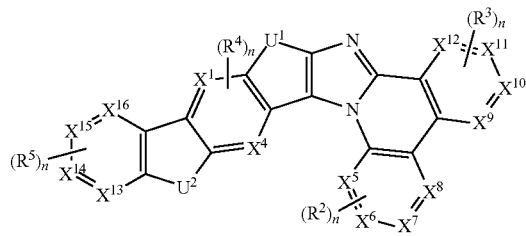
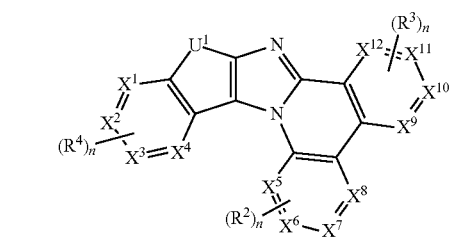
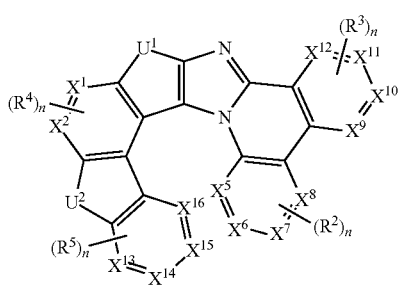
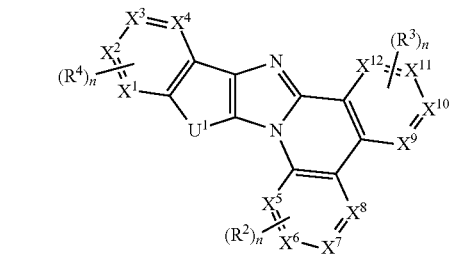
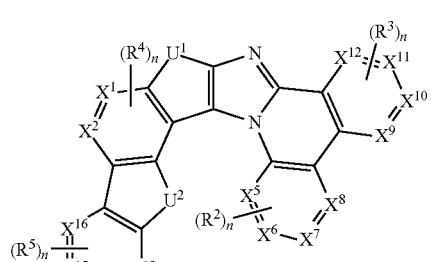
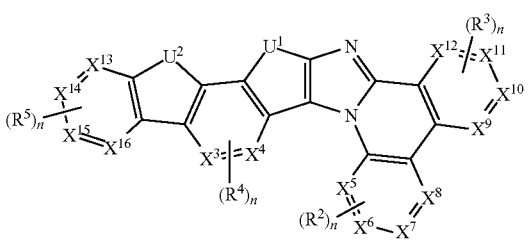
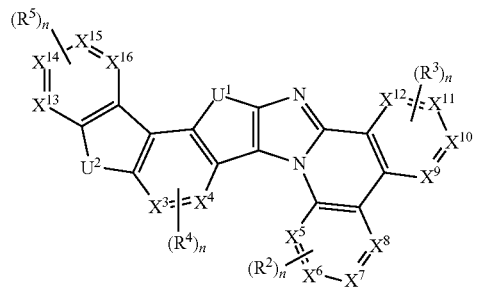
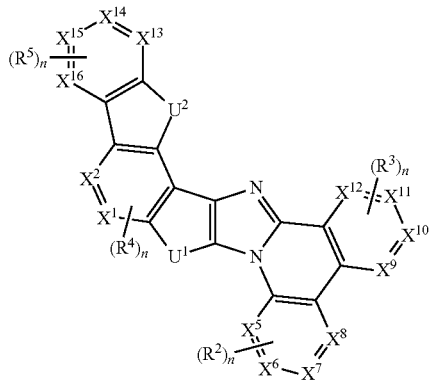

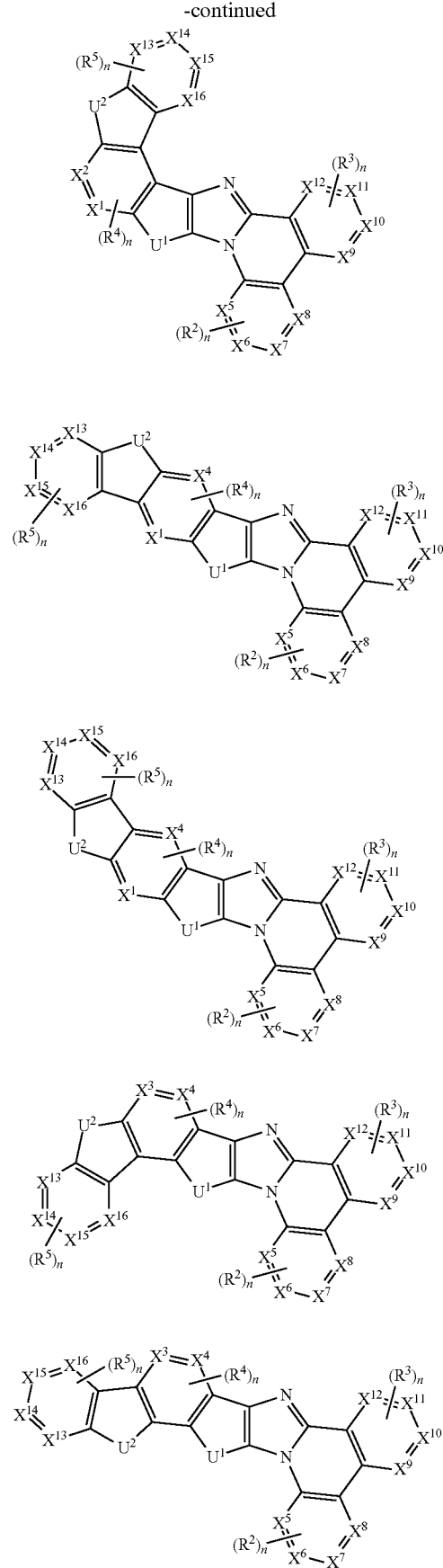

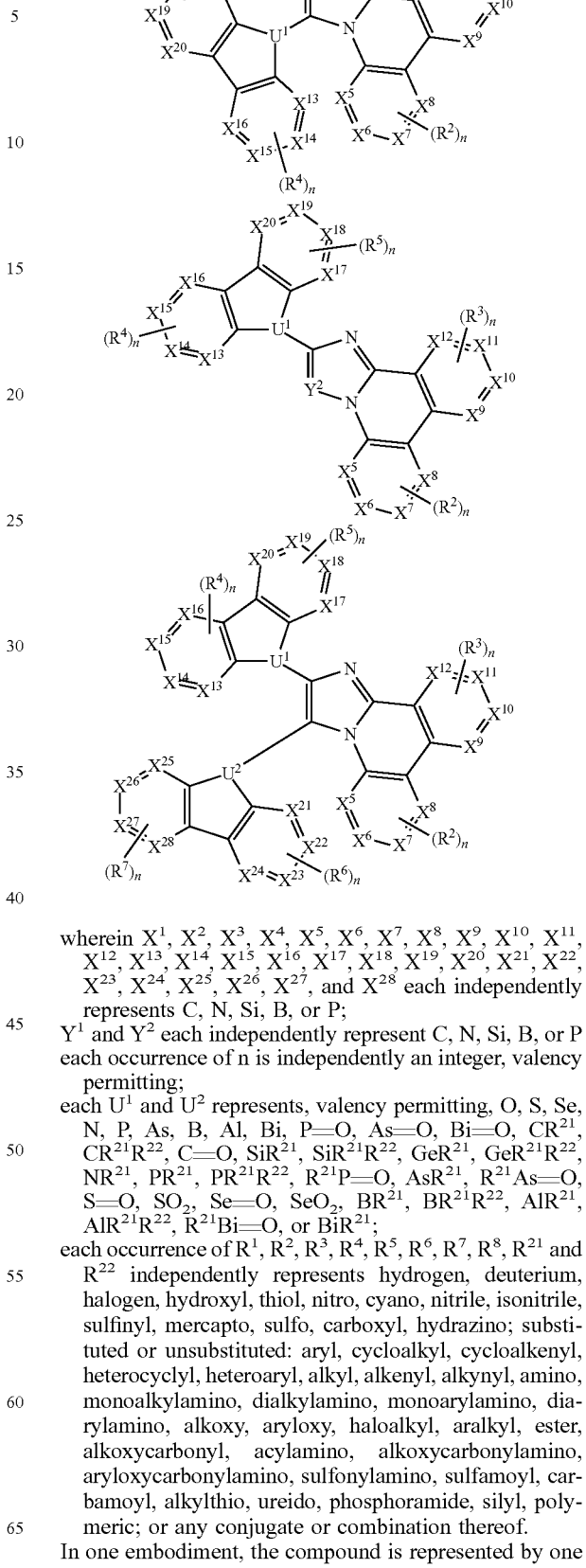

wherein $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$, $X^{25}$, $X^{26}$, $X^{27}$, and $X^{28}$ each independently represents C, N, Si, B, or P;

$Y^1$ and $Y^2$ each independently represent C, N, Si, B, or P each occurrence of n is independently an integer, valency permitting;

each $U^1$ and $U^2$ represents, valency permitting, O, S, Se, N, P, As, B, Al, Bi, P=O, As=O, Bi=O, $CR^{21}$, $CR^{21}R^{22}$, C=O, $SiR^{21}$, $SiR^{21}R^{22}$, $GeR^{21}$, $GeR^{21}R^{22}$, $NR^{21}$, $PR^{21}$, $PR^{21}R^{22}$, $R^{21}P$=O, $AsR^{21}$, $R^{21}As$=O, S=O, $SO_2$, Se=O, $SeO_2$, $BR^{21}$, $BR^{21}R^{22}$, $AlR^{21}$, $AlR^{21}R^{22}$, $R^{21}Bi$=O, or $BiR^{21}$;

each occurrence of $R^1$, $R^2$, $R^3$, $R^4$, $R^5$, $R^6$, $R^7$, $R^8$, $R^{21}$ and $R^{22}$ independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one embodiment, the compound is represented by one of the following structures:

63
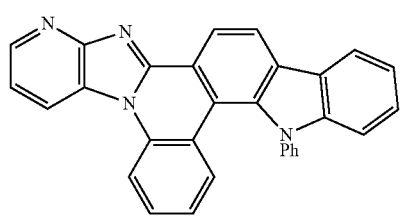
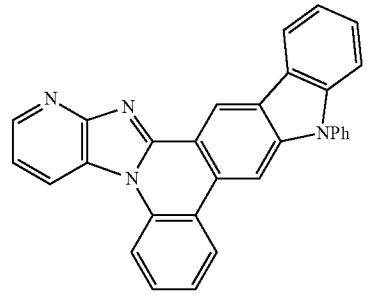
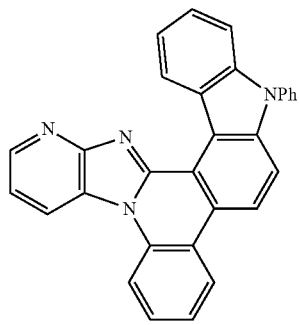
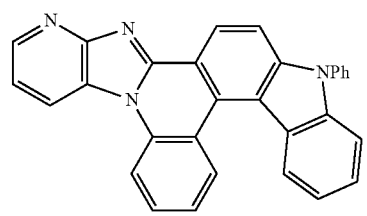
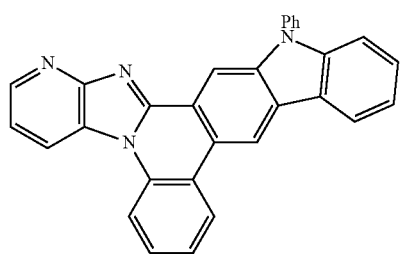
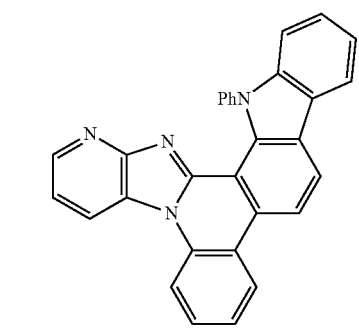
64
-continued
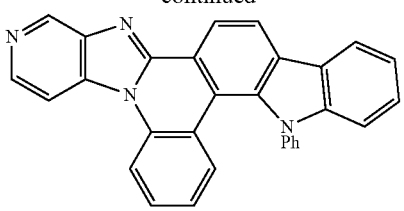
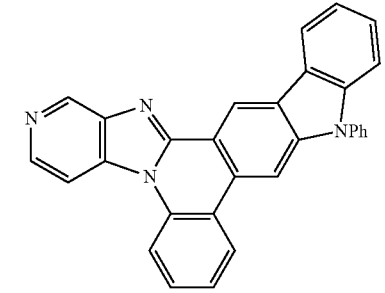
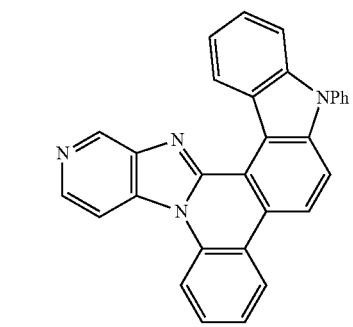
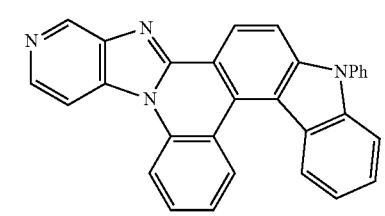
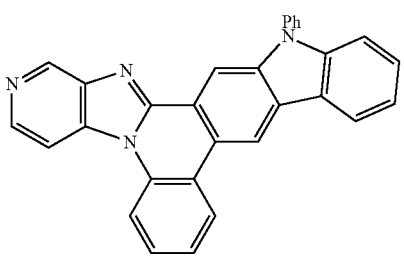

-continued
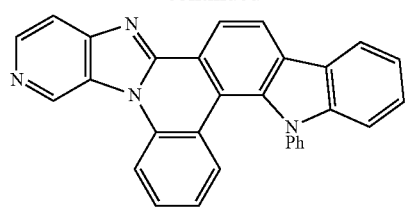
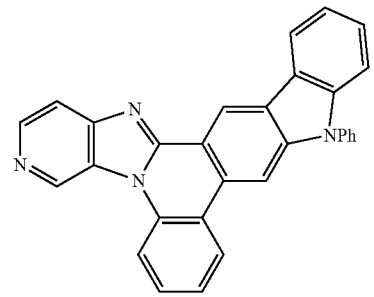
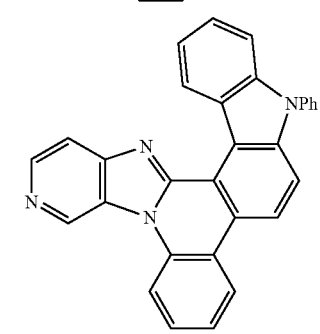
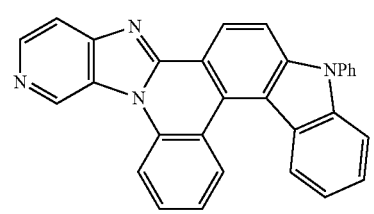
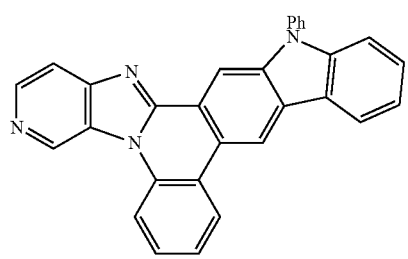
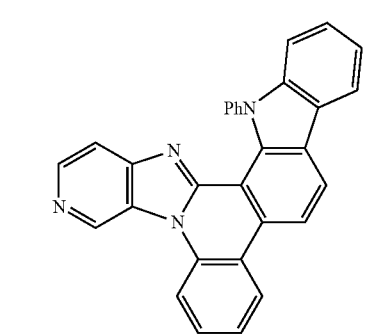
-continued
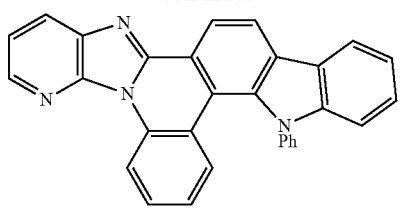
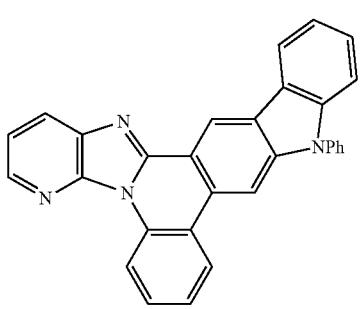
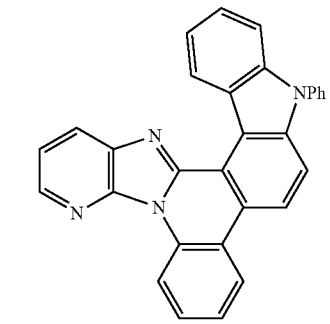
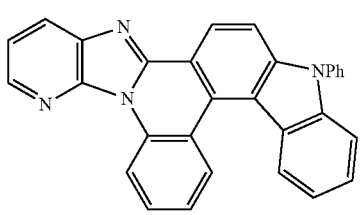
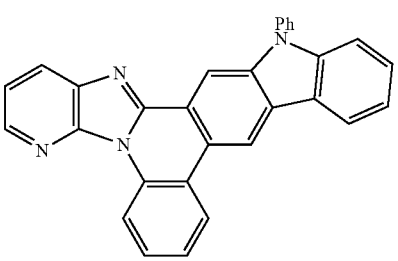
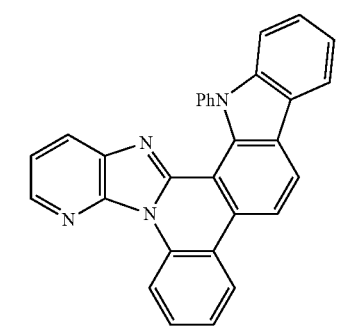

67
-continued
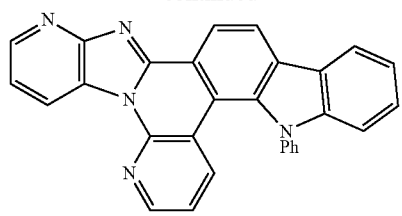
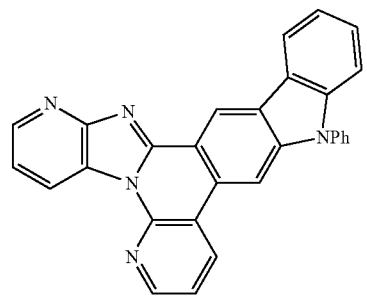
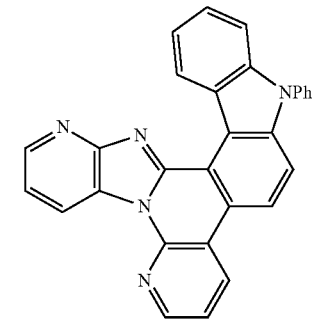
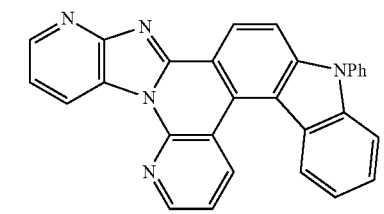
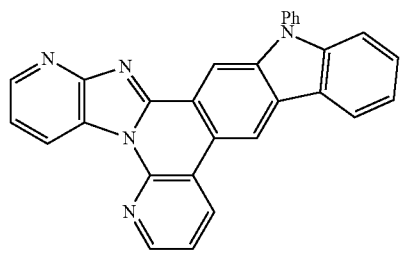
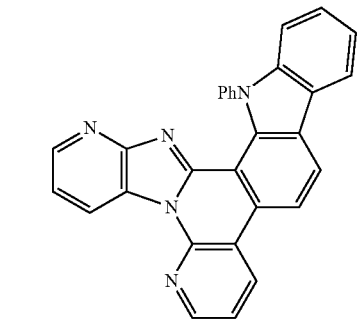
68
-continued
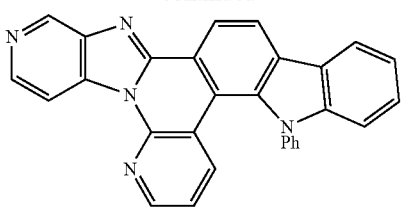
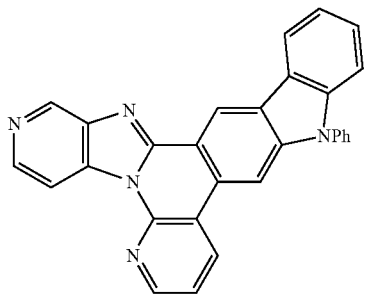
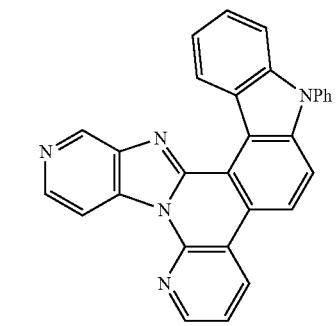
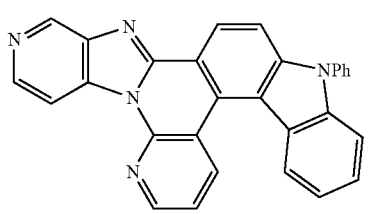
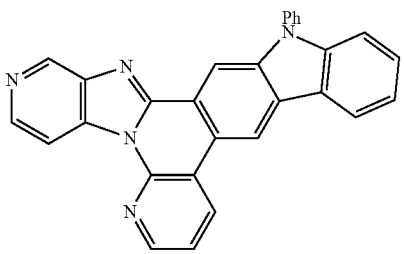
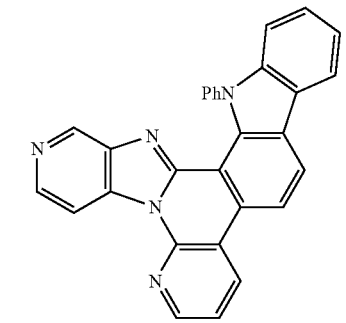

-continued
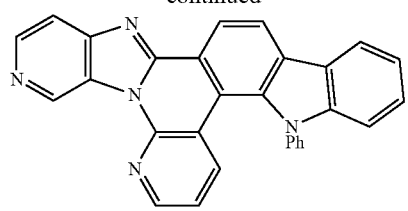
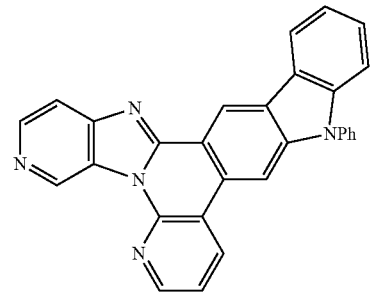
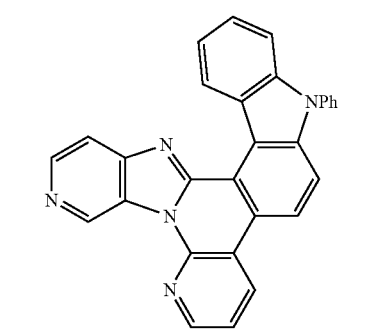
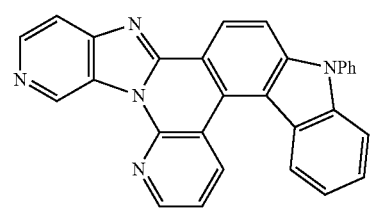
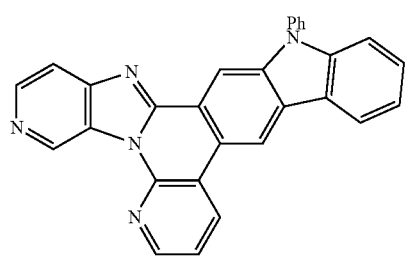
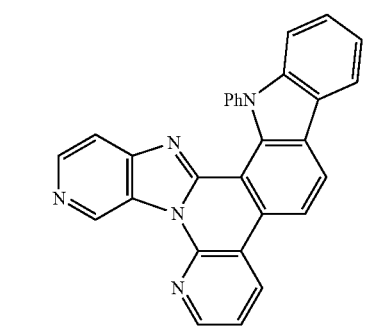
-continued
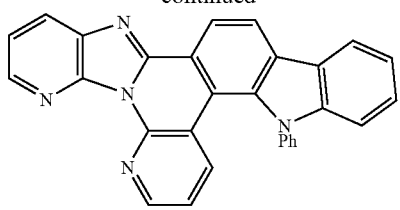
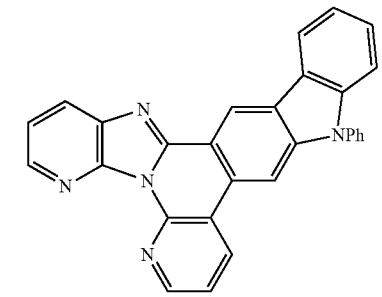
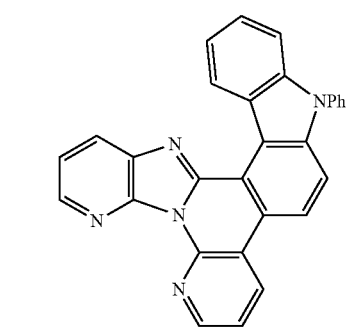
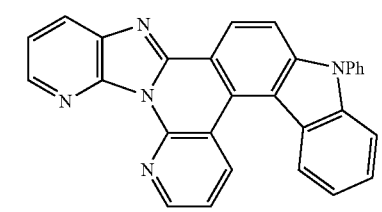
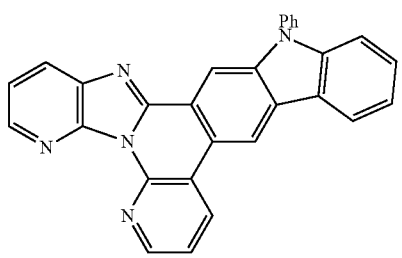
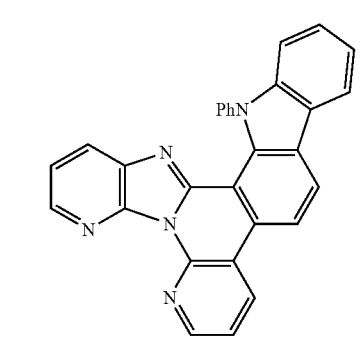

71
-continued
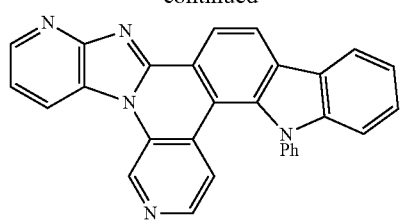
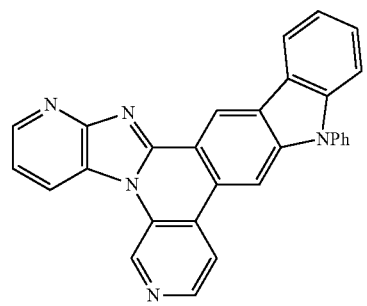
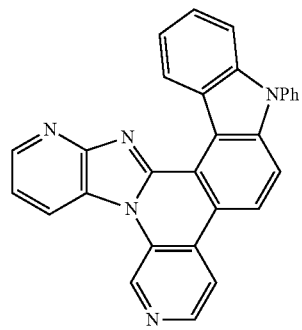
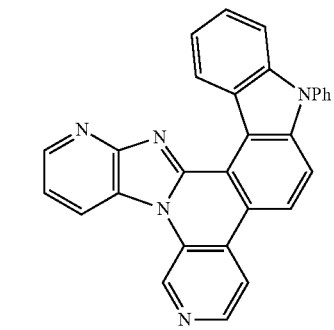
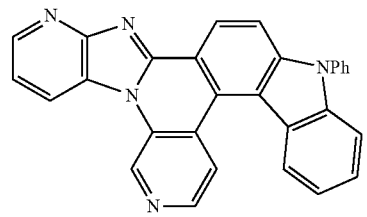
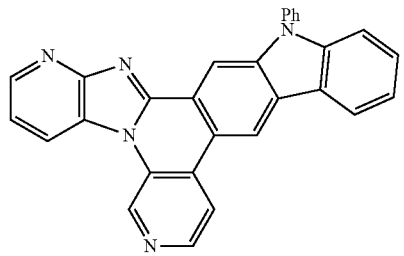

72
-continued
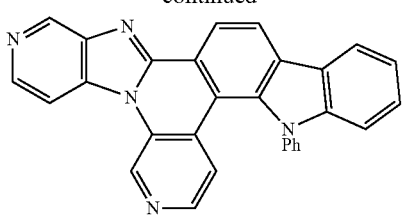
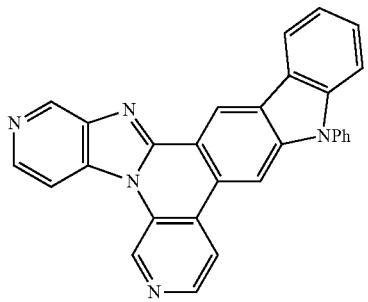
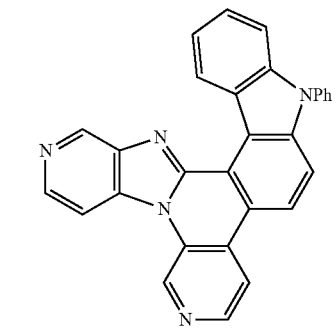
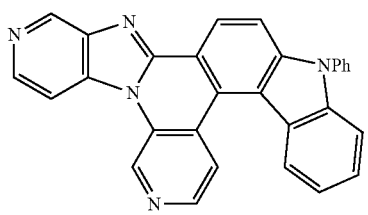
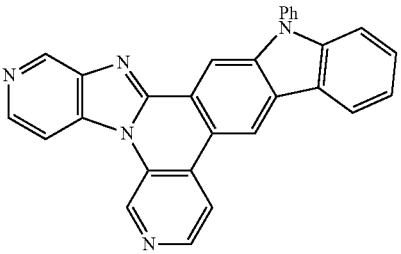
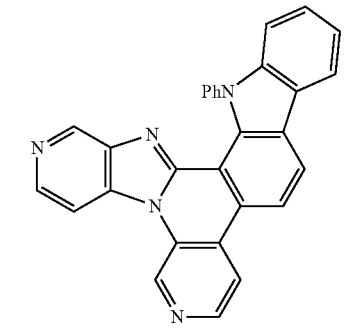

73
-continued
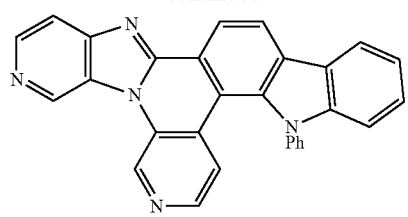
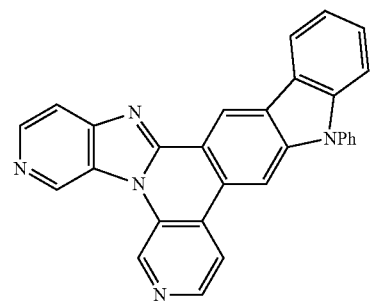
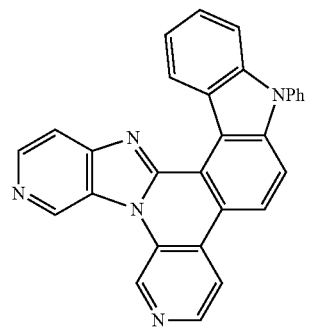
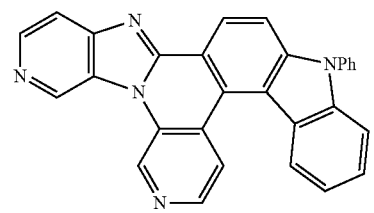
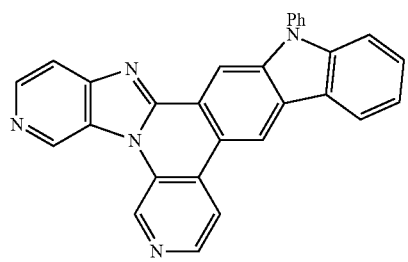
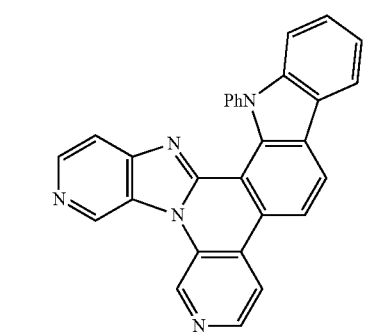
74
-continued
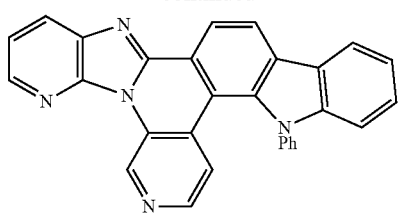
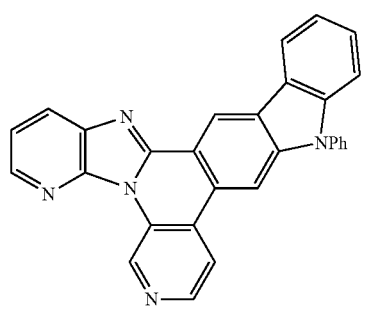
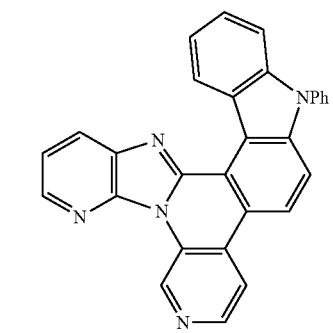
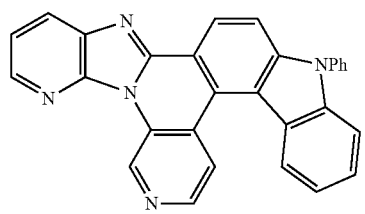
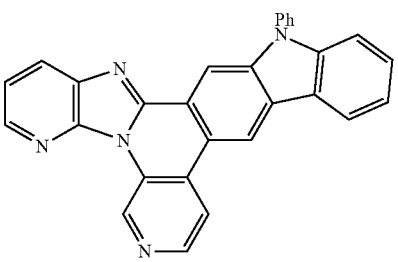
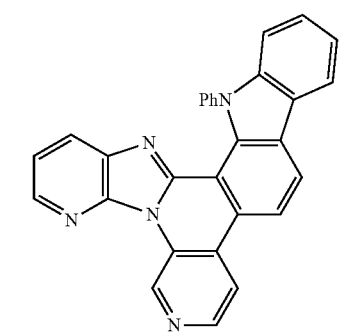

75
-continued
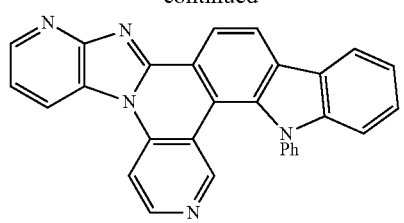
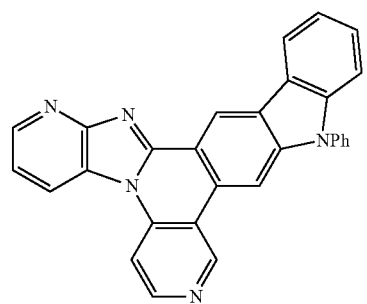
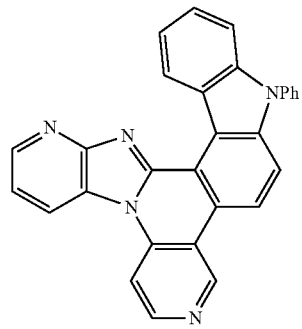
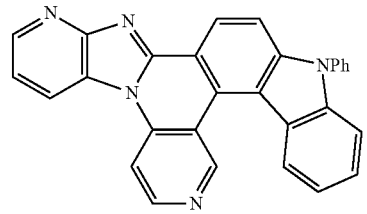
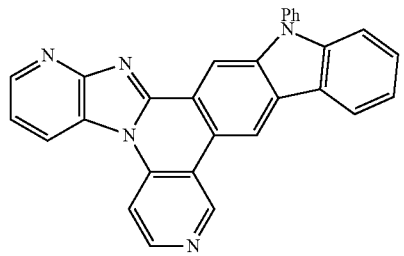
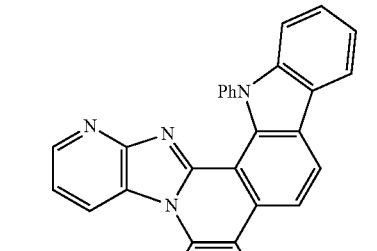
76
-continued
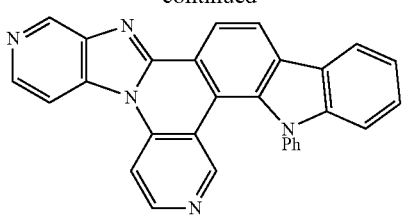
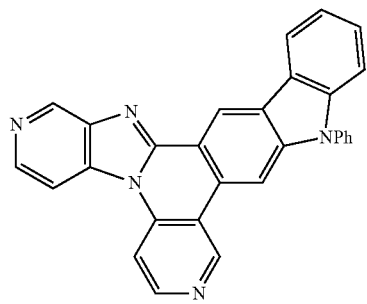
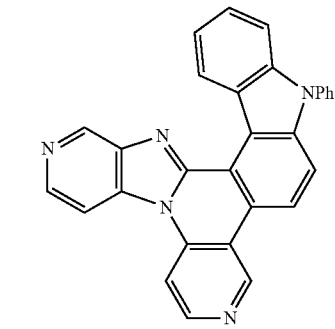
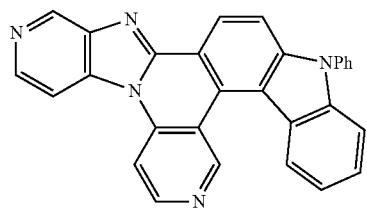
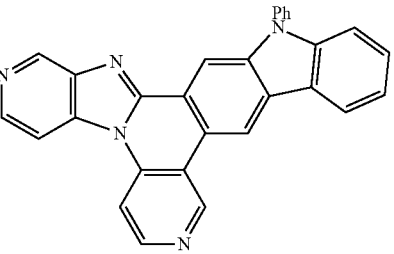
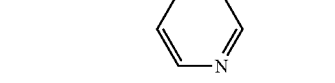

77
-continued
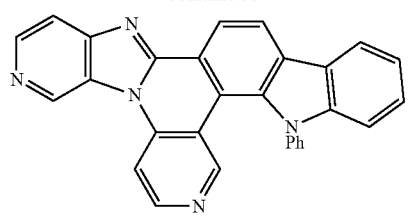
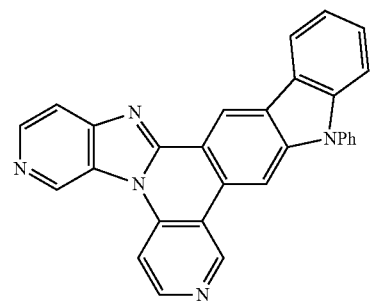
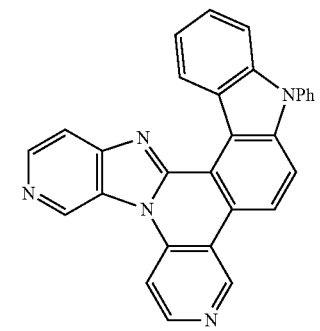
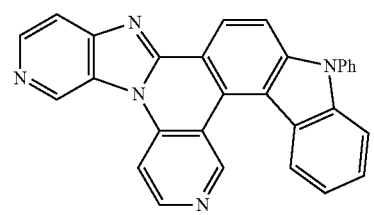
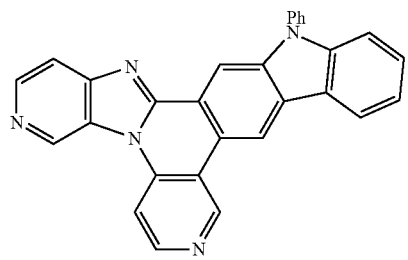
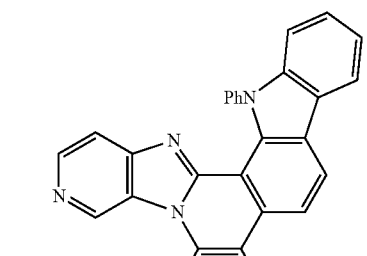
78
-continued
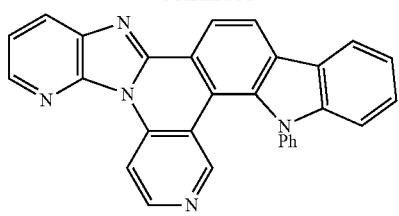
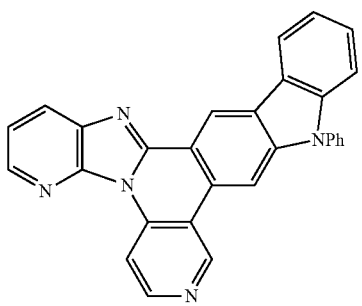
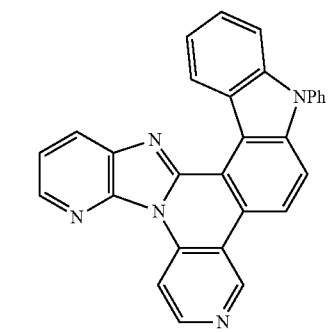
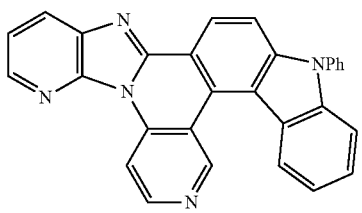
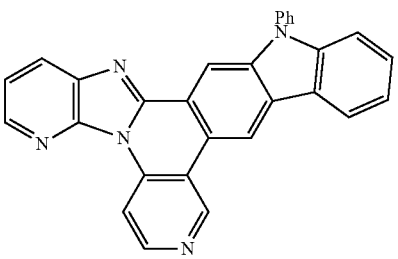
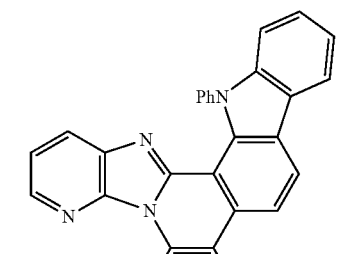

79
-continued
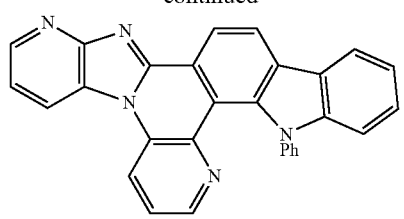
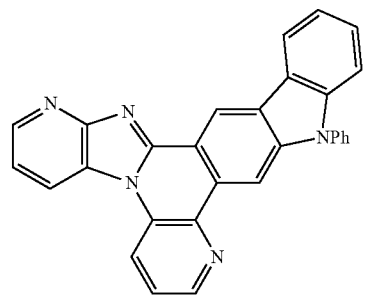
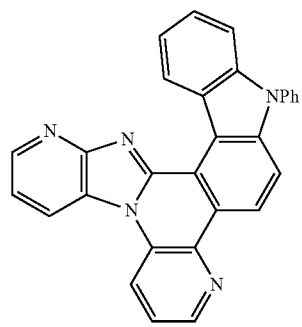
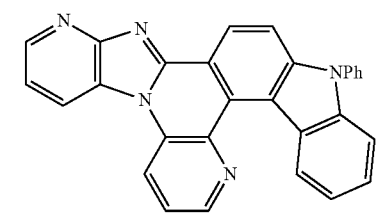
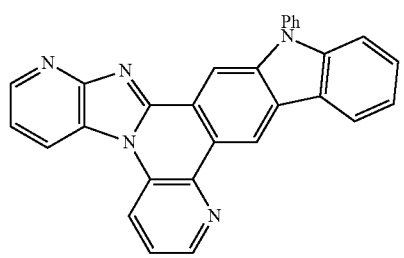
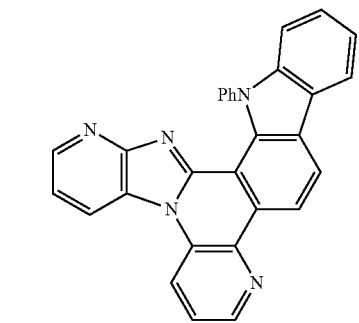
80
-continued
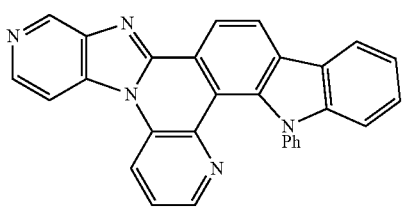
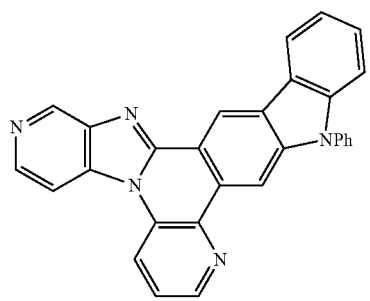
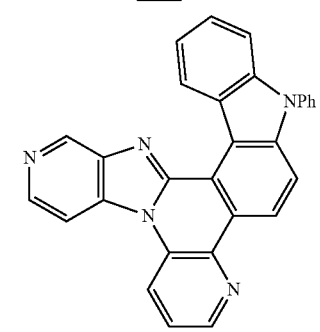
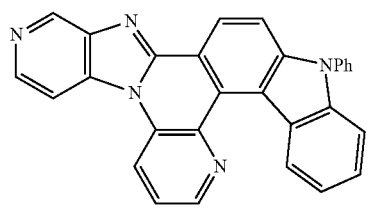
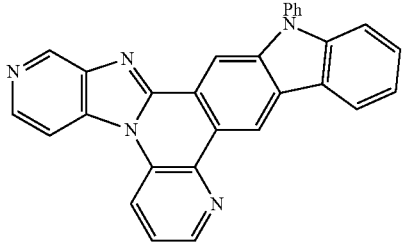
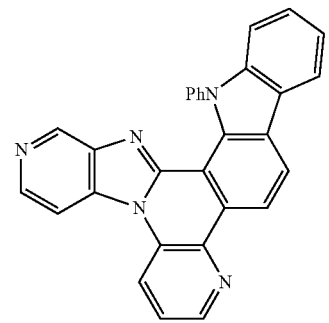

81
-continued
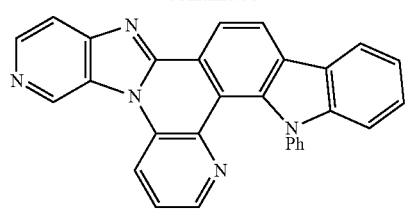
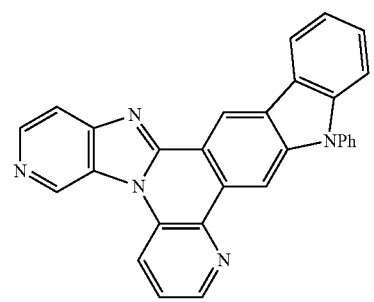
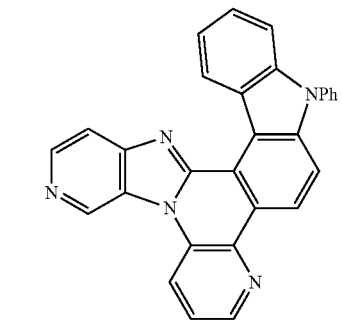
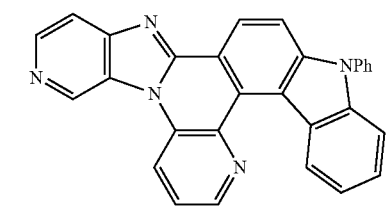
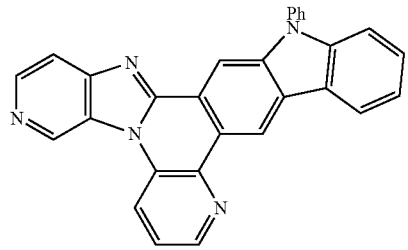
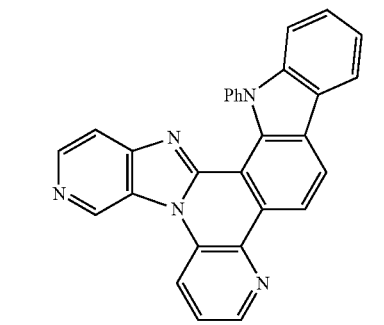
82
-continued
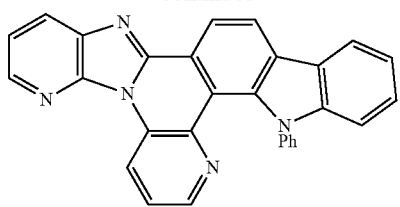
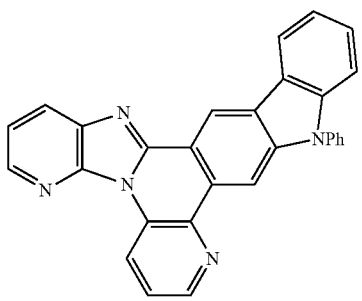

-continued
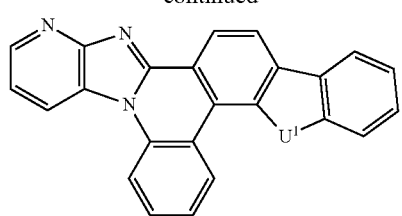
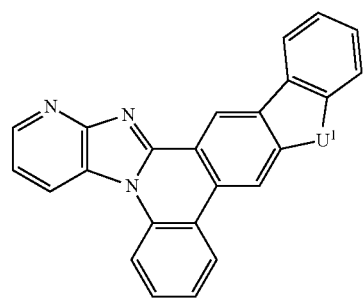
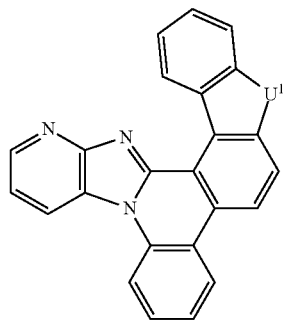
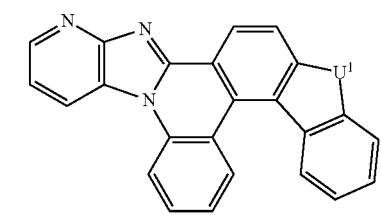
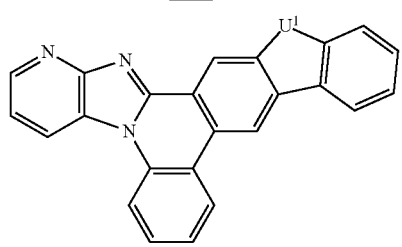
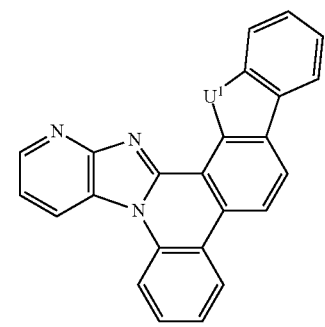
-continued
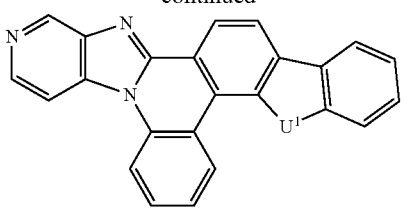
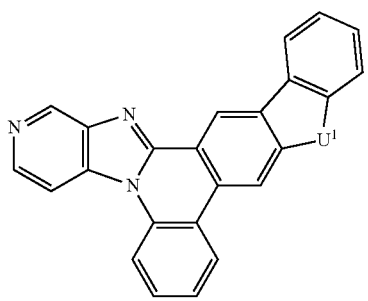
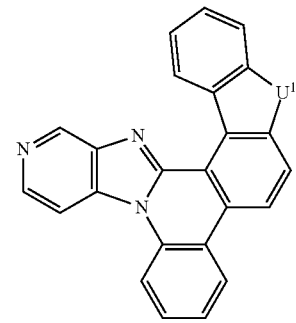
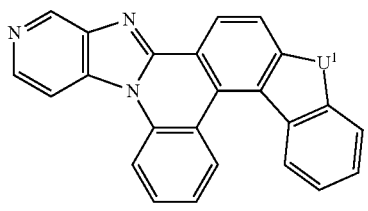
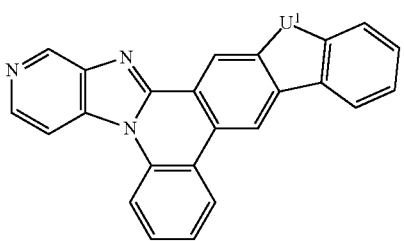
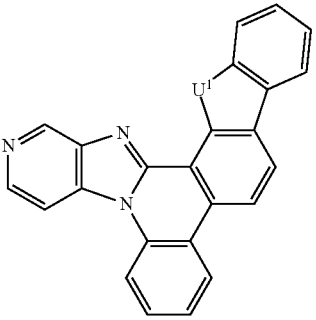

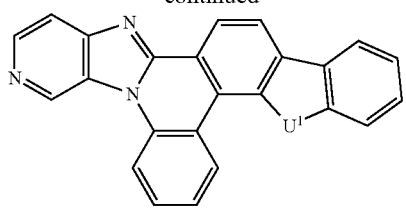
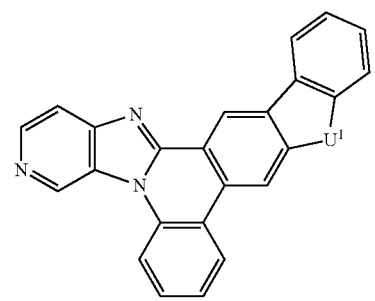
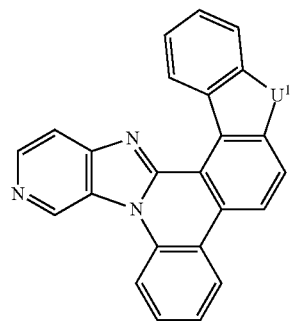
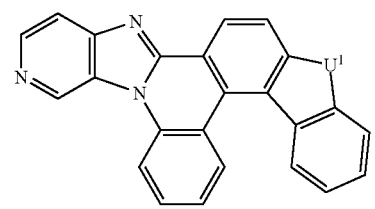
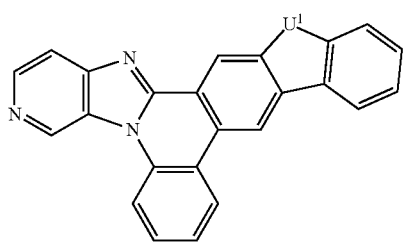
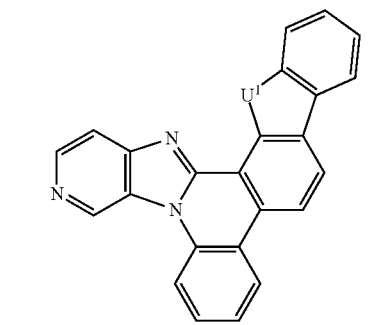
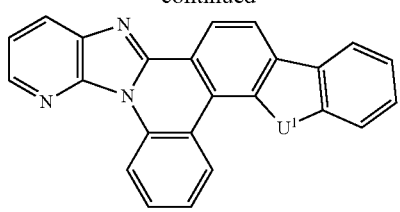
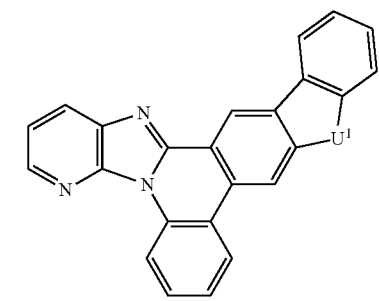
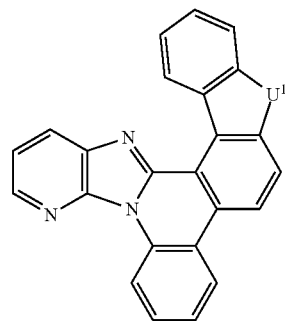
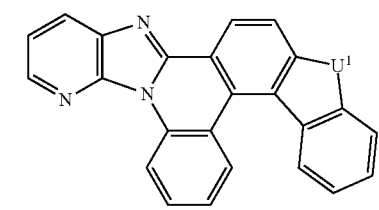
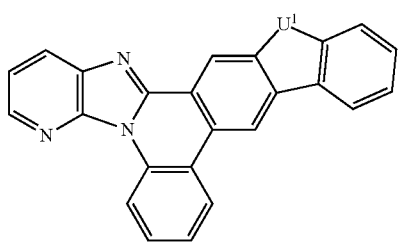
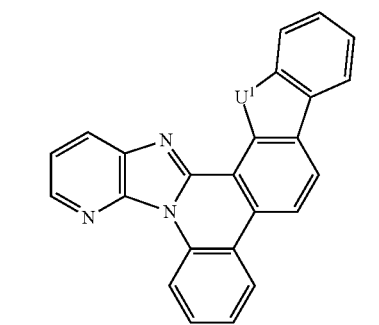

87
-continued
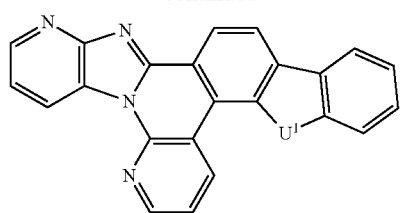
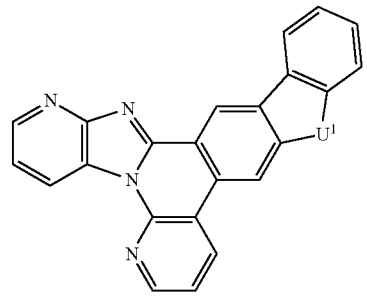
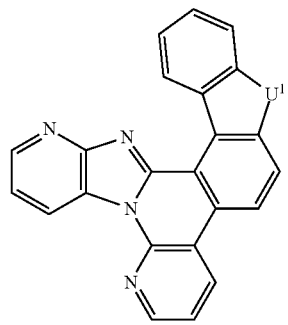
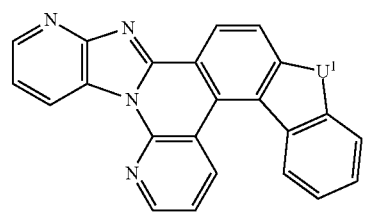
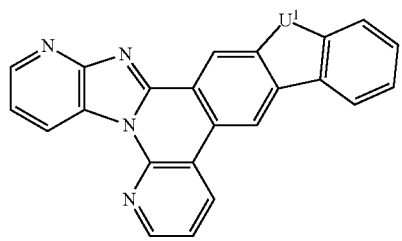
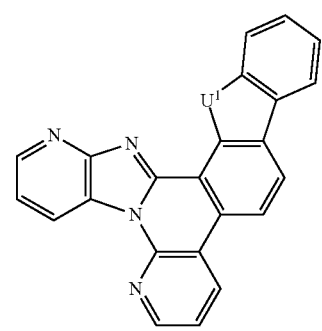
88
-continued
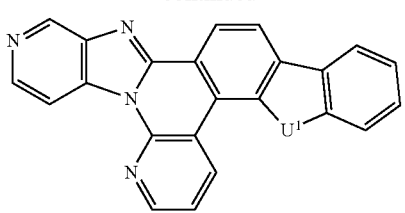
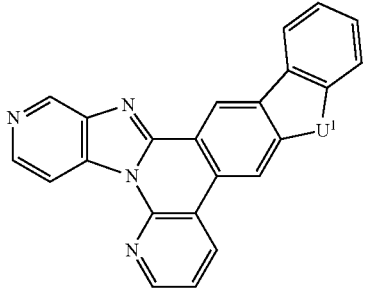
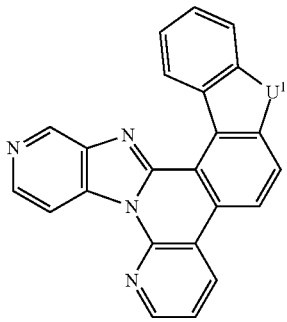
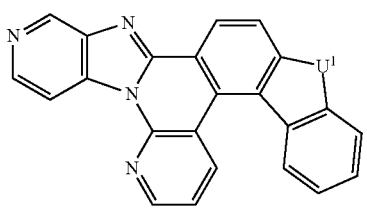
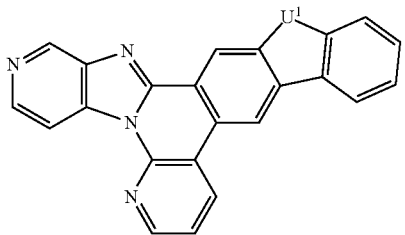
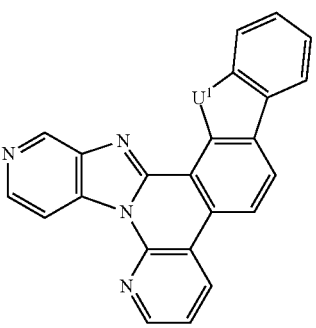

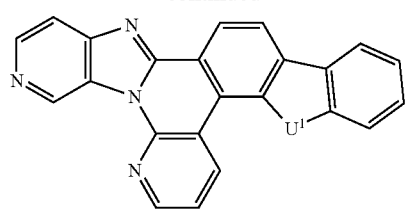
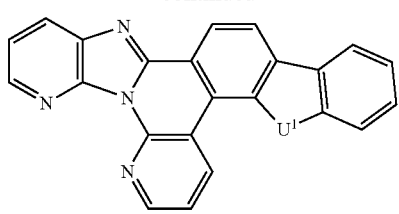
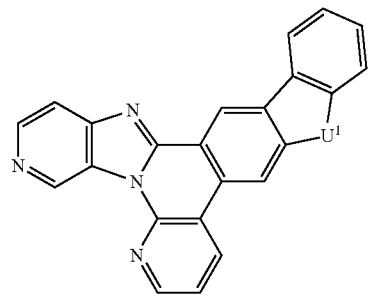
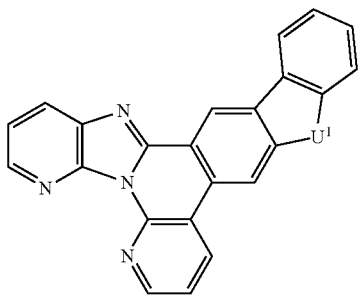
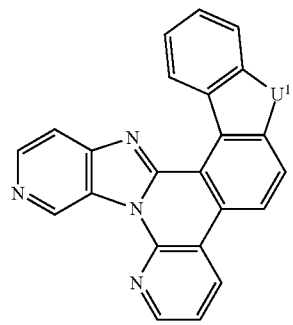
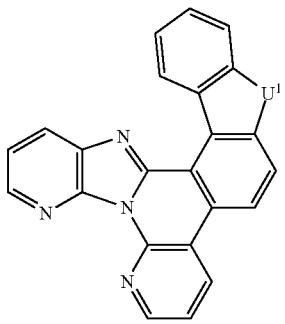
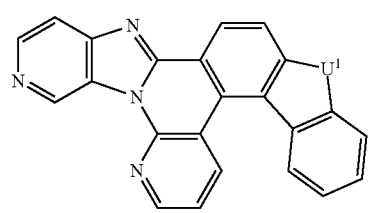
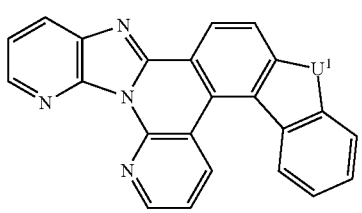
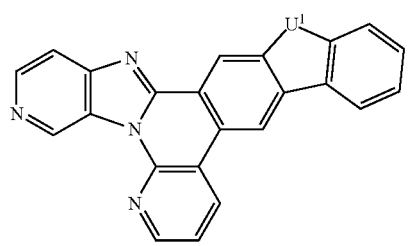
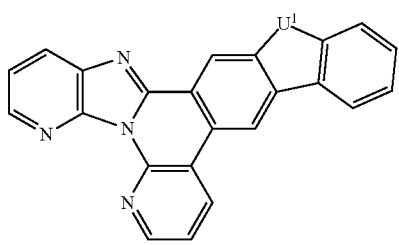
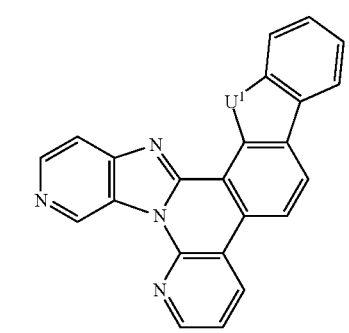
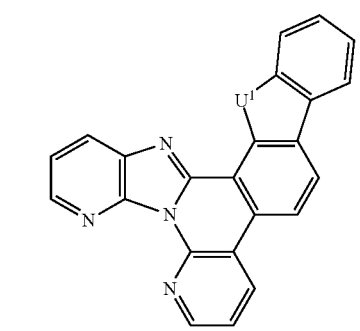

91
-continued
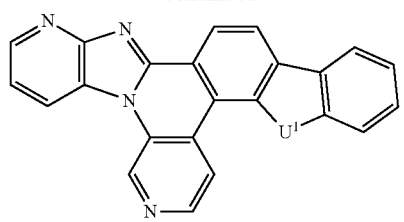
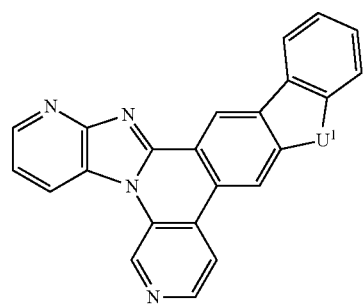
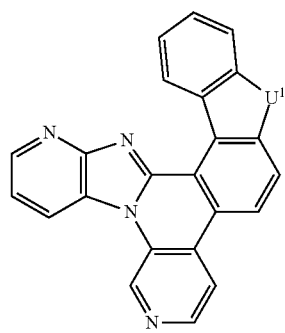
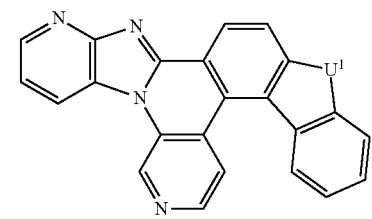
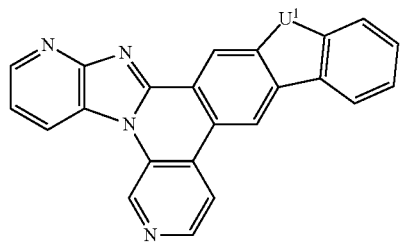
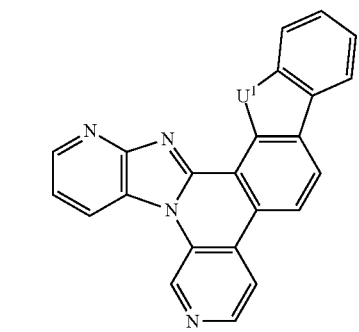
92
-continued
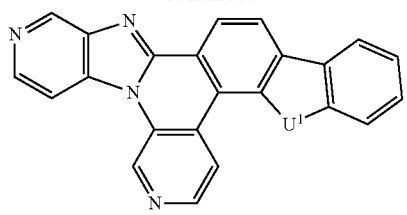
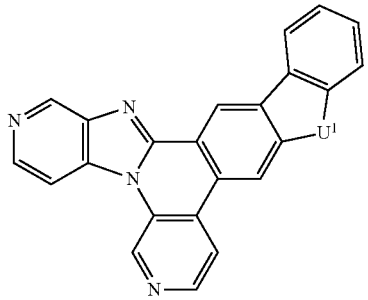
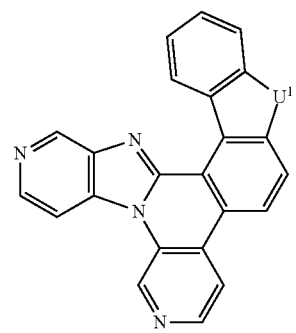
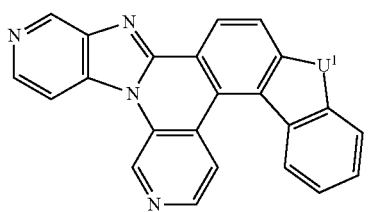
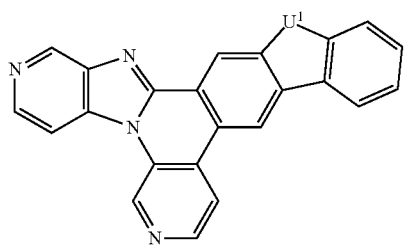
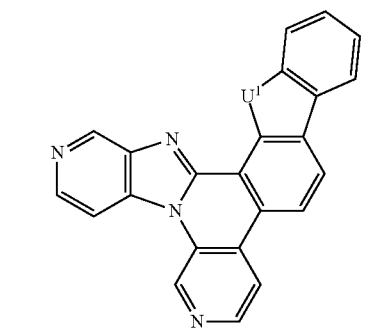

93
-continued
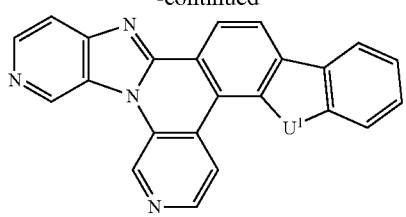
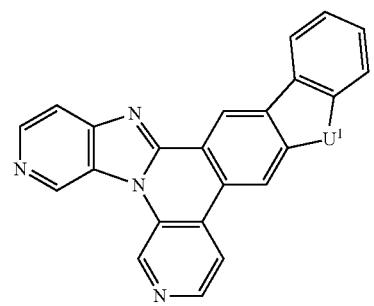
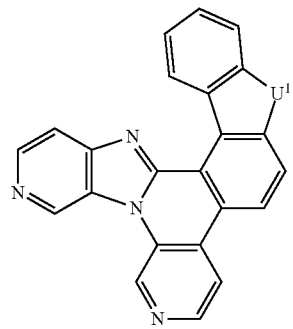
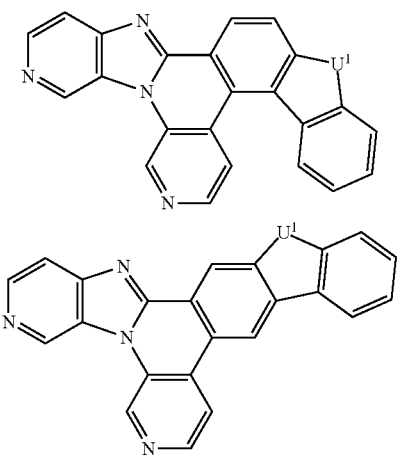
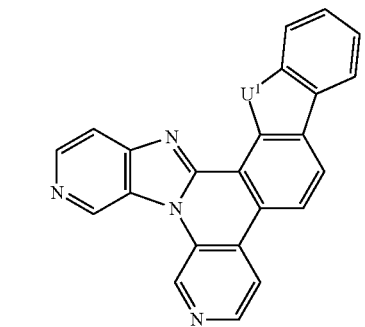
94
-continued
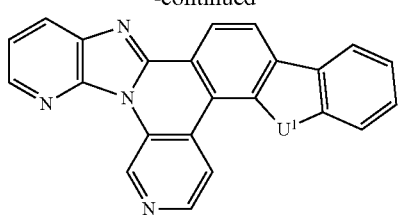
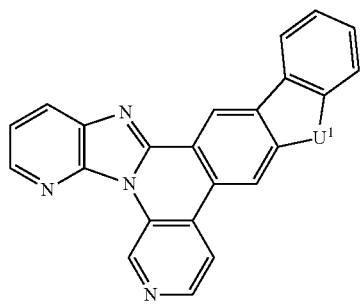
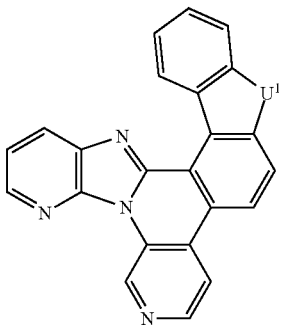
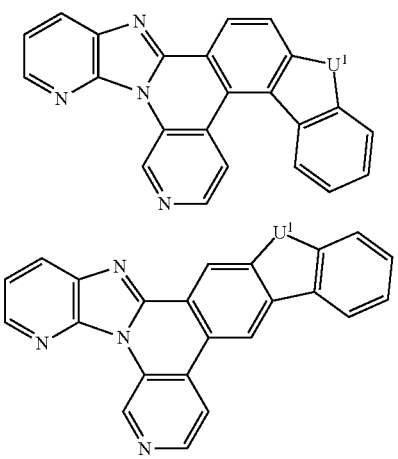
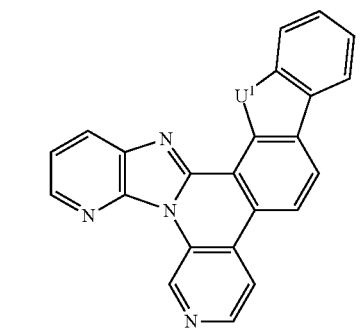

95
-continued
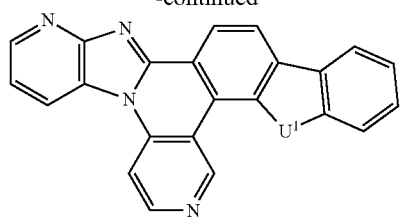
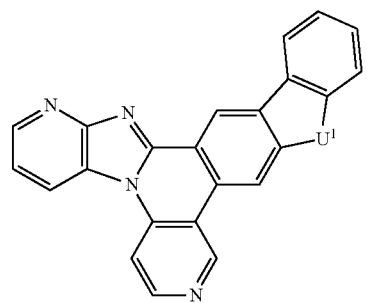
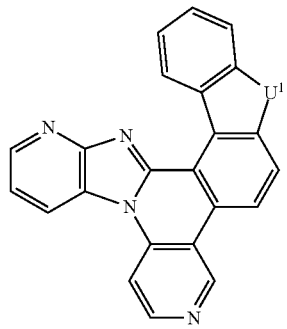
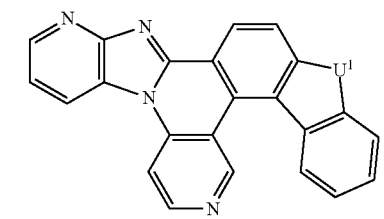
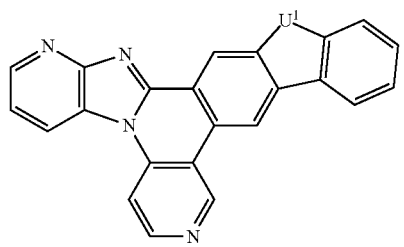
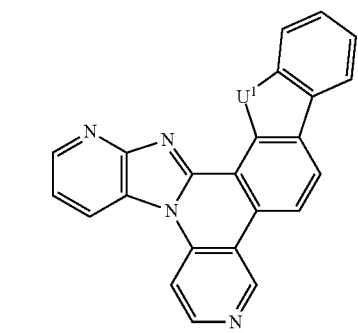
96
-continued
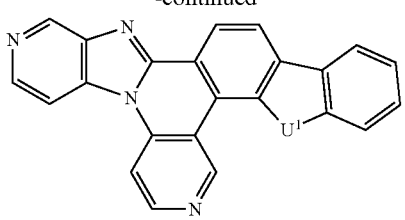
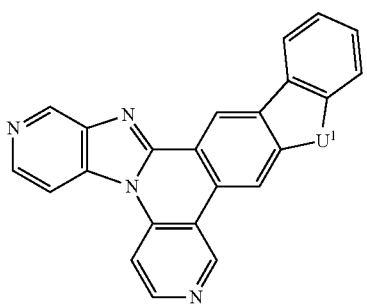
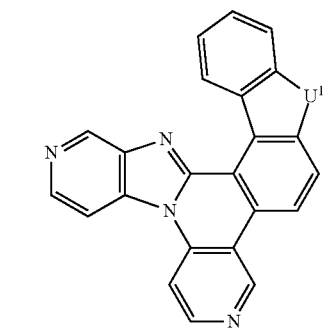
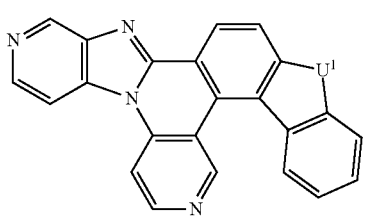
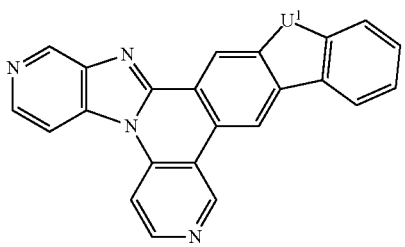
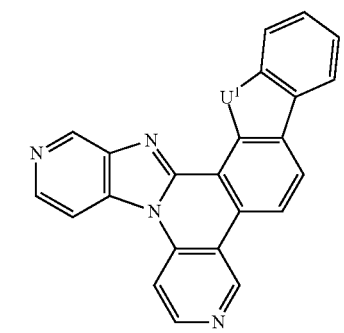

97
-continued
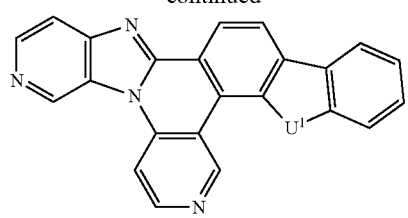
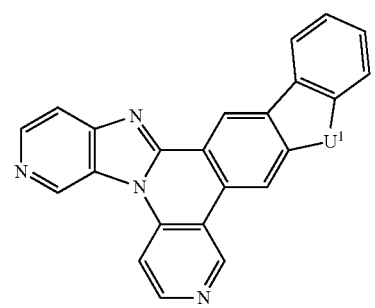
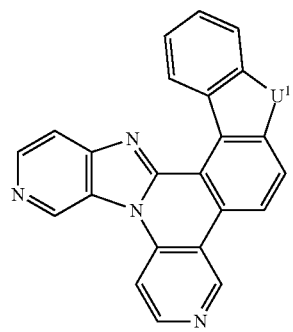
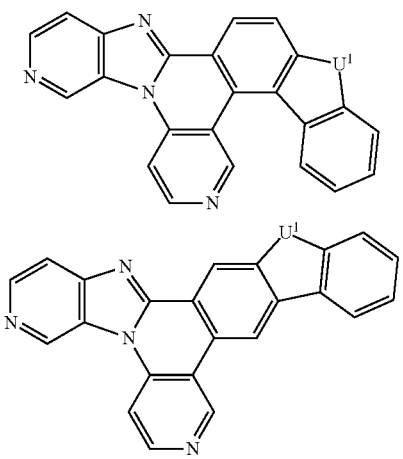
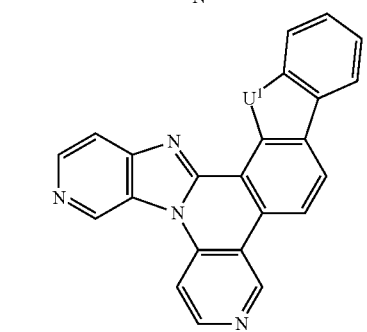
98
-continued
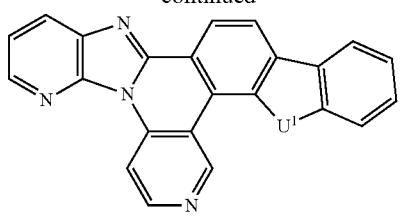
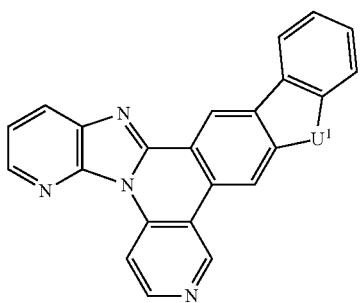
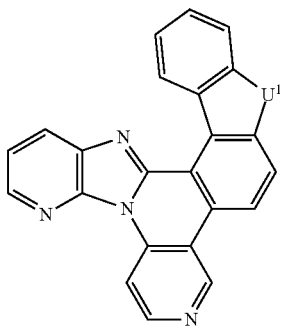
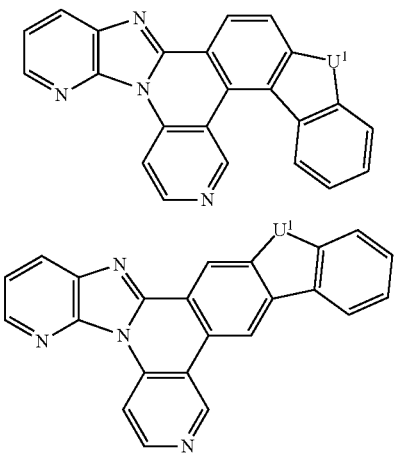
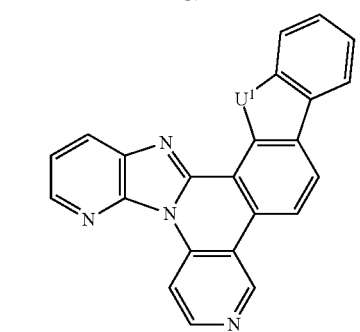

99
-continued
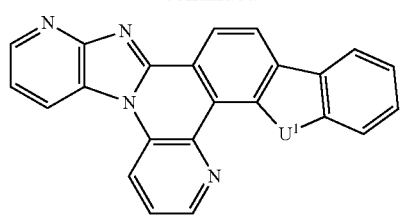
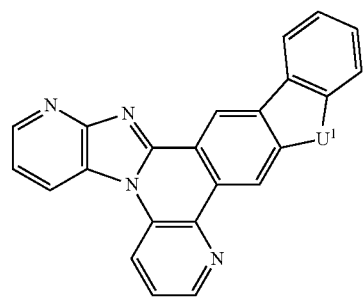
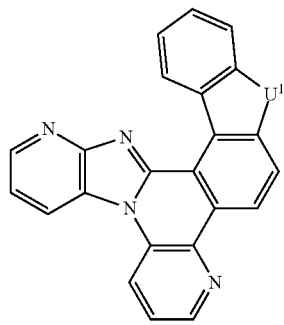
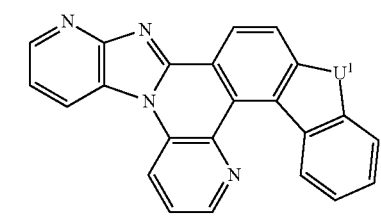
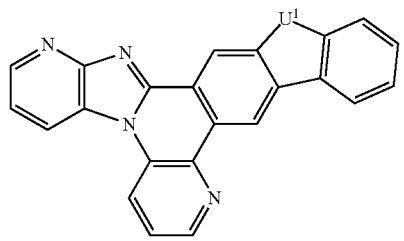
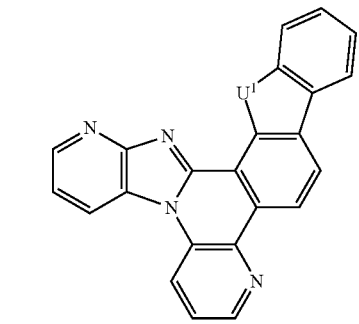
100
-continued
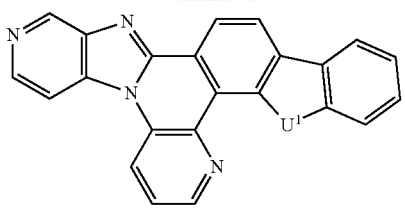
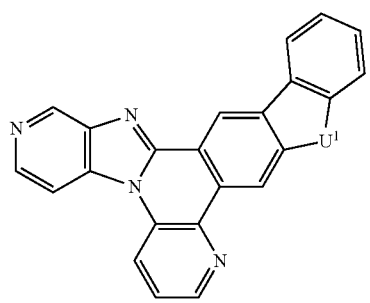
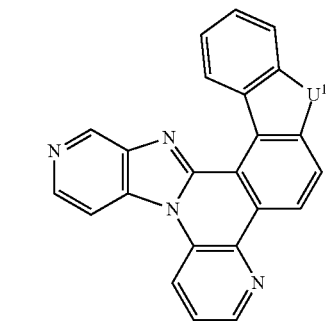
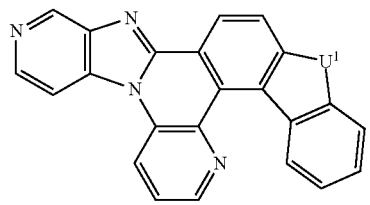
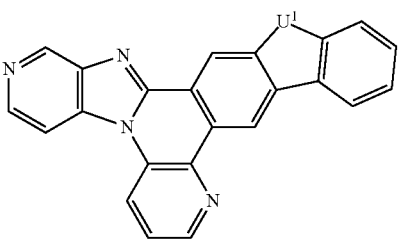
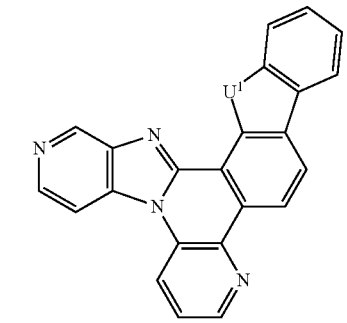

101
-continued
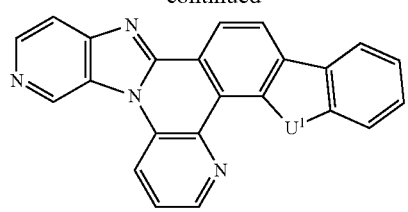
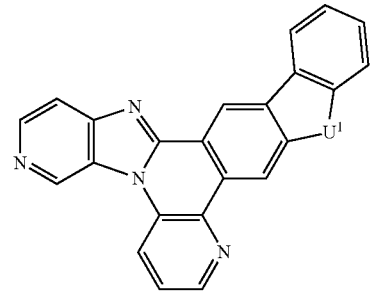
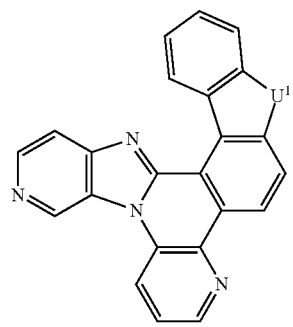
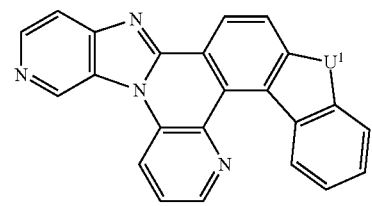
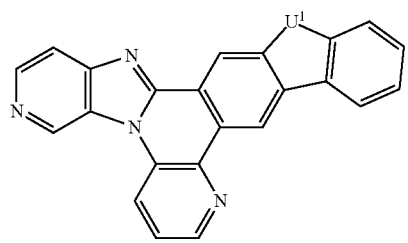
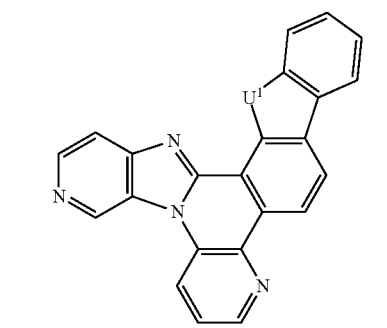
102
-continued
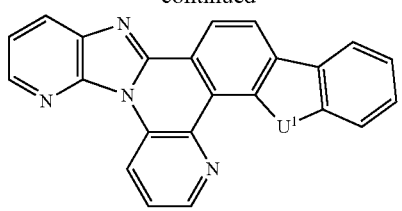
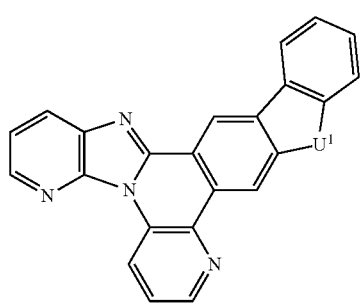
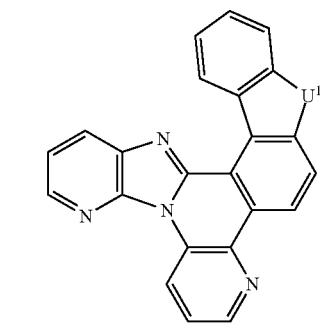
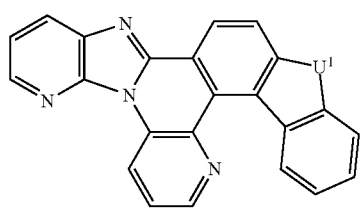
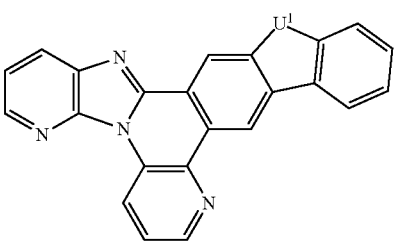
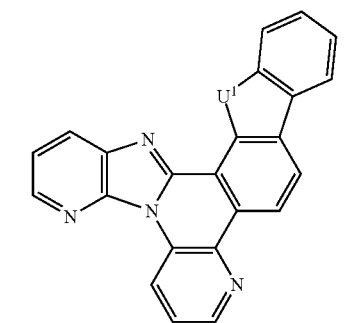

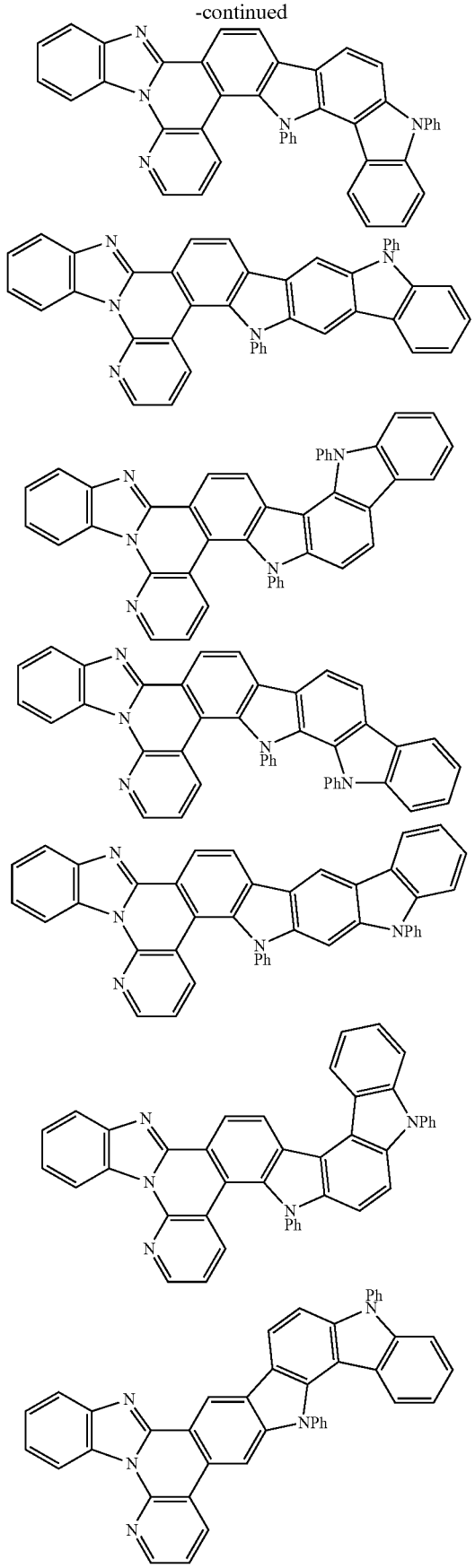
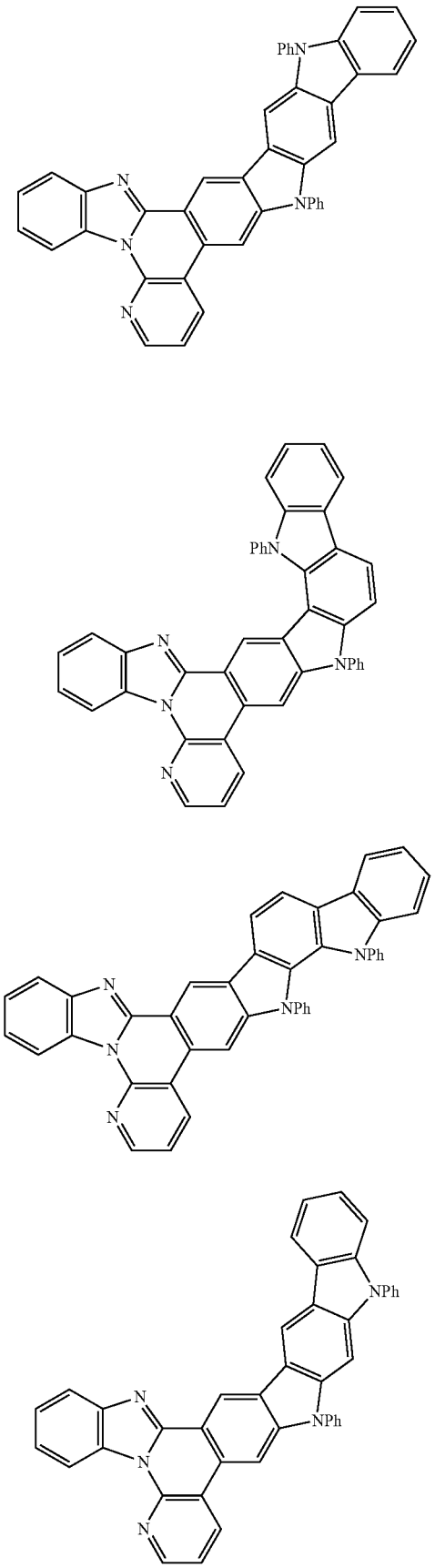

-continued
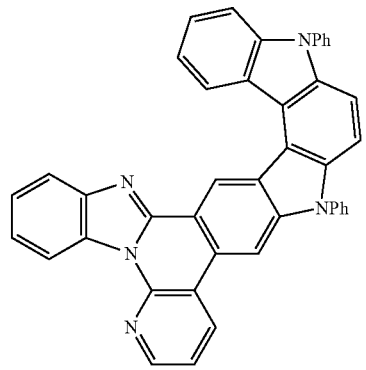
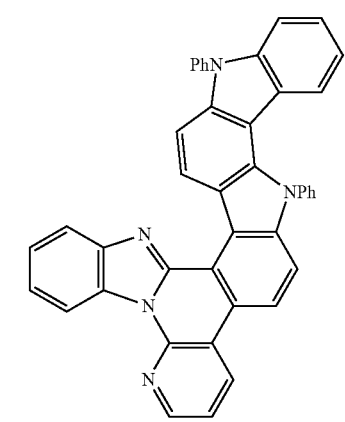
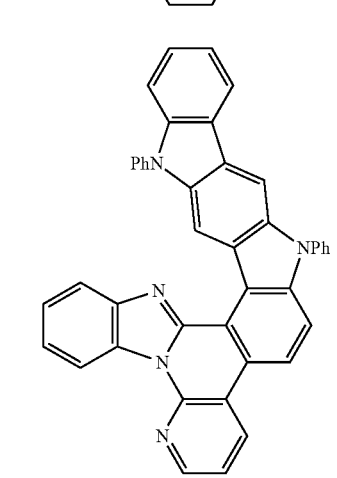
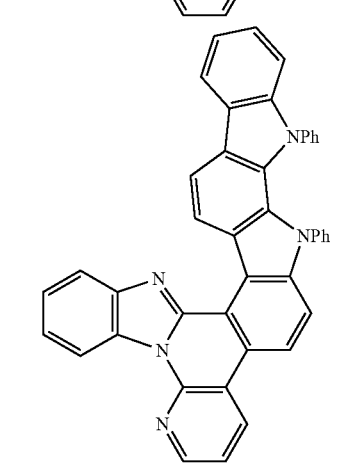
-continued
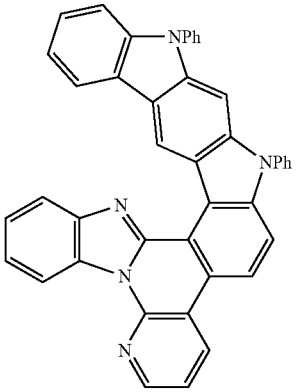
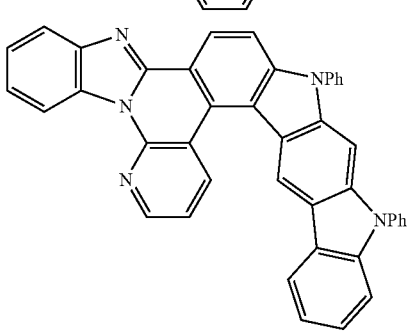
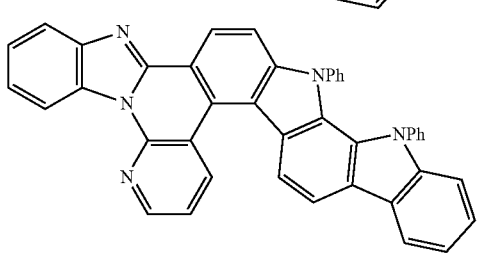
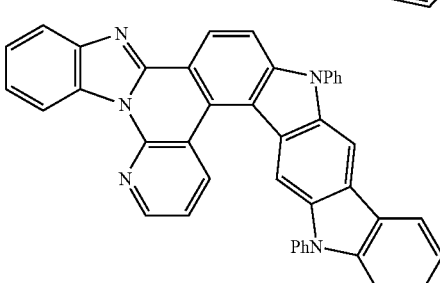
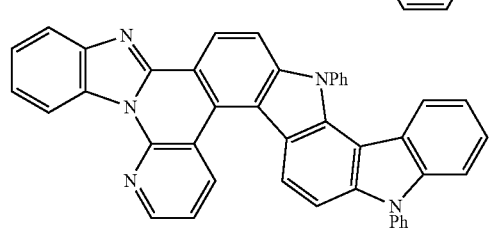
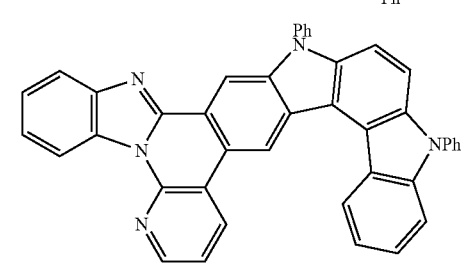

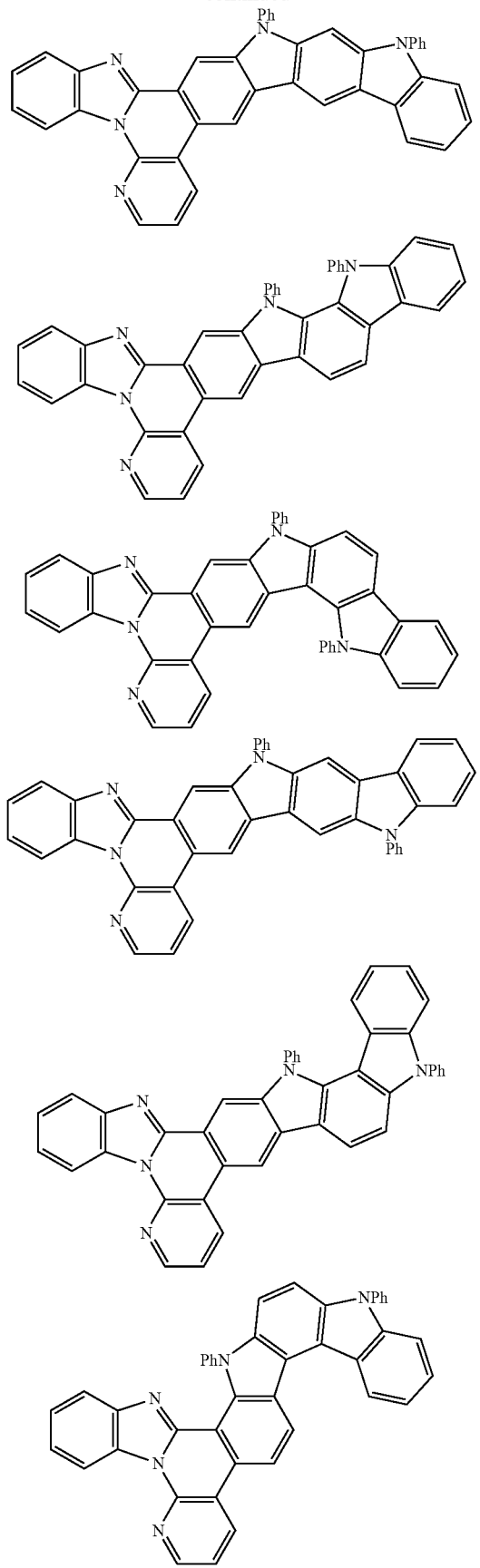
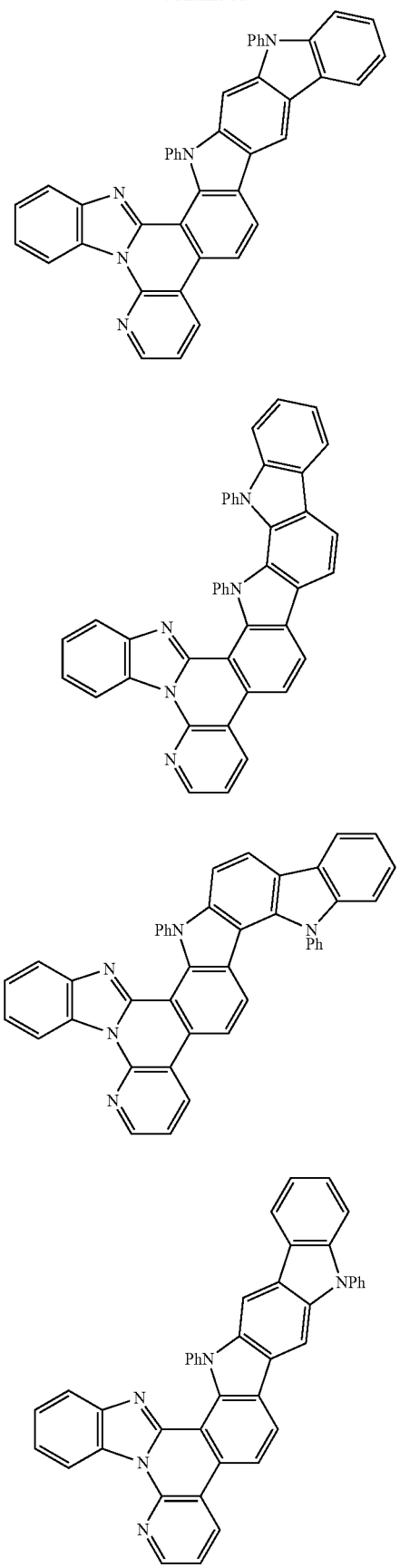

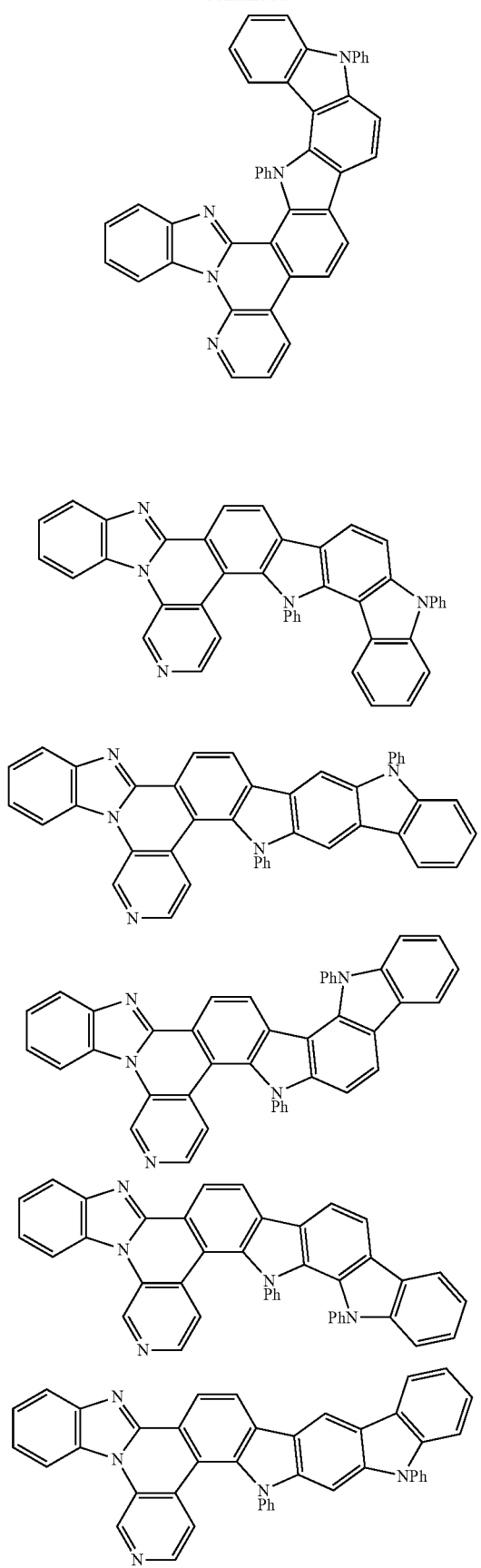

-continued
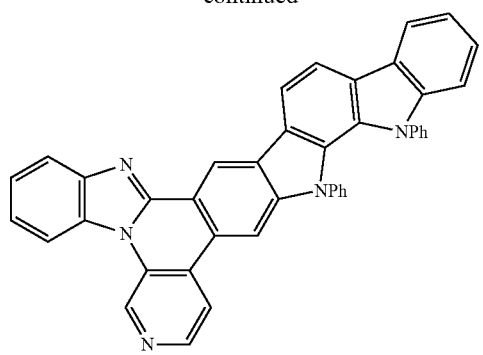
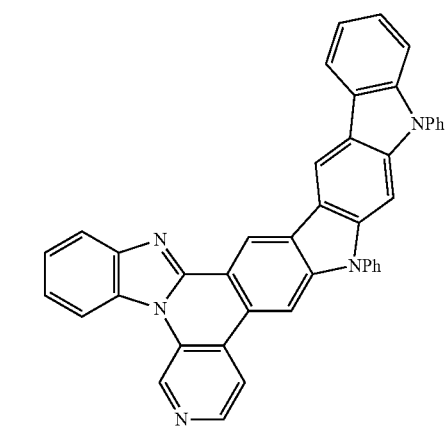
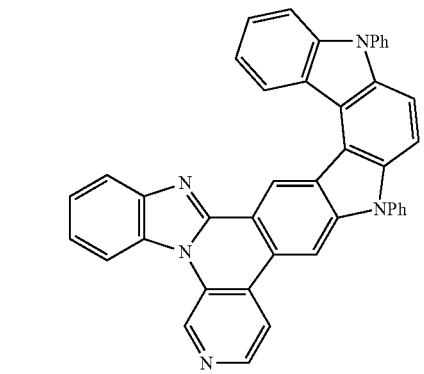
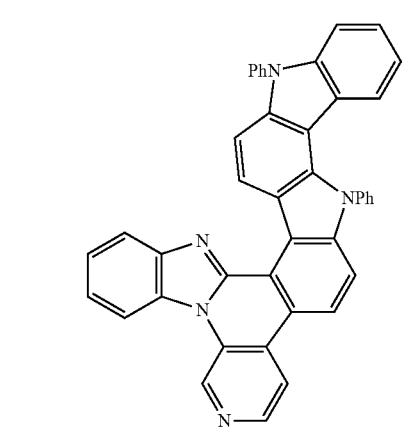
-continued
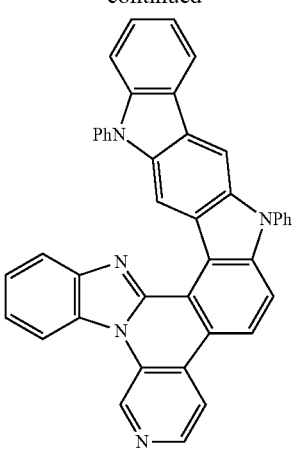
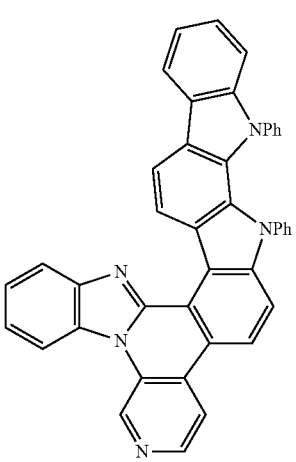
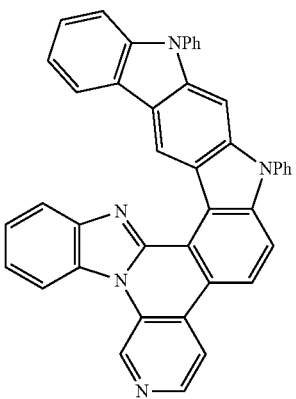
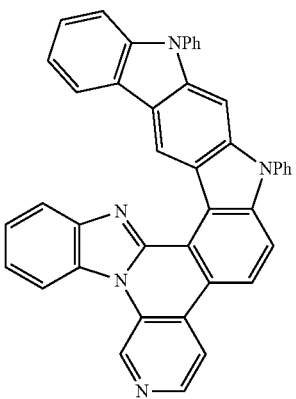

113
-continued
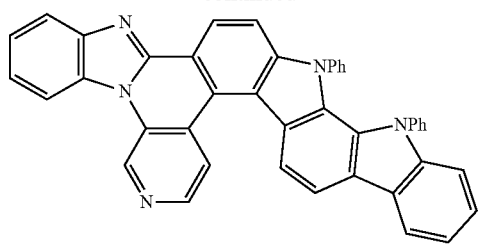
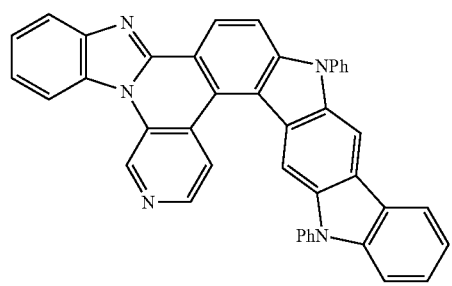
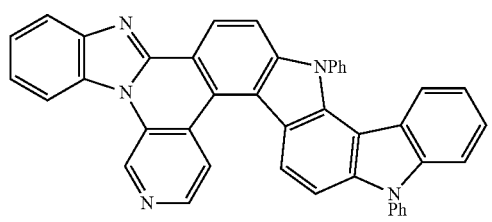
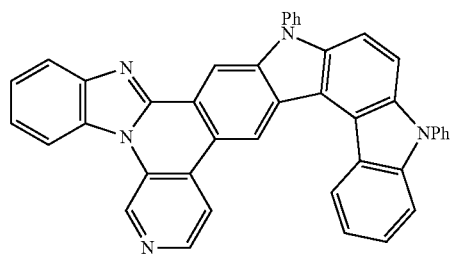
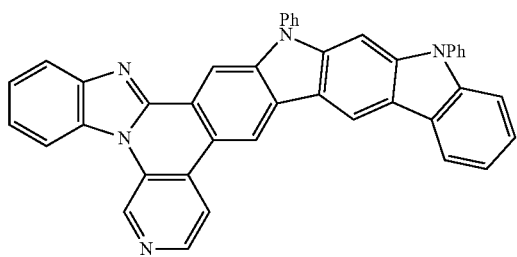
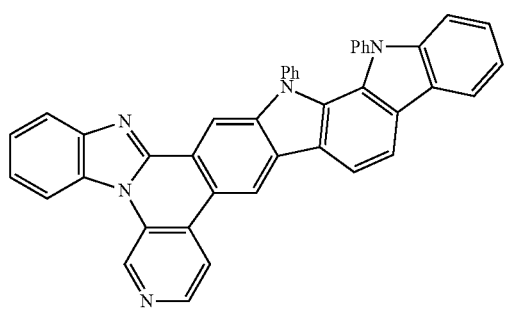
114
-continued
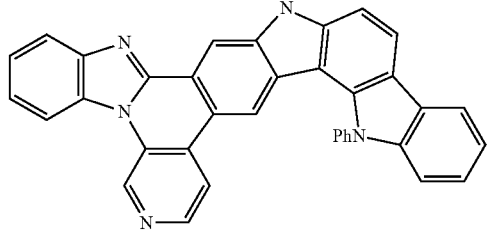
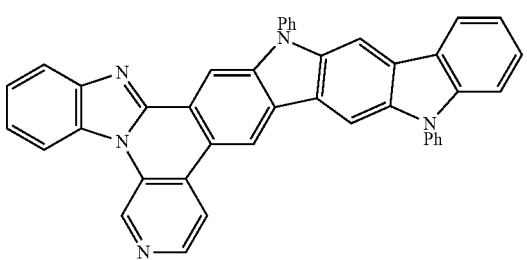
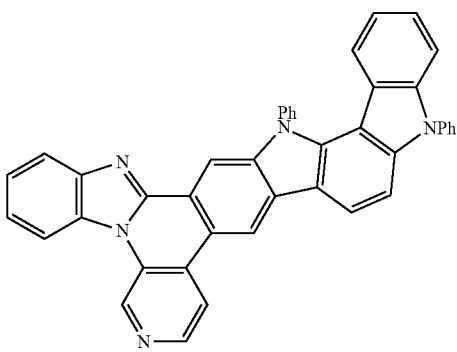
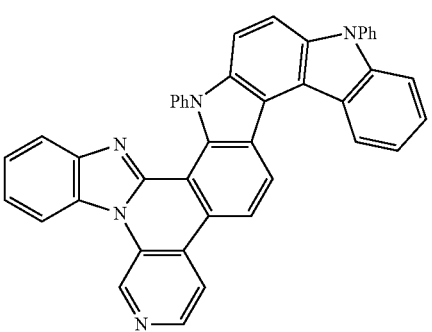
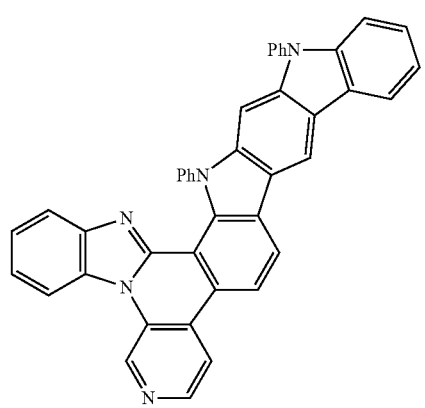

-continued
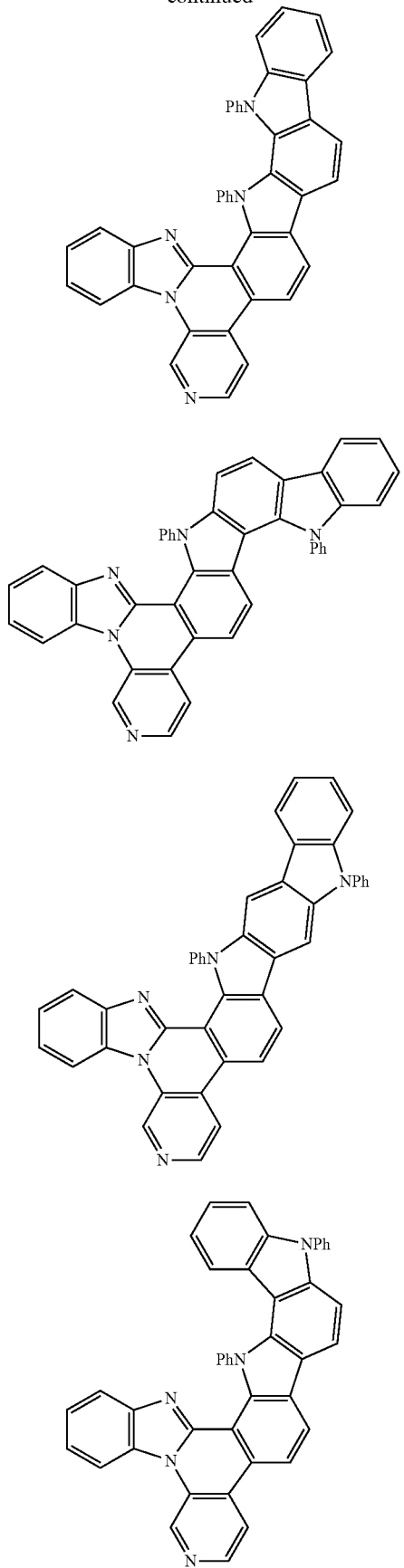
-continued
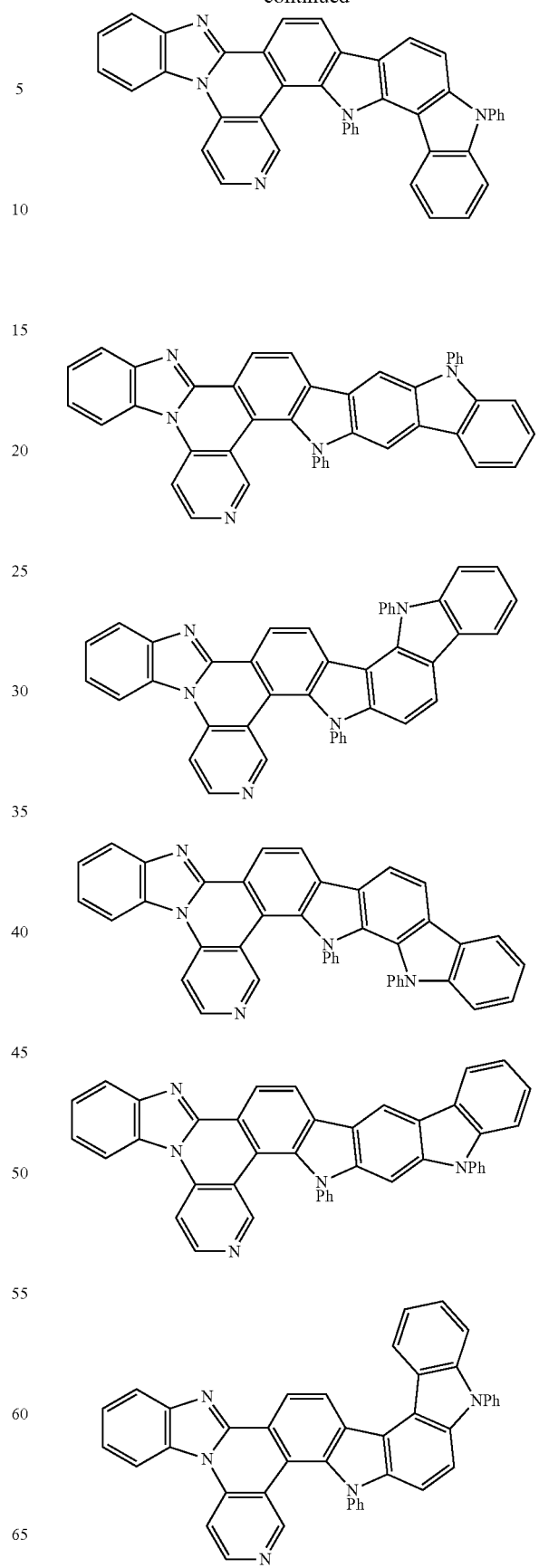

-continued
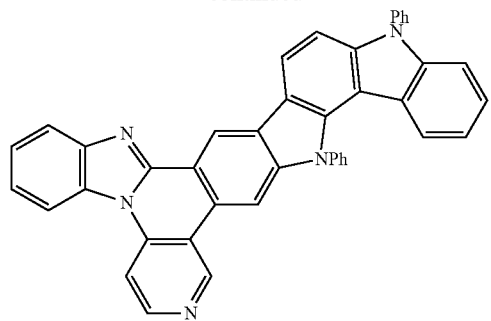
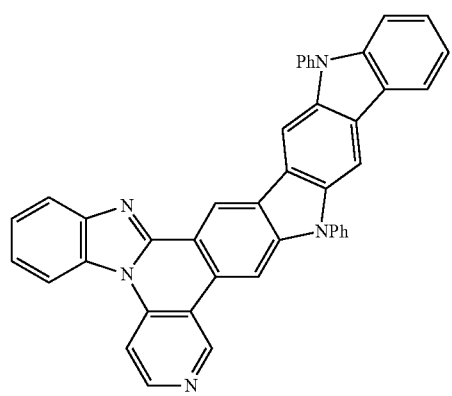
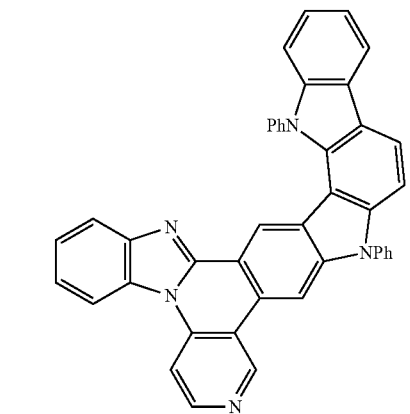
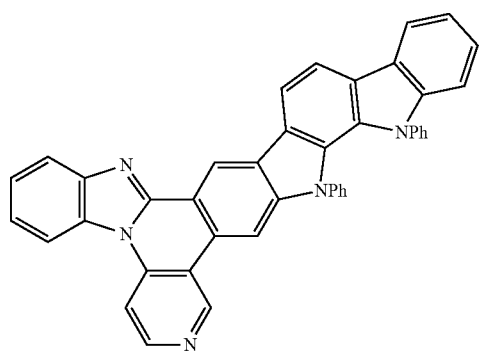
-continued
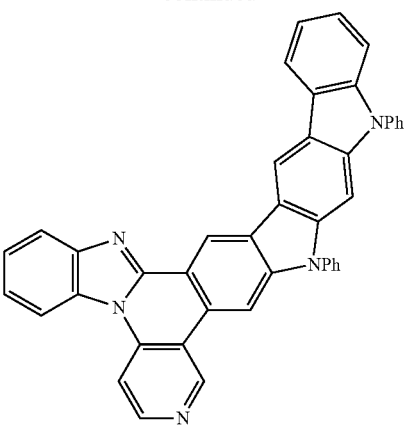
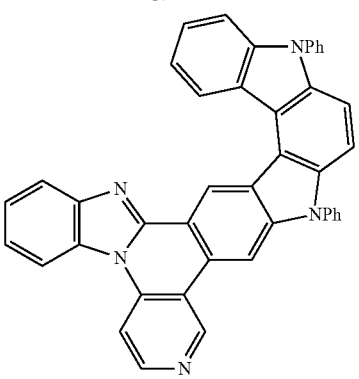
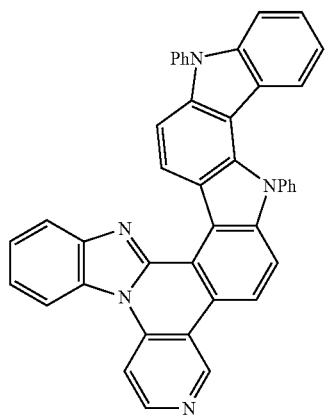
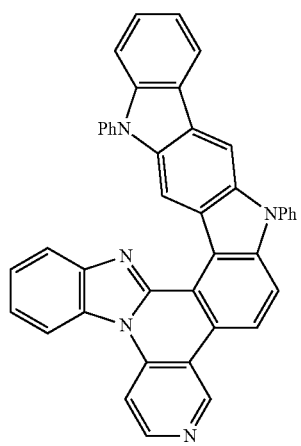

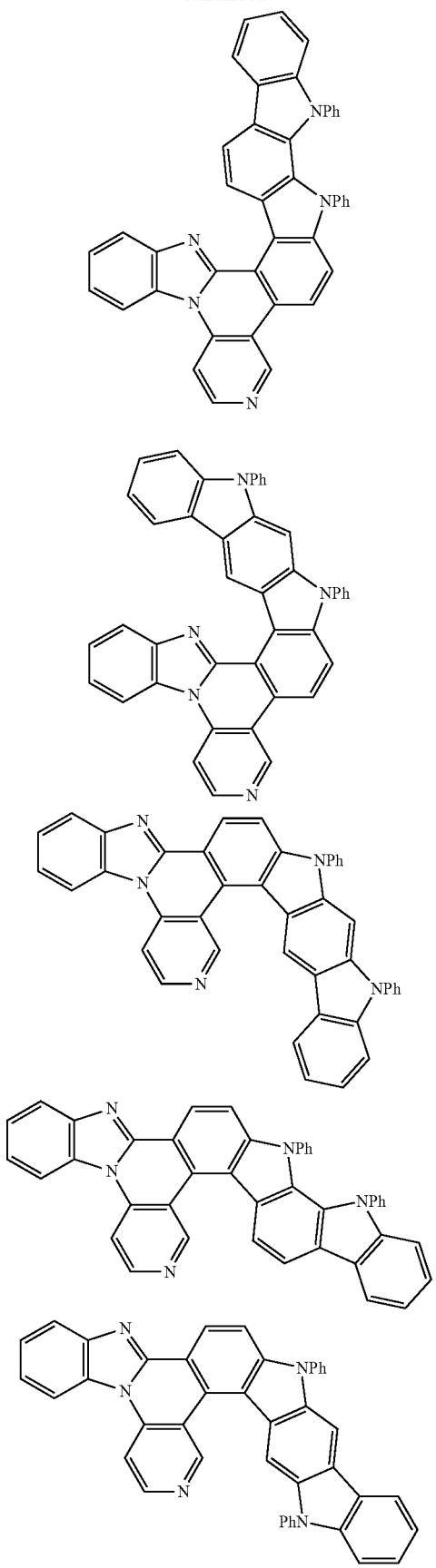
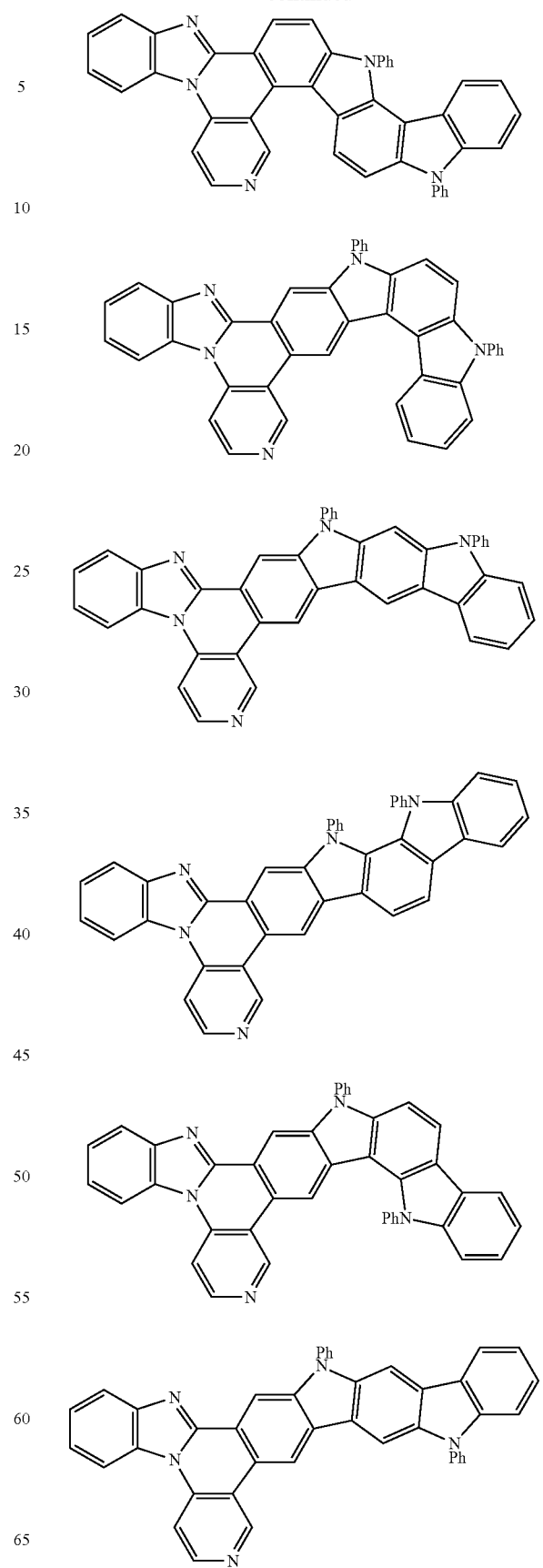

121
-continued
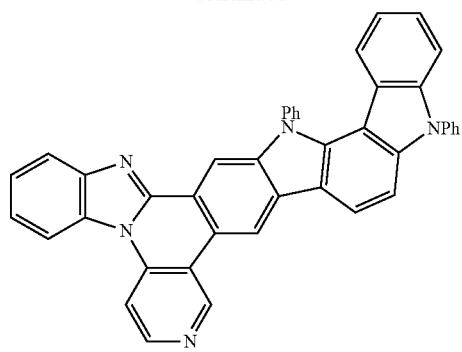
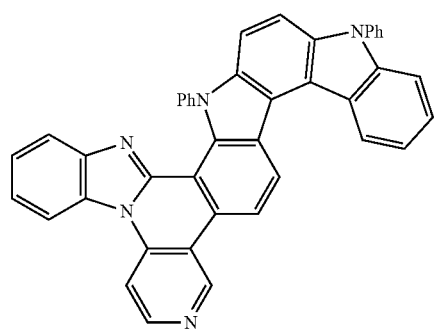
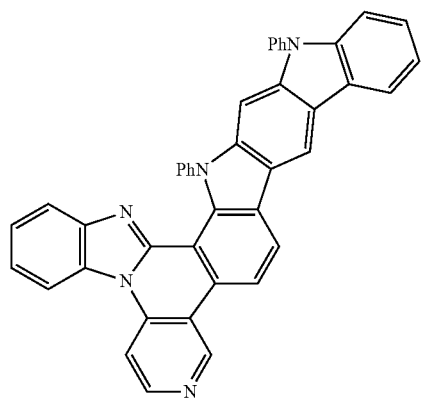
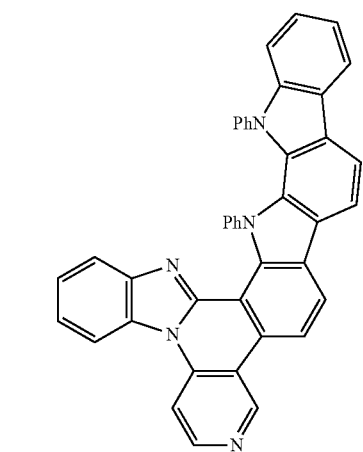
122
-continued
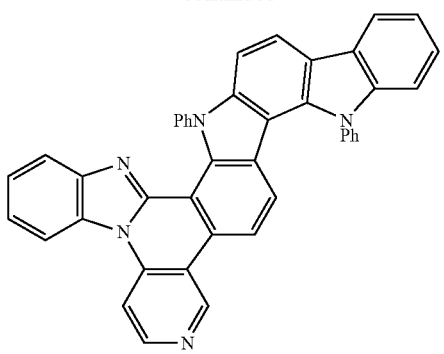
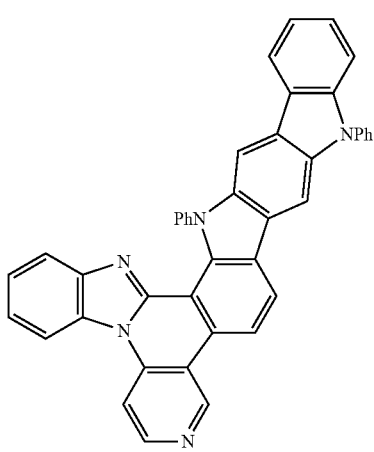
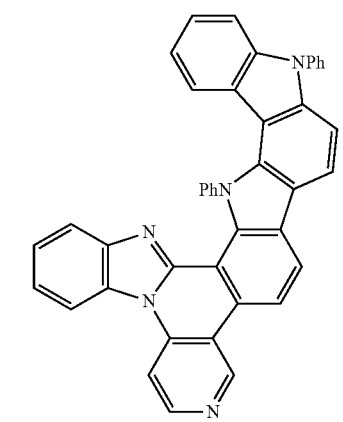
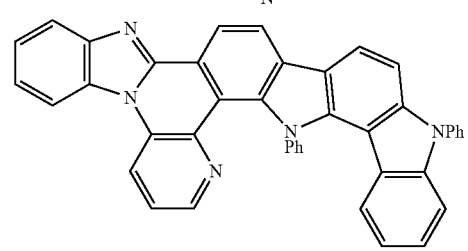
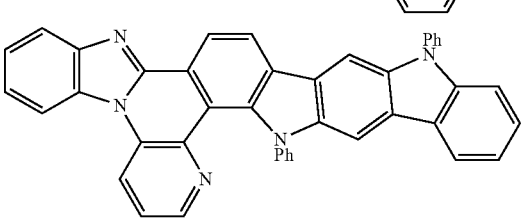

123
-continued
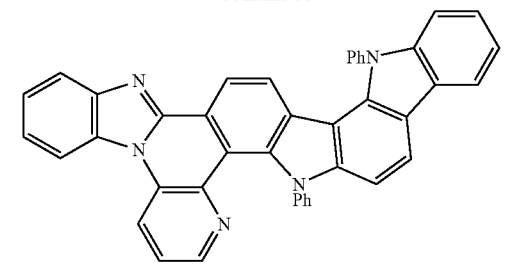
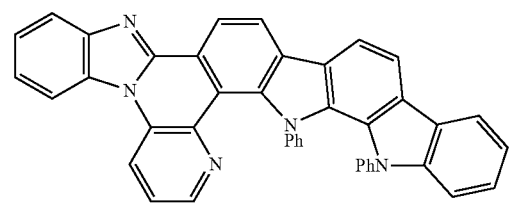
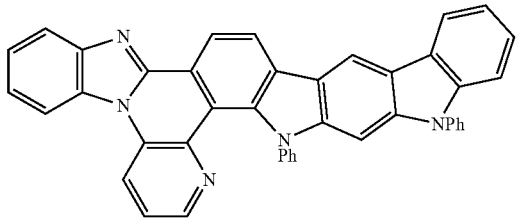
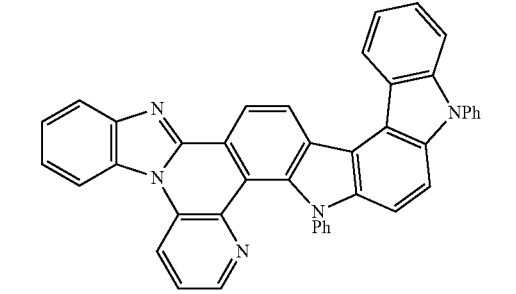
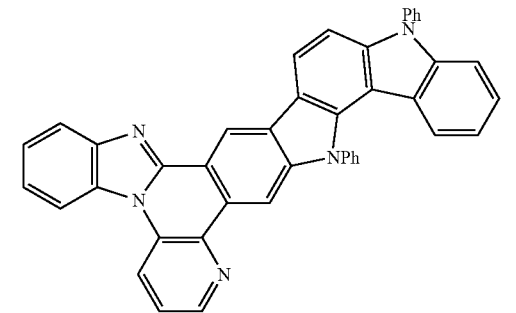
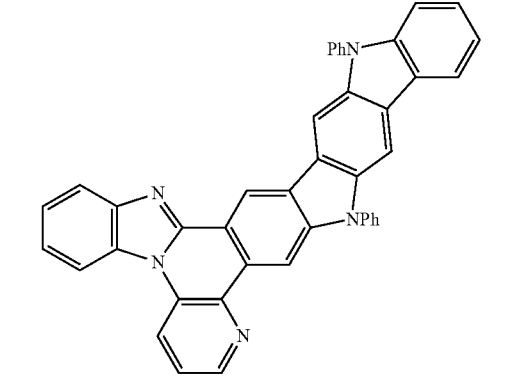
124
-continued
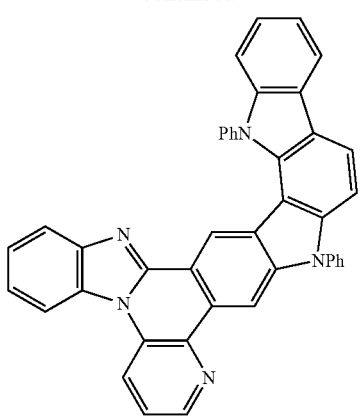
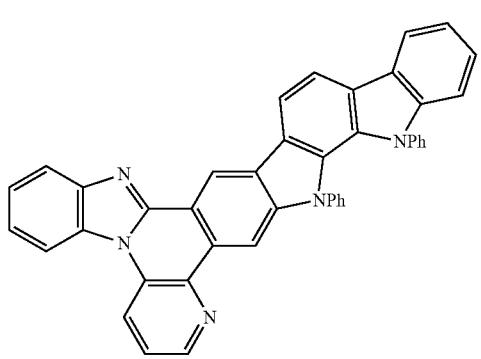
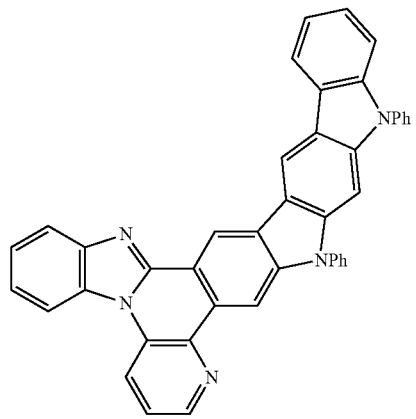
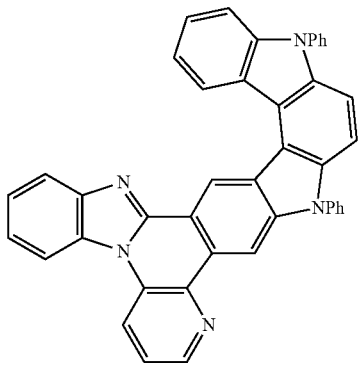

-continued
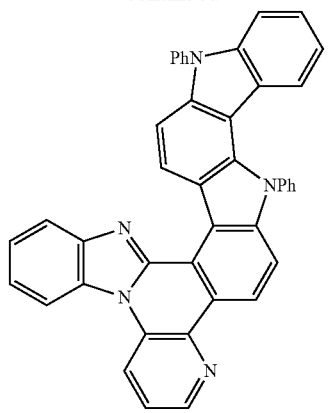
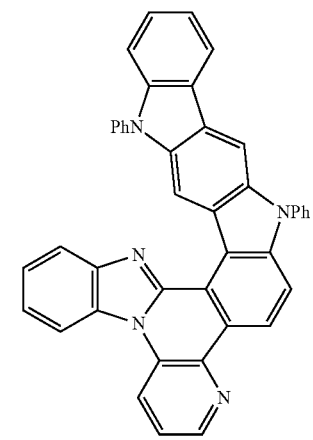
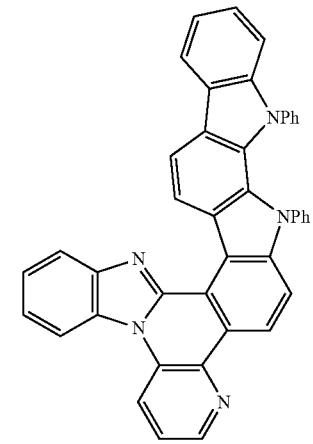
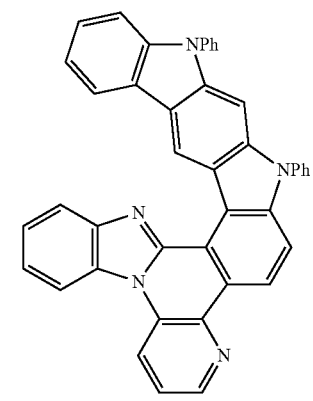
-continued
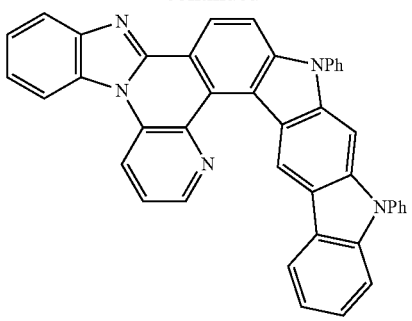
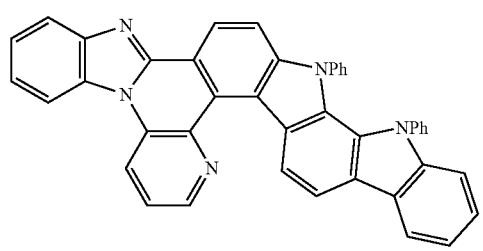

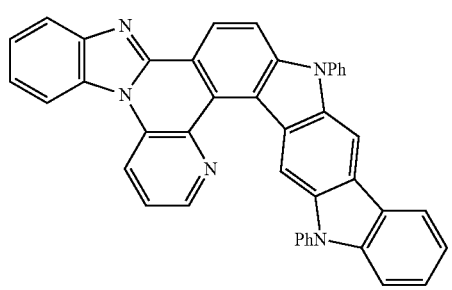

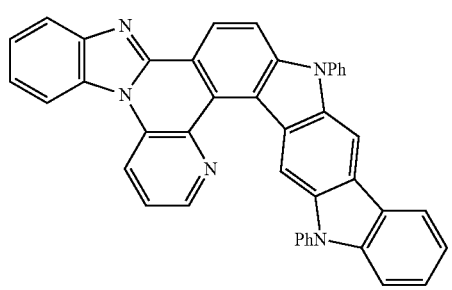
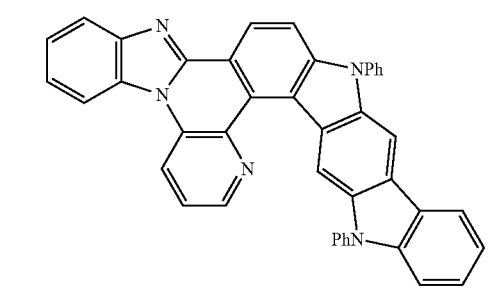

-continued
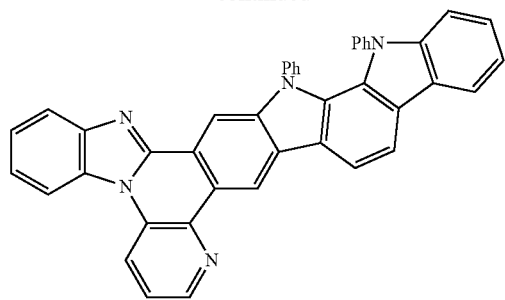
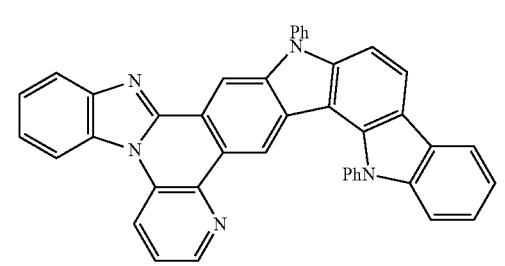
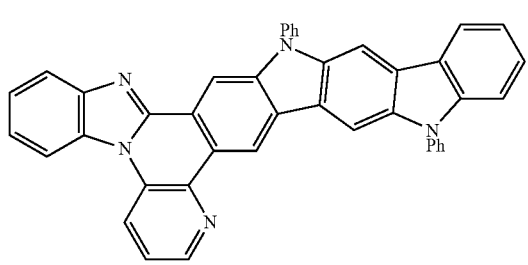
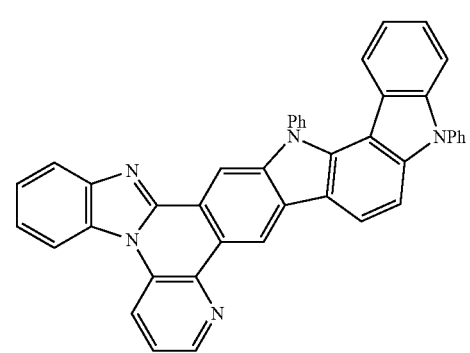
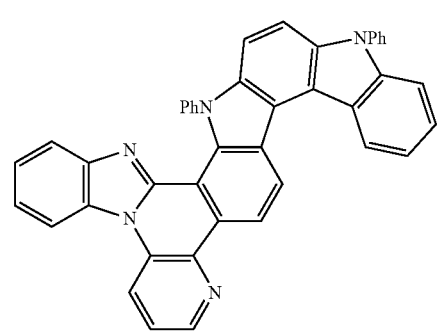
-continued
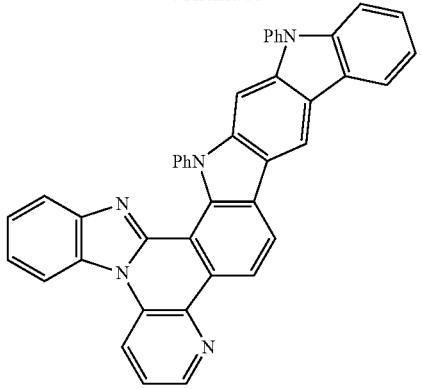
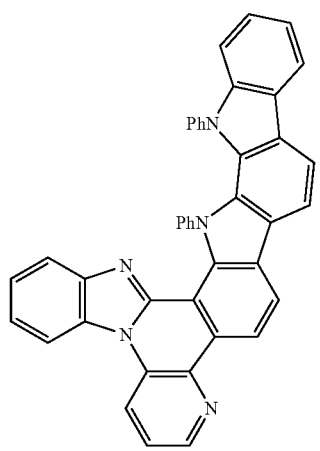
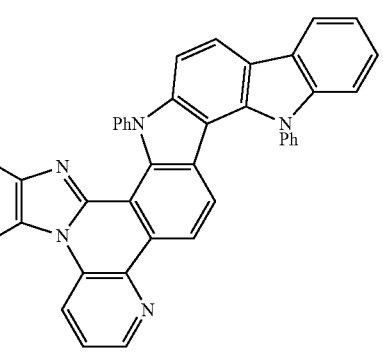
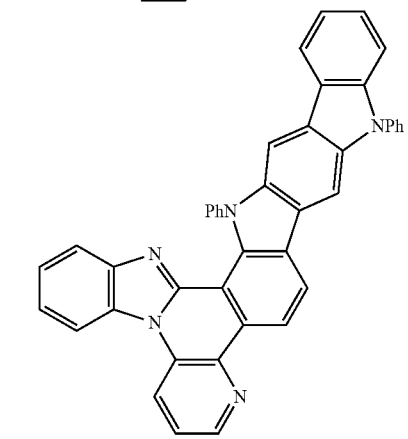

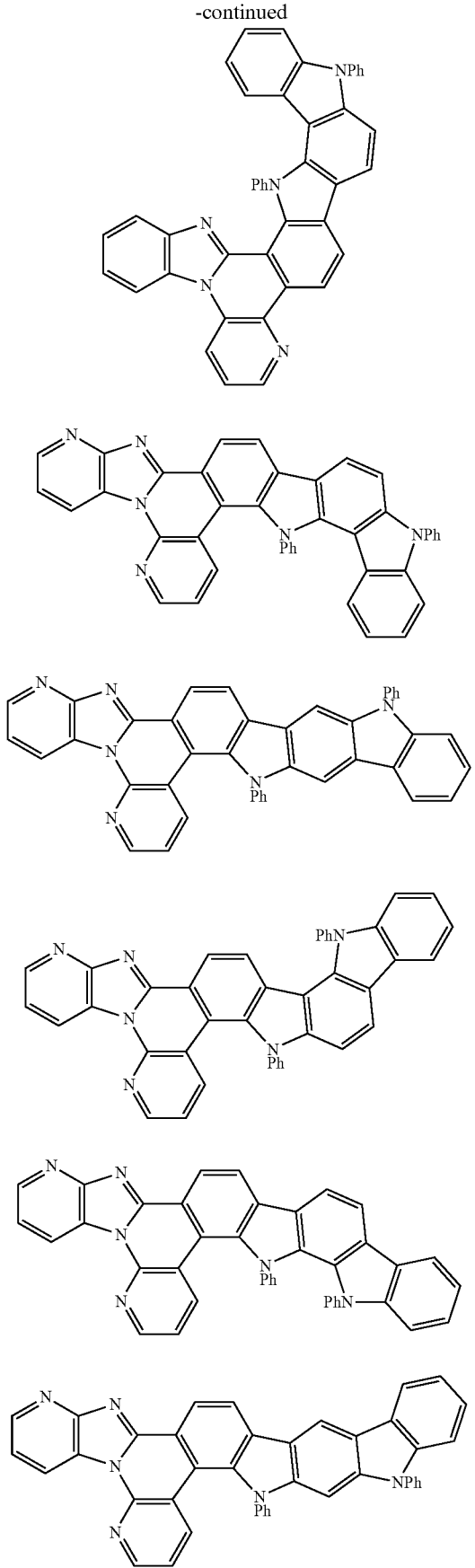
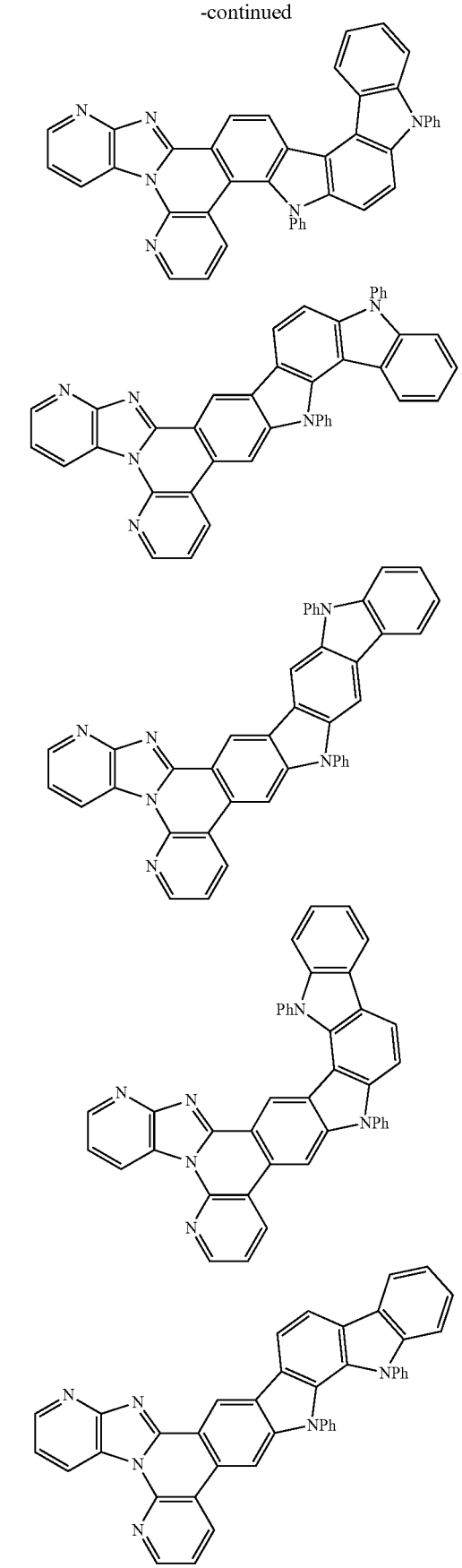

131
-continued
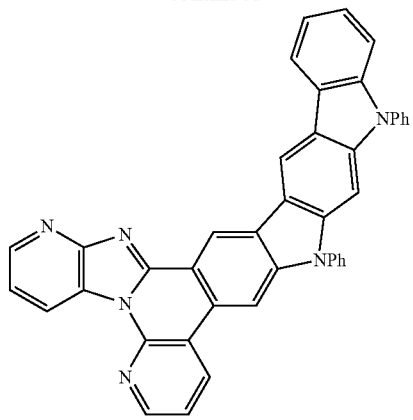
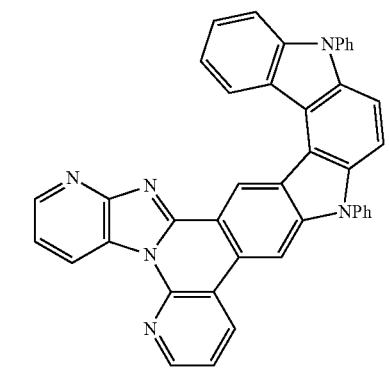
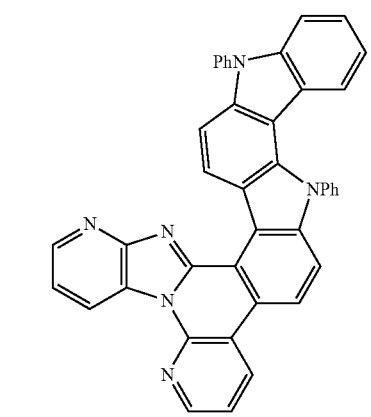
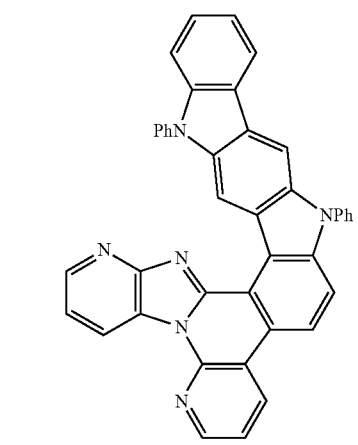
132
-continued
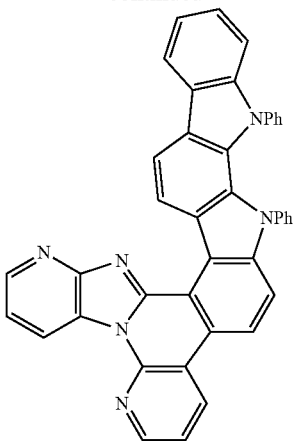
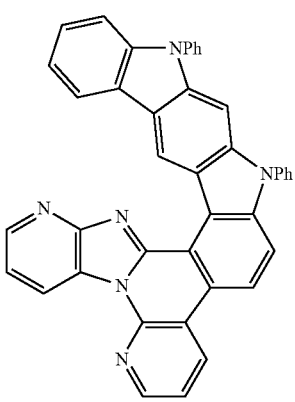
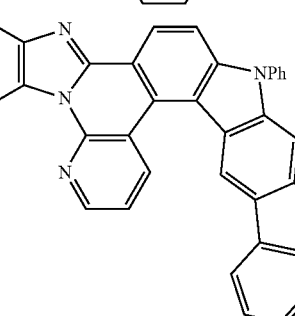
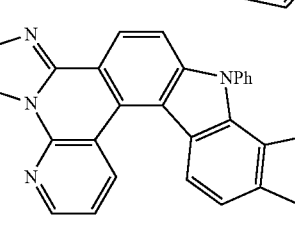
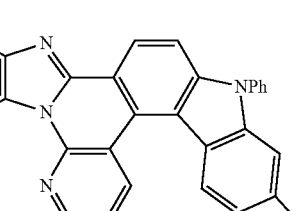
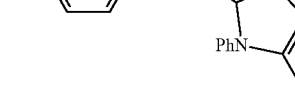

-continued
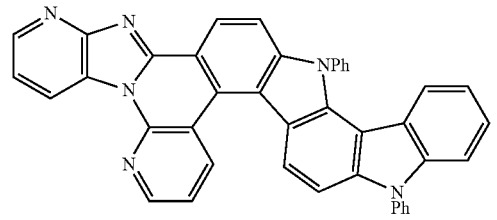
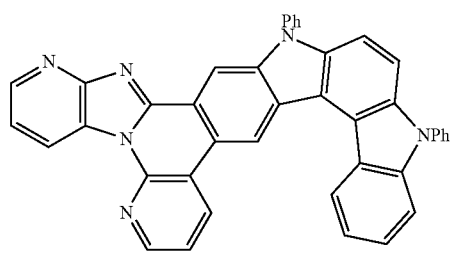
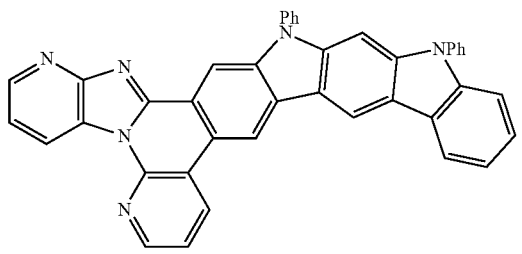
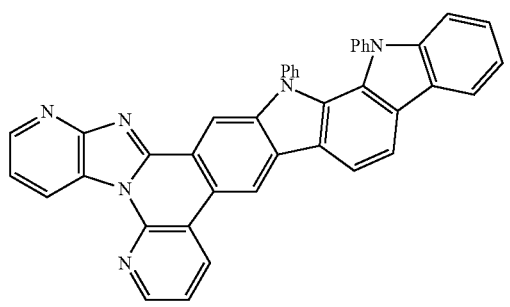
-continued
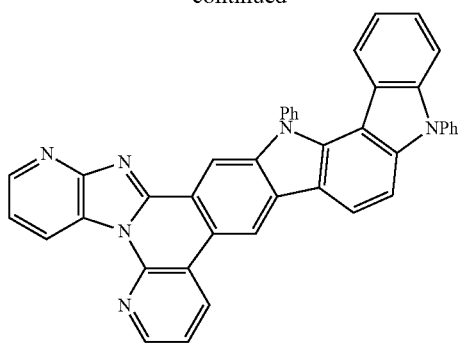
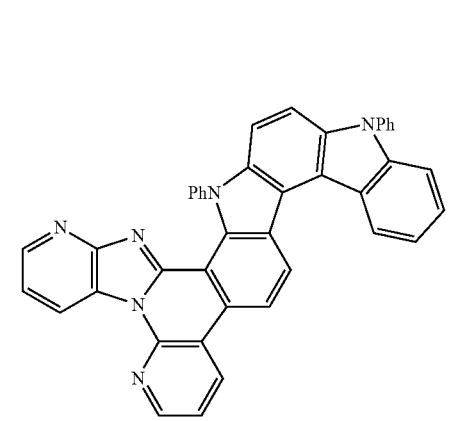
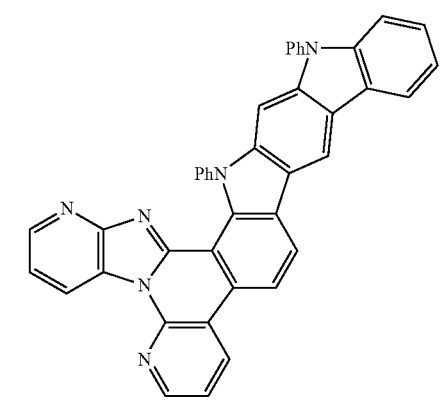
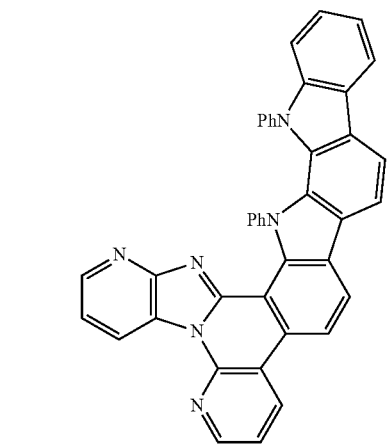
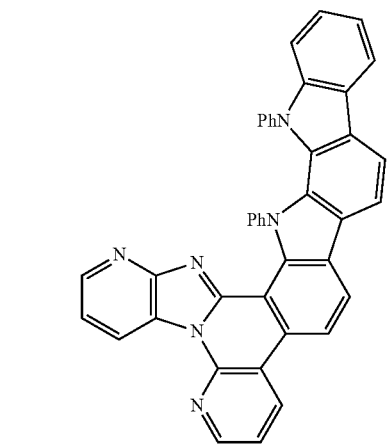

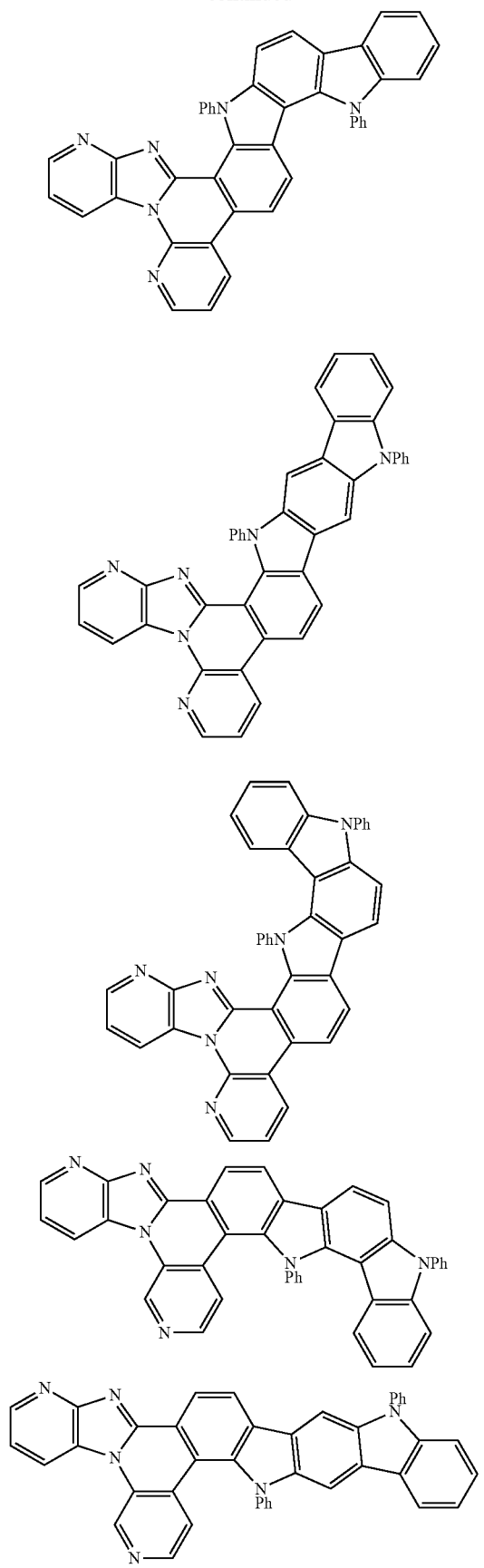
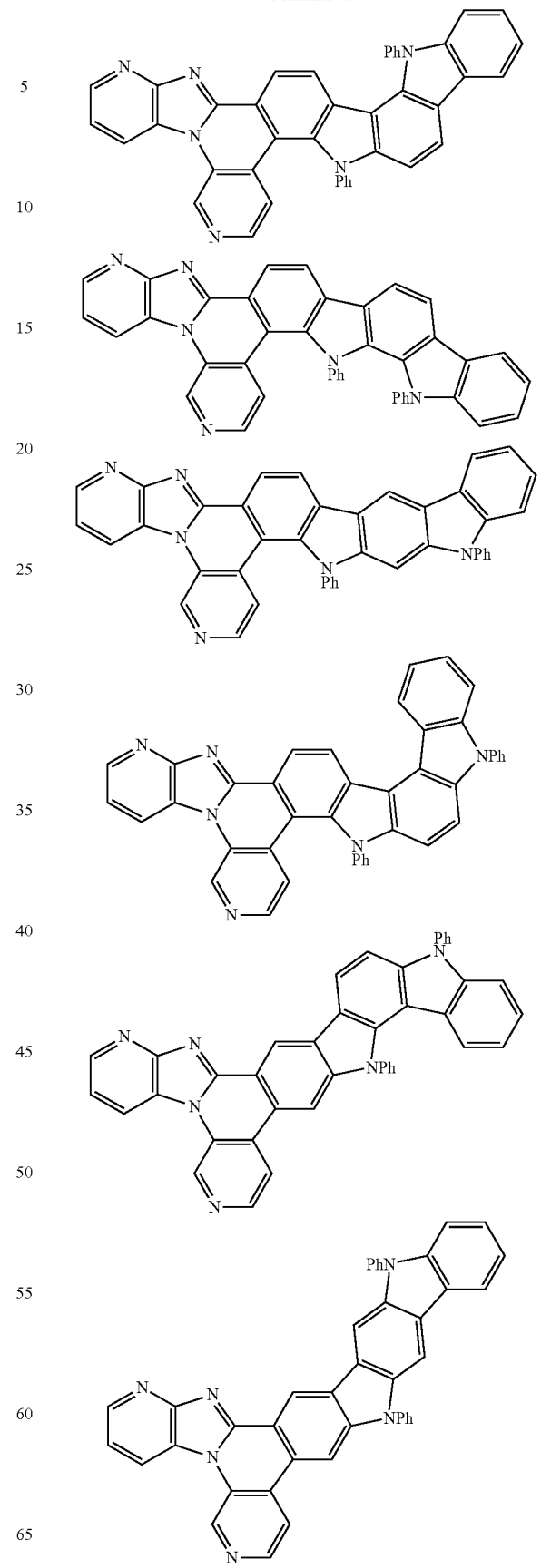

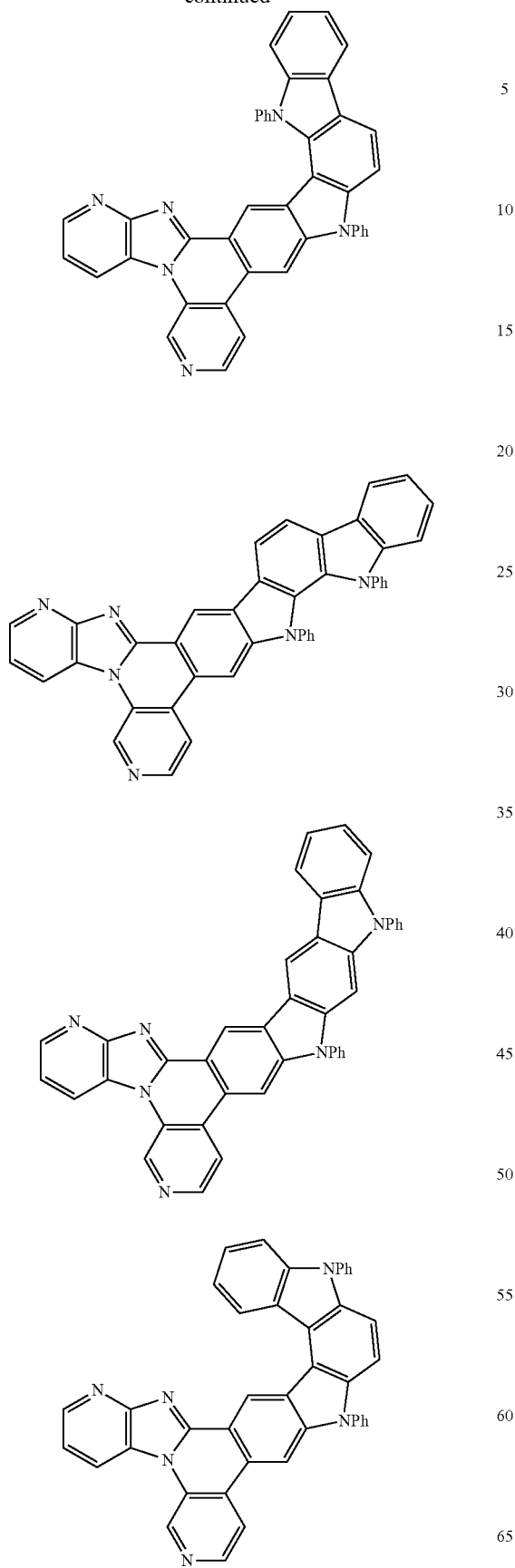
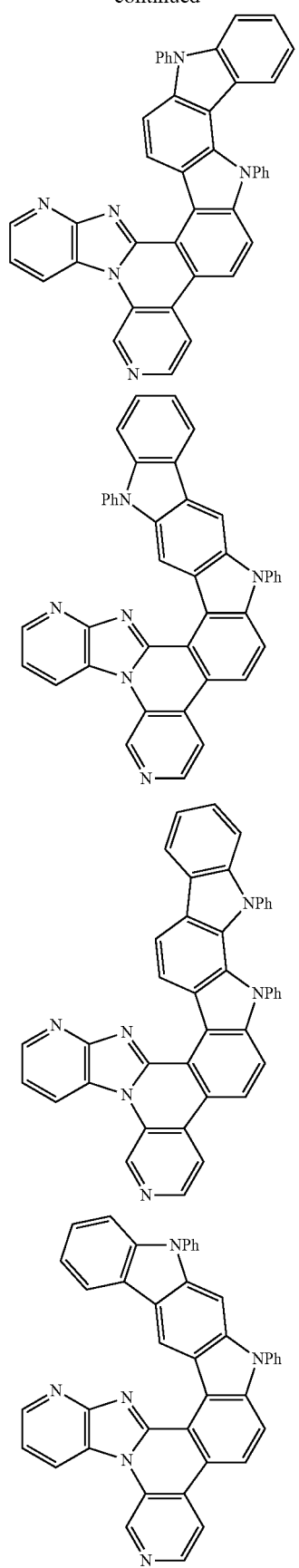

139
-continued
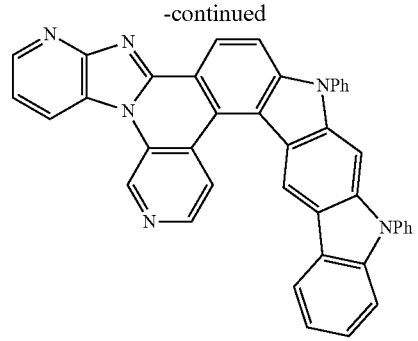
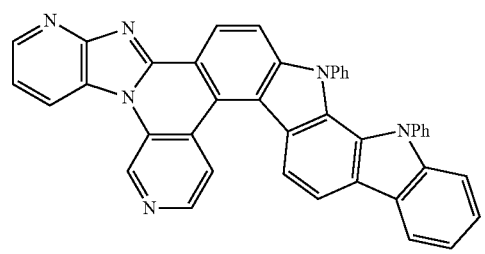
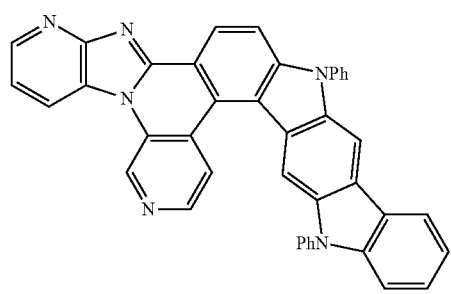
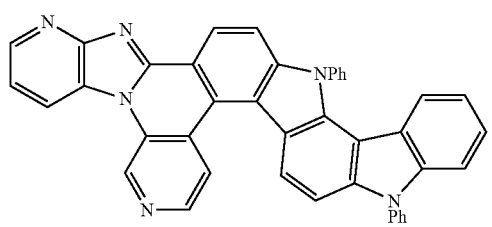
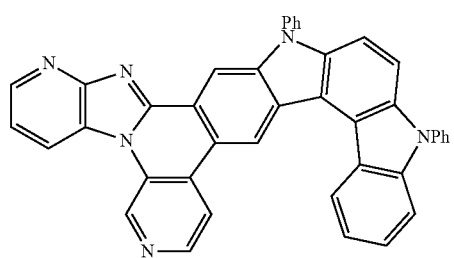
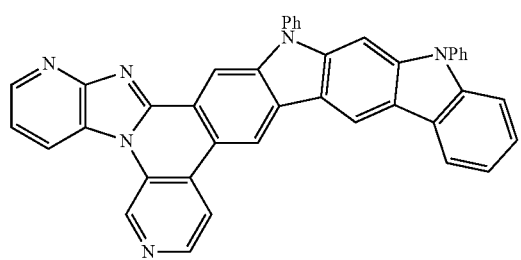
140
-continued
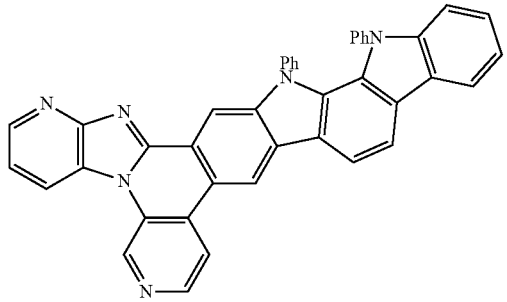
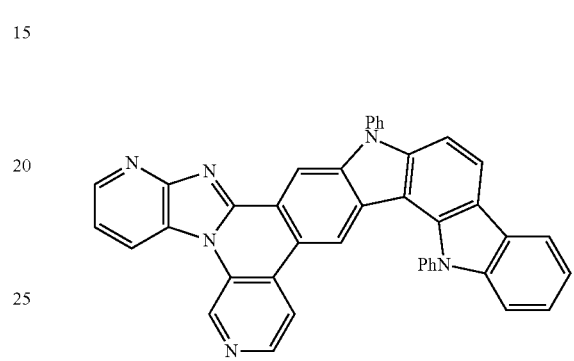
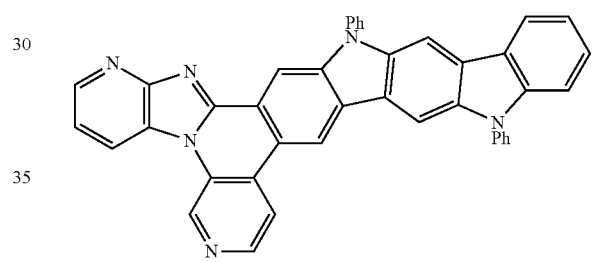
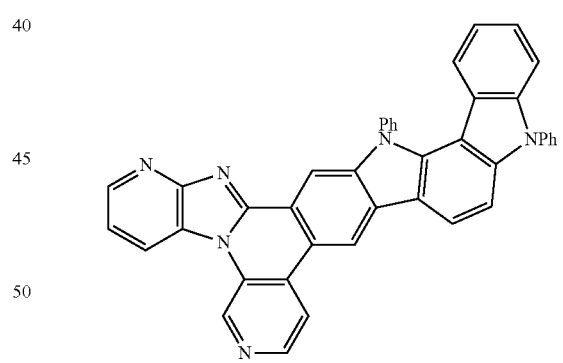
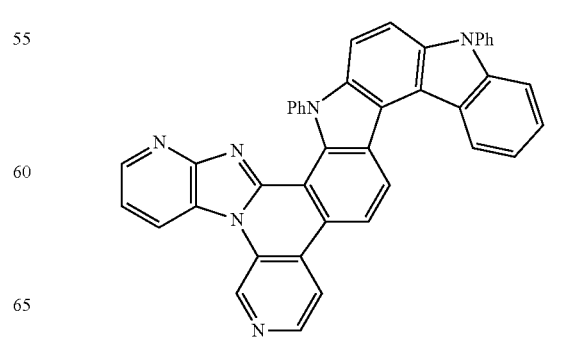

-continued
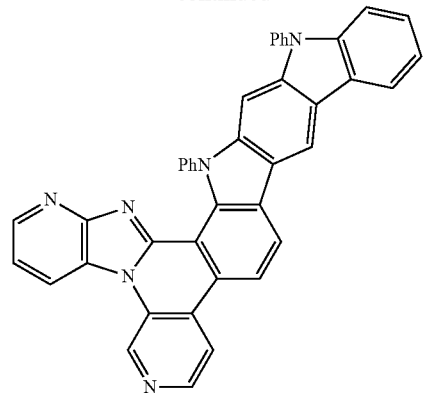
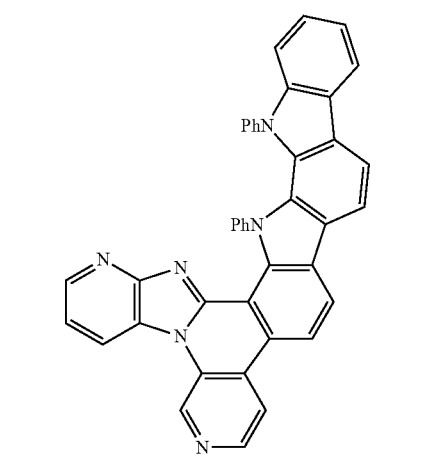
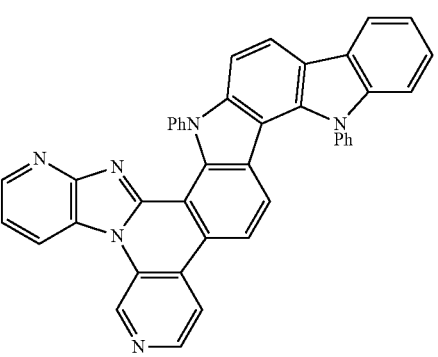
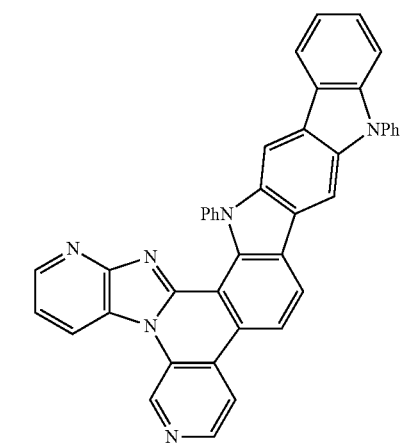
-continued
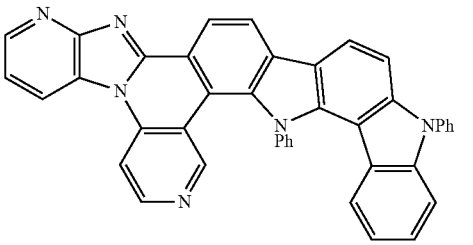
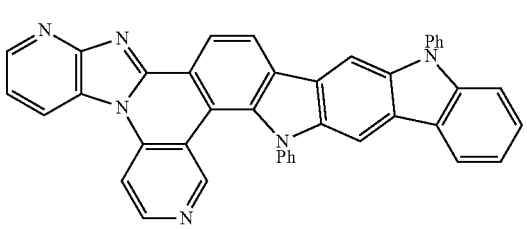
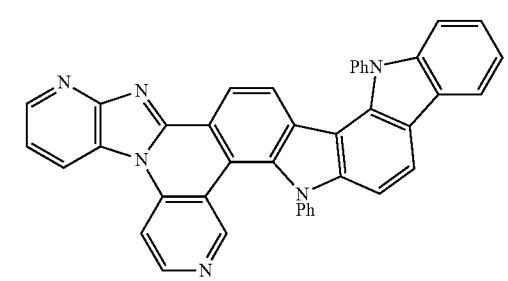
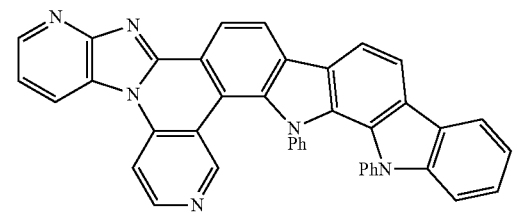
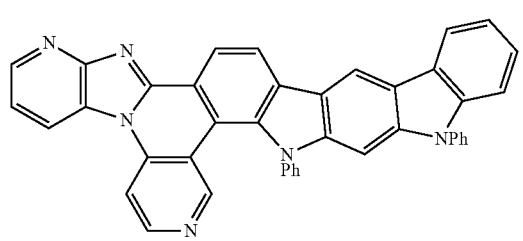

-continued
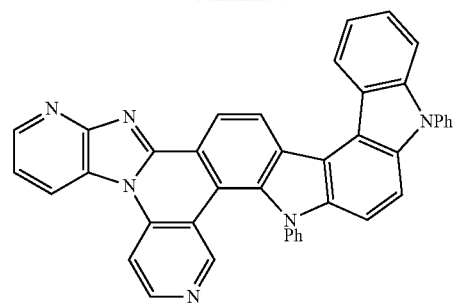
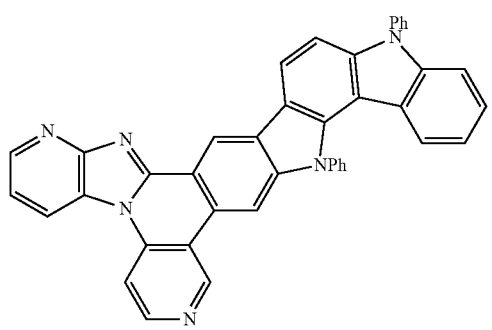
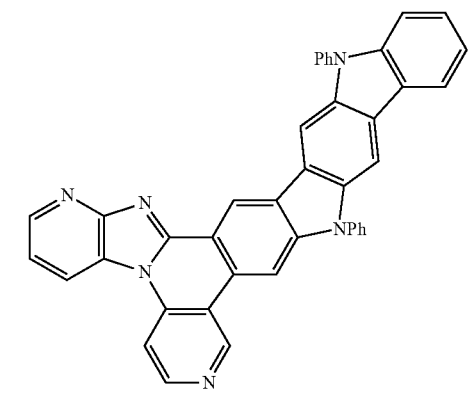
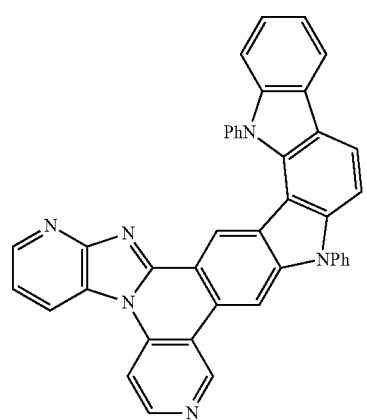
-continued
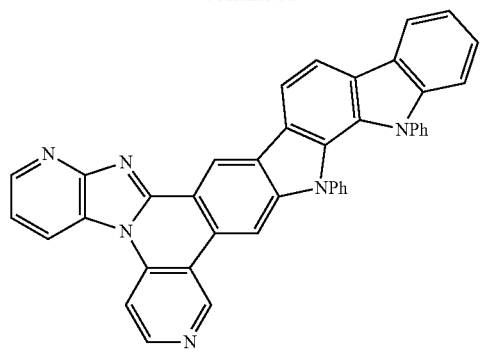
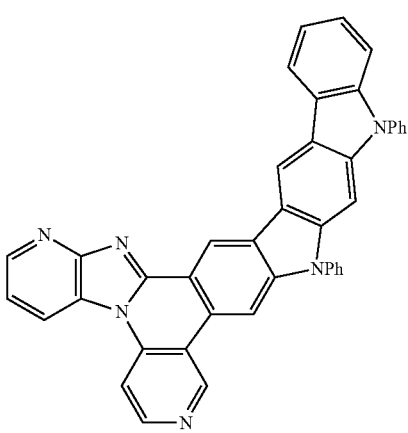
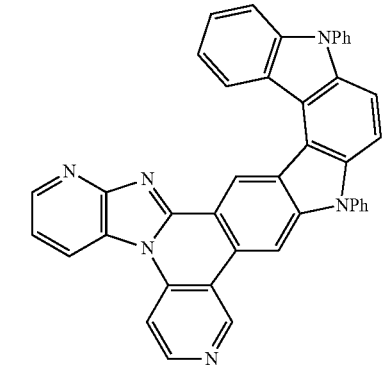
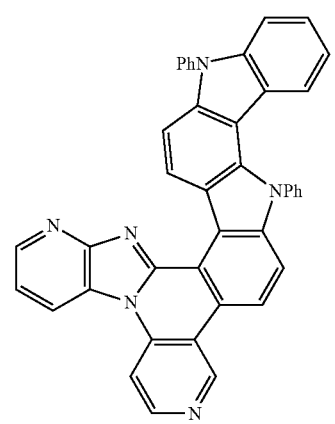

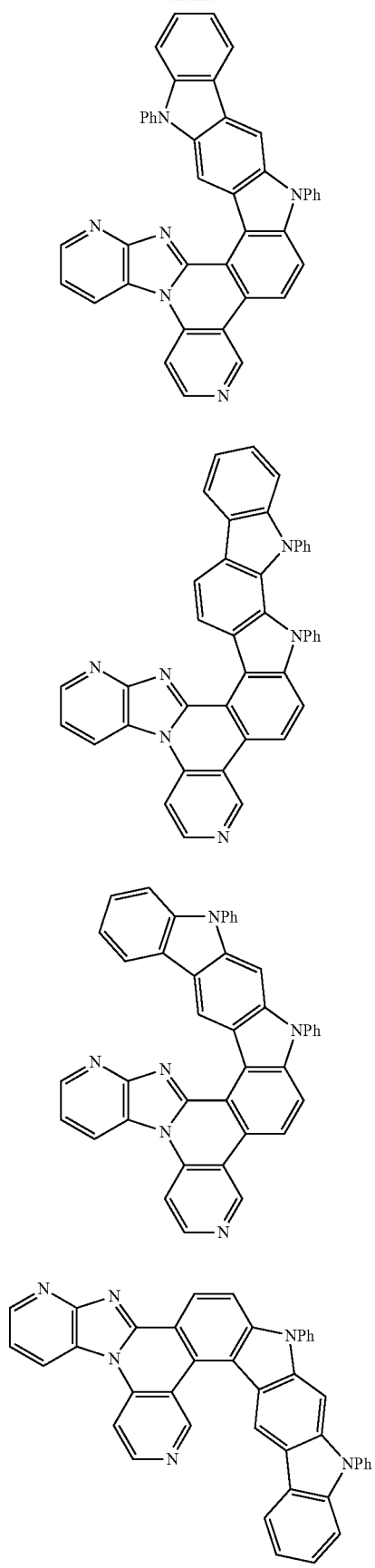

-continued
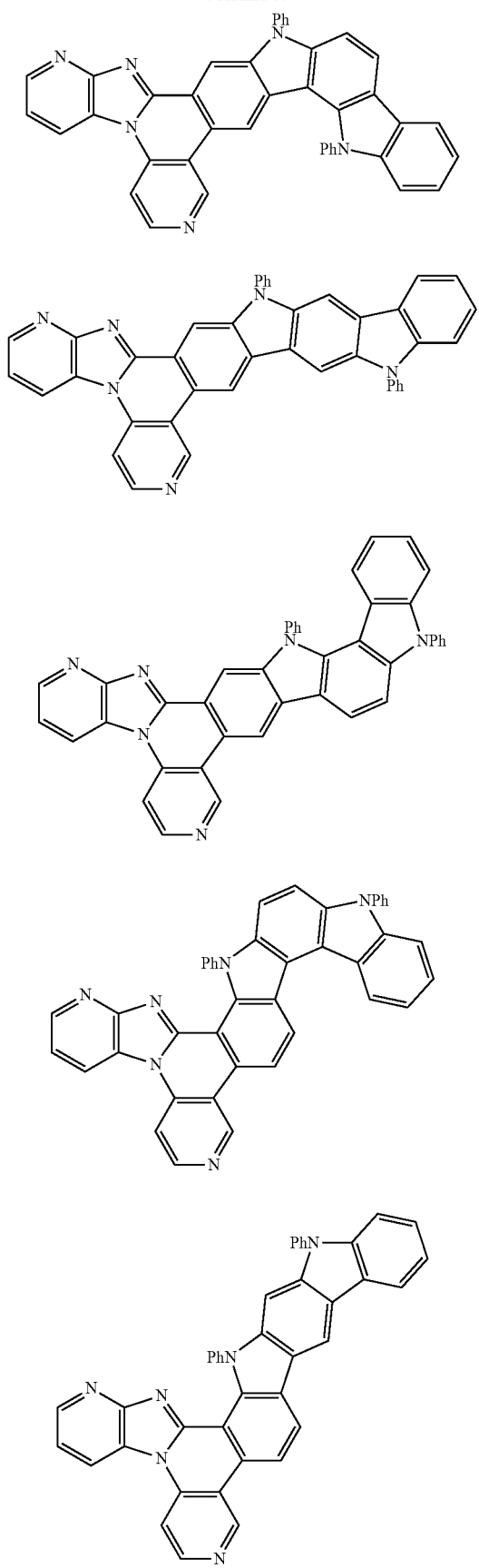
-continued
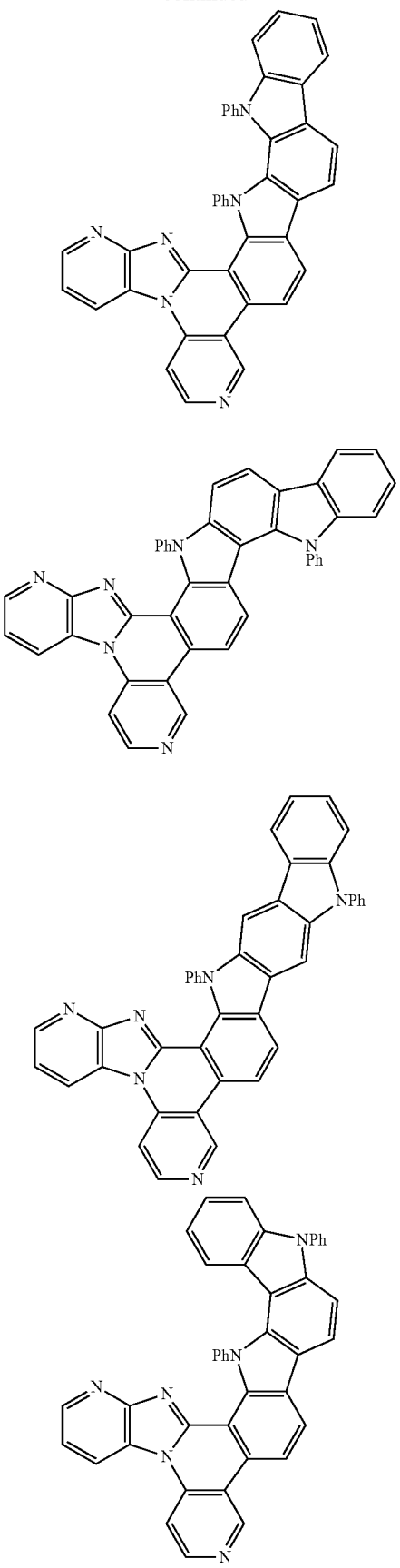

149
-continued
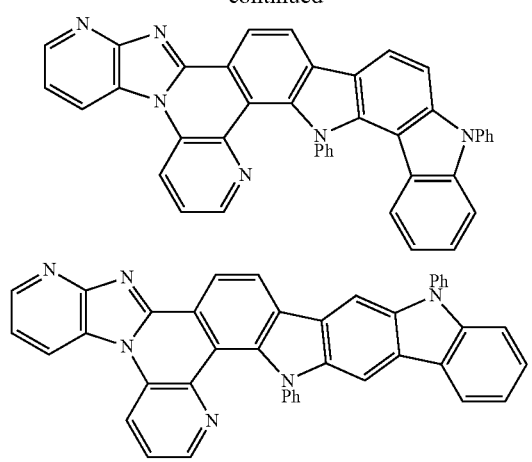
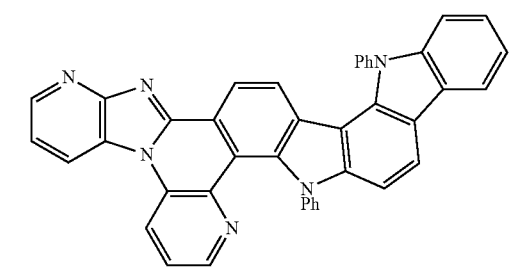
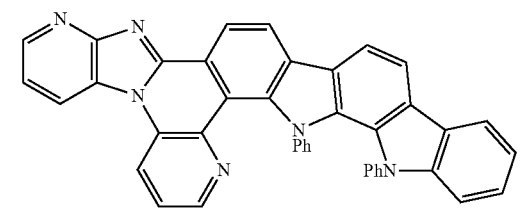
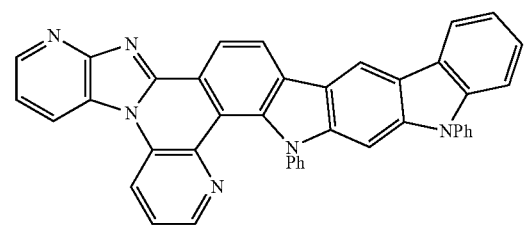
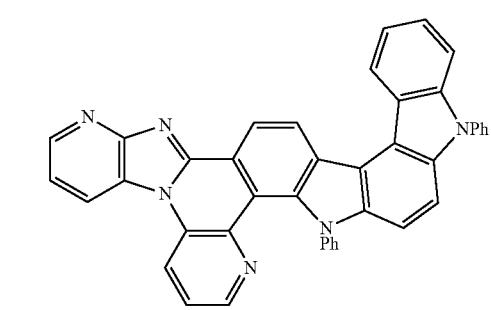
150
-continued
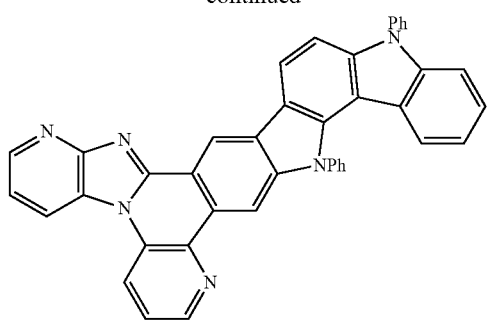
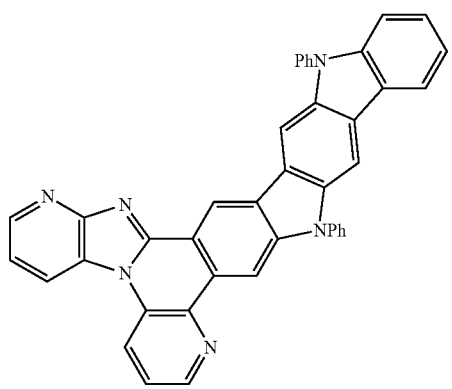
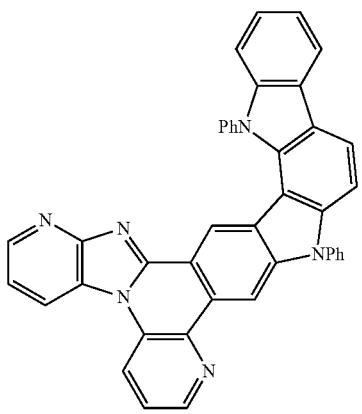
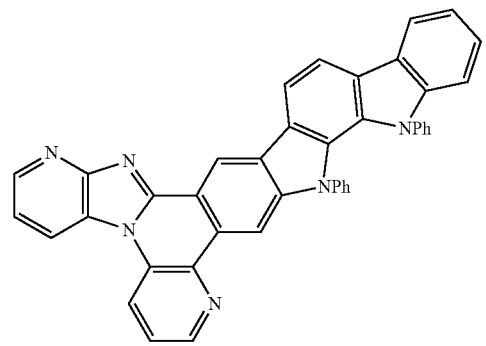

-continued
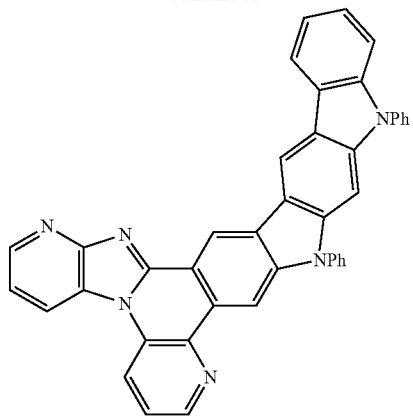
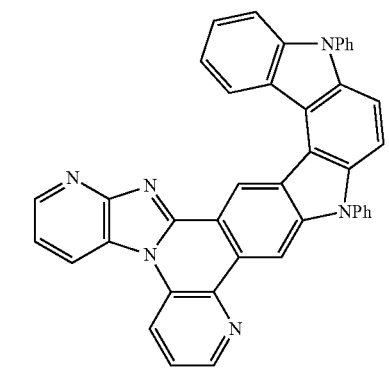
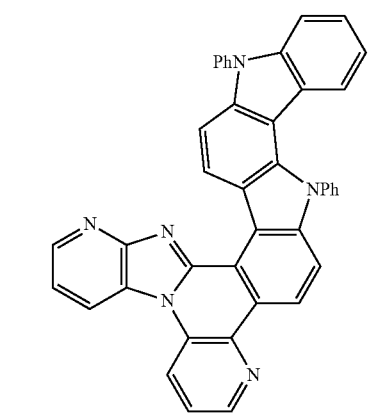
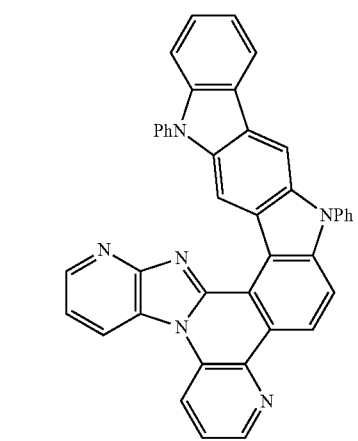
-continued
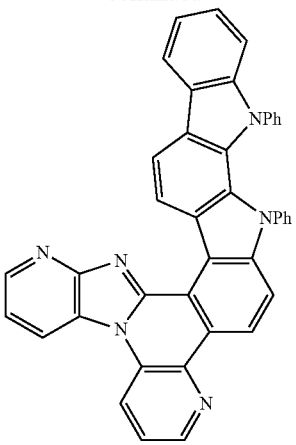
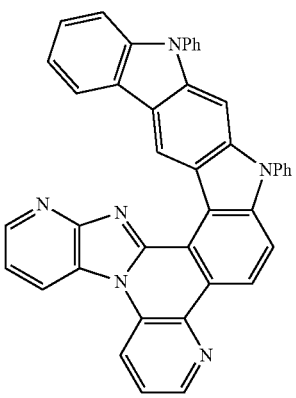
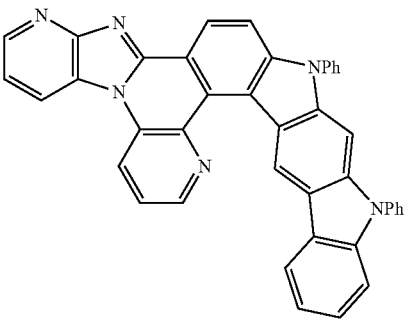
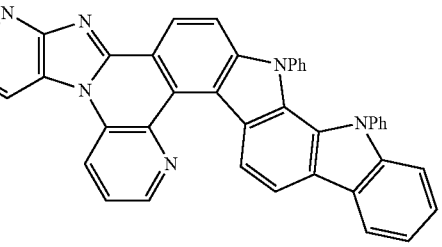
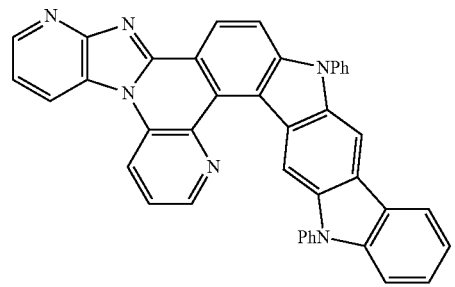

153
-continued
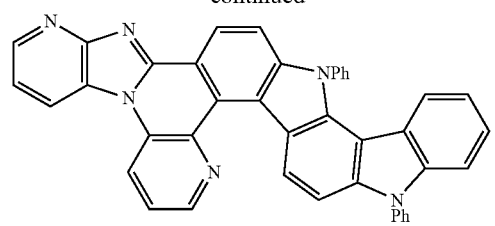
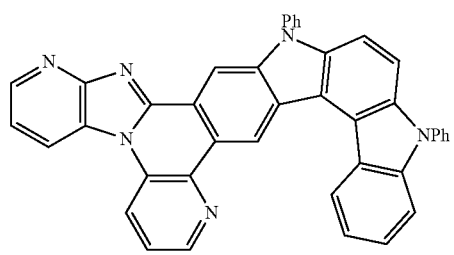
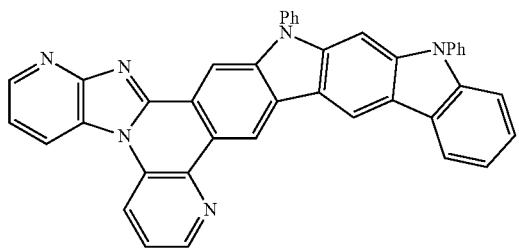
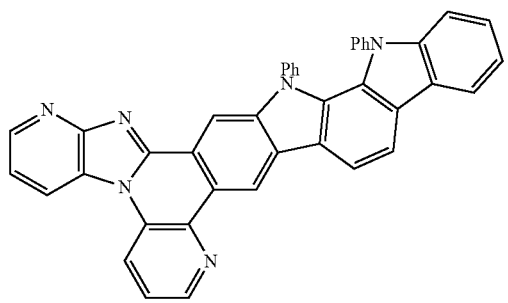
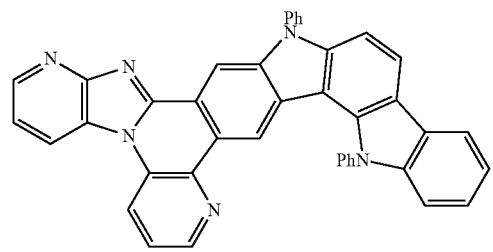
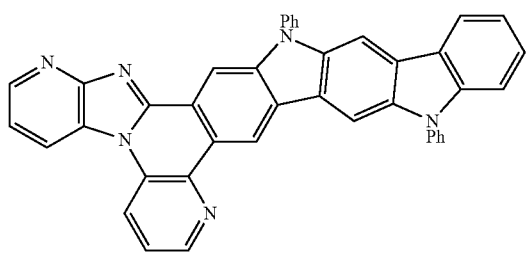
154
-continued
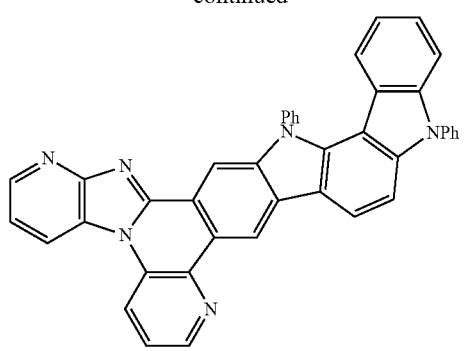
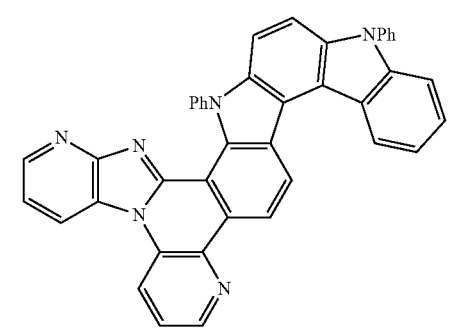
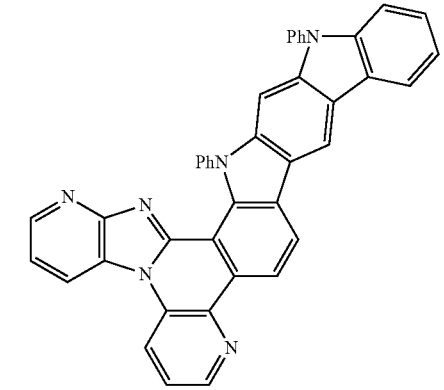
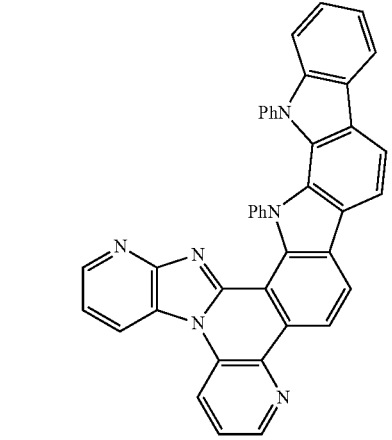

-continued
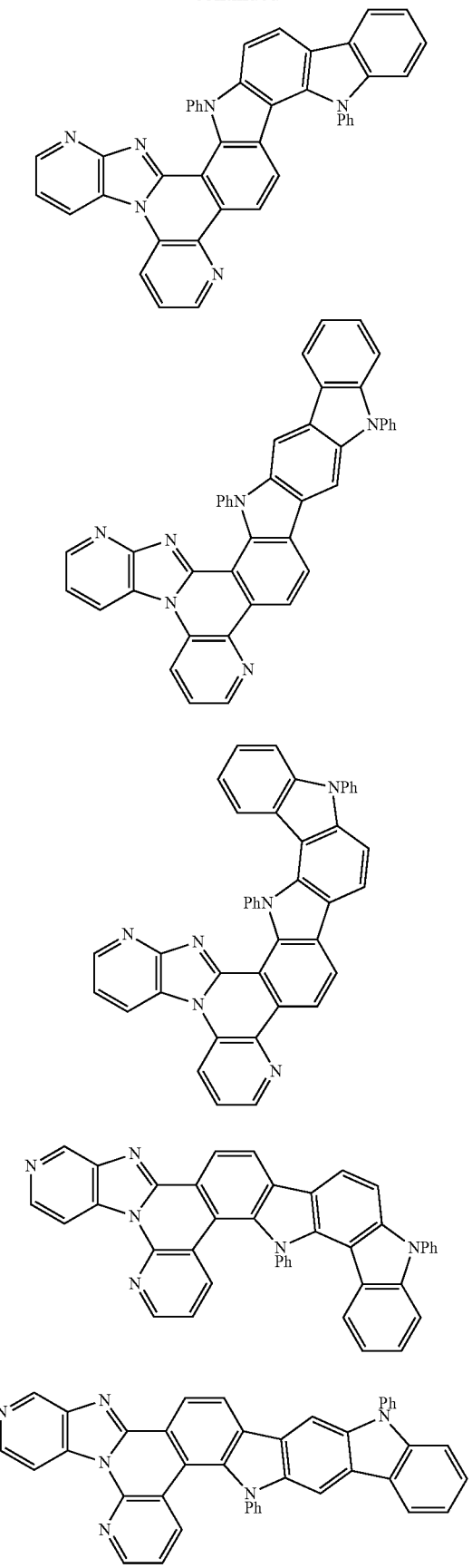
-continued
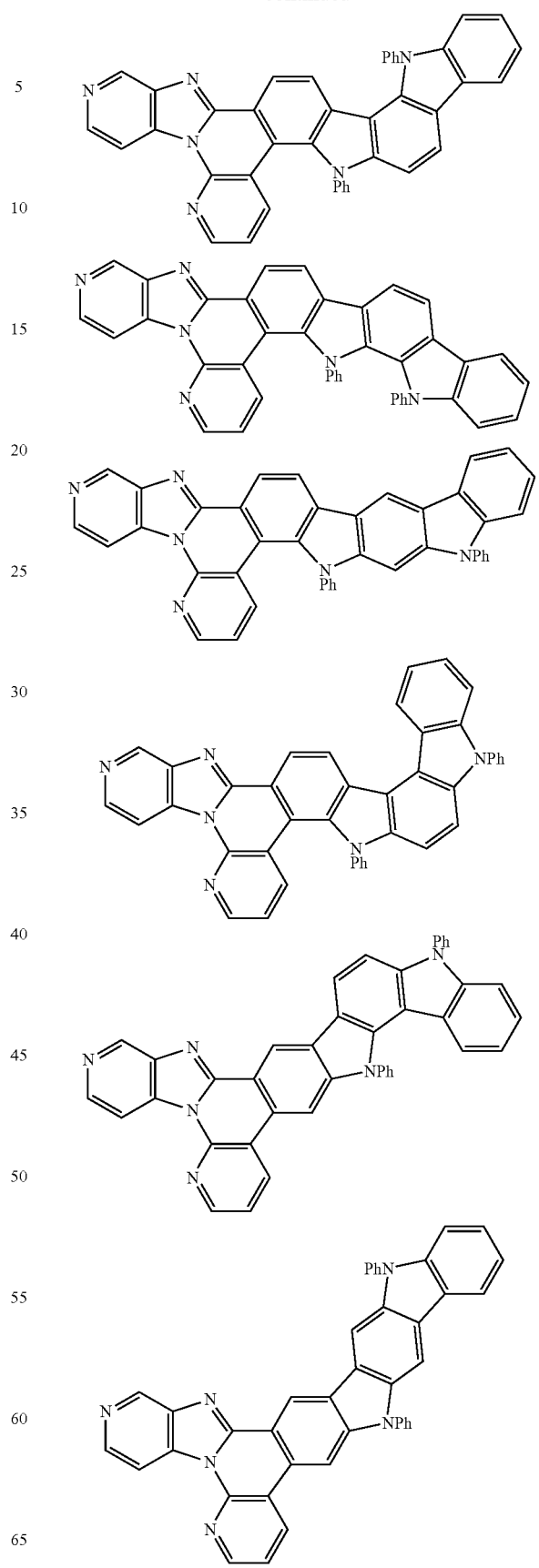

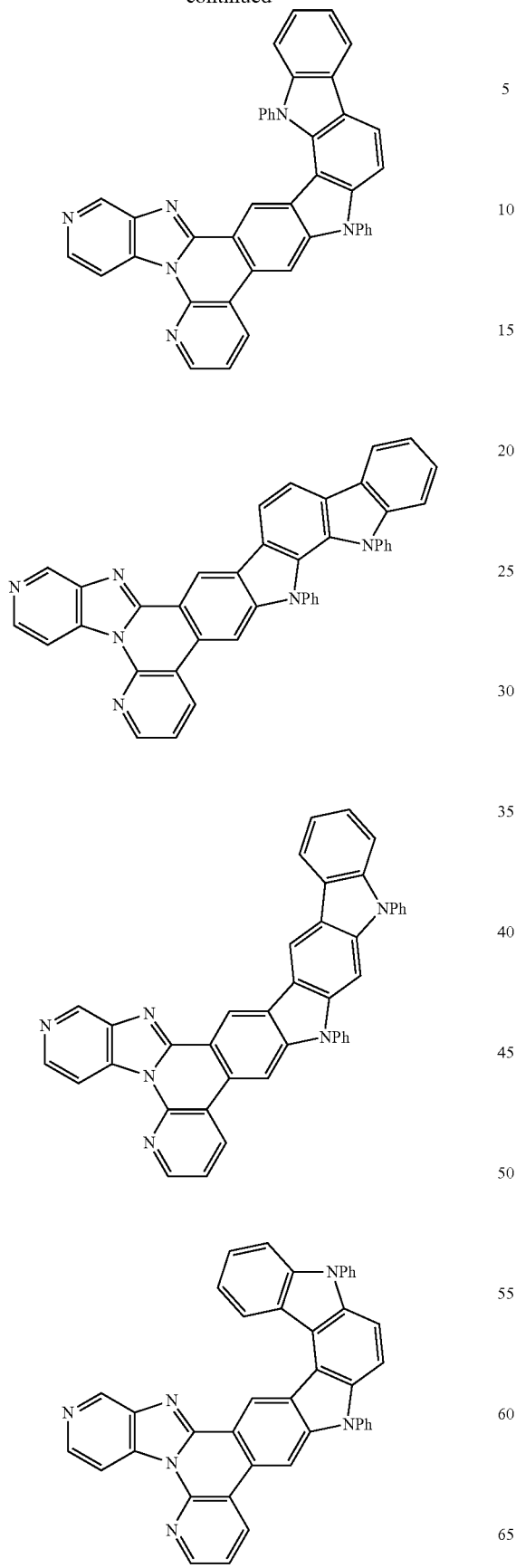
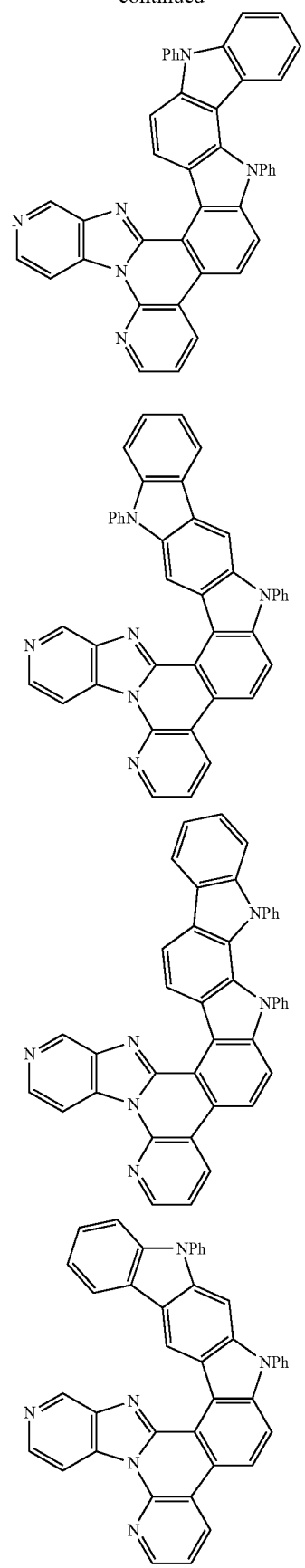

159
-continued
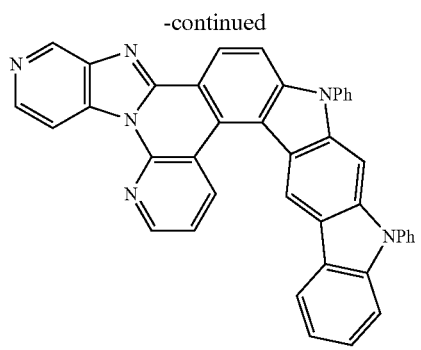
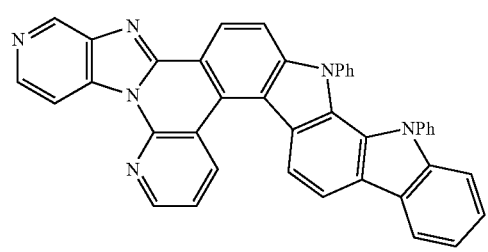
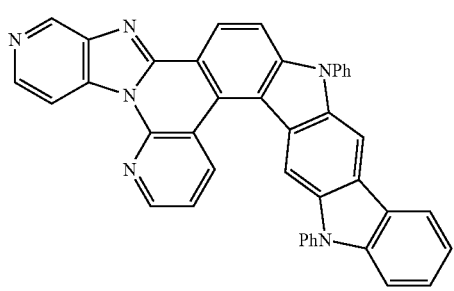
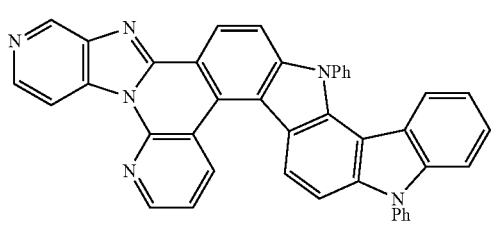
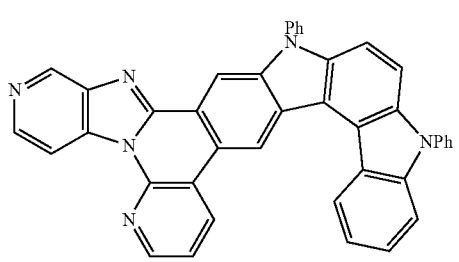
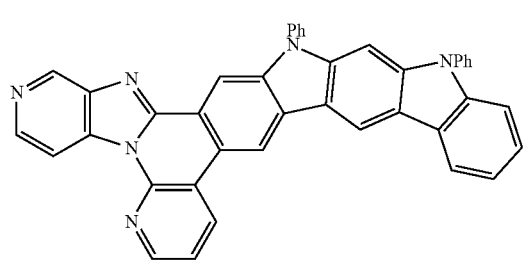
160
-continued
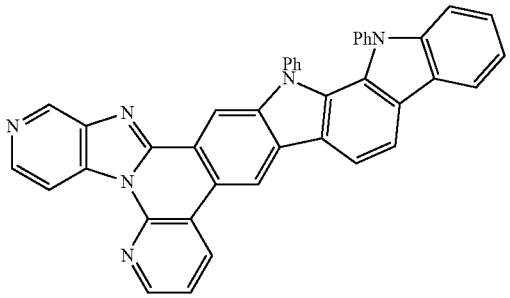
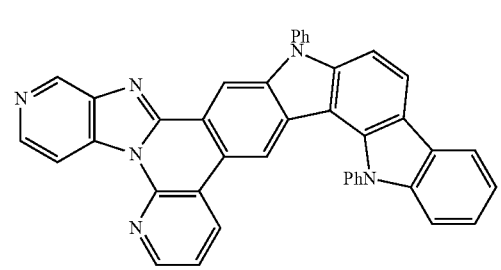
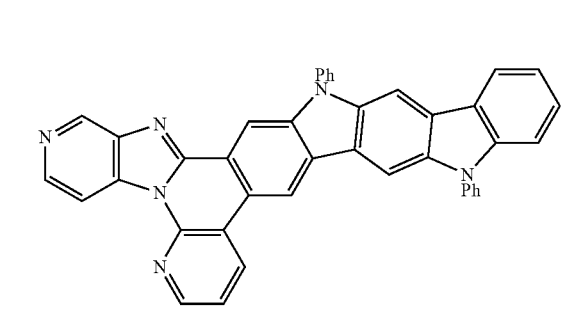
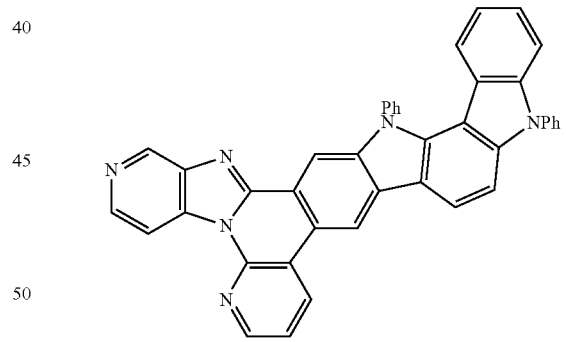
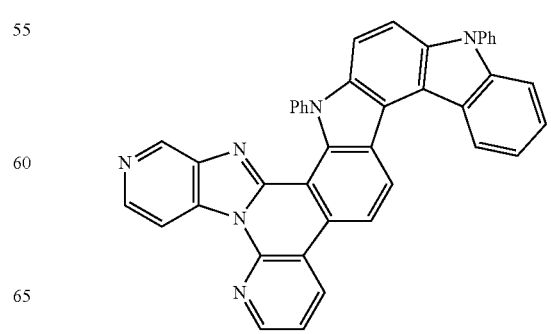

-continued
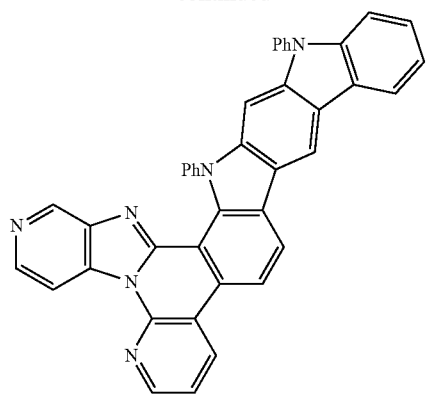
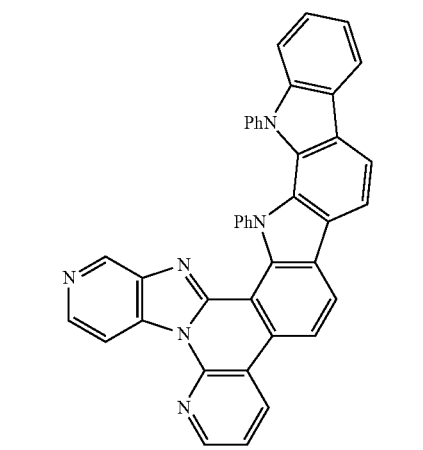
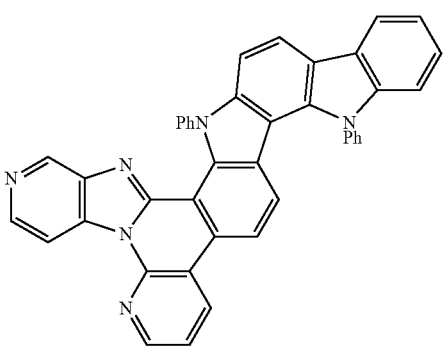
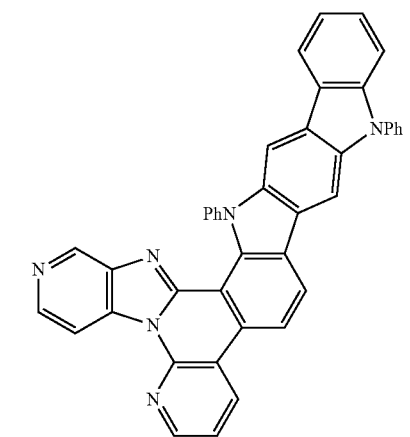
-continued
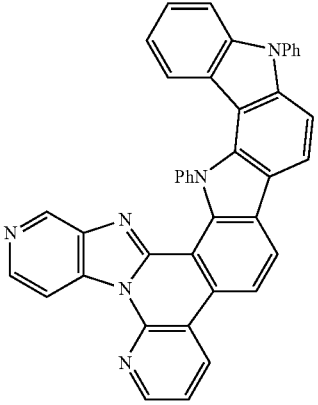
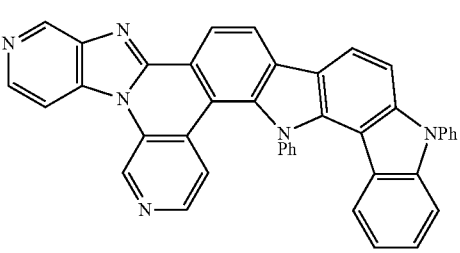
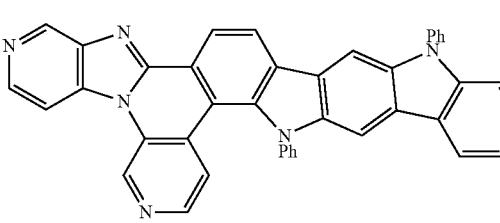
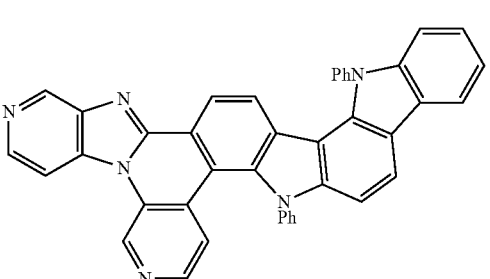
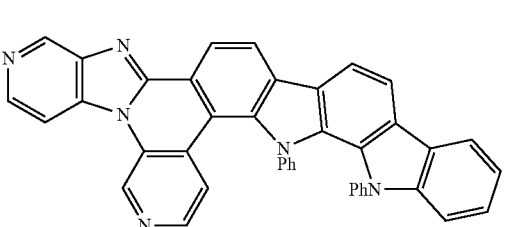
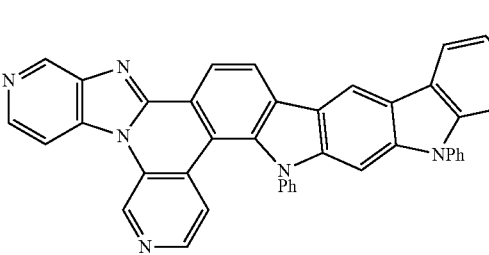

163
-continued
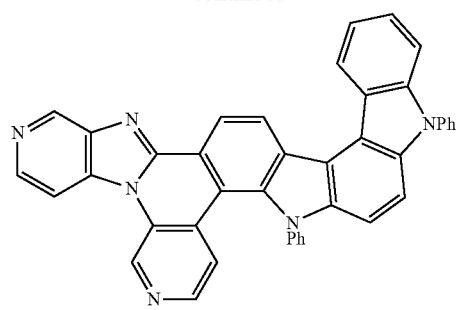
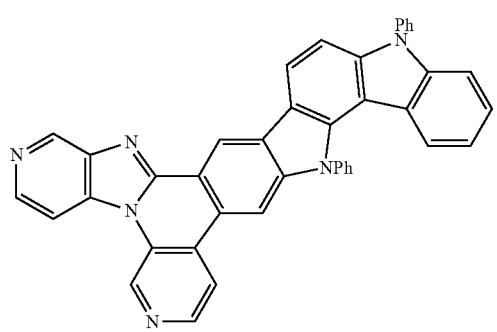
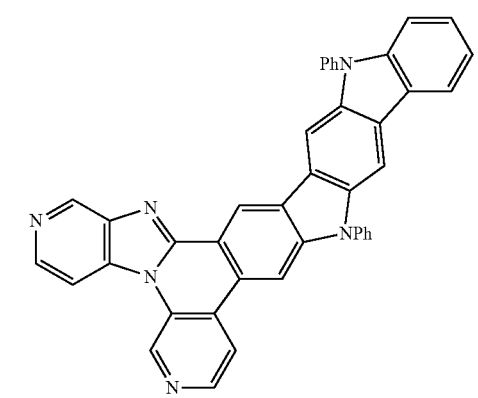
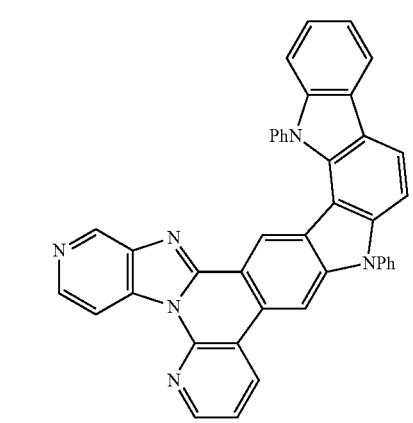
164
-continued
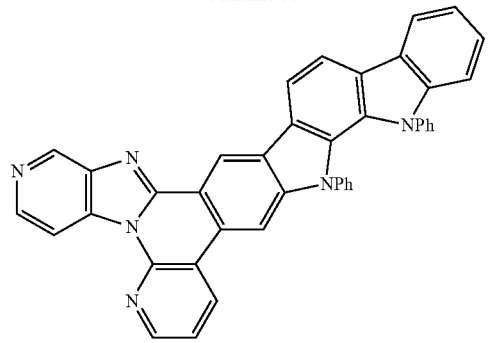
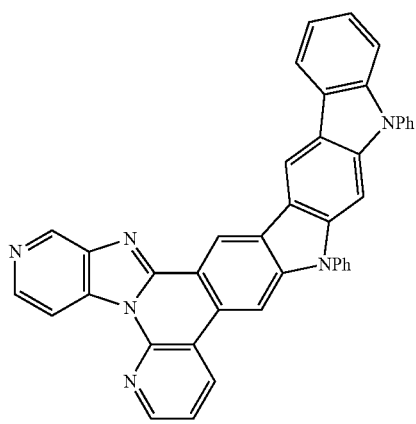
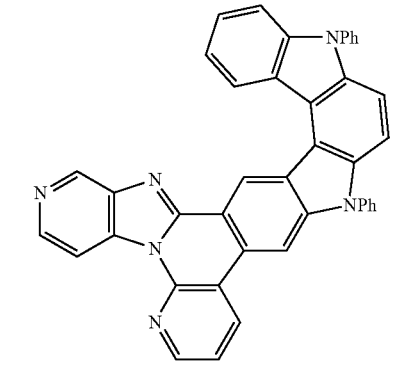
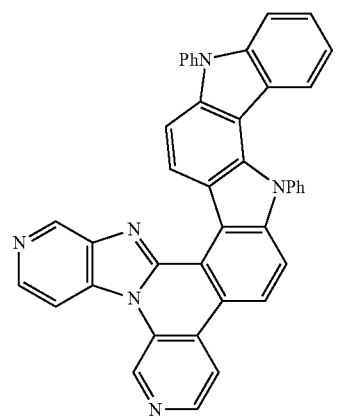

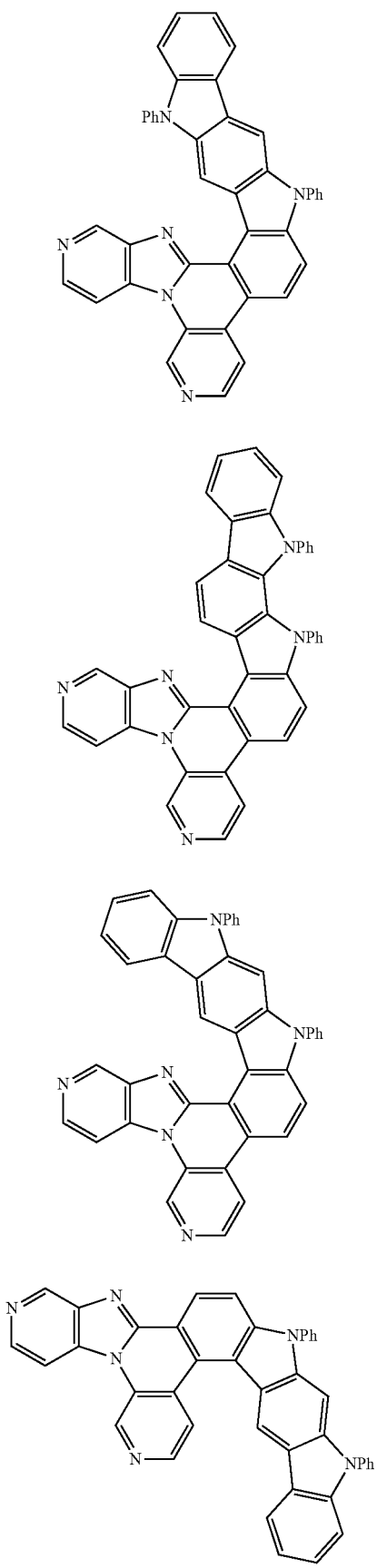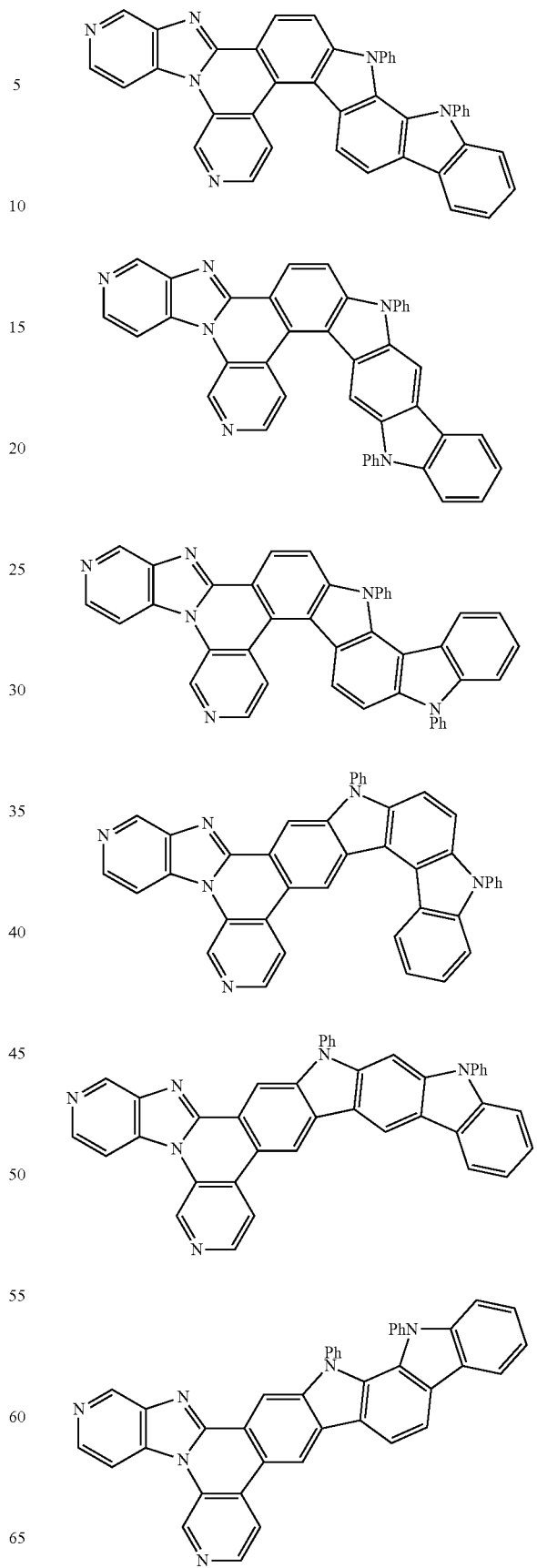

-continued
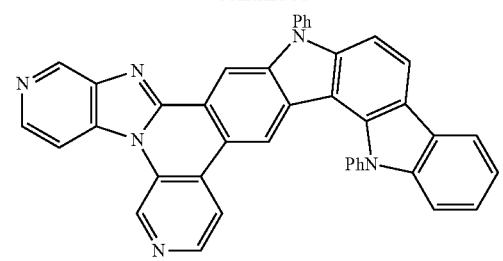
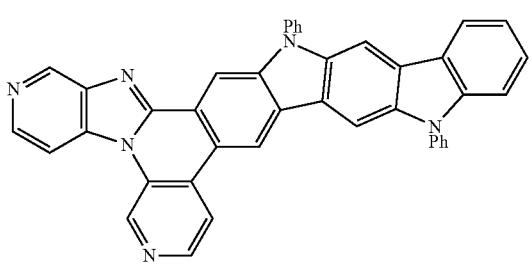
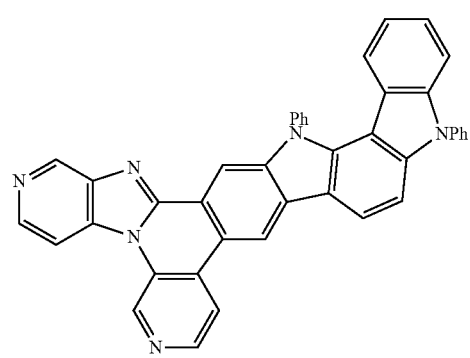
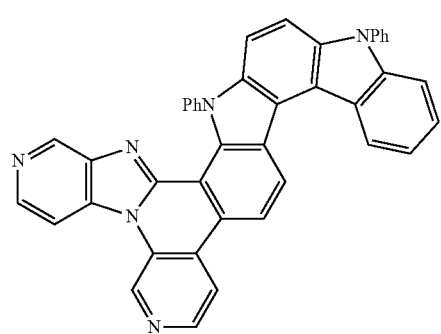
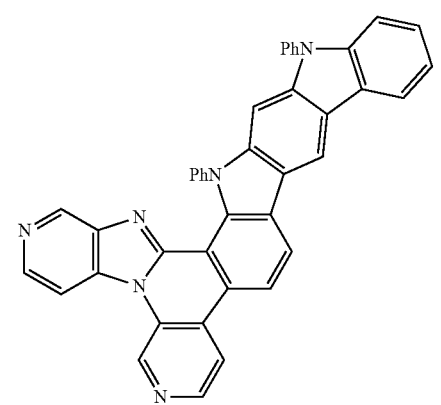
-continued
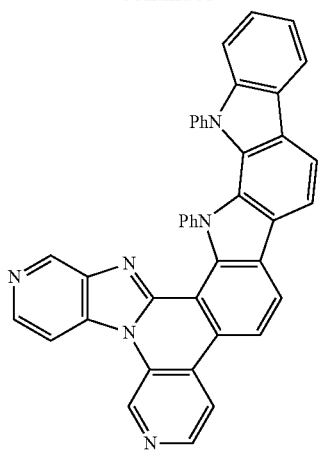
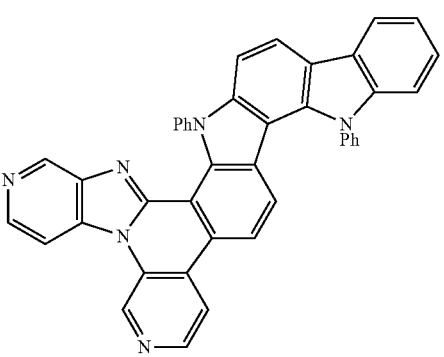
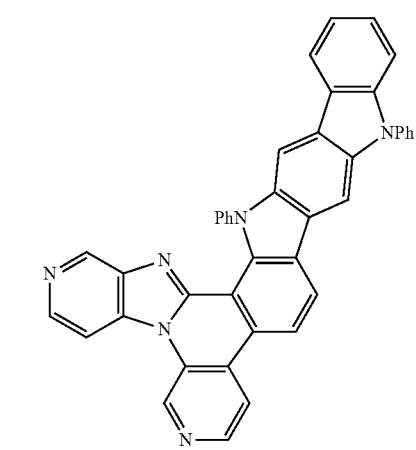
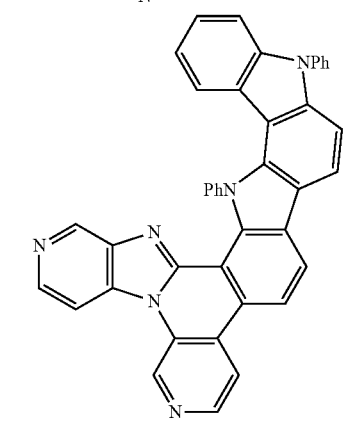

169
-continued
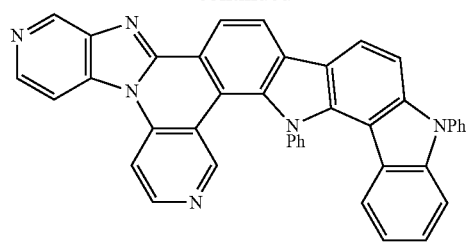
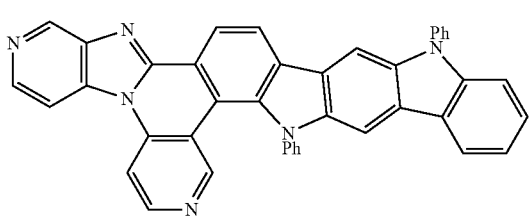
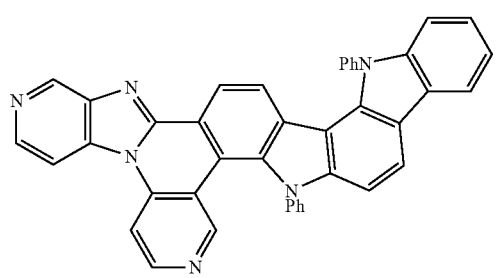
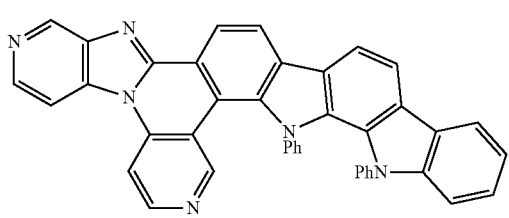
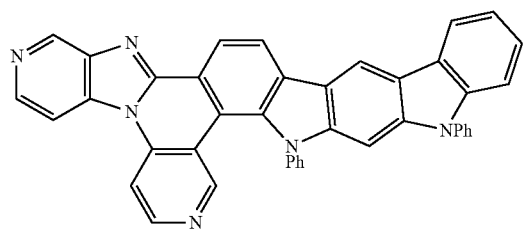
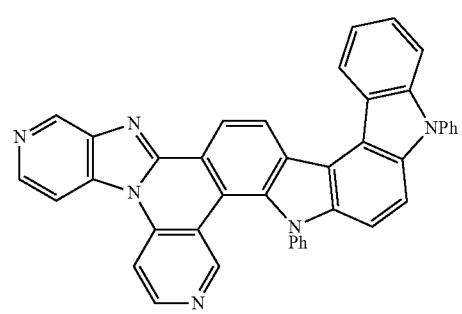
170
-continued
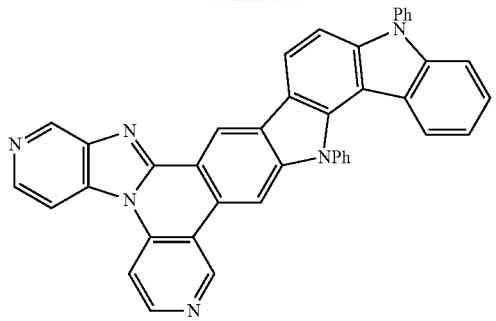
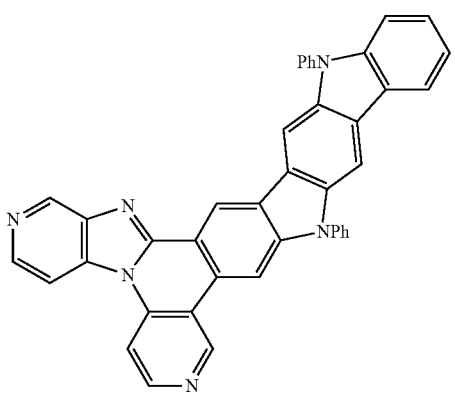
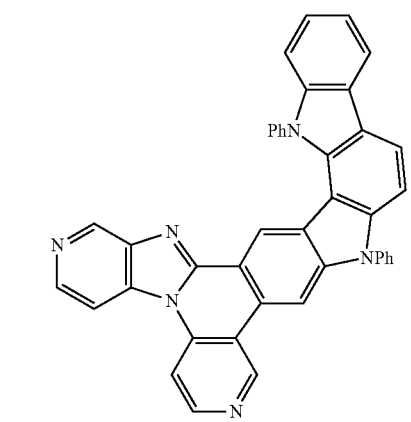
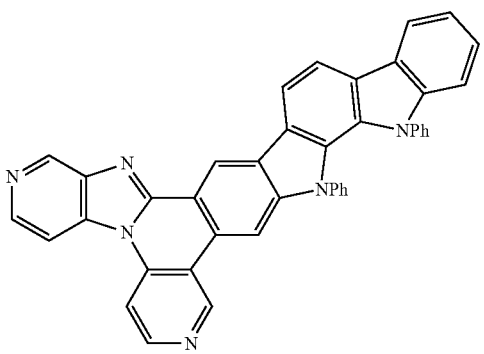

-continued
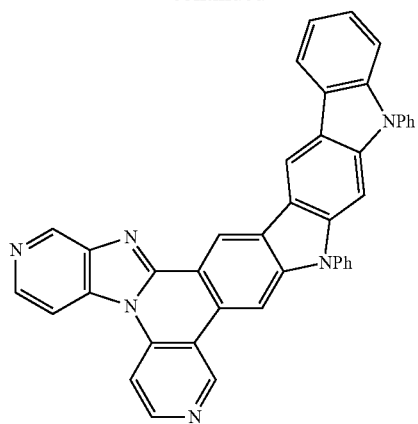
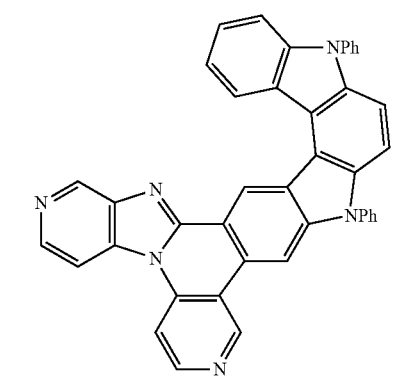
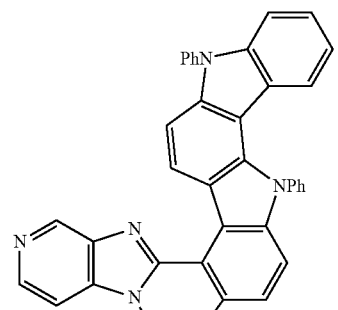
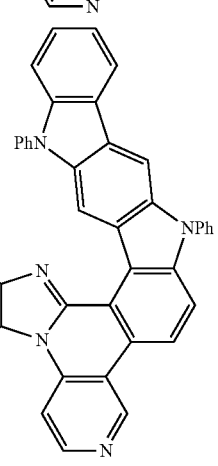
-continued
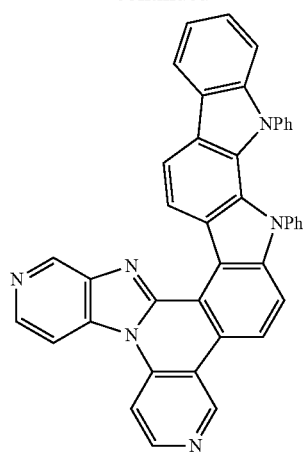
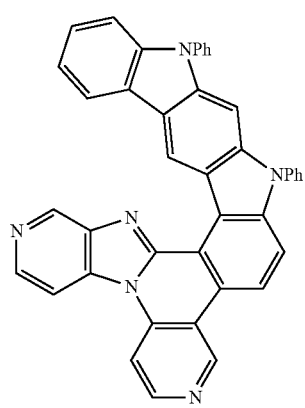
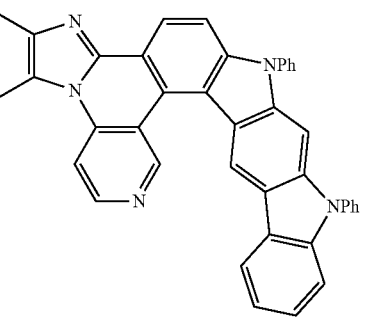
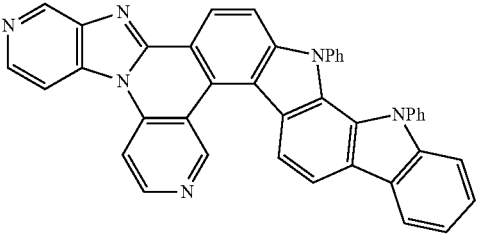
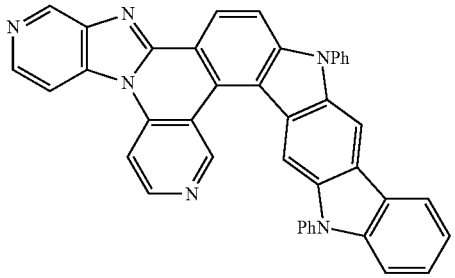

-continued
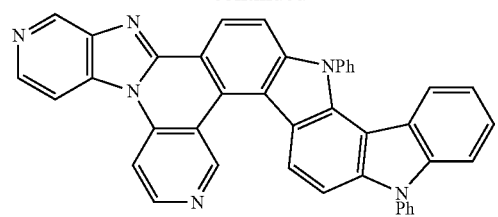
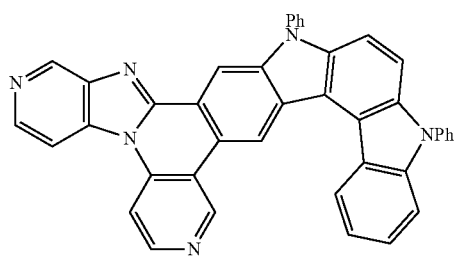
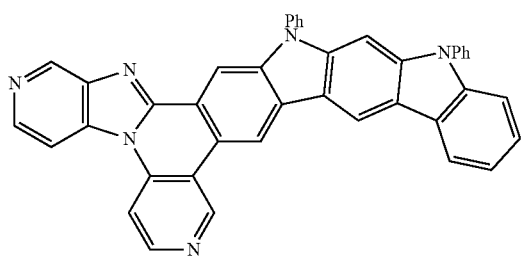
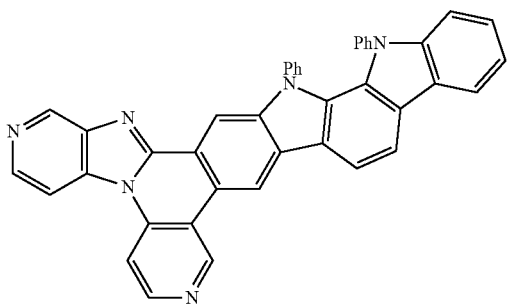
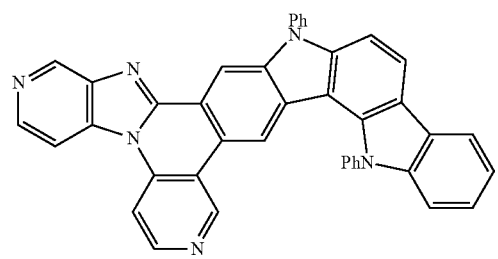
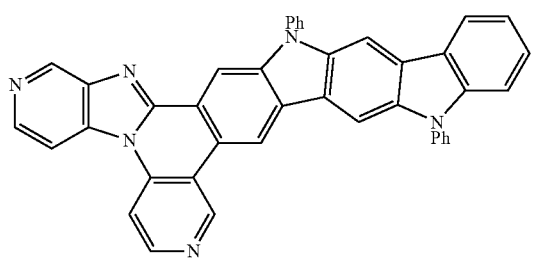
-continued
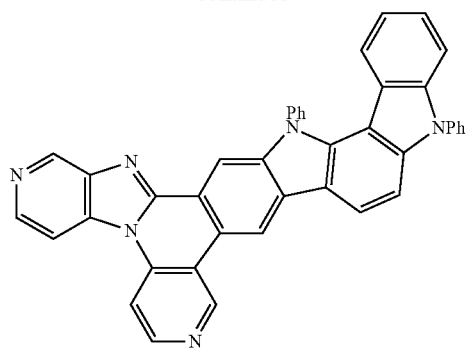
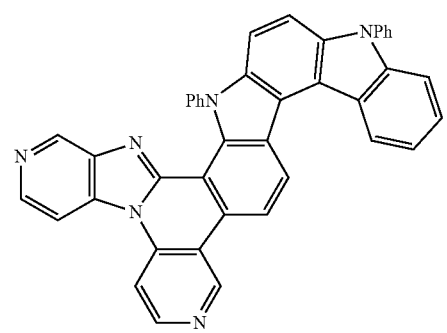
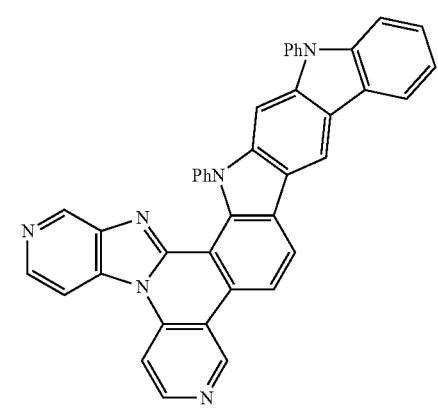

-continued
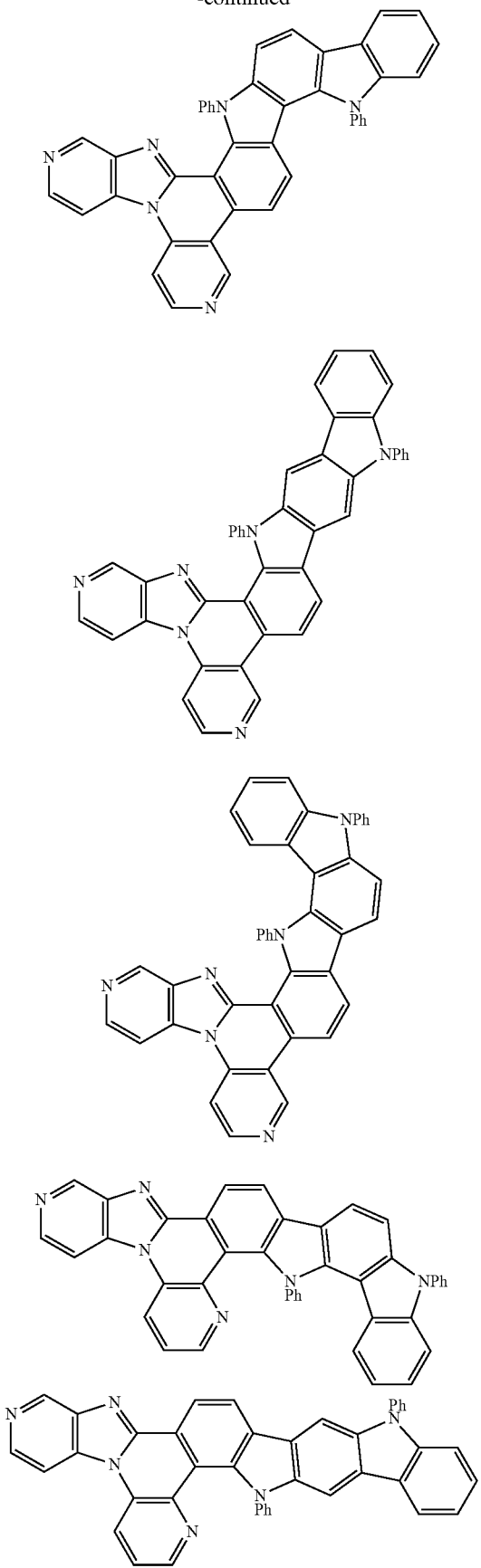
-continued
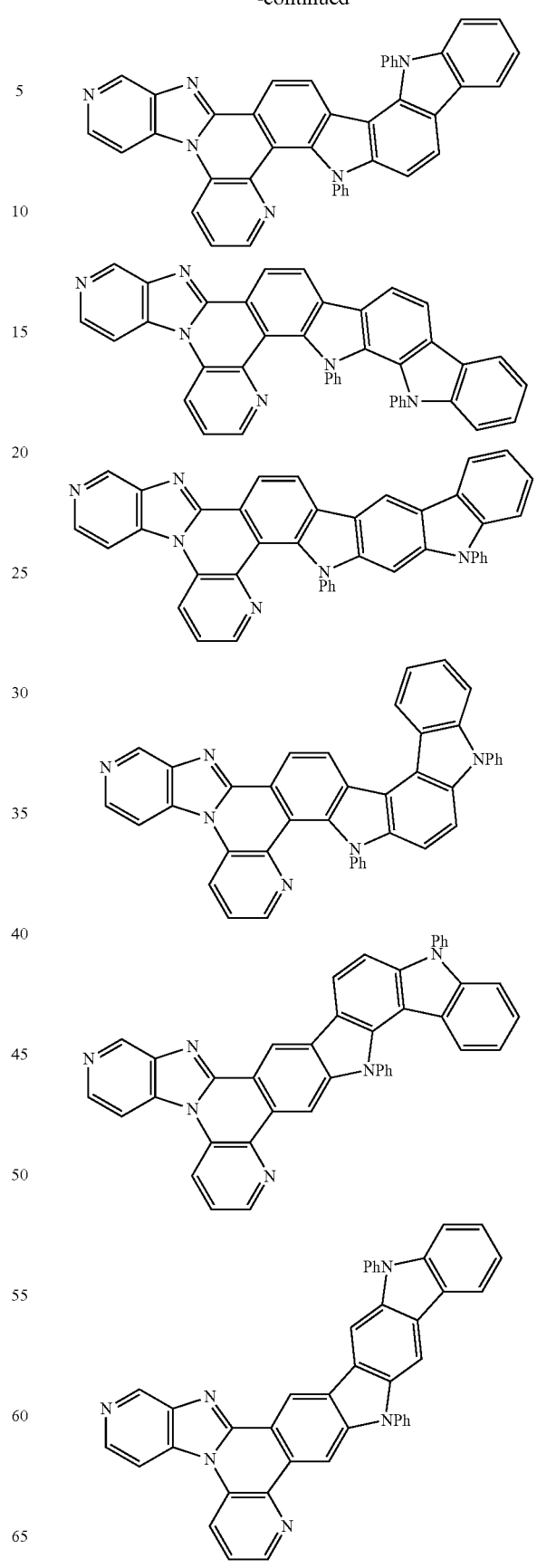

-continued
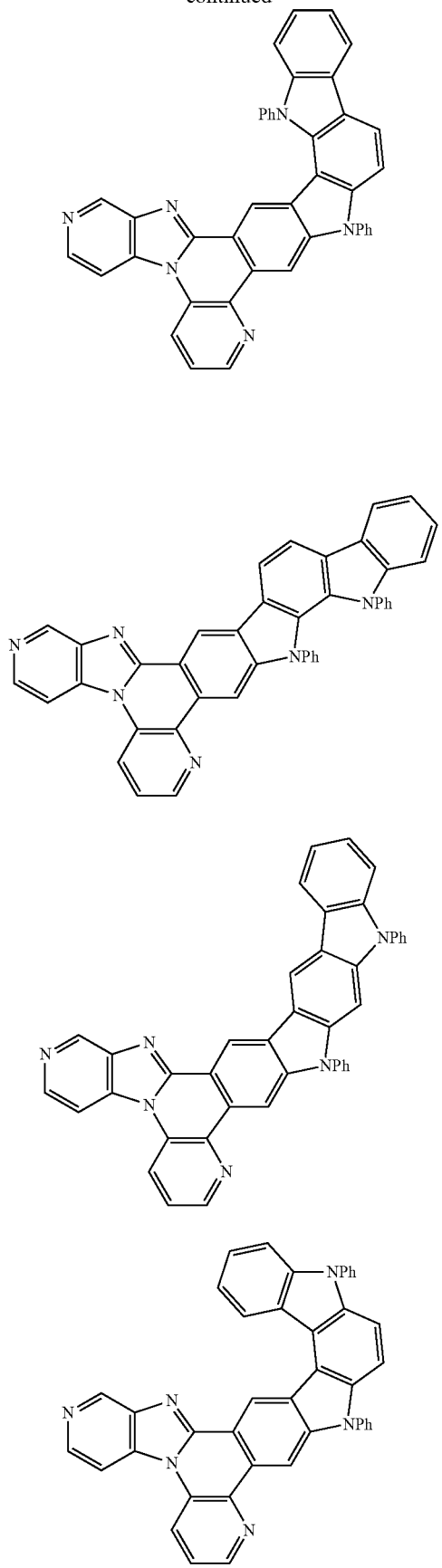
-continued
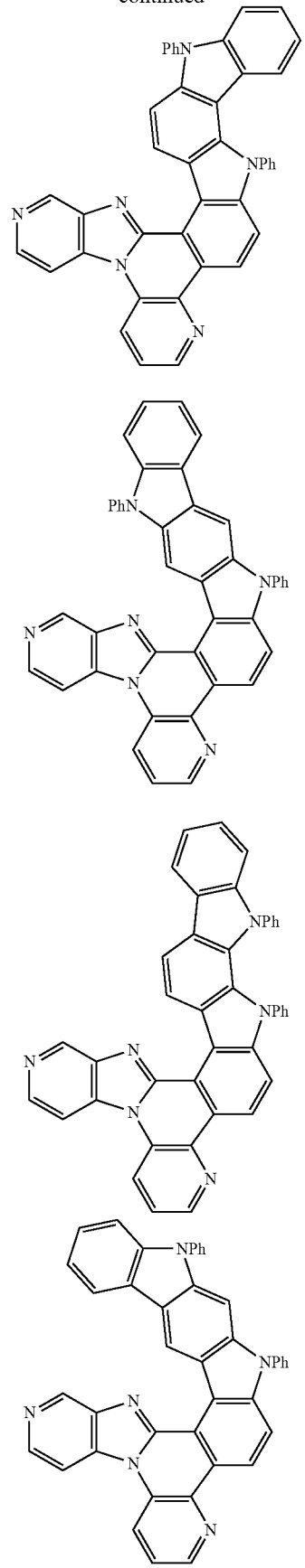

179
-continued
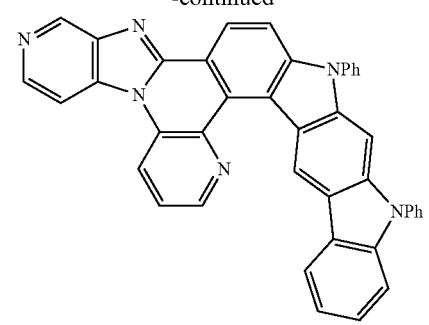
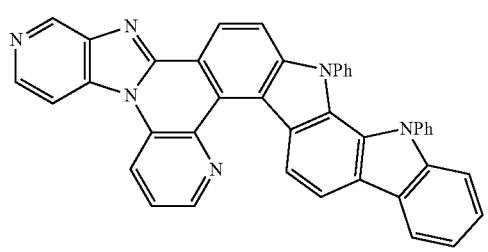
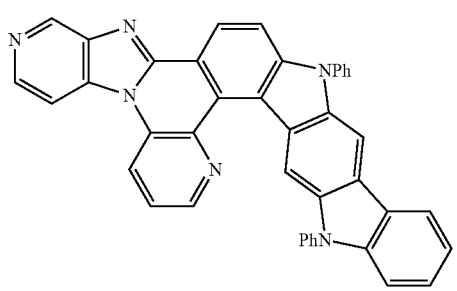
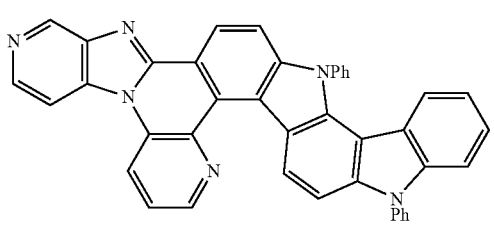
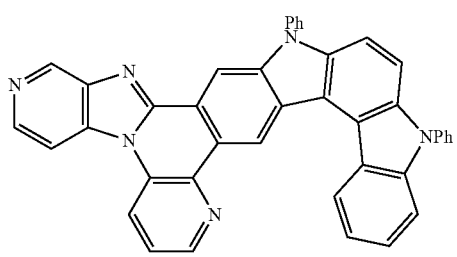
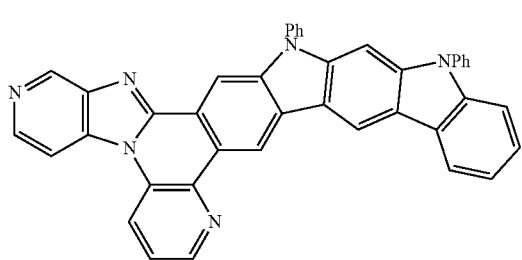
180
-continued
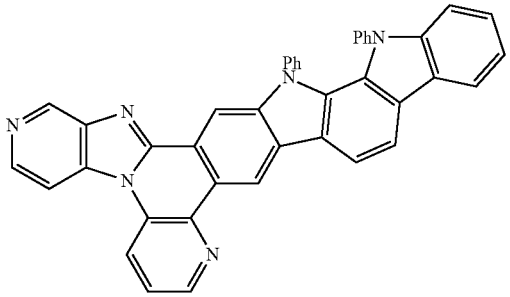
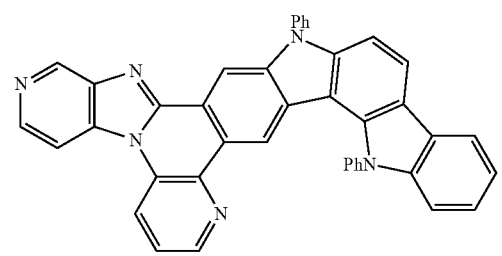
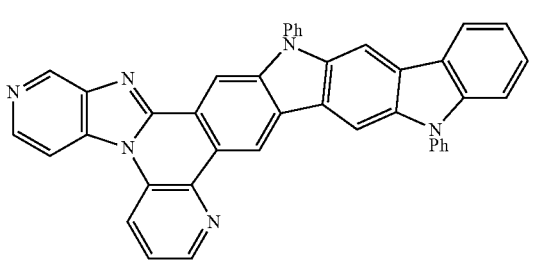
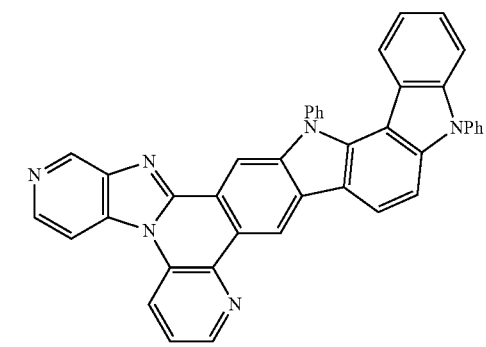

-continued
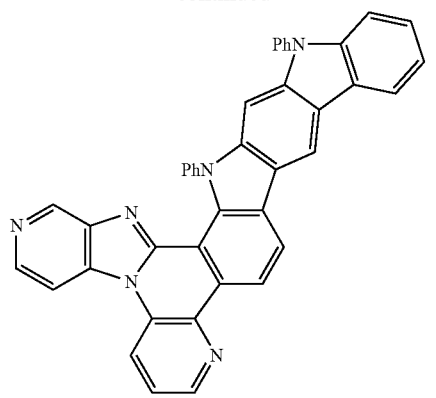
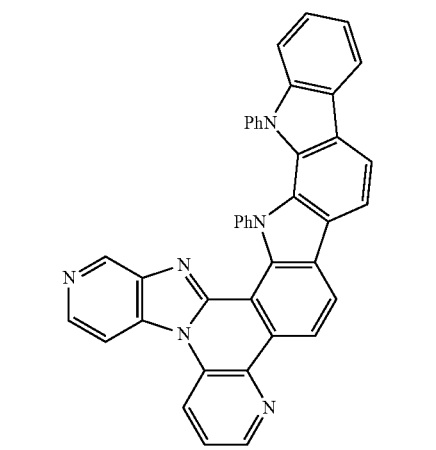
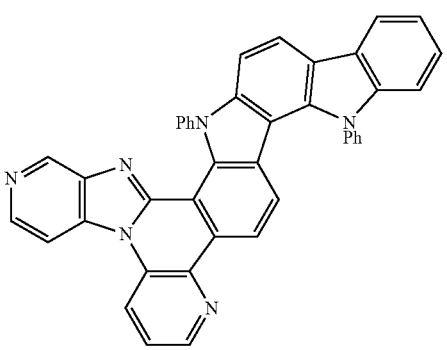
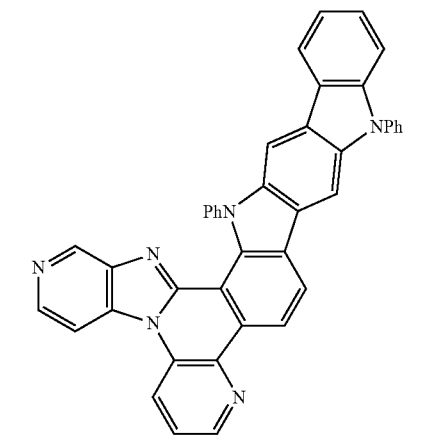
-continued
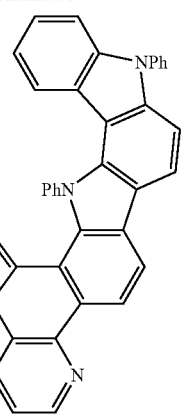
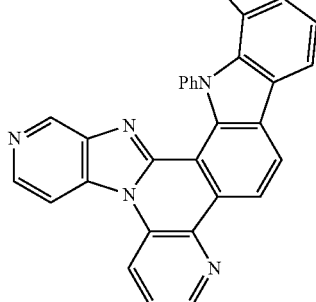
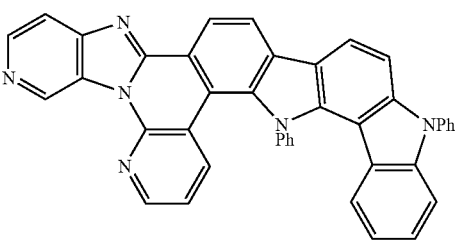
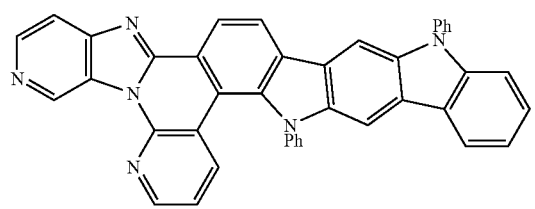
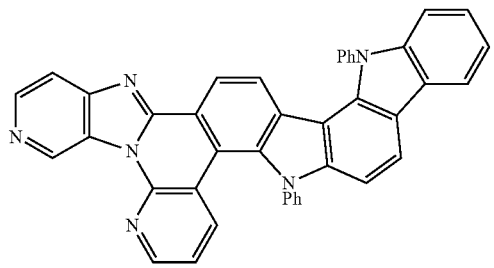
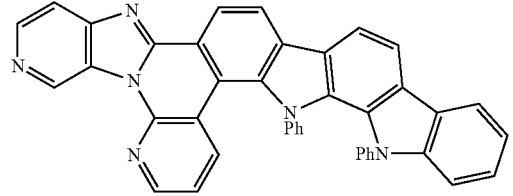
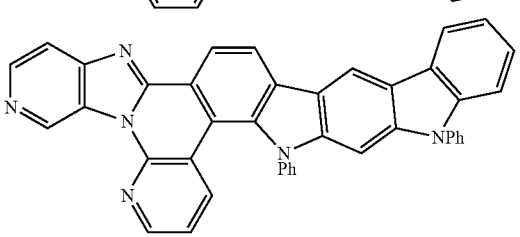

-continued
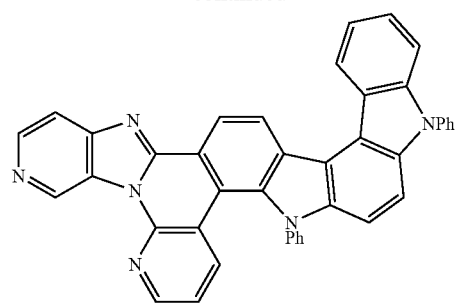
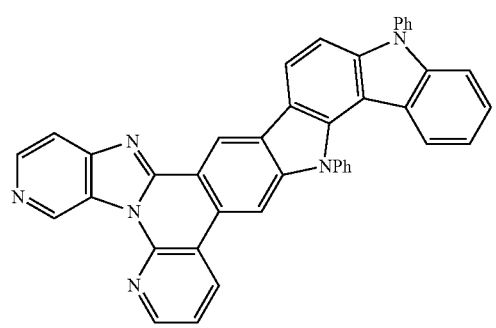
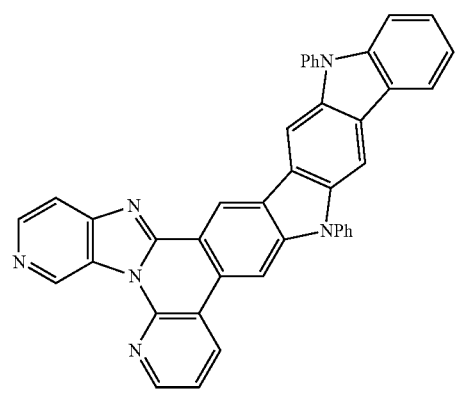
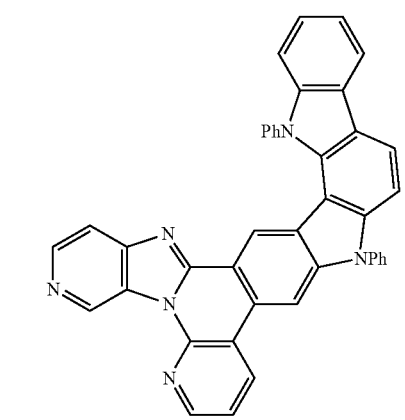
-continued
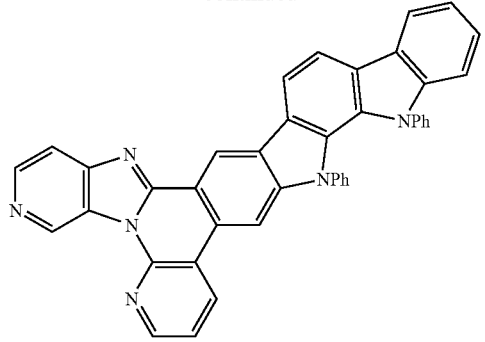
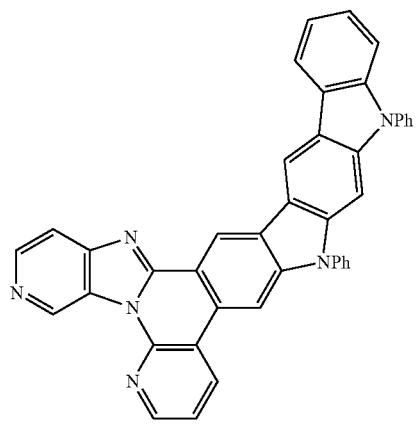
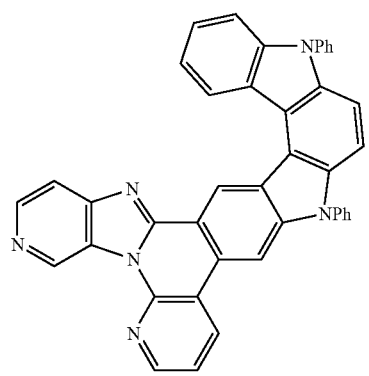
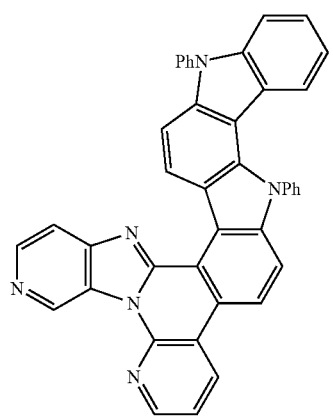

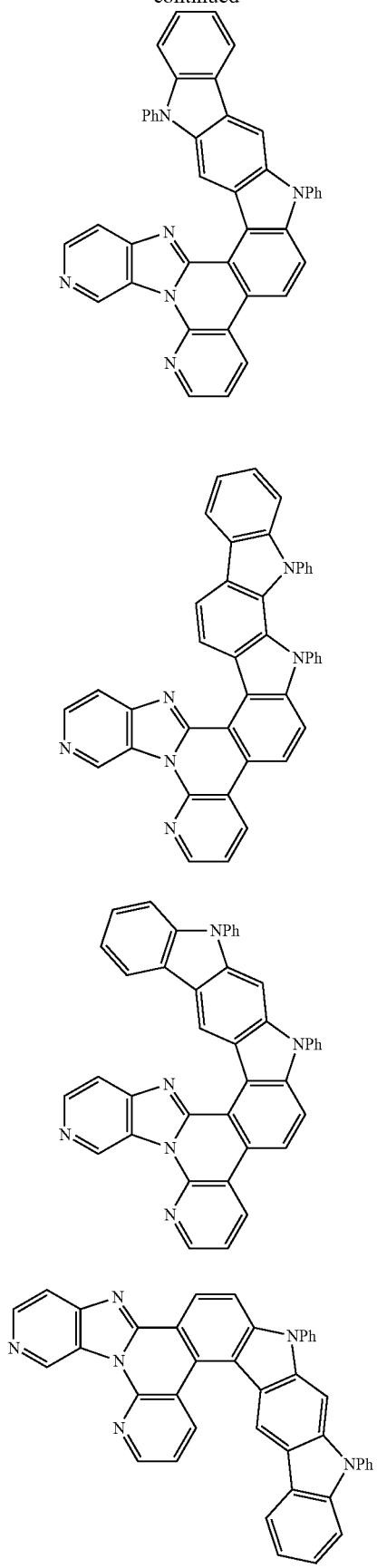
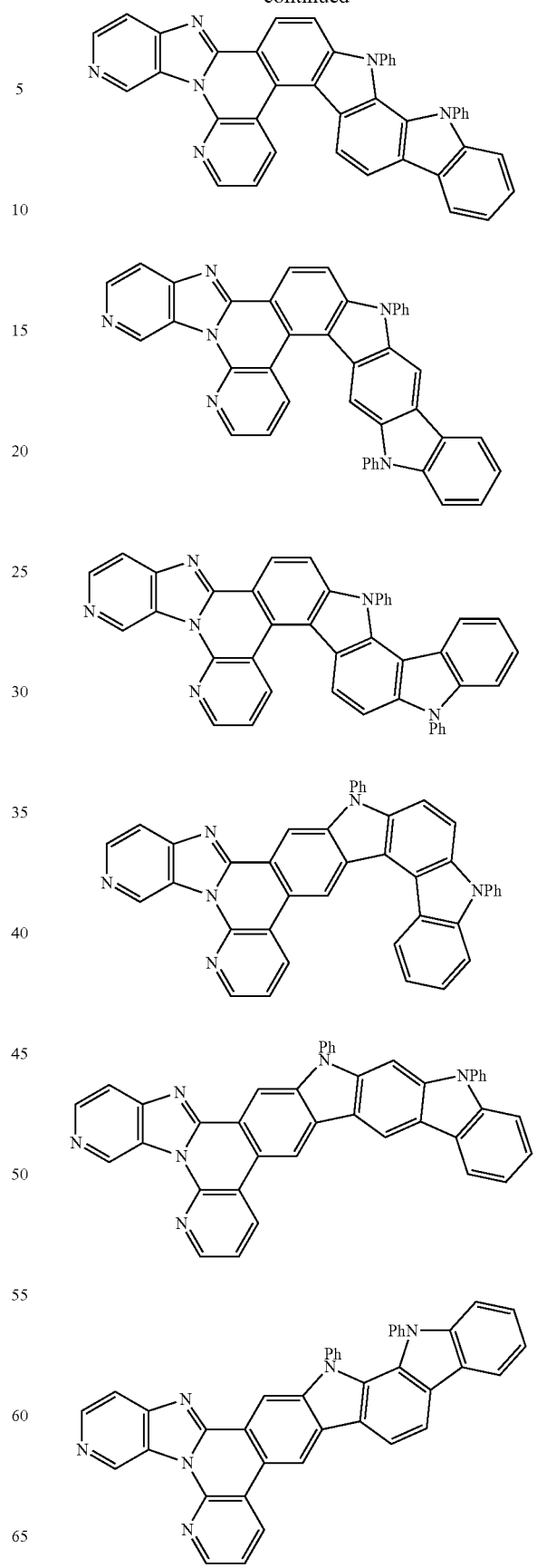

187
-continued
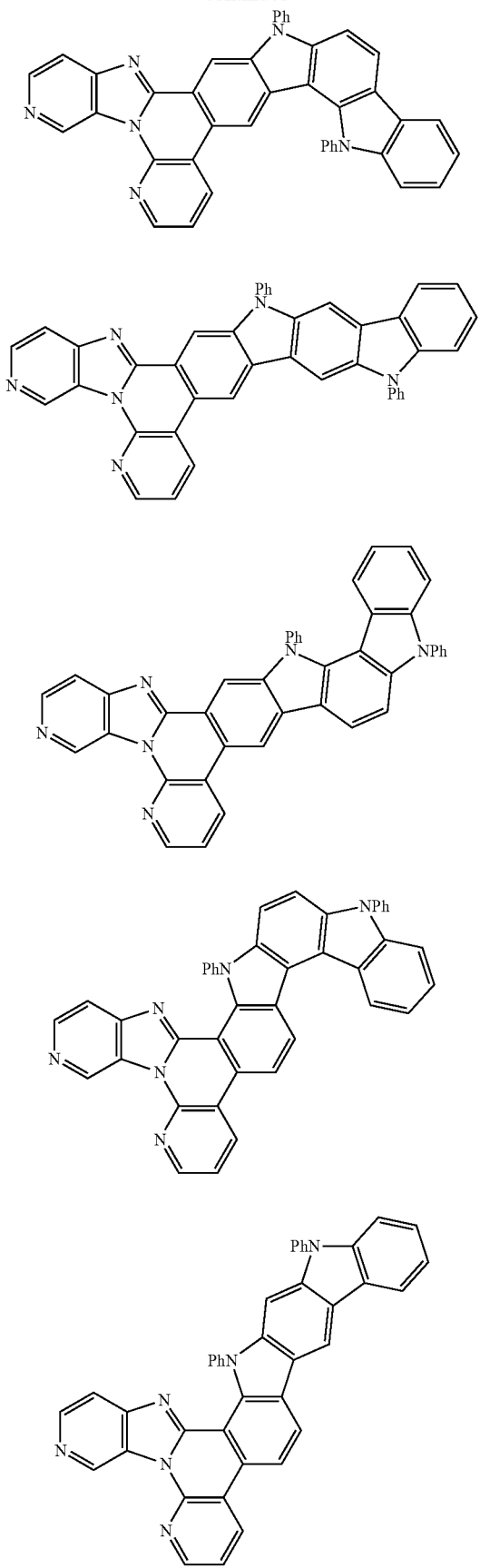
188
-continued
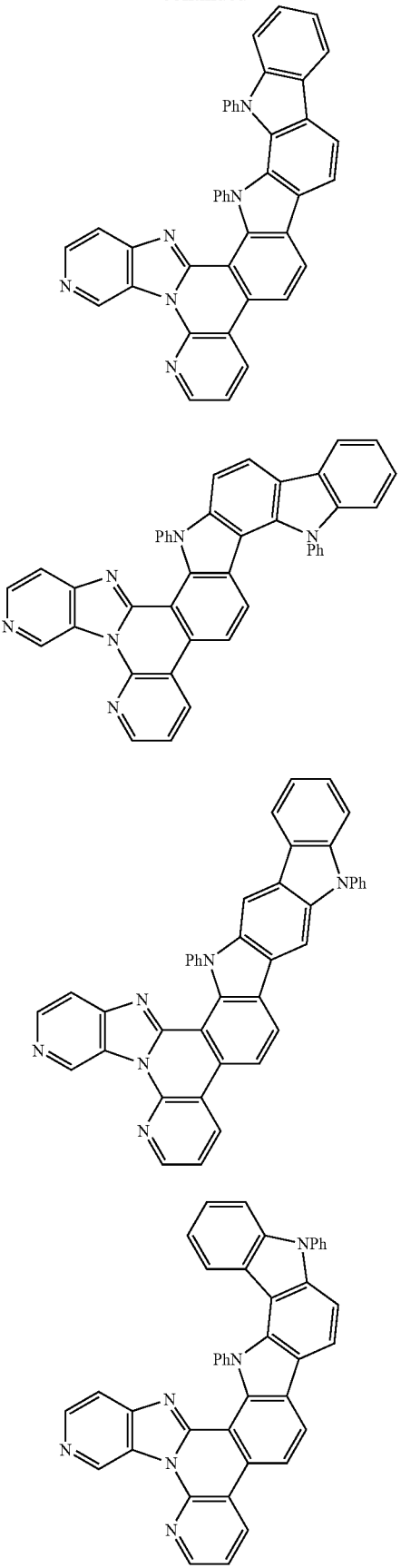

189
-continued
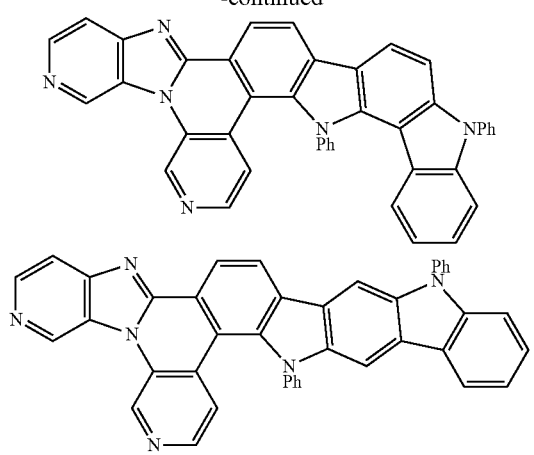
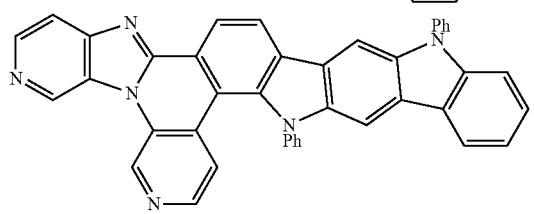
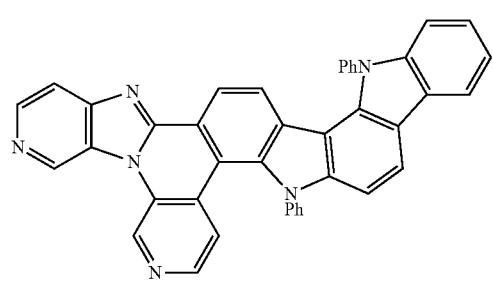
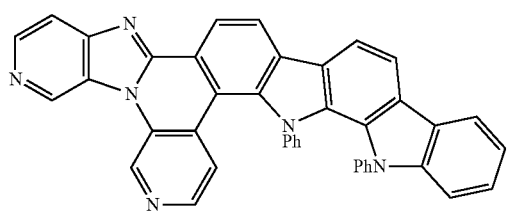
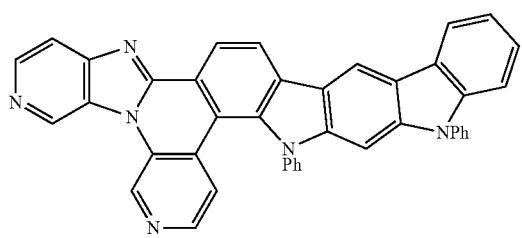
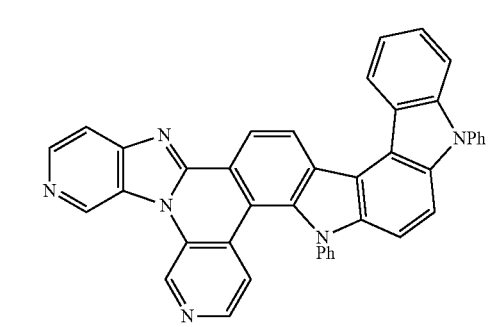
190
-continued
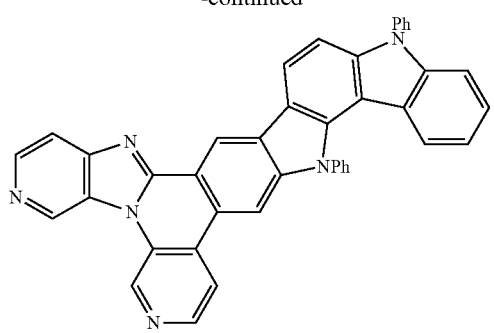
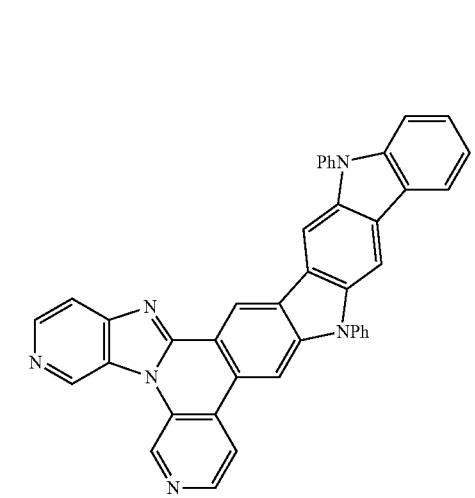
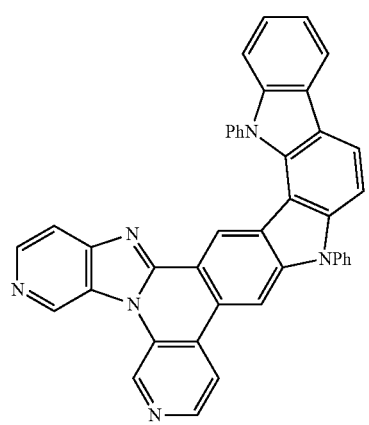
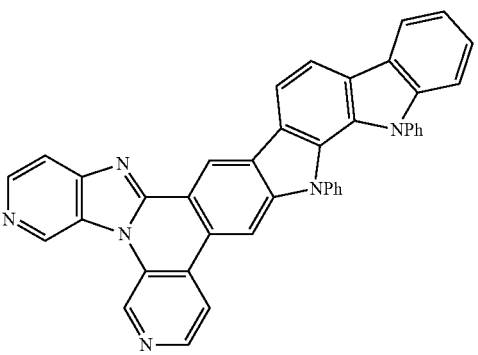

-continued
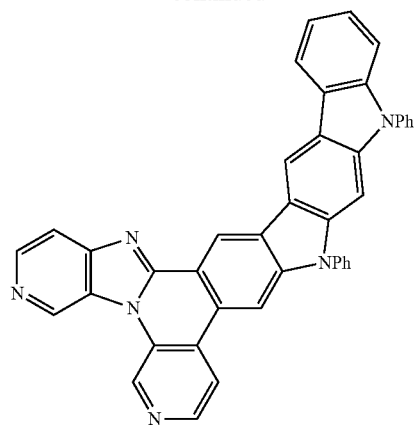
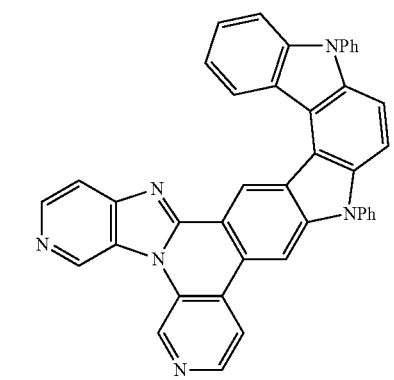
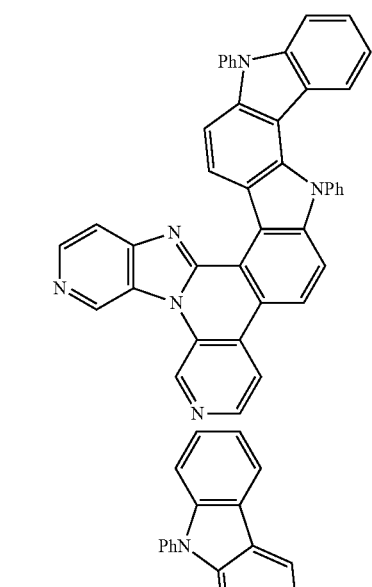
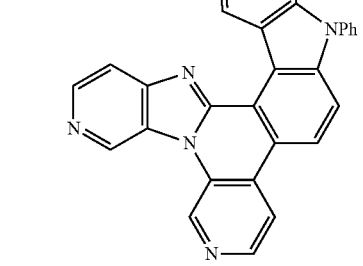
-continued
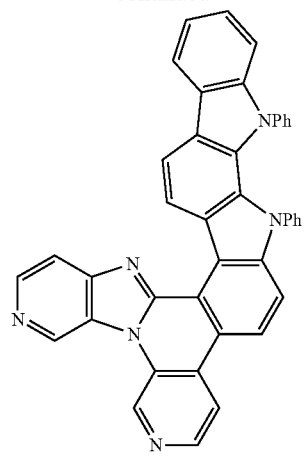
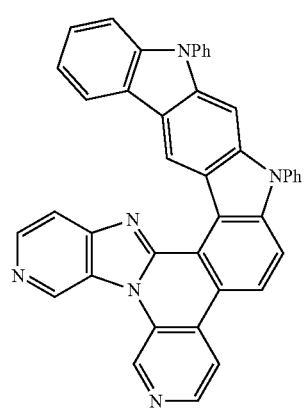
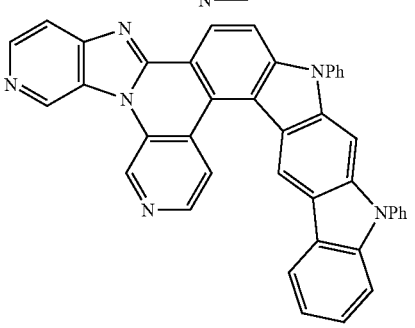
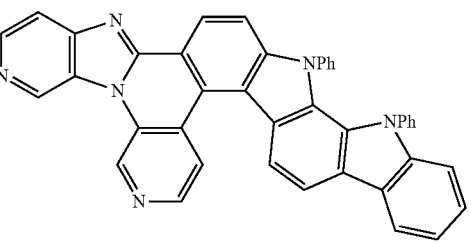
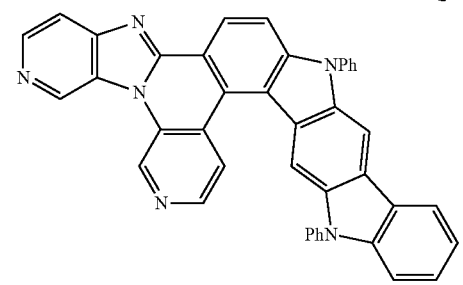

193
-continued
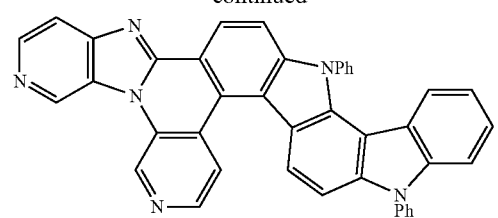
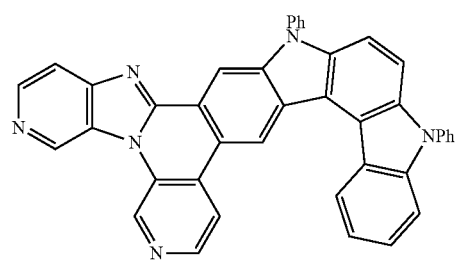
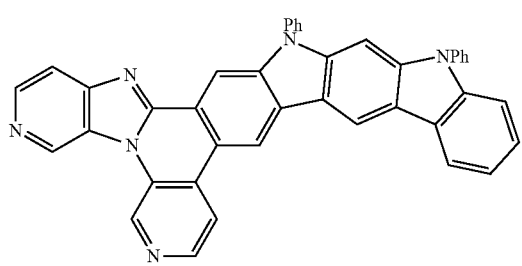
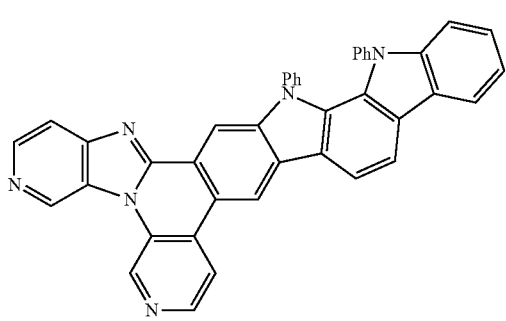
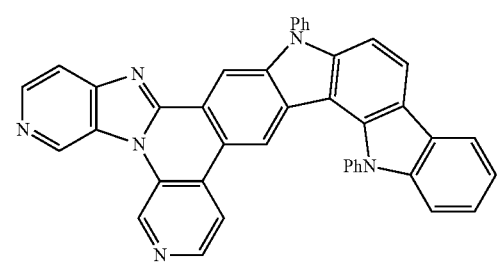
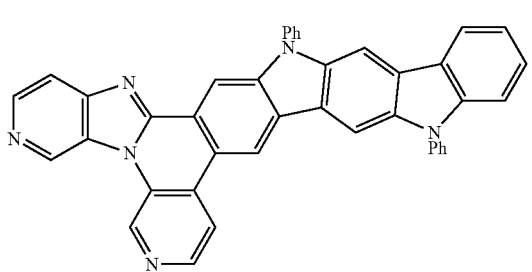
194
-continued
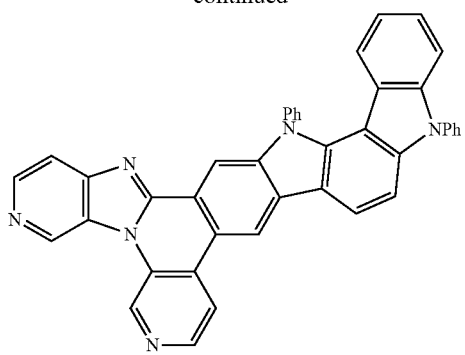
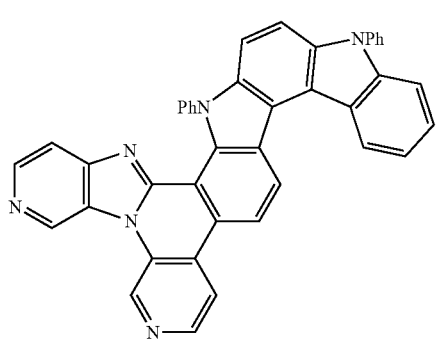
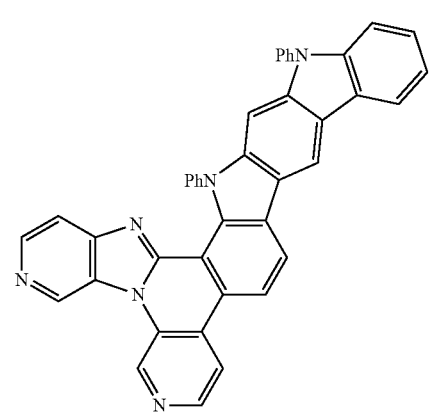
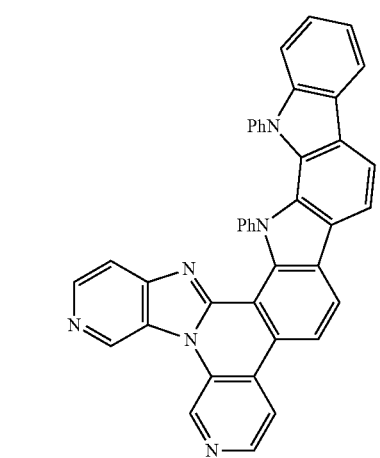

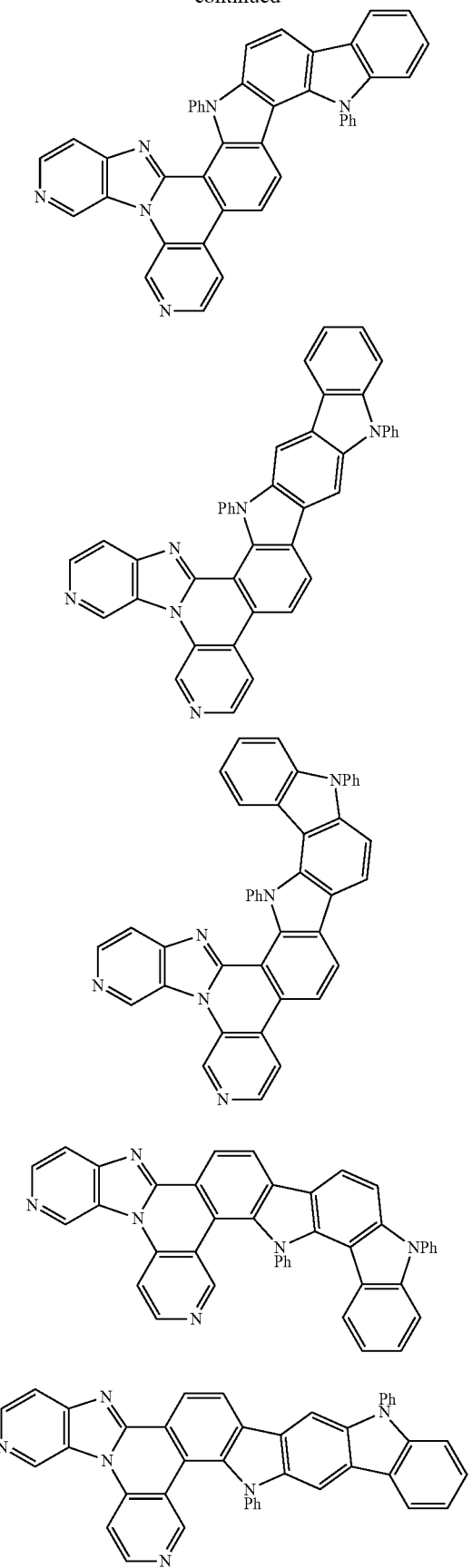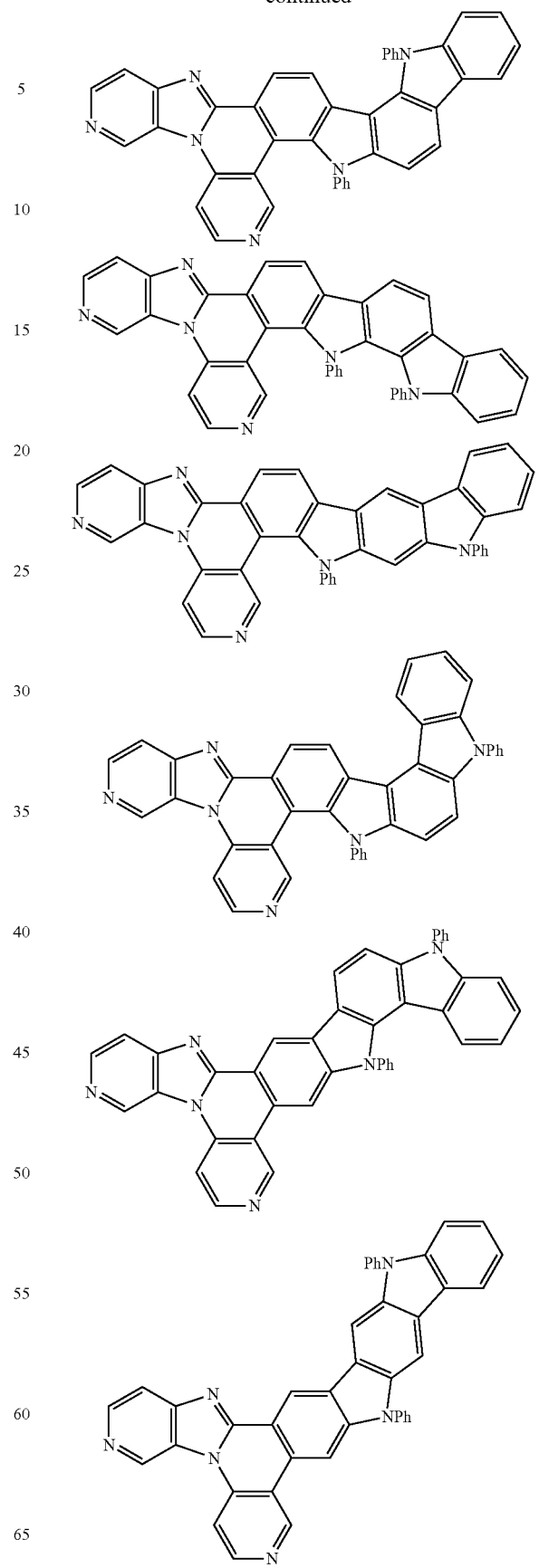

-continued
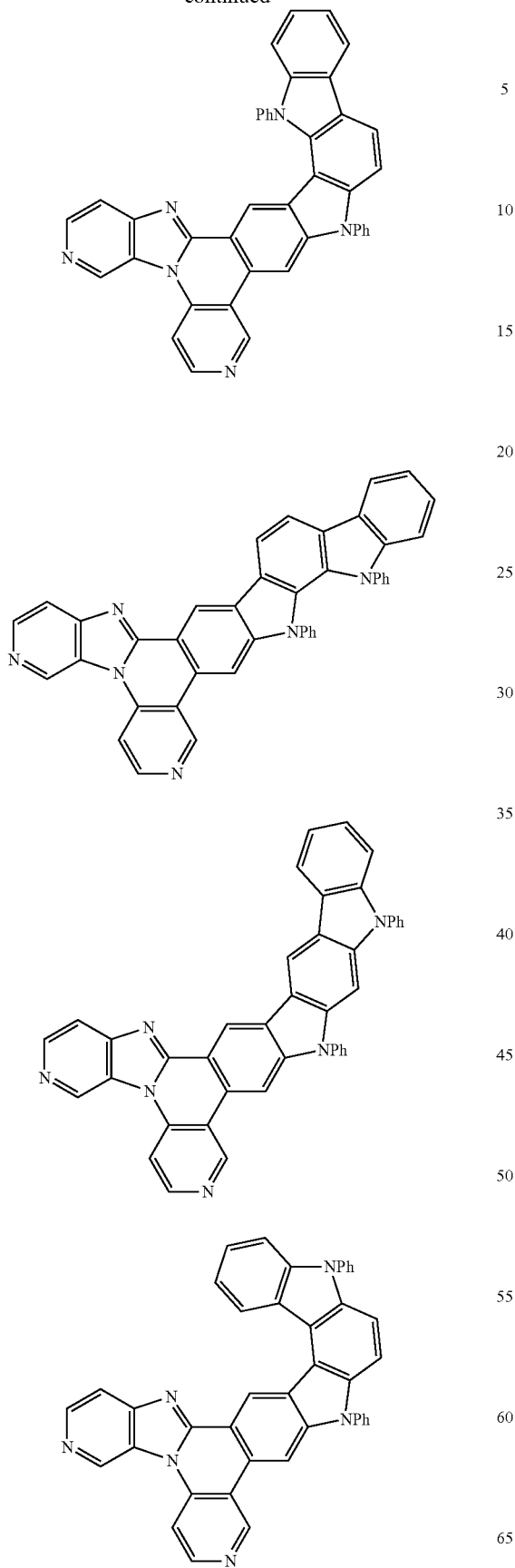
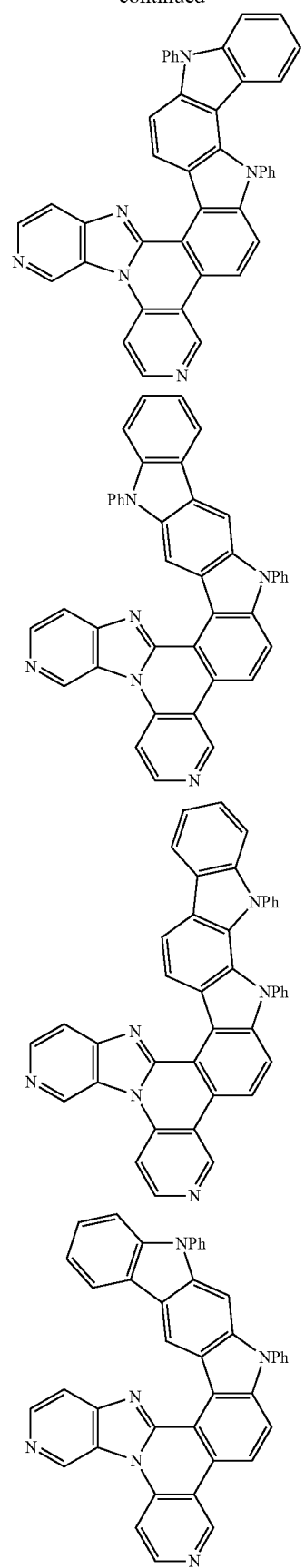

199
-continued
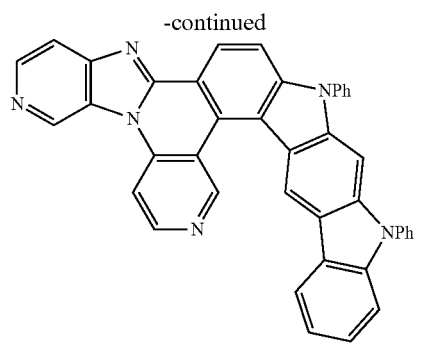
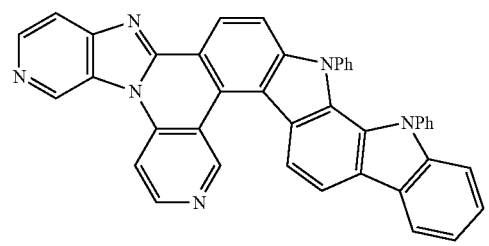
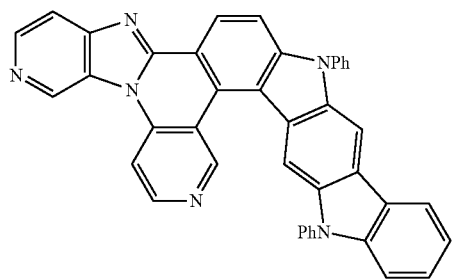
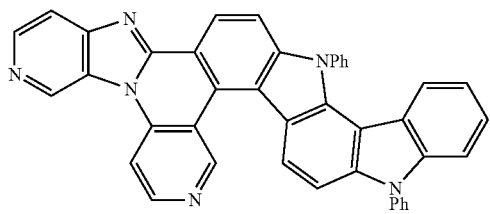
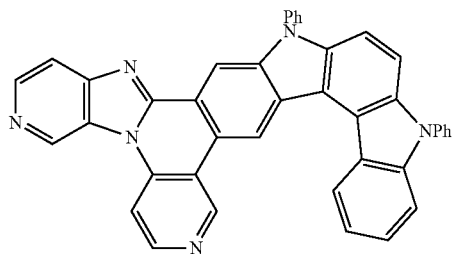
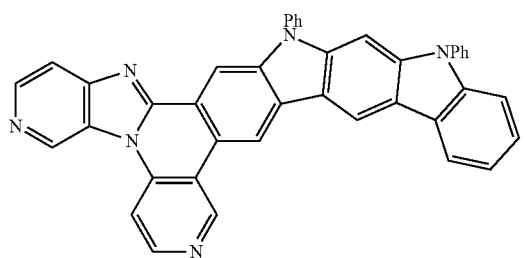
200
-continued
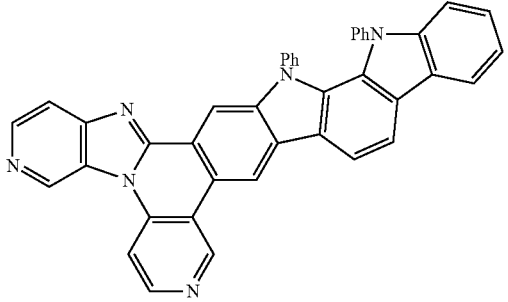
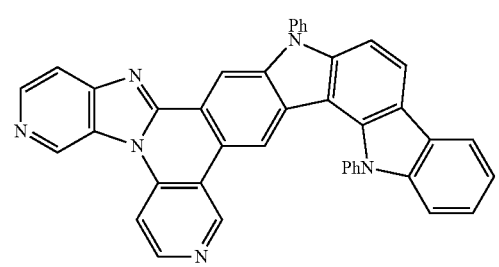
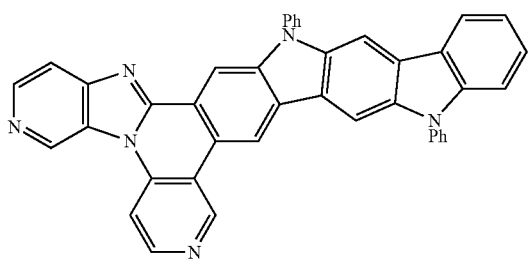
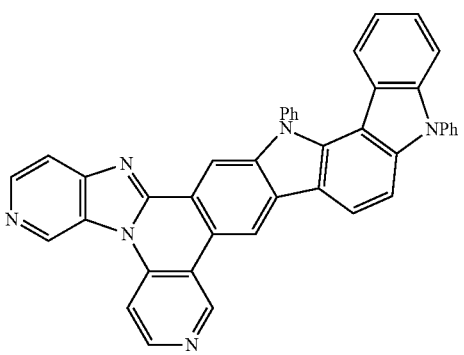
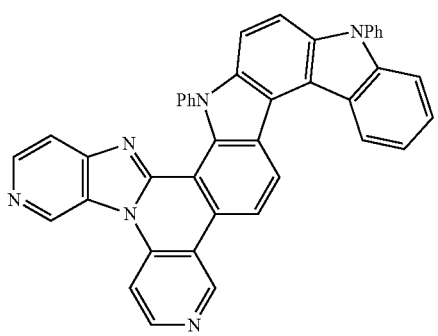

-continued
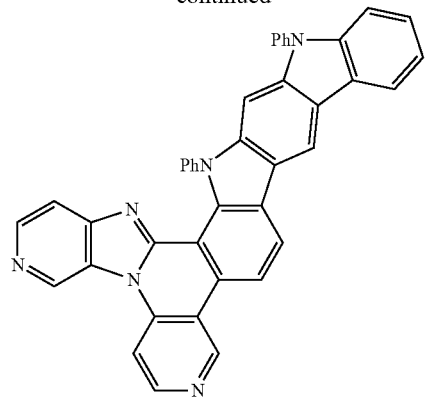
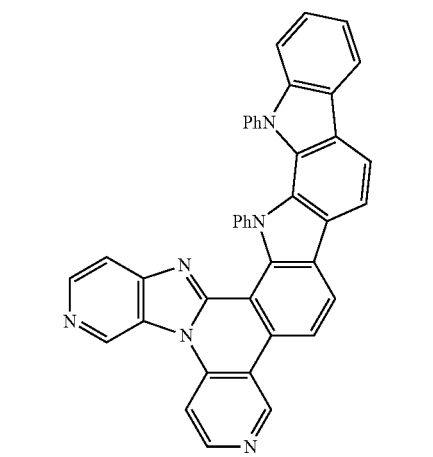
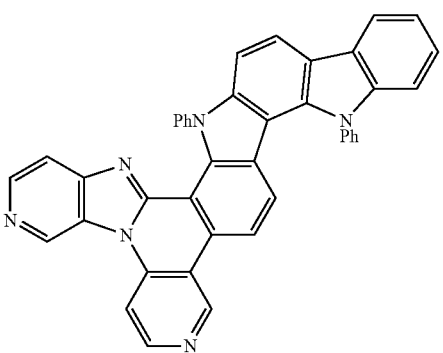
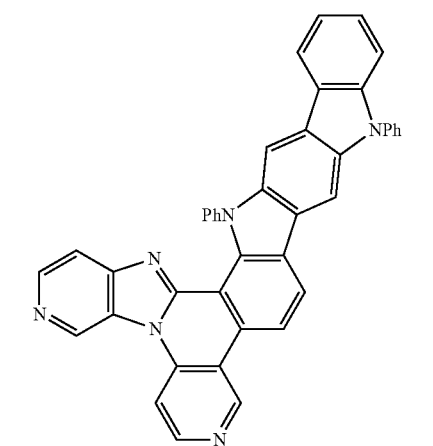
-continued
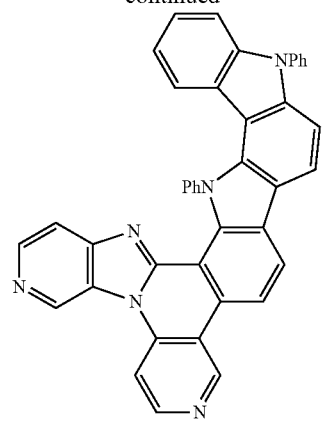
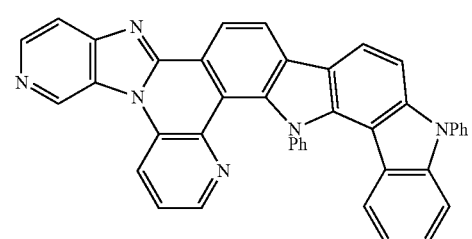
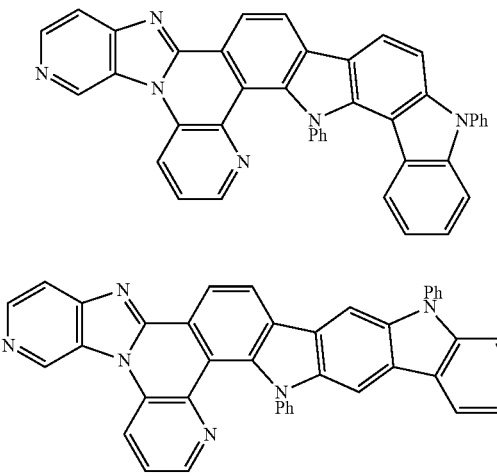
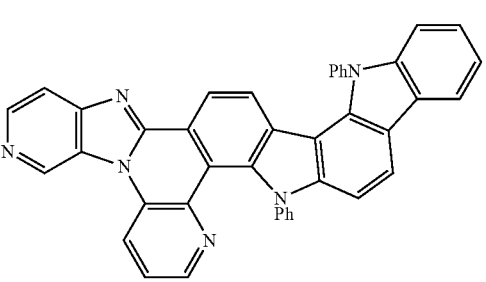
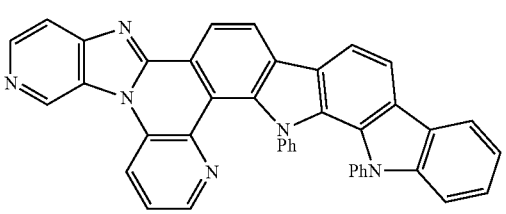
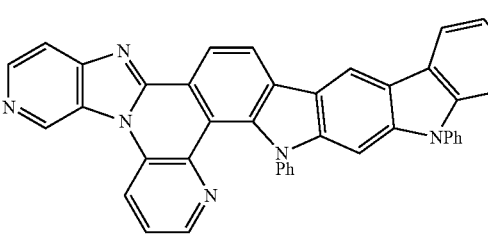

203
-continued
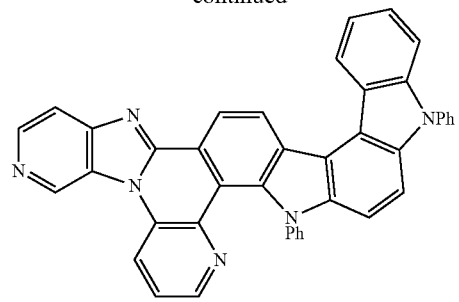
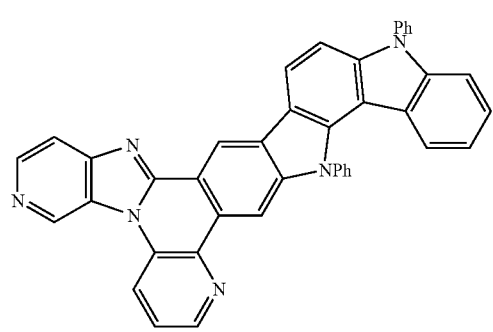
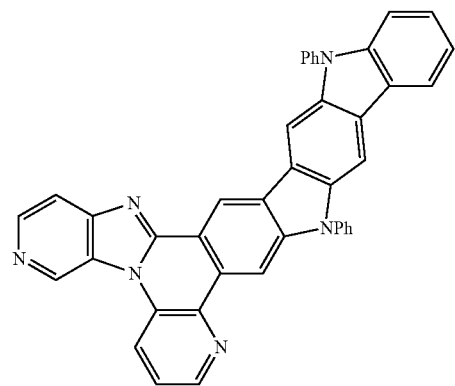
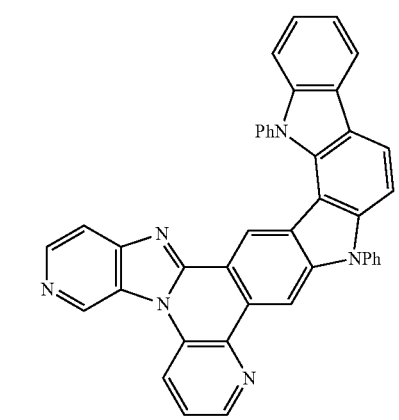
204
-continued
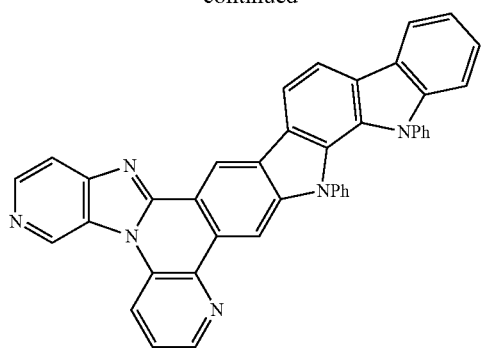
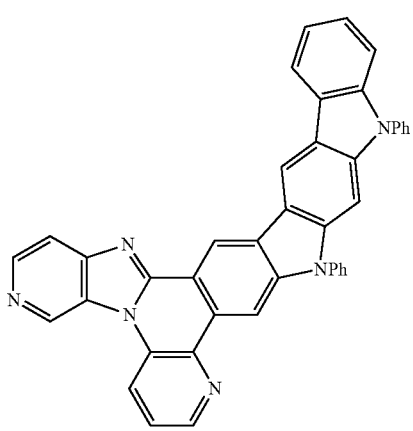
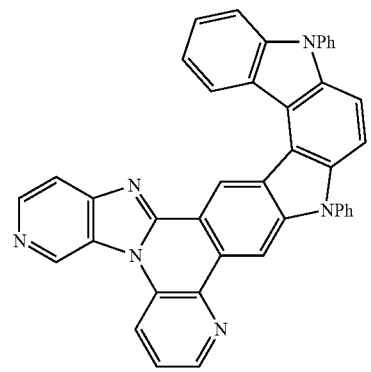
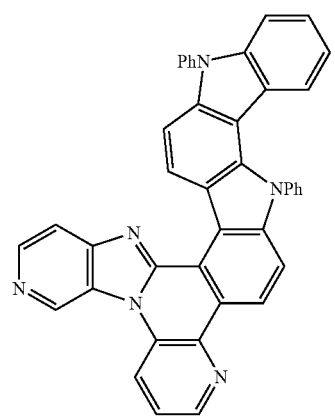

205
-continued
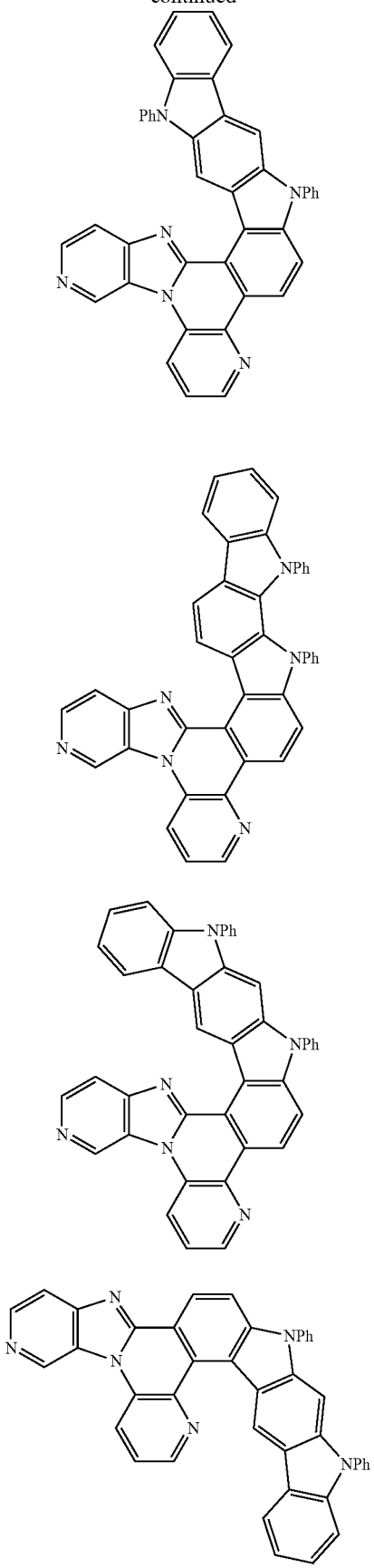
206
-continued
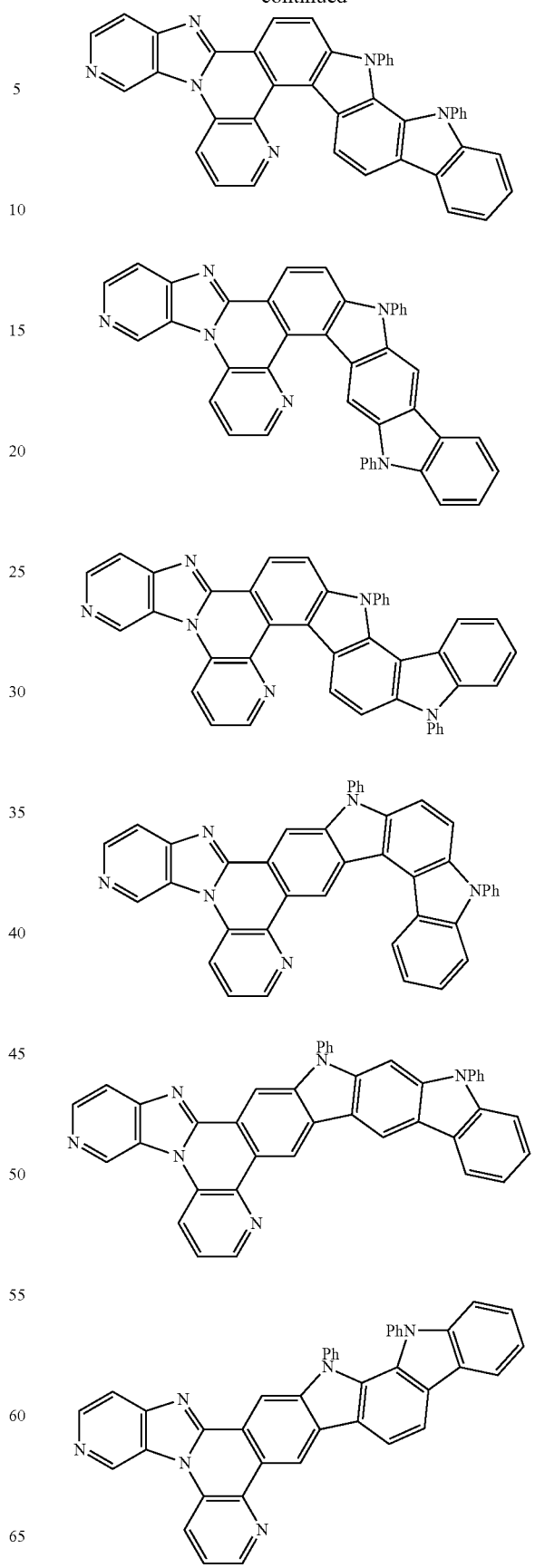

-continued
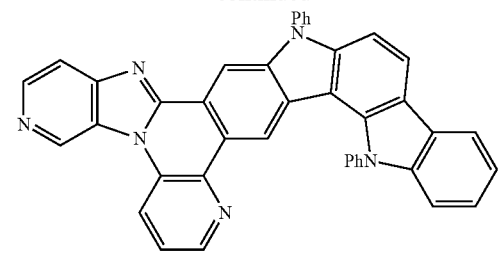
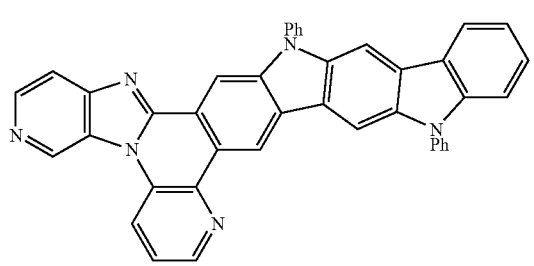
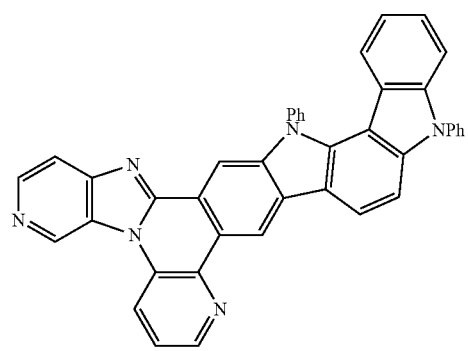
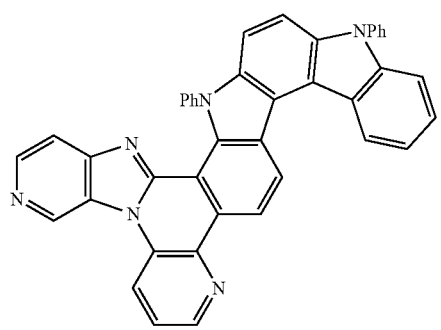
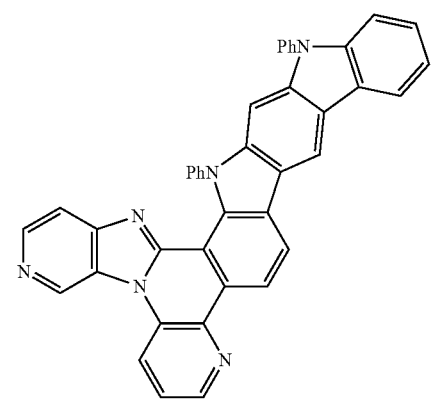
-continued
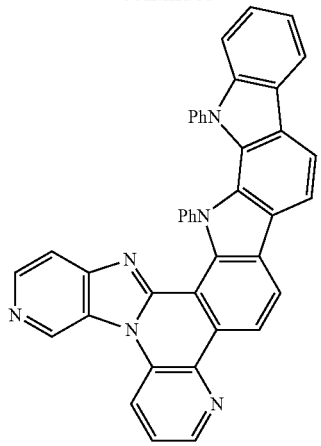
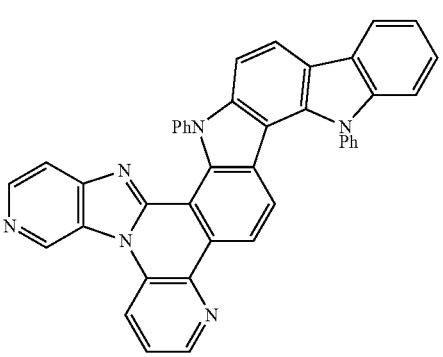
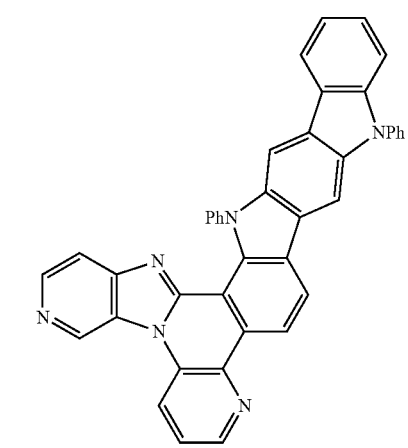
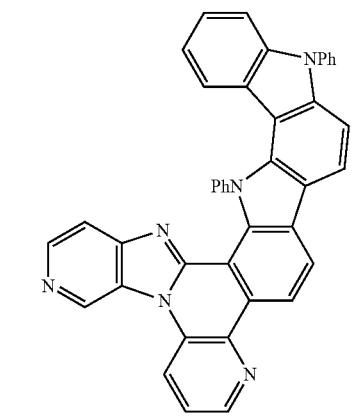

-continued
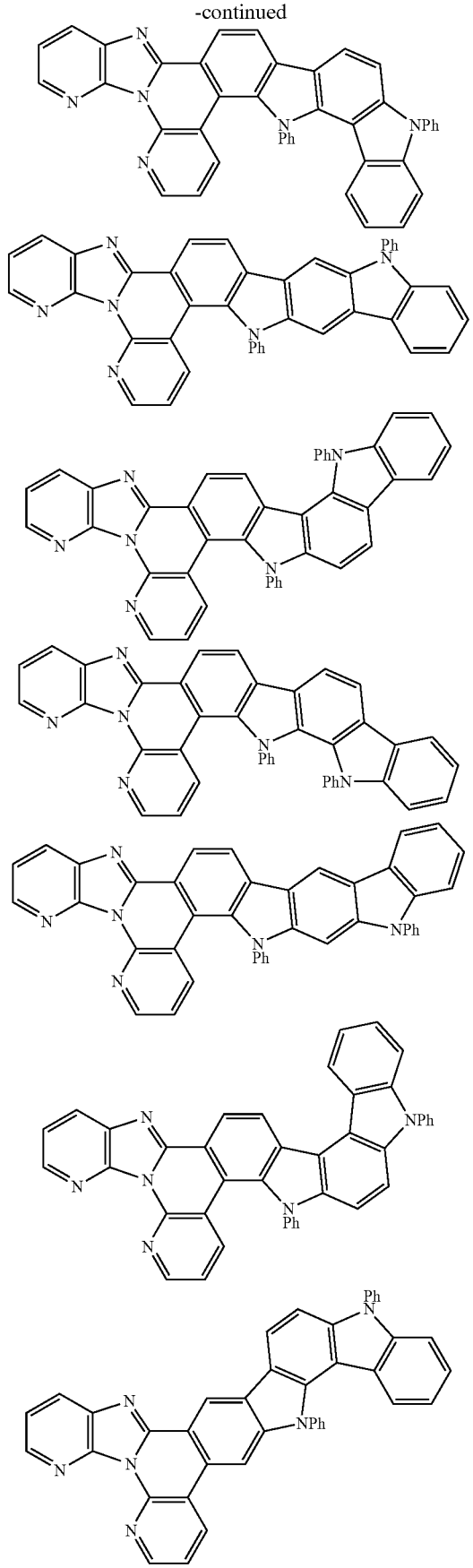
-continued
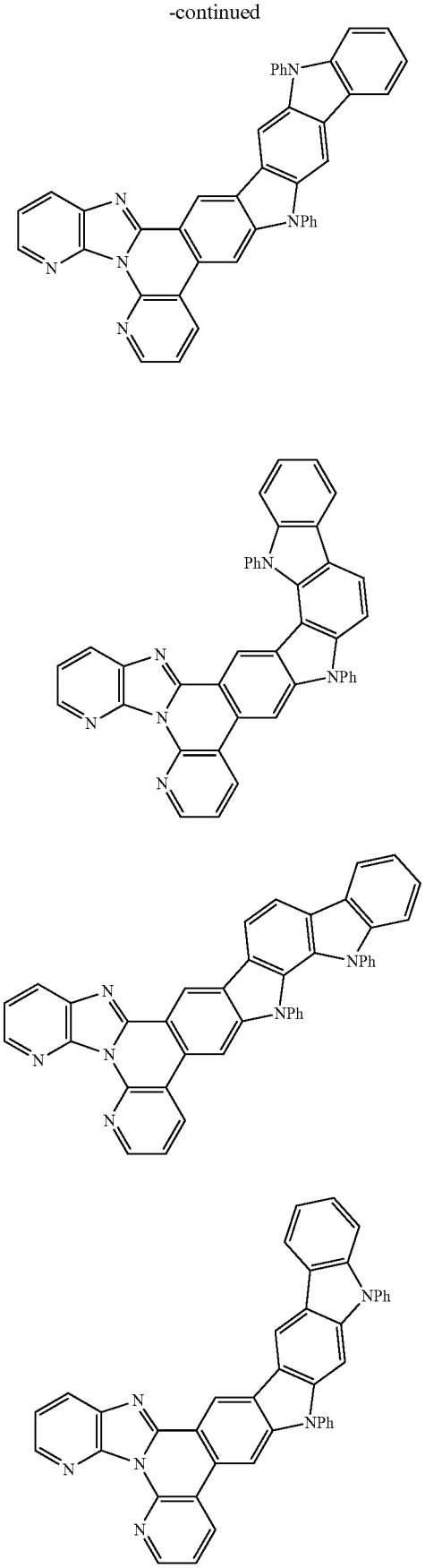

211
-continued
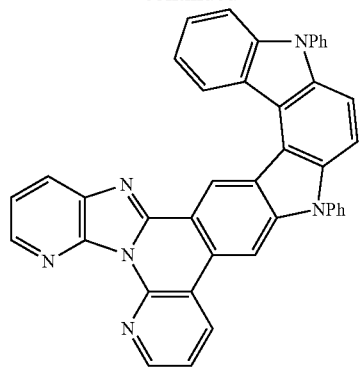
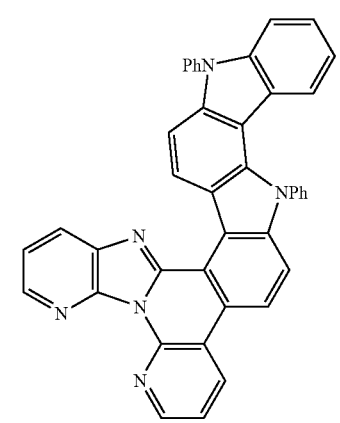
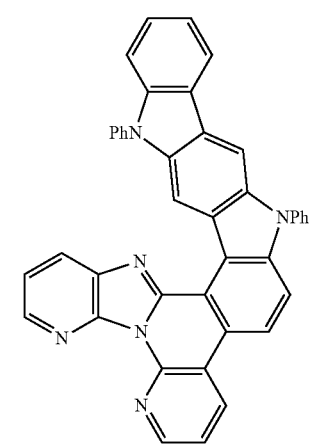
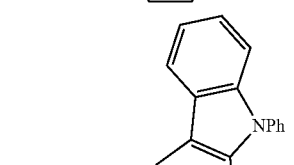
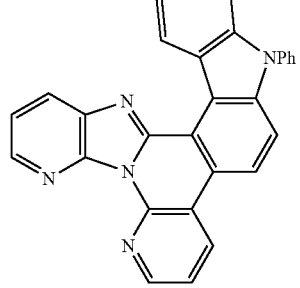
212
-continued
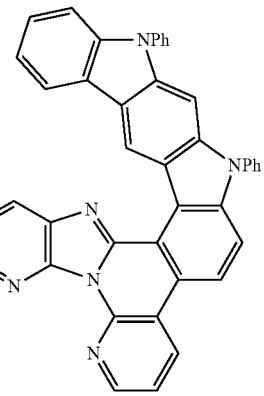
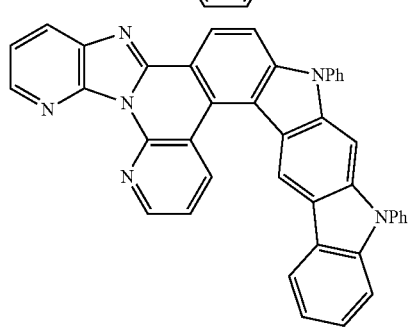
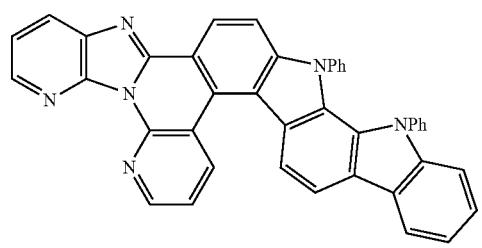
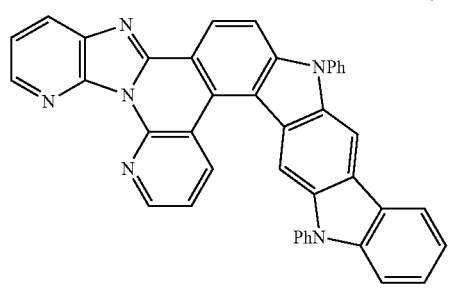
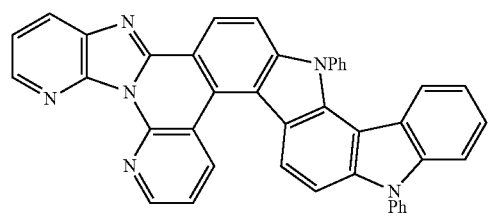
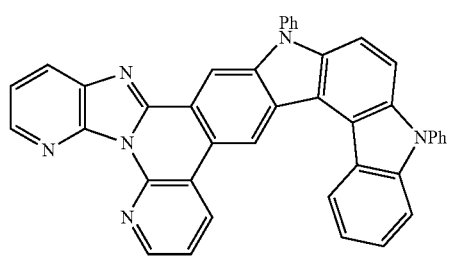

-continued
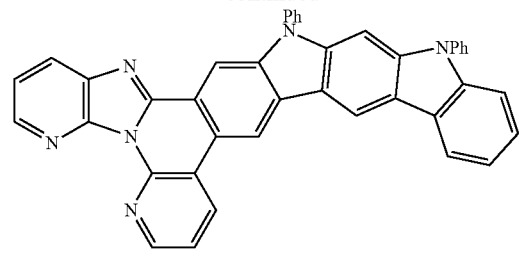
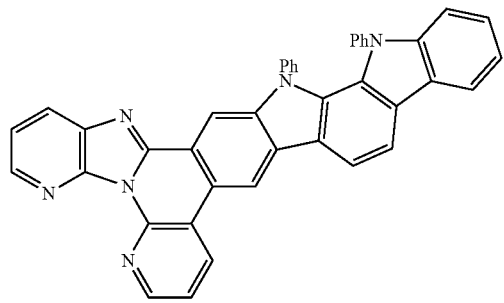
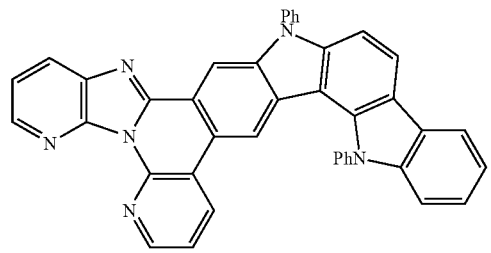
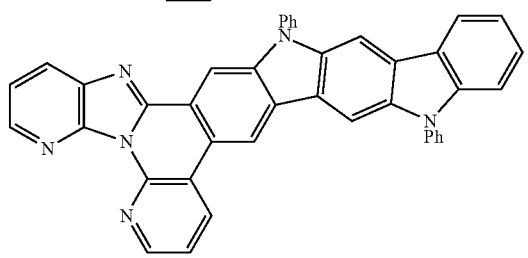
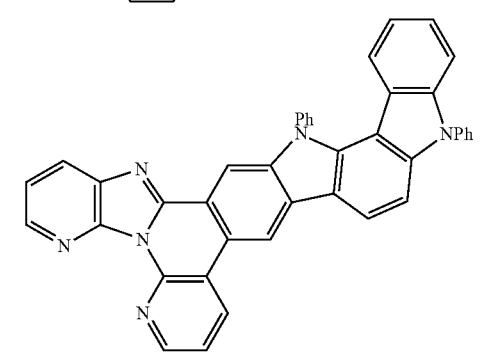
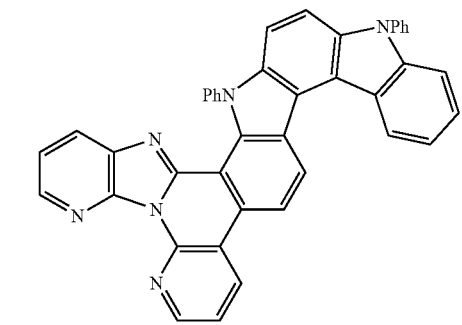
-continued
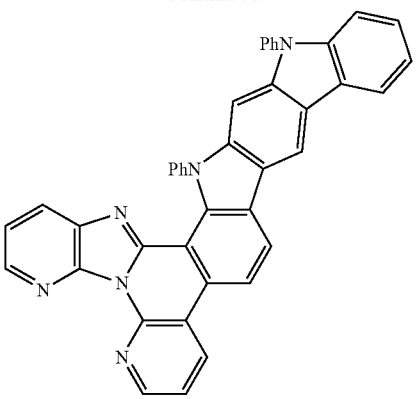
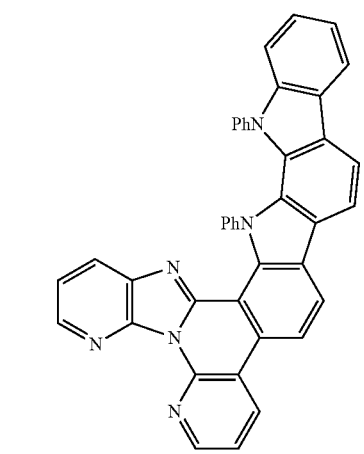
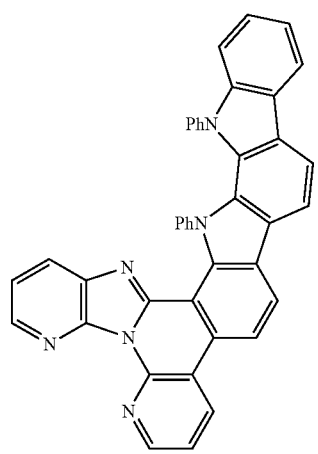
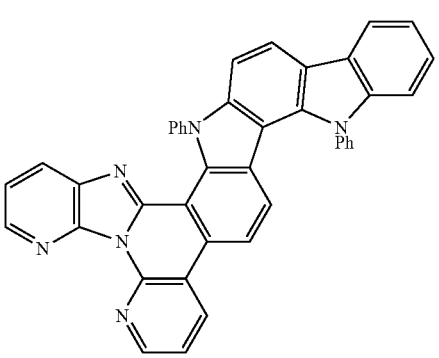
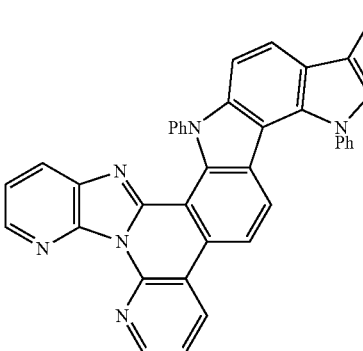

215
-continued
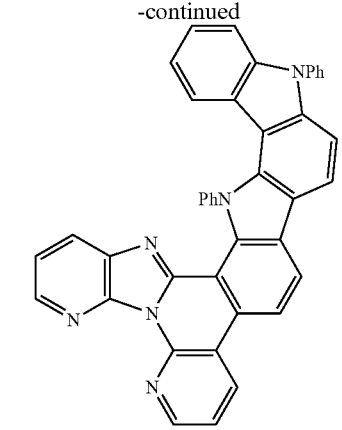
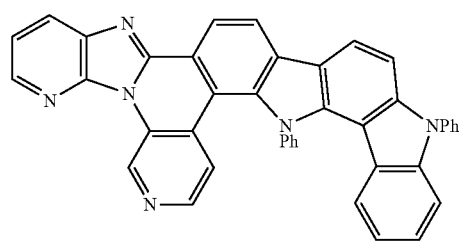
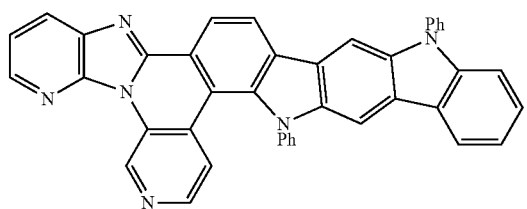
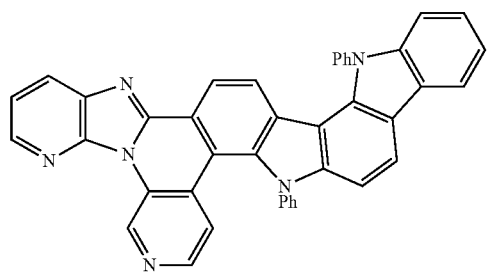
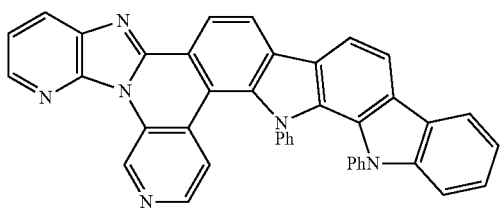
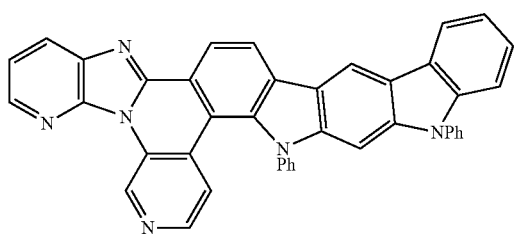
216
-continued
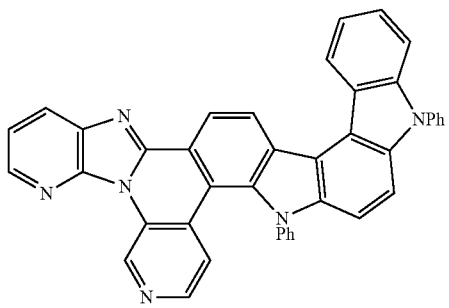
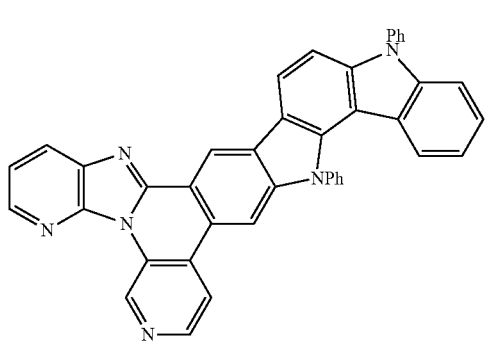
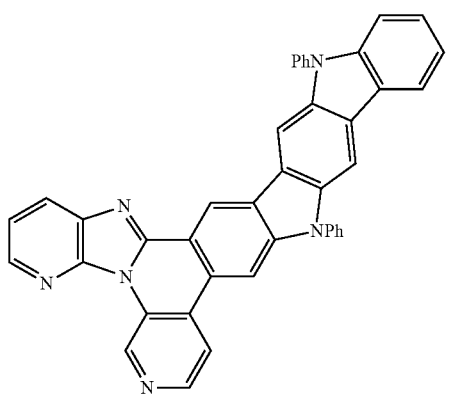
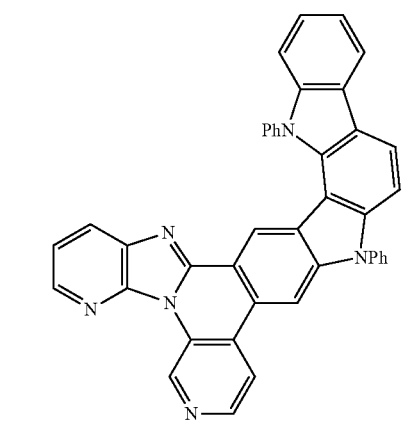

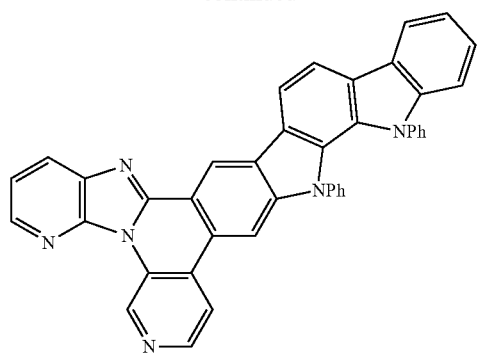
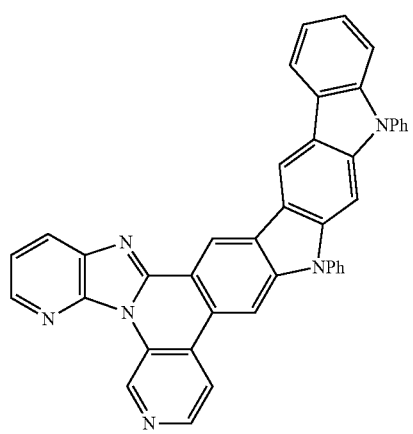
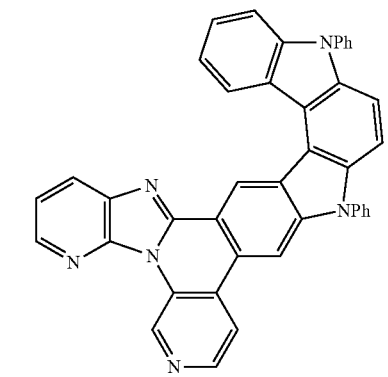
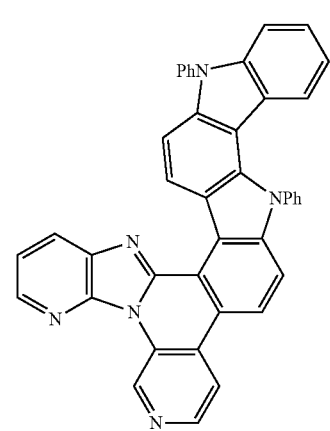
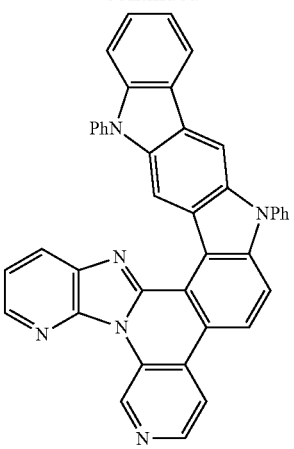
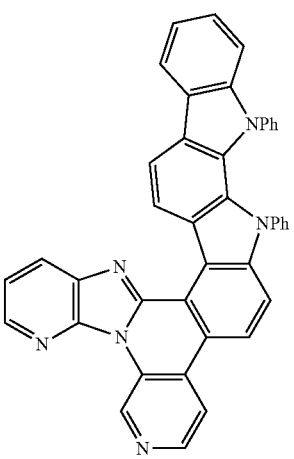
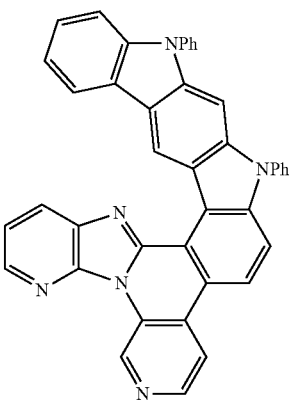
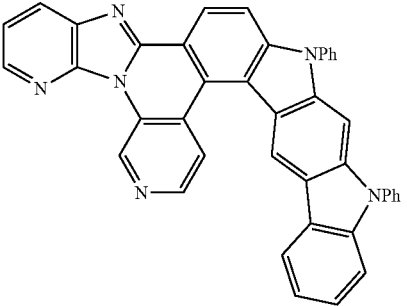

219
-continued
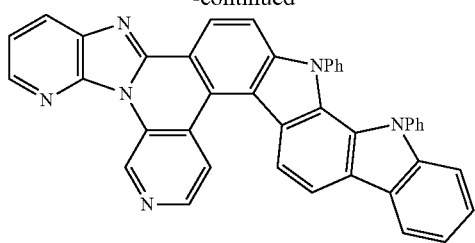
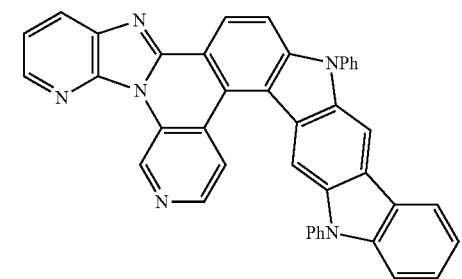
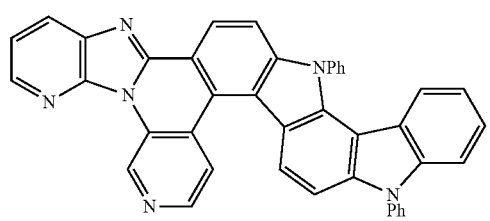
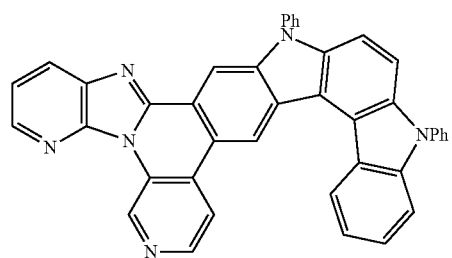
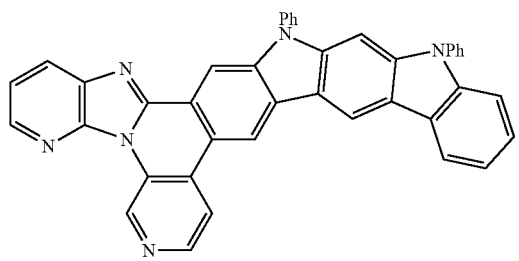
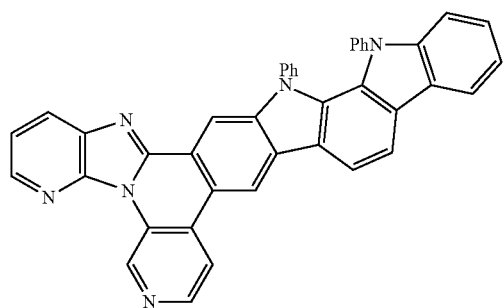
220
-continued
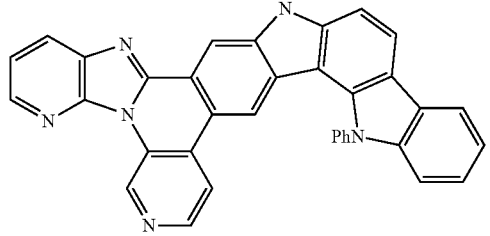
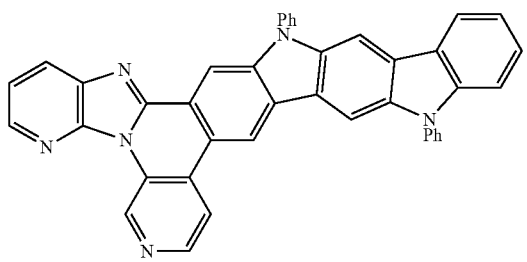
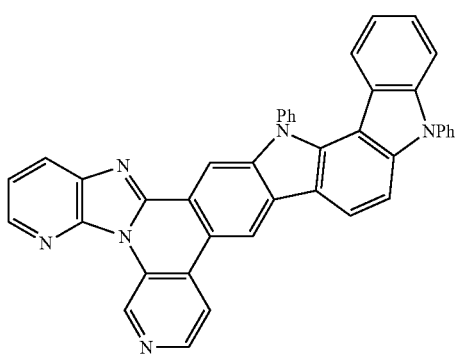
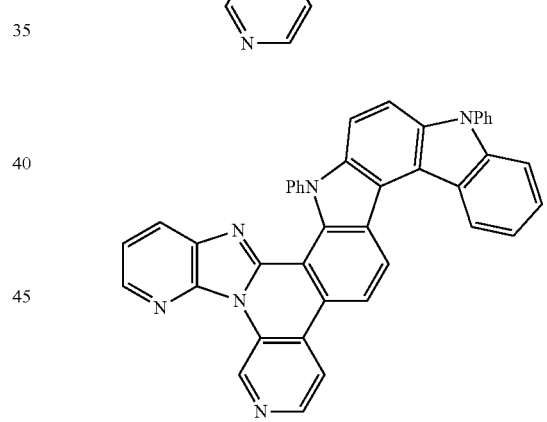
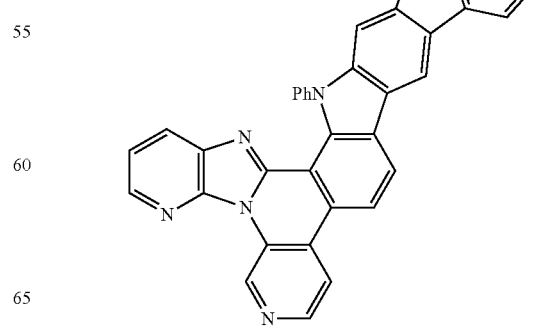

221
-continued
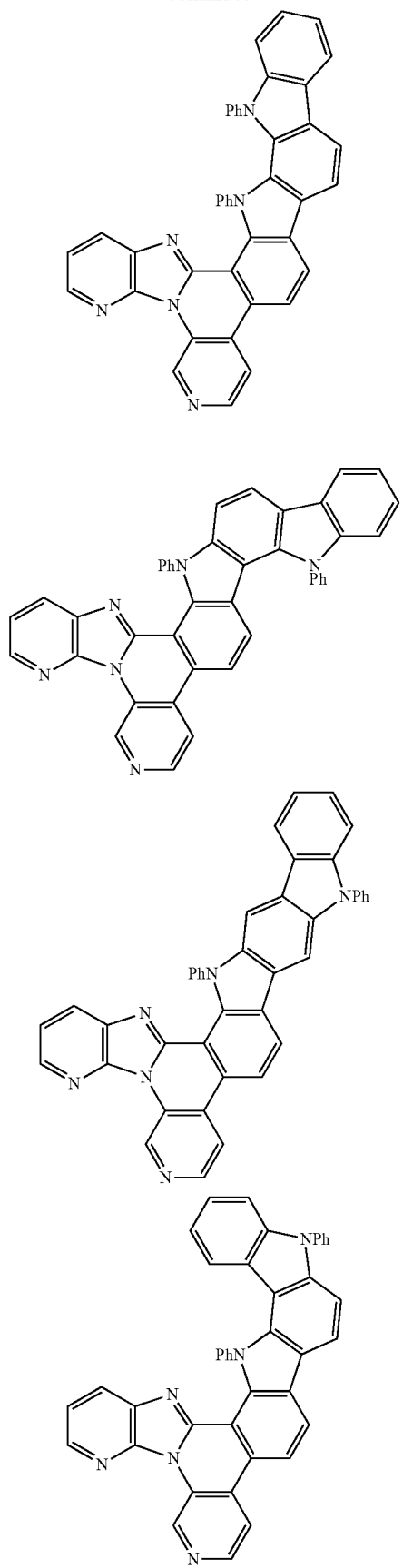
222
-continued
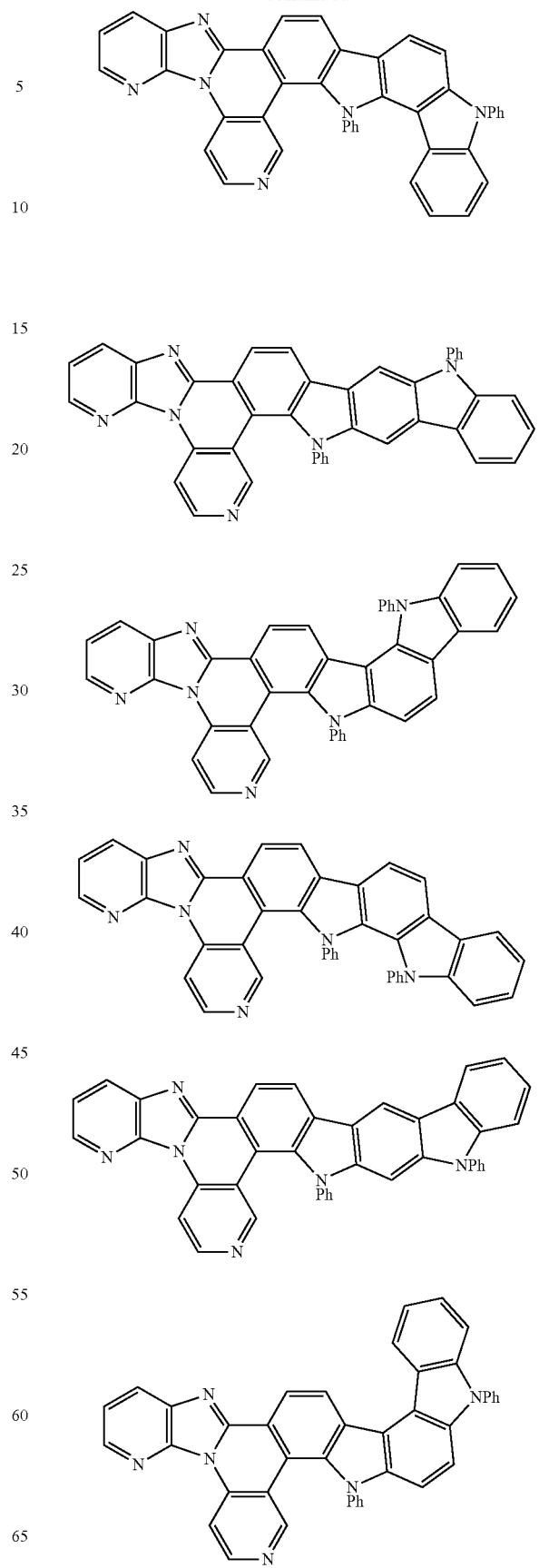

223
-continued
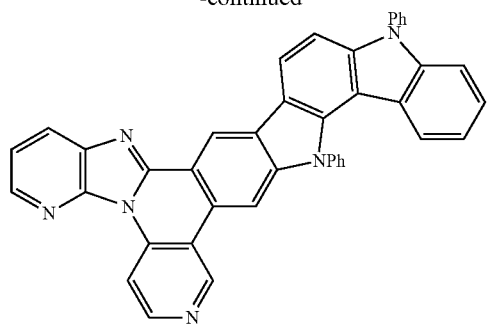
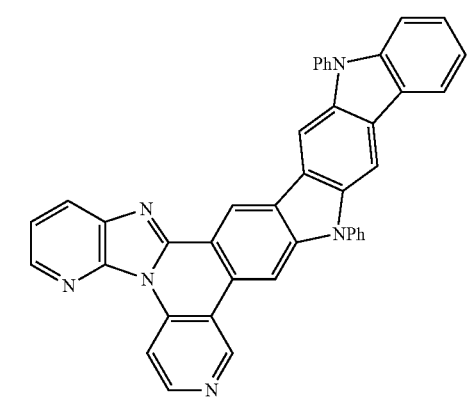
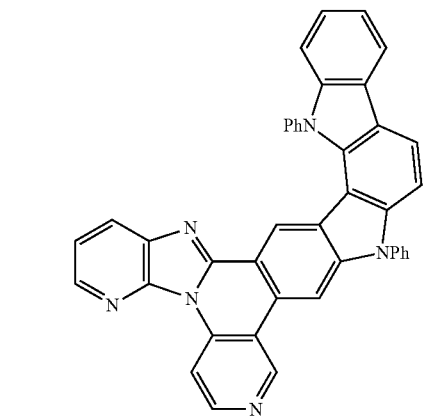
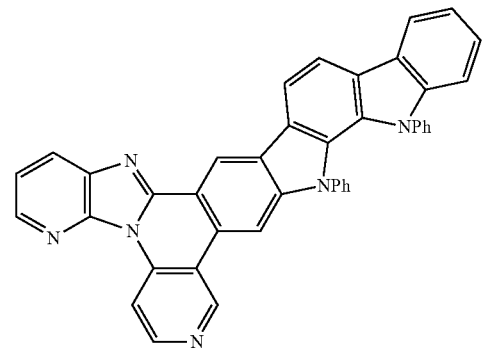
224
-continued
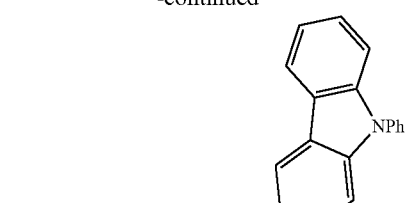
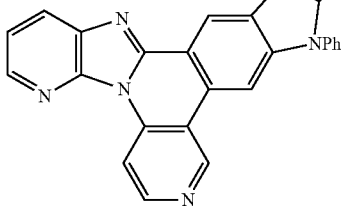
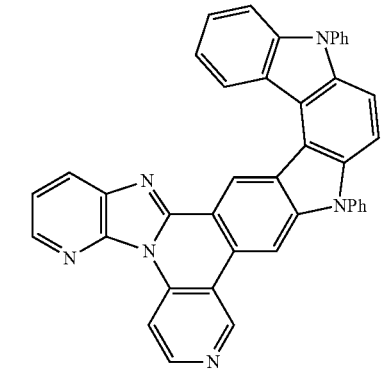
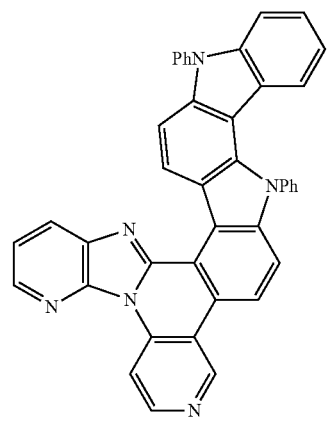
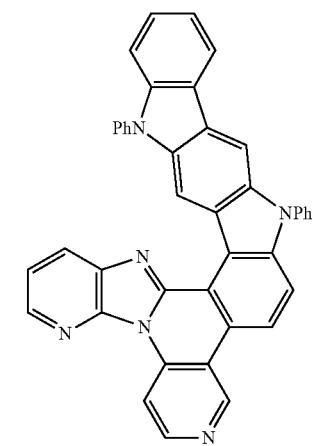

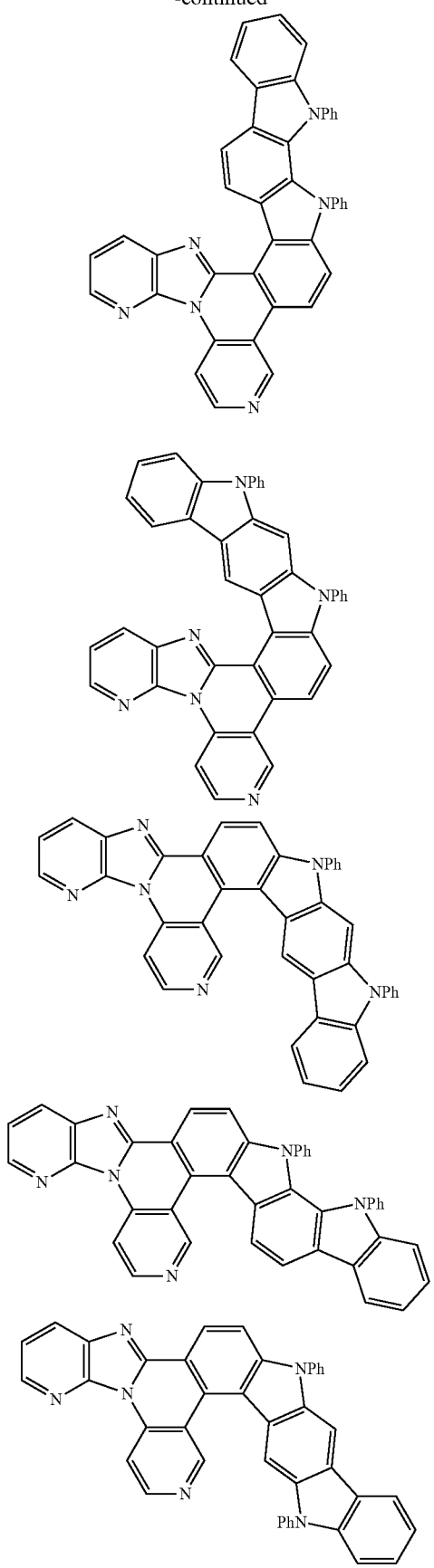
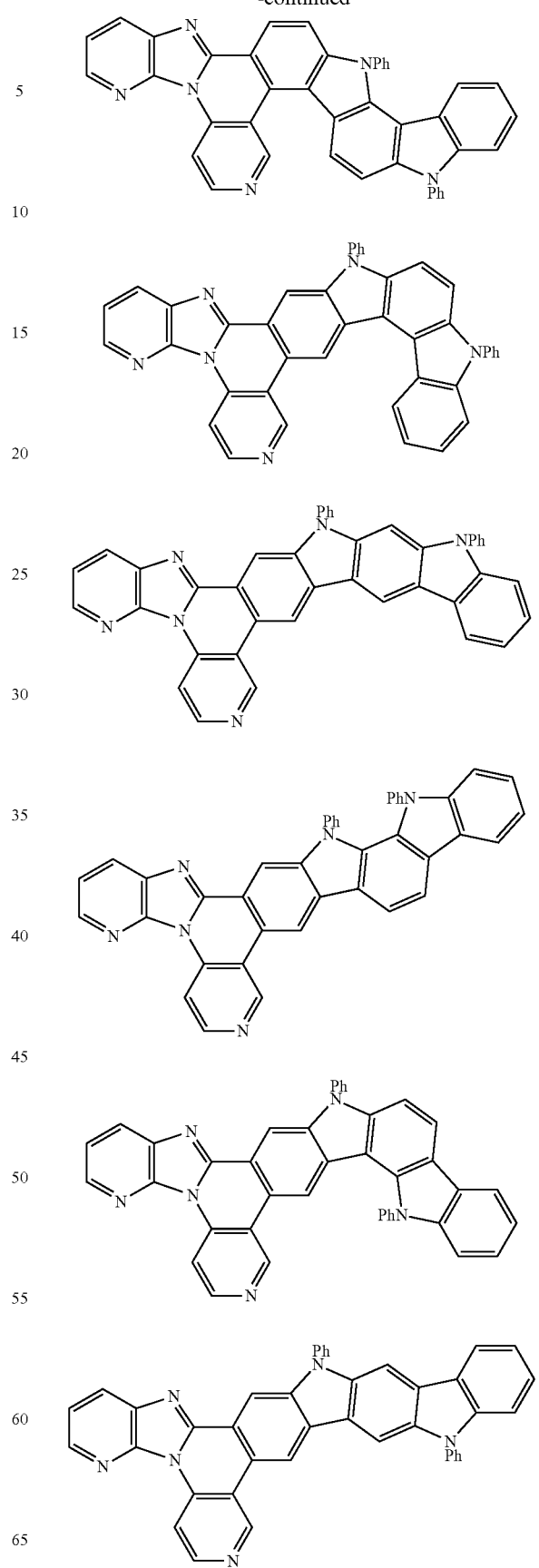

227
-continued
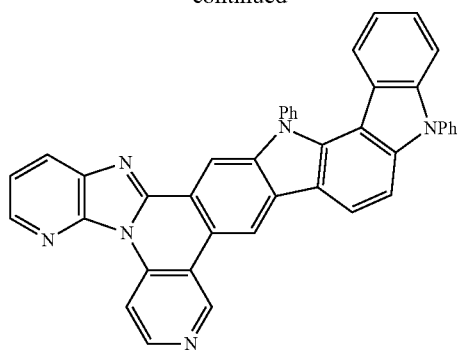
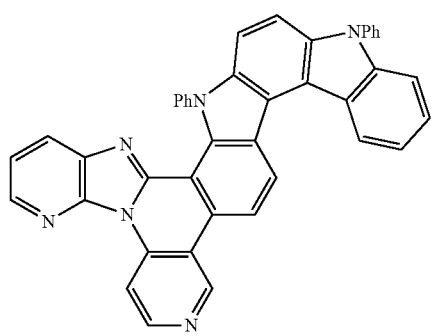
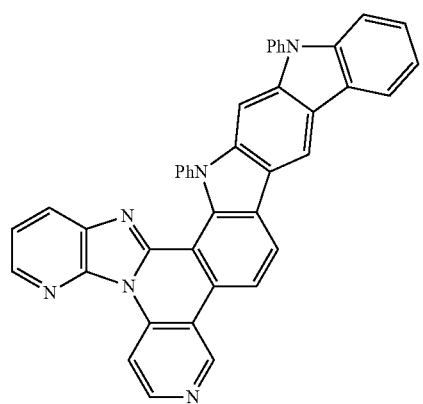
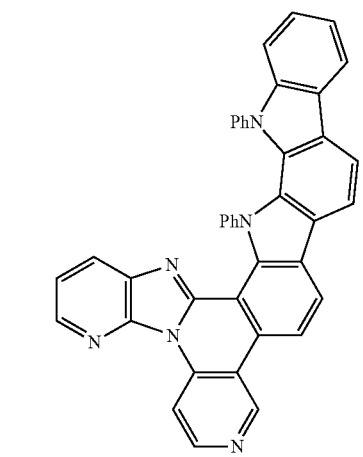
228
-continued
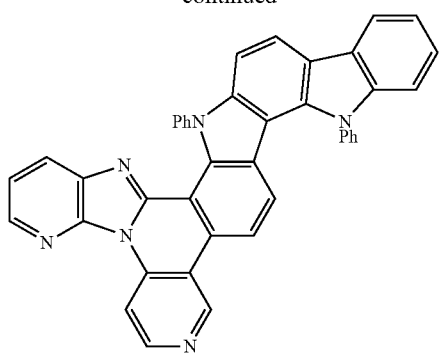
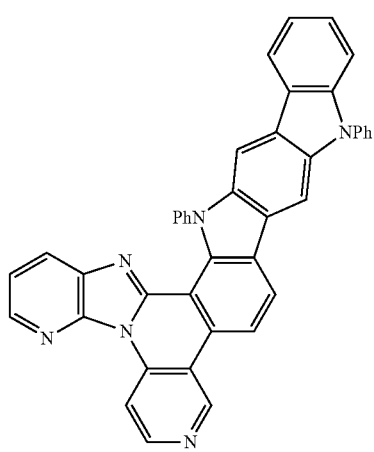
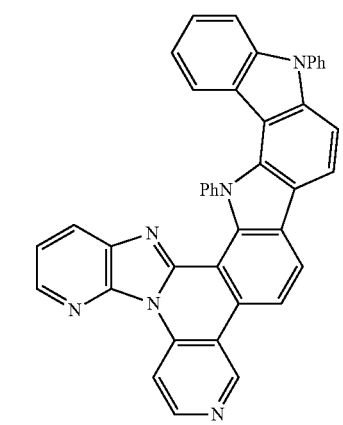
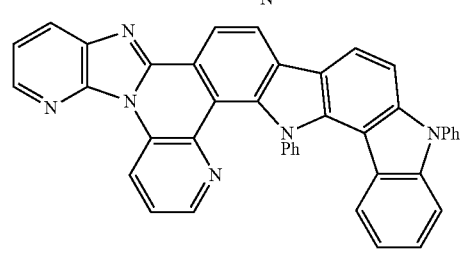
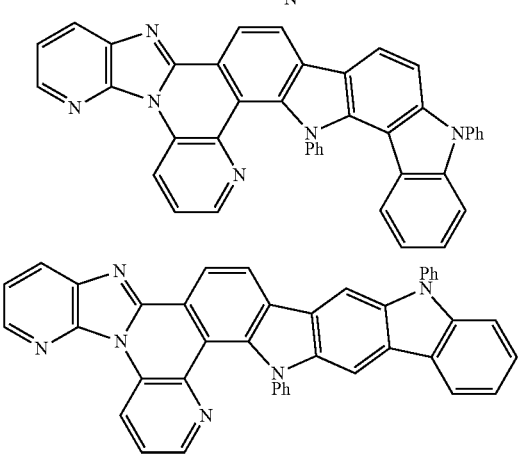

-continued
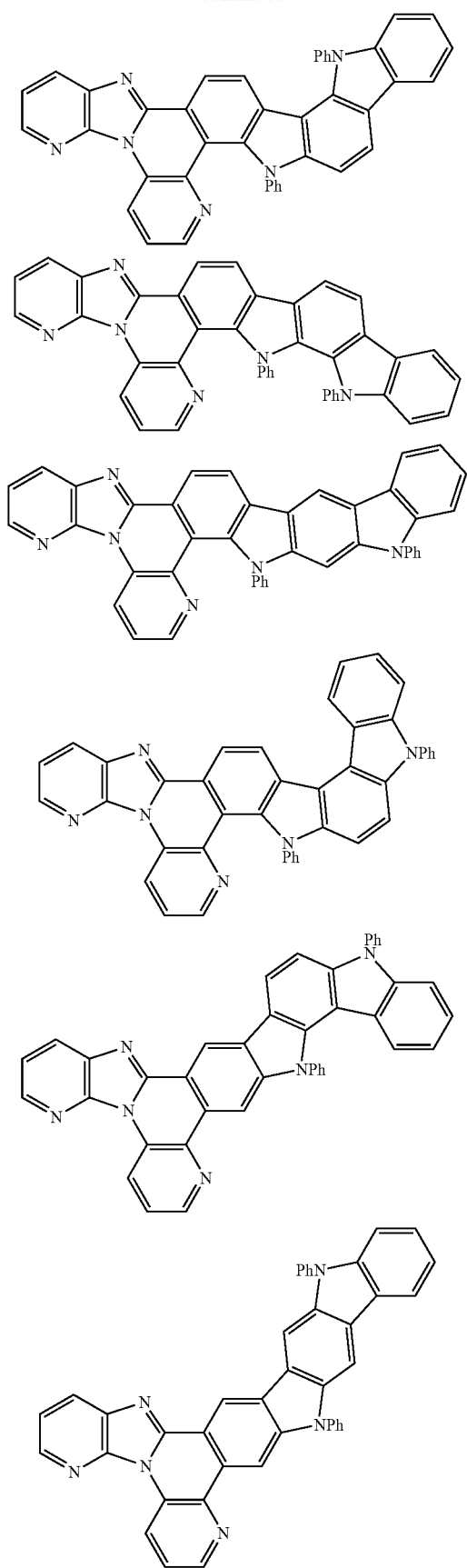
-continued
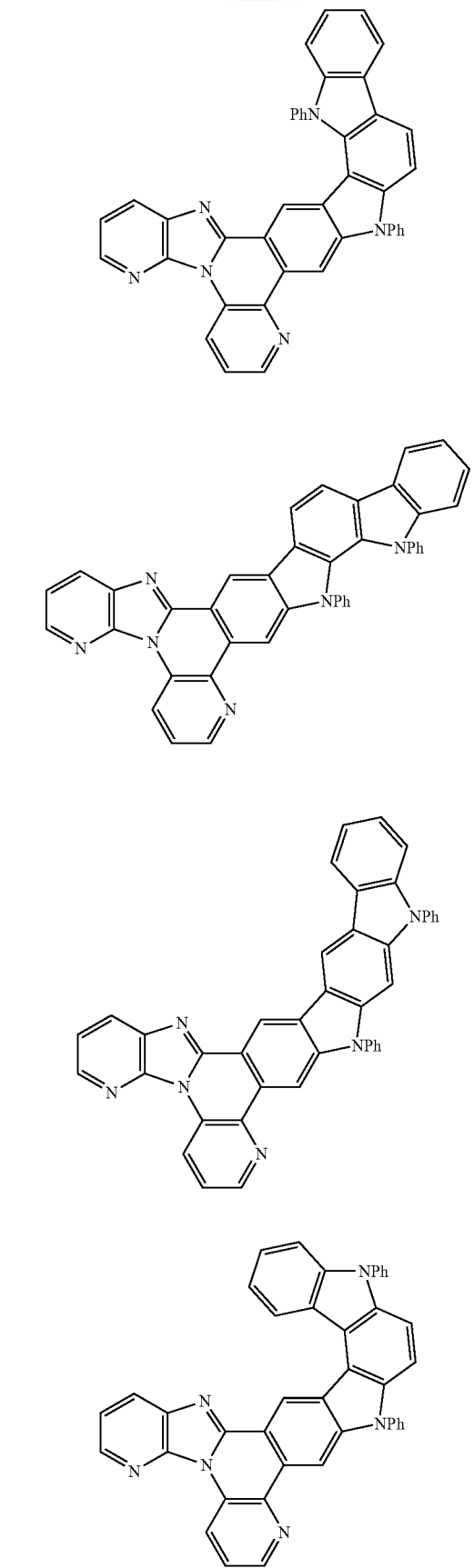

231
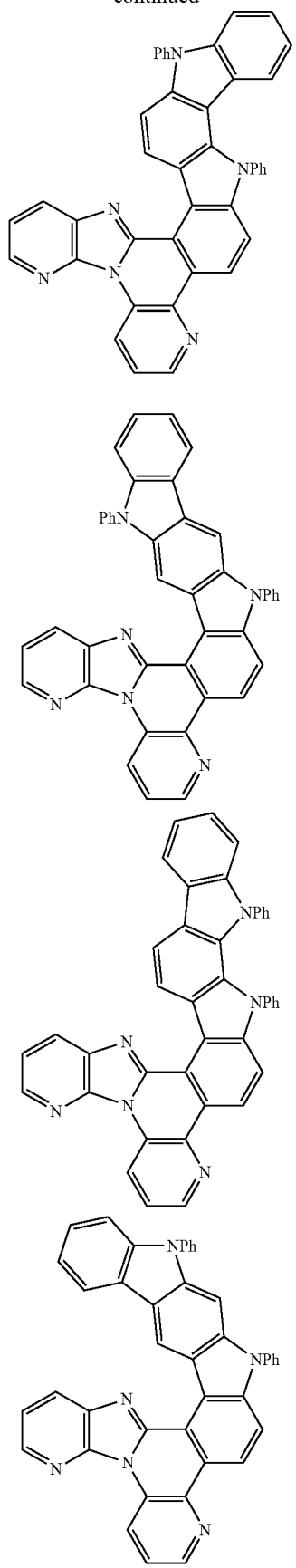
232
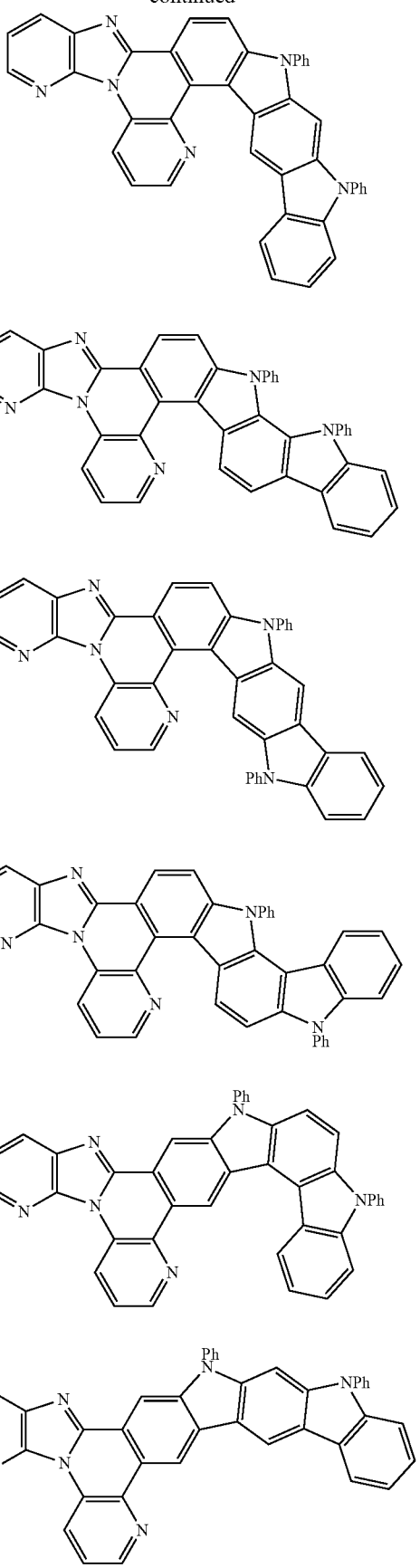

-continued
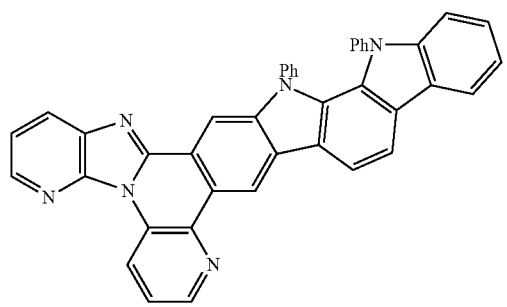
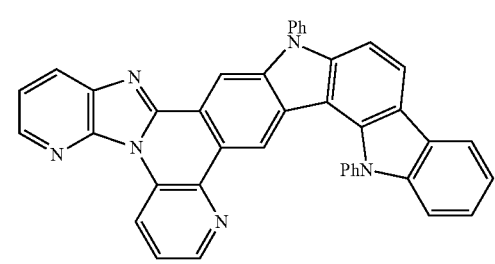
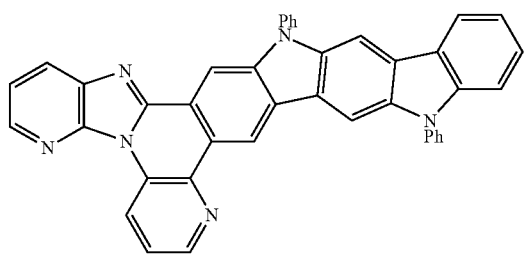
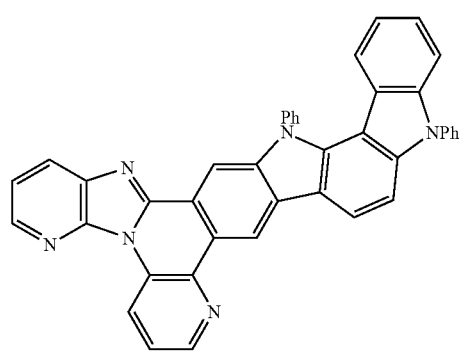
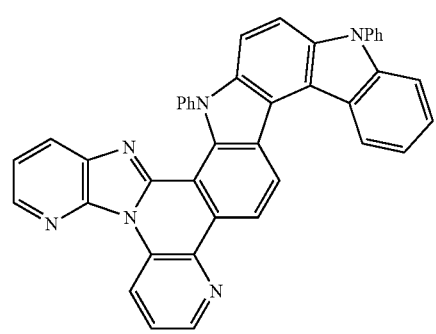
-continued
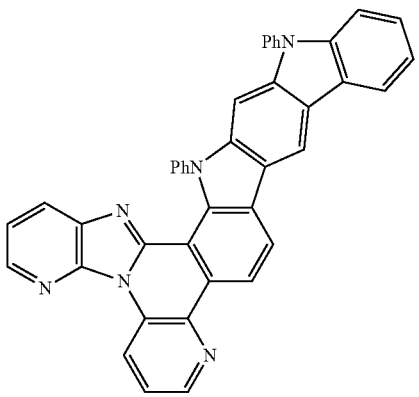
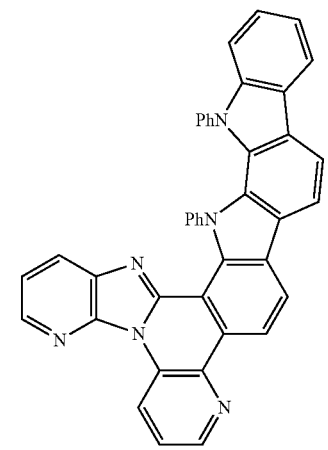
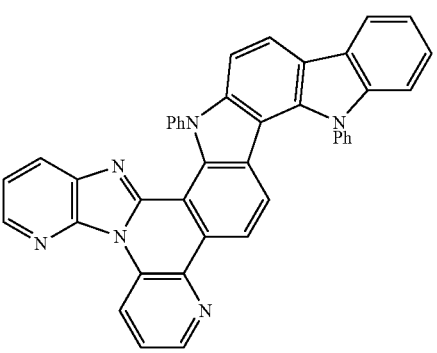
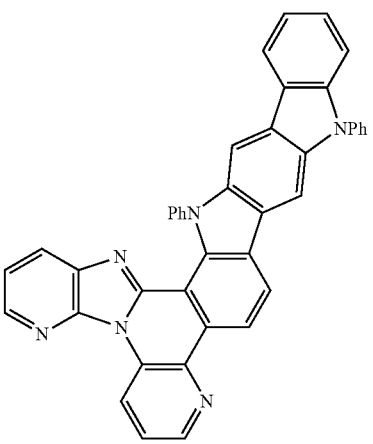

-continued
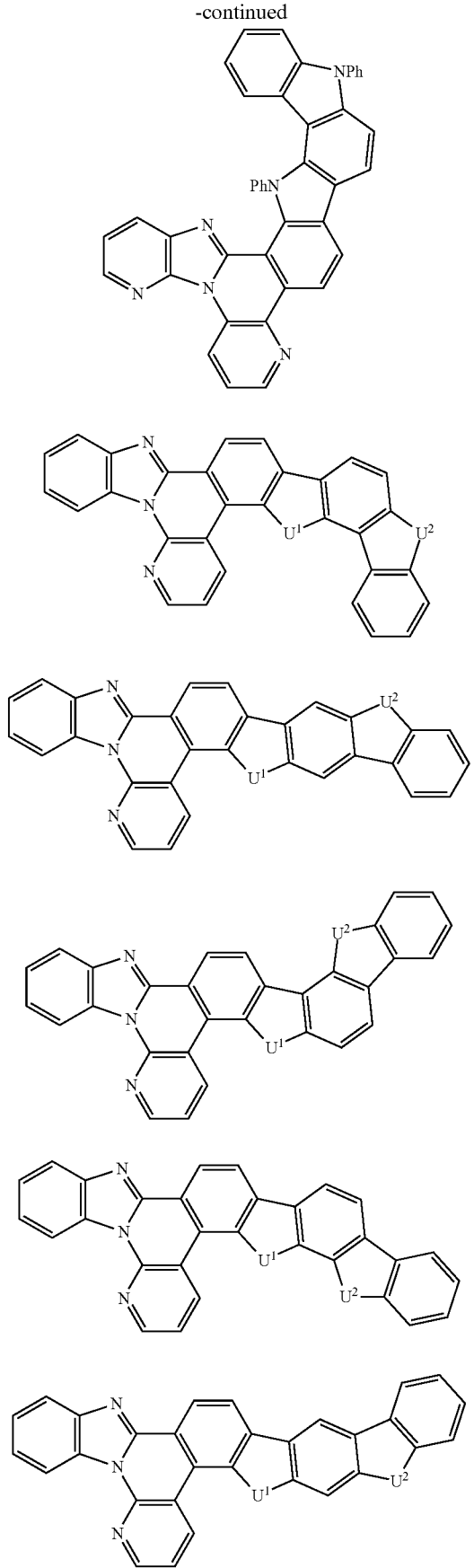
-continued
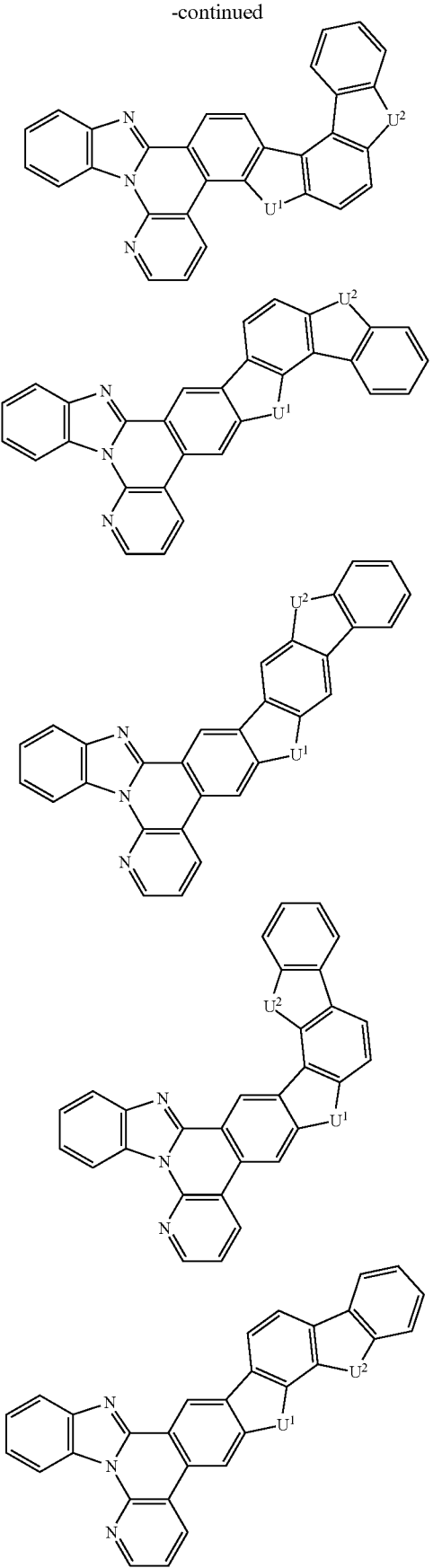

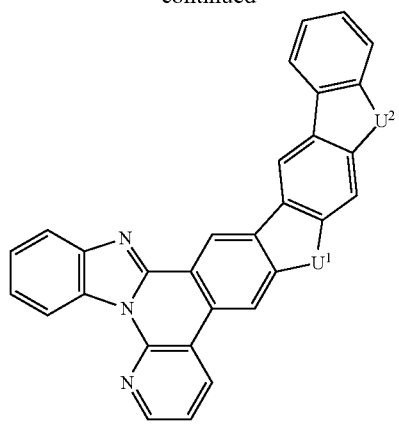
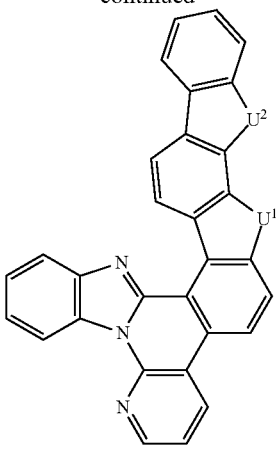
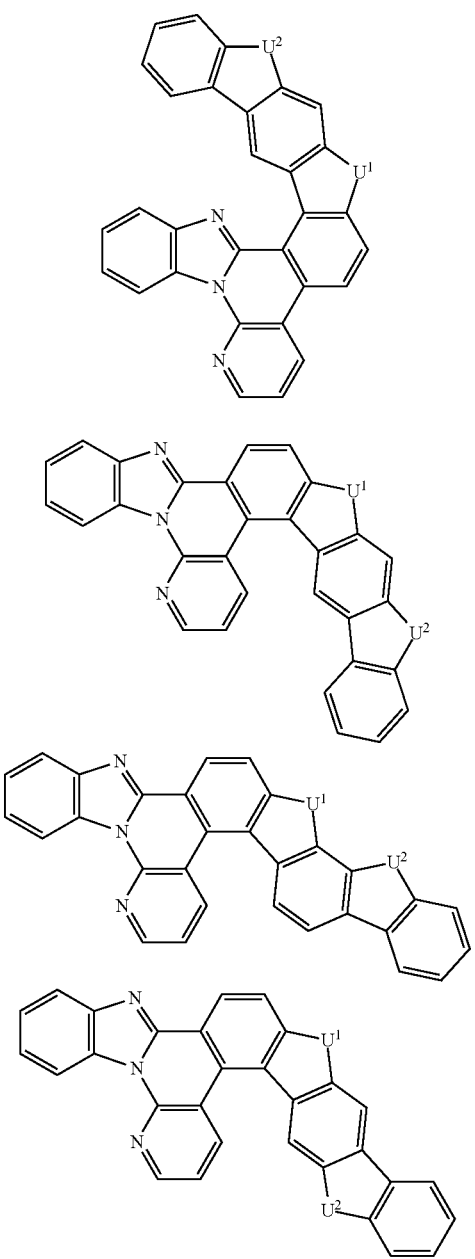

239
-continued
240
-continued
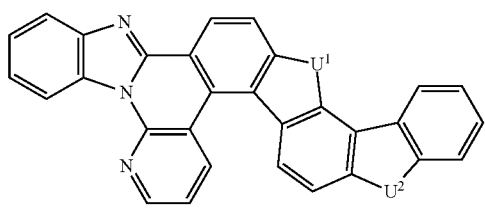
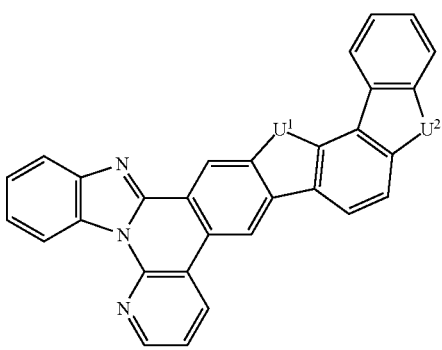
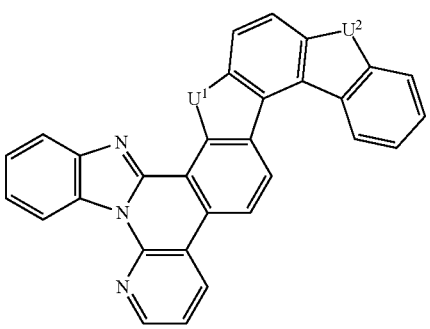
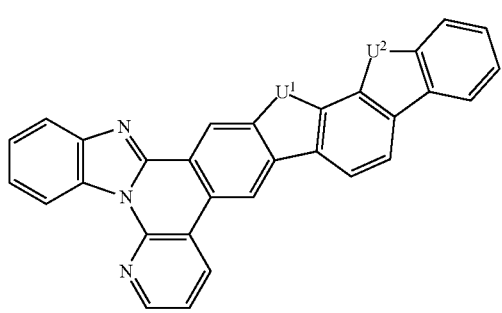
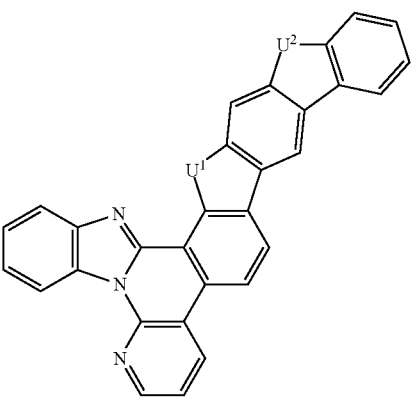
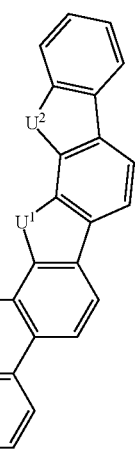

241
-continued
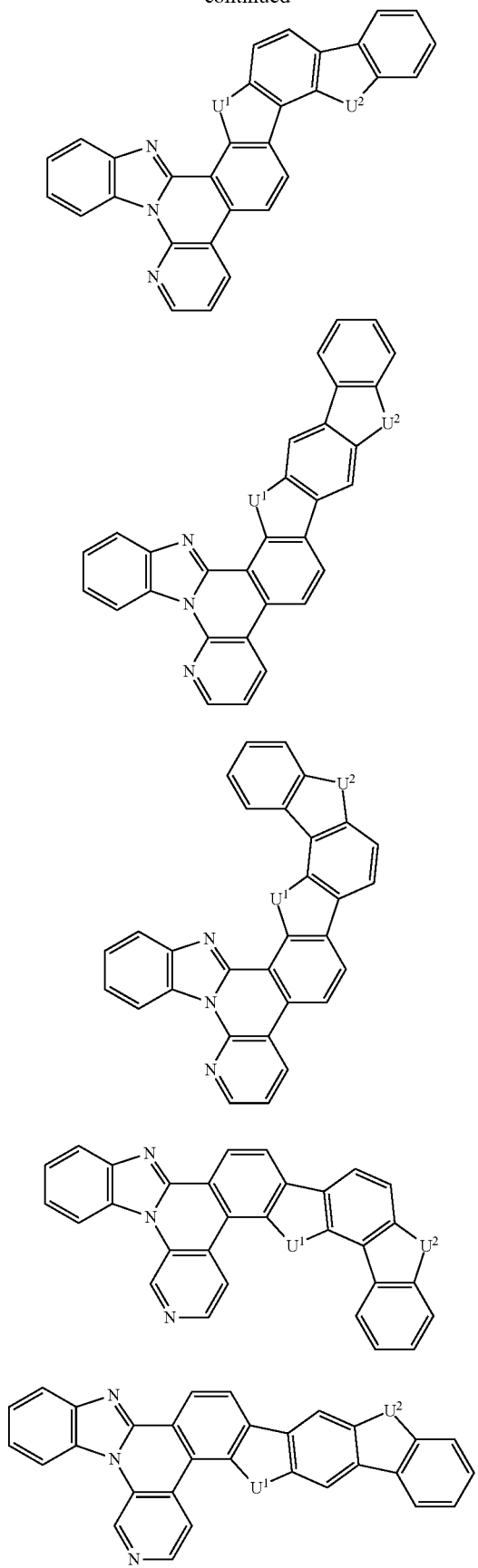
242
-continued
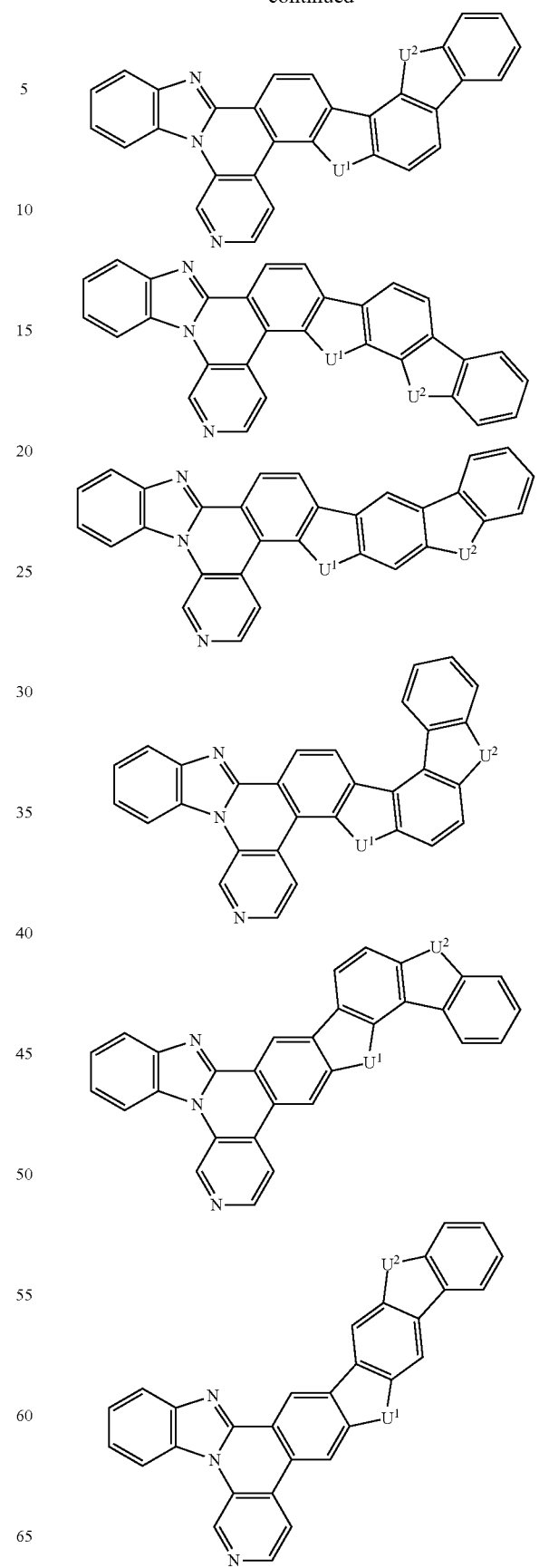

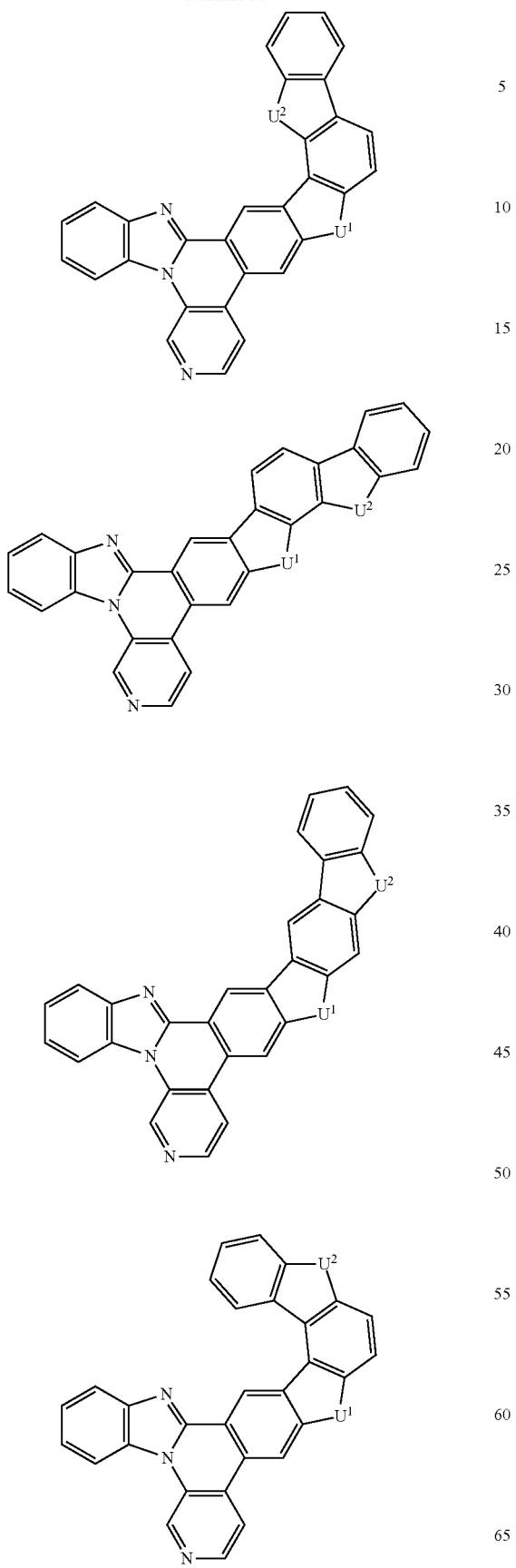
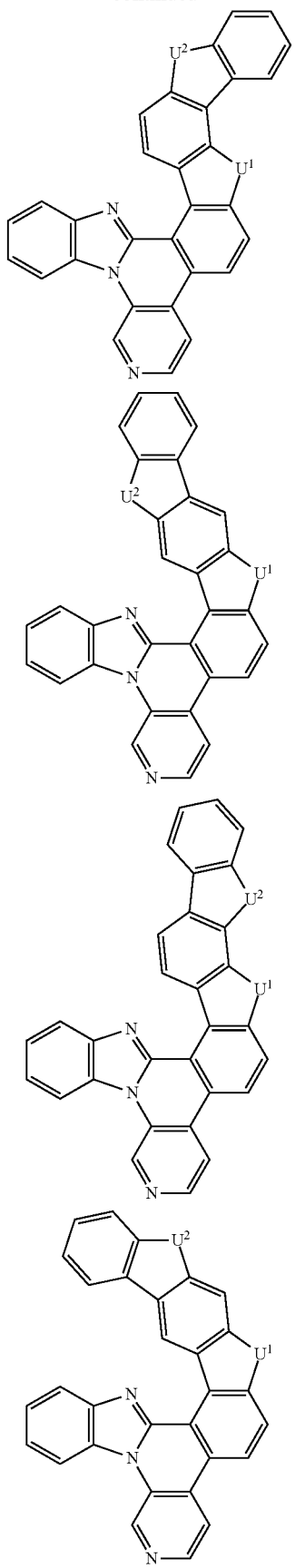

245
-continued
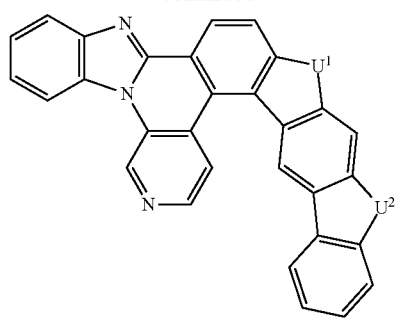
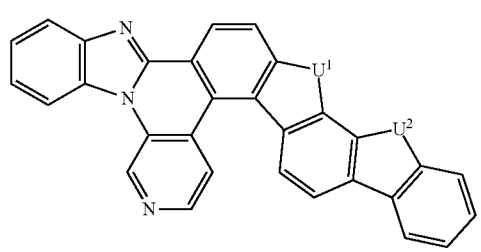
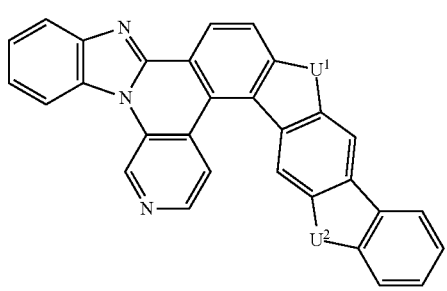
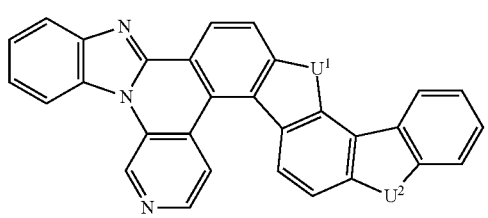
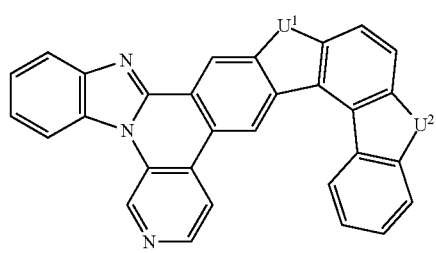
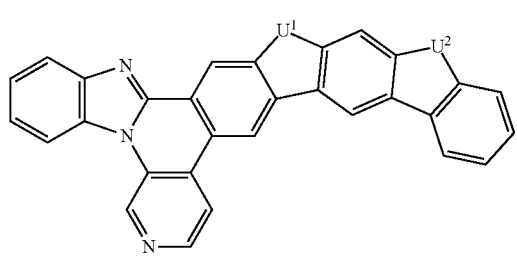
246
-continued
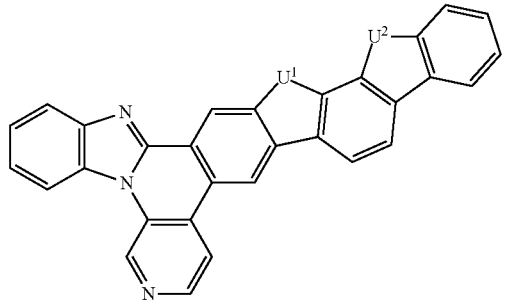
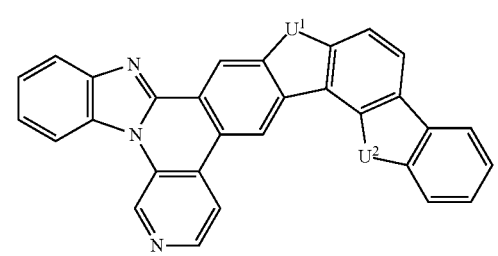
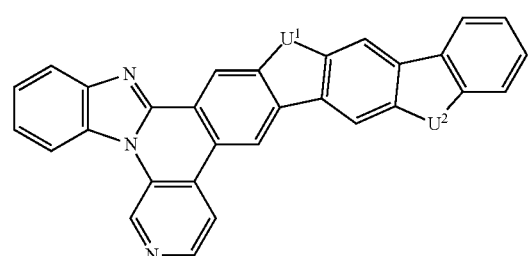
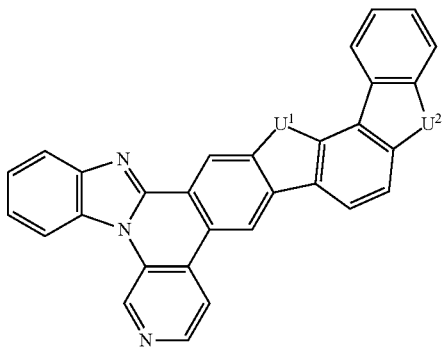
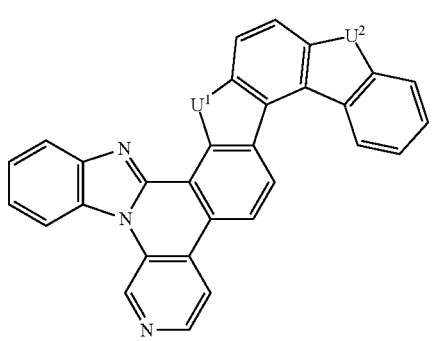

247
-continued
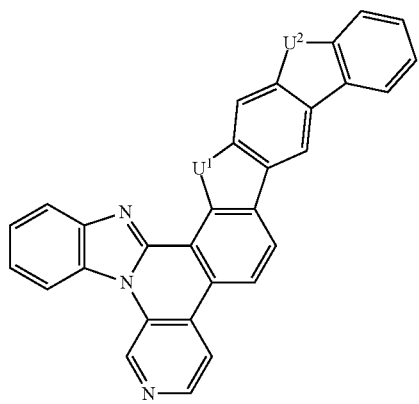
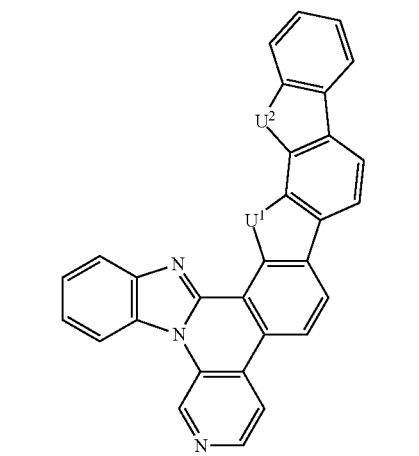
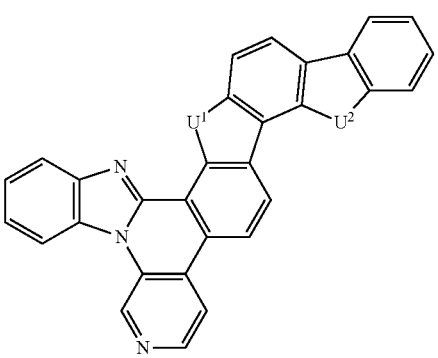
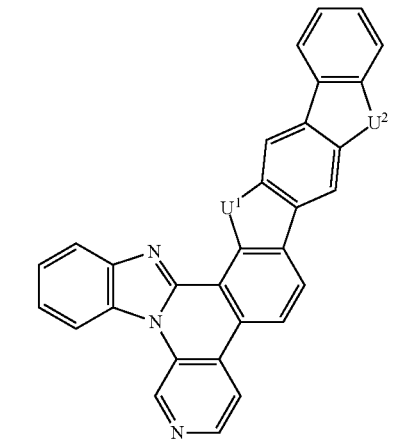
248
-continued
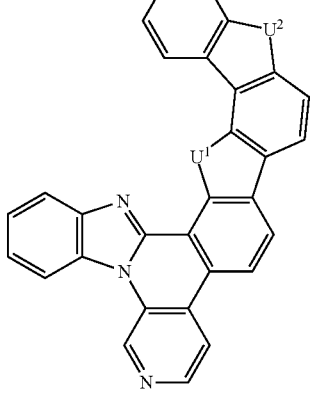
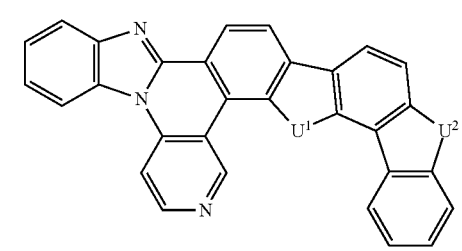
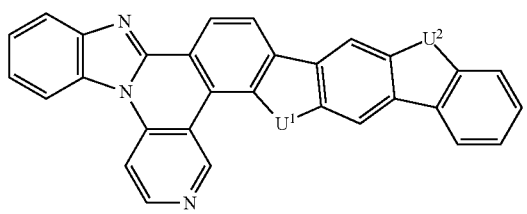
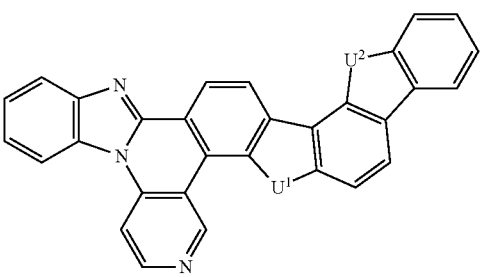
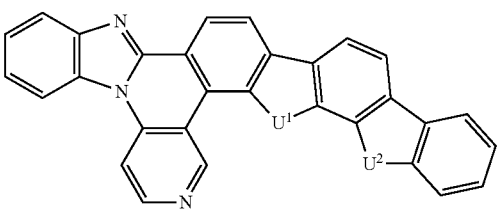
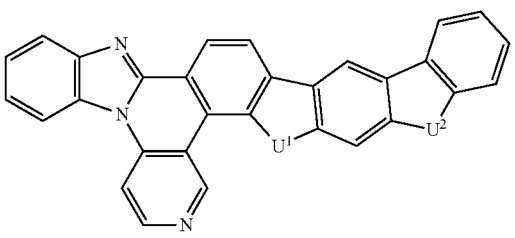

249
-continued
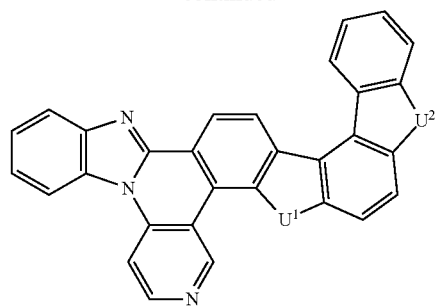
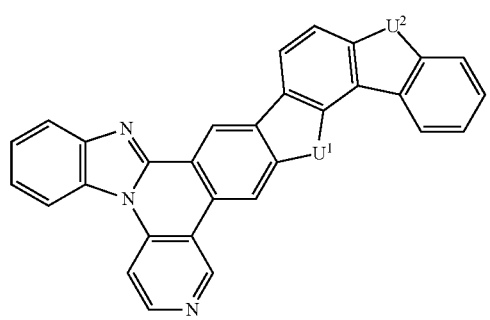
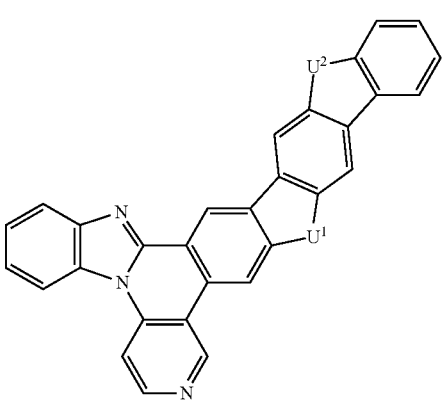
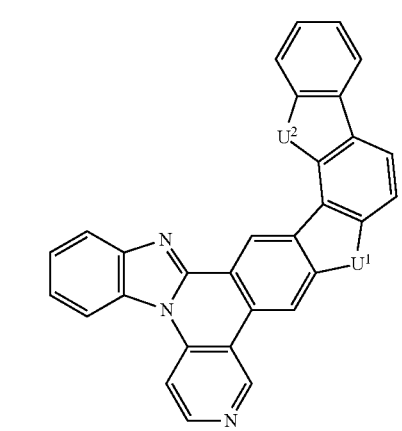
250
-continued
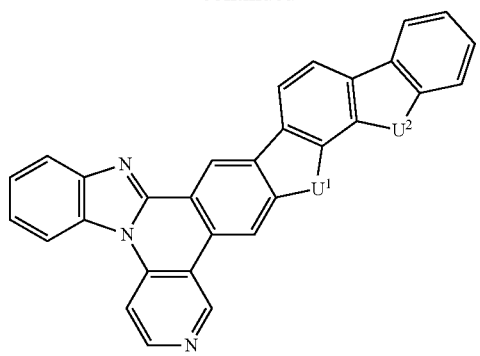
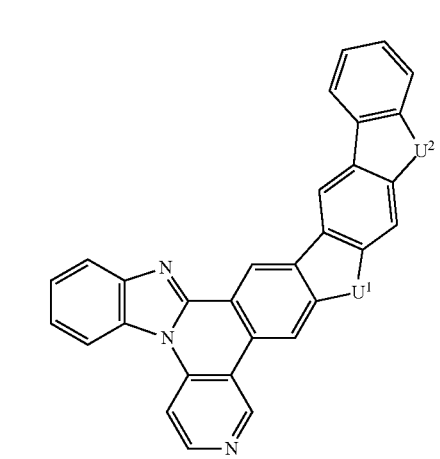
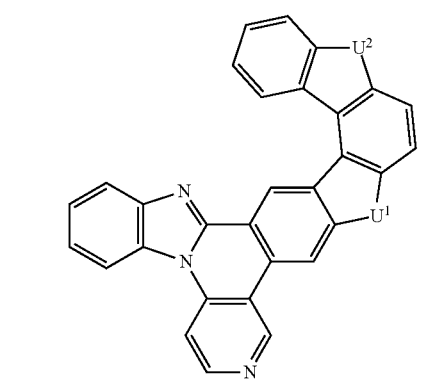
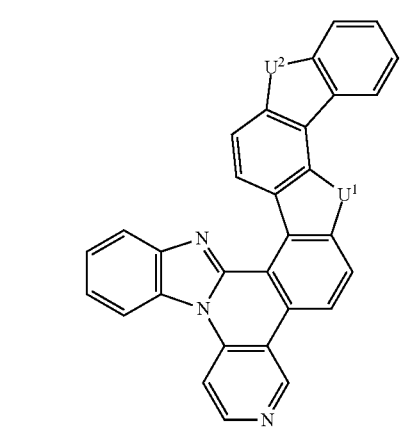

-continued
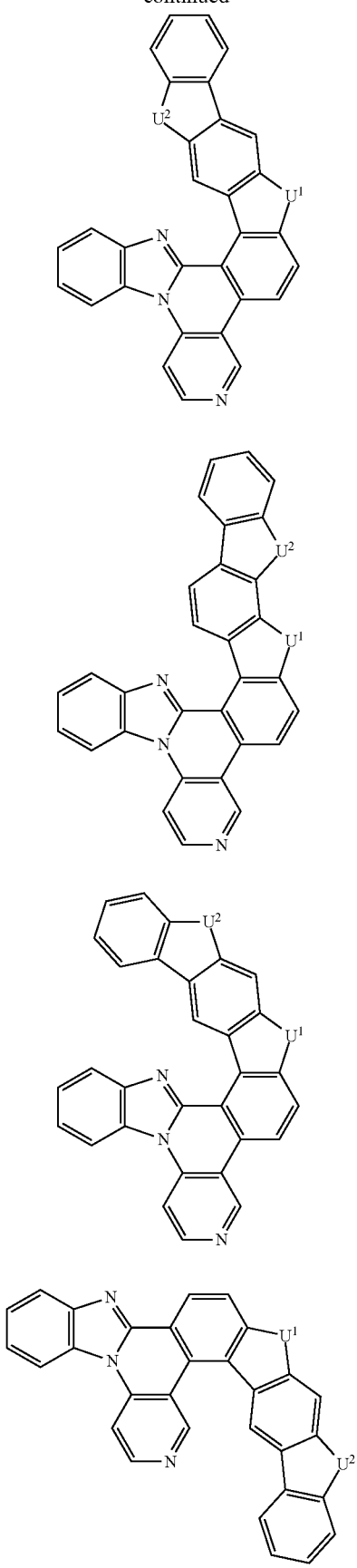

253
-continued
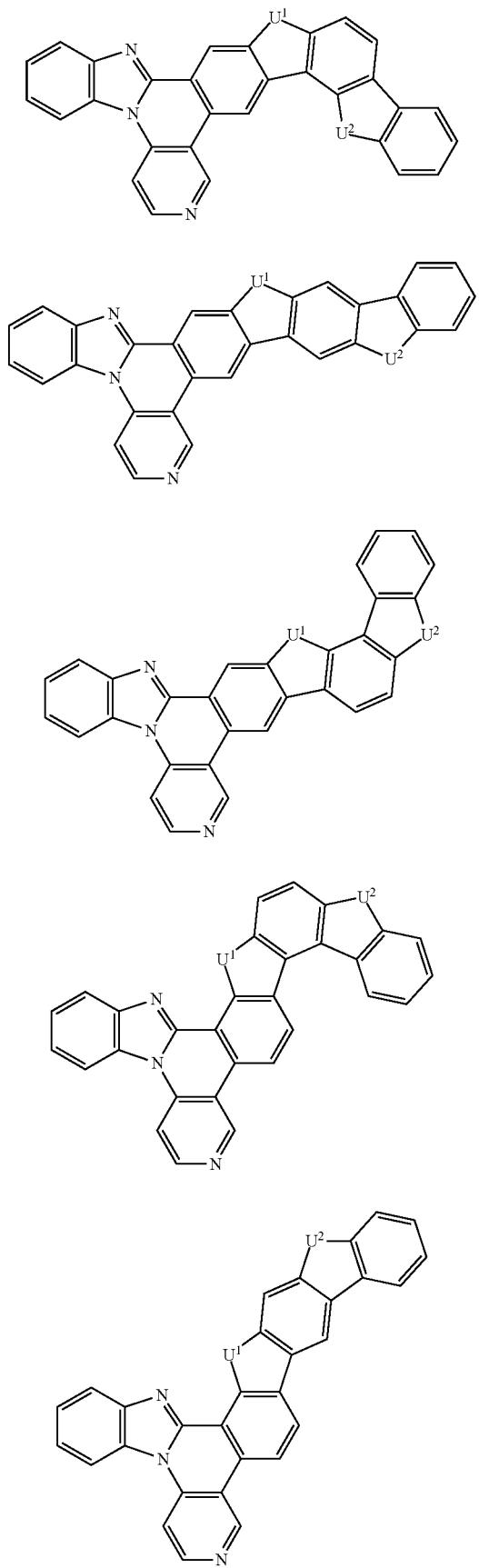
254
-continued
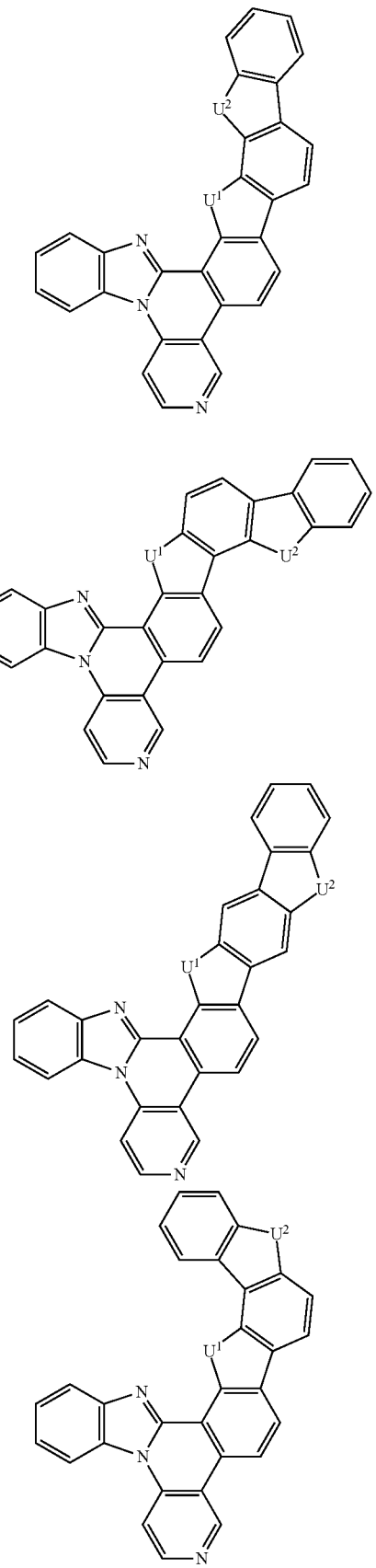

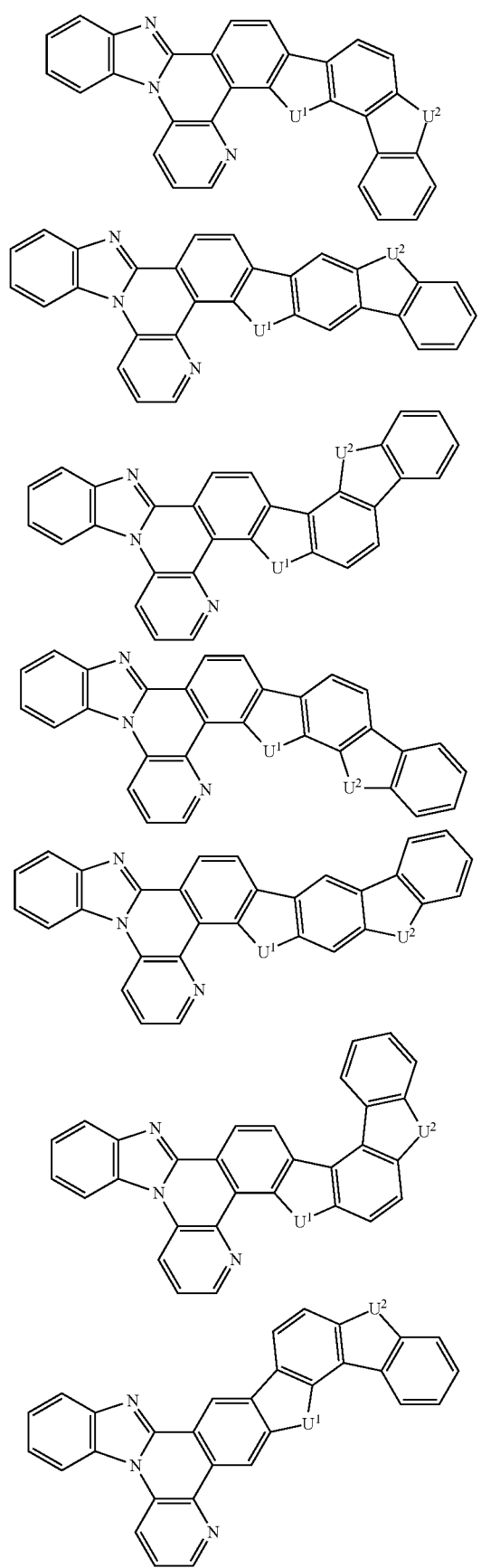
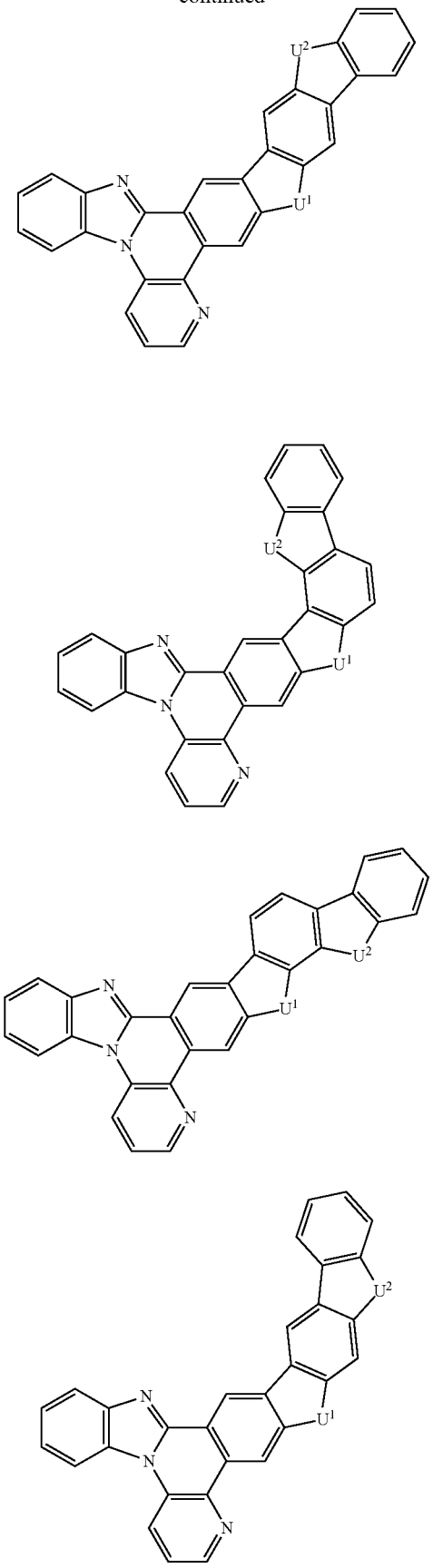

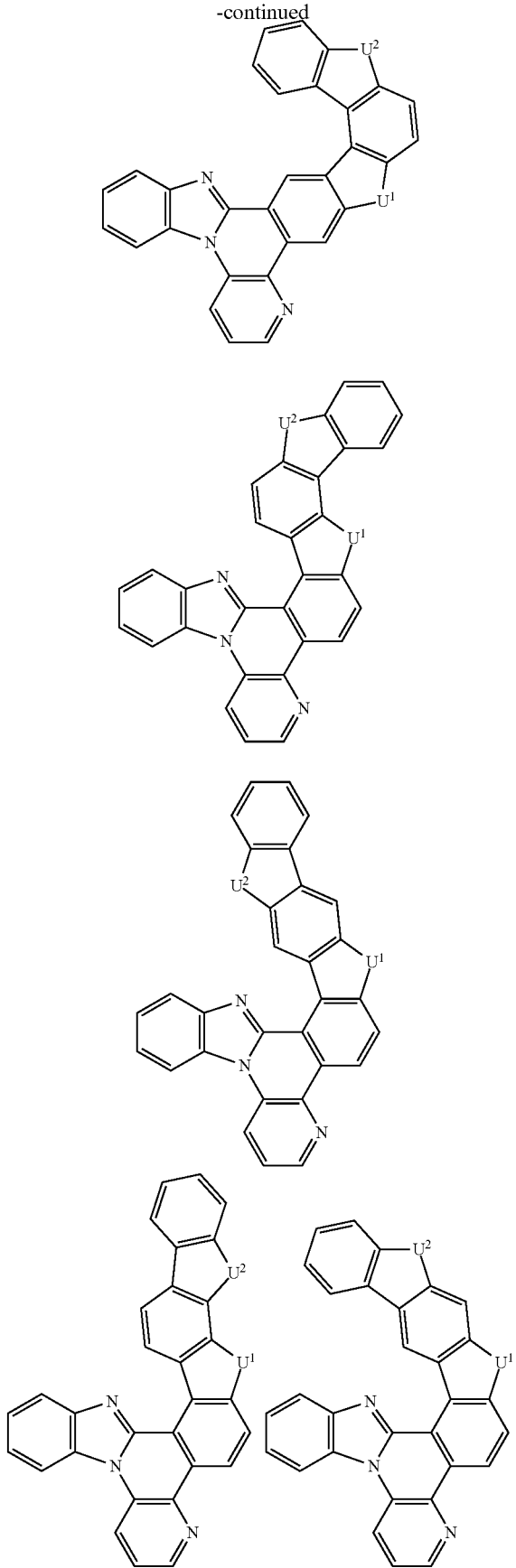
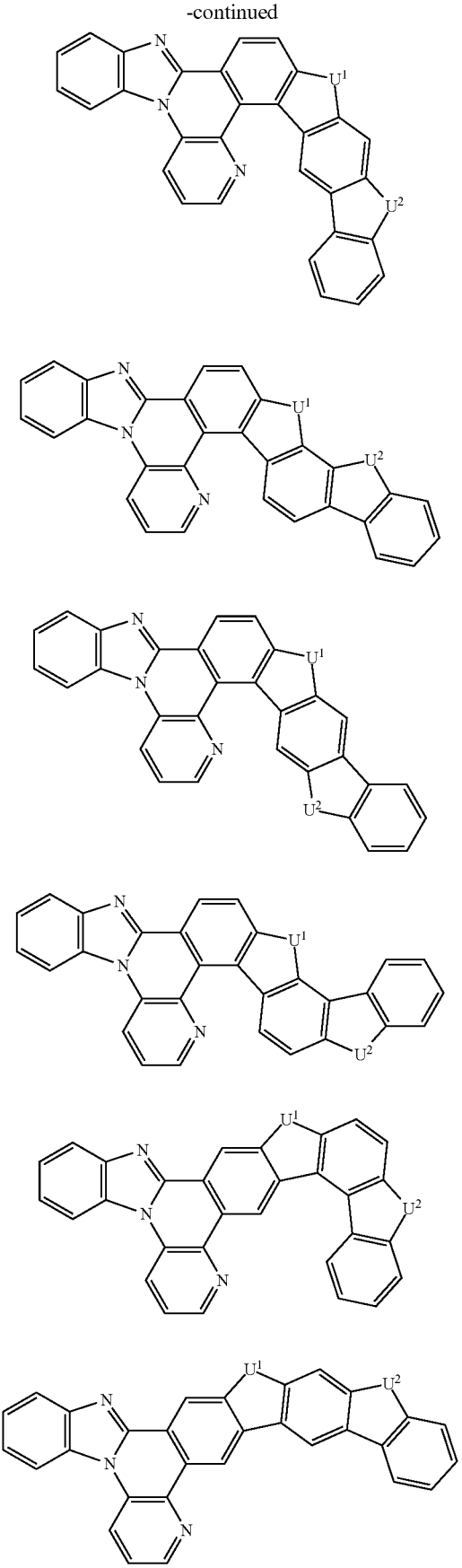

259
-continued
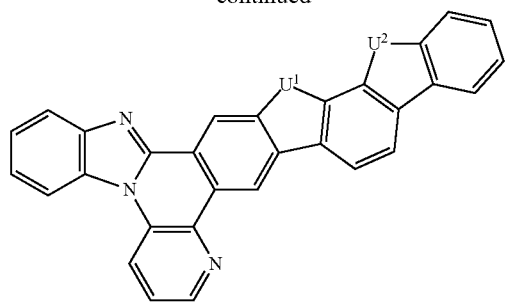
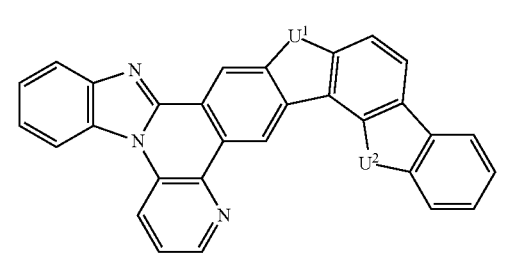
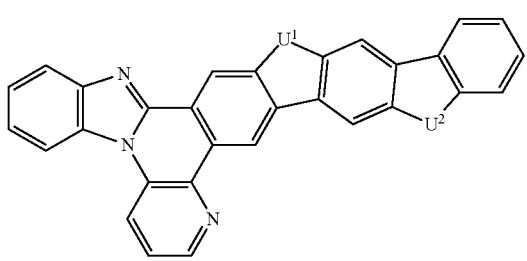
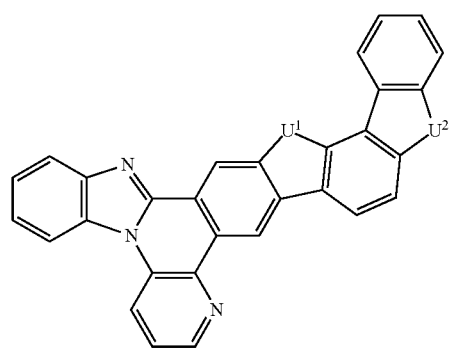
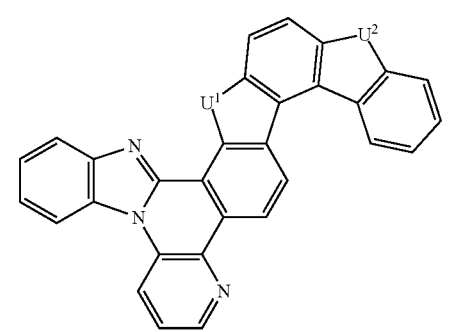
260
-continued
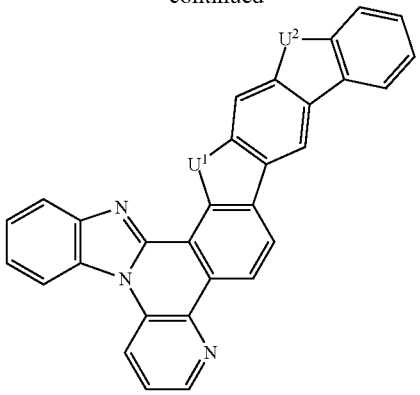
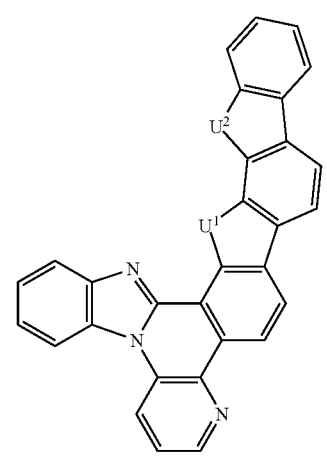
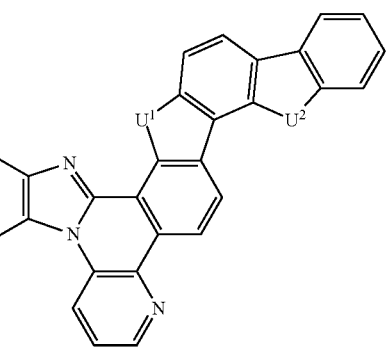
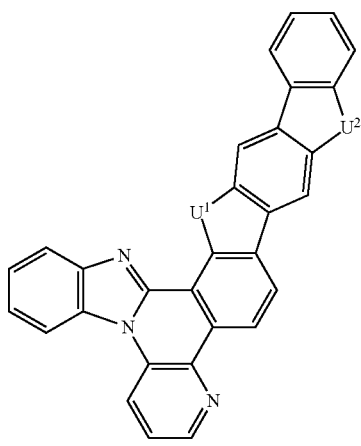

261
-continued
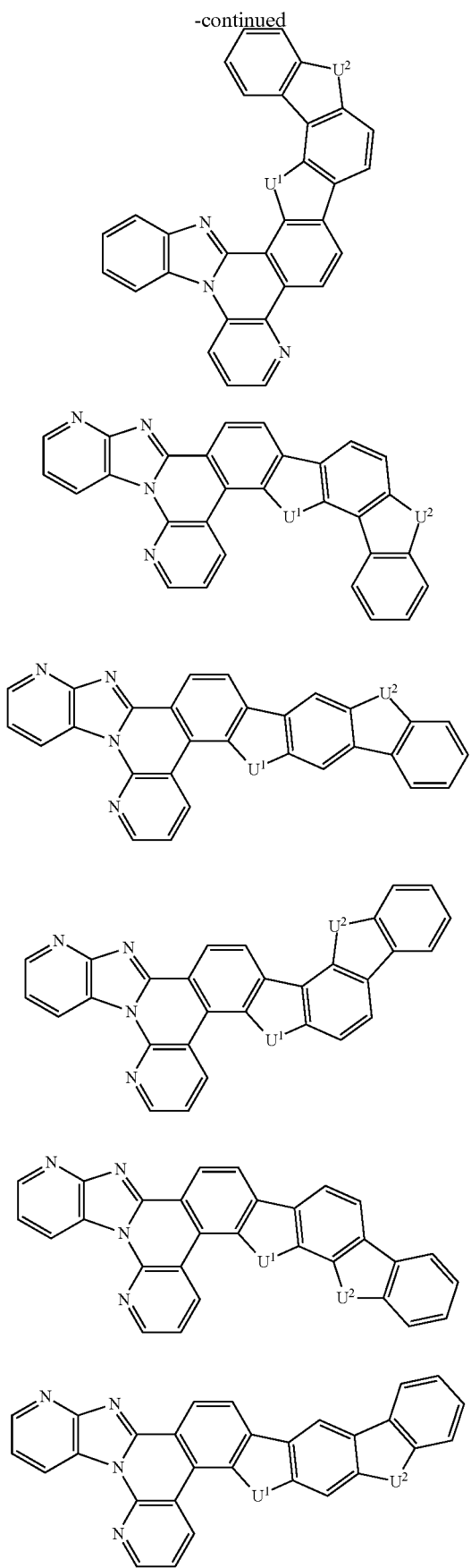
262
-continued
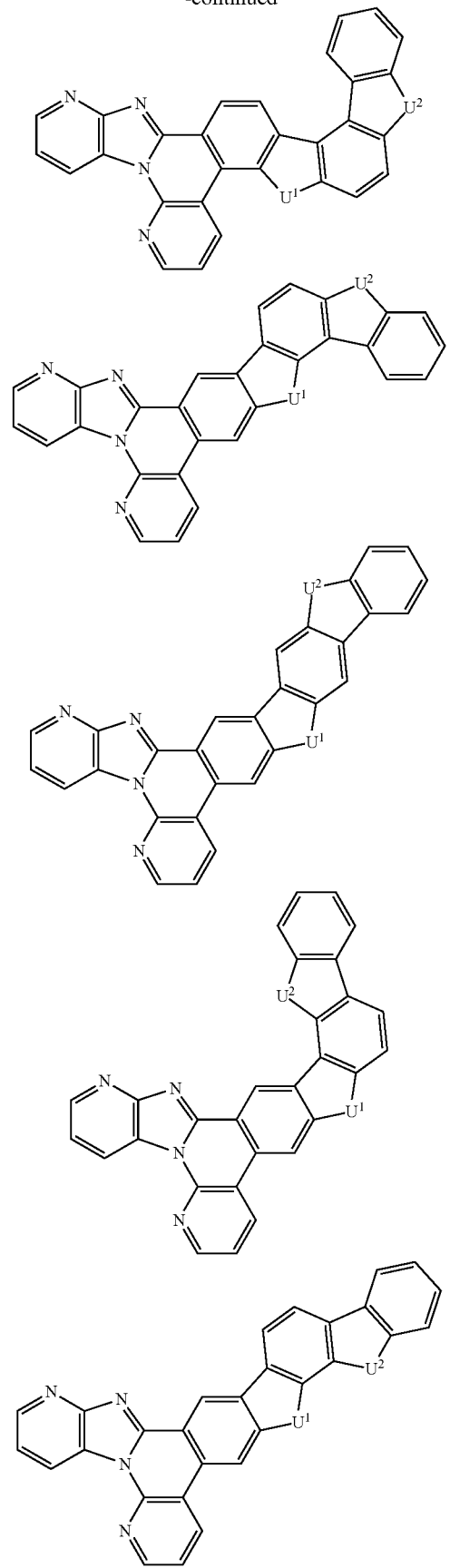

-continued
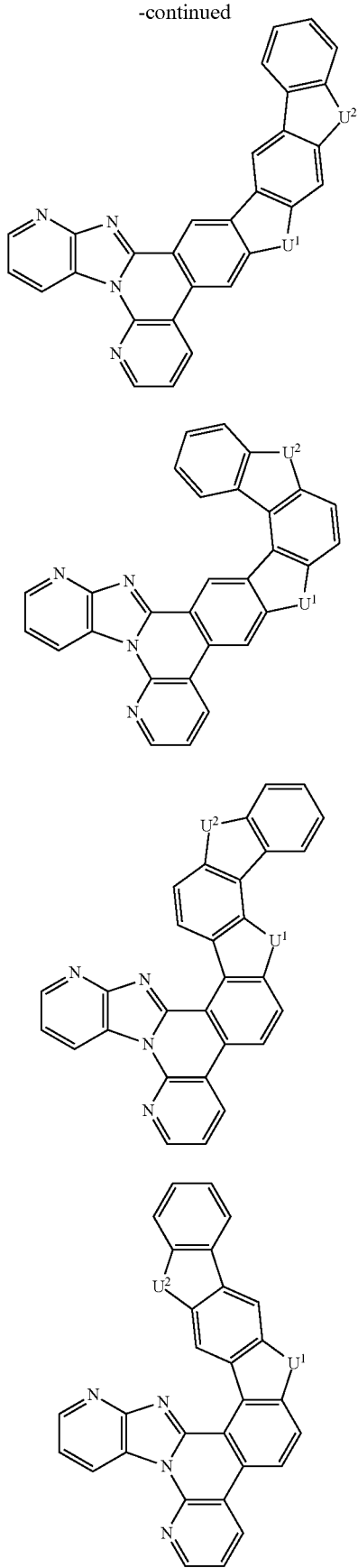
-continued
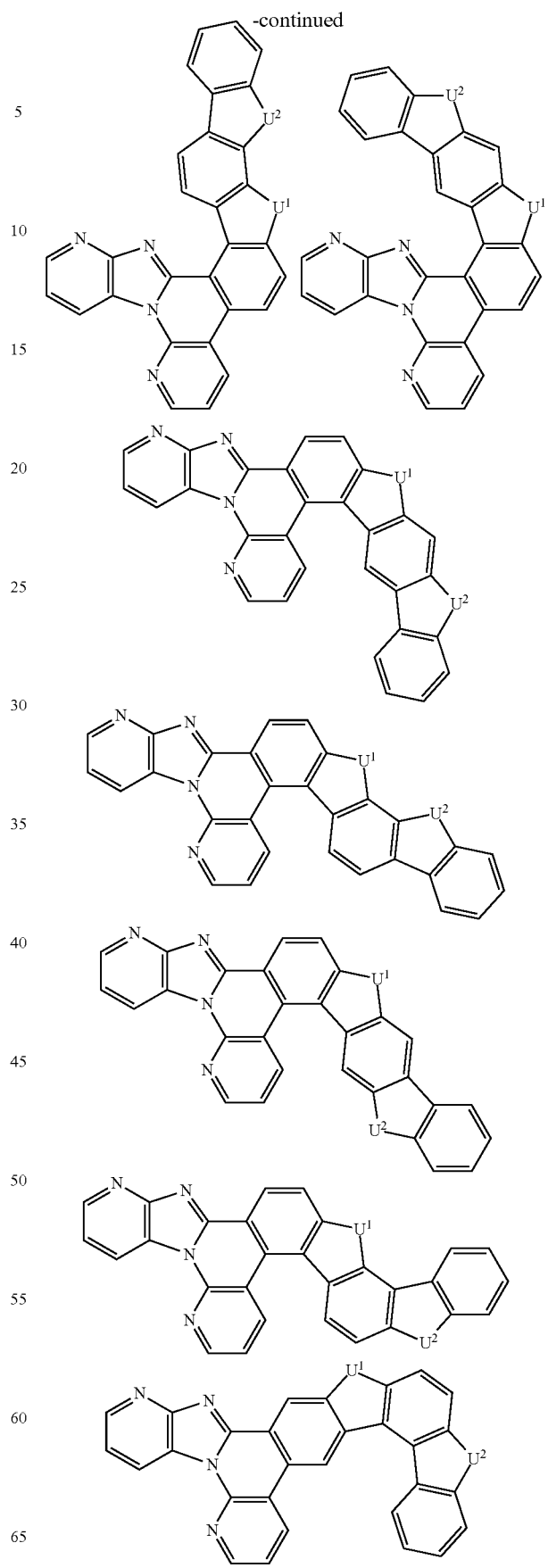

265
-continued
266
-continued
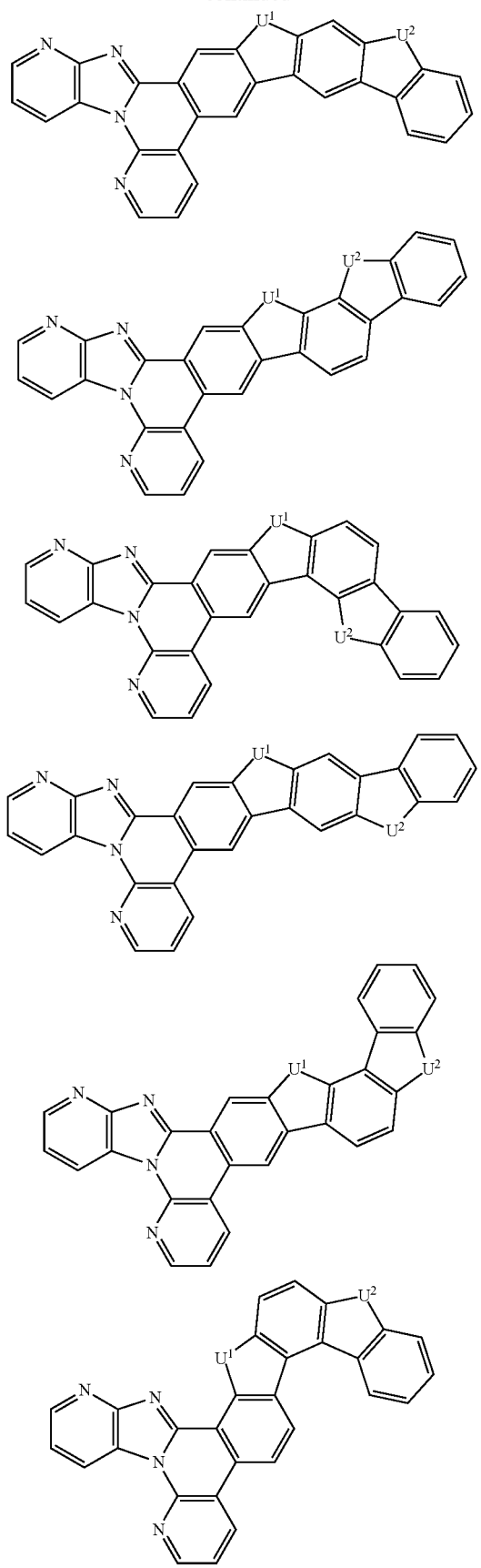
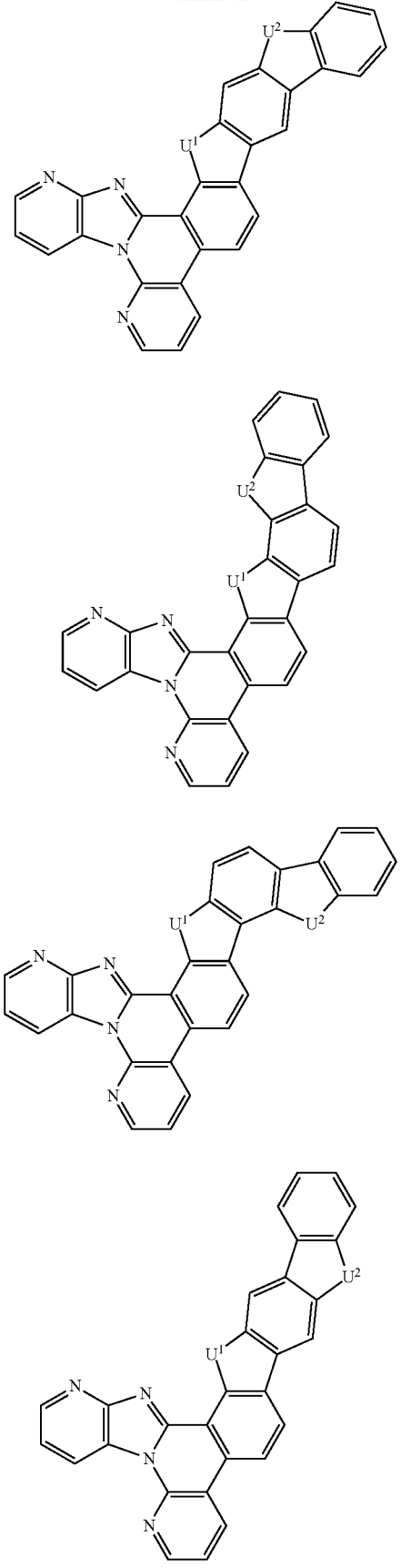

267
-continued
268
-continued
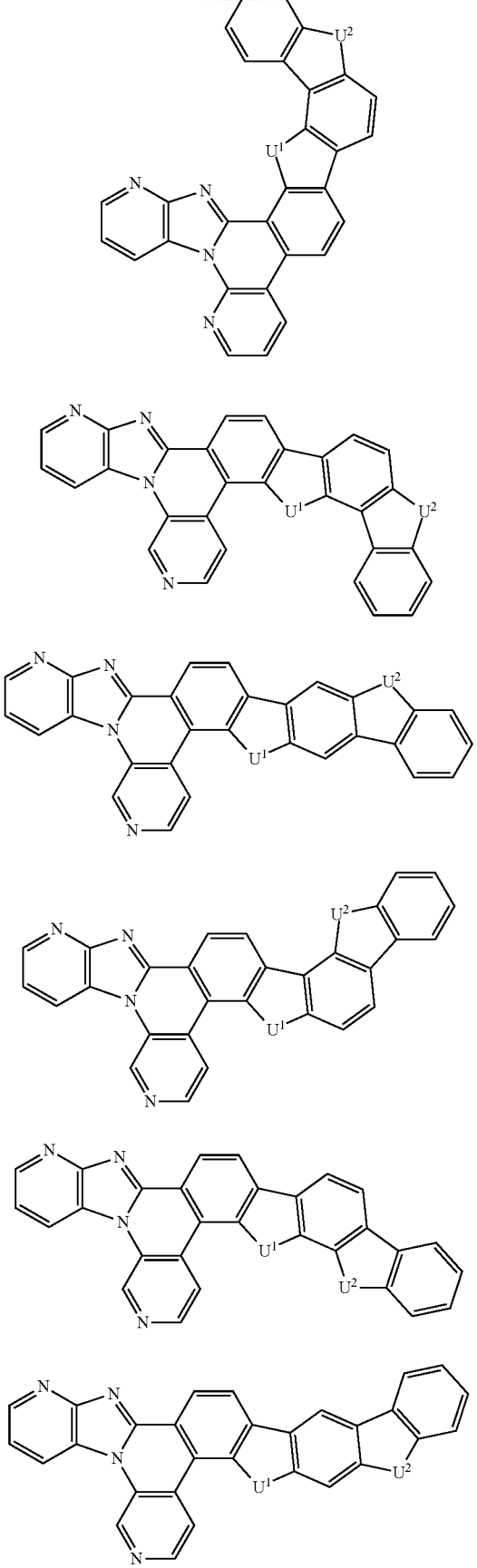
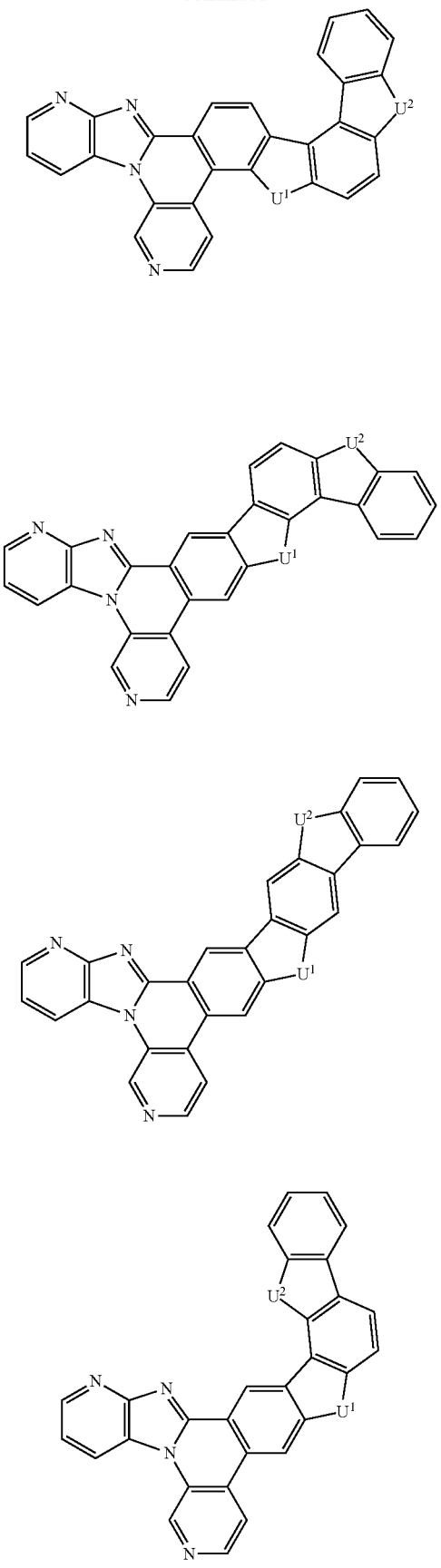

-continued
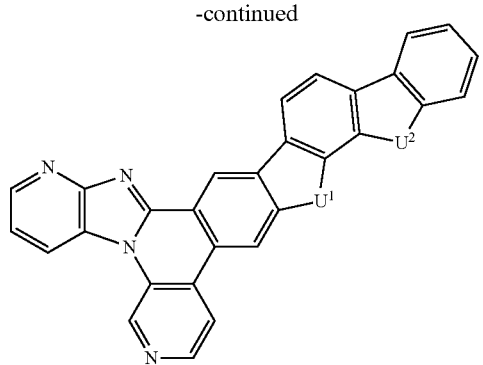
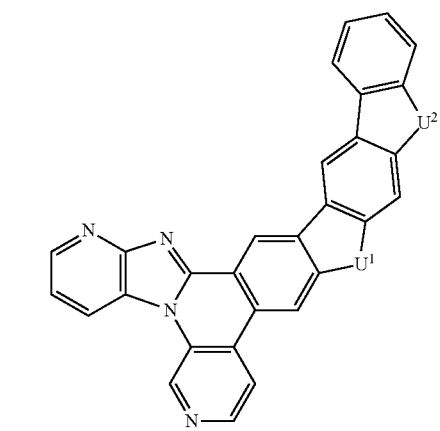
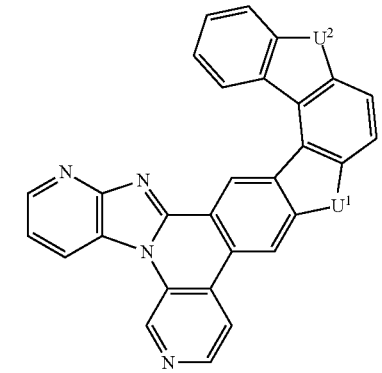
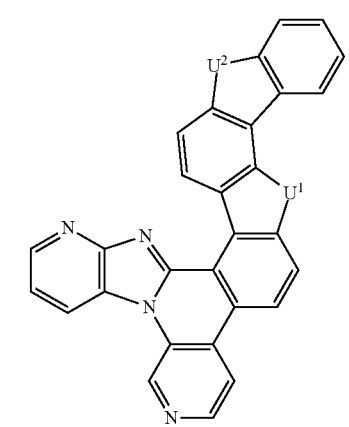
-continued
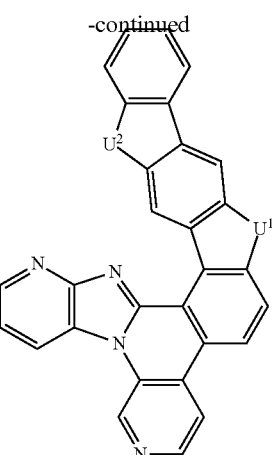
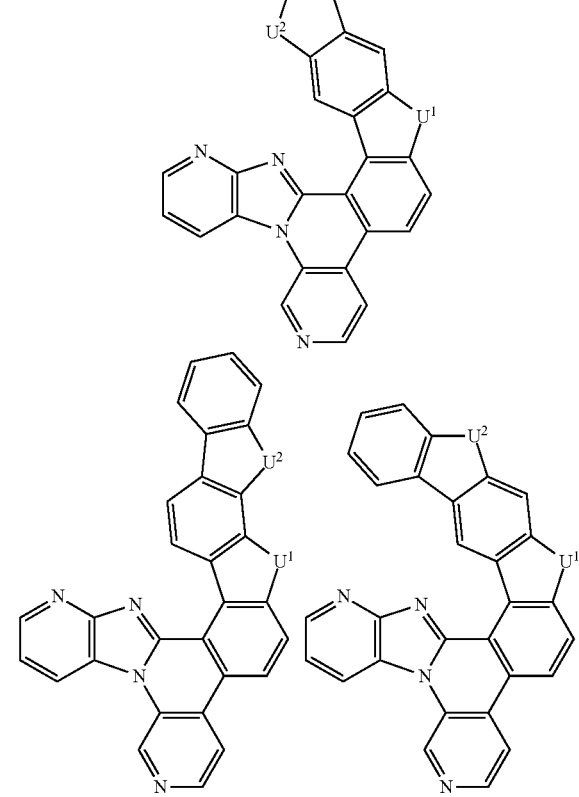
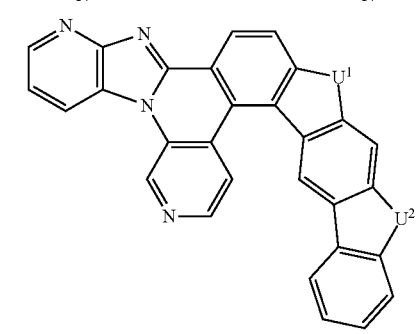
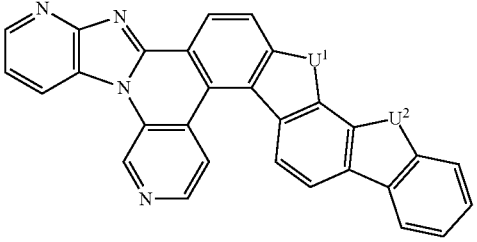
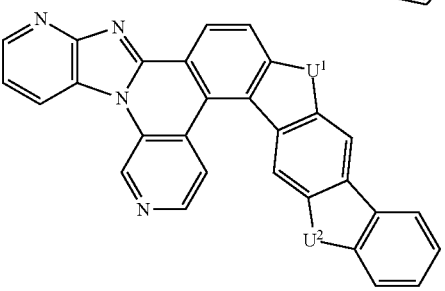

271
-continued
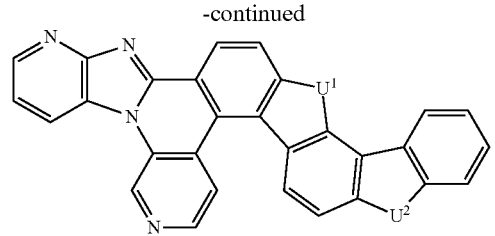
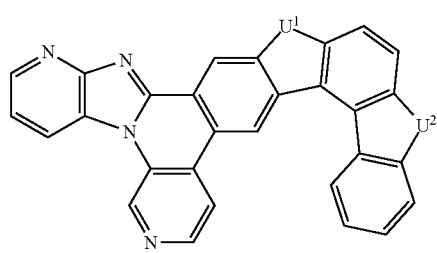
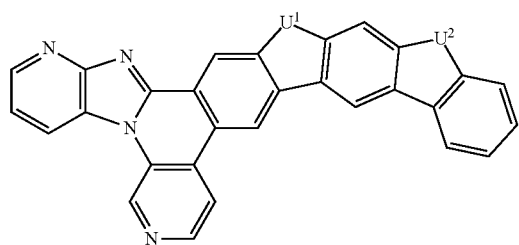
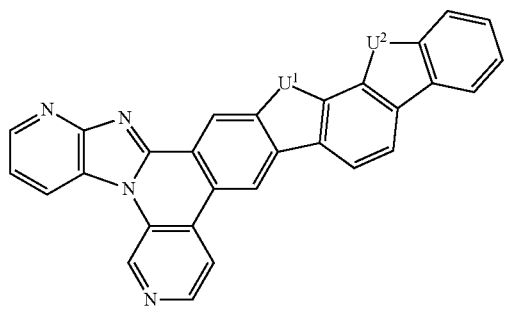
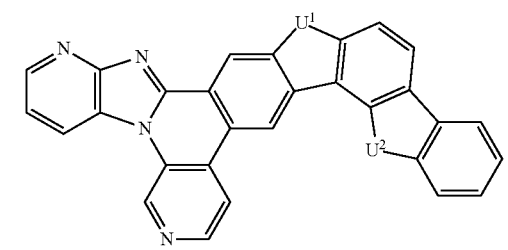
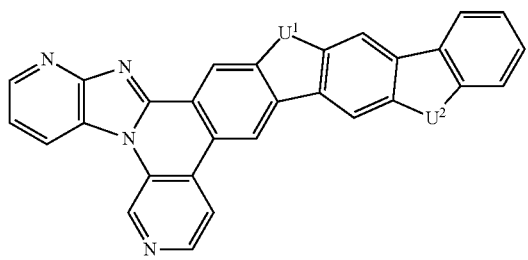
272
-continued
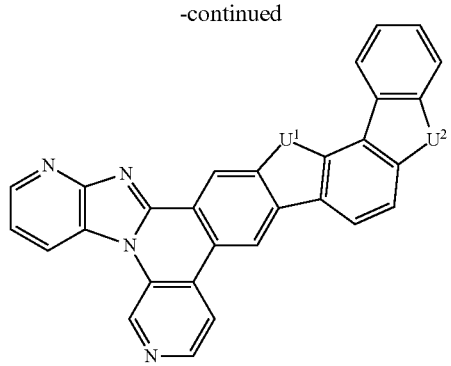
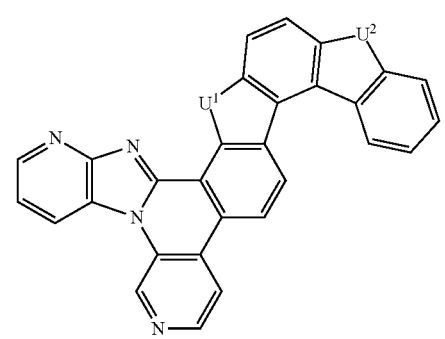
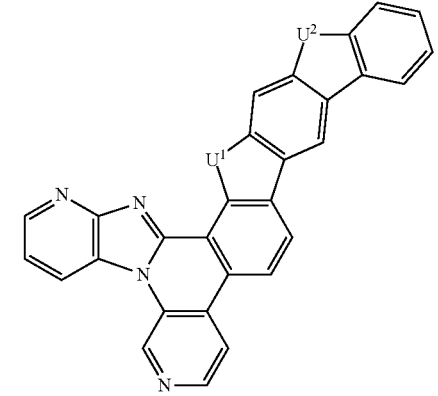
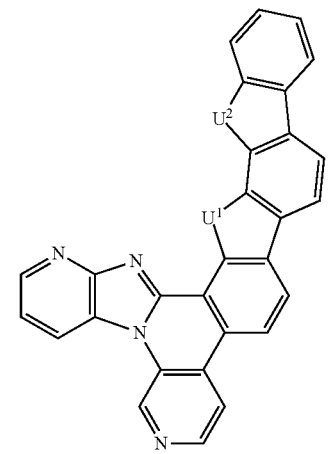

-continued
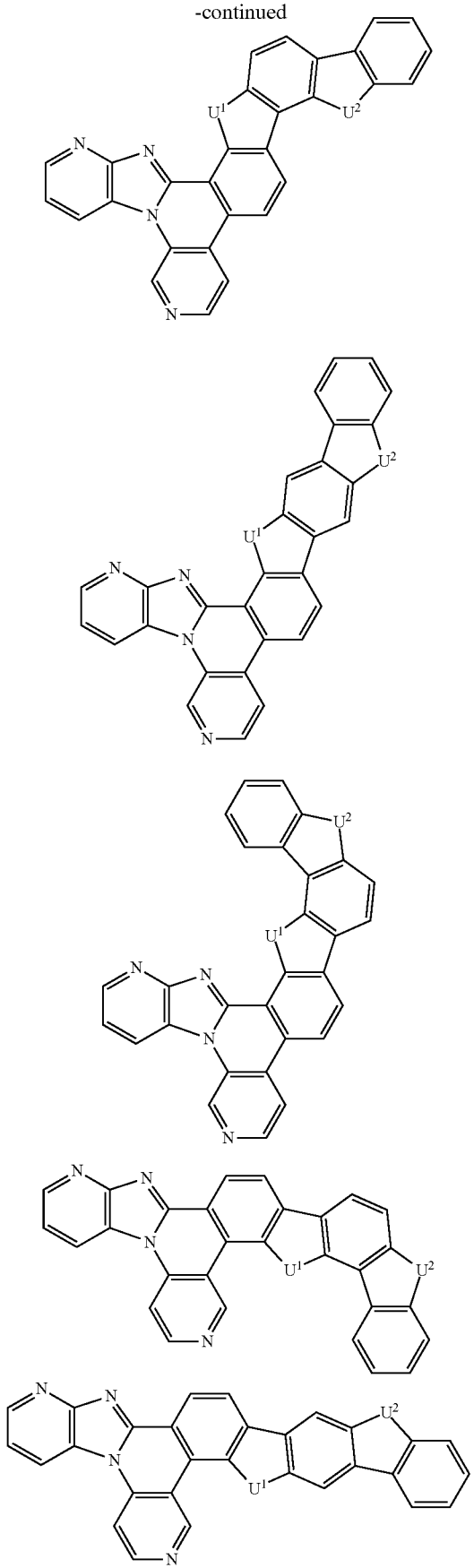
-continued
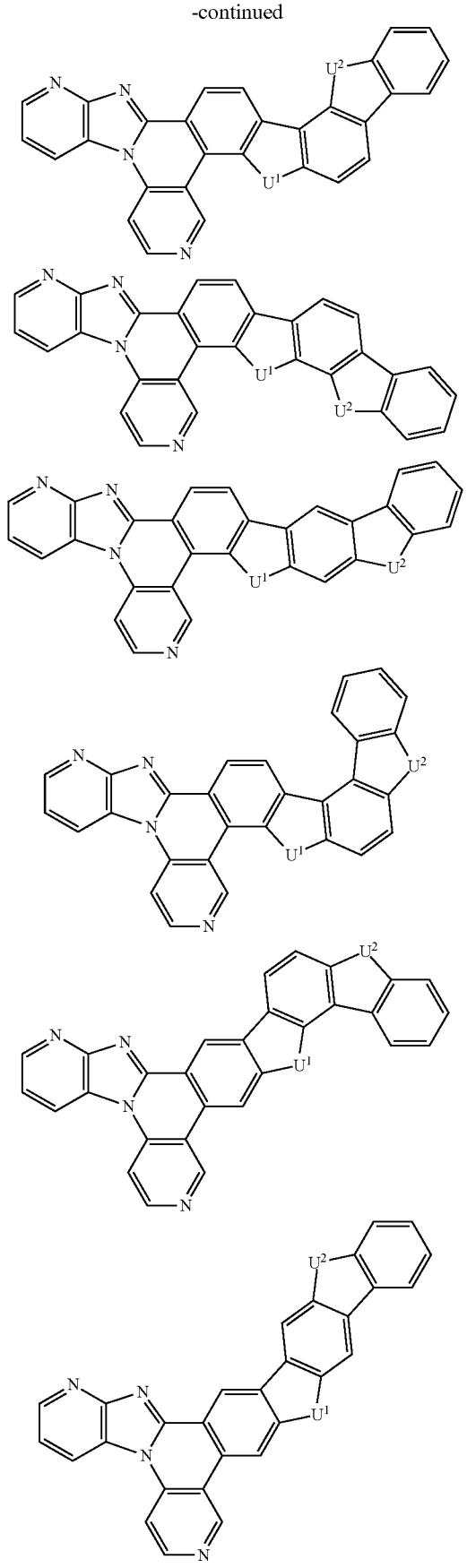

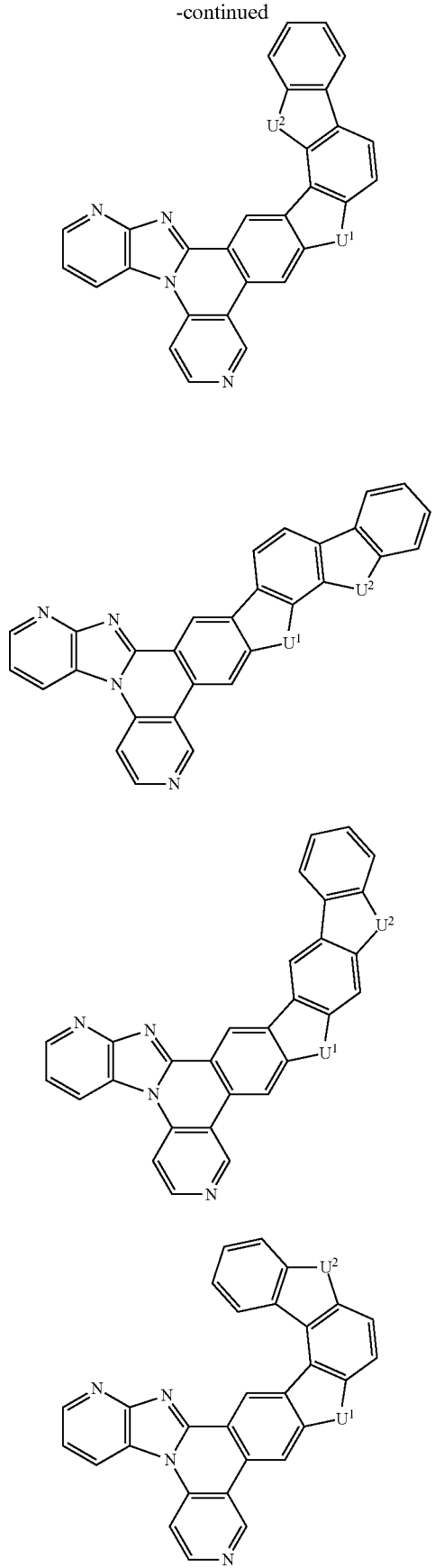
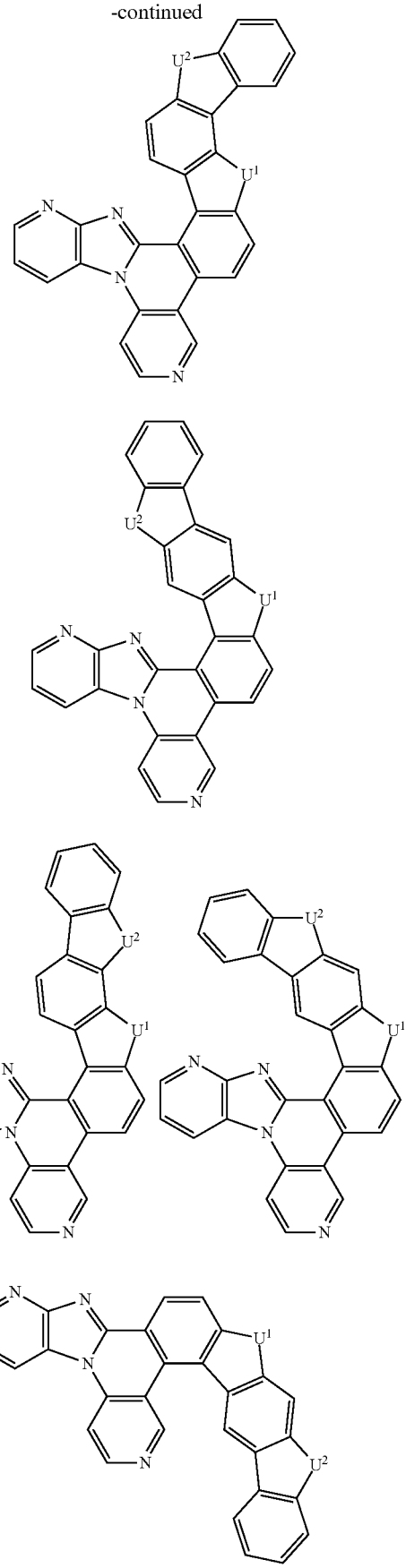

277
-continued
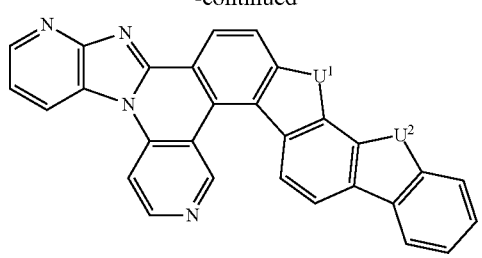
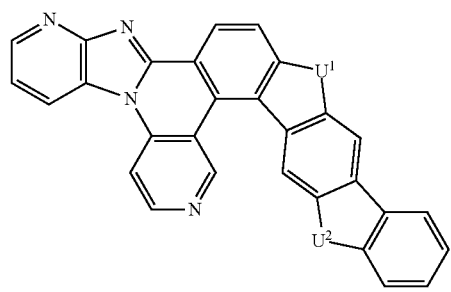
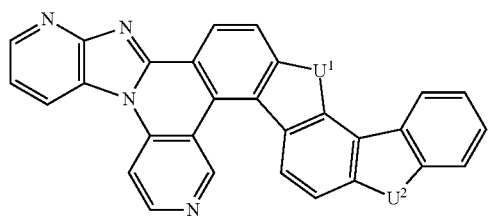
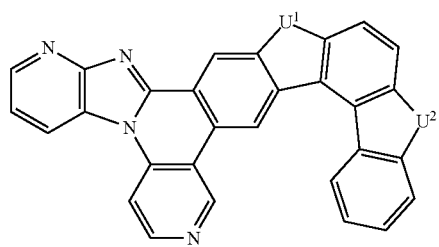
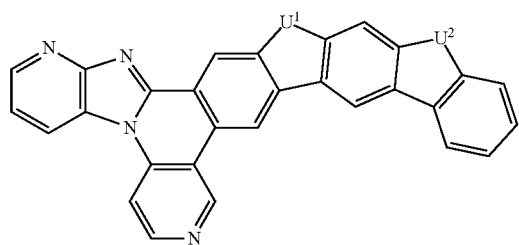
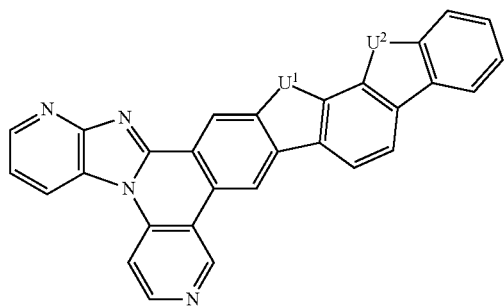
278
-continued
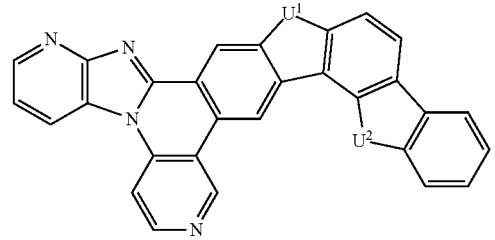
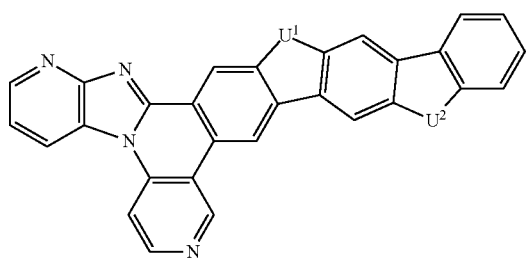
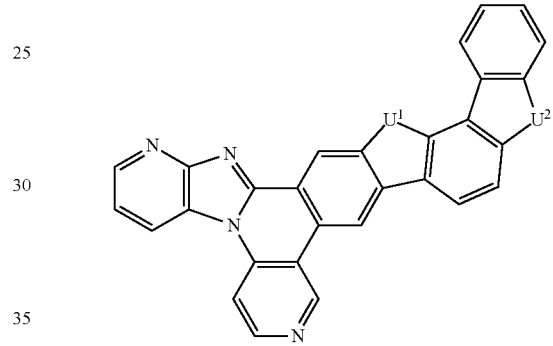
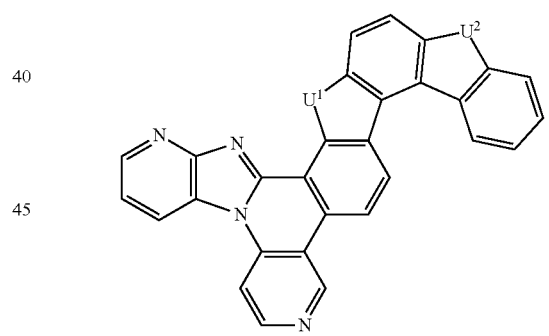
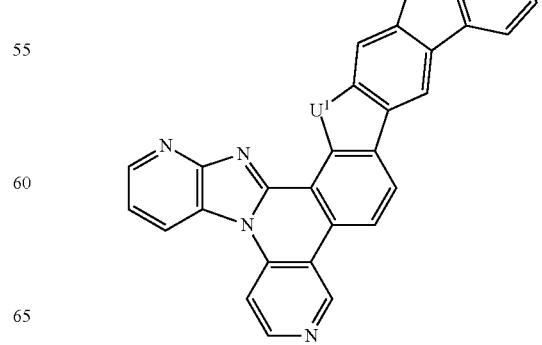

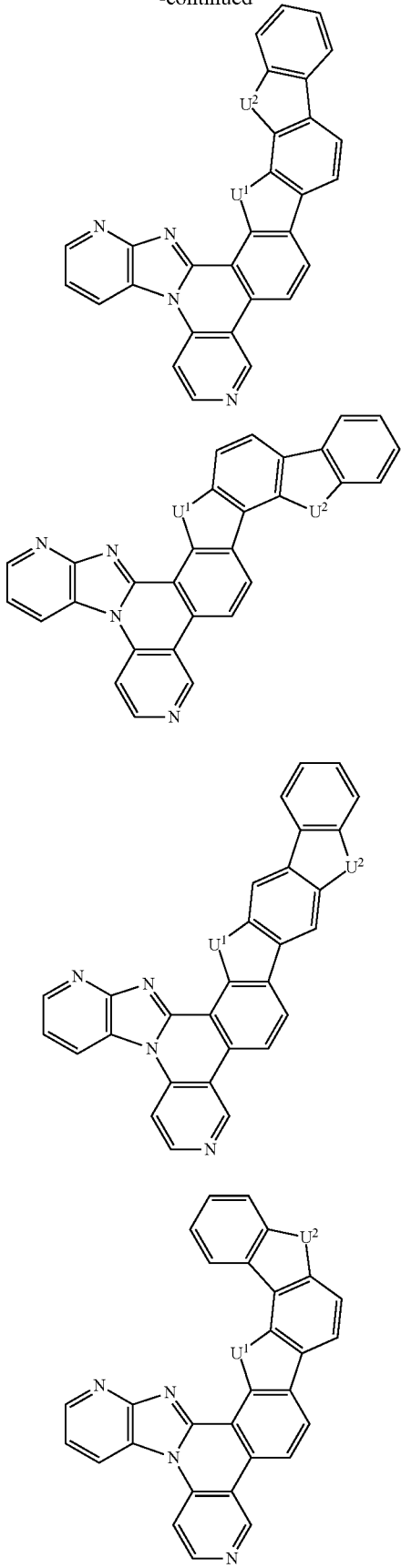
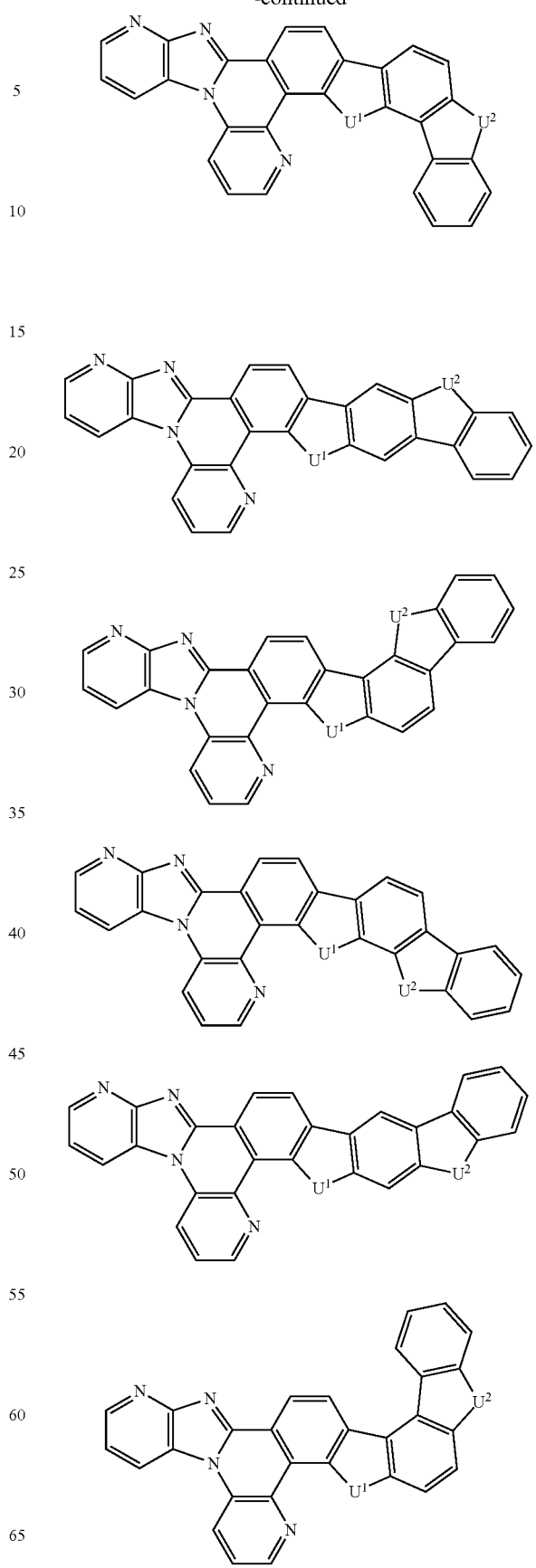

-continued
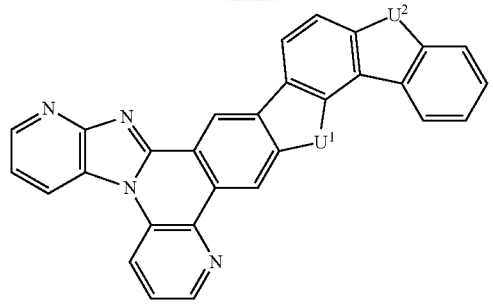
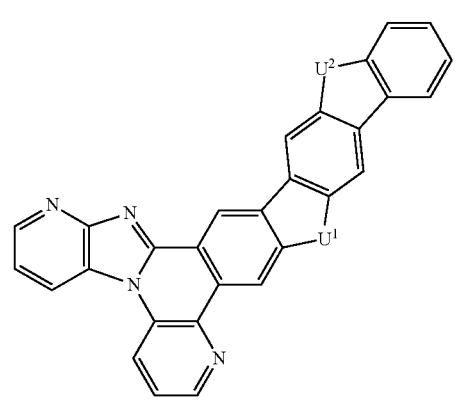
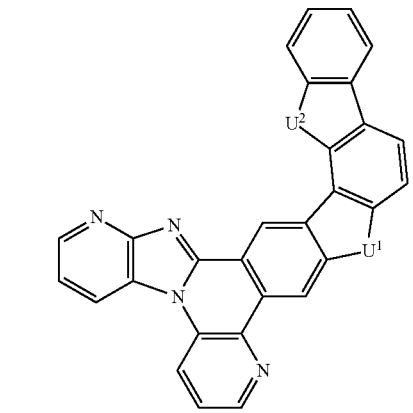

-continued
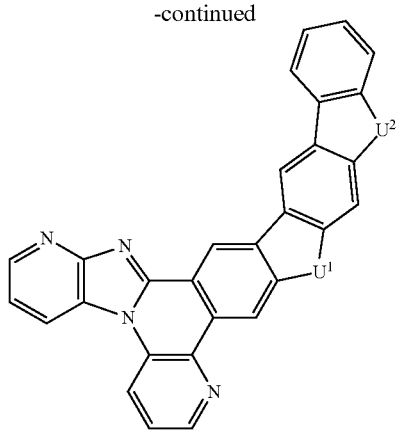
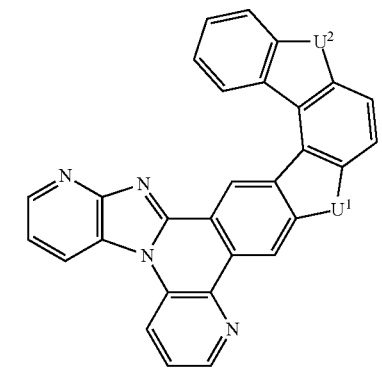
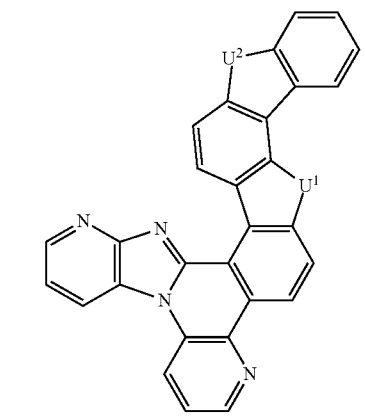

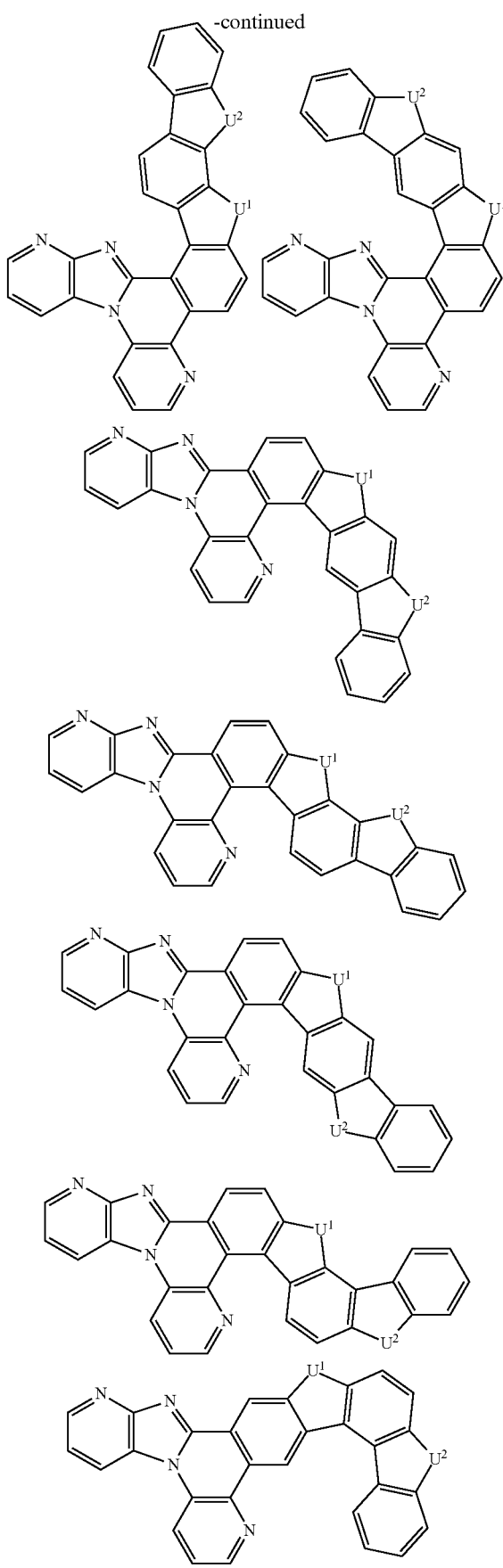
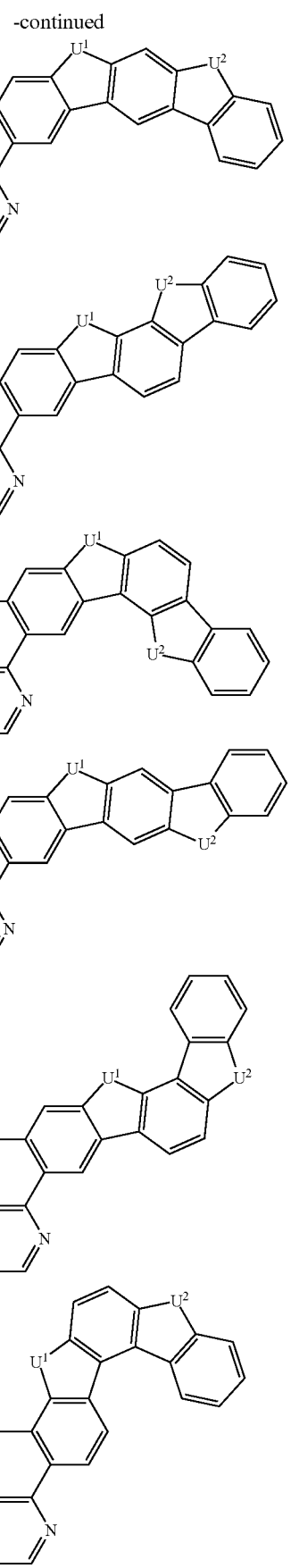

-continued
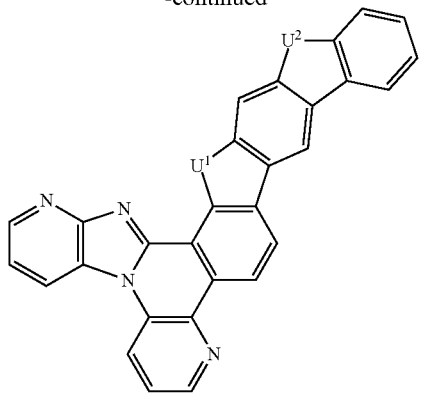
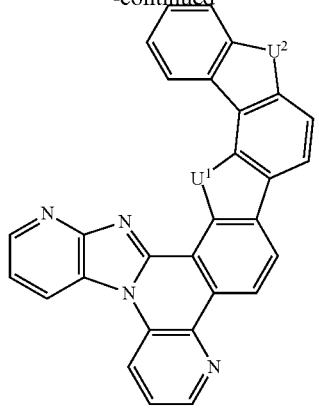
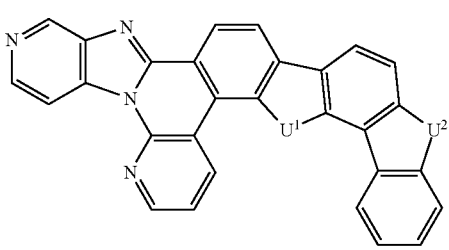
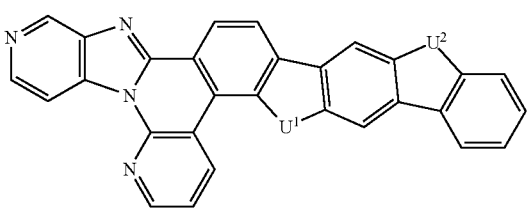
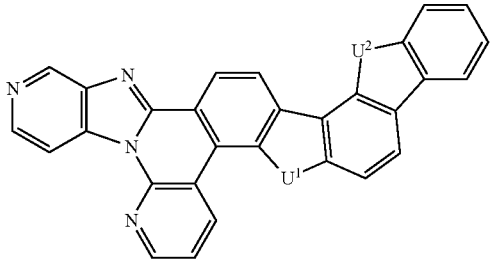
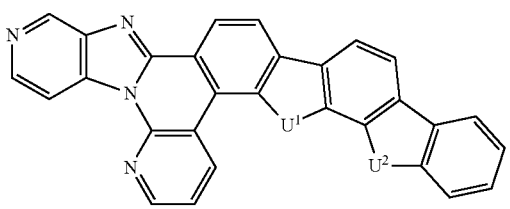
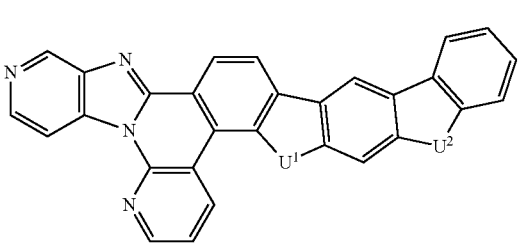

287
-continued
288
-continued
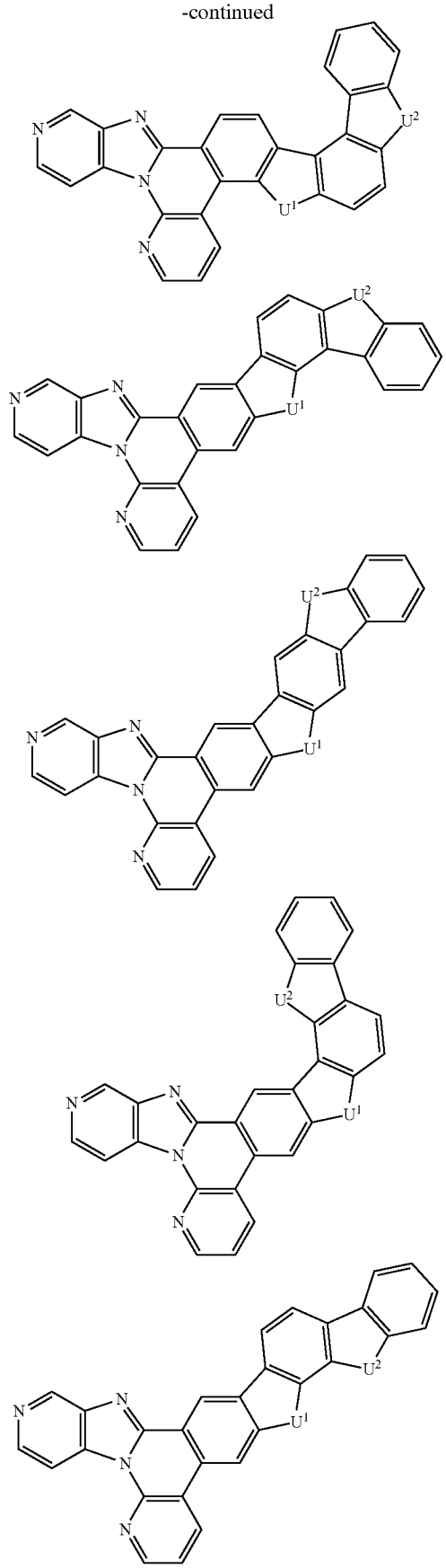
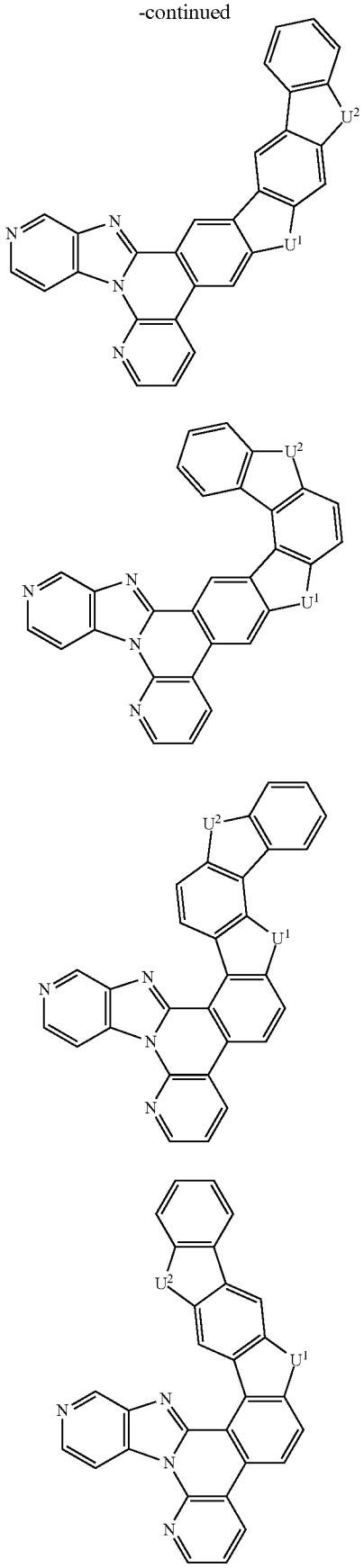

-continued
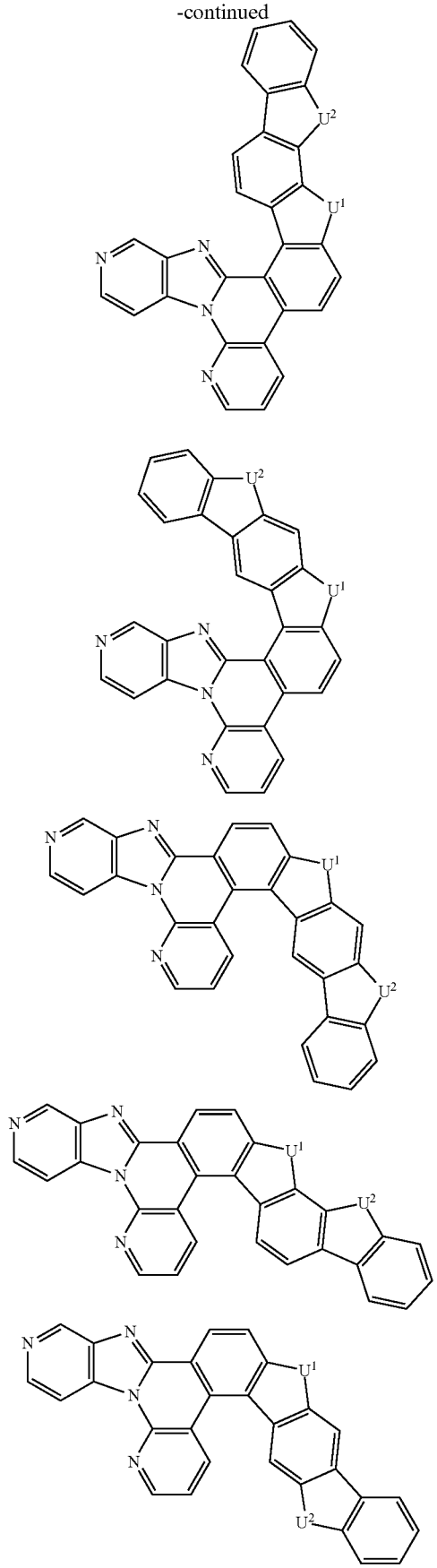
-continued
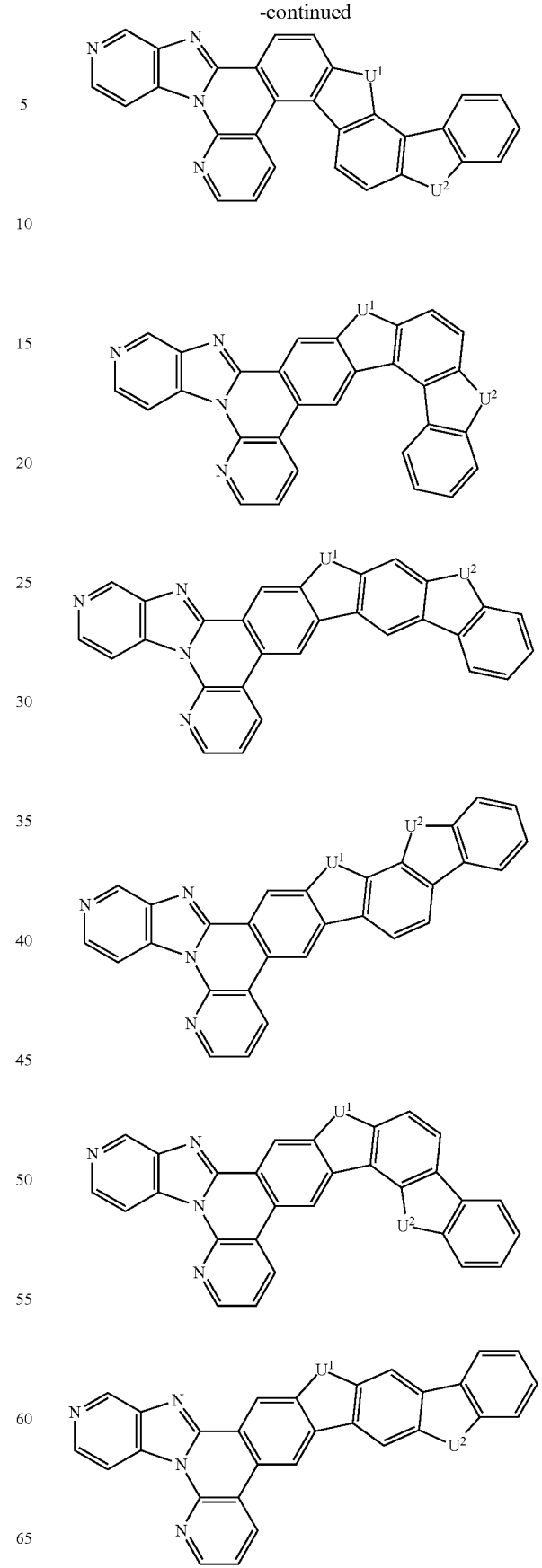

-continued
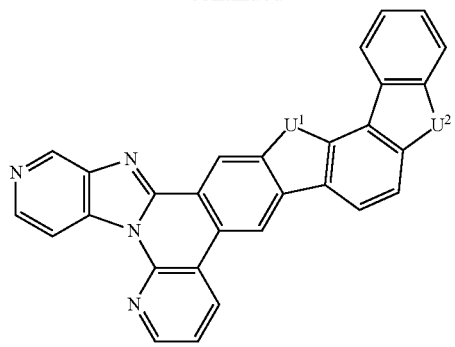
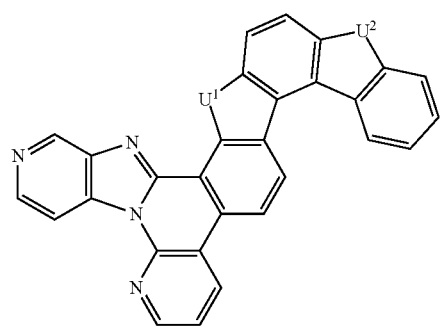
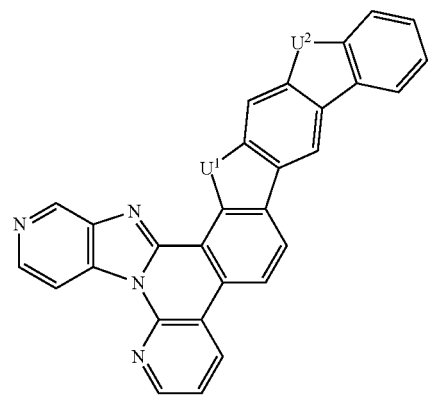
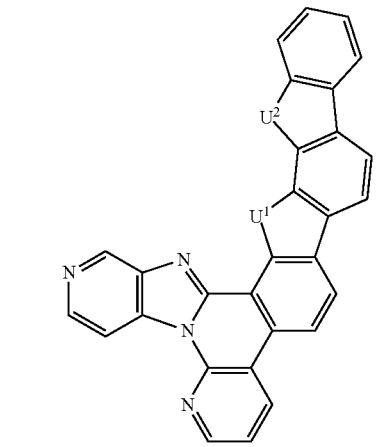
-continued
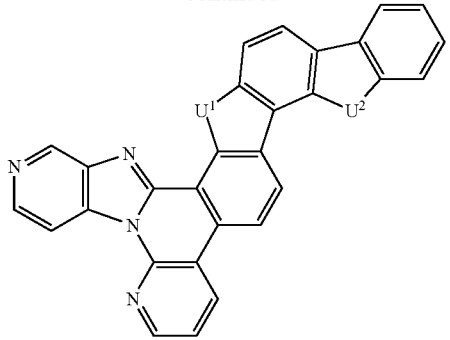
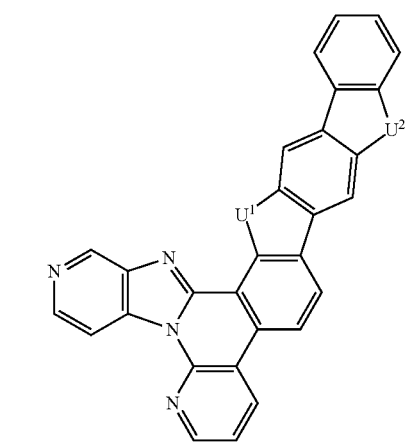
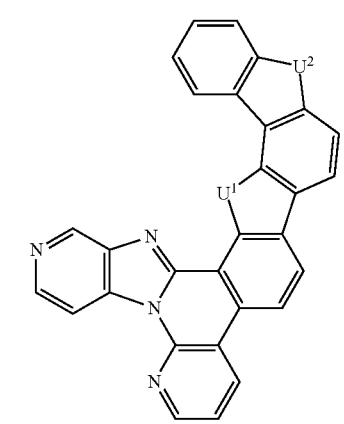
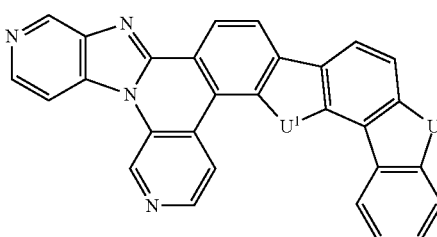
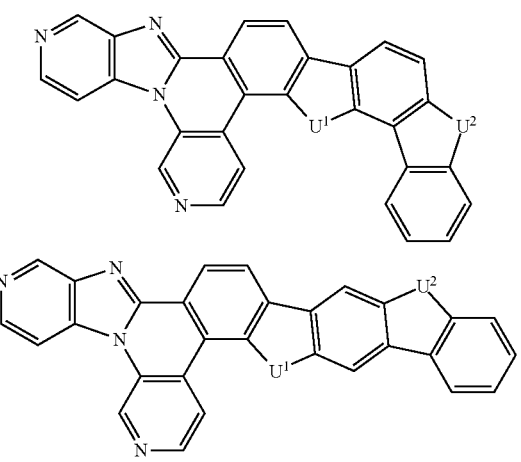

-continued
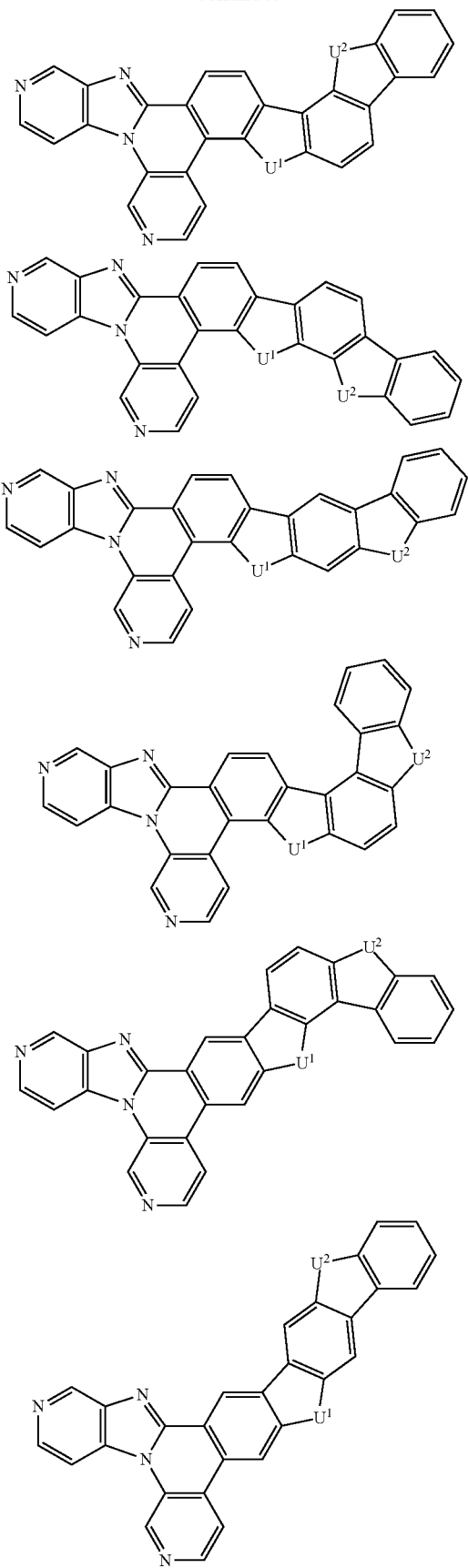
-continued
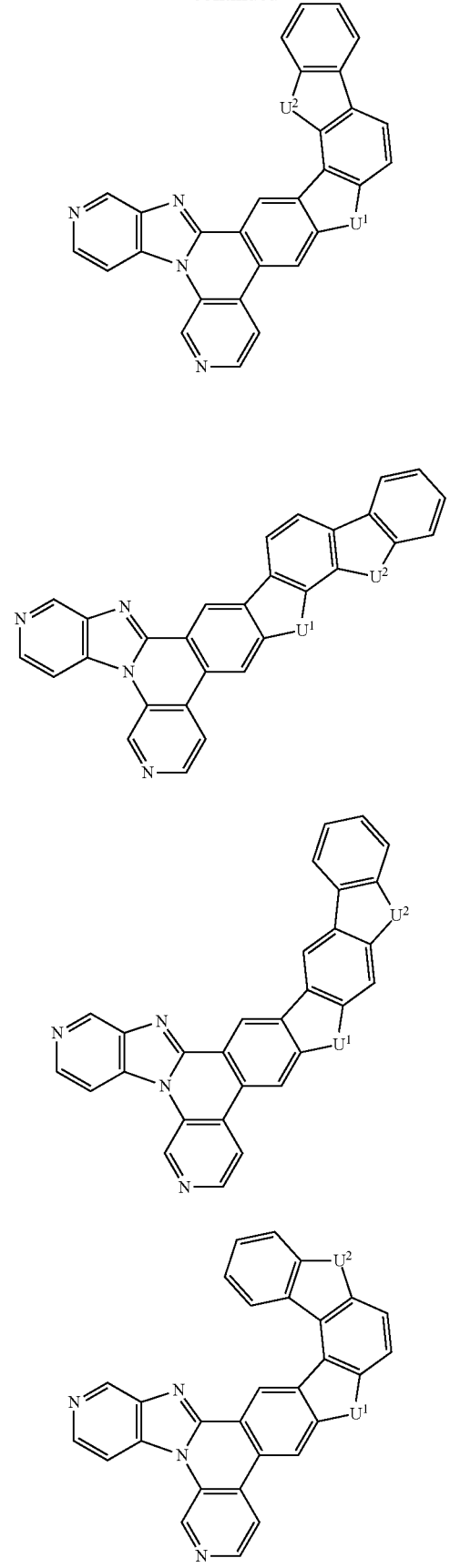

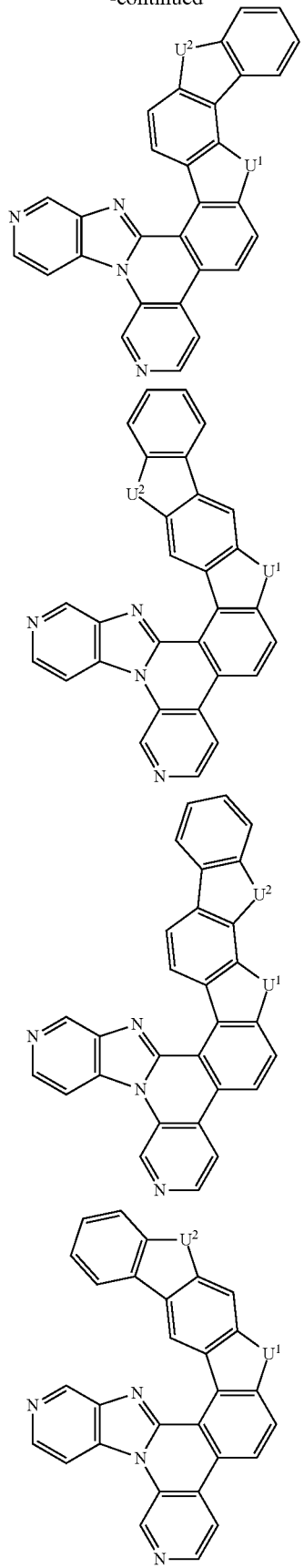
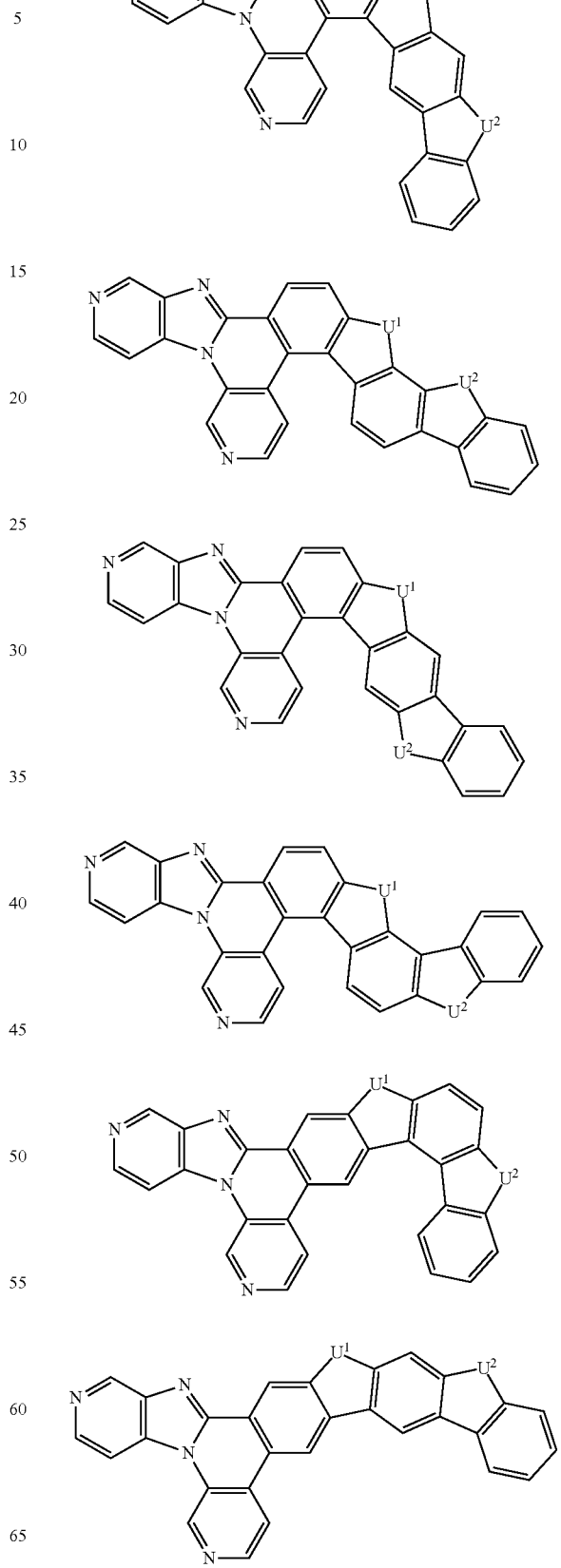

-continued
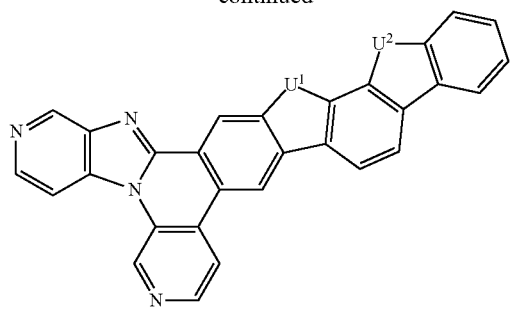
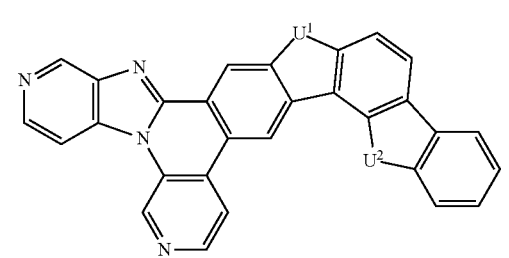
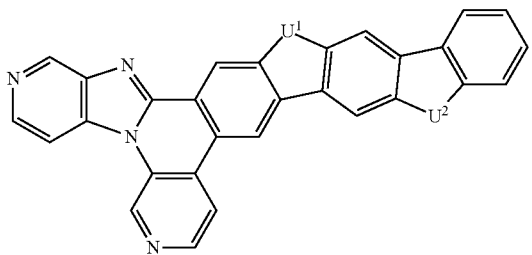
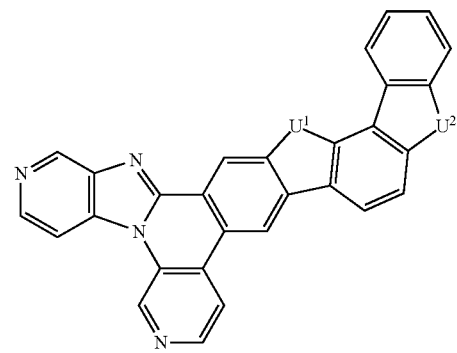
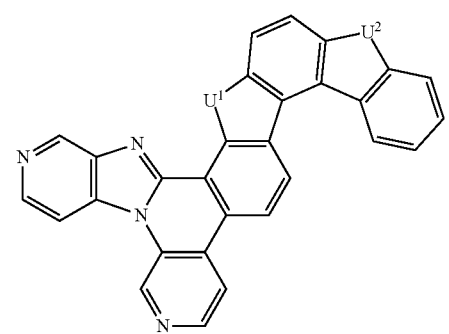
-continued
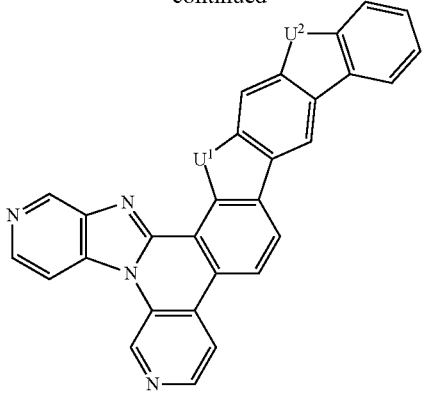
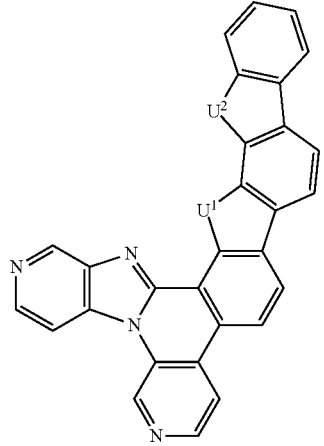
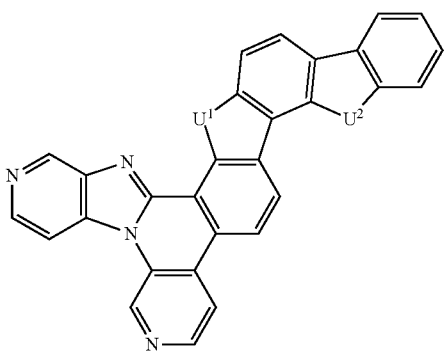
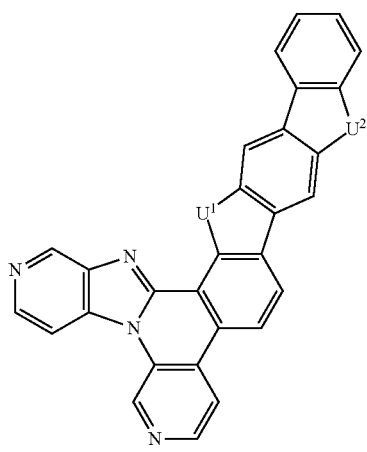

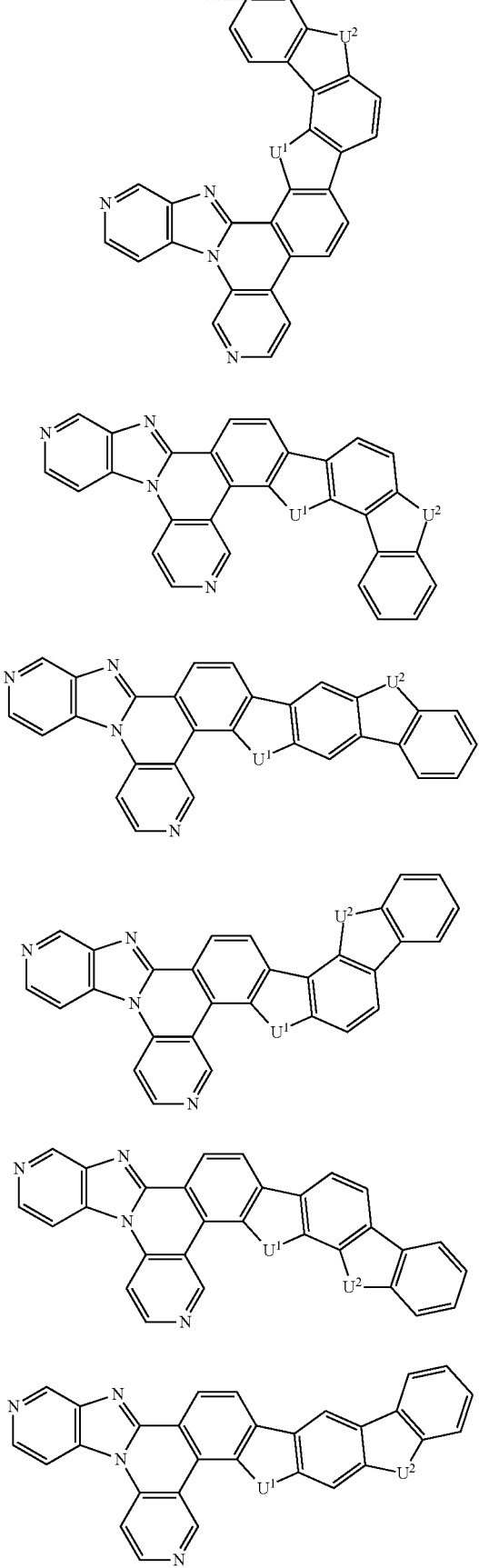
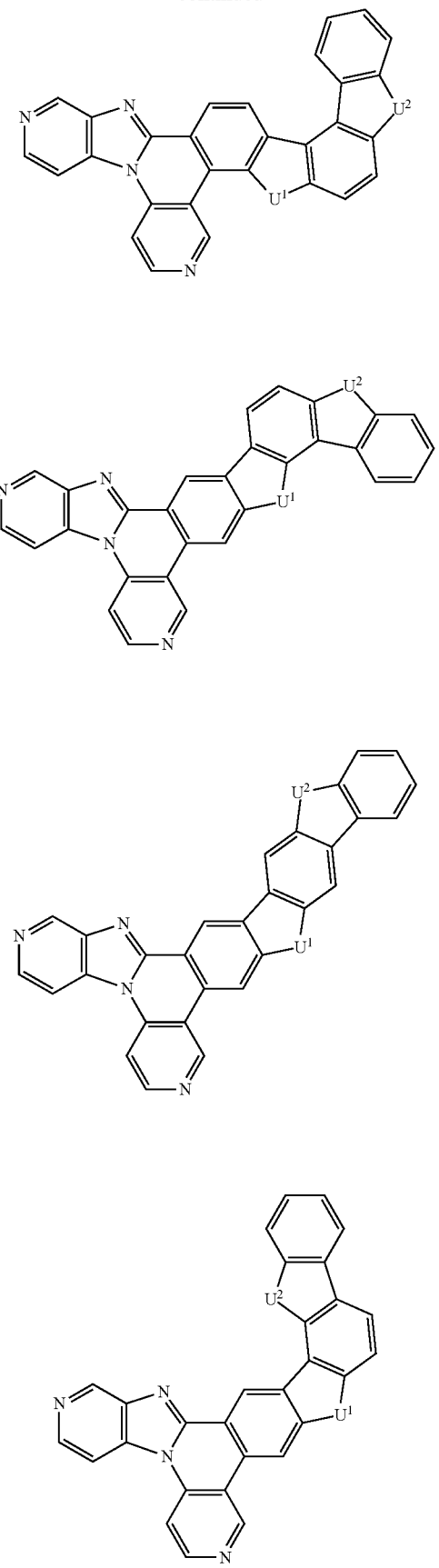

301
-continued
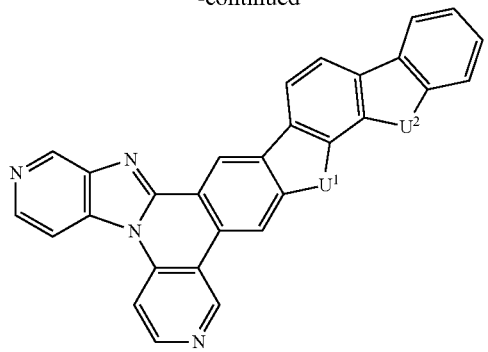
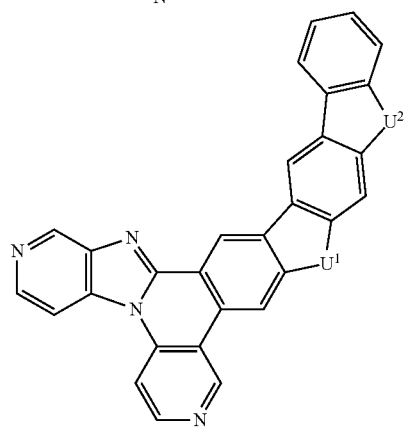
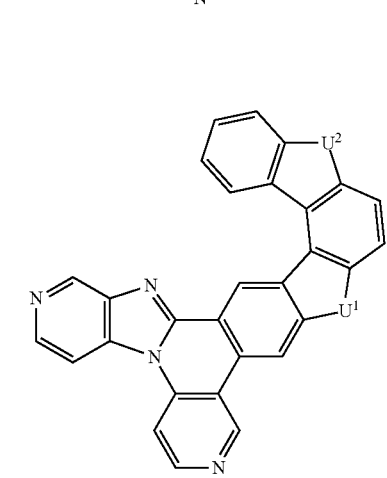
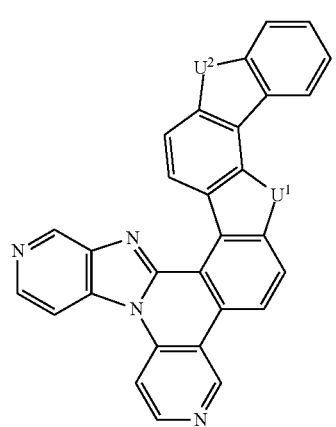
302
-continued
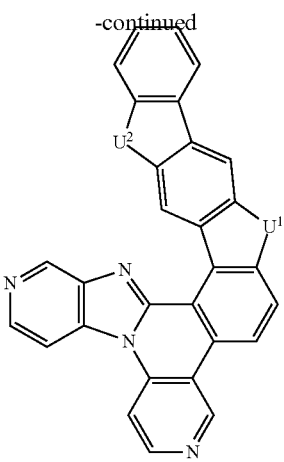
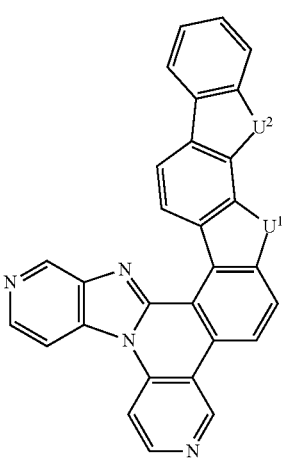
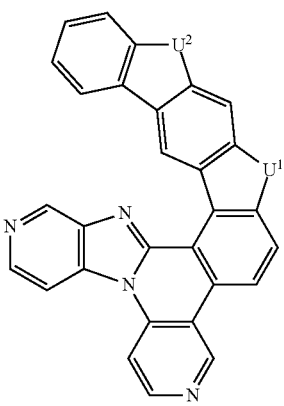
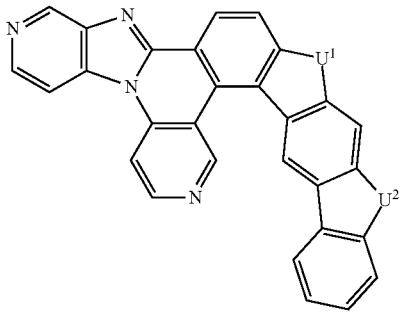

303
-continued
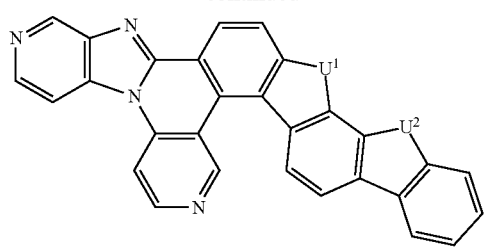
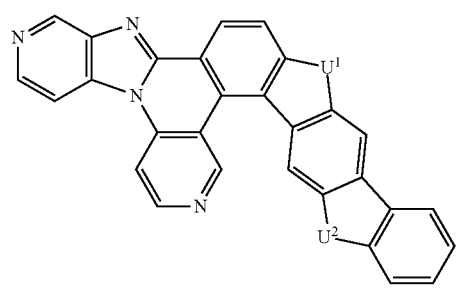
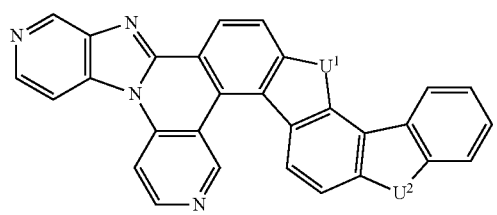
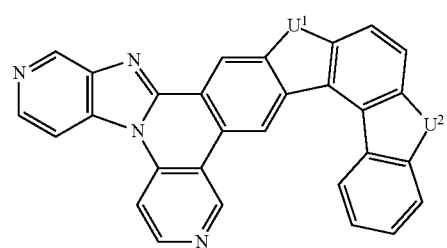
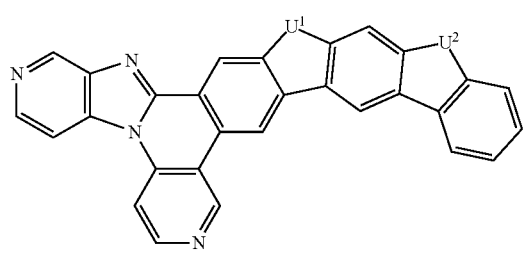
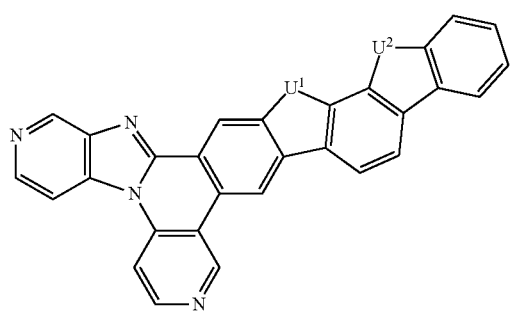
304
-continued
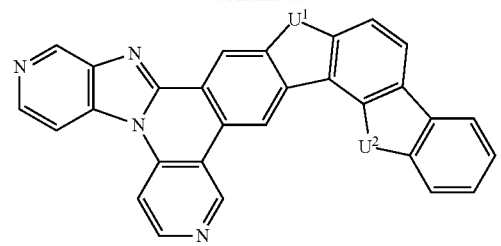
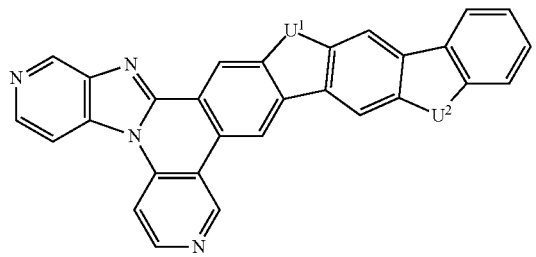
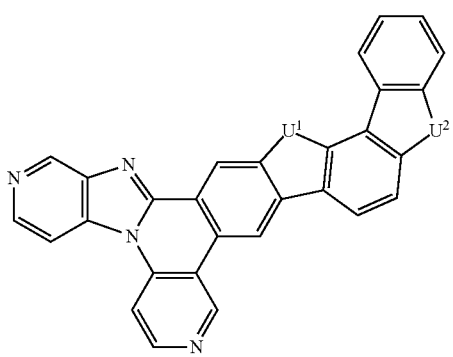
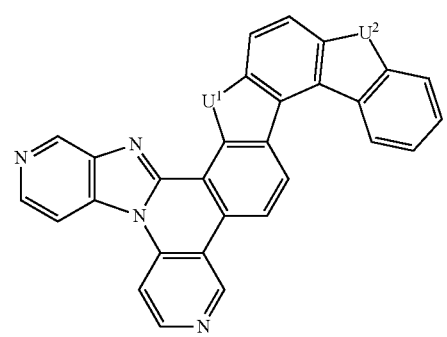
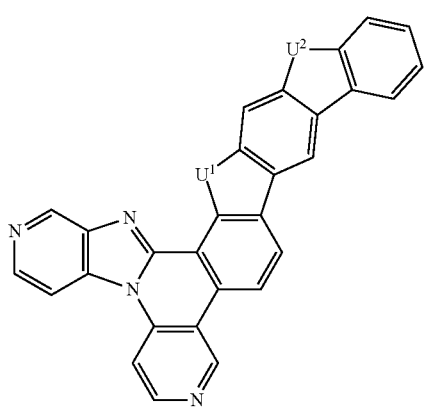

305
-continued
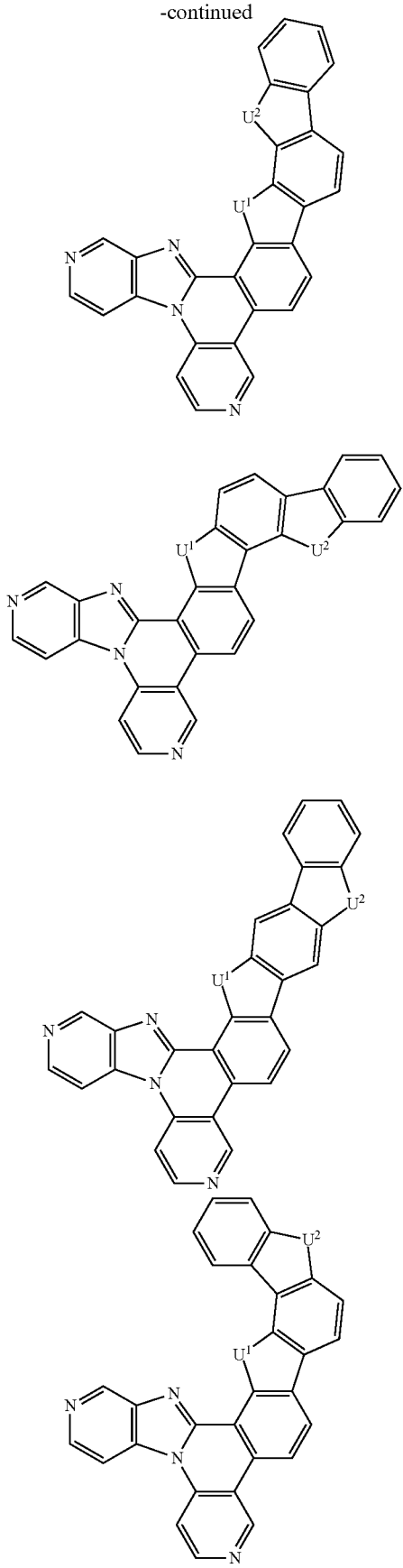
306
-continued
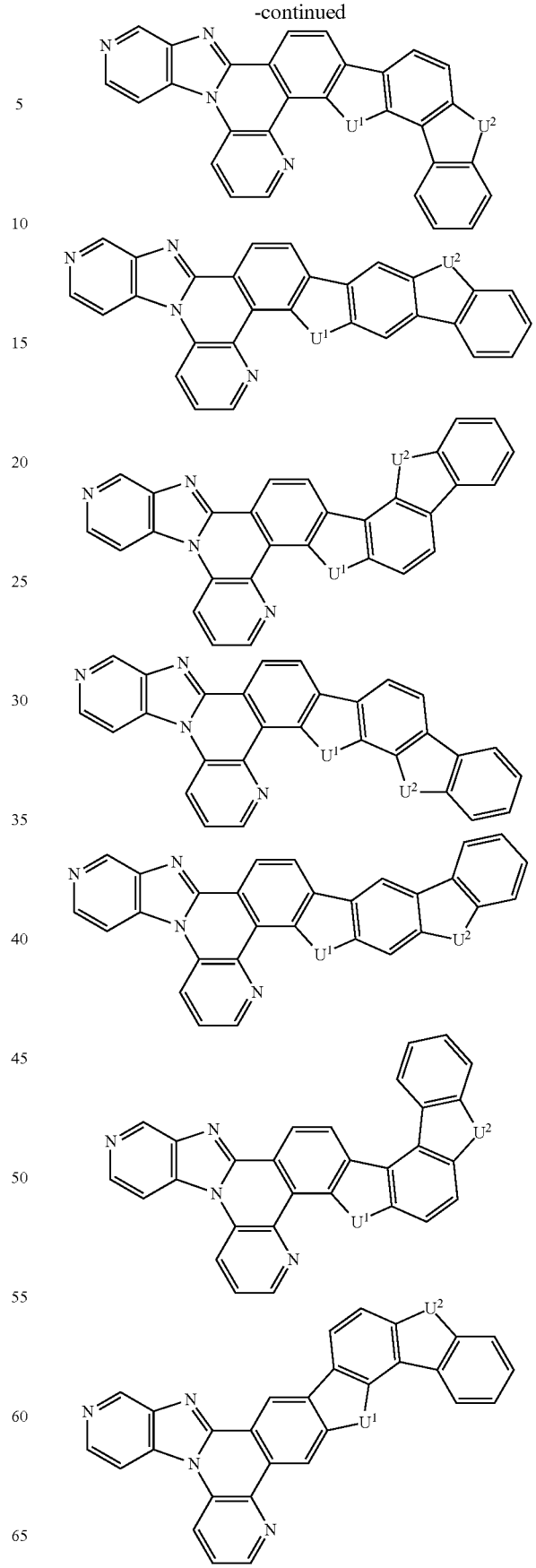

307
-continued
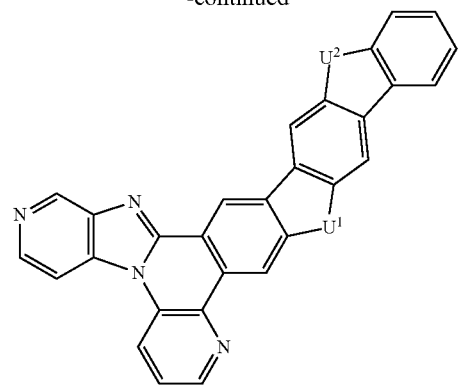
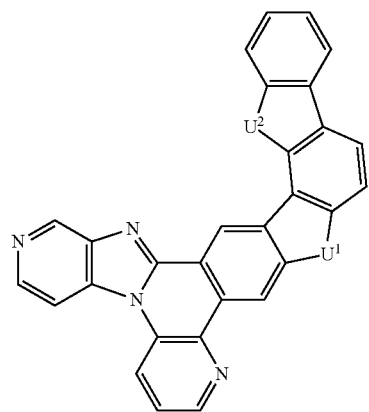
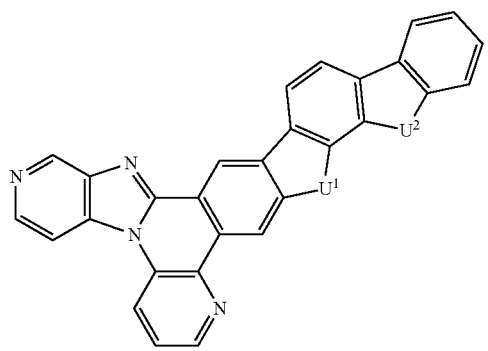
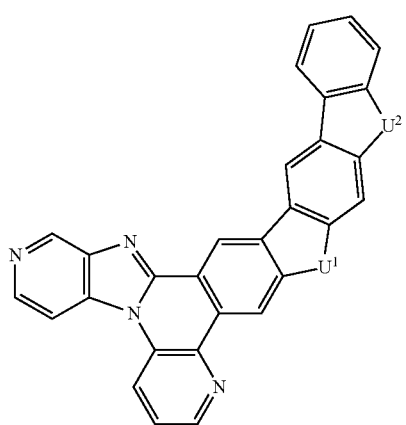
308
-continued
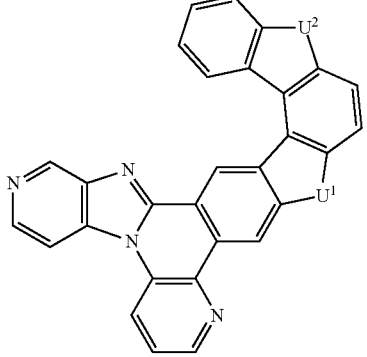
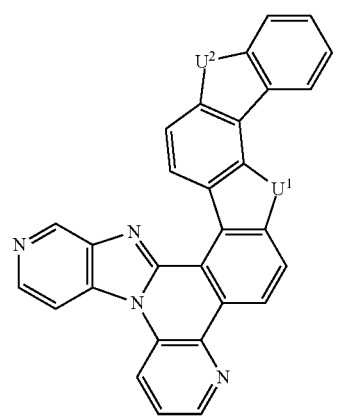
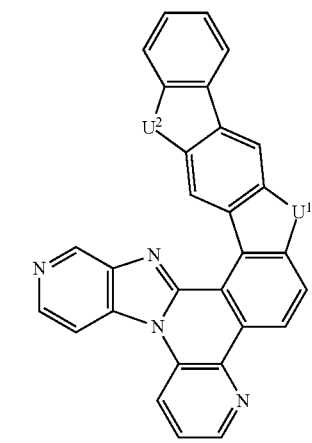
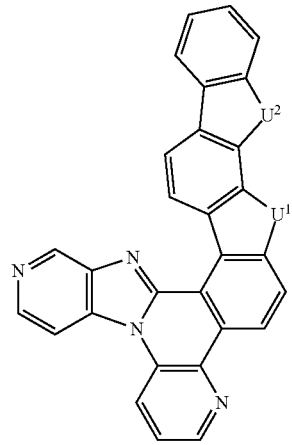

309
-continued
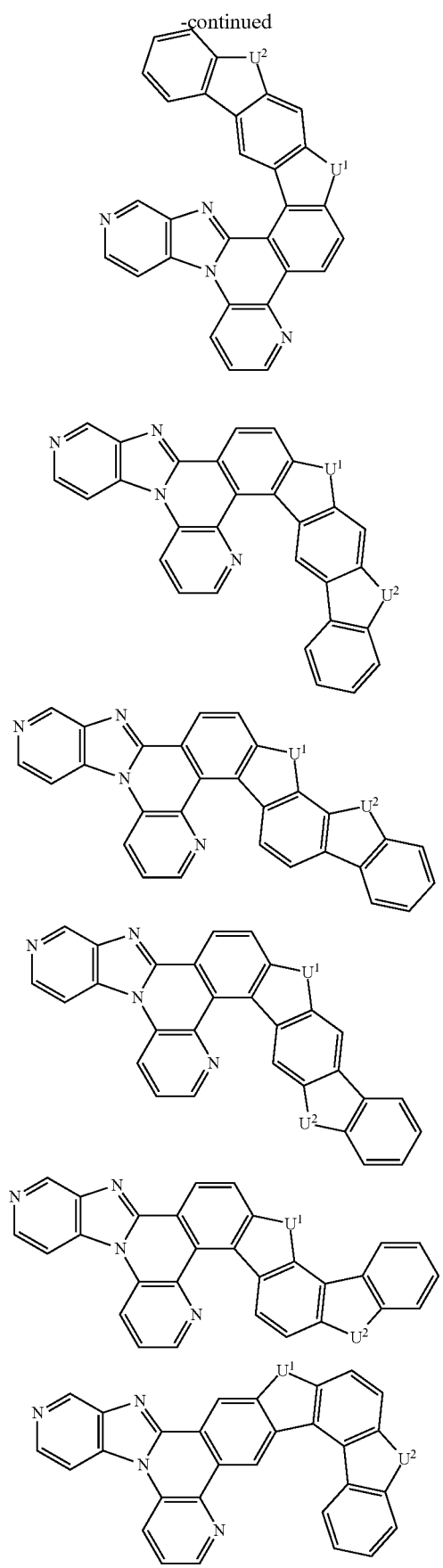
310
-continued
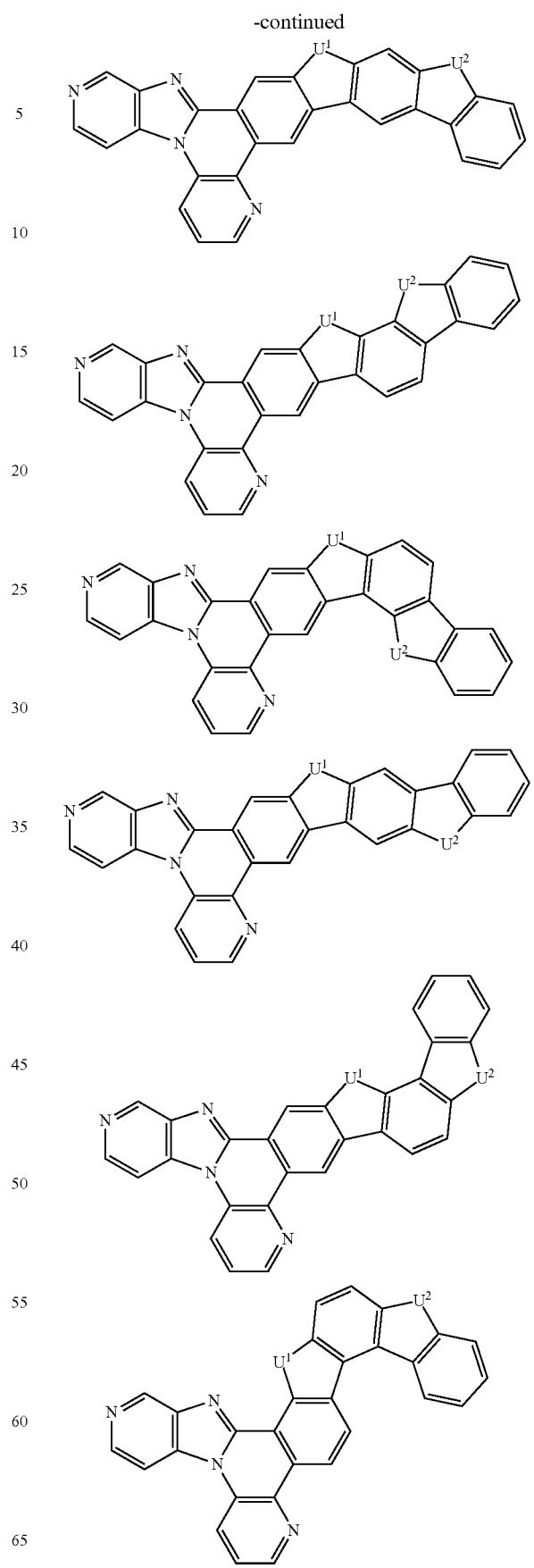

311
-continued
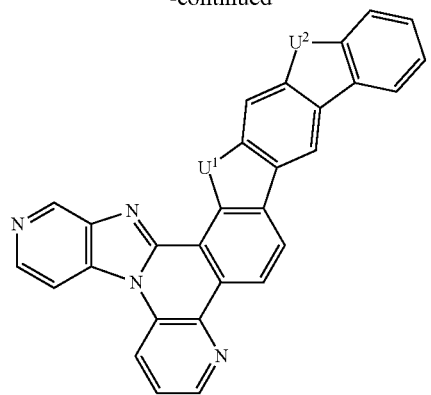
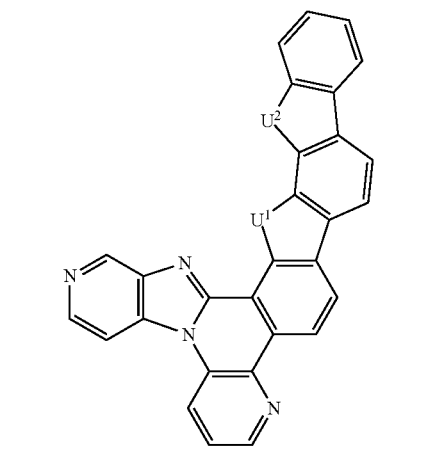
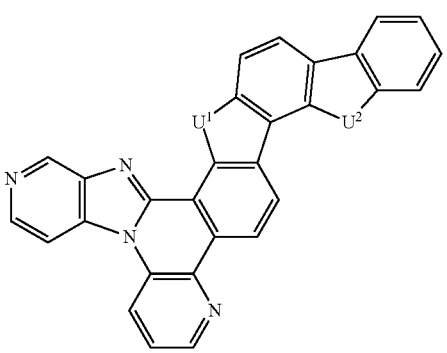
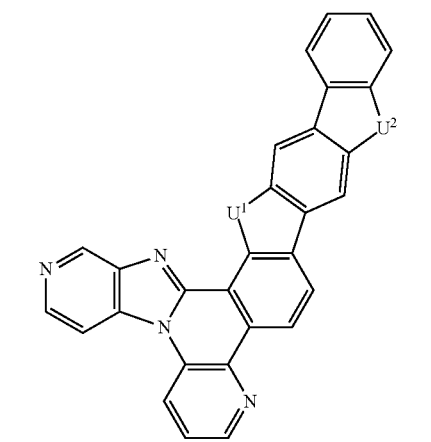
312
-continued
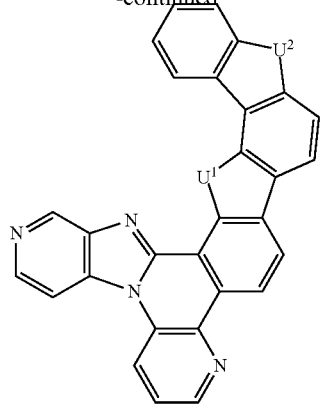
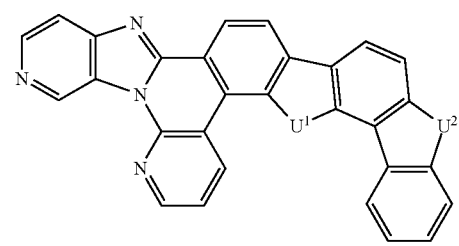
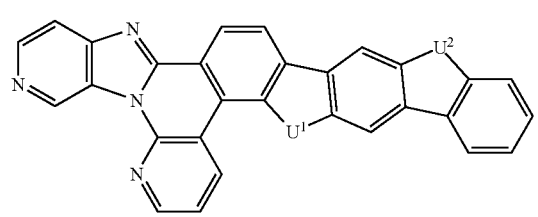
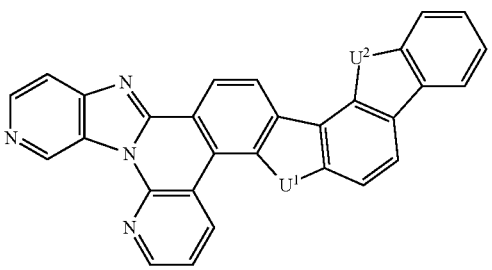
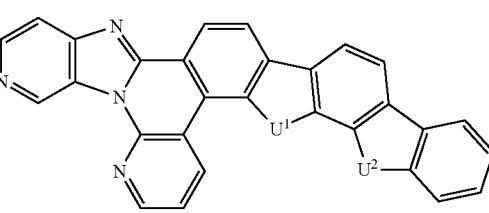
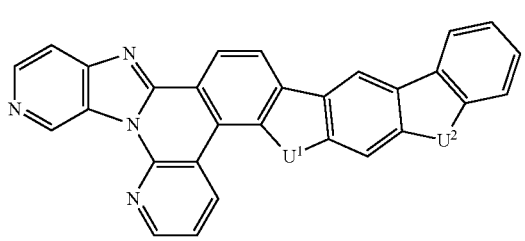

313
-continued
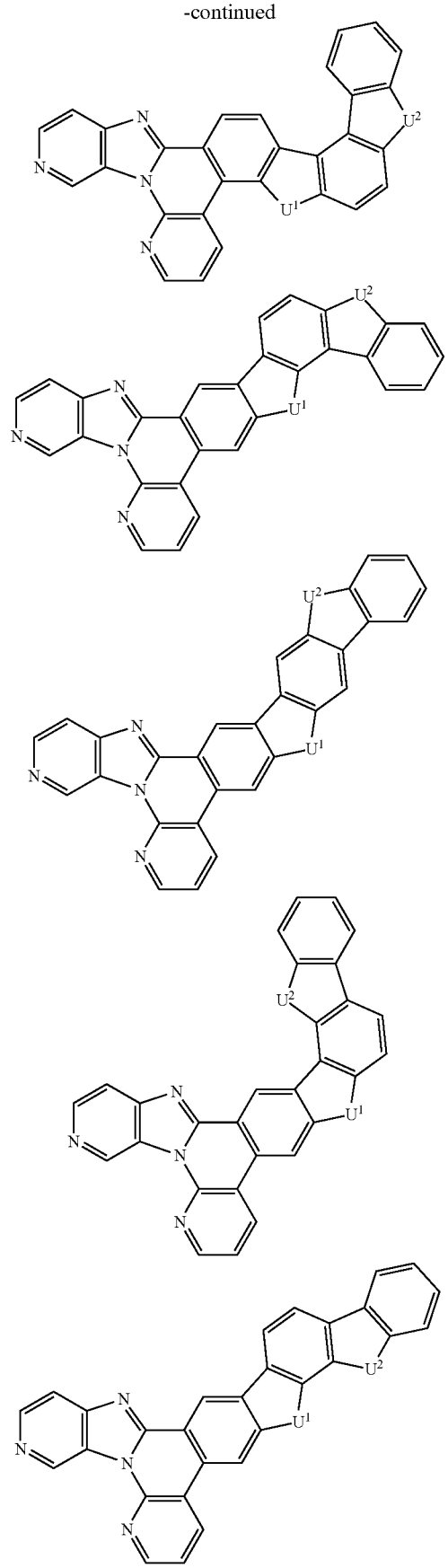
314
-continued
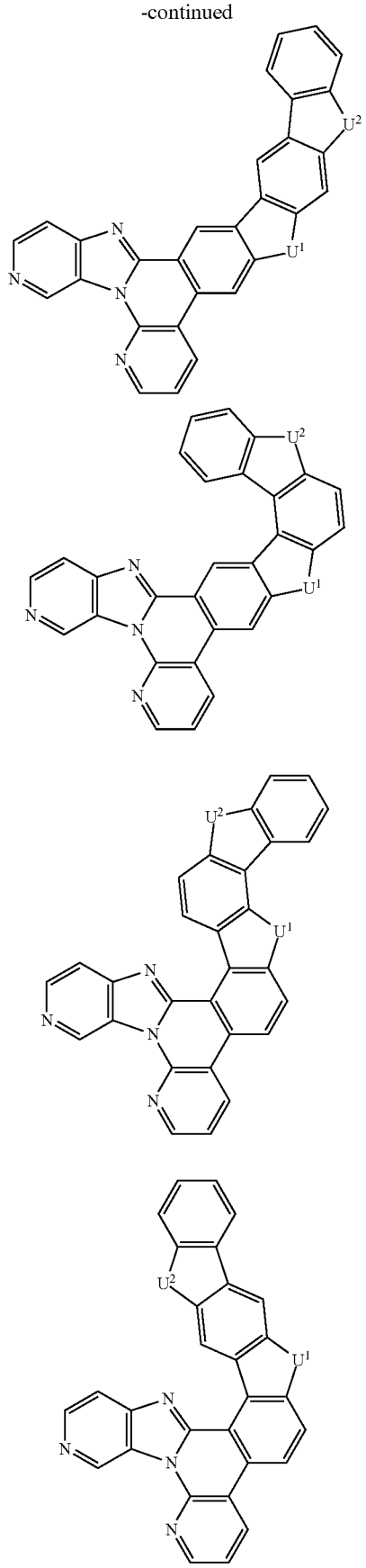

315
-continued
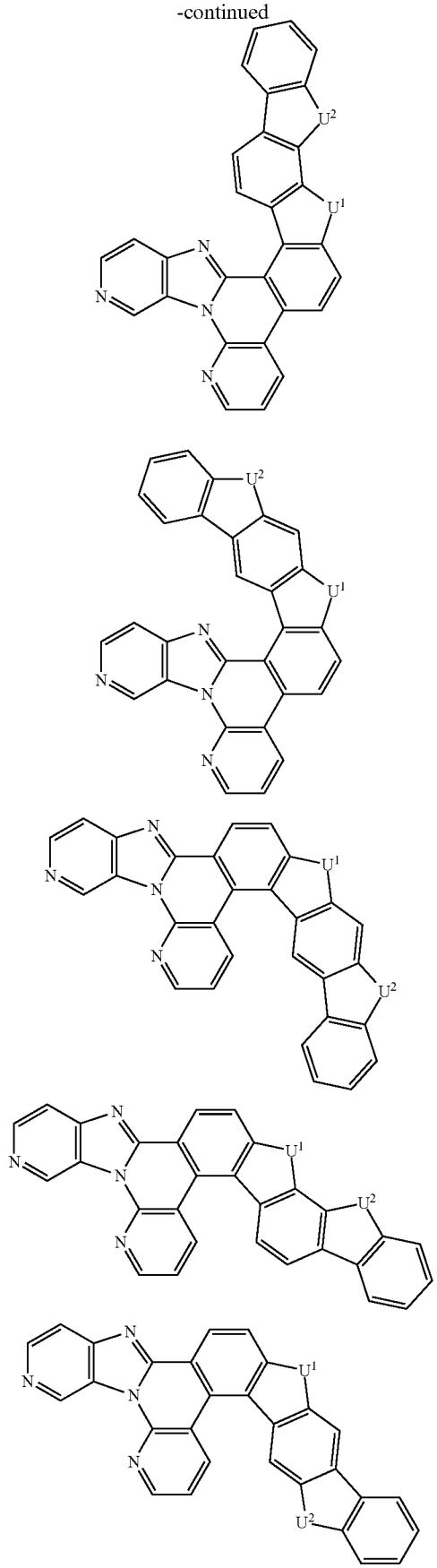
316
-continued
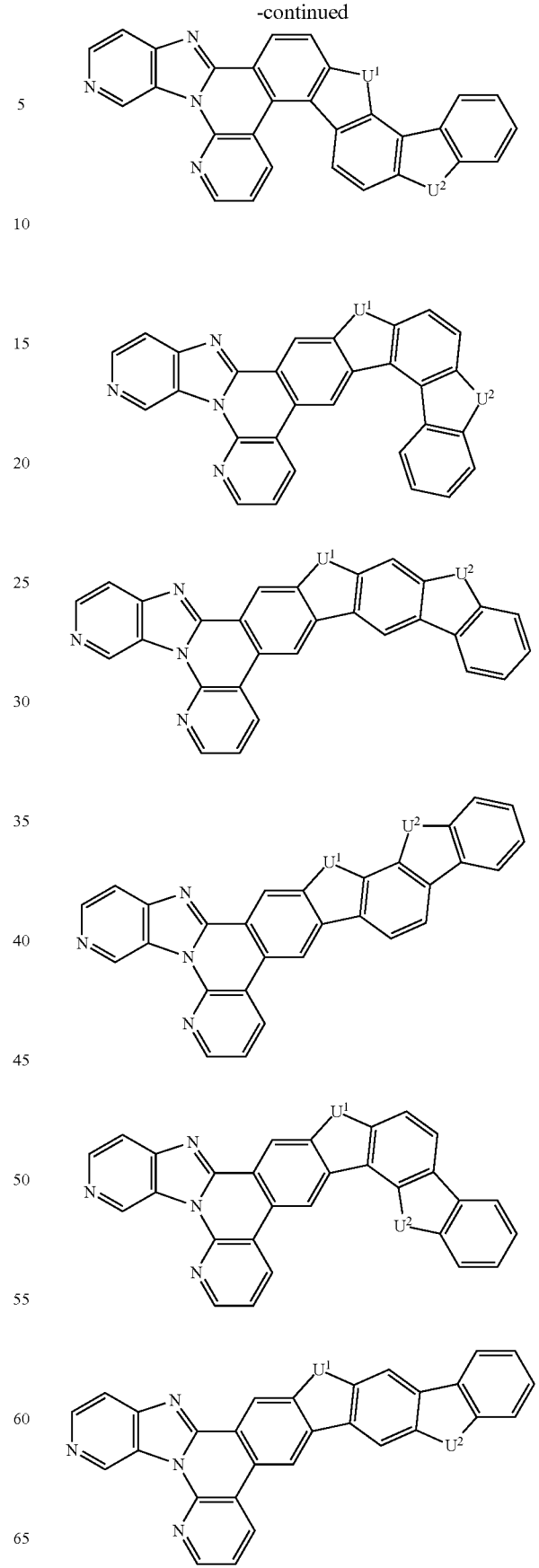

317
-continued
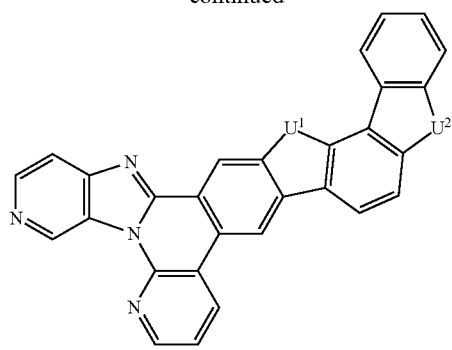
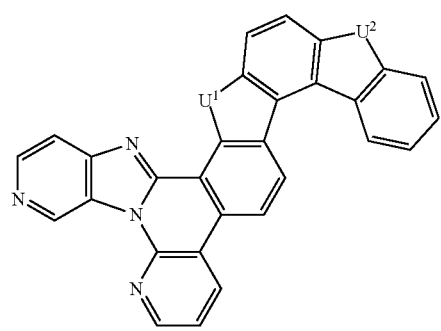
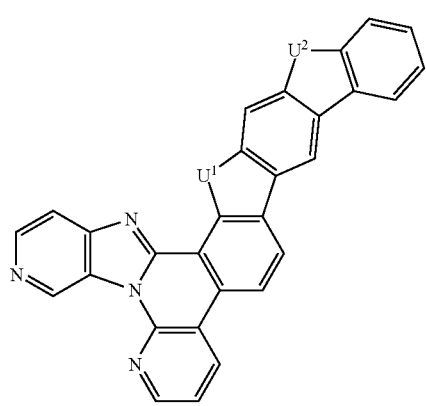
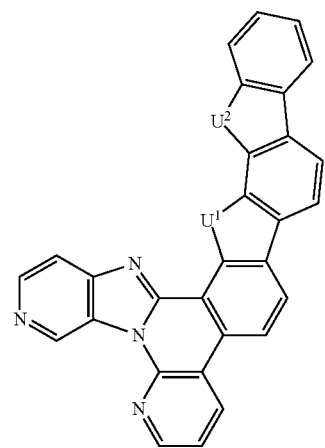
318
-continued
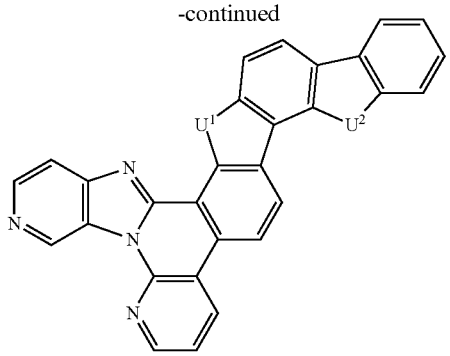
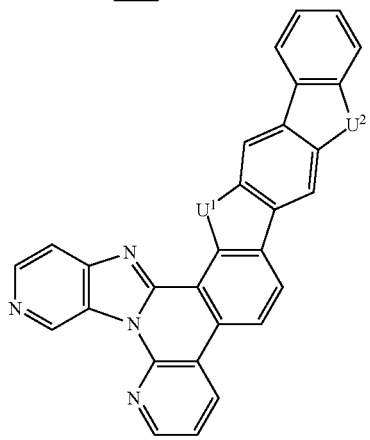
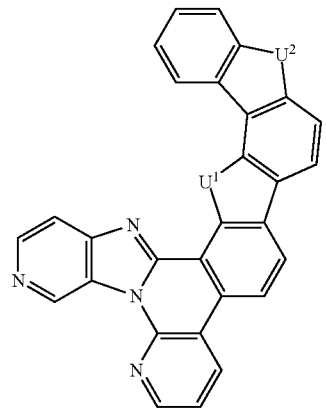
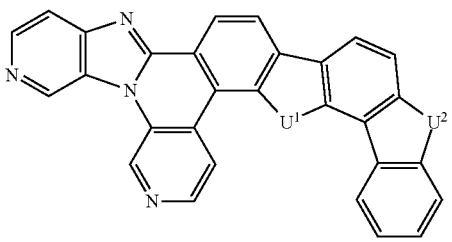
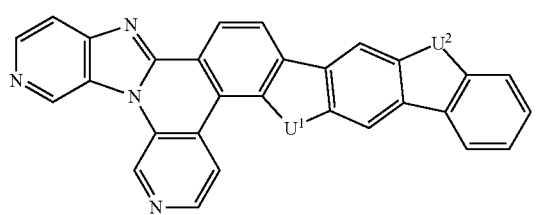

319
-continued
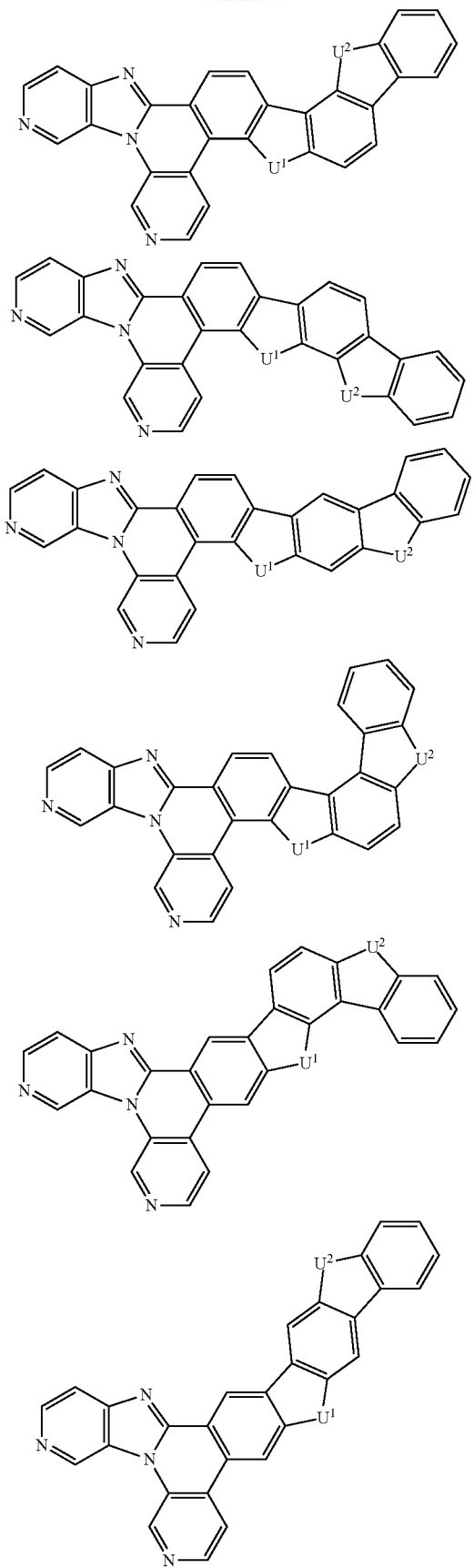
320
-continued
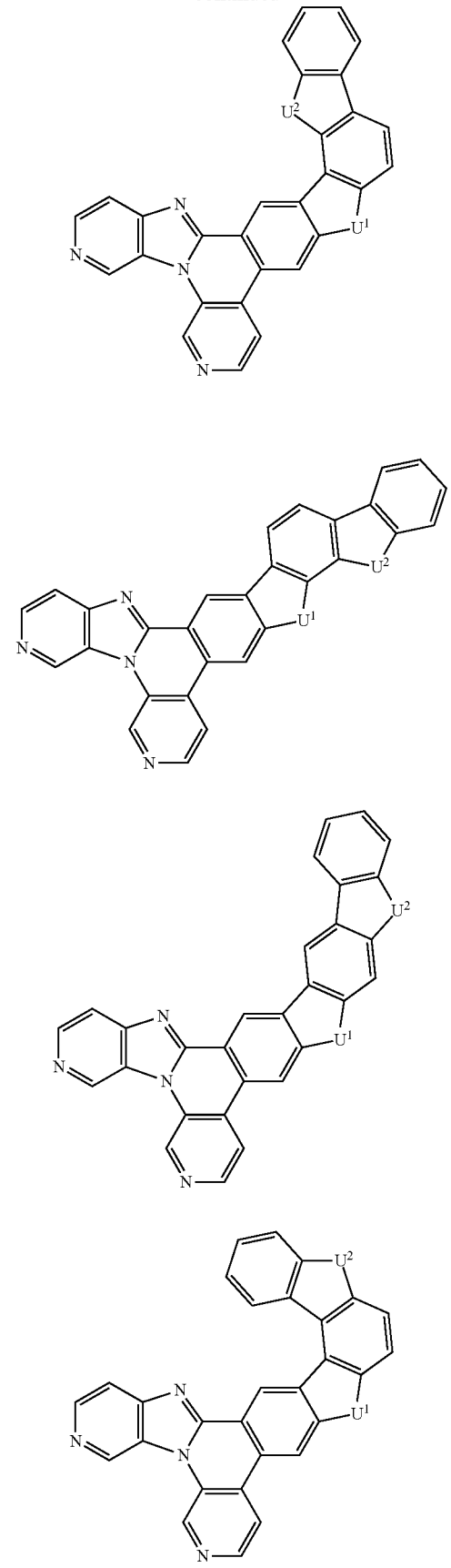

321
-continued
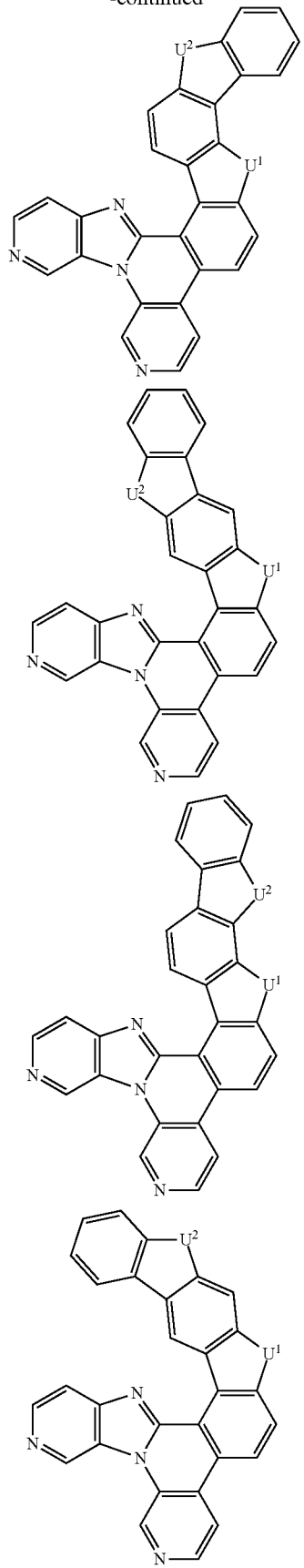
322
-continued
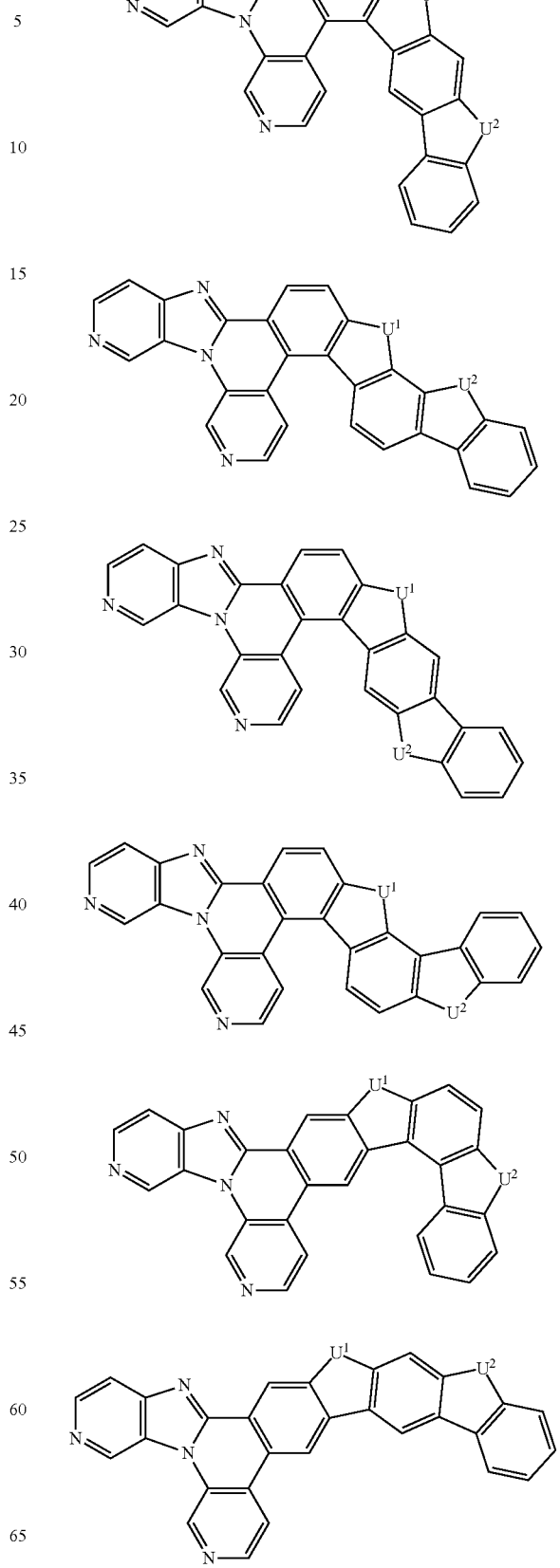

323
-continued
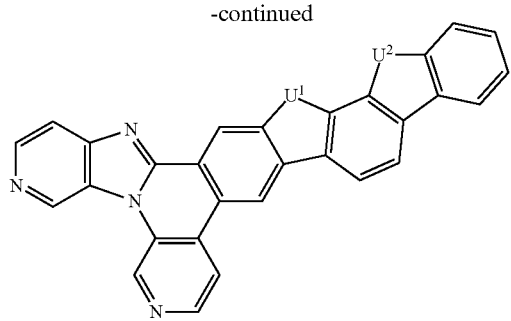
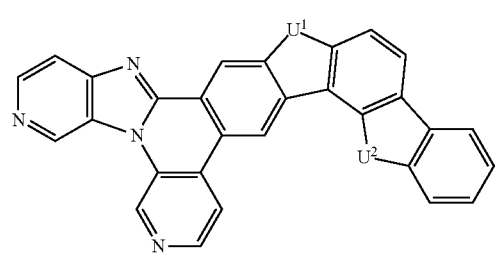
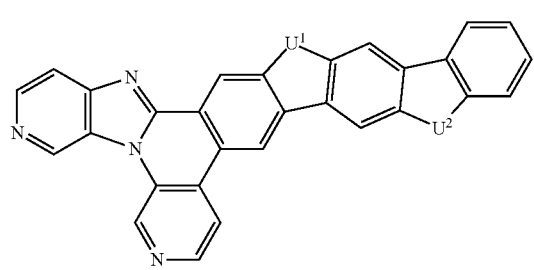
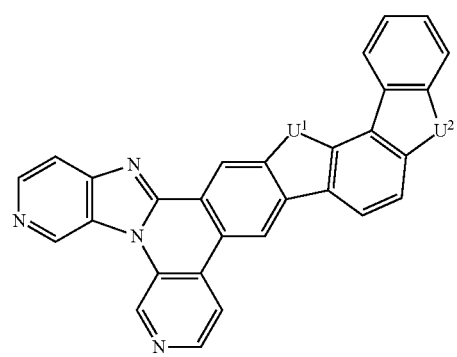
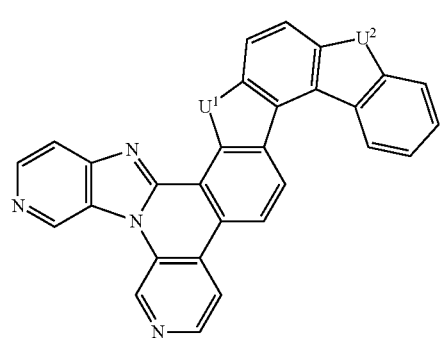
324
-continued
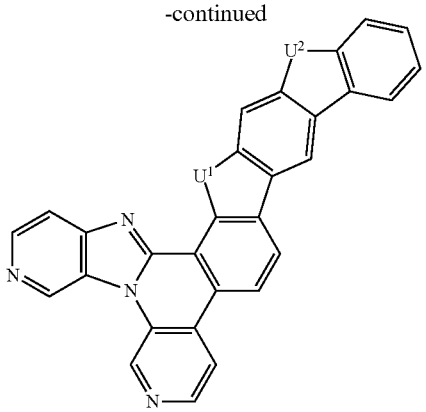
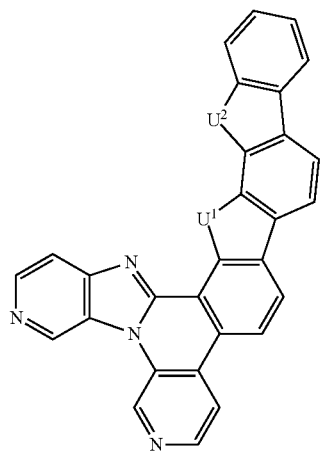
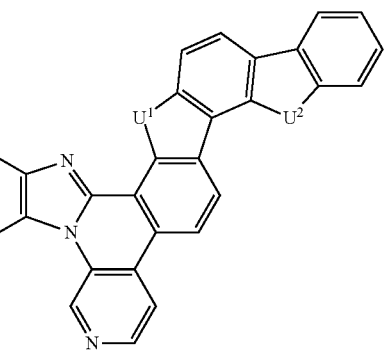
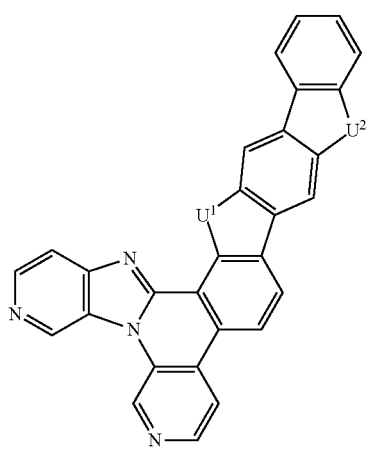

325
-continued
326
-continued
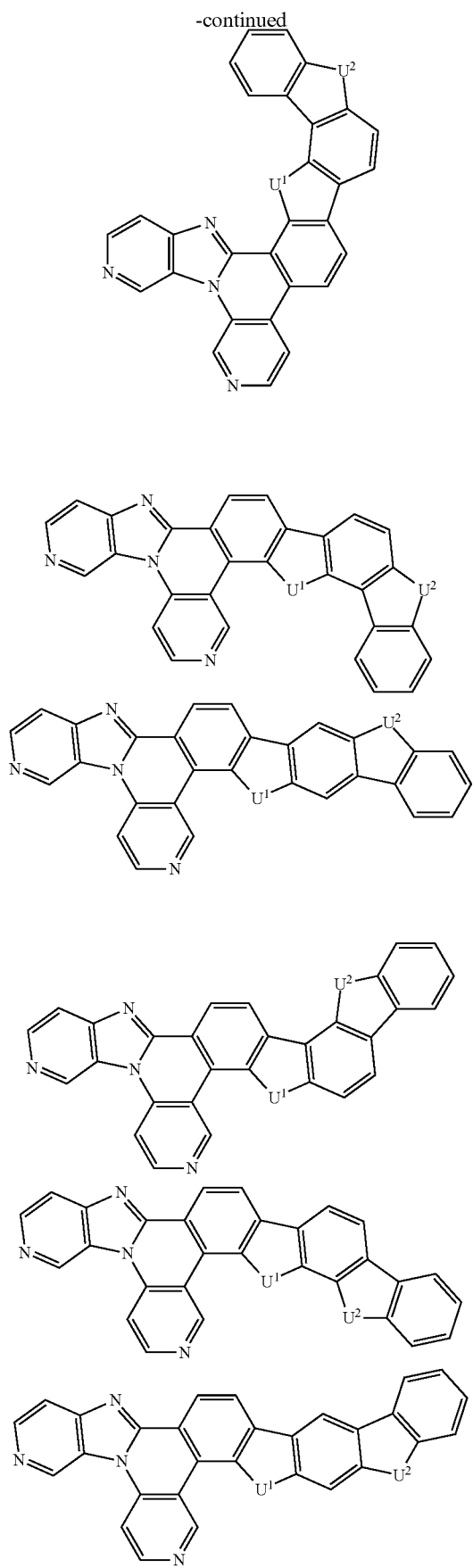
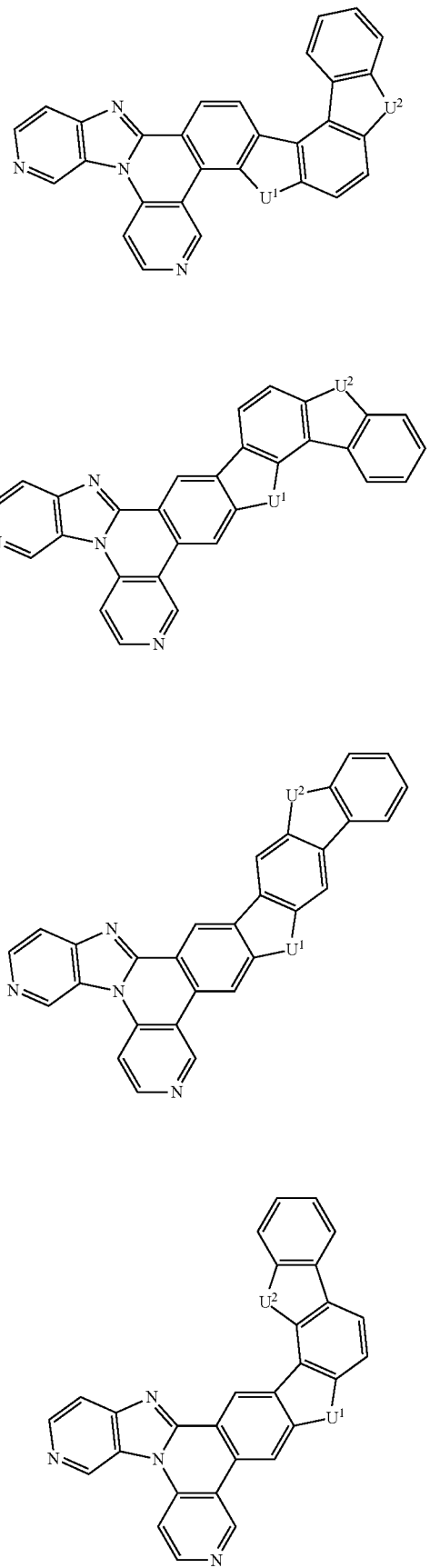

327
-continued
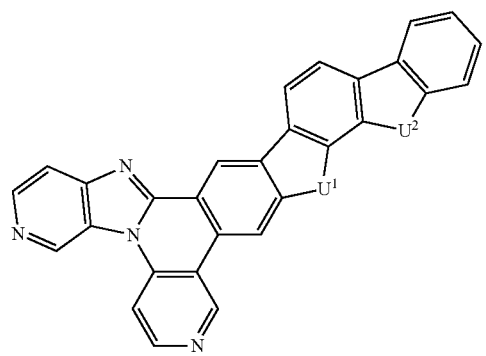
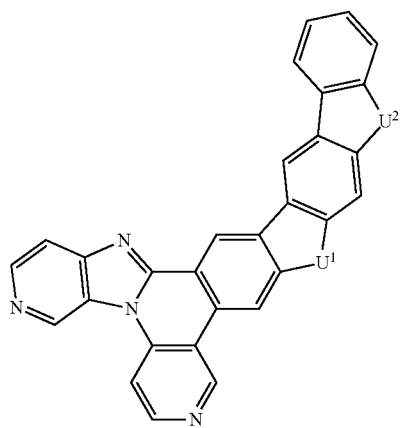
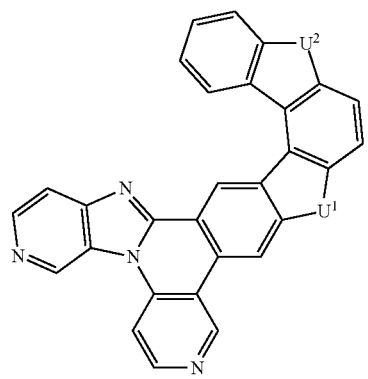
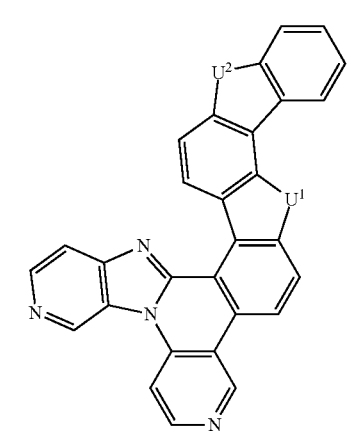
328
-continued
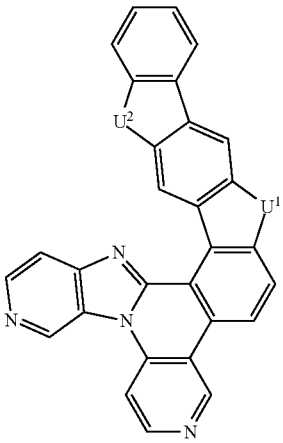
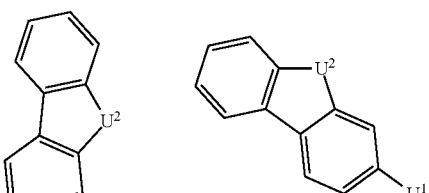
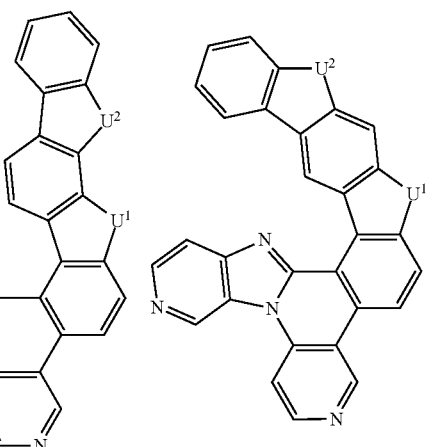
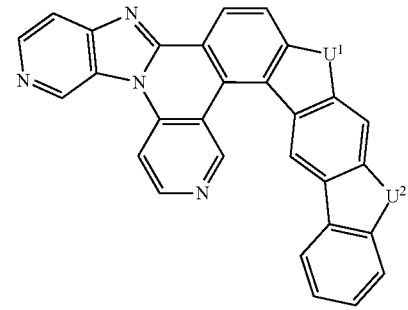
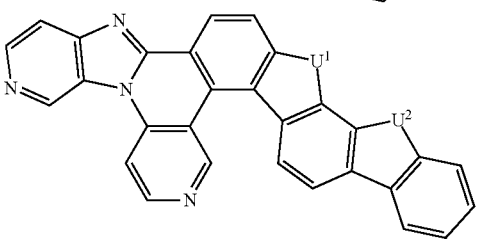
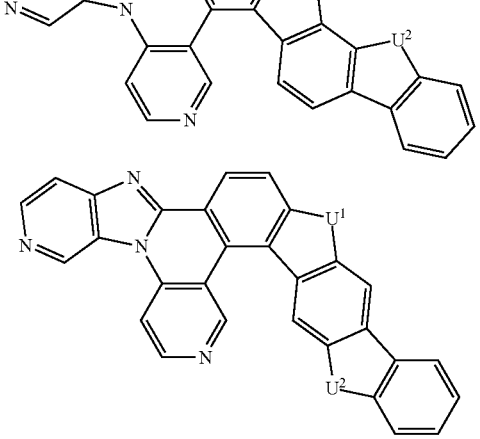

329
-continued
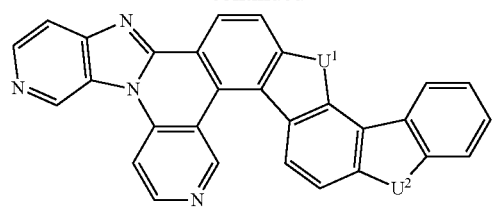
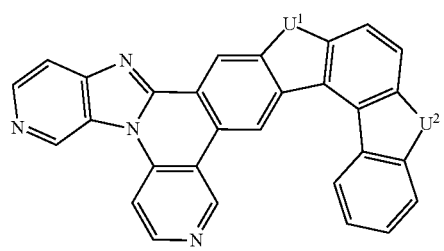
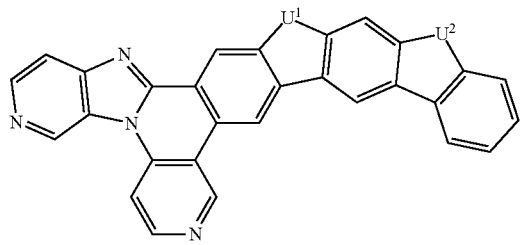
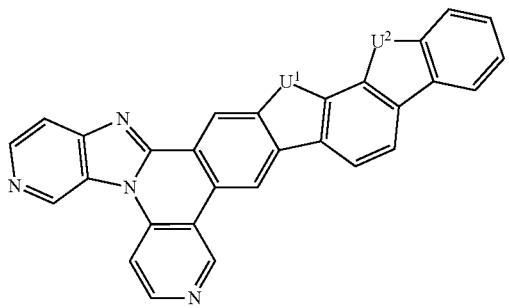
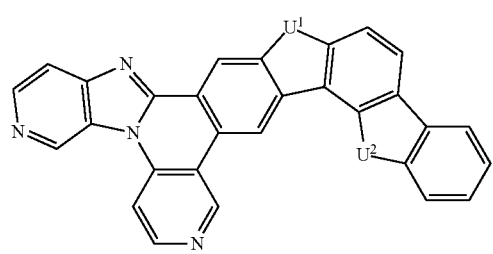
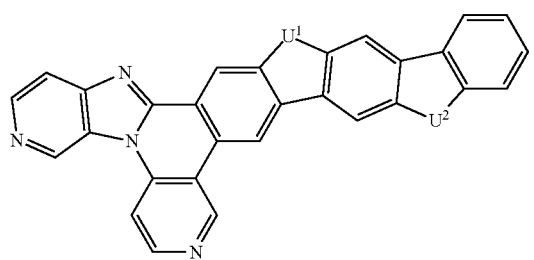
330
-continued
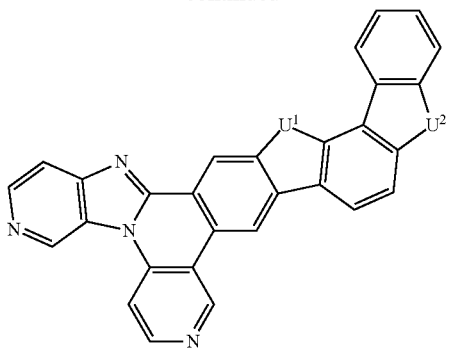
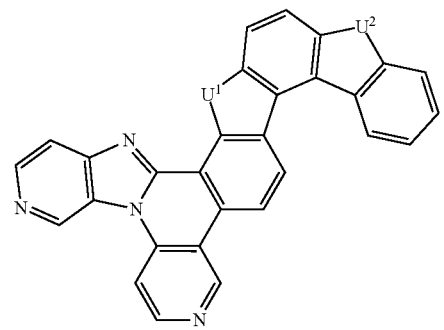
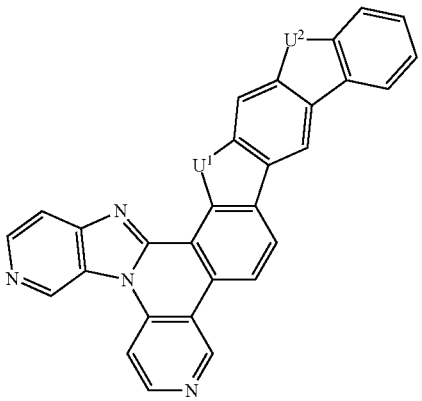
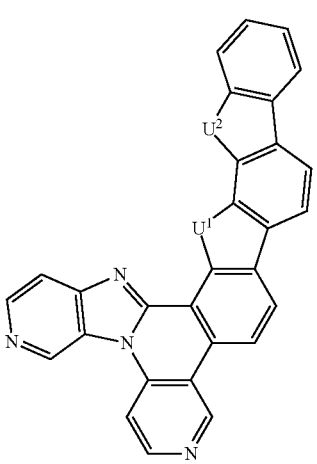

331
-continued
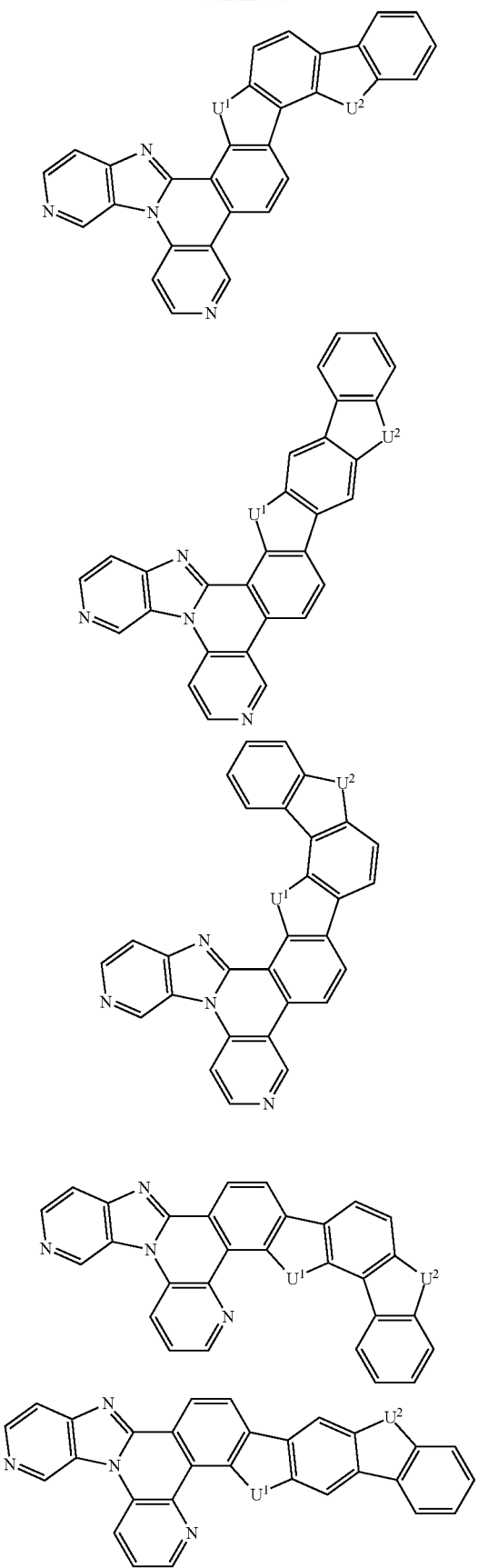
332
-continued
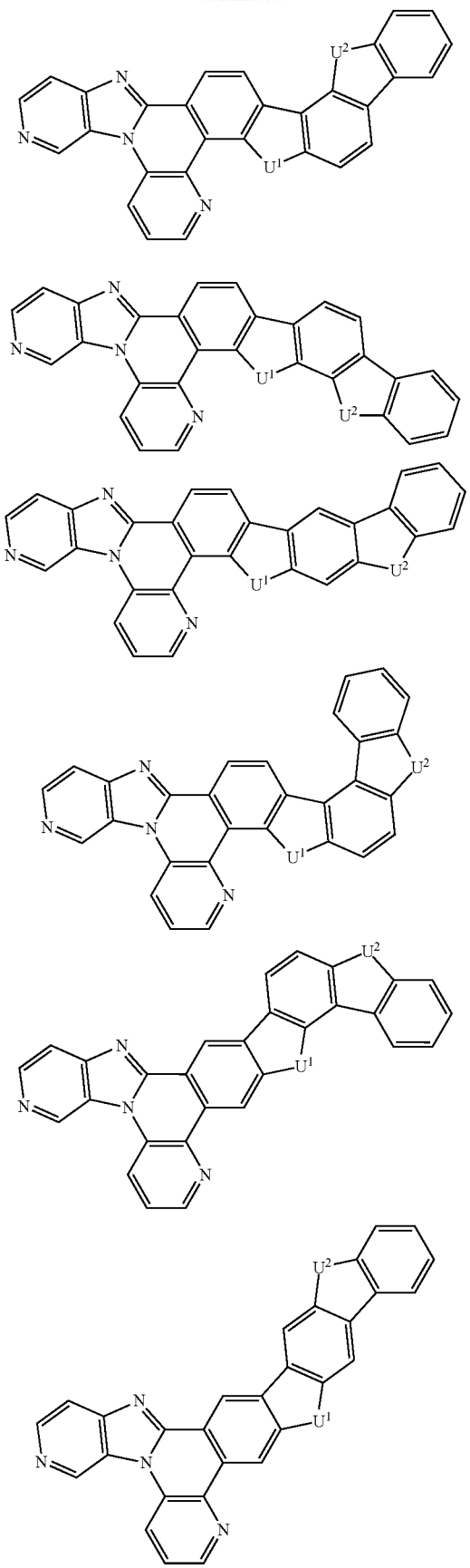

333
-continued
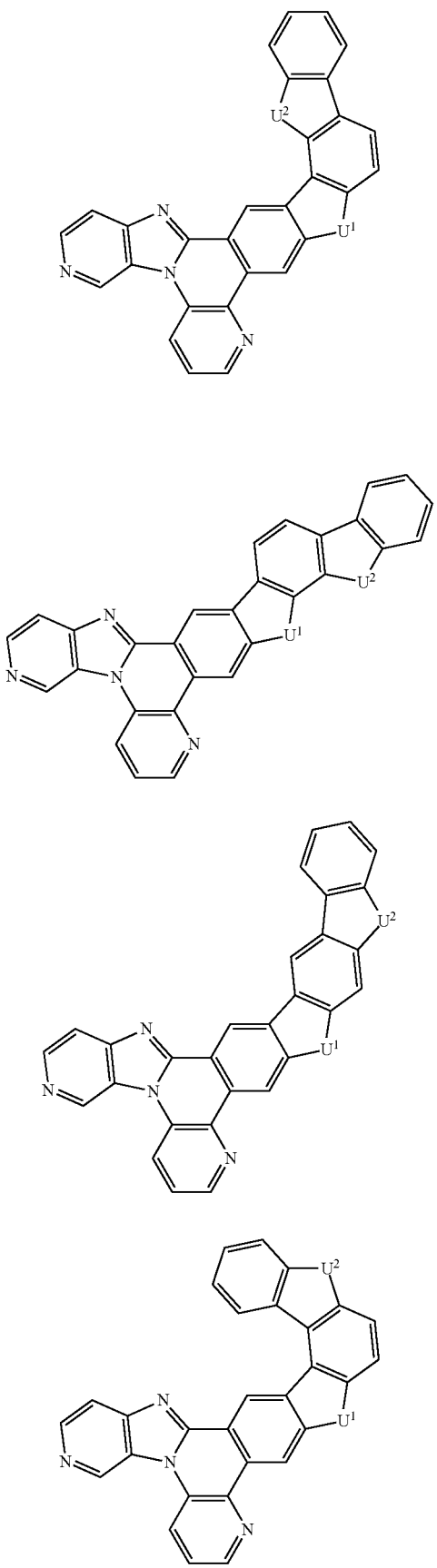
334
-continued
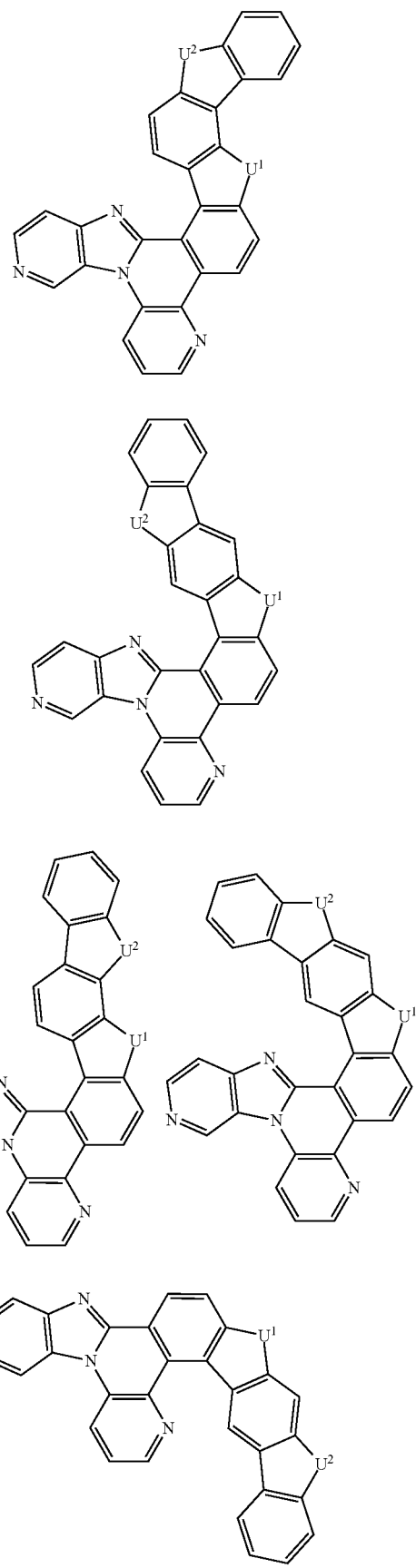

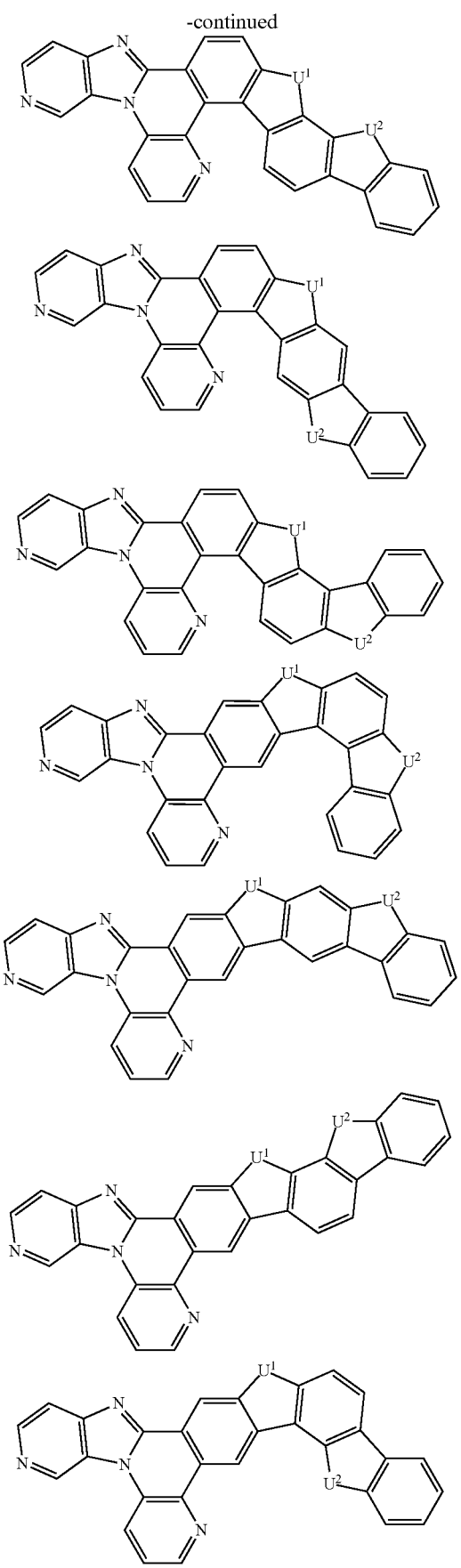
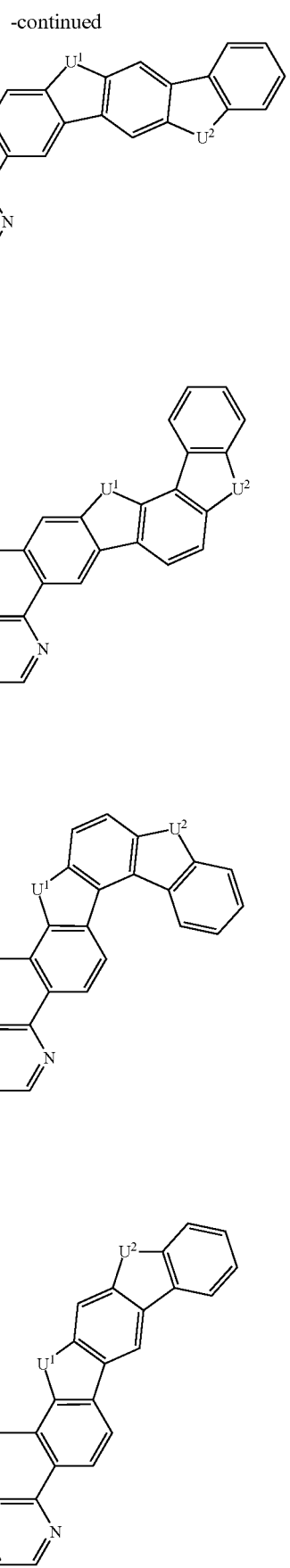

337
-continued
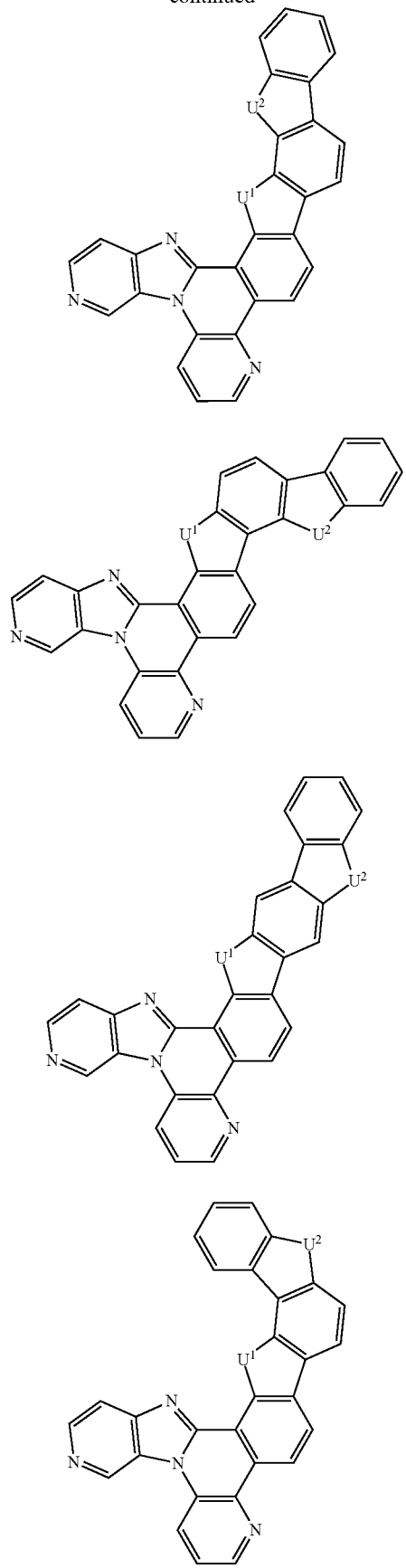
338
-continued
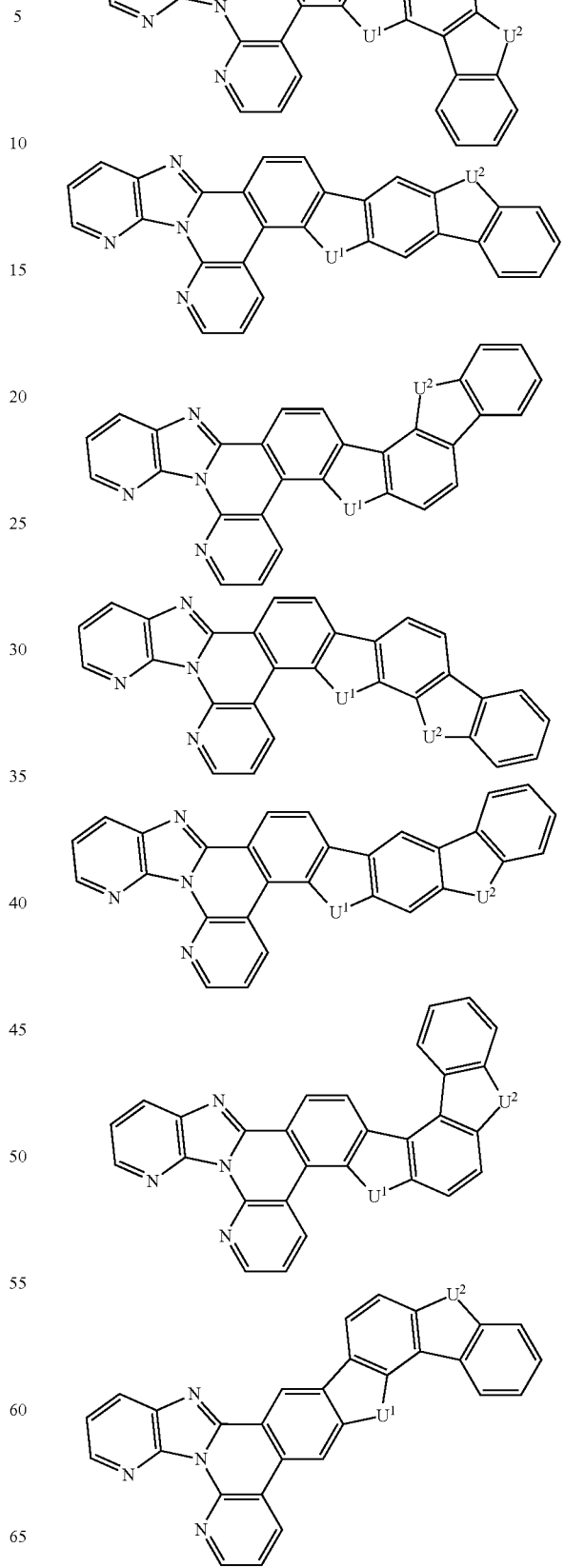

339
-continued
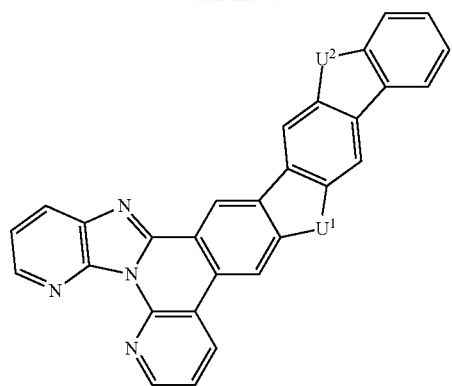
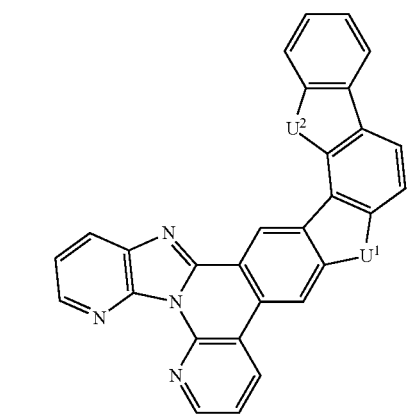
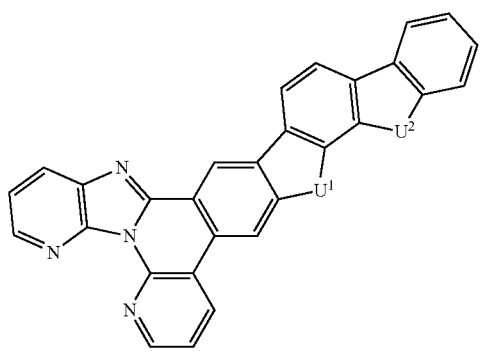
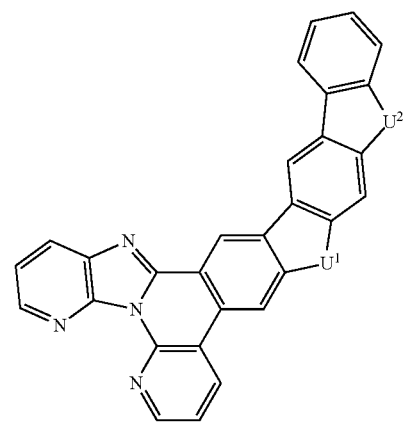
340
-continued
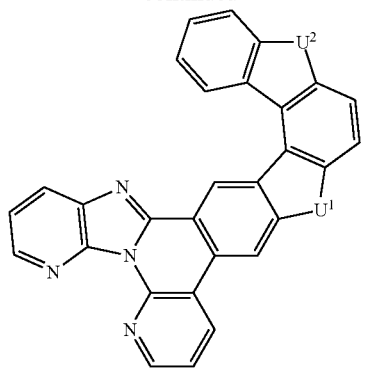
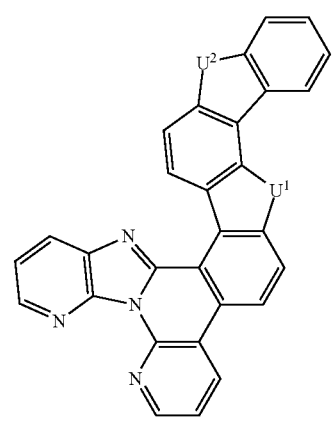
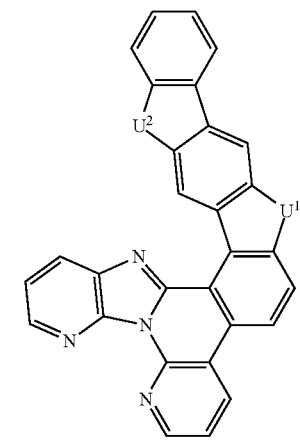
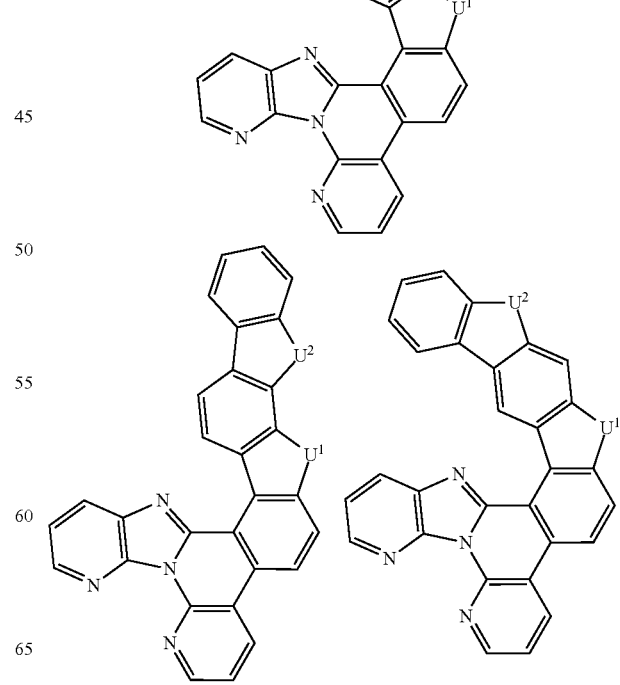

341
-continued
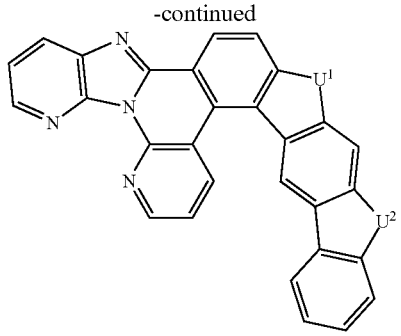
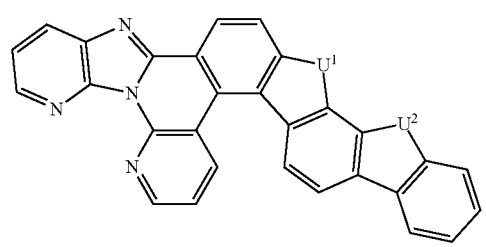
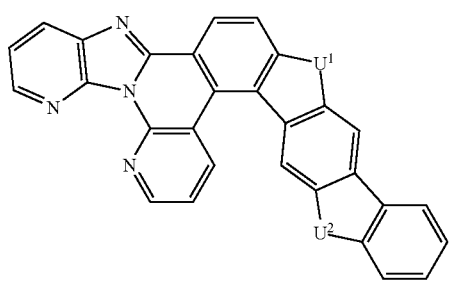
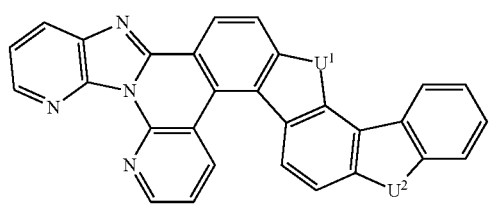
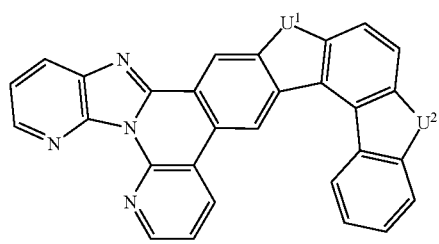
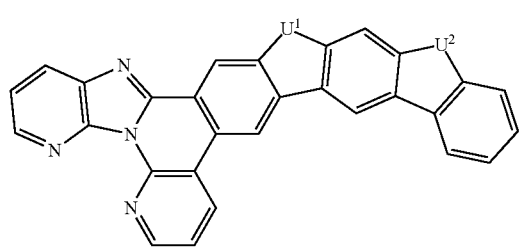
342
-continued
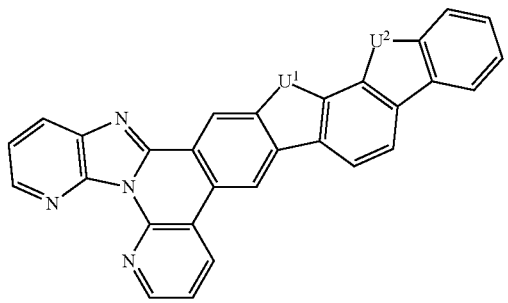
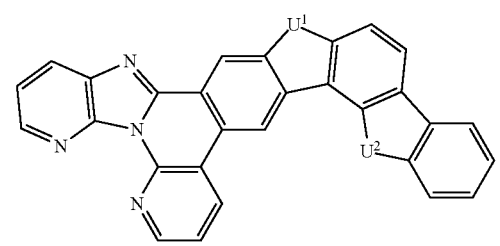
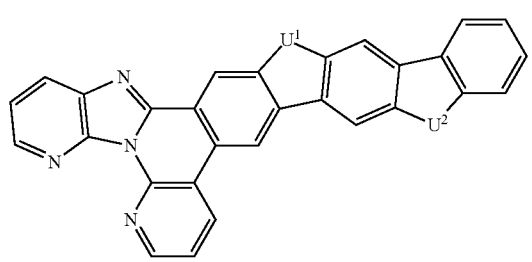
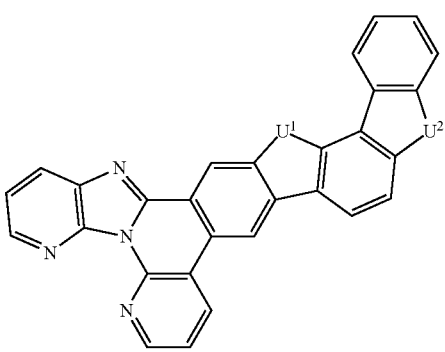
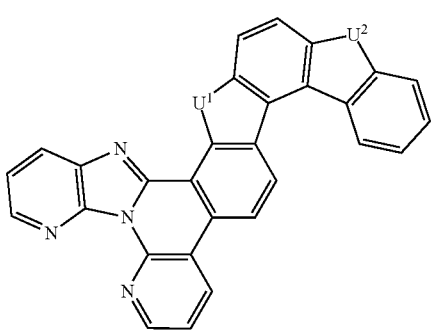

-continued
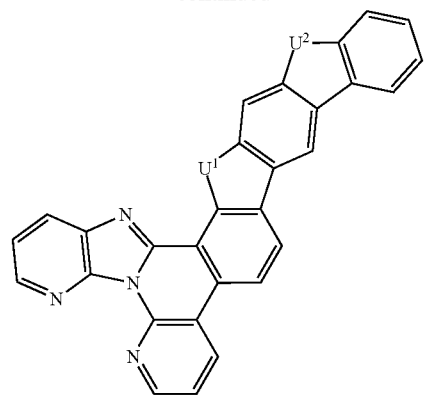
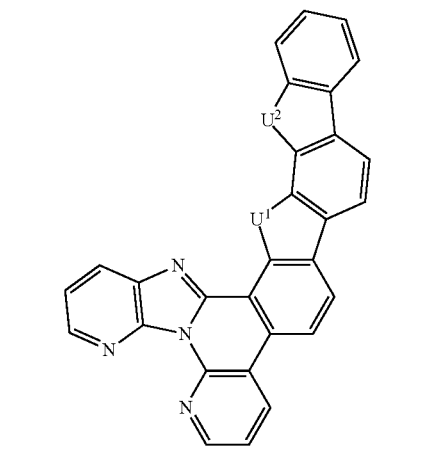
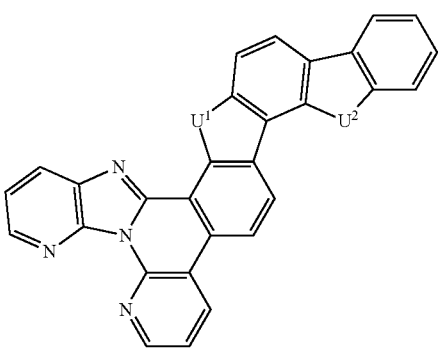
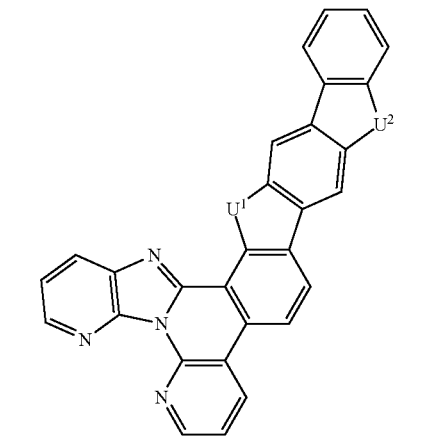
-continued
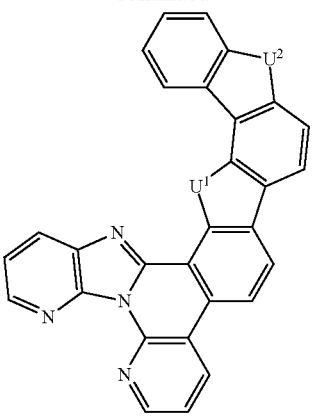
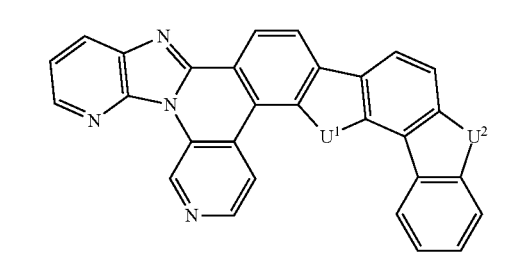
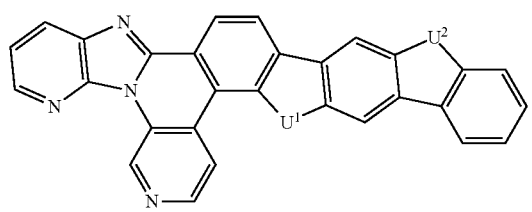
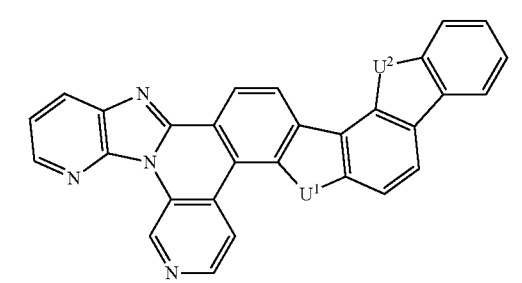
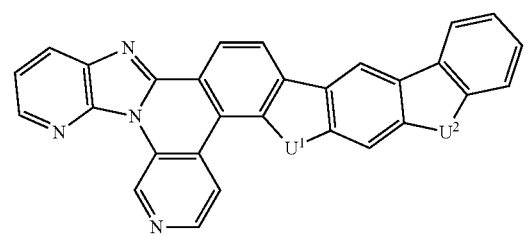

345
-continued

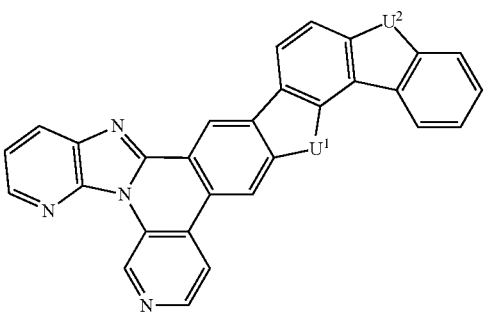
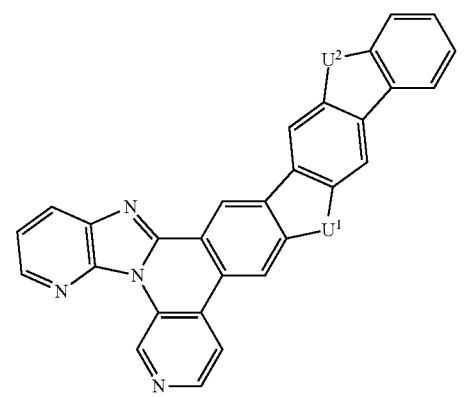
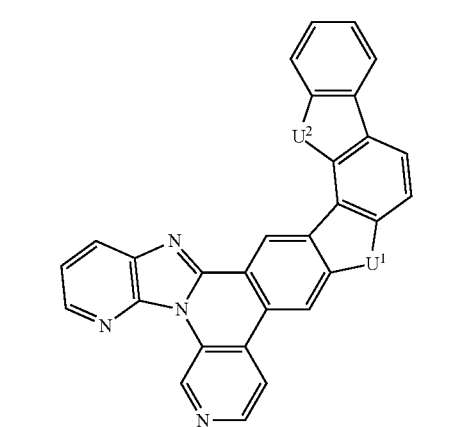
346
-continued
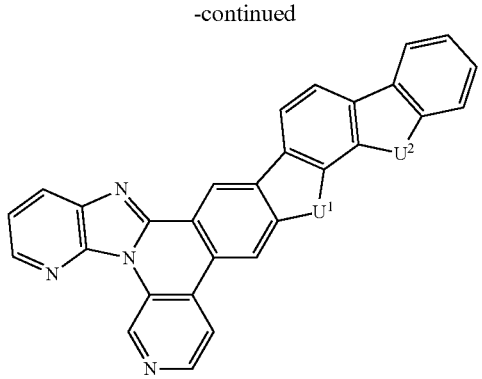
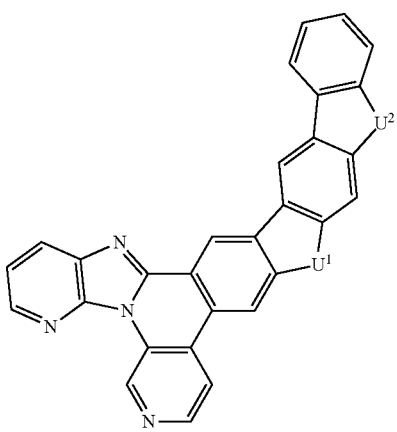
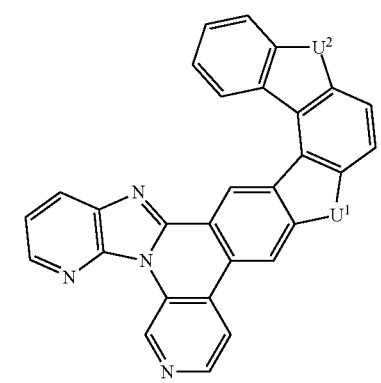
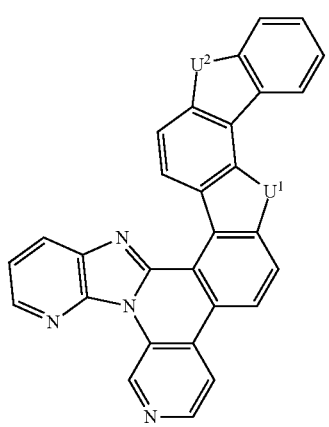

-continued
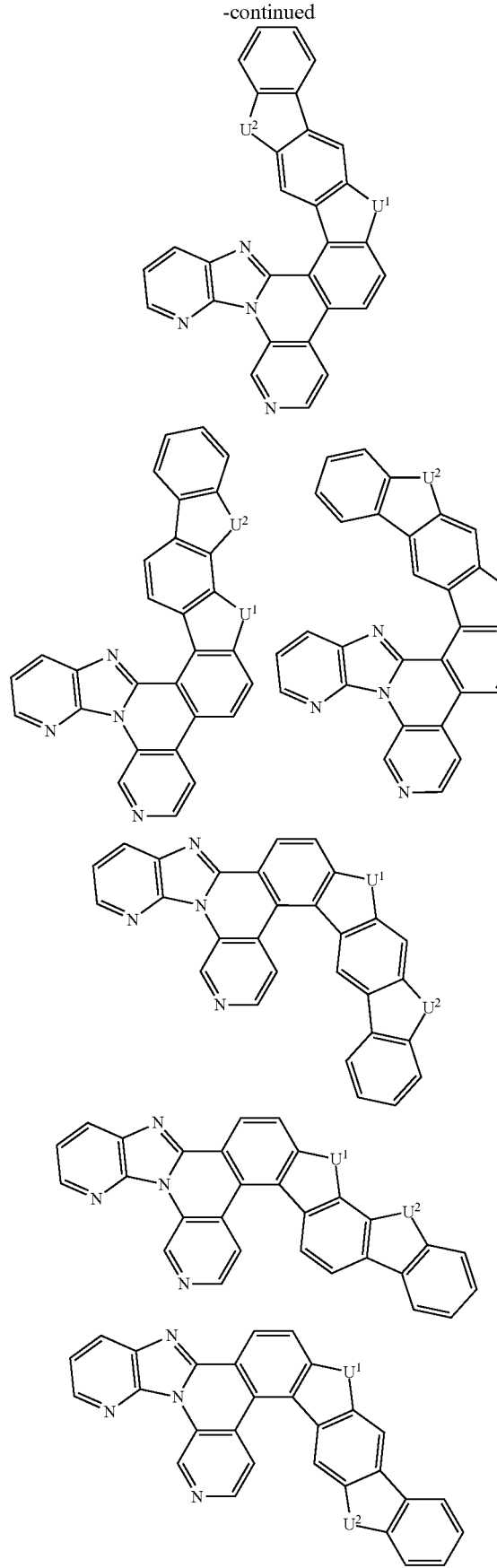
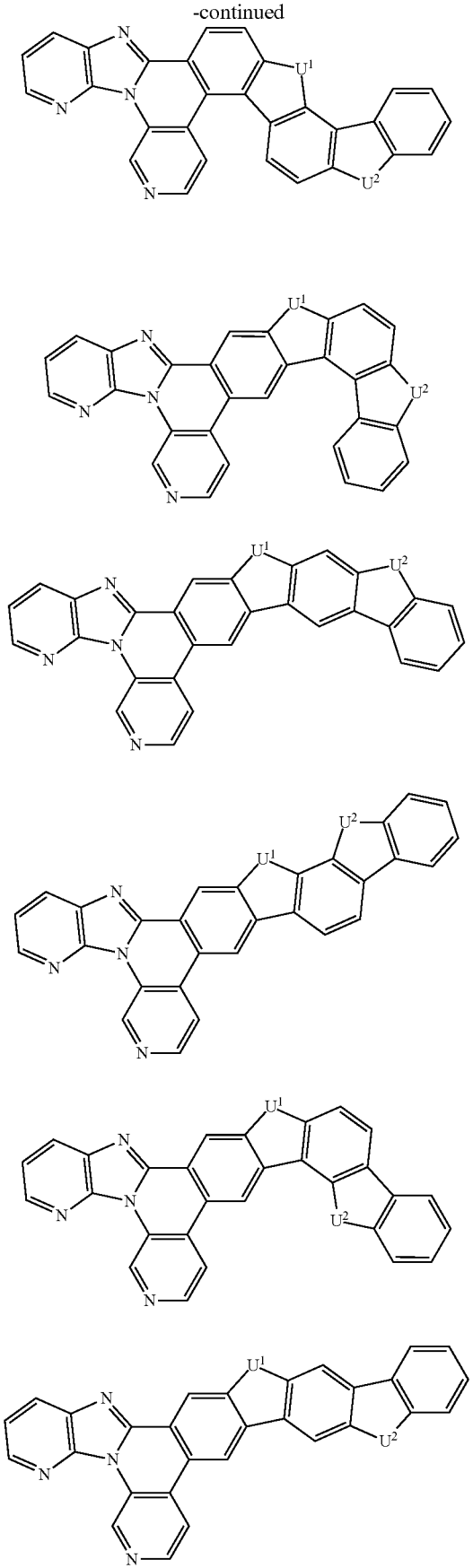

349
-continued
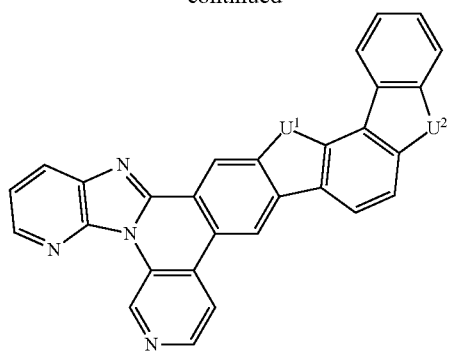
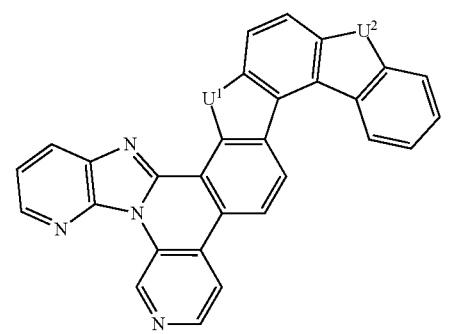
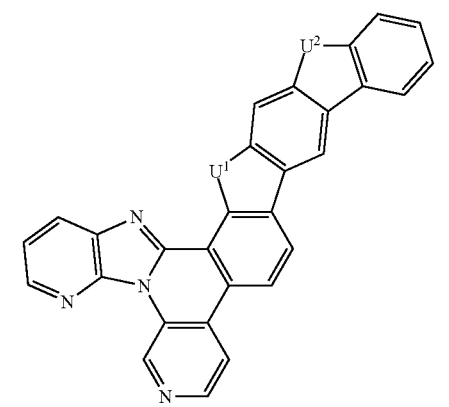
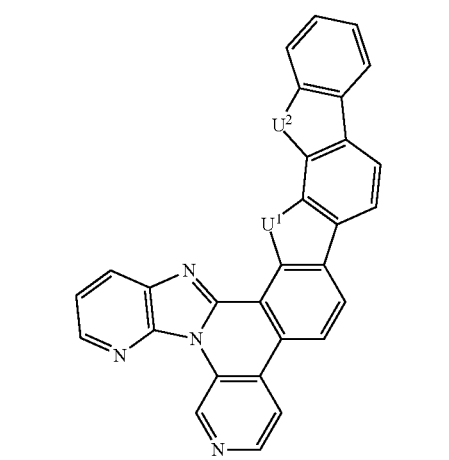
350
-continued
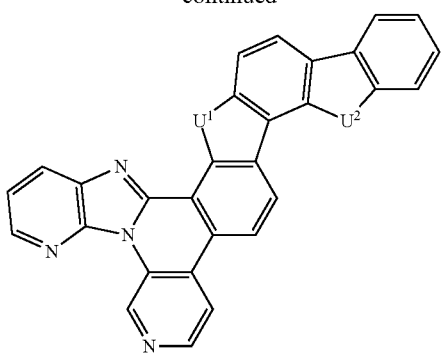

351
-continued
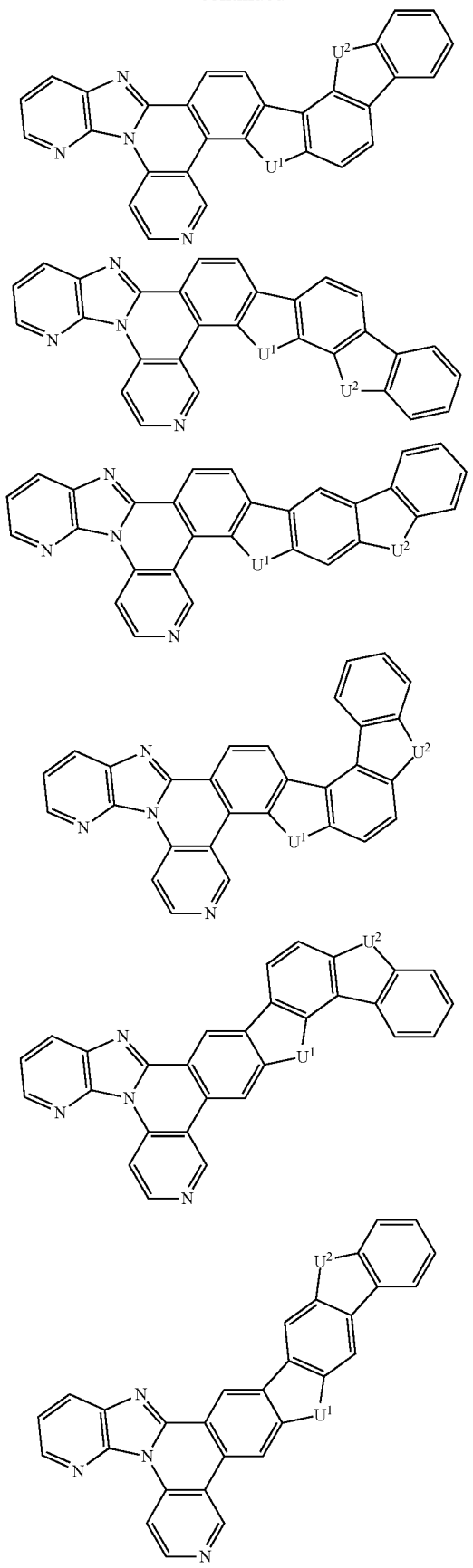
352
-continued
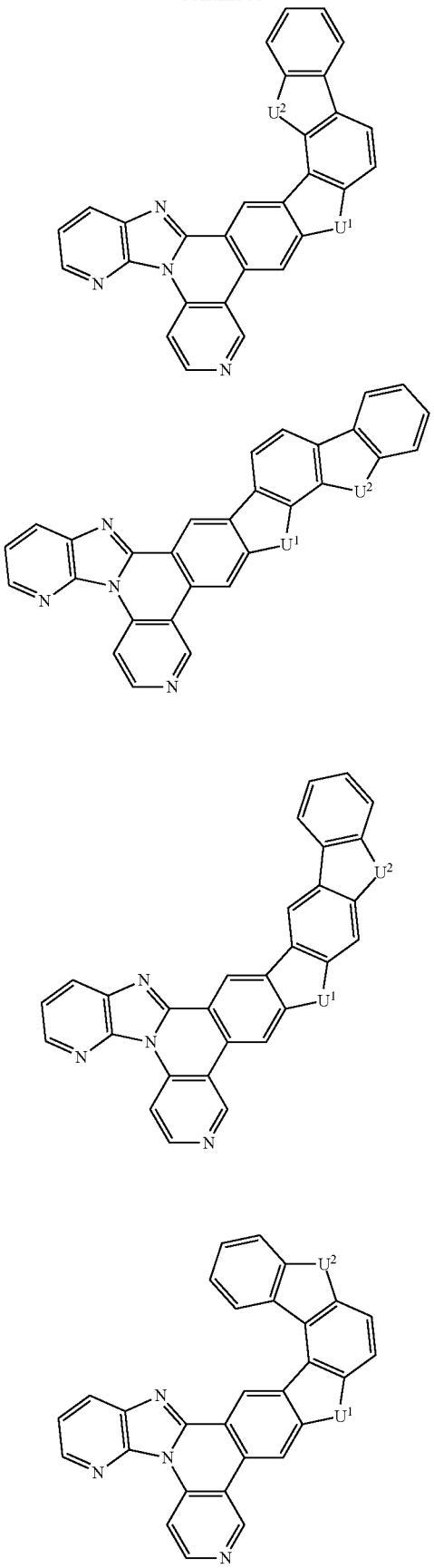

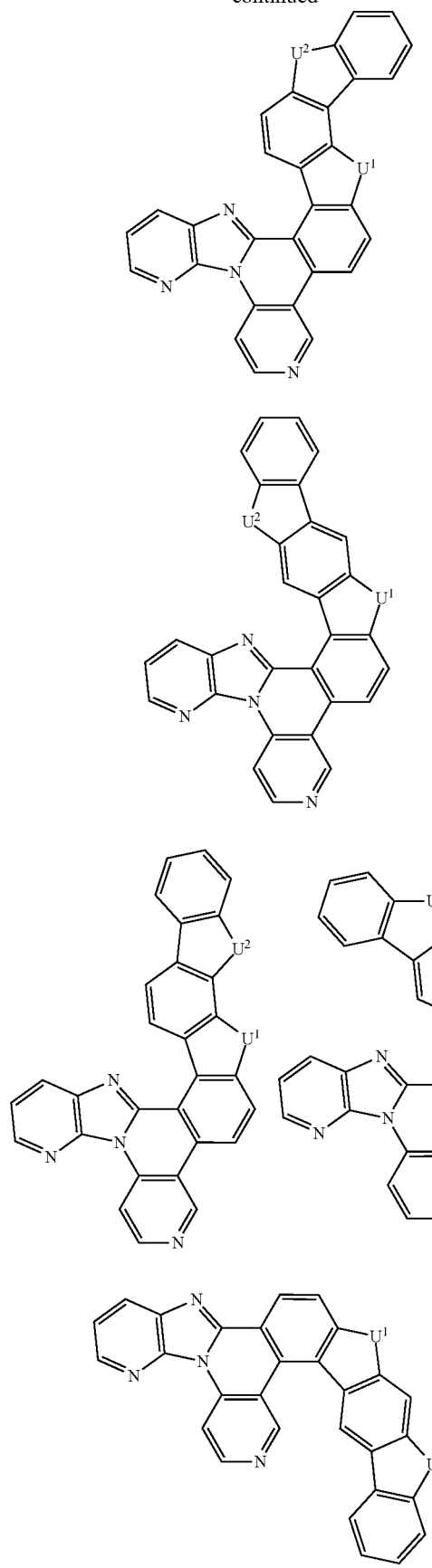
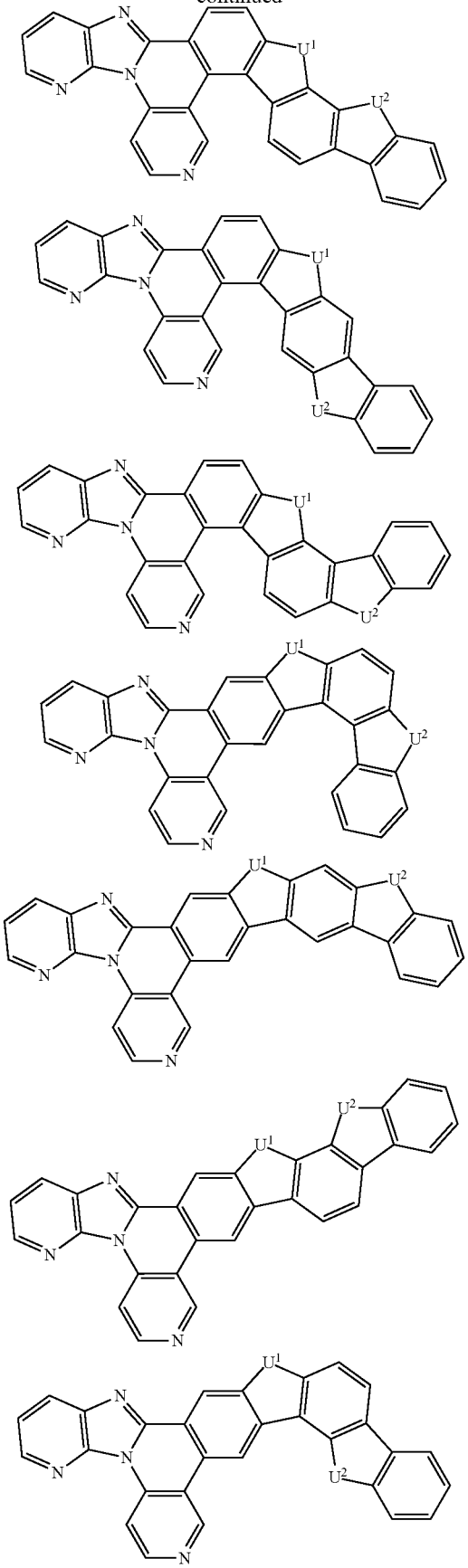

355
-continued
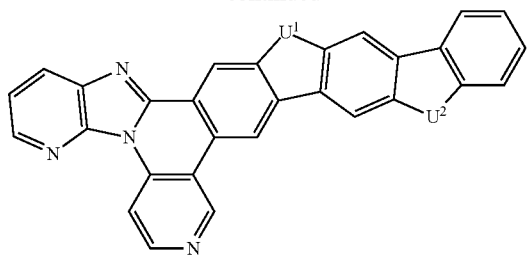
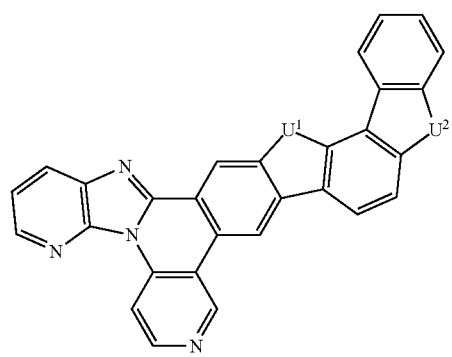
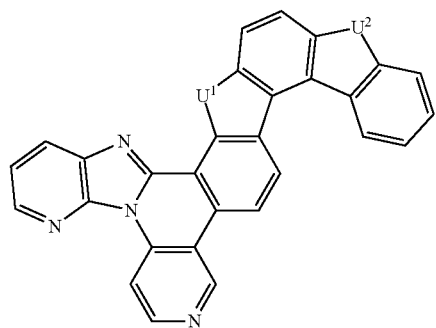
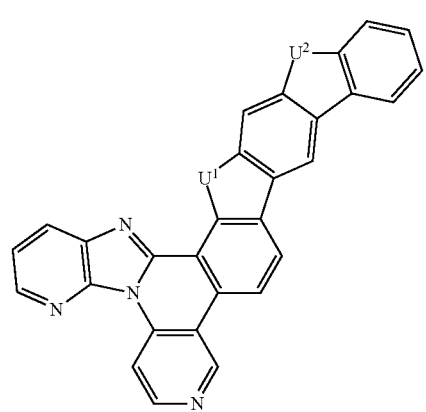
356
-continued
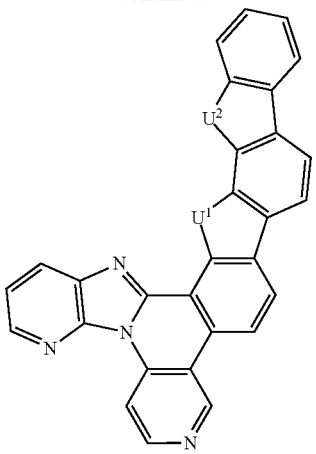
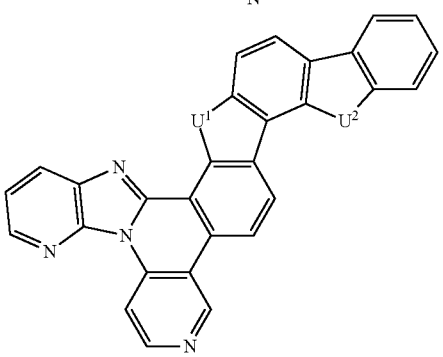
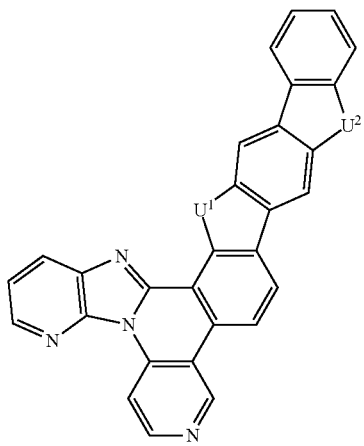
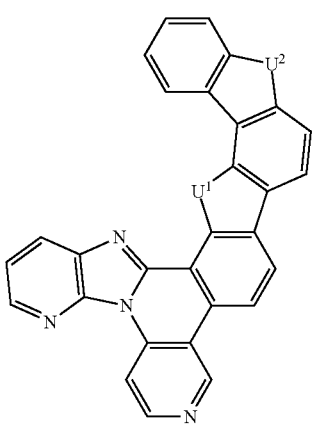

357
-continued
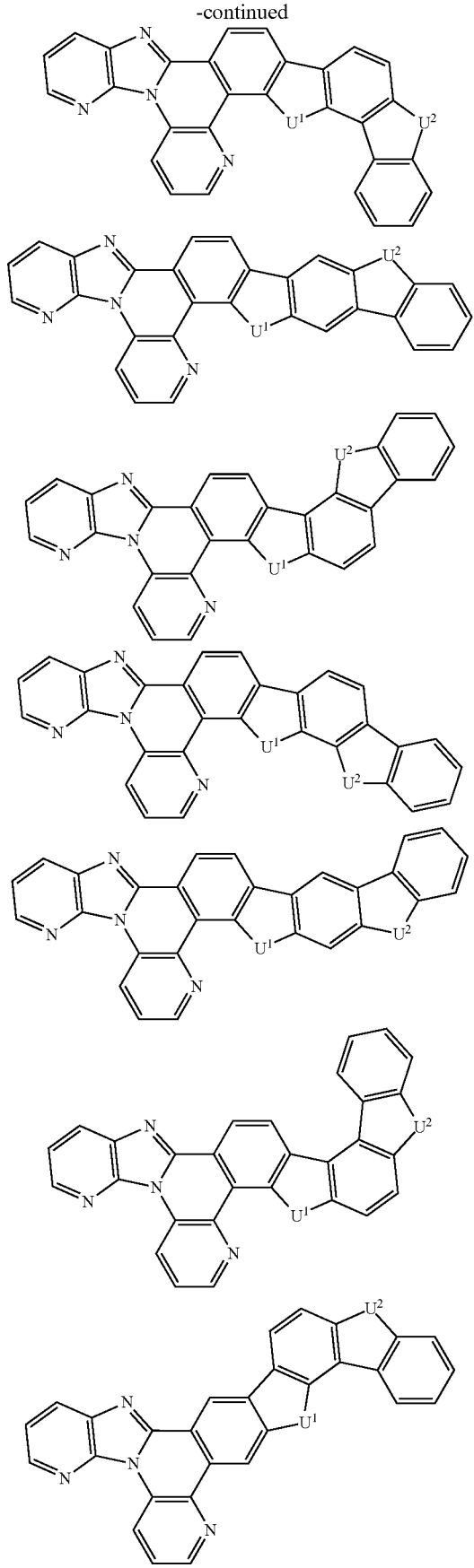
358
-continued
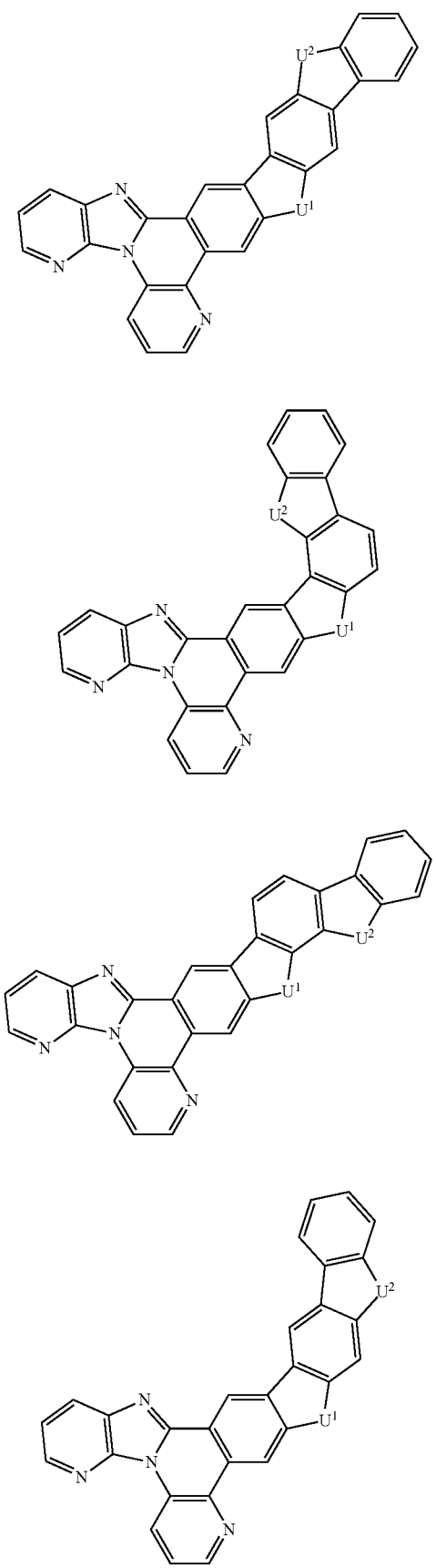

359
-continued
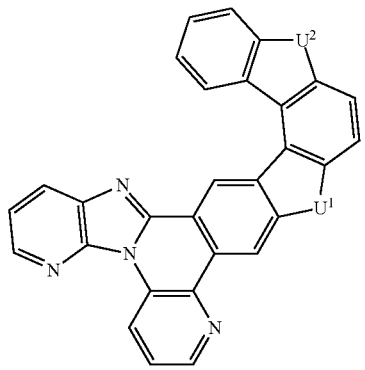
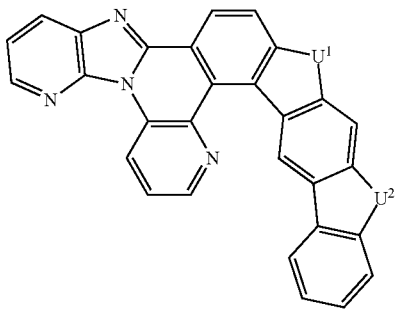
360
-continued
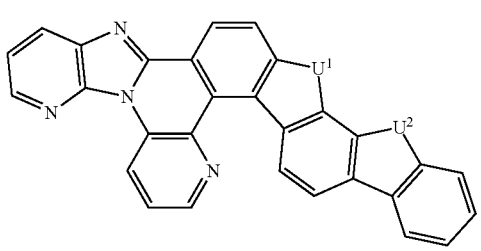
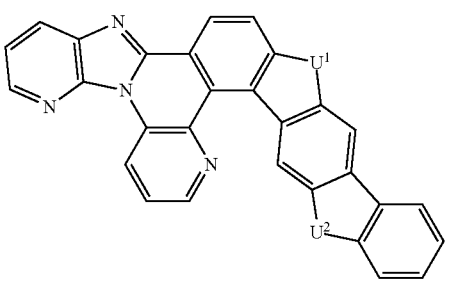
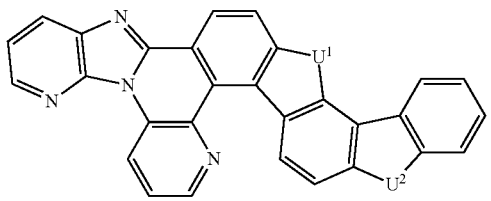
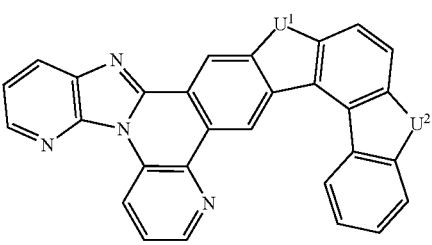
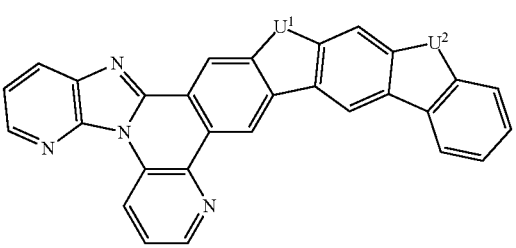

361
-continued
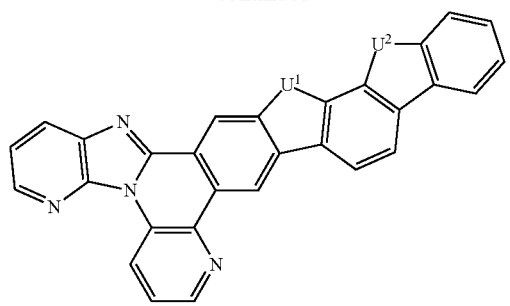
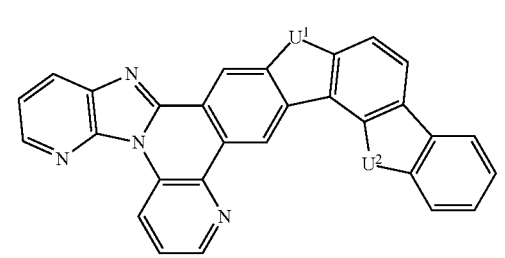
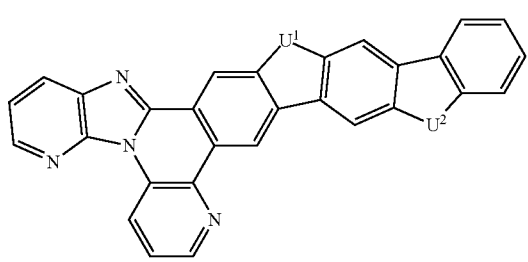
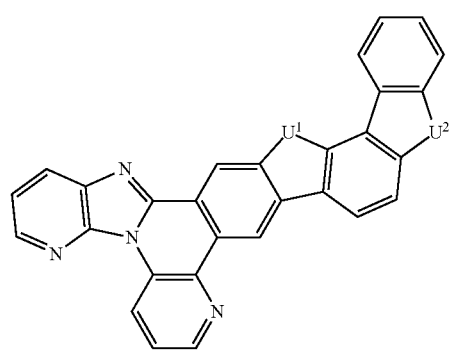
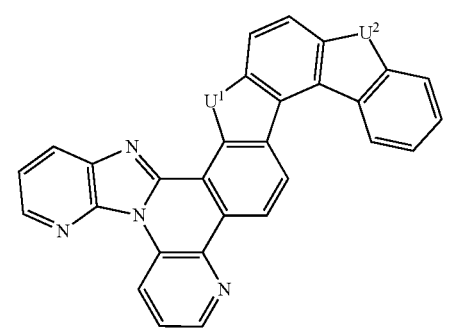
362
-continued
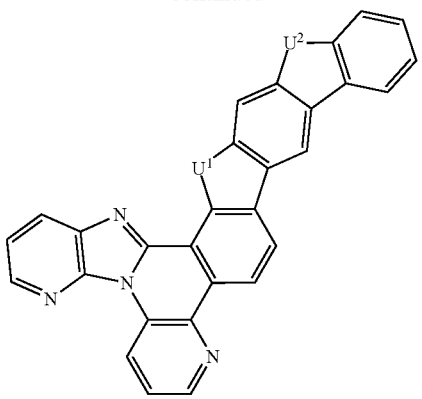
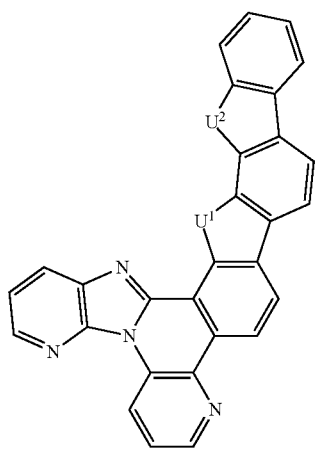
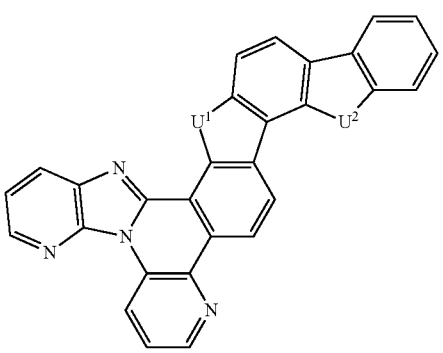
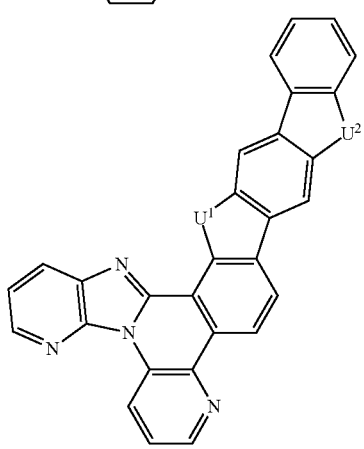

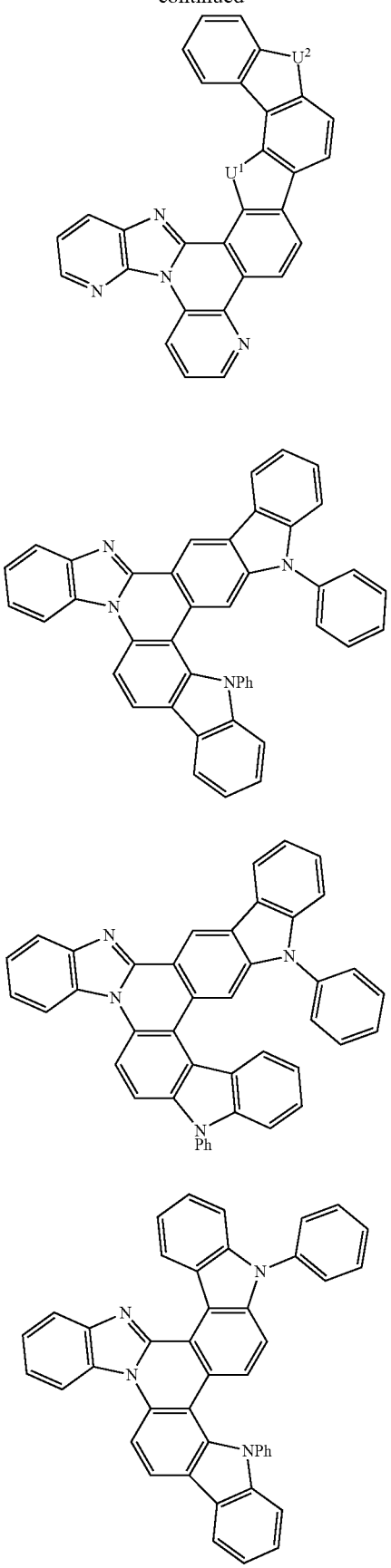

365
-continued
366
-continued
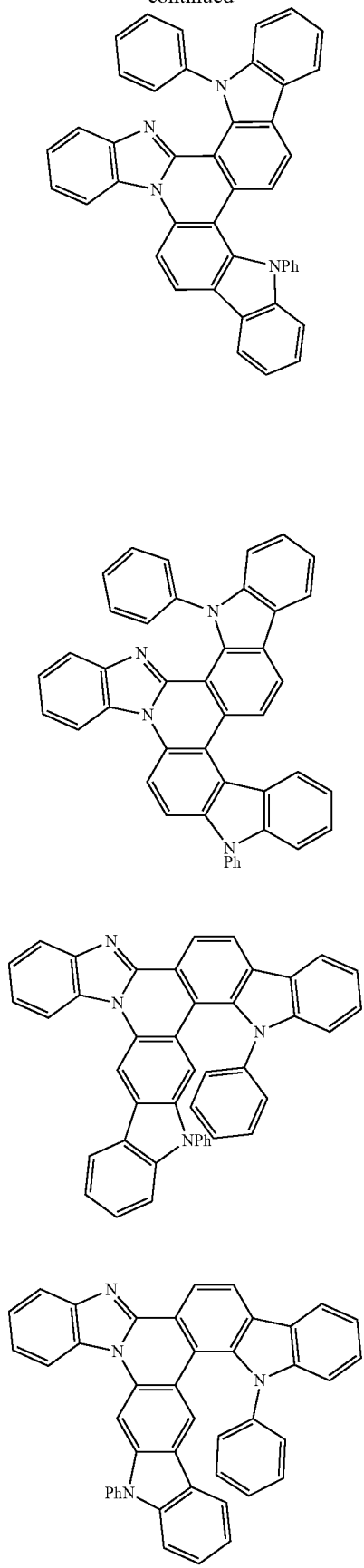

367
-continued
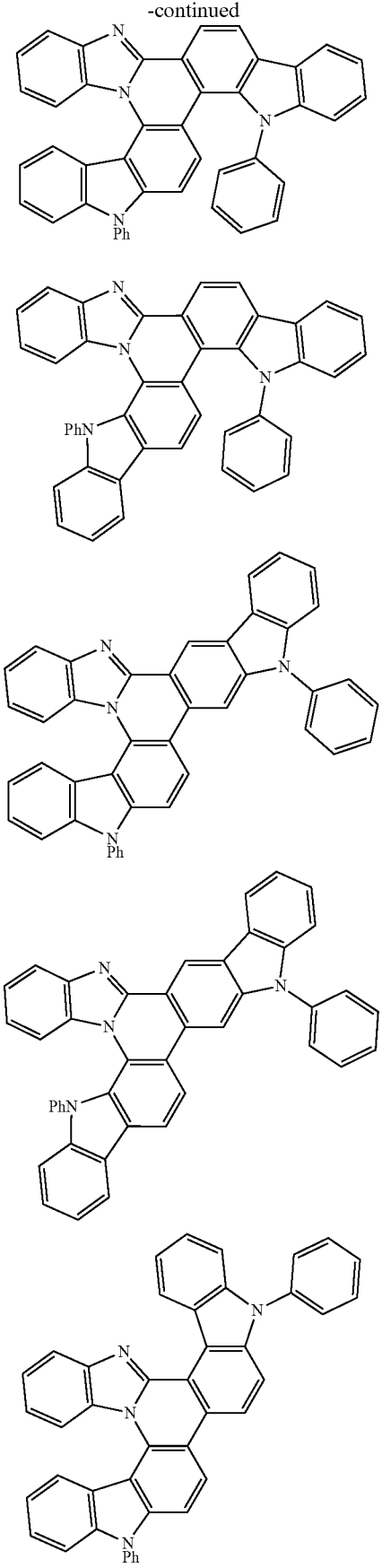
368
-continued
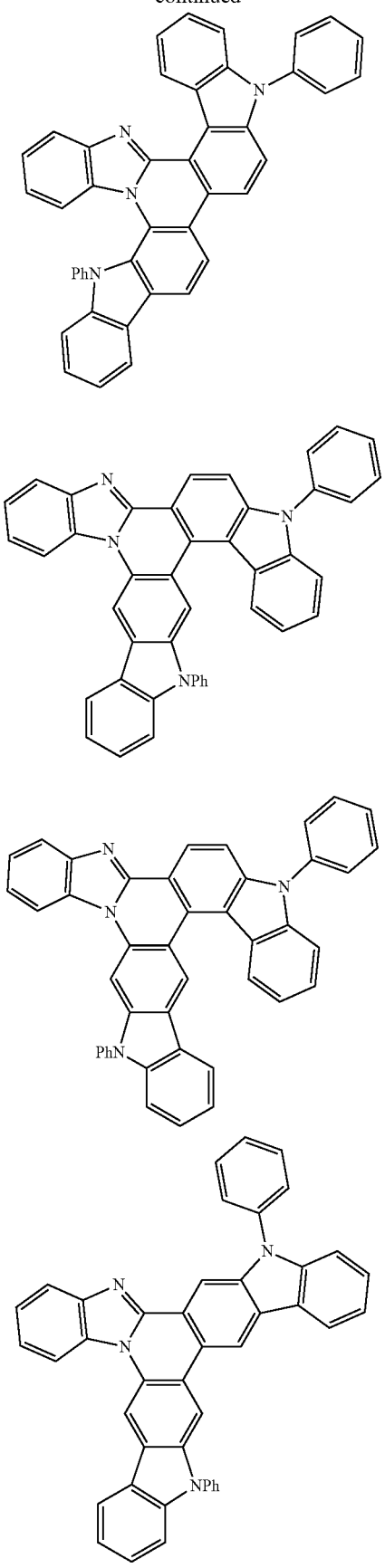

369
-continued
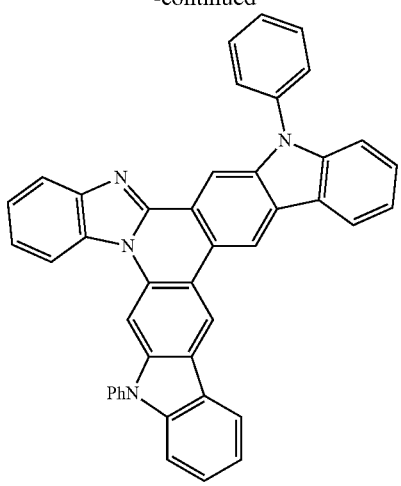
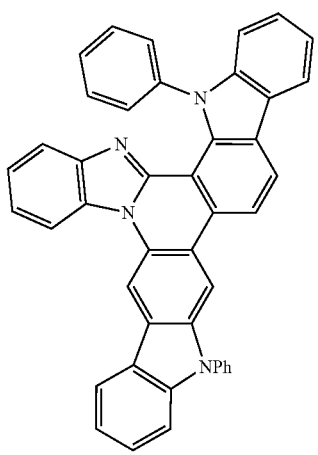
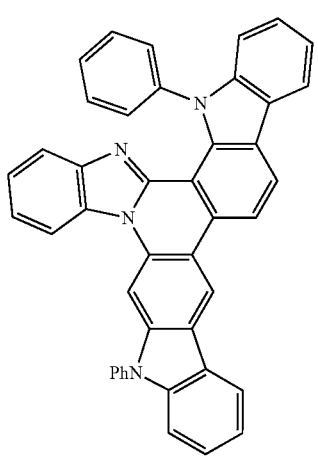
370
-continued
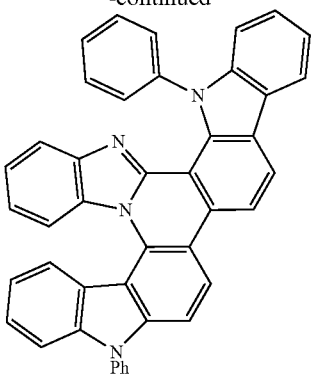
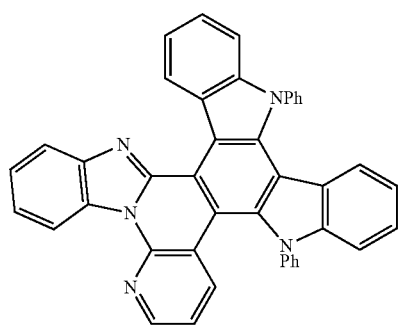
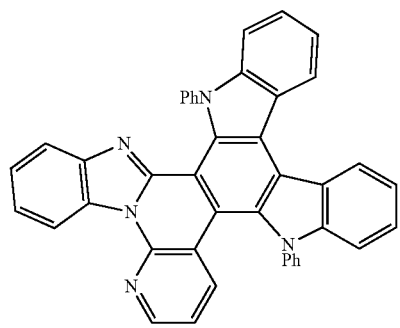
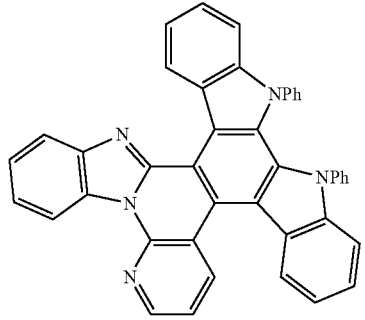
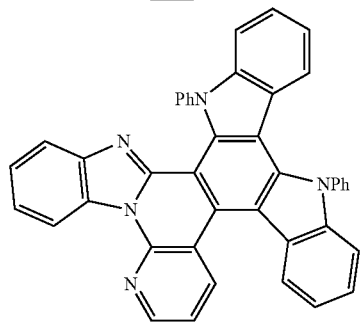

371
-continued
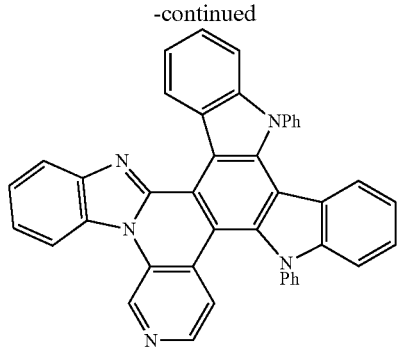
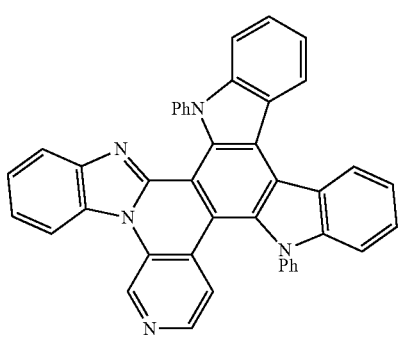
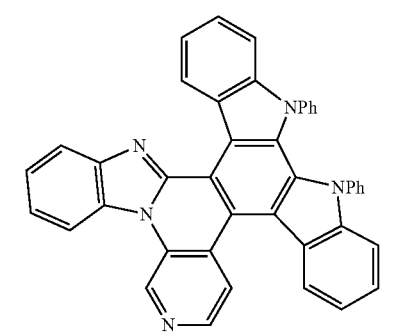
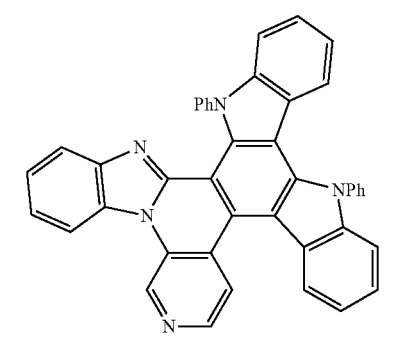
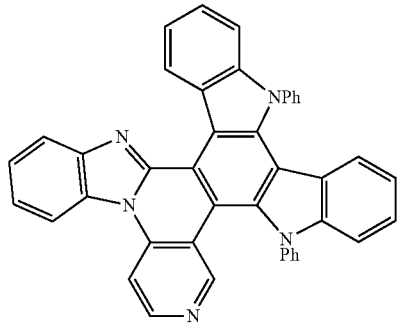
372
-continued
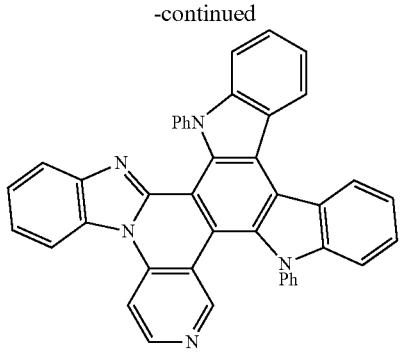
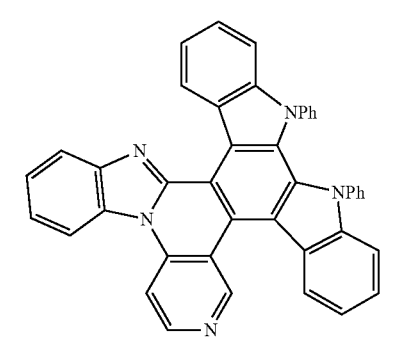
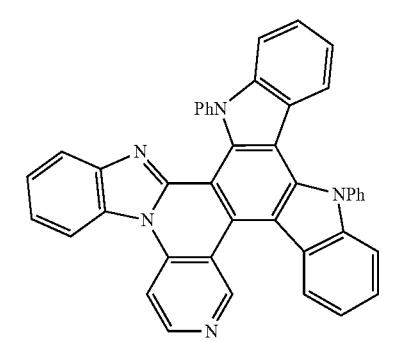
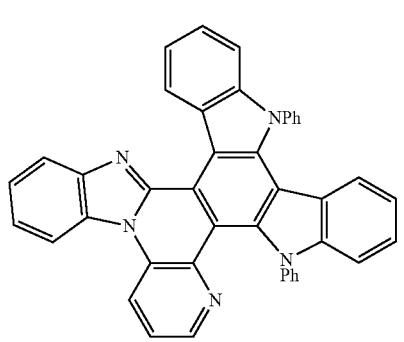
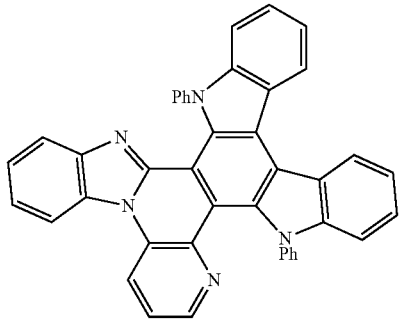

373
-continued
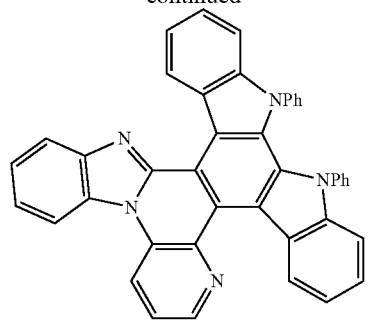
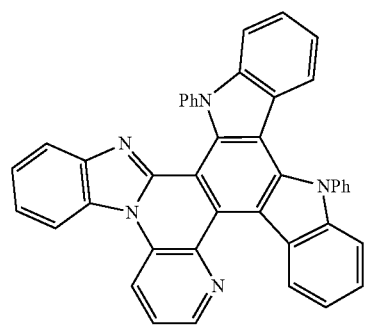
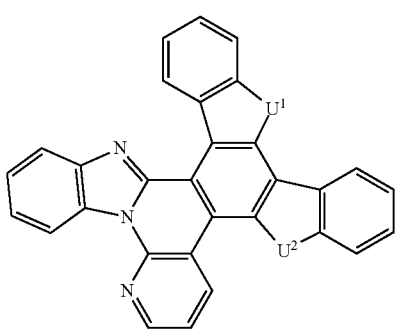
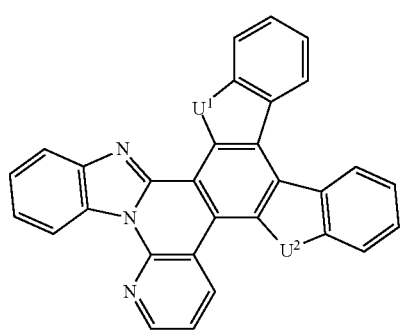
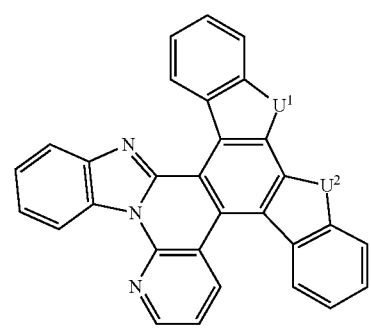
374
-continued
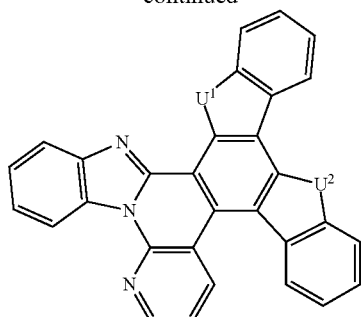
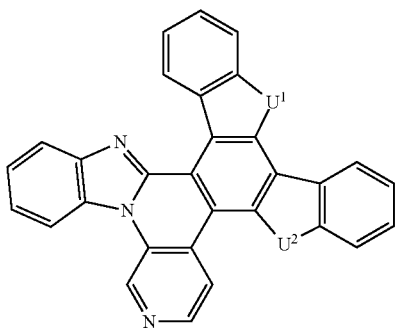
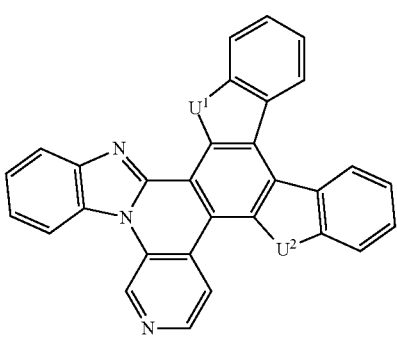
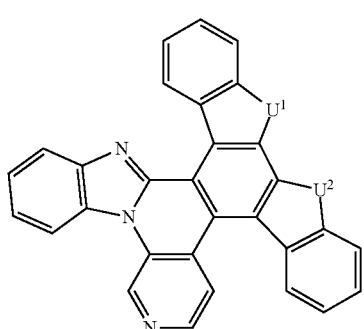
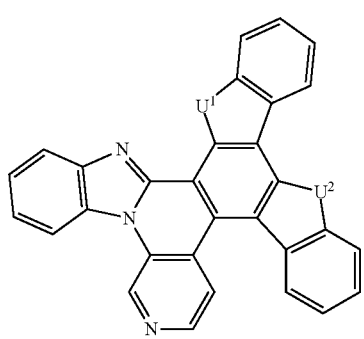

375
-continued
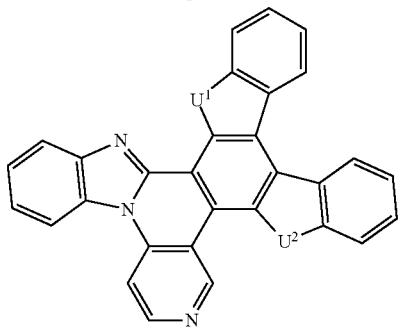
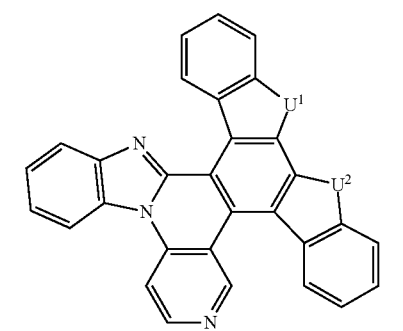
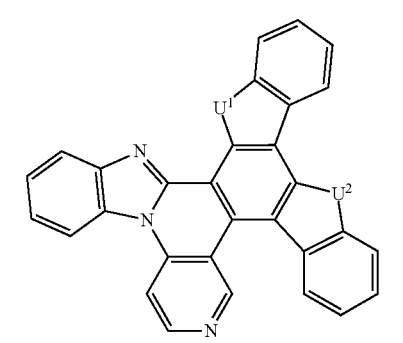
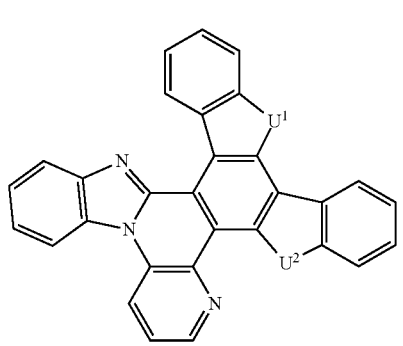
376
-continued
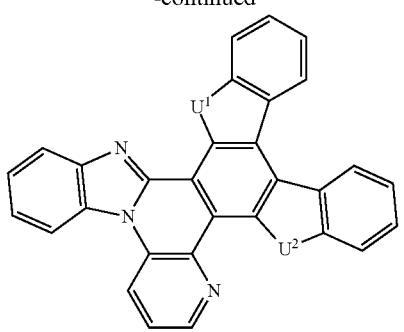
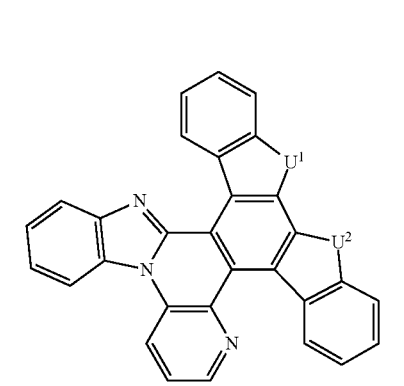
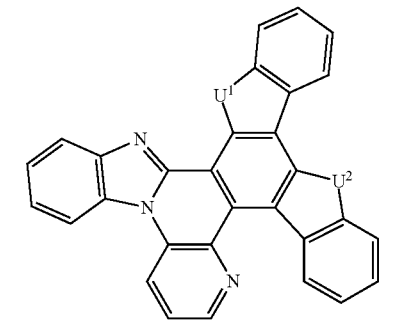
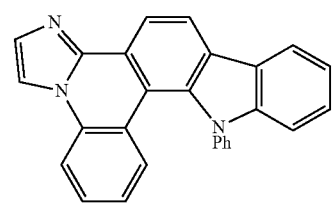
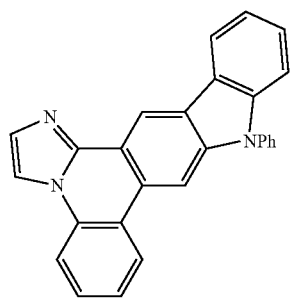

377
-continued
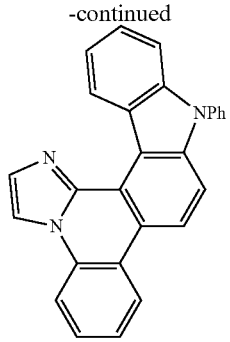
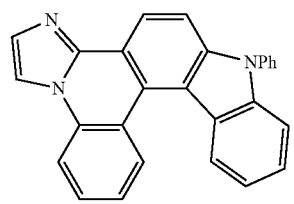
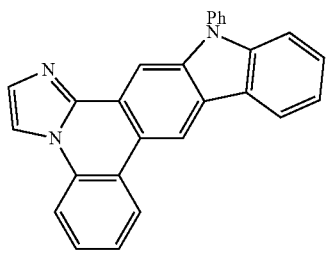
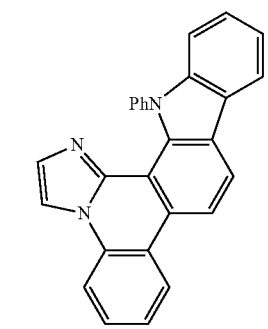
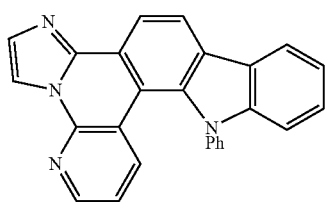
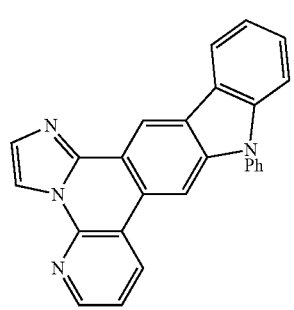
378
-continued
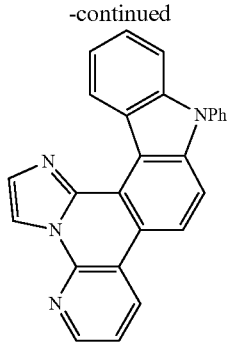
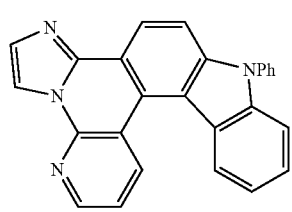
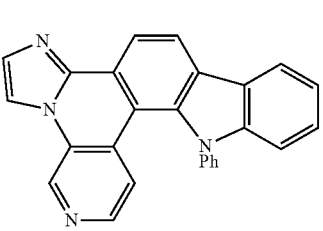
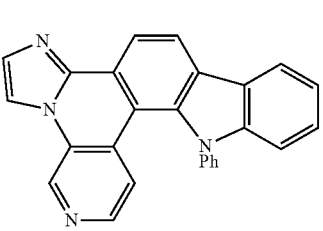
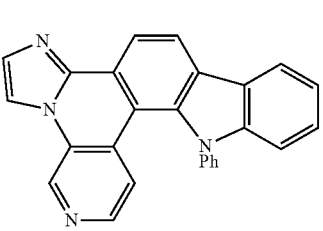
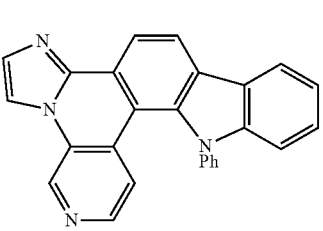

-continued
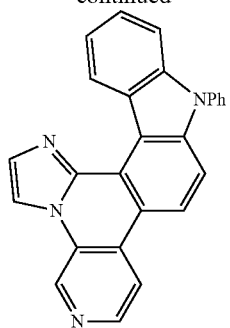
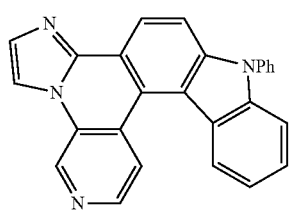
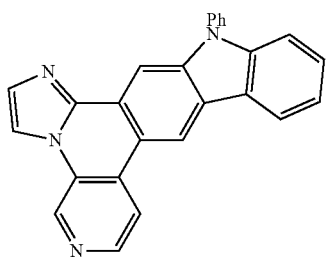
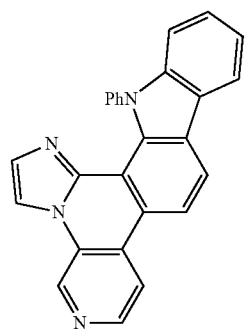
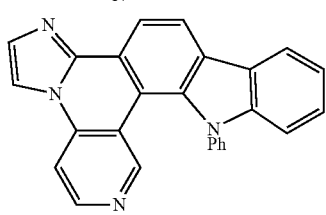
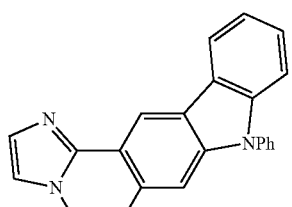
-continued
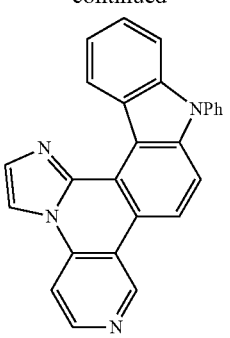
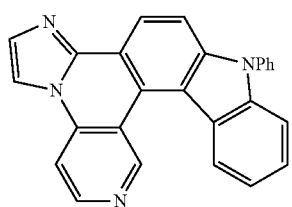
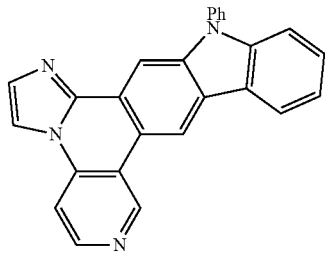
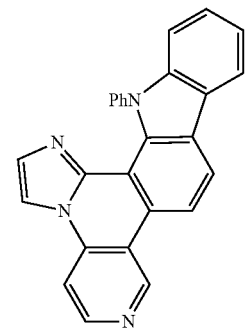
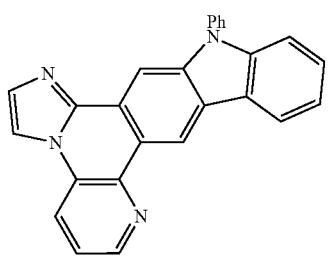
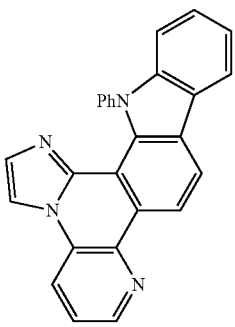

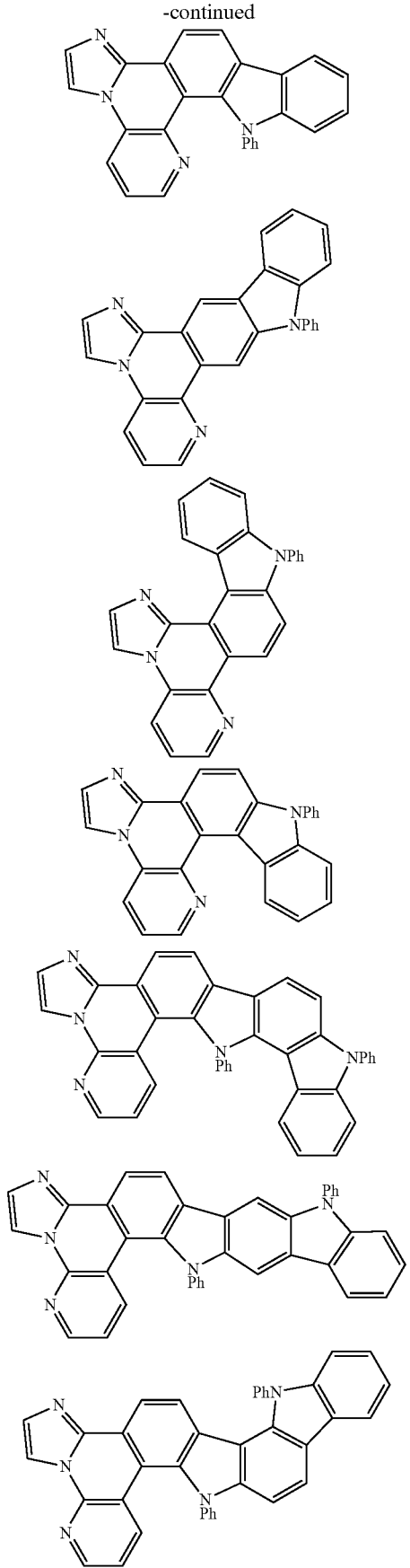

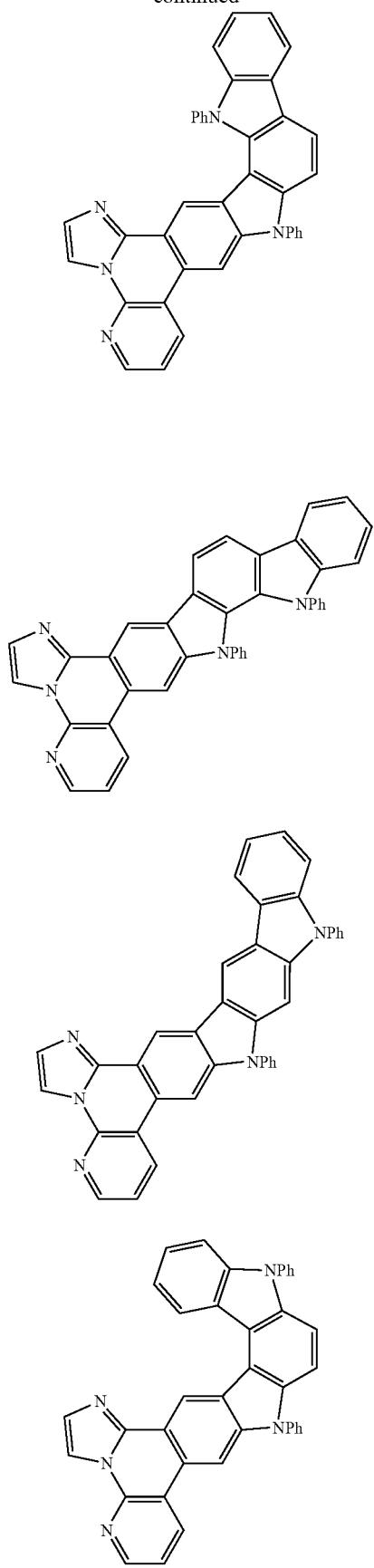

385
-continued
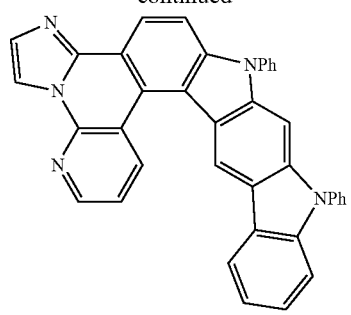
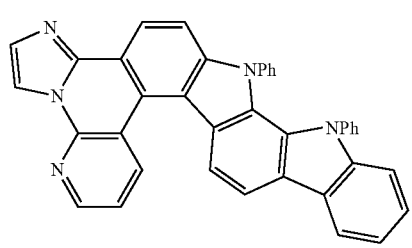
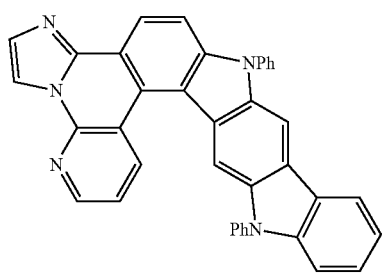
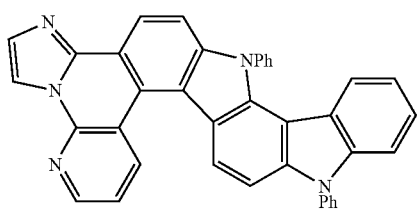
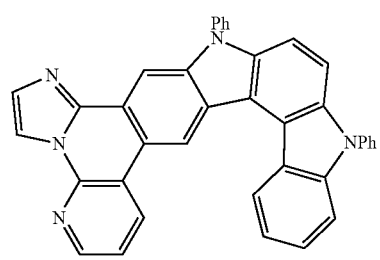
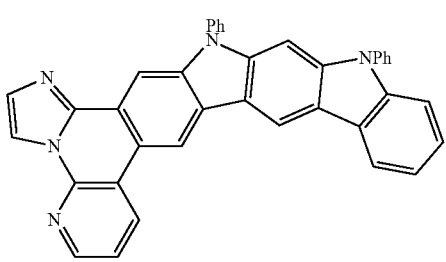
386
-continued
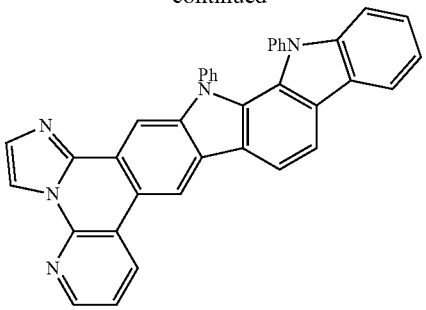
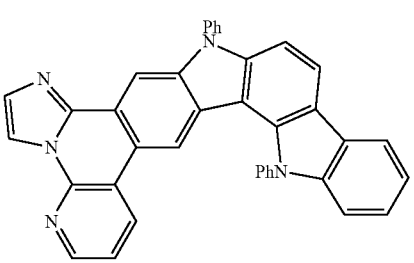
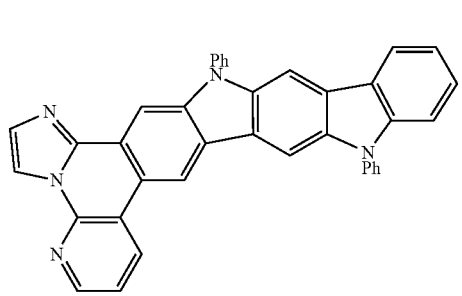
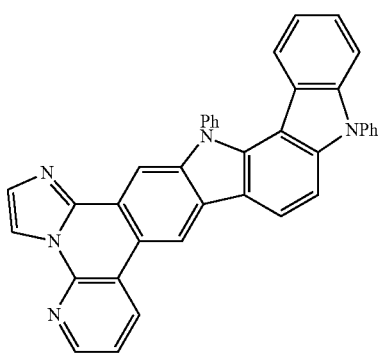
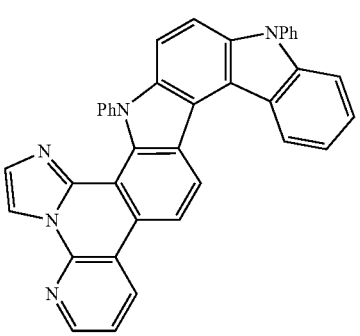

387
-continued
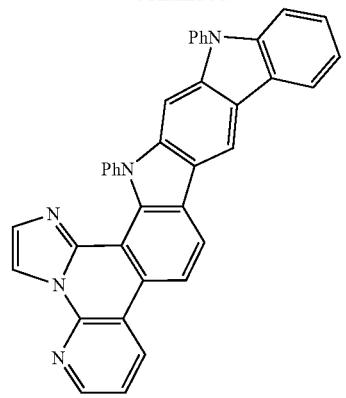
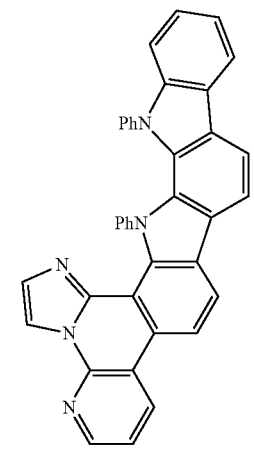
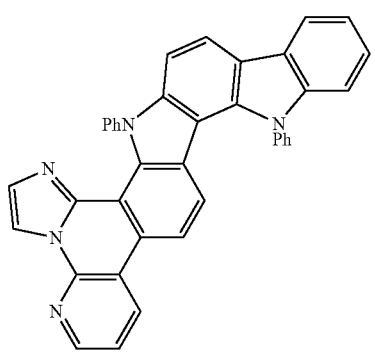
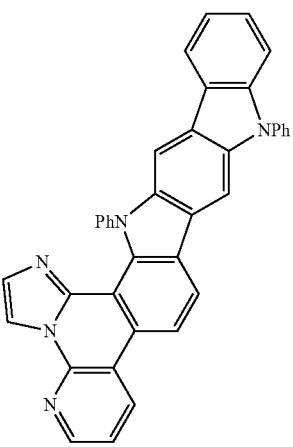
388
-continued
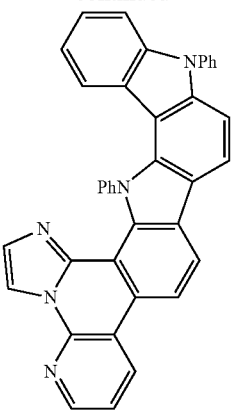
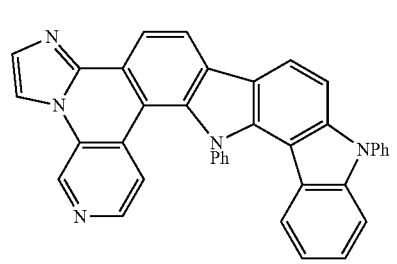
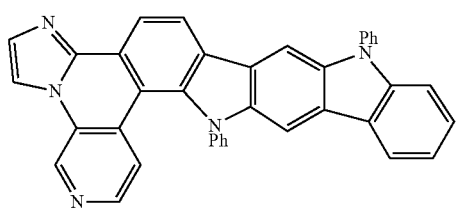
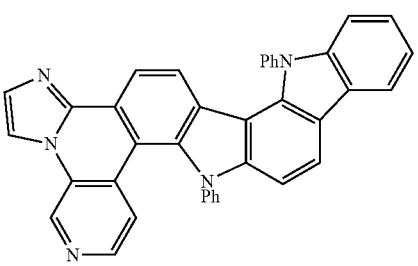
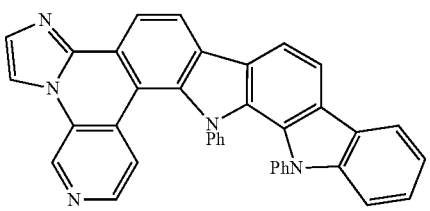
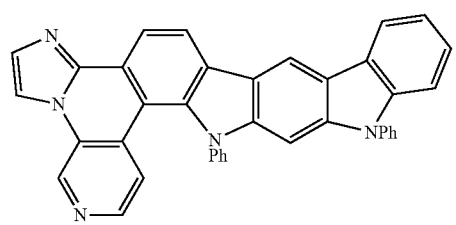

389
-continued
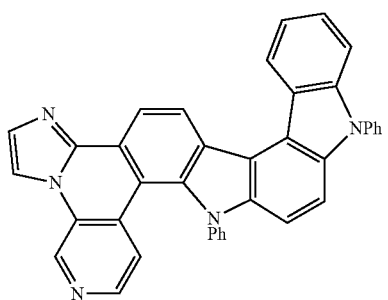
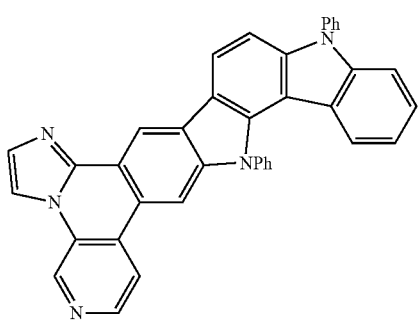
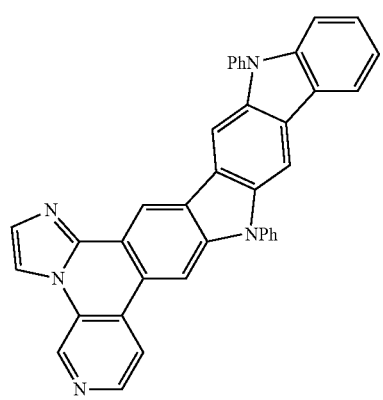
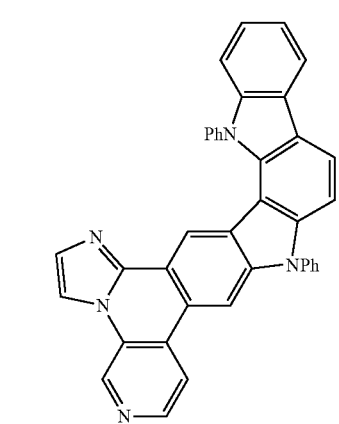
390
-continued
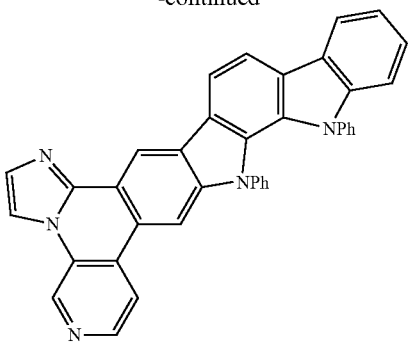
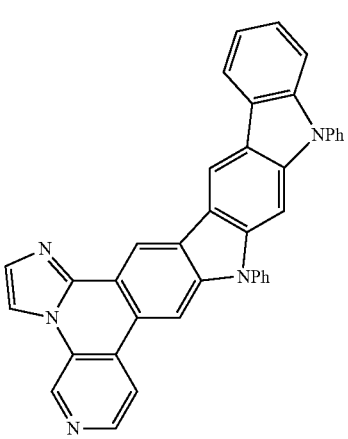
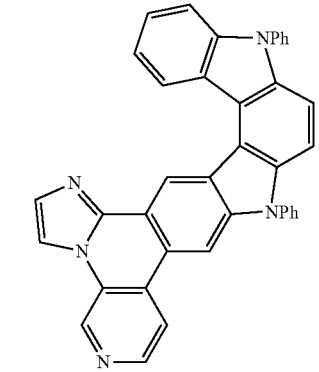
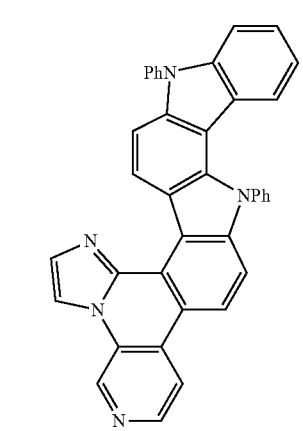

391
-continued
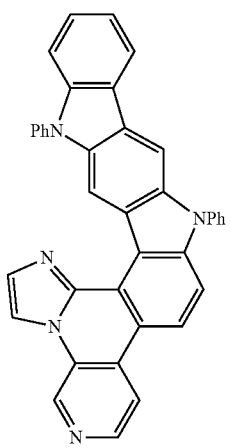
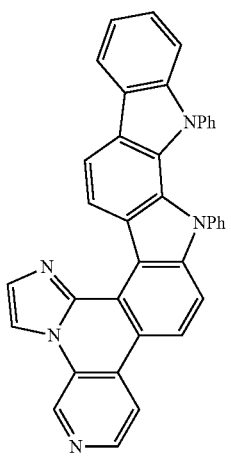
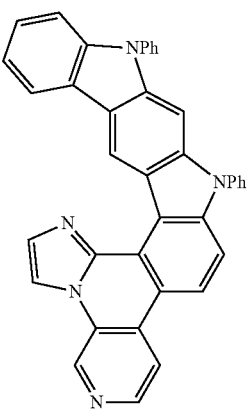
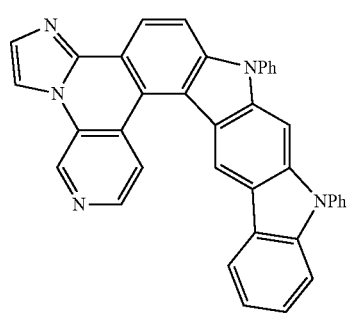
392
-continued
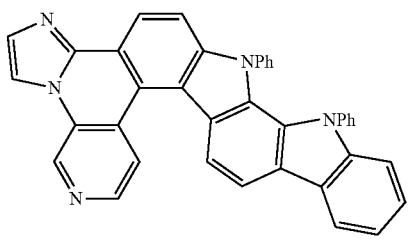
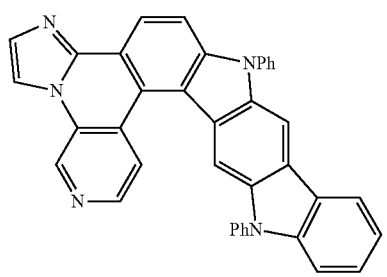
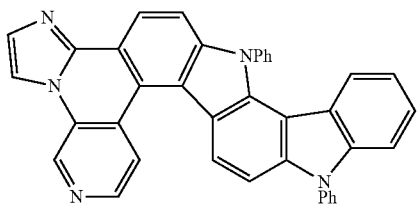
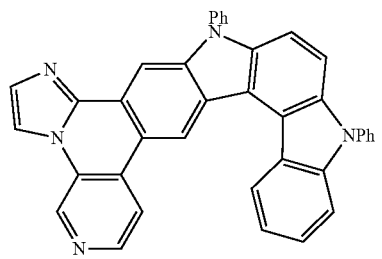
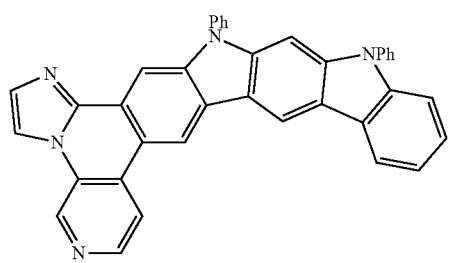
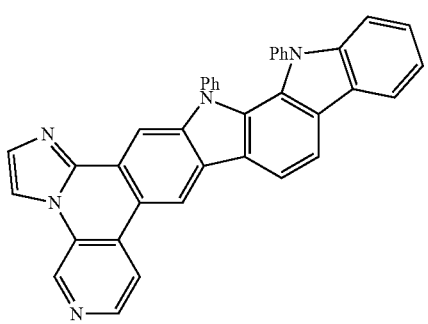

393
-continued
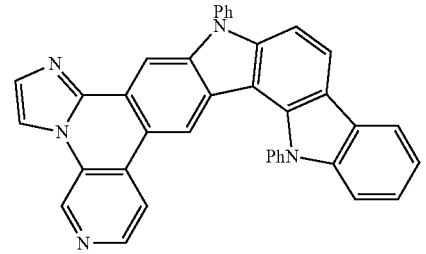
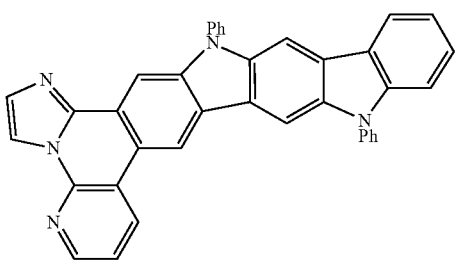
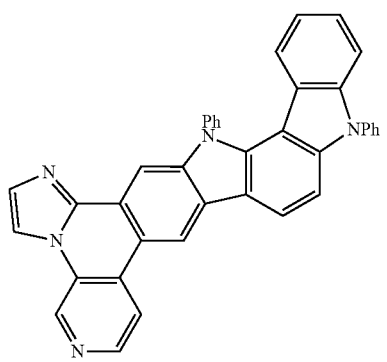
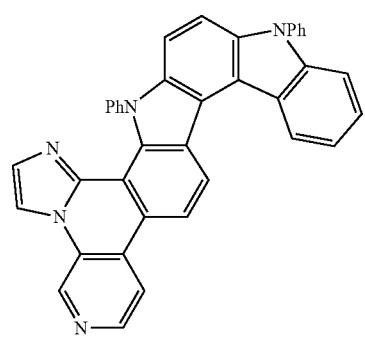
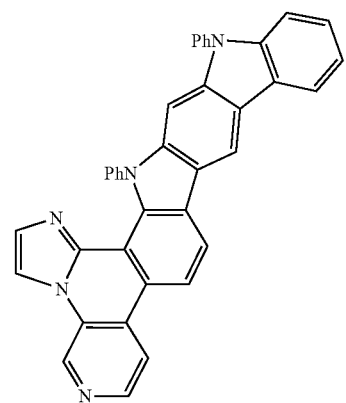
394
-continued
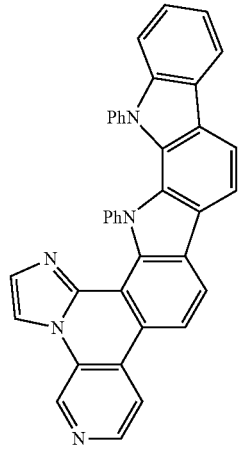
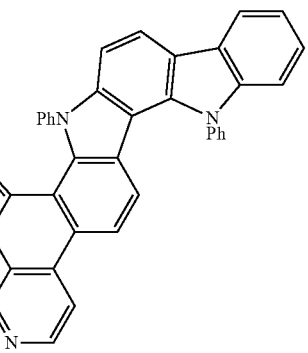
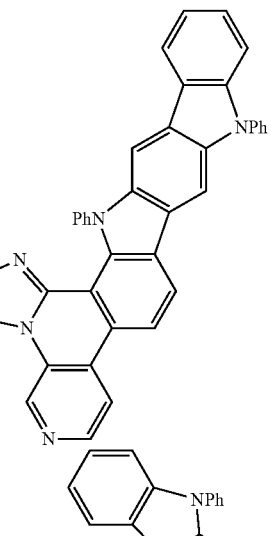
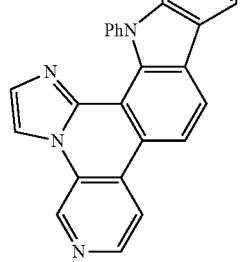

395
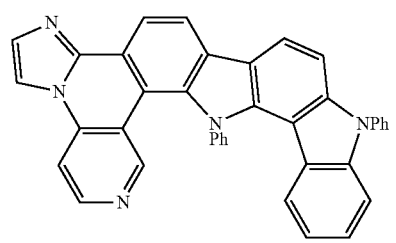
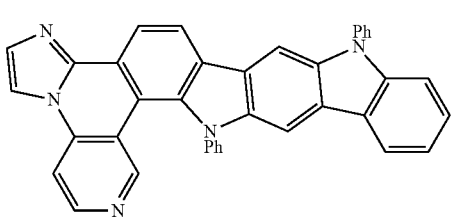
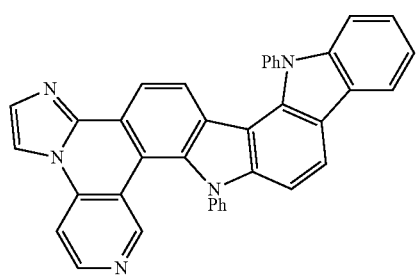
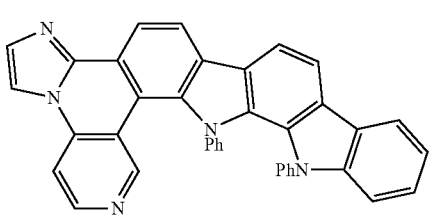
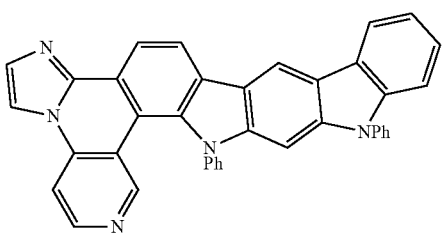
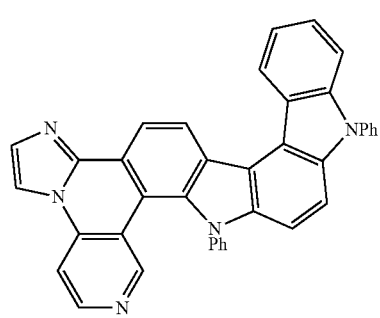
396
-continued
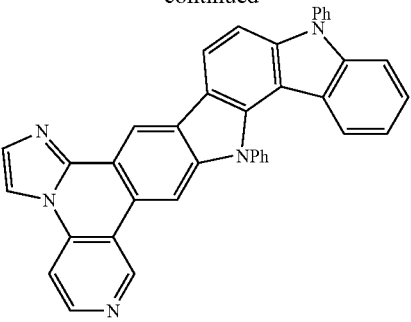
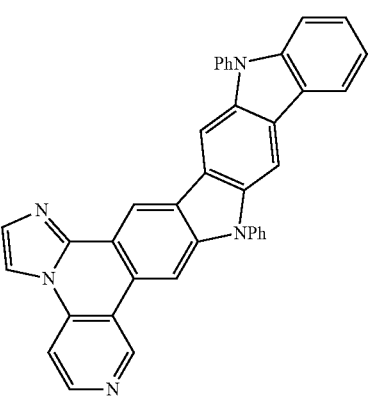
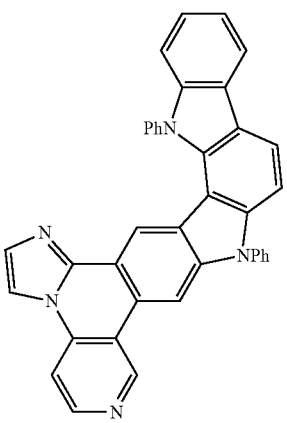
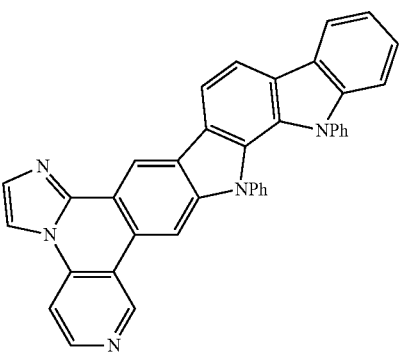

397
-continued
398
-continued
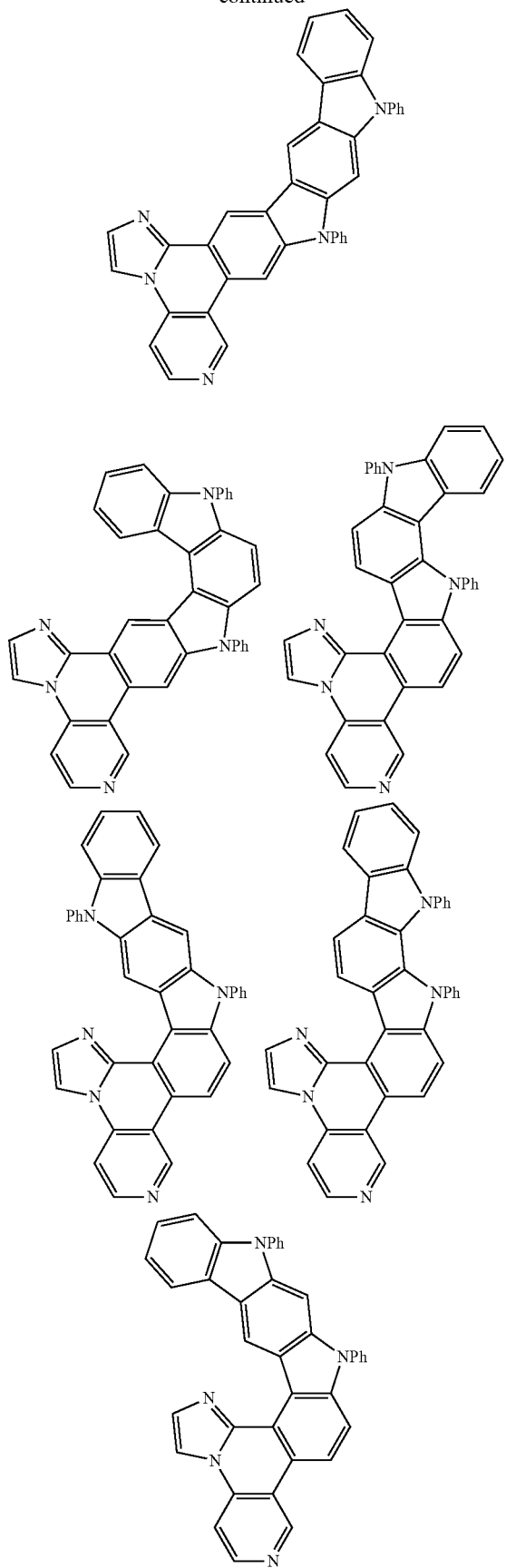
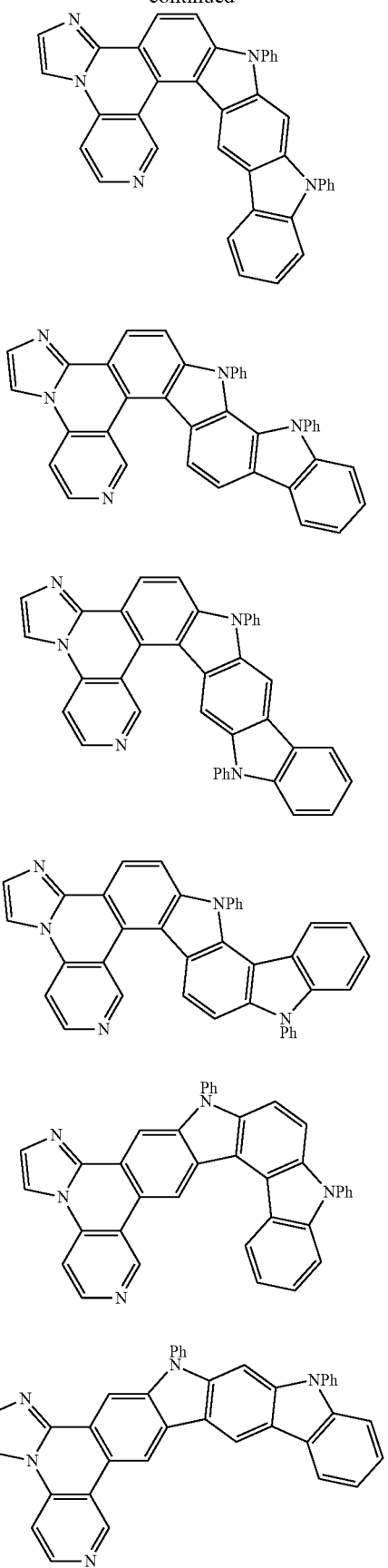

399
-continued
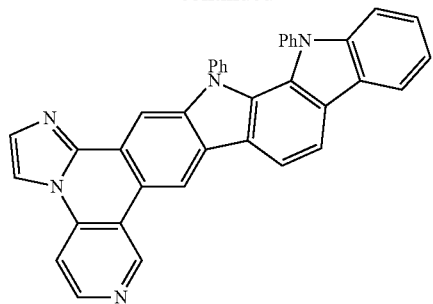
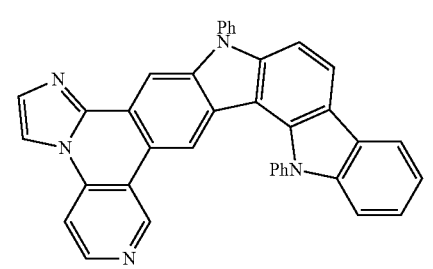
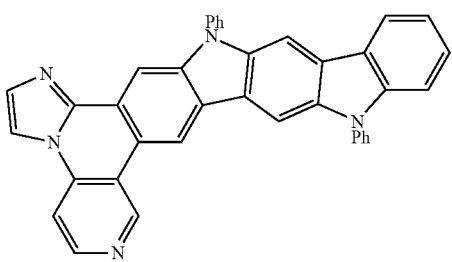
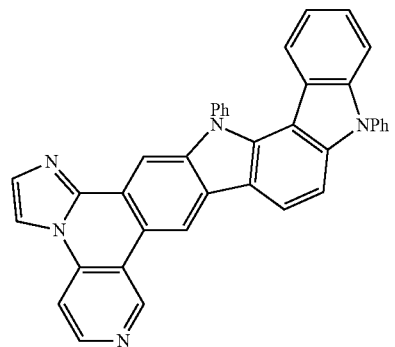
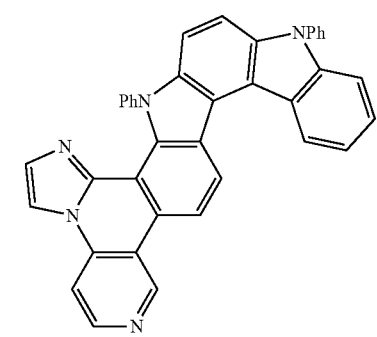
400
-continued
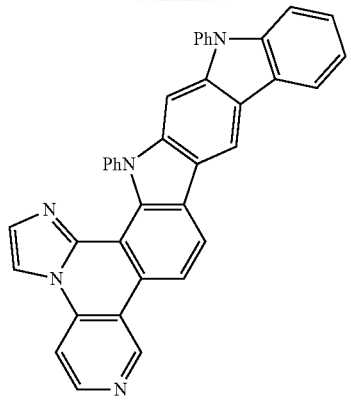
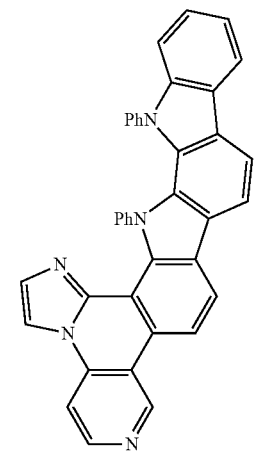
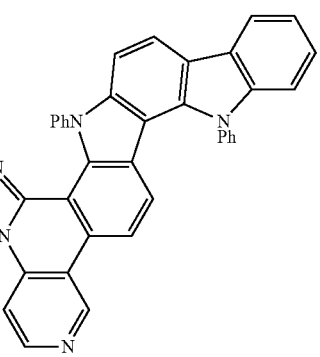
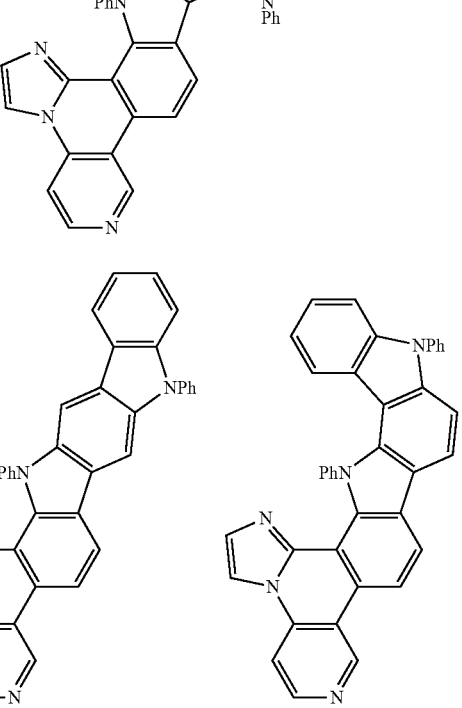

401
-continued
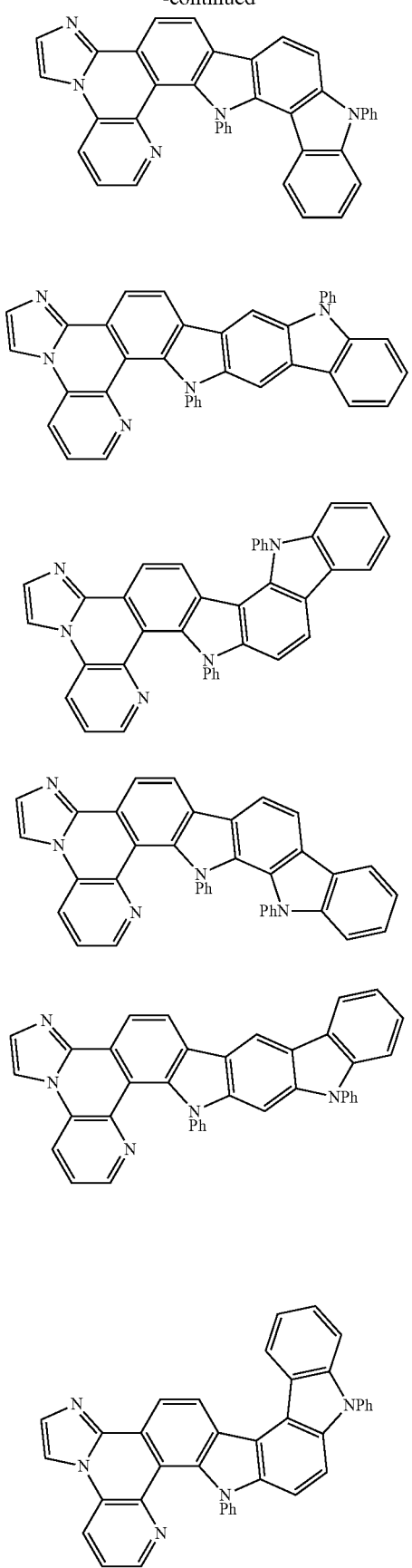
402
-continued
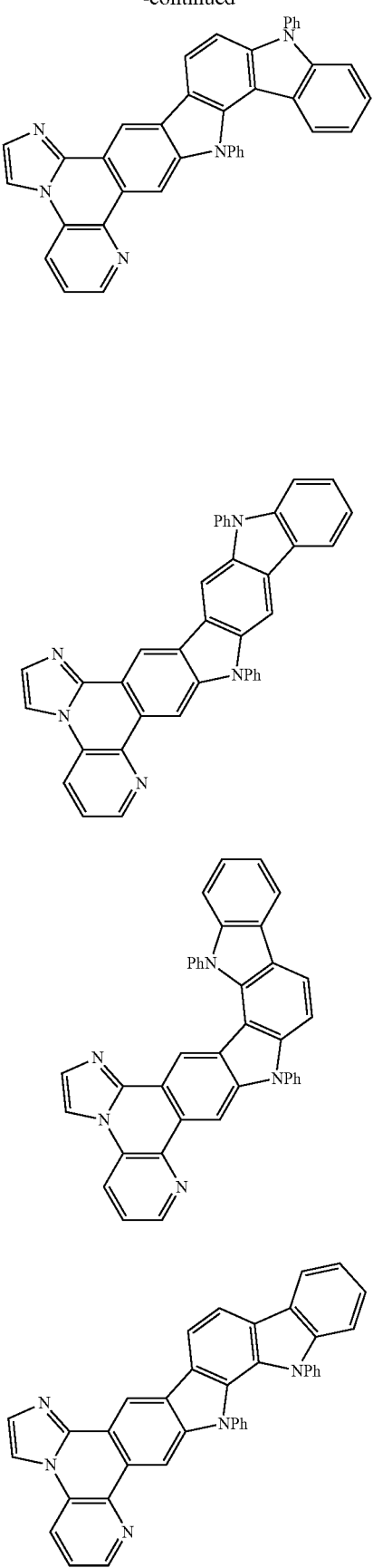

403
-continued
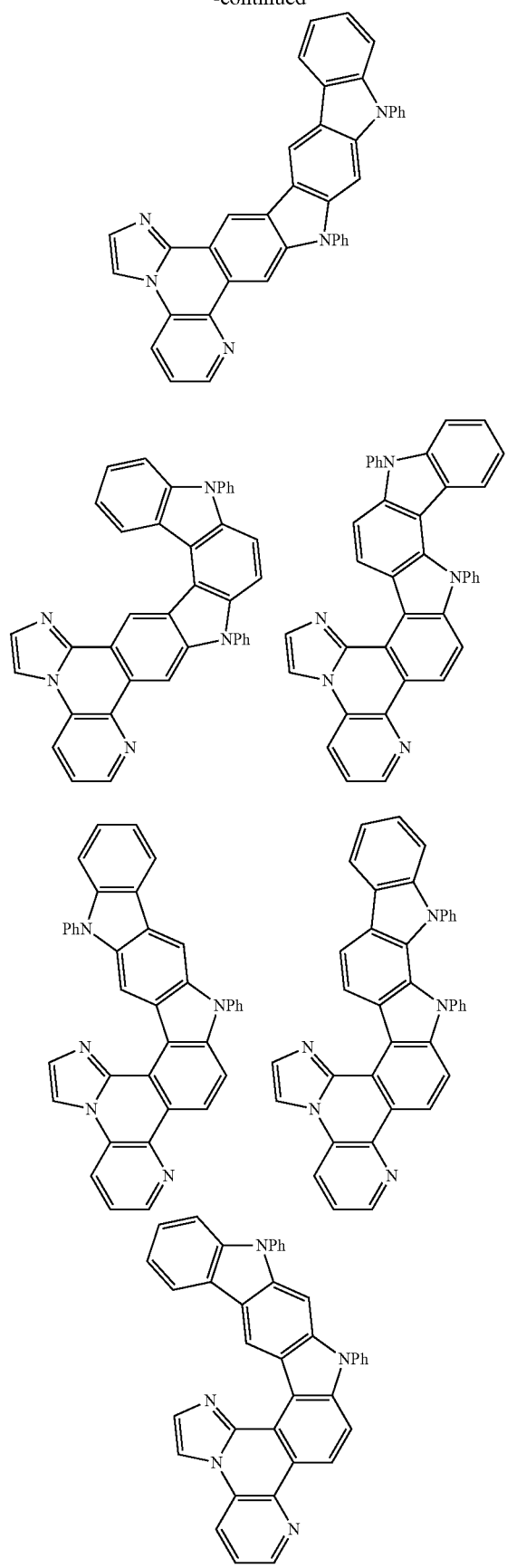
404
-continued
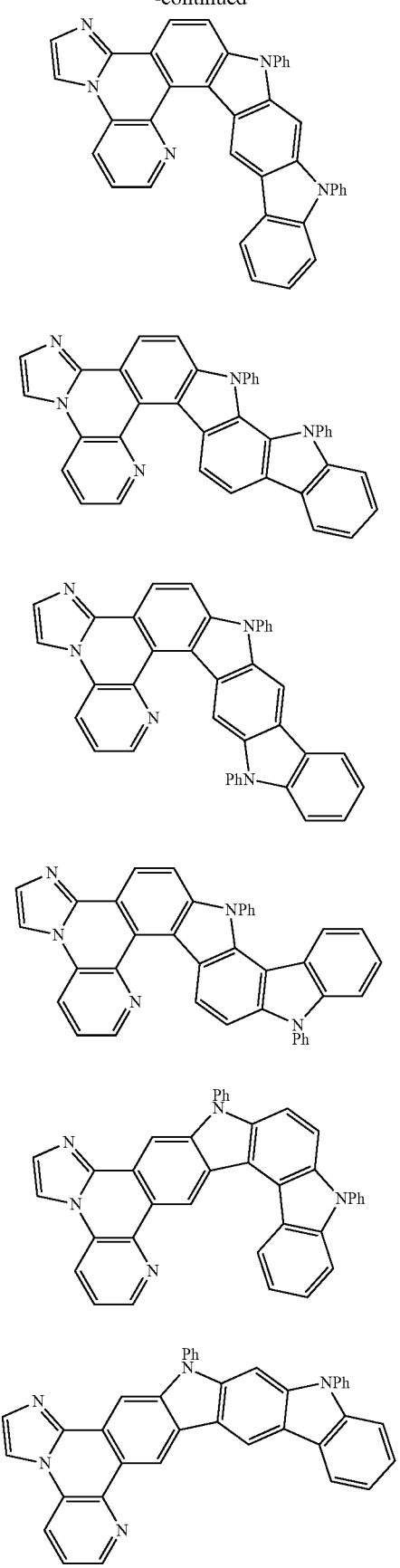

405
-continued
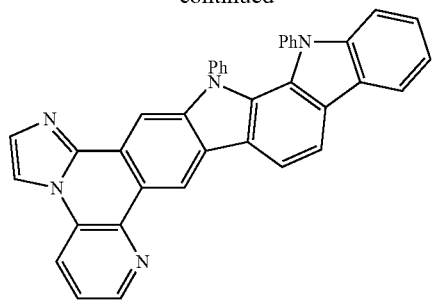
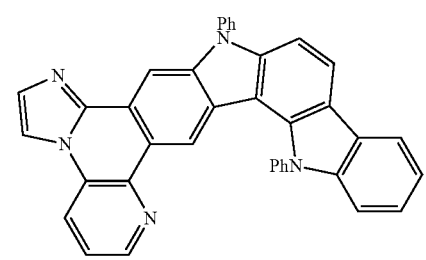
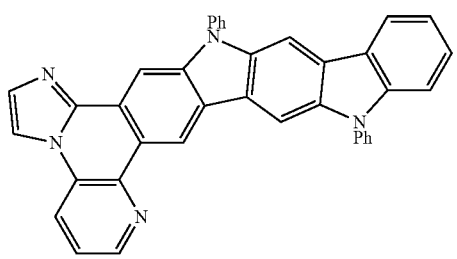
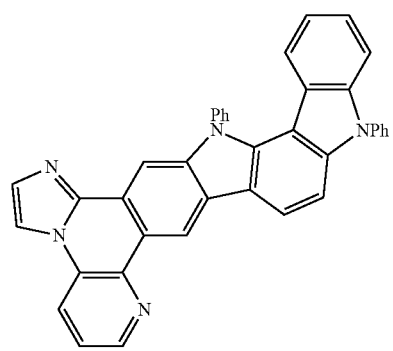
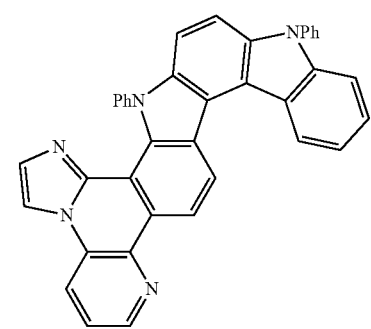
406
-continued
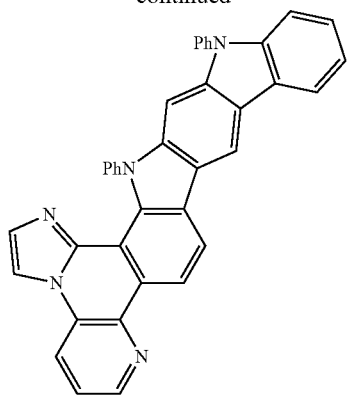
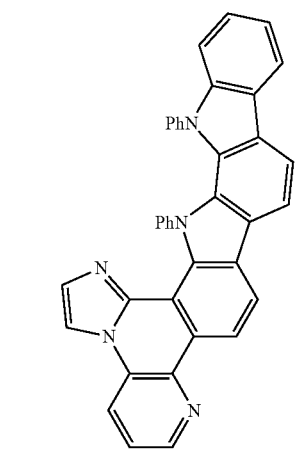
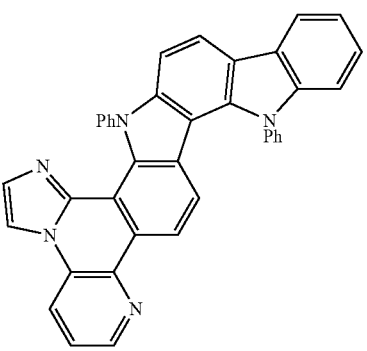
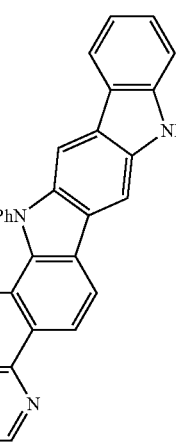 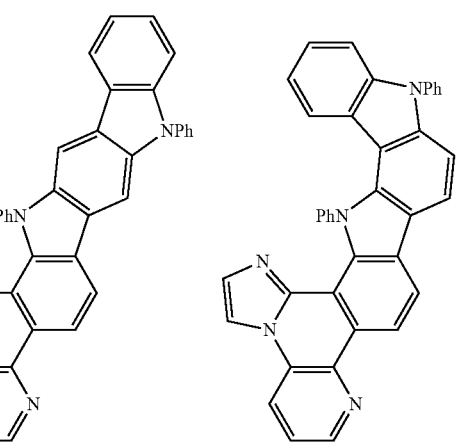

407
-continued
408
-continued
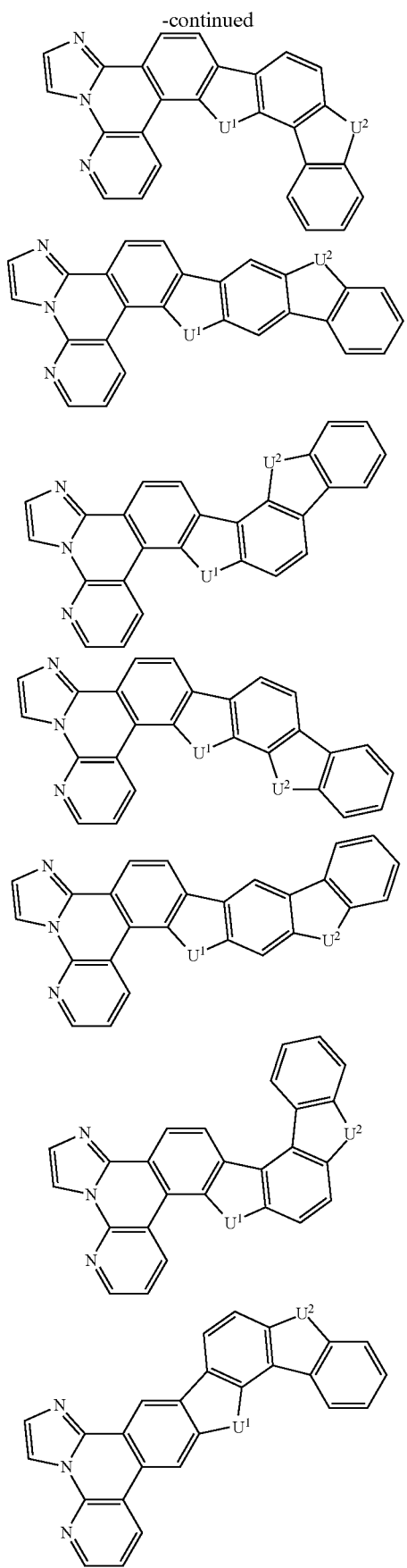
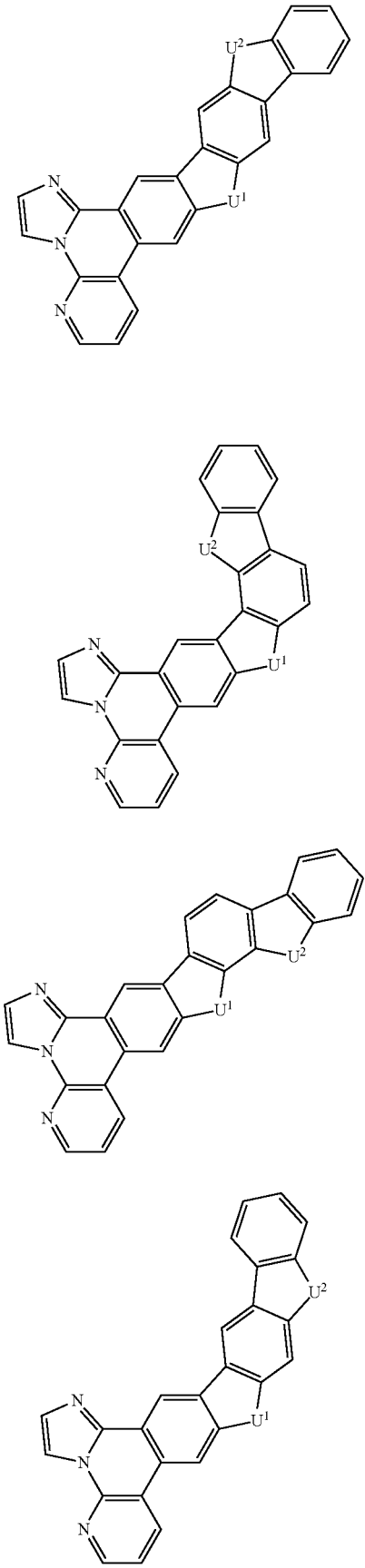

409
-continued
410
-continued
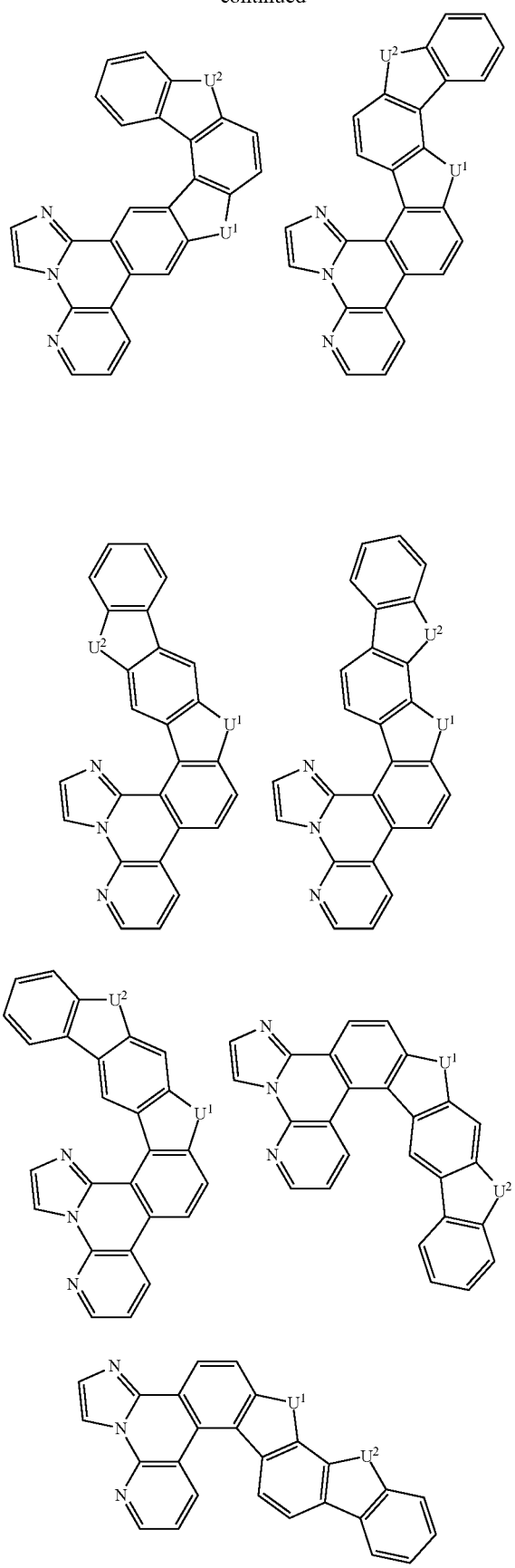
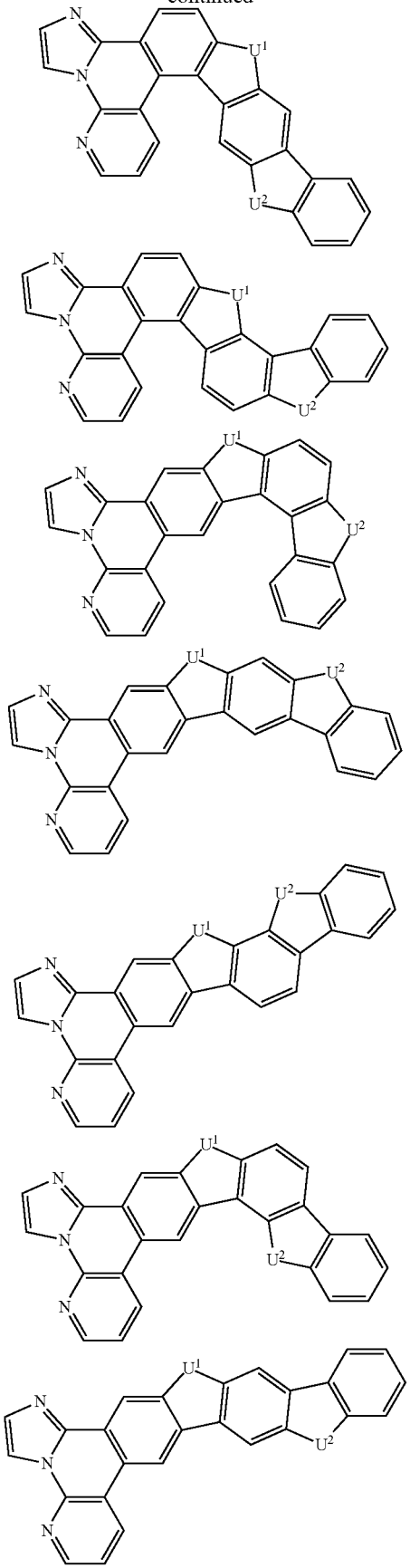

411
-continued
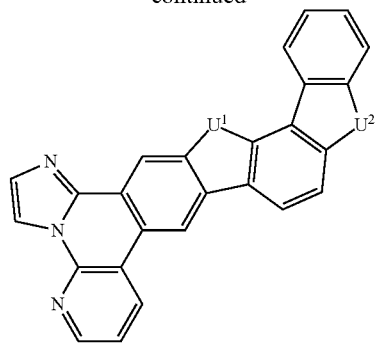
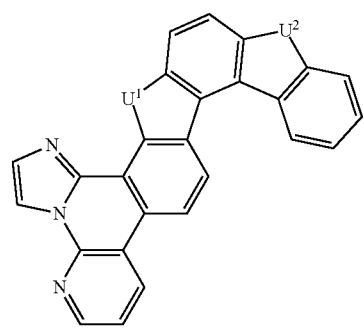
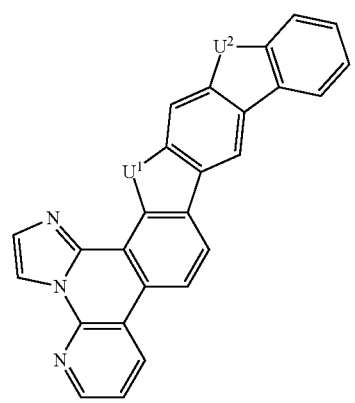
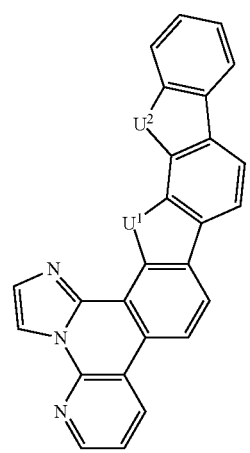
412
-continued
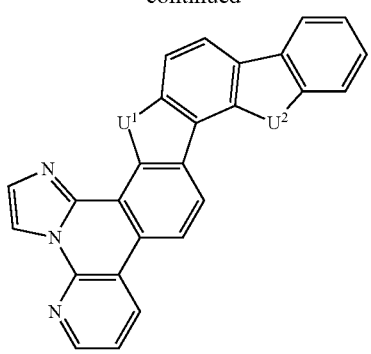
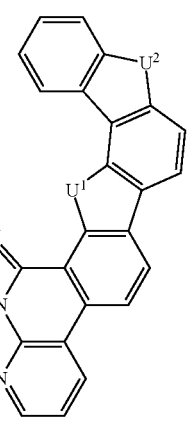
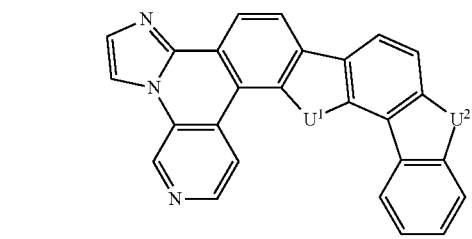
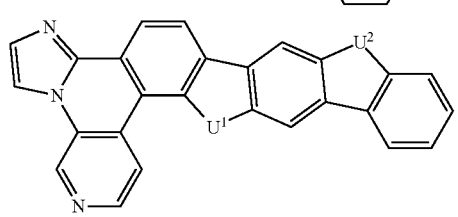
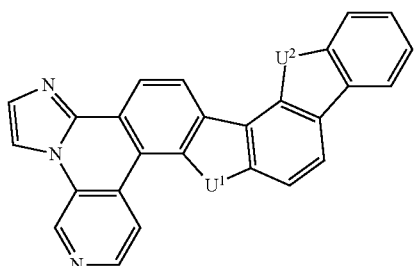
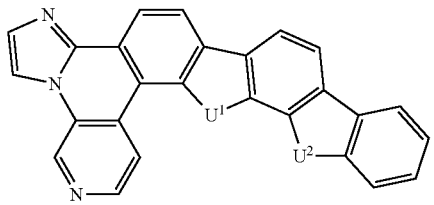

413
-continued
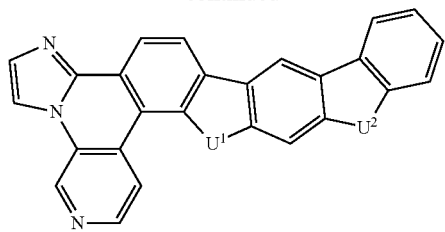
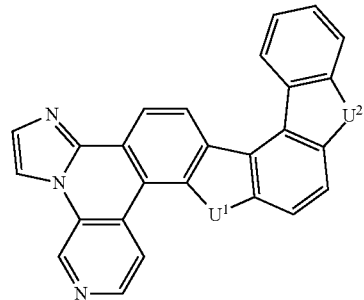
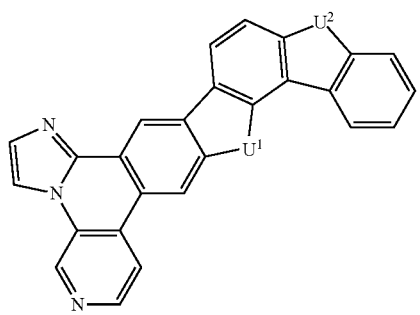
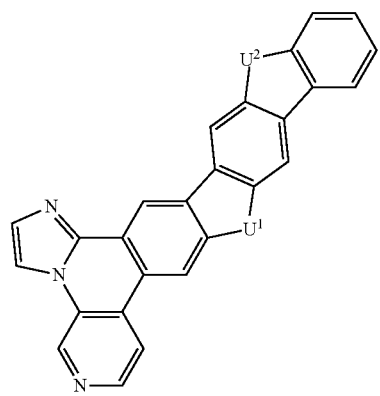
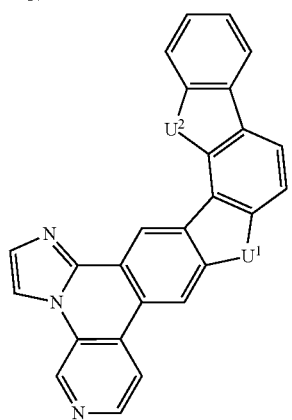
414
-continued
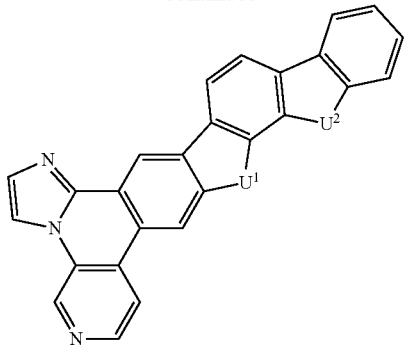
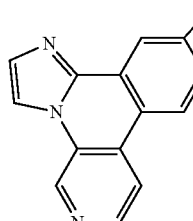
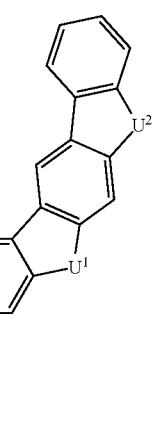
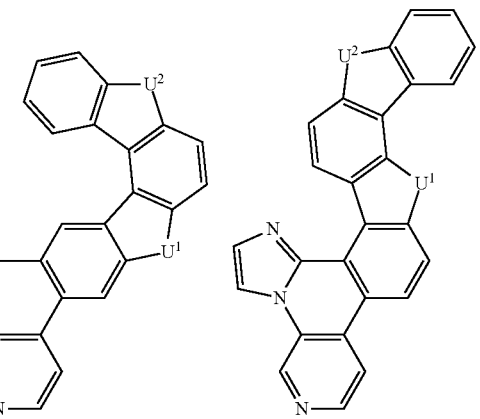
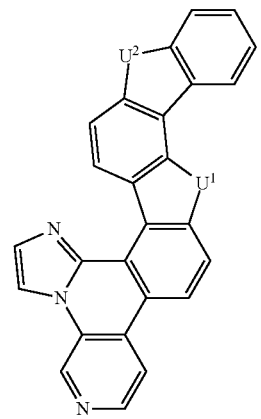
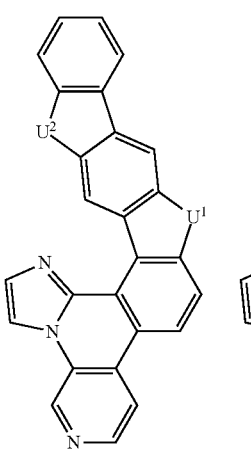
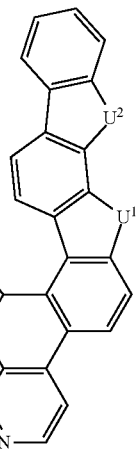

415
-continued
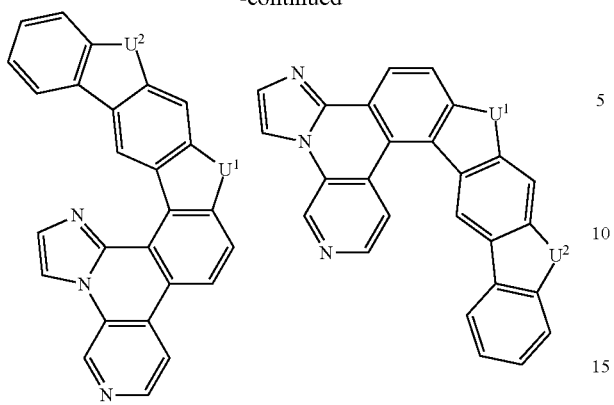
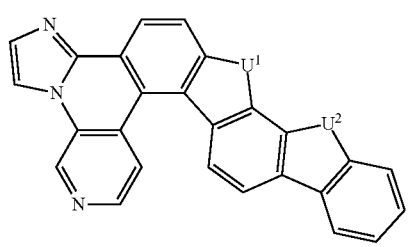
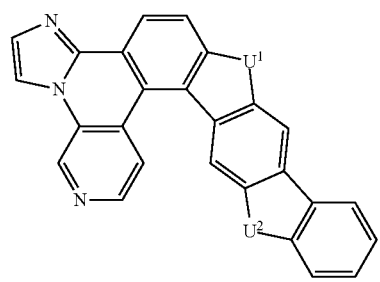
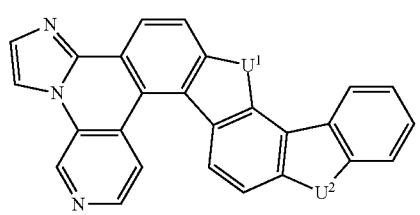
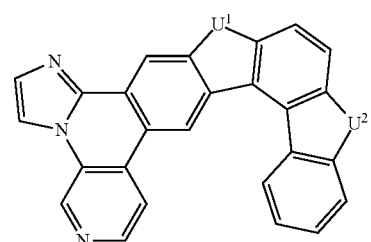
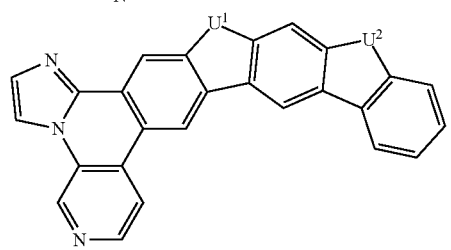
416
-continued
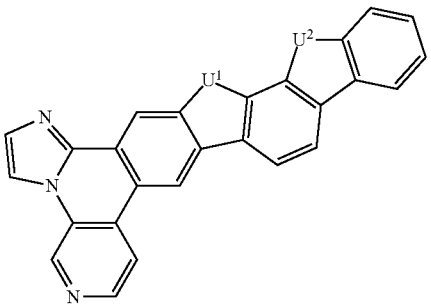
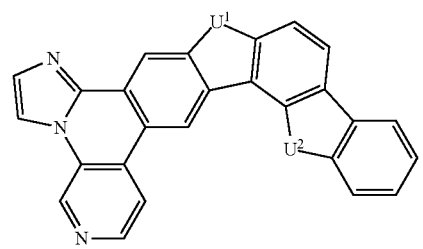
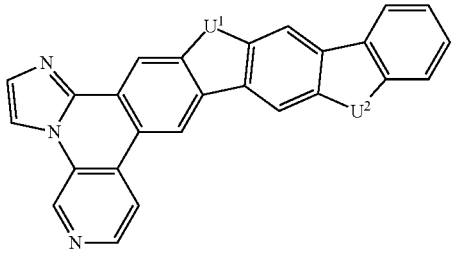
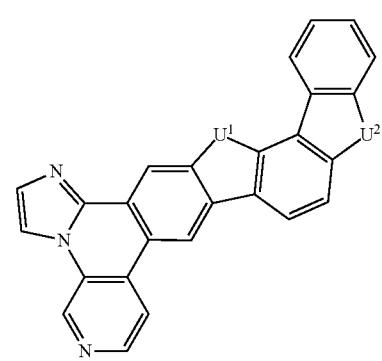
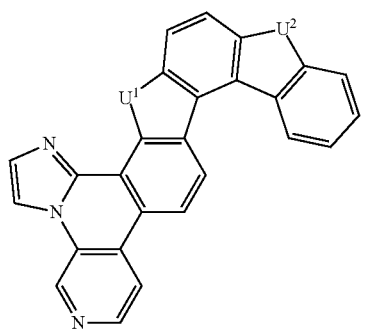

417
-continued
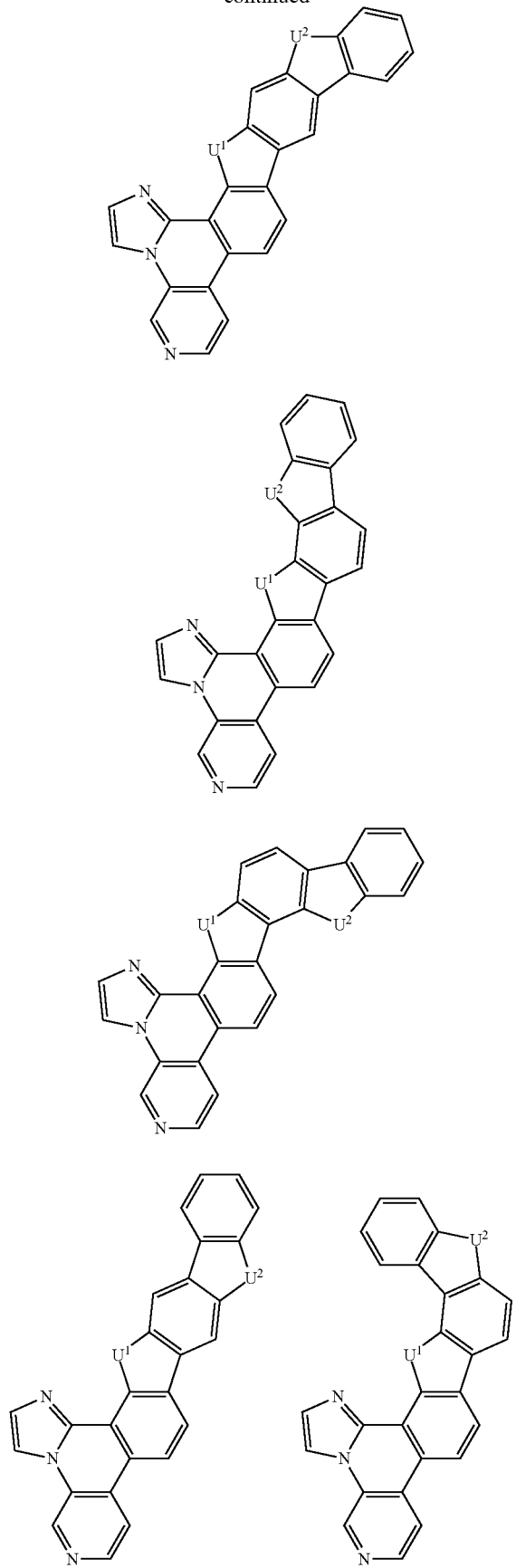
418
-continued
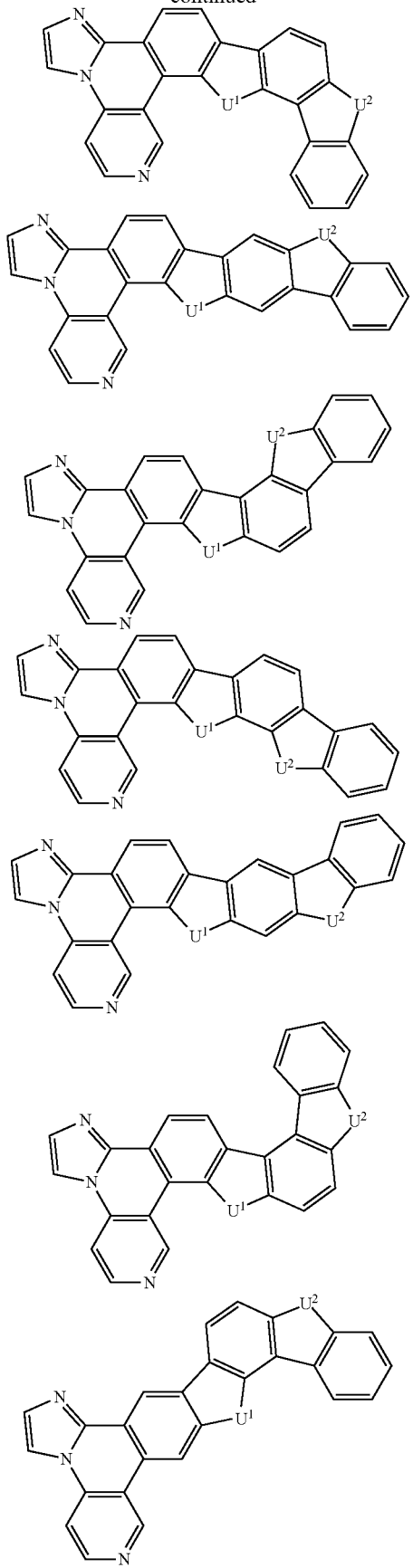

-continued
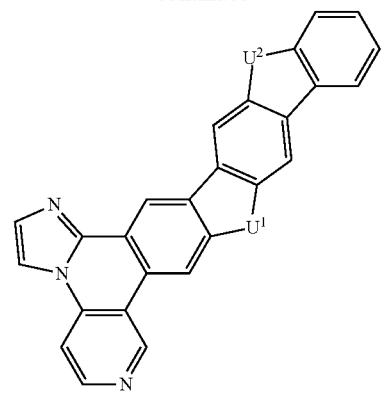
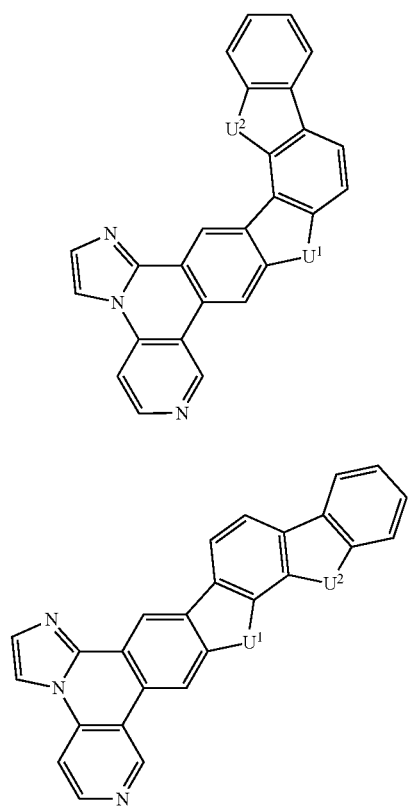
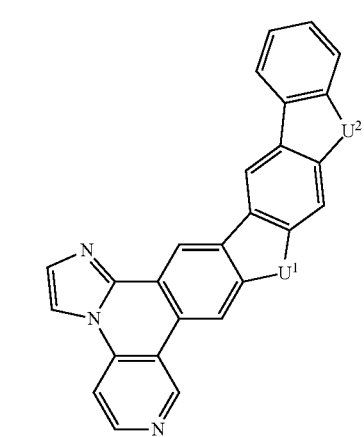
-continued
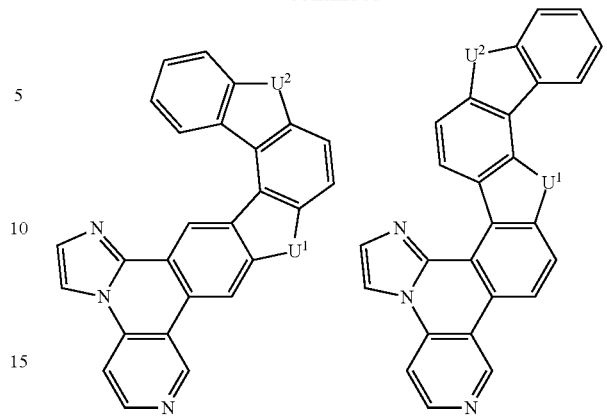
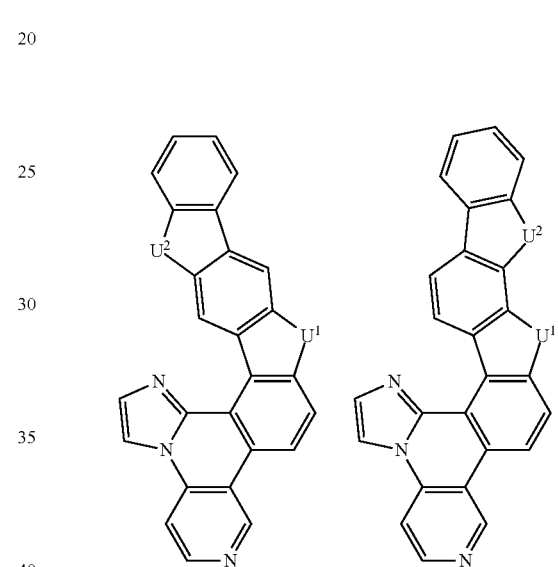
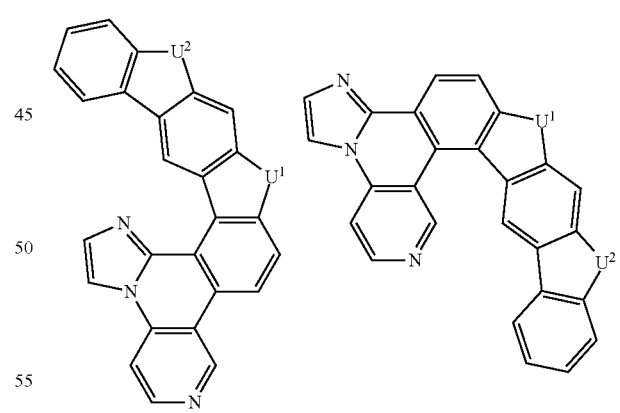
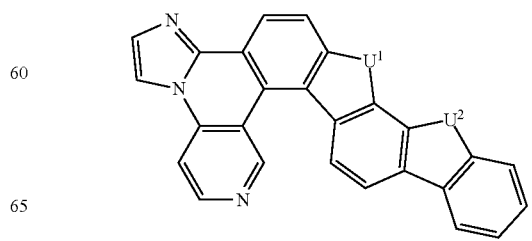

421
-continued
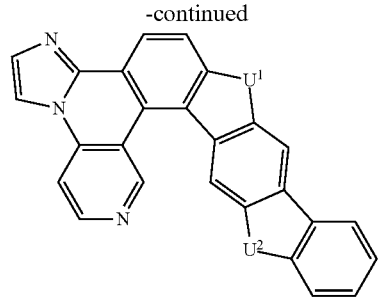
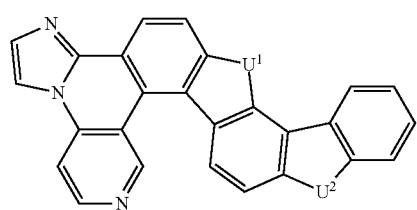
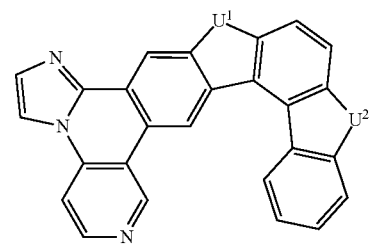
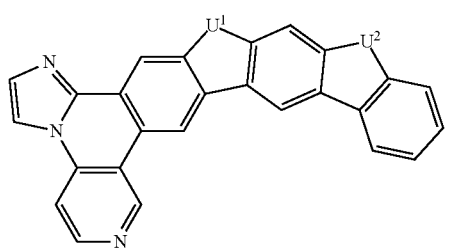
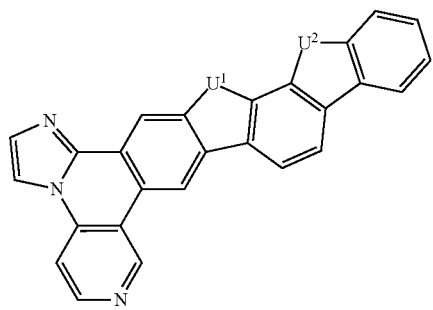
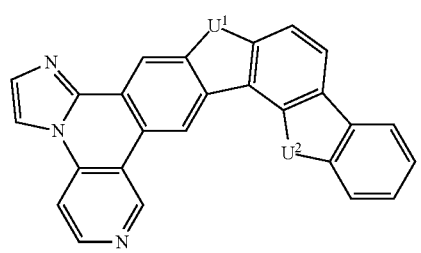
422
-continued
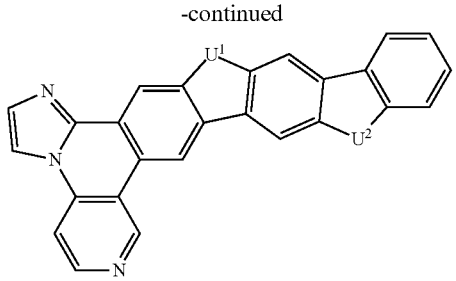
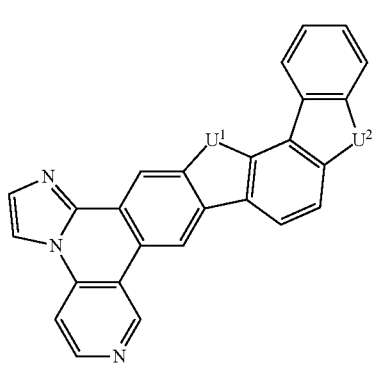
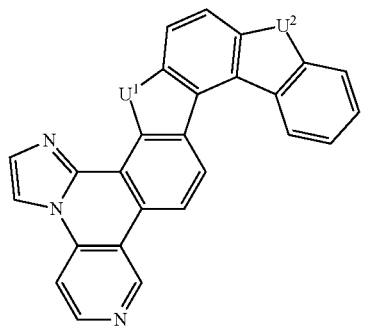
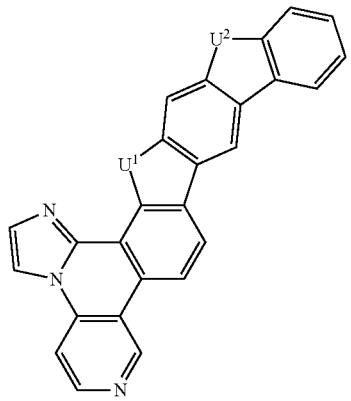

-continued
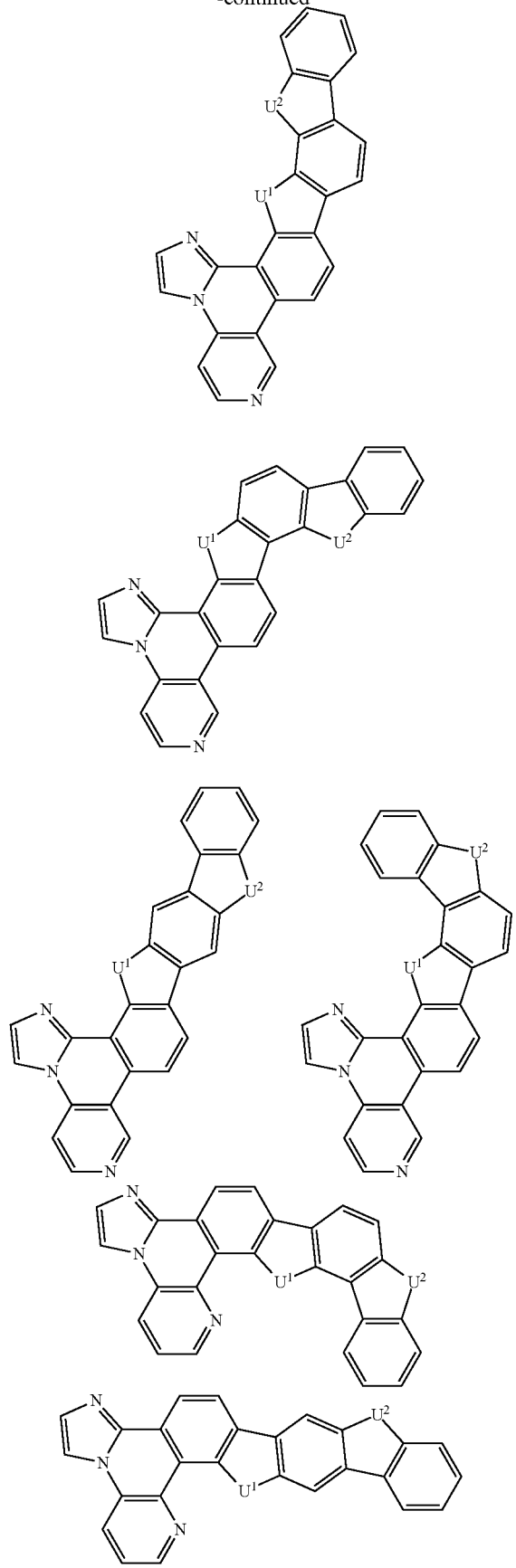
-continued
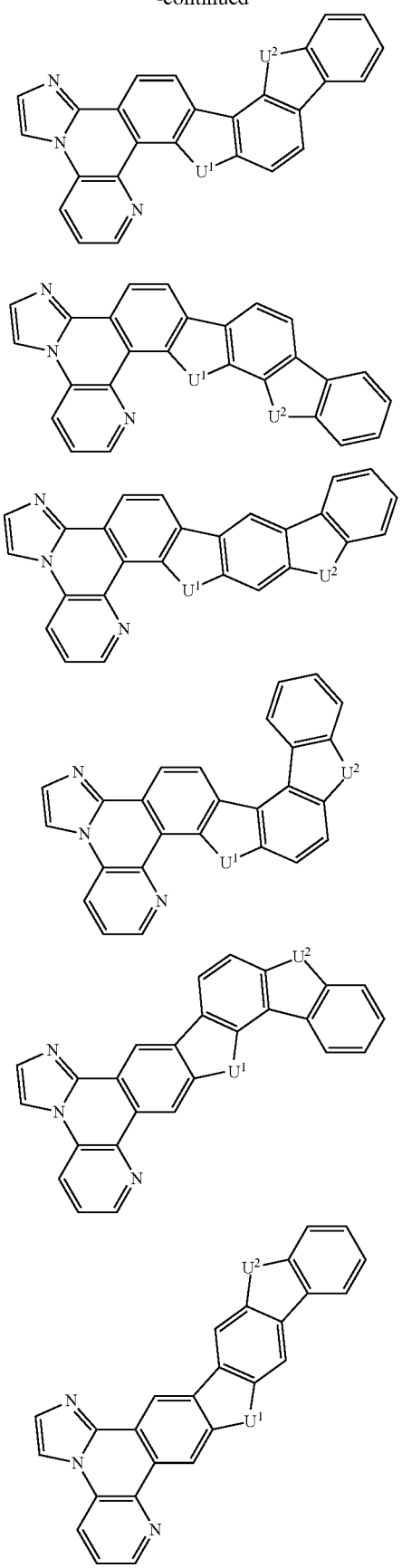

425
-continued
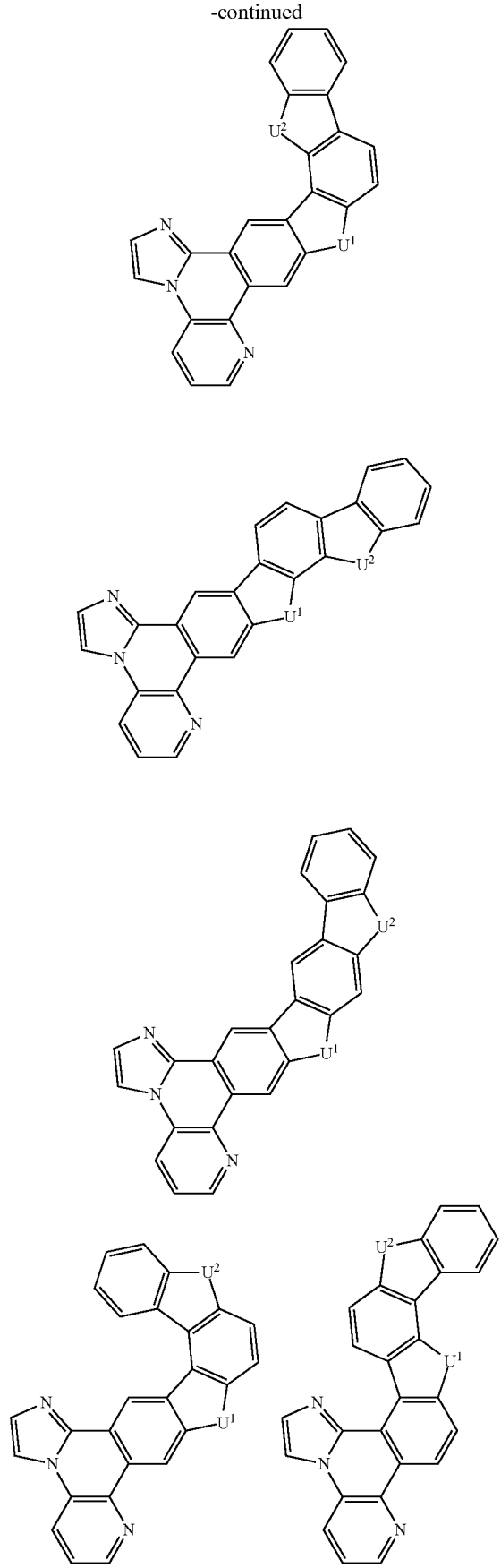
426
-continued
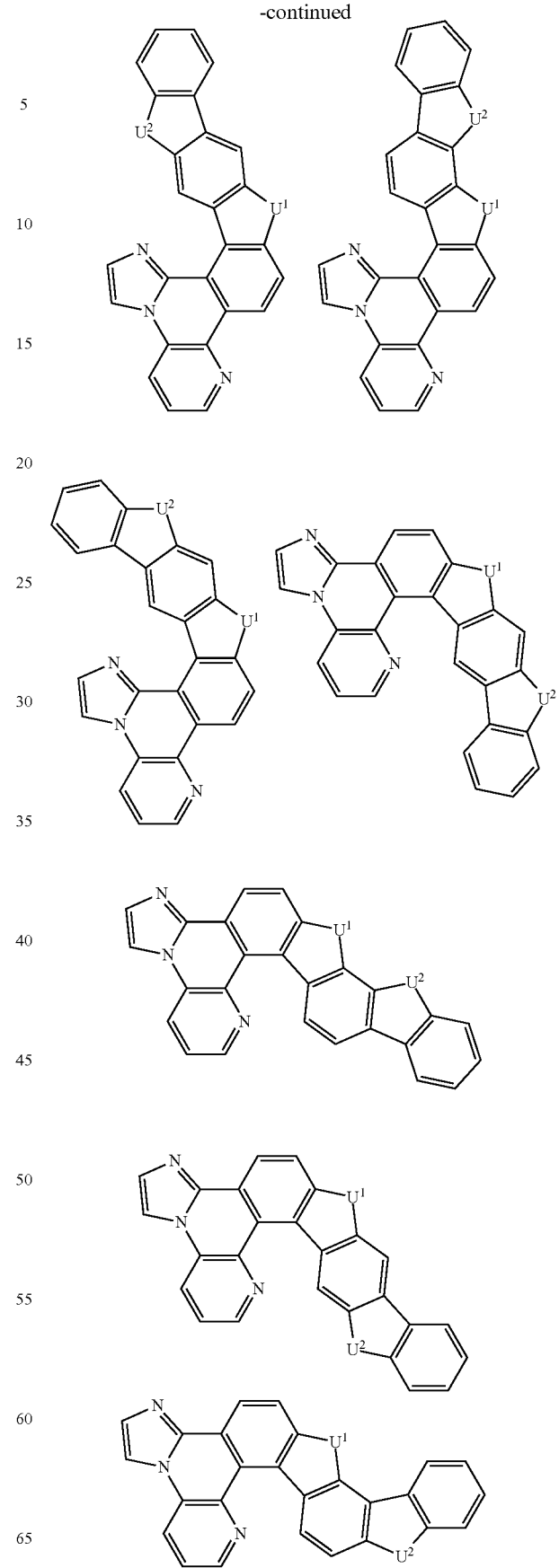

427
-continued
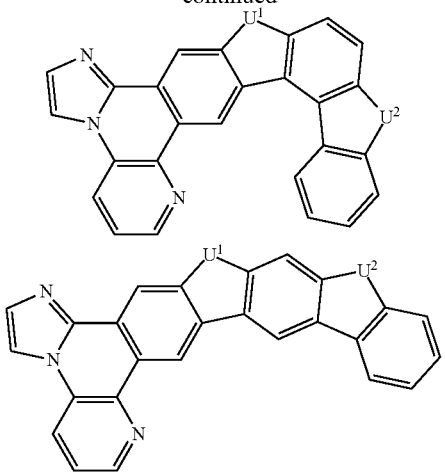
428
-continued
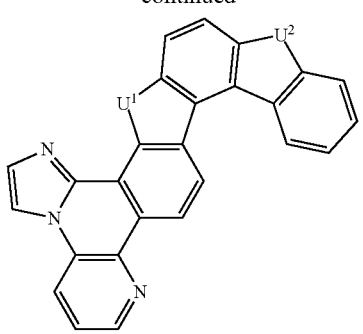
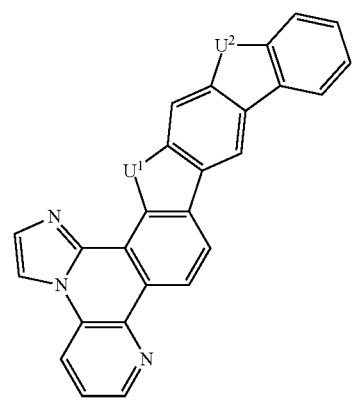
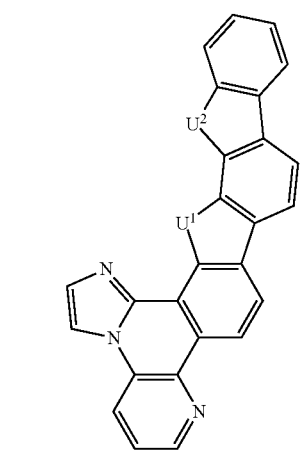
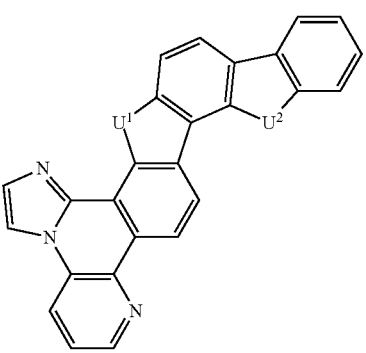

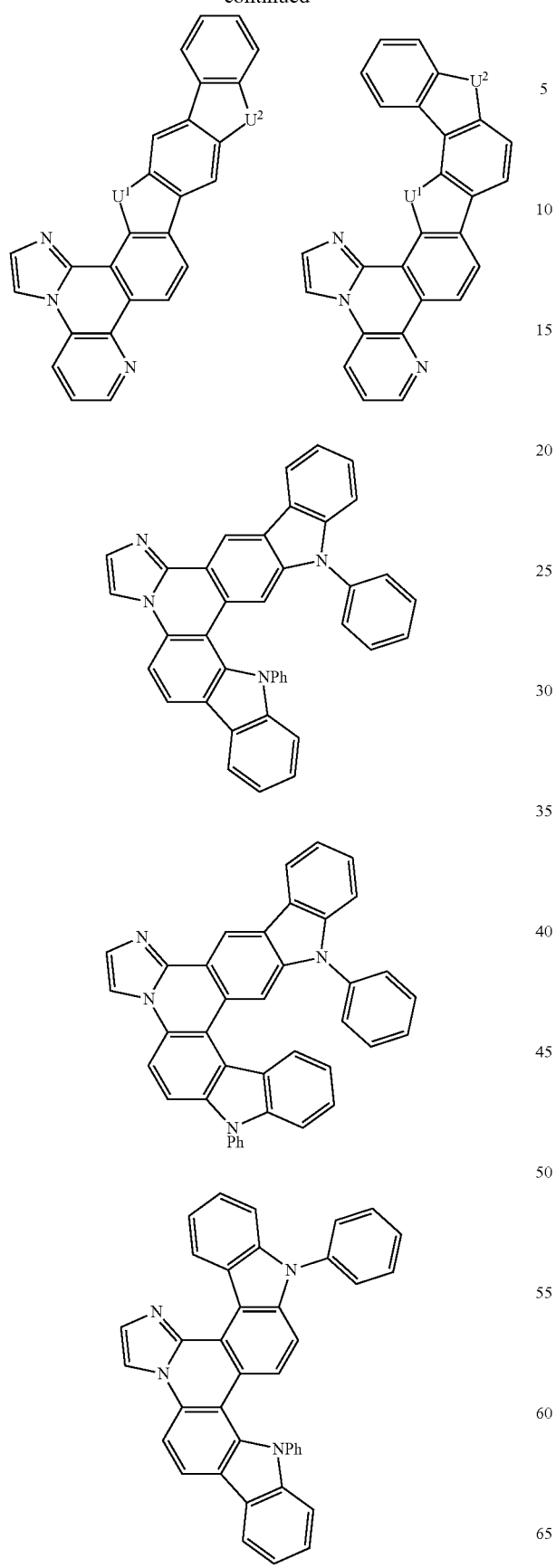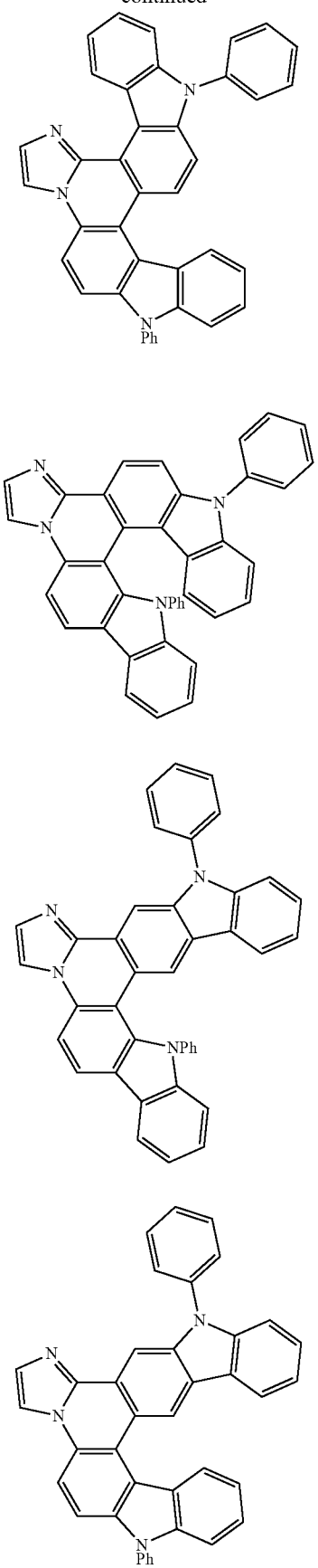

431
-continued
432
-continued
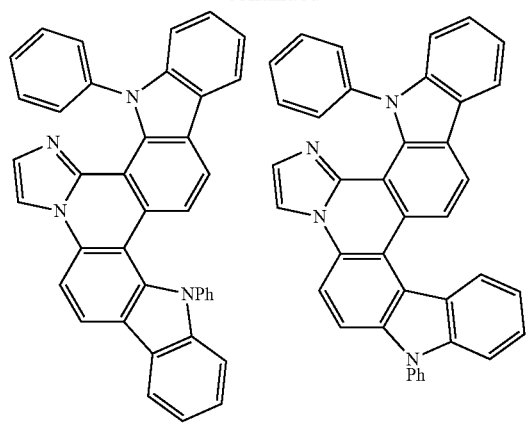
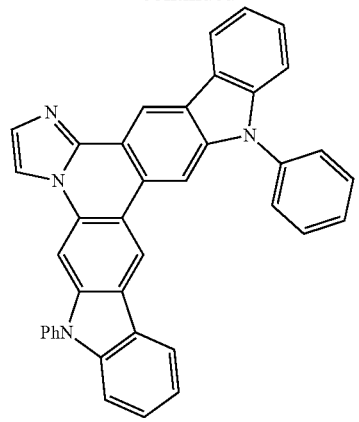
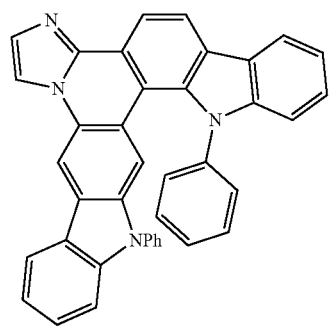
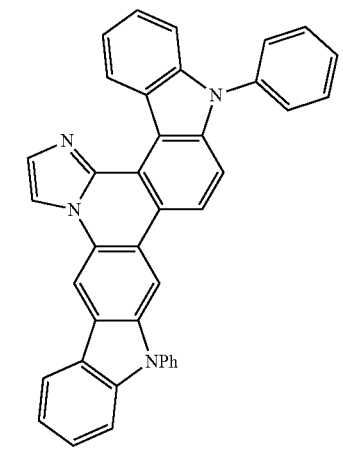
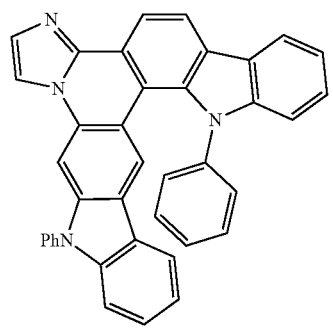
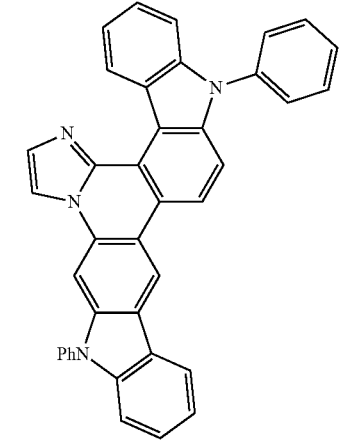
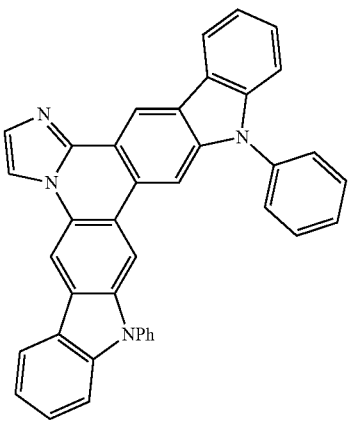
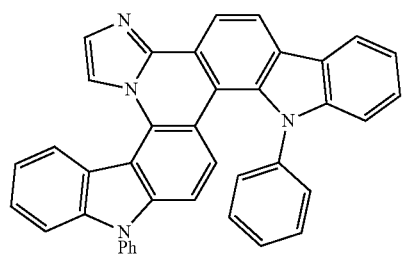

433
-continued
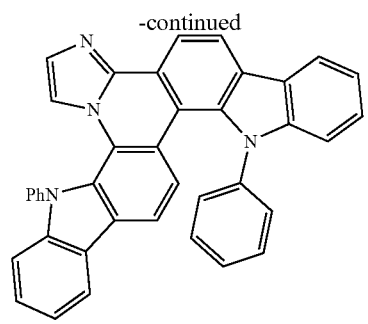
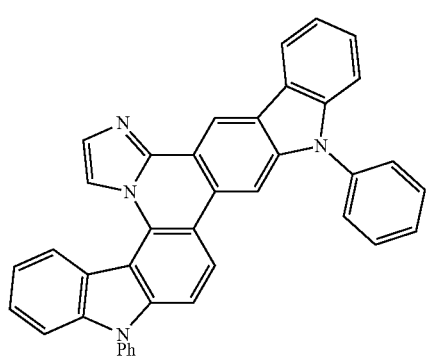
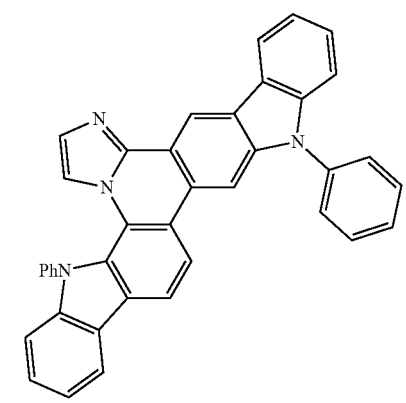
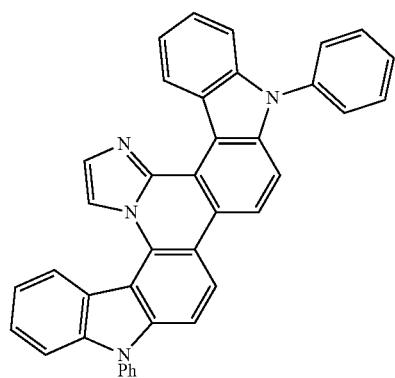
434
-continued
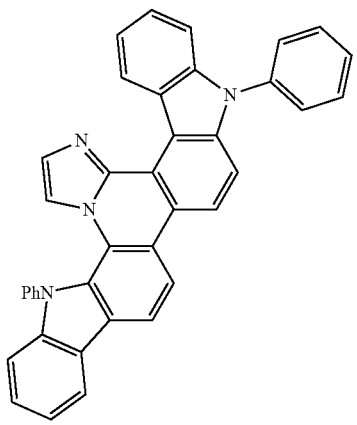
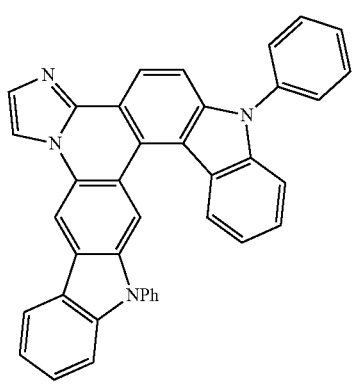
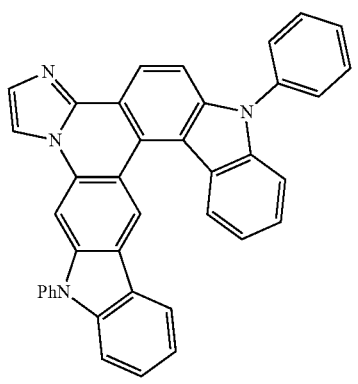
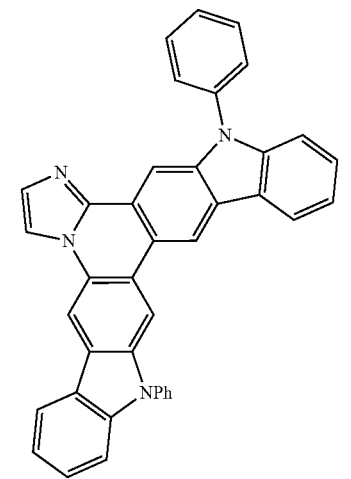

435
-continued
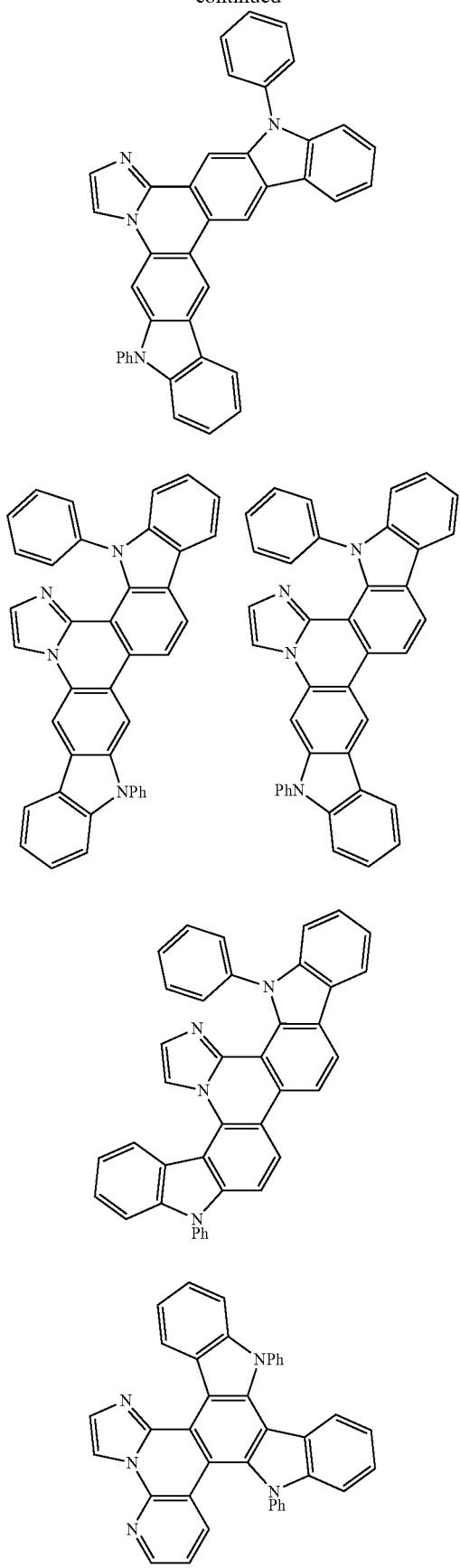
436
-continued
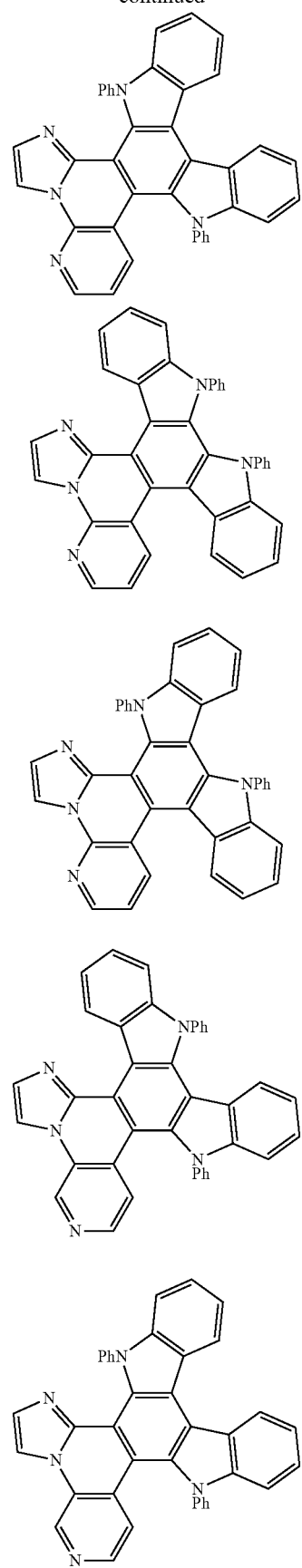

437
-continued
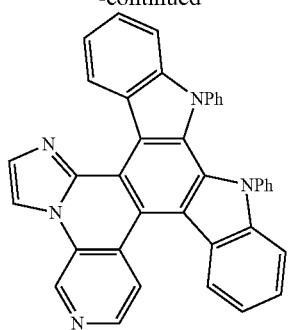
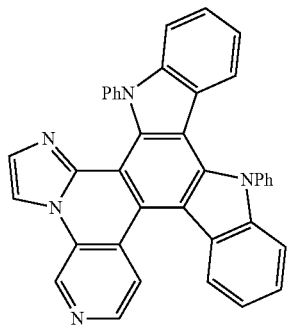
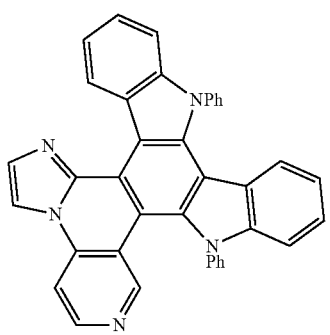
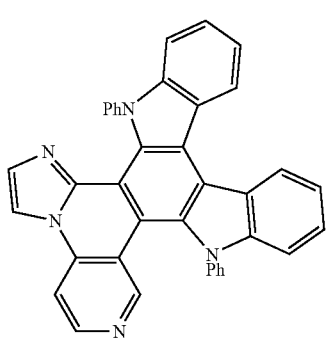
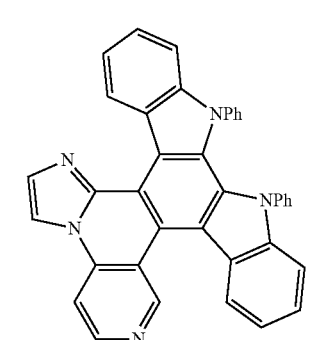
438
-continued
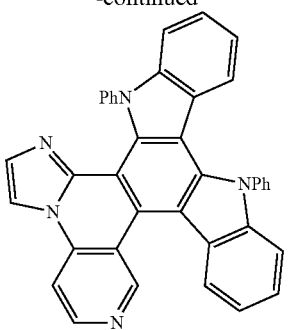
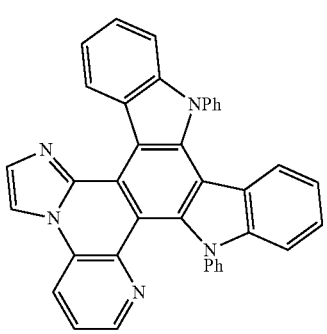
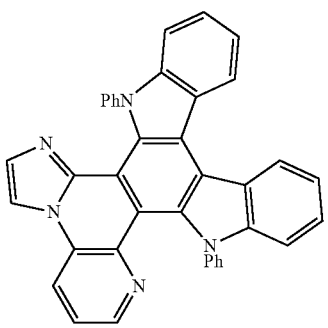
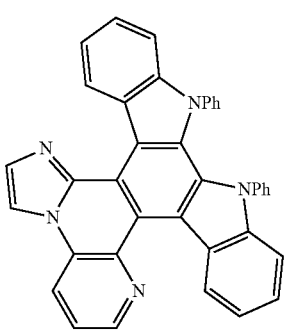

439
-continued
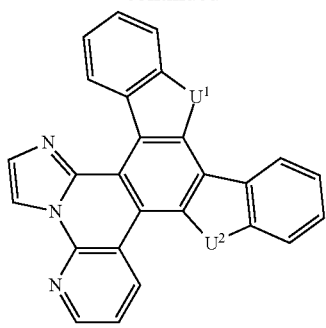
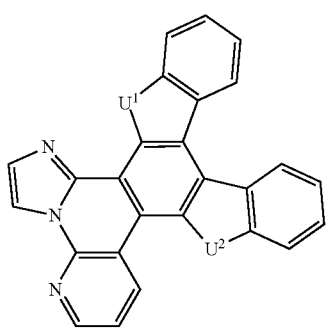
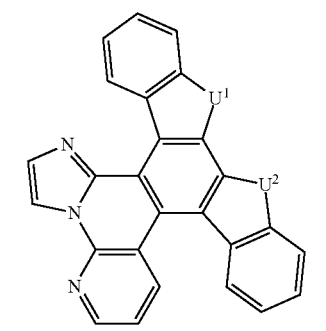
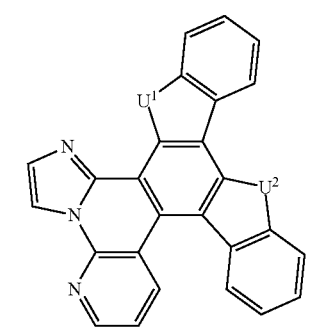
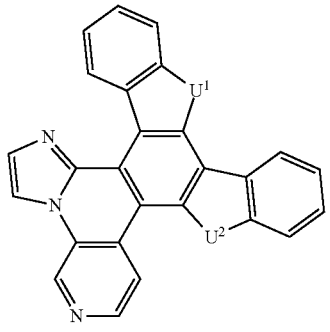
440
-continued
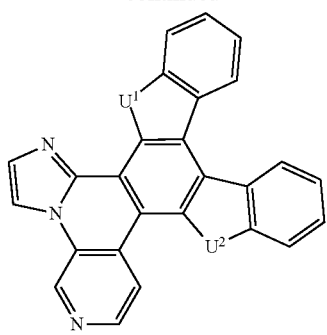
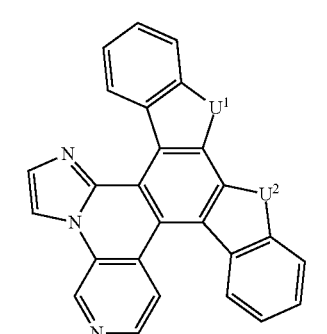
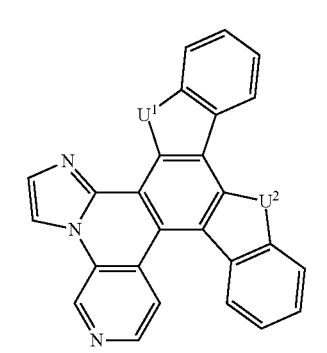
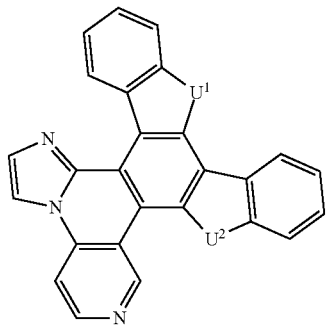
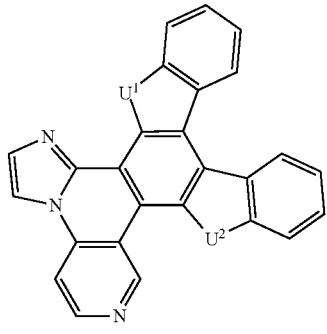

441
-continued
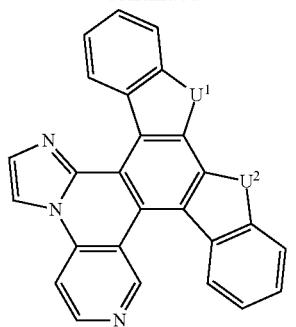
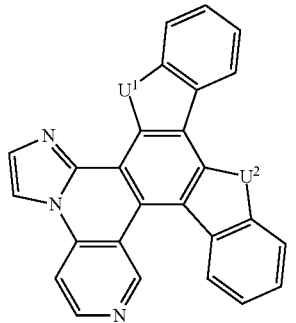
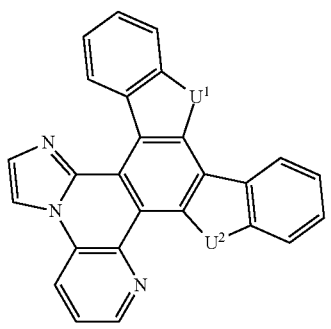
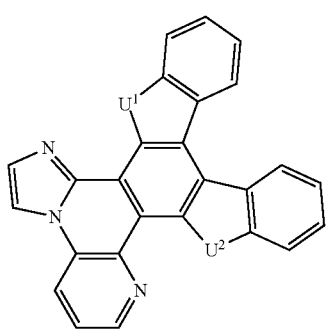
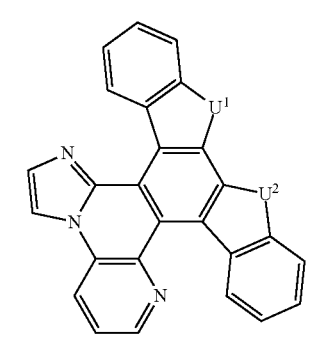
442
-continued
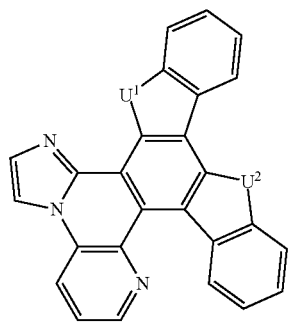
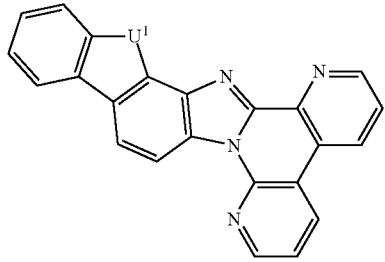
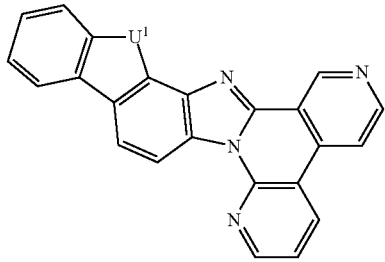
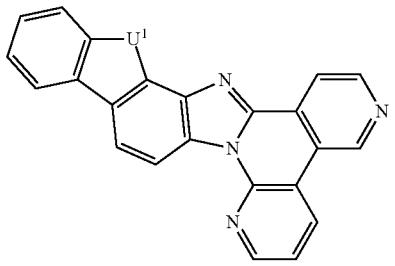
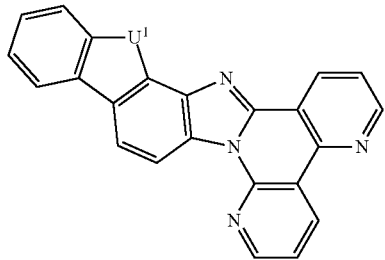
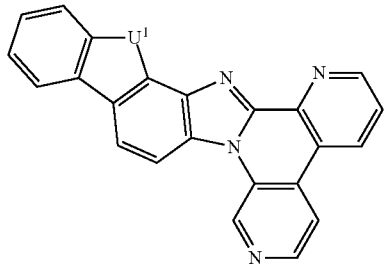

443
-continued
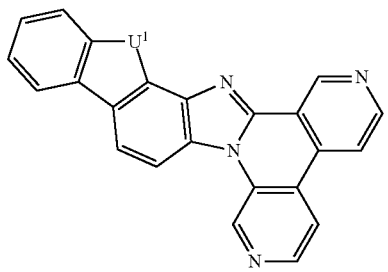
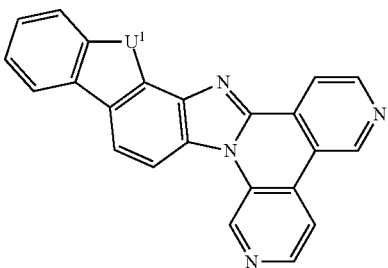
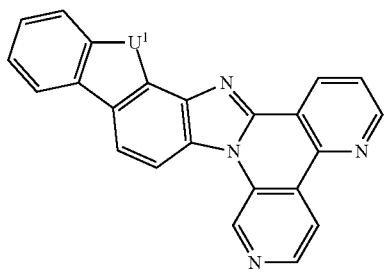
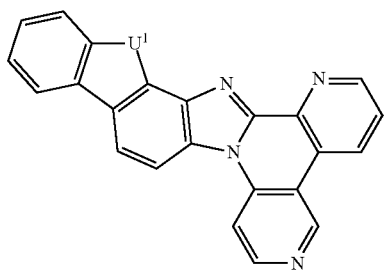
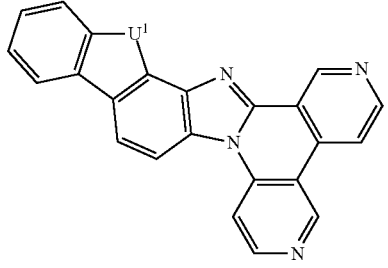
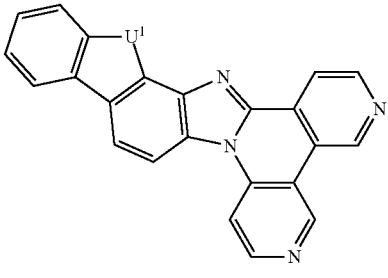
444
-continued
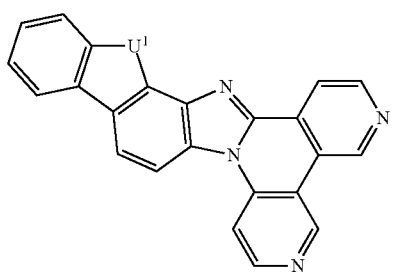
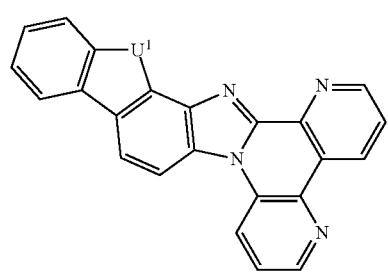
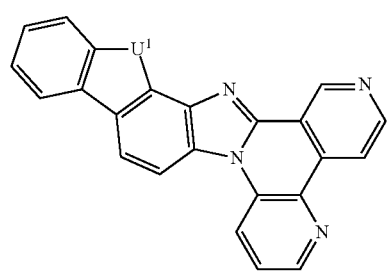
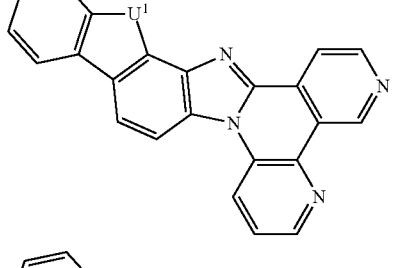
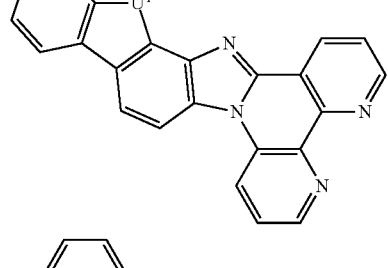
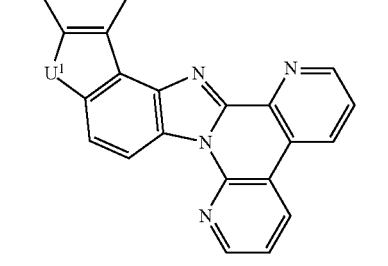

445
-continued
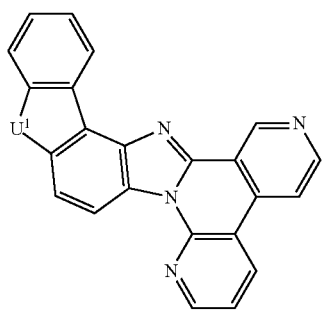
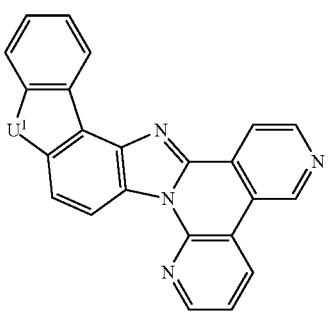
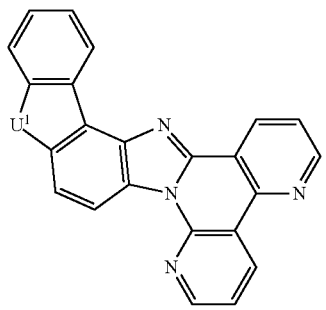
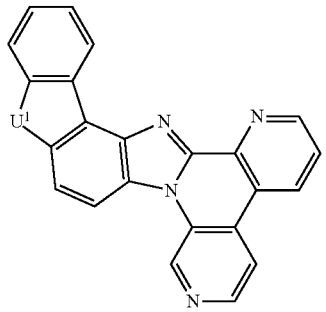
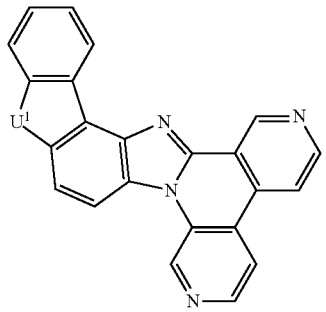
446
-continued
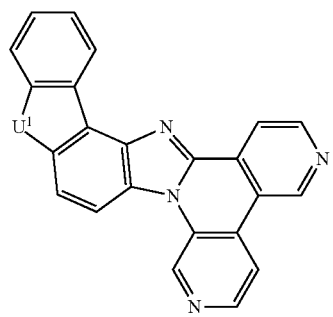
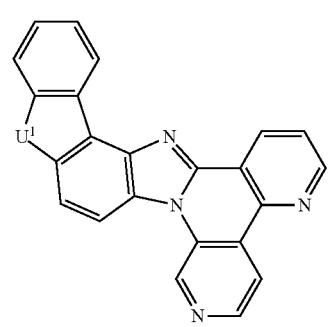
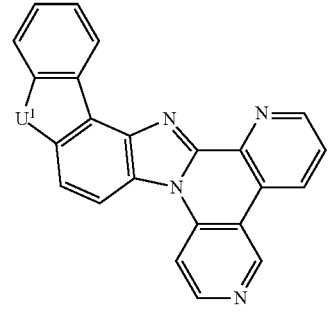
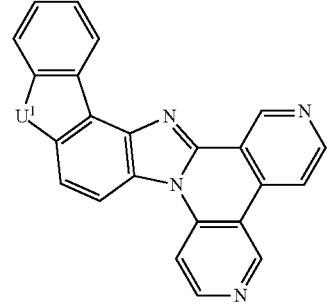
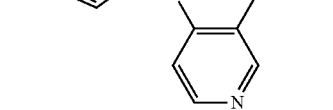

447
-continued
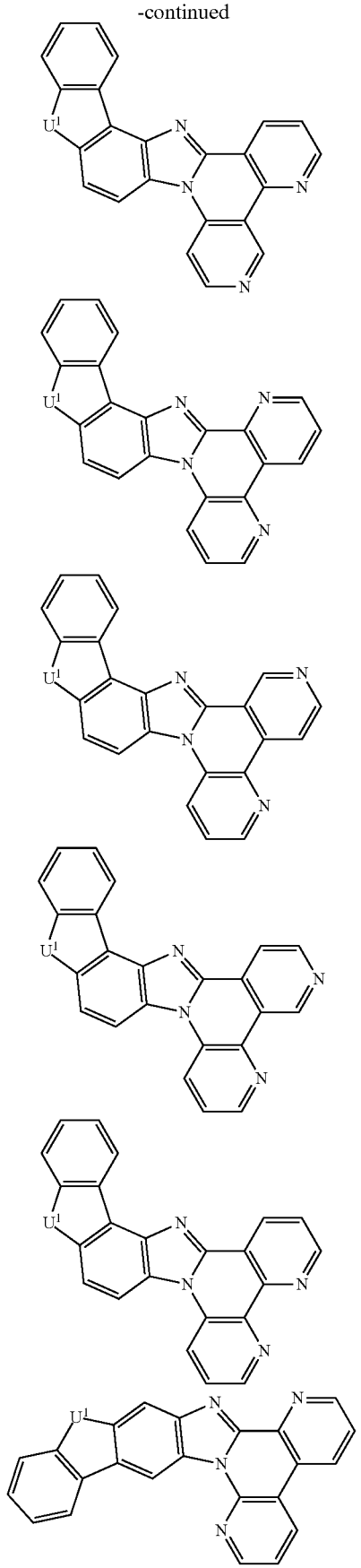
448
-continued
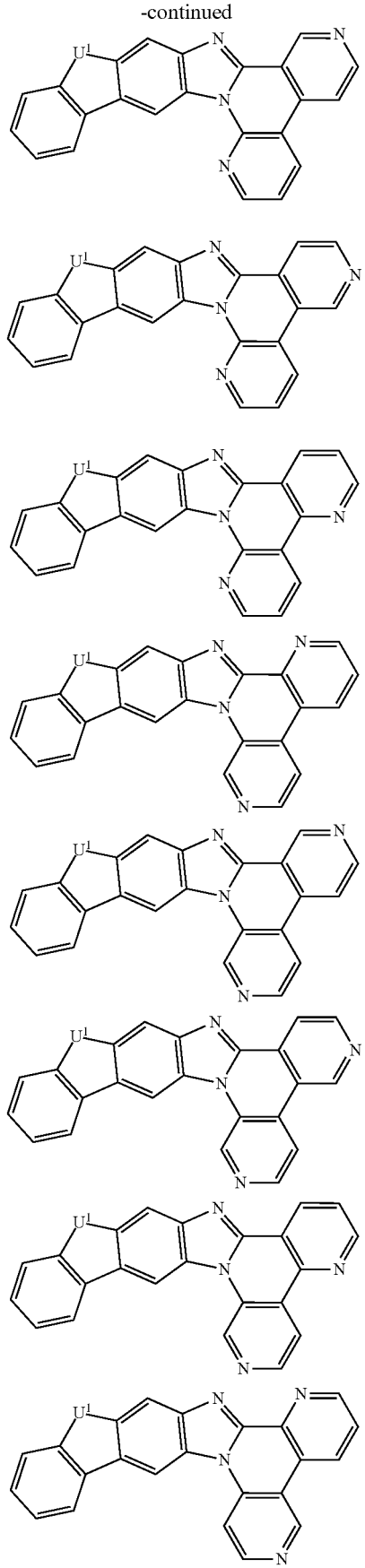

449
-continued
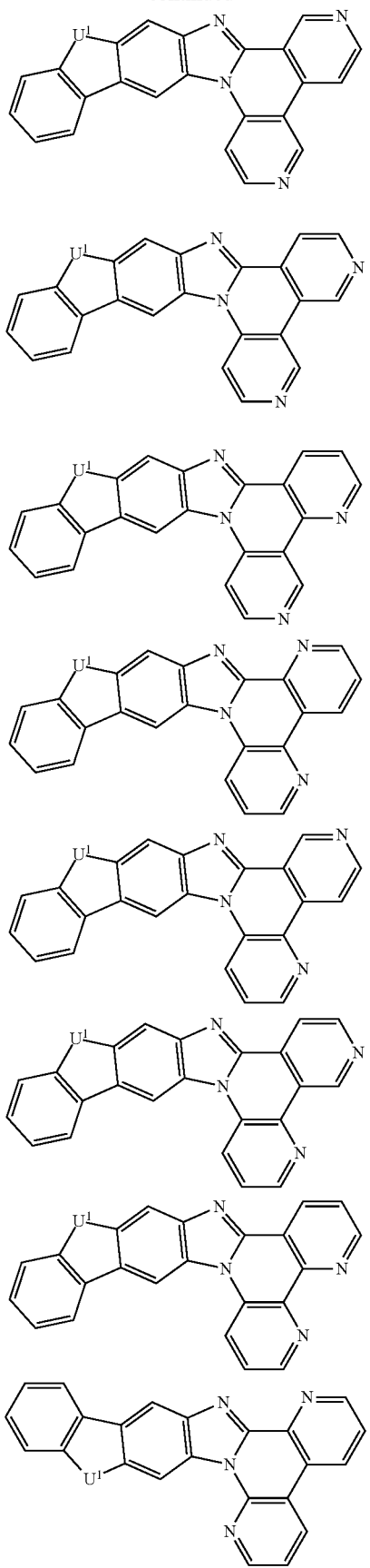
450
-continued
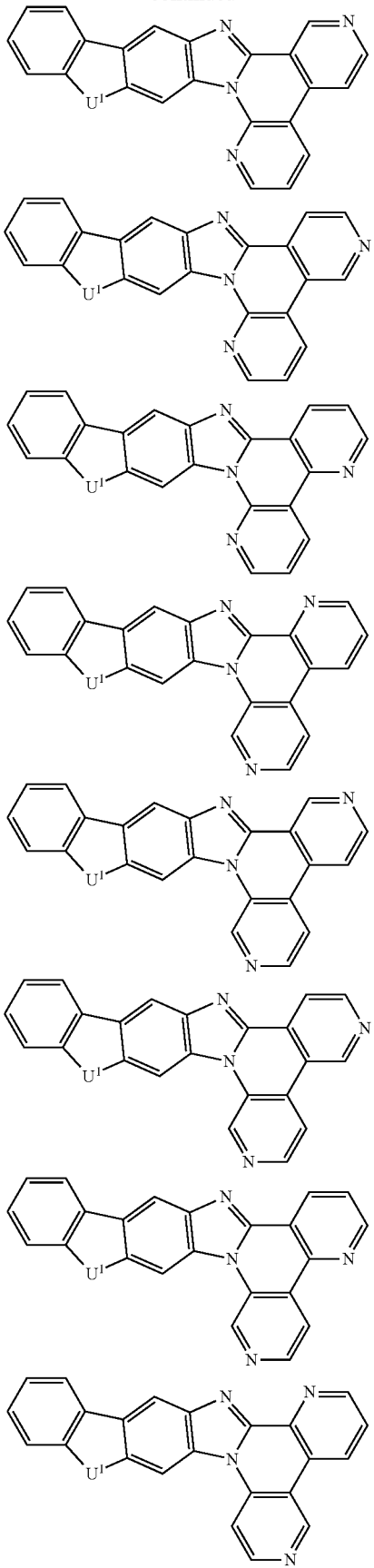

451
-continued
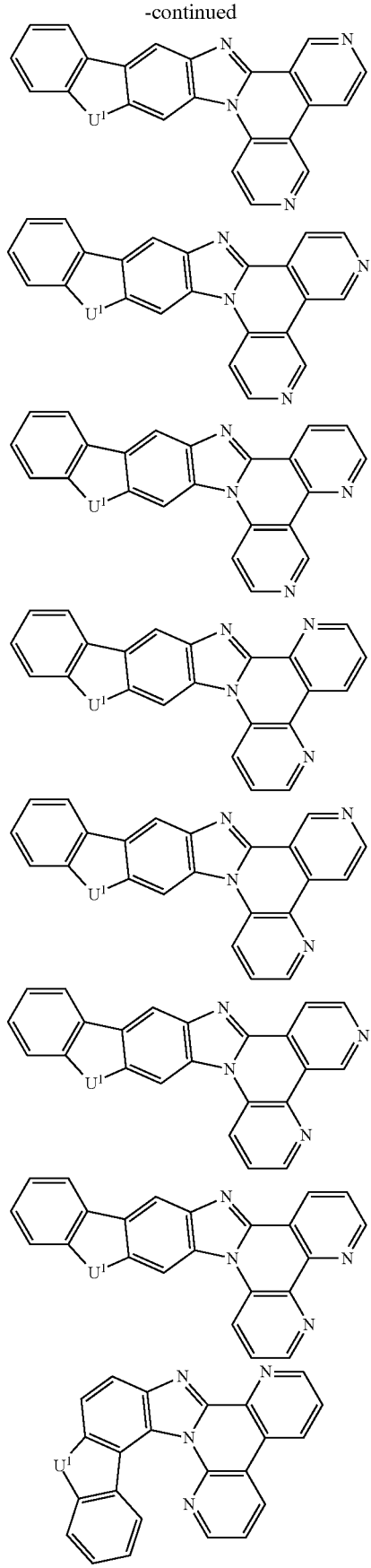
452
-continued
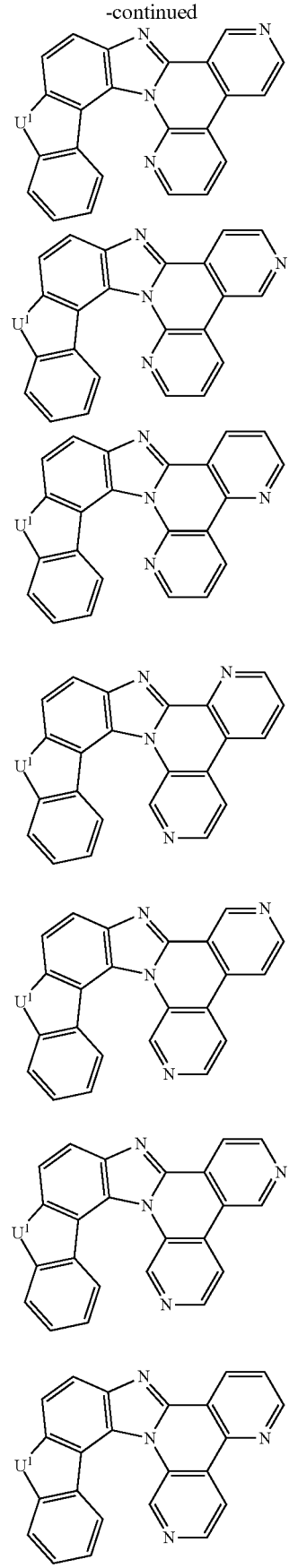

453
-continued
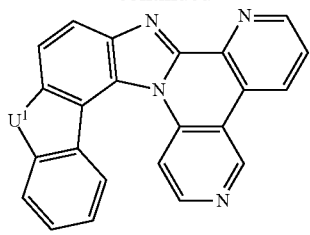
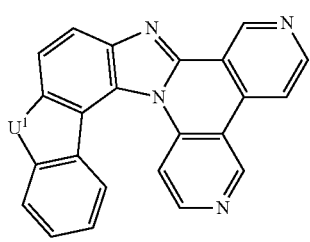
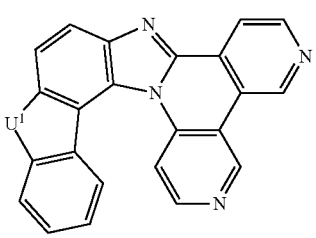
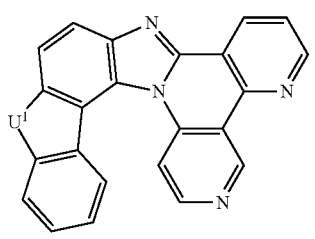
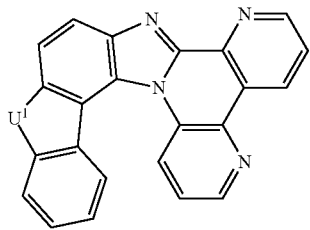
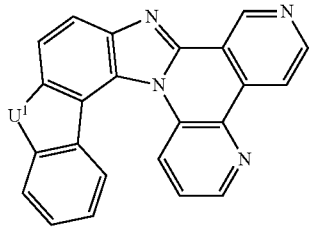
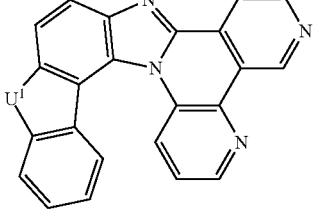
454
-continued
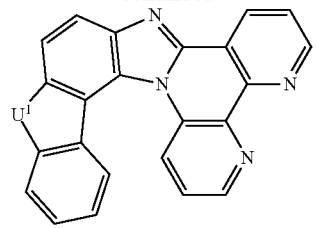
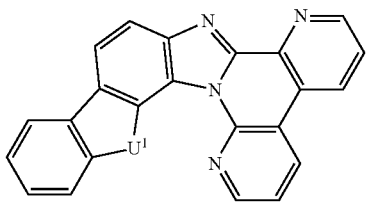
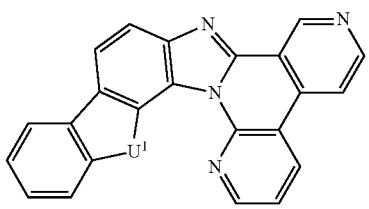
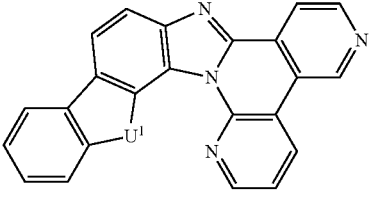
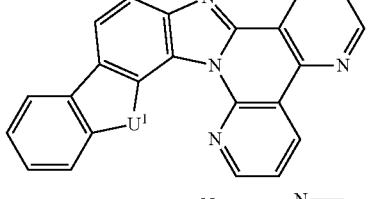
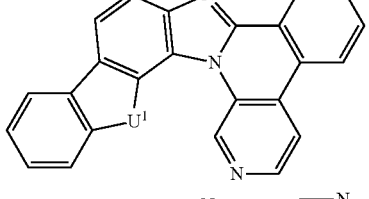
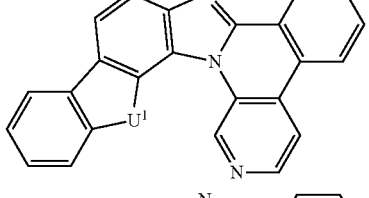

455
-continued
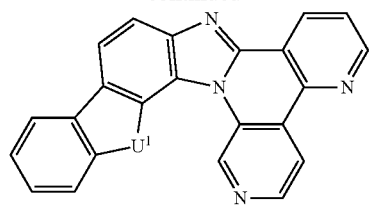
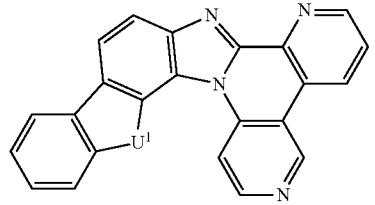
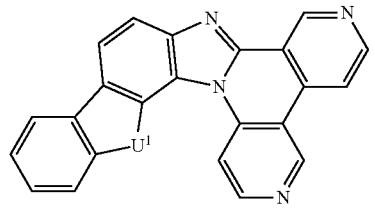
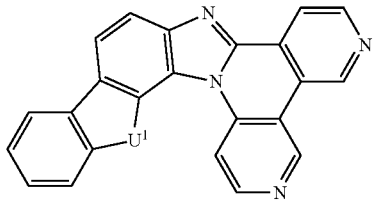
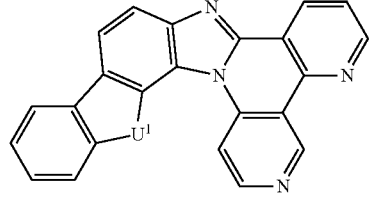
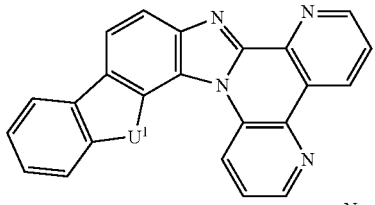
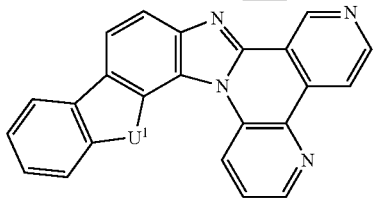
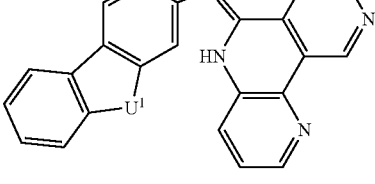
456
-continued
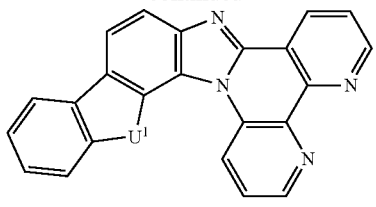
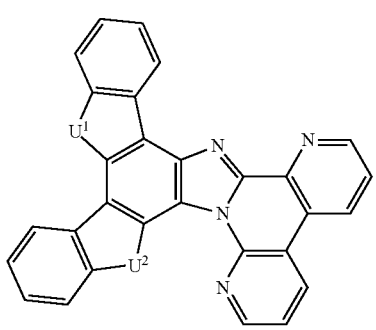
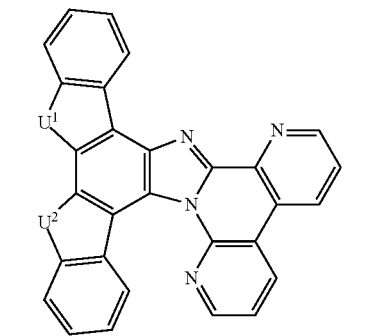
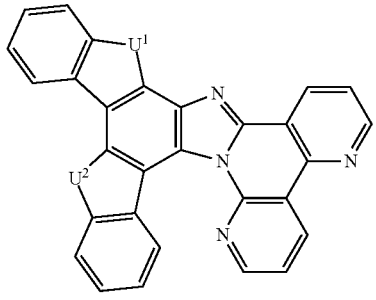
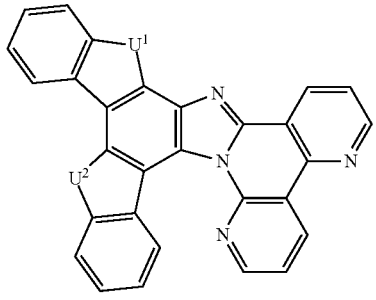
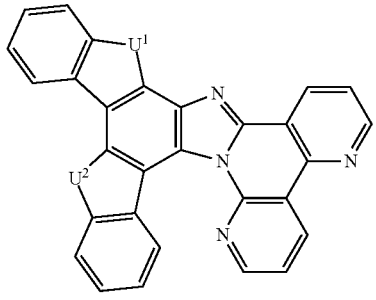

457
-continued
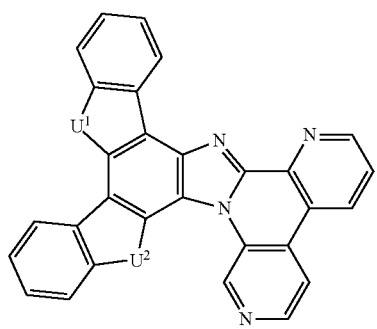
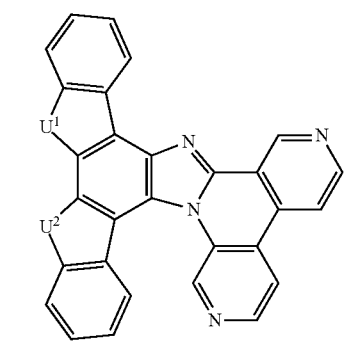
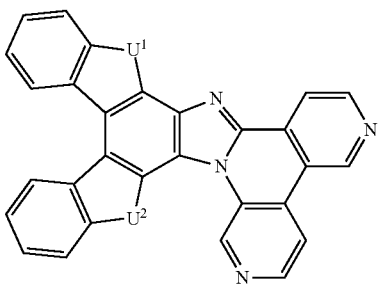
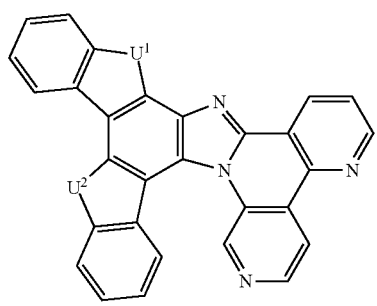
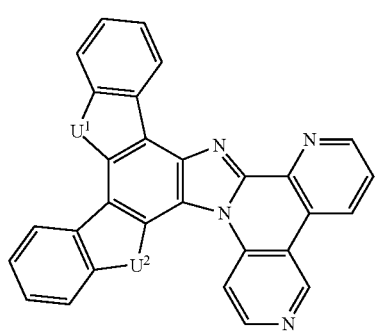
458
-continued
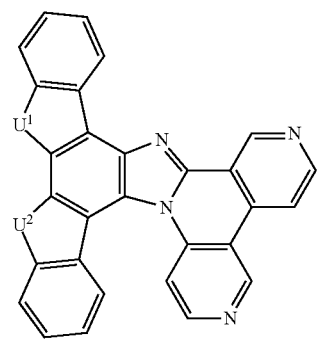
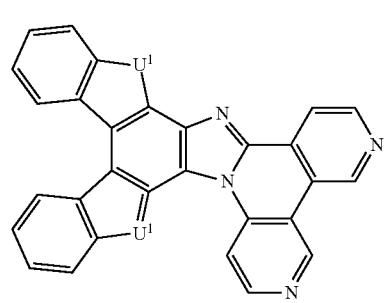
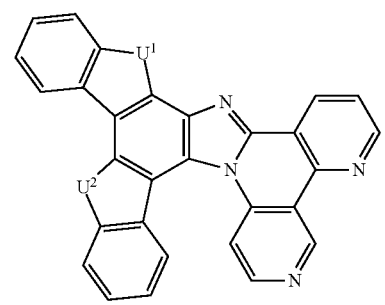
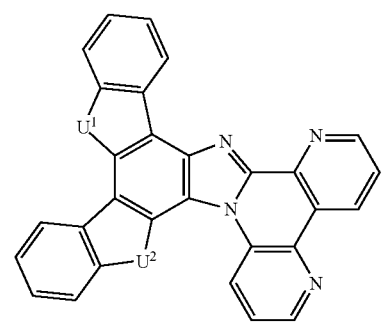
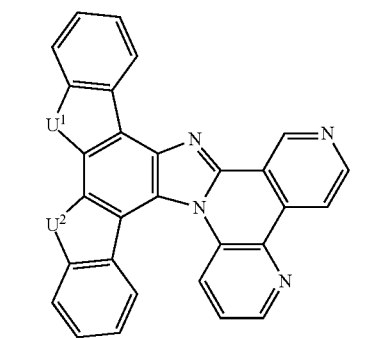

459
-continued
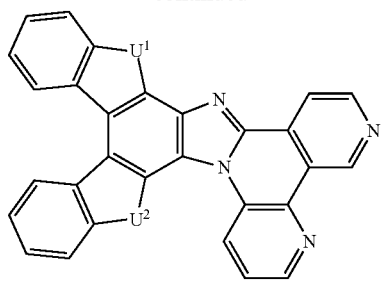
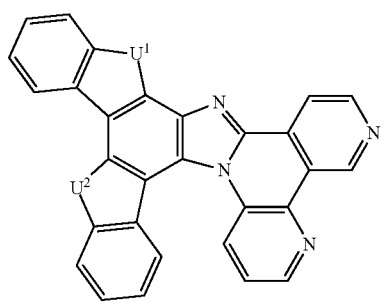
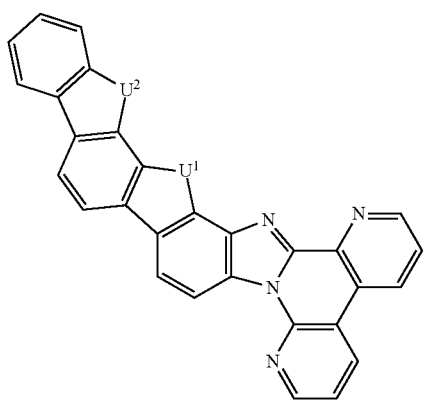
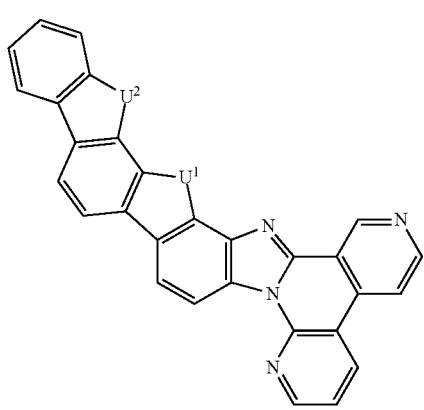
460
-continued
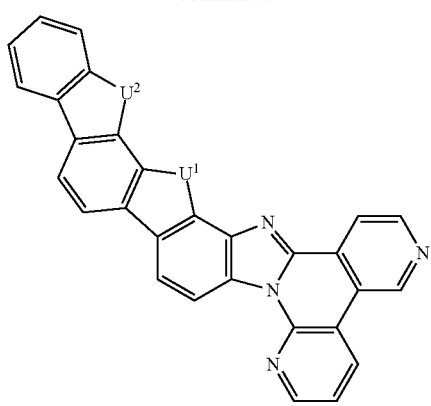
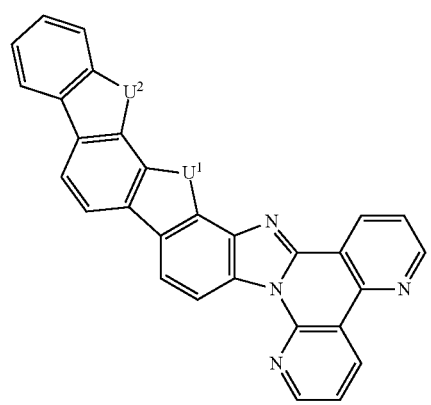
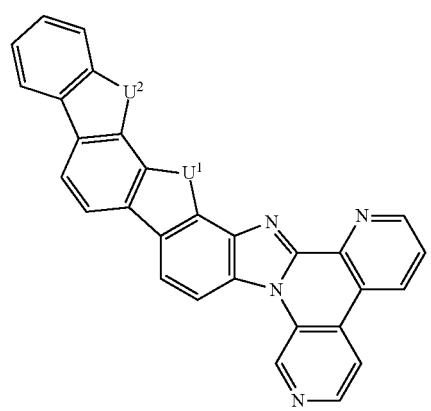
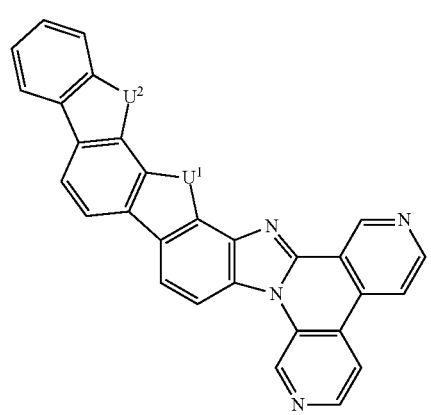

461
-continued
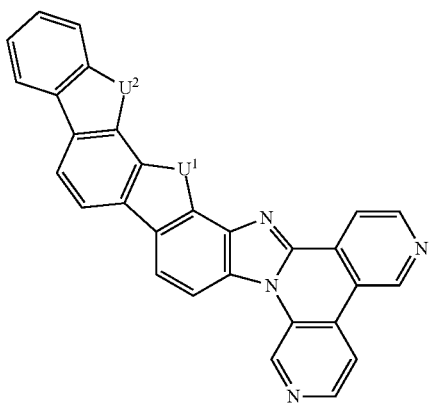
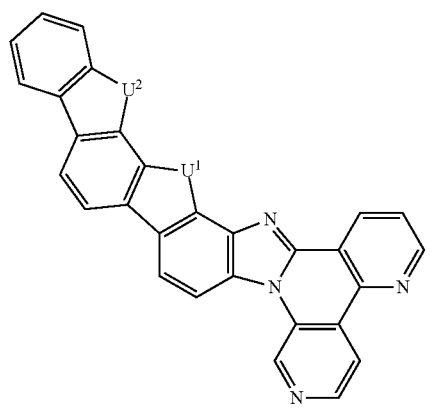
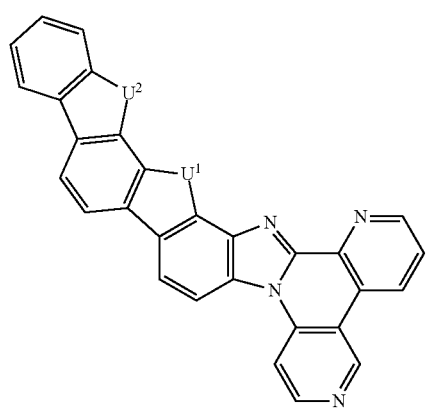
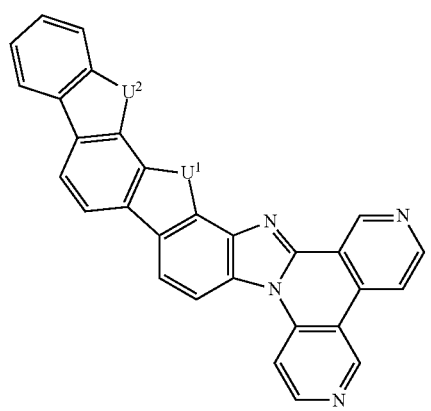
462
-continued
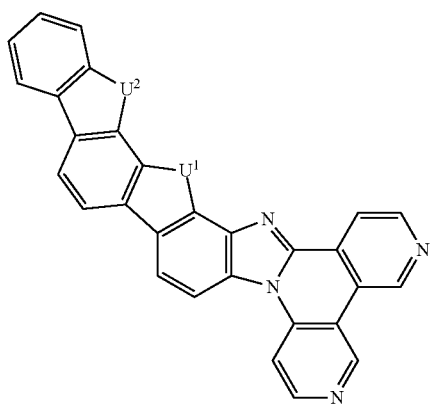
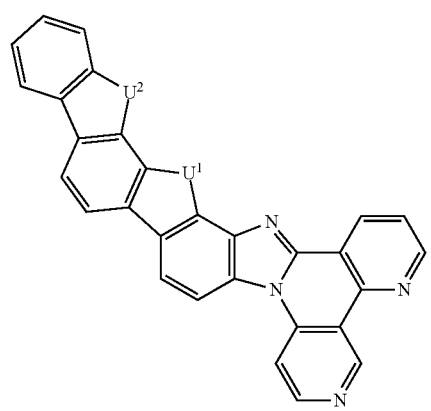
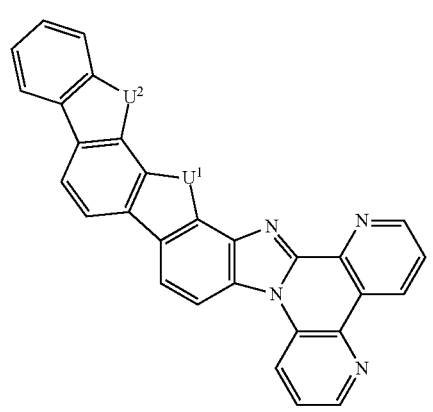
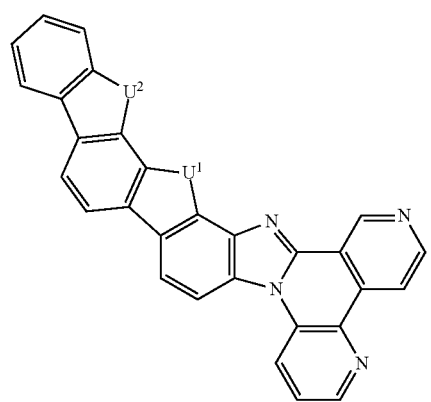

463
-continued
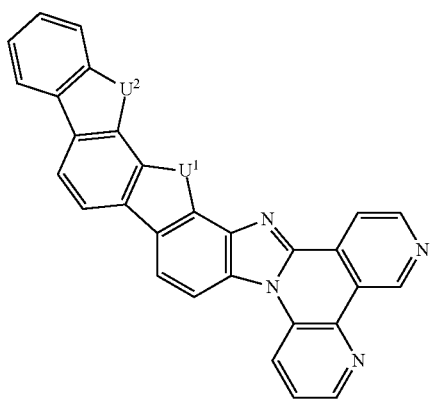
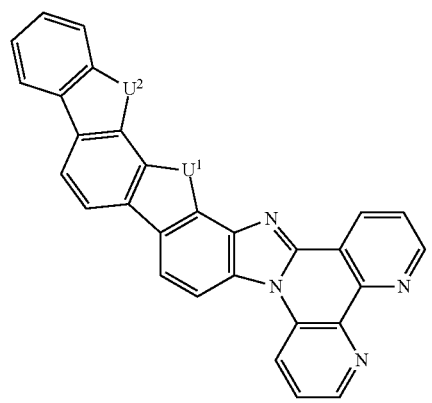
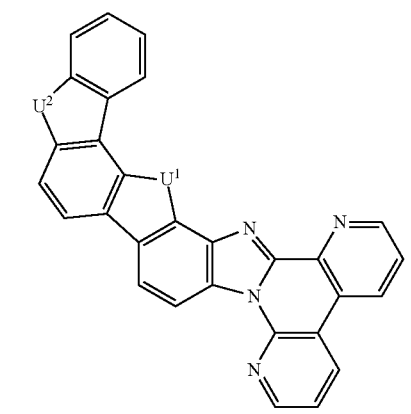
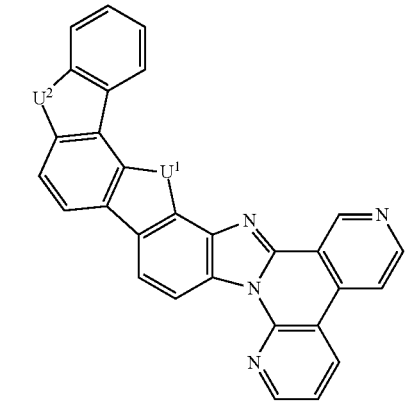
464
-continued
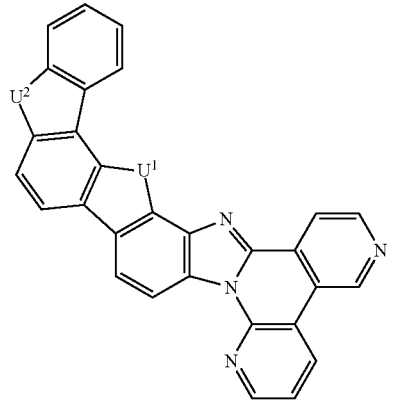
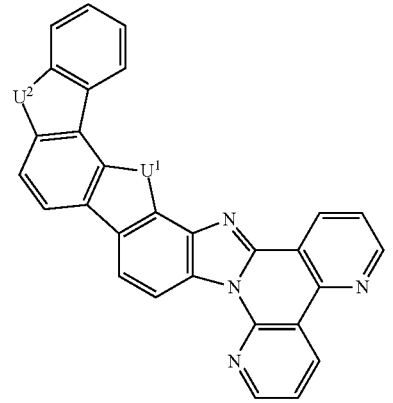
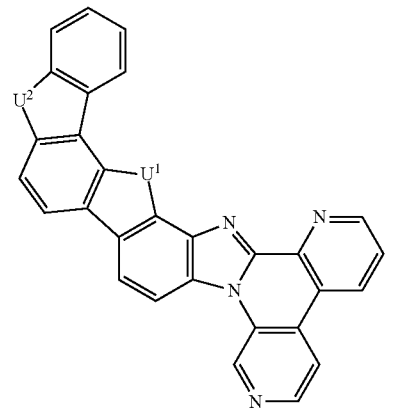
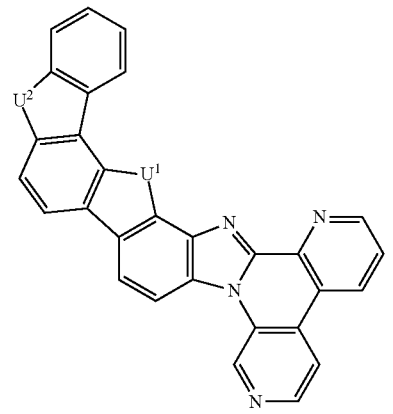

465
-continued
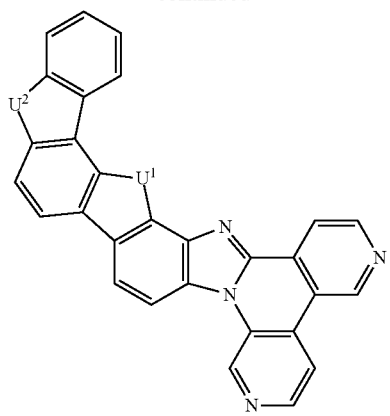
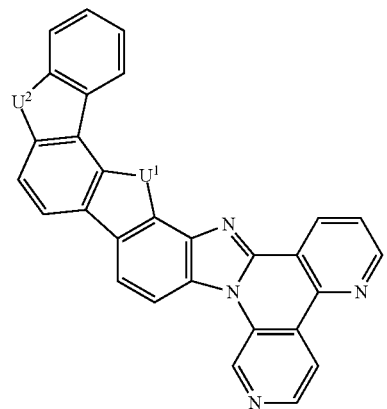
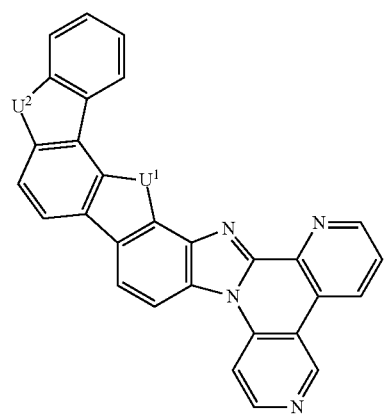
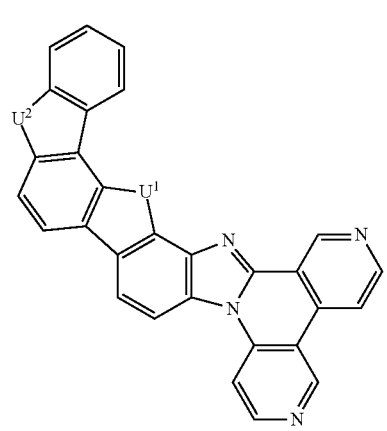
466
-continued
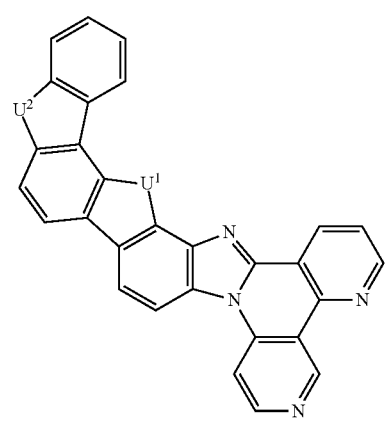
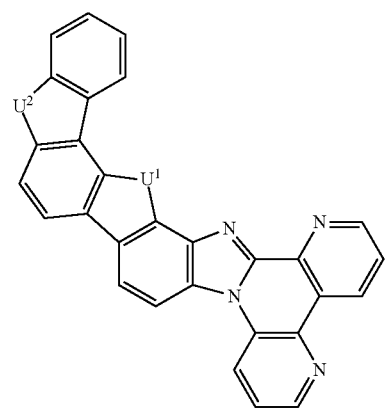

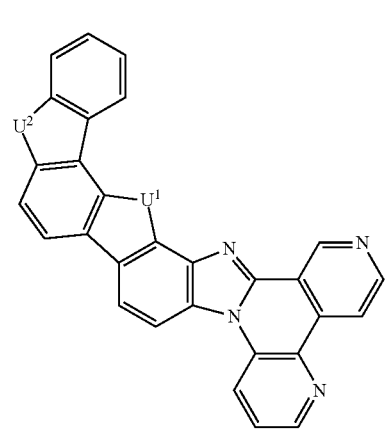

467
-continued
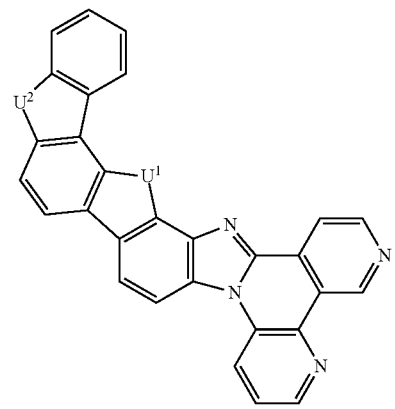
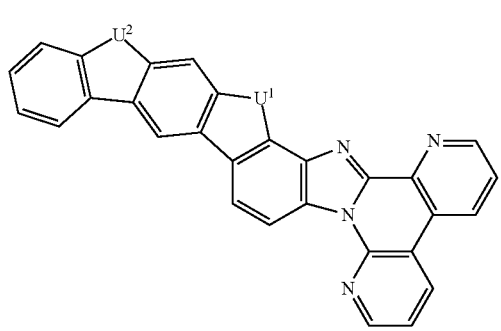
468
-continued
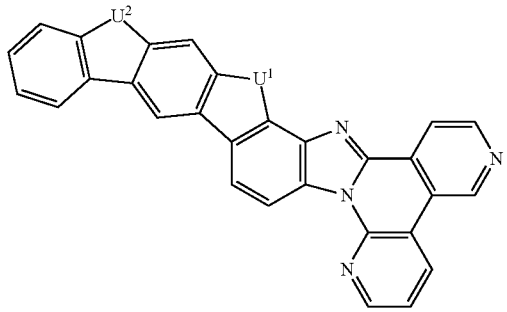
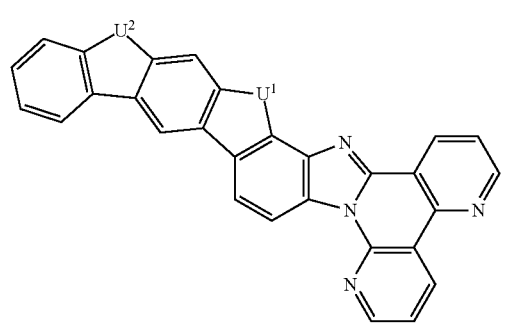
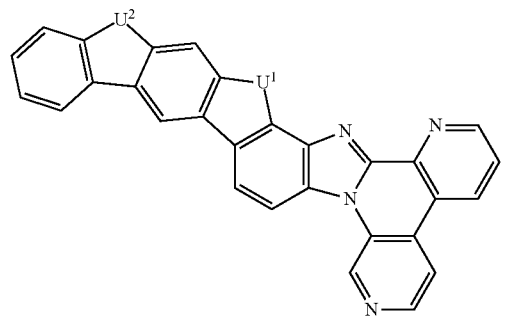
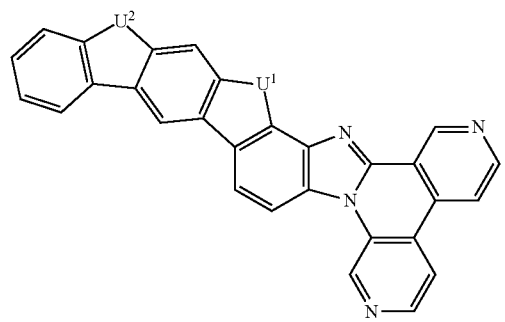
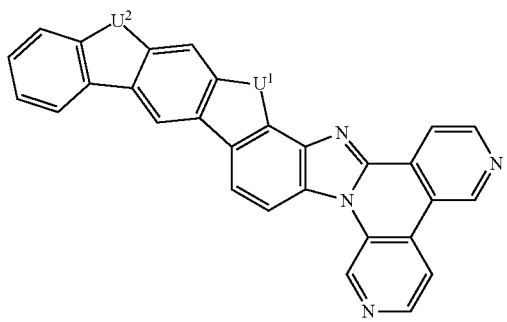

469
-continued
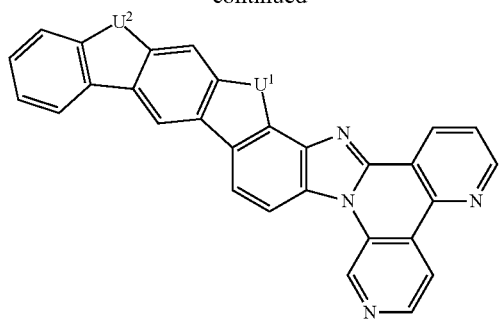
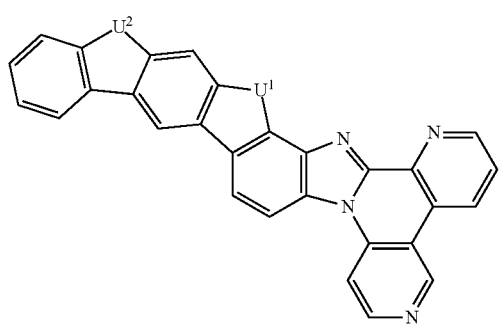
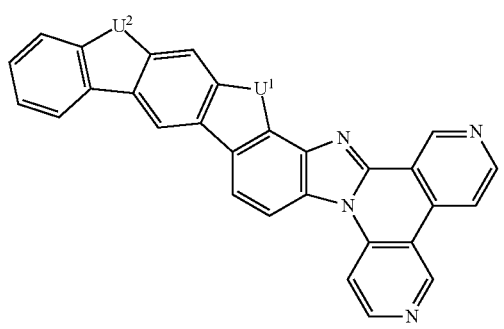
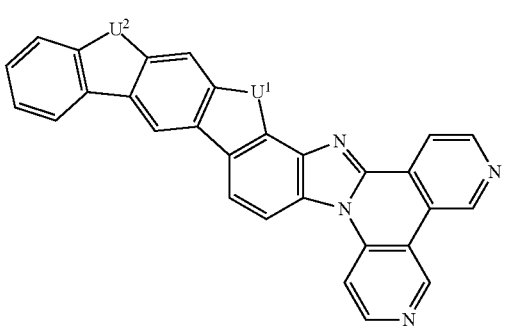
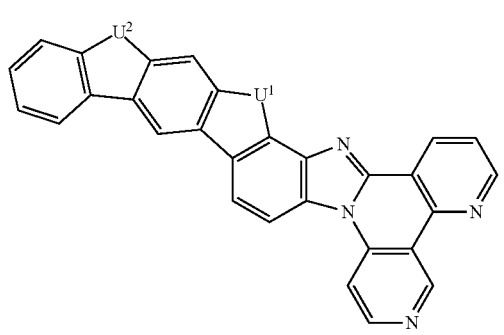
470
-continued
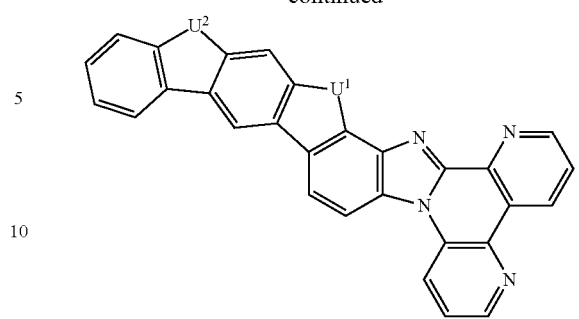

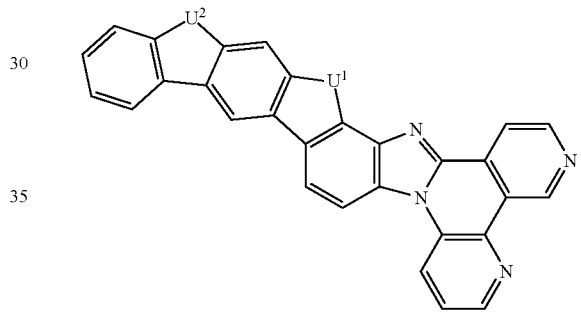

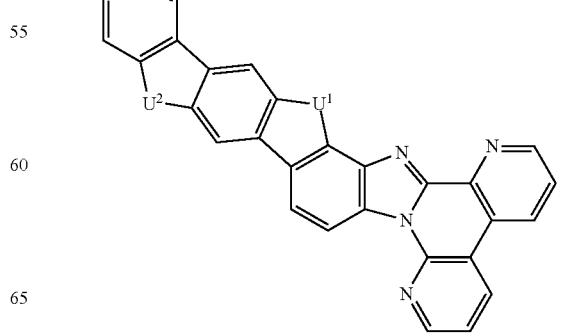

471
-continued
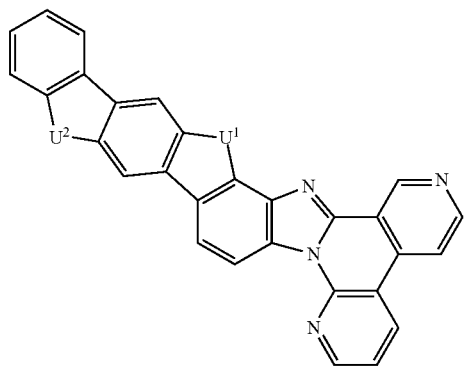
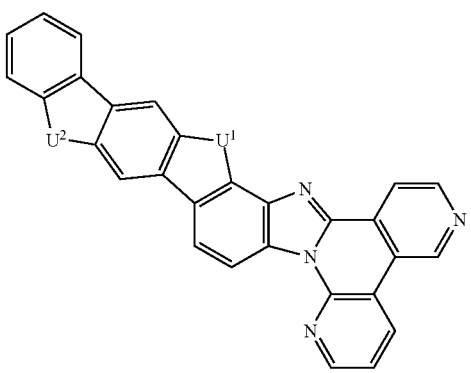
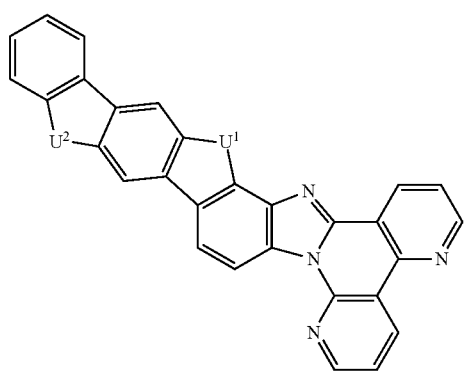
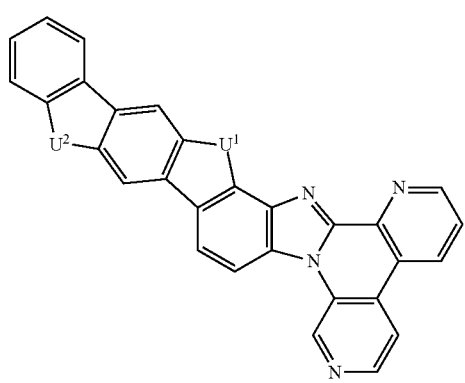
472
-continued
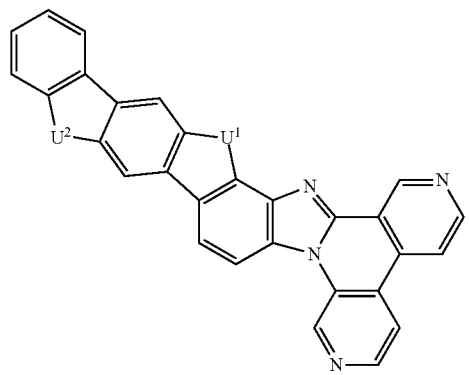
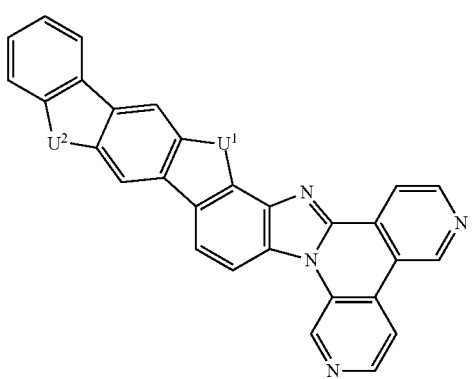
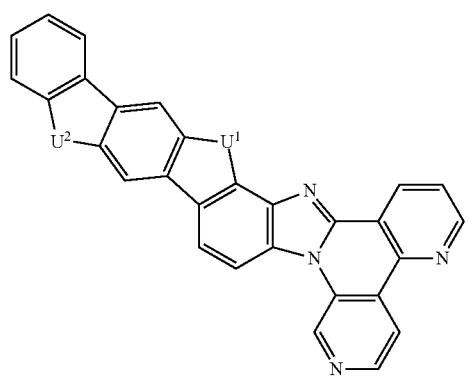
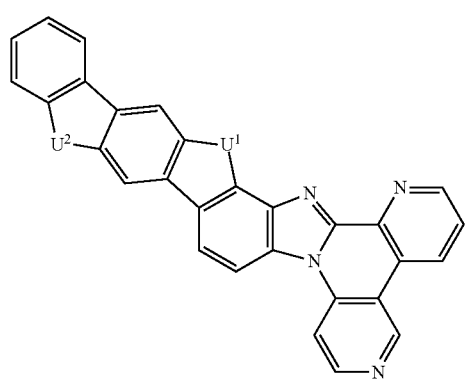

473
-continued
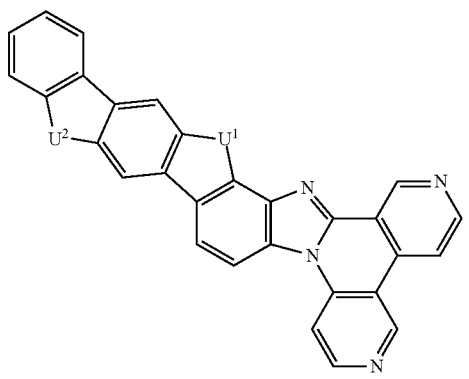
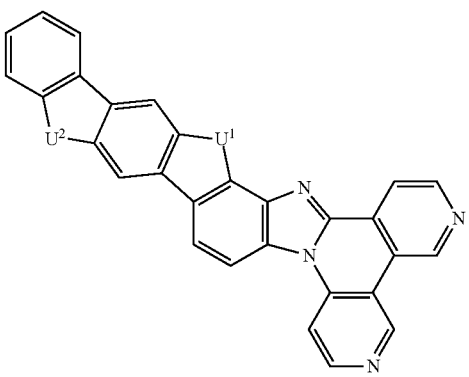
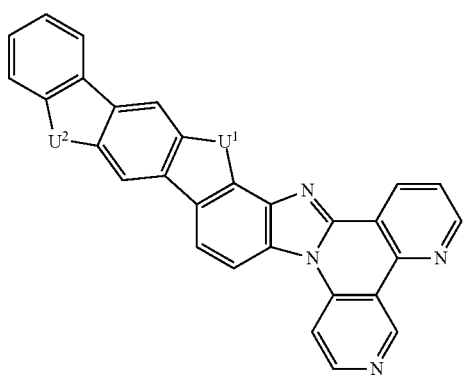
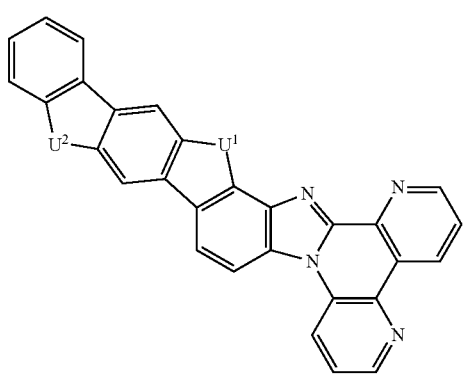
474
-continued
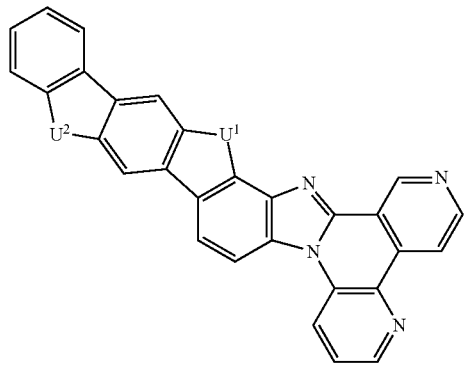
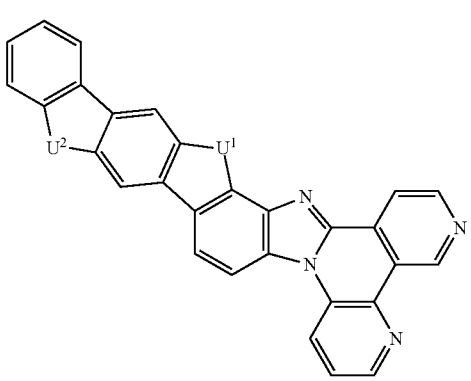
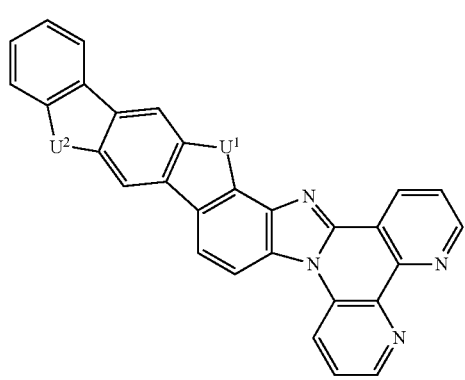
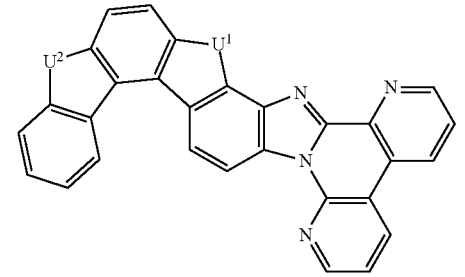
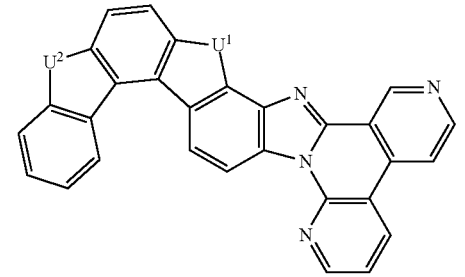

475
-continued
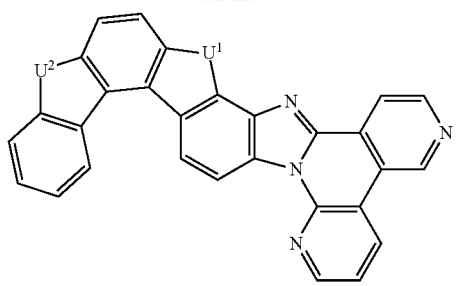
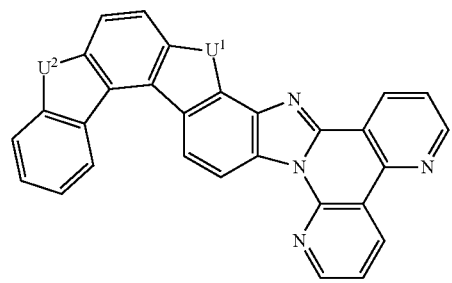
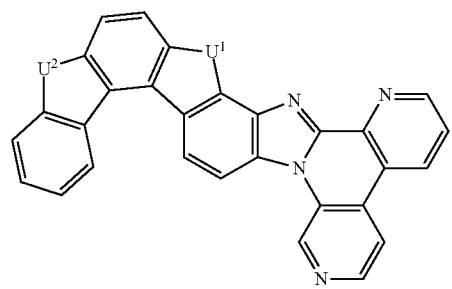
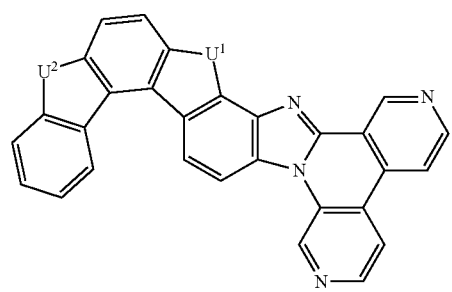
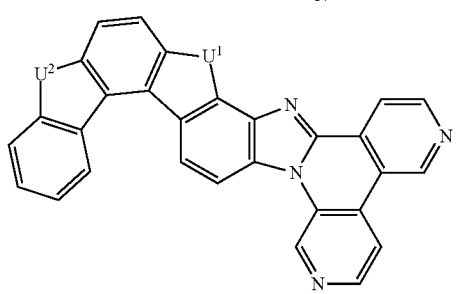
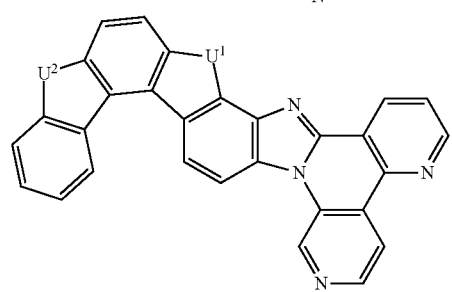
476
-continued
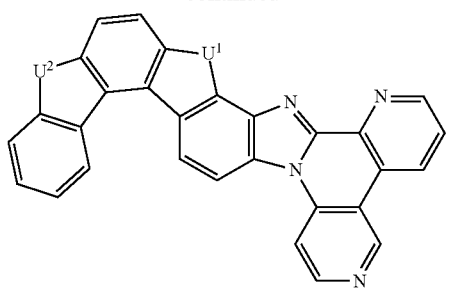
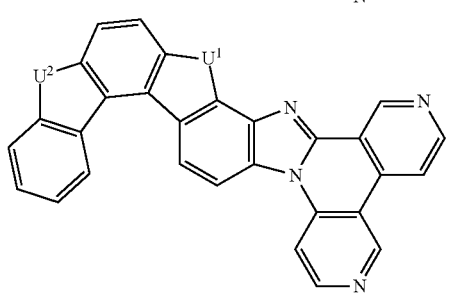
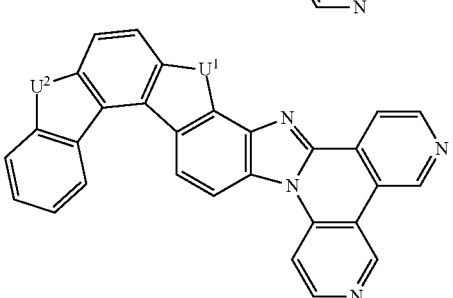
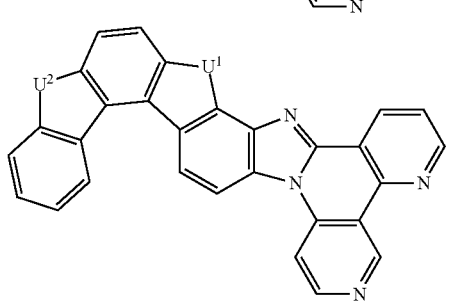
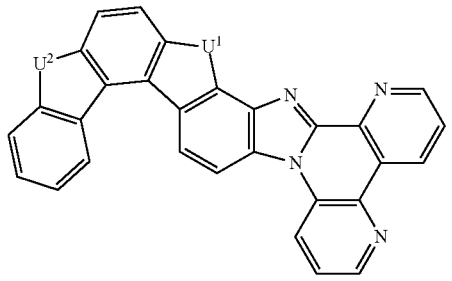
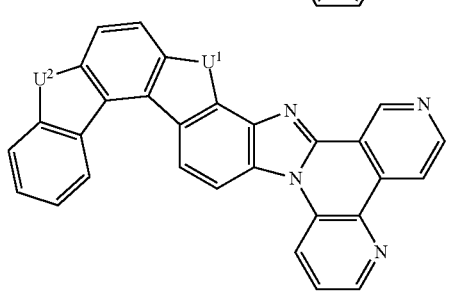

477
-continued
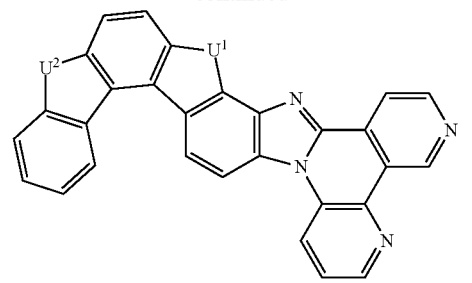
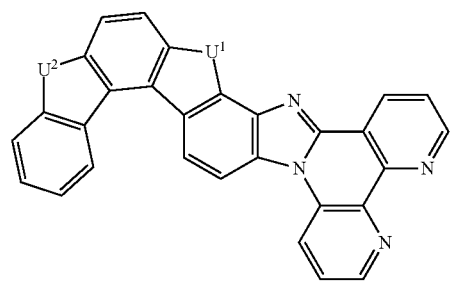
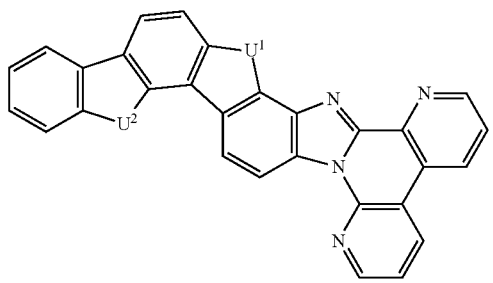
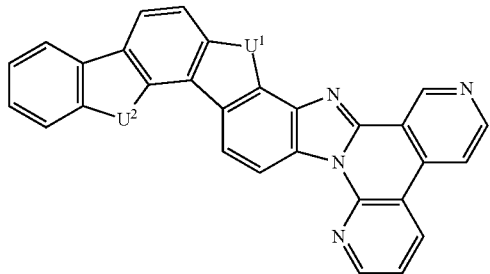
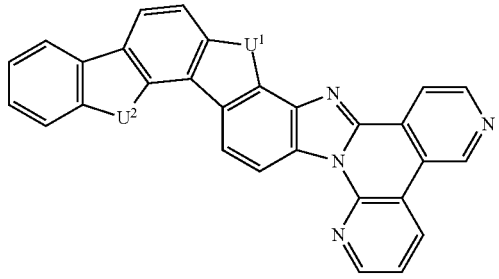
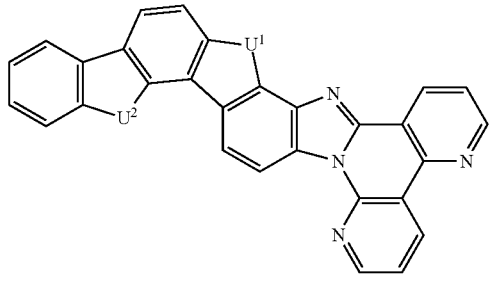
478
-continued
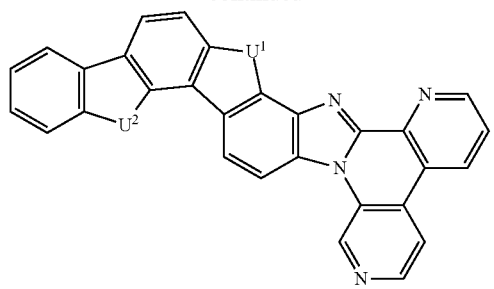
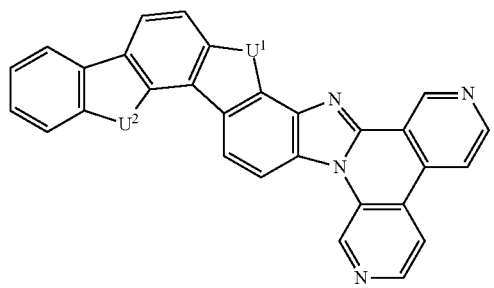
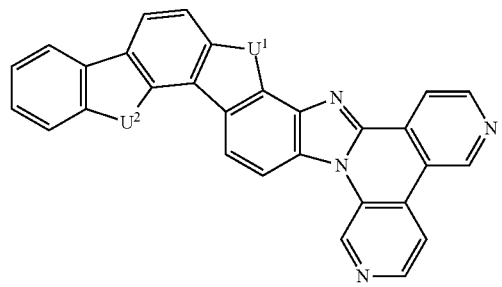
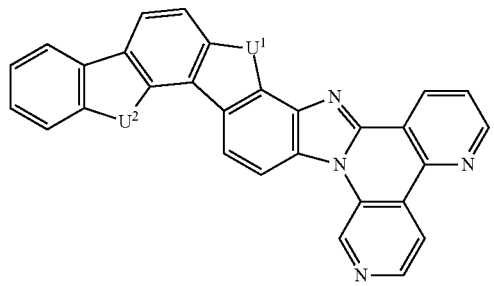
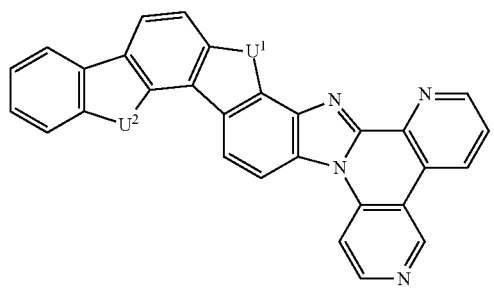
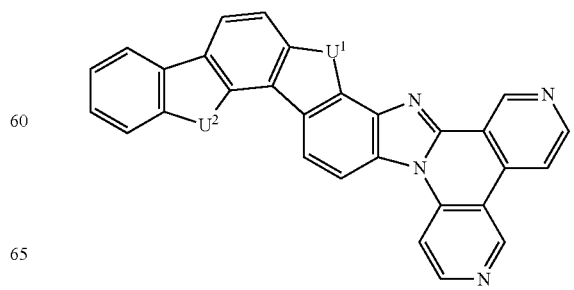

479
-continued
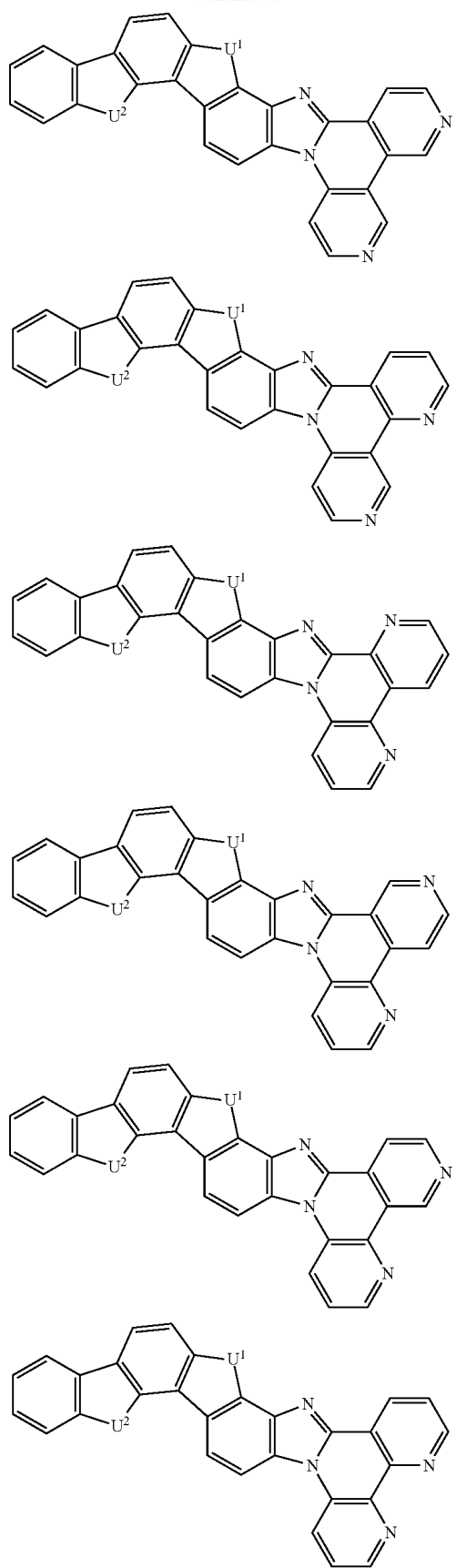
480
-continued
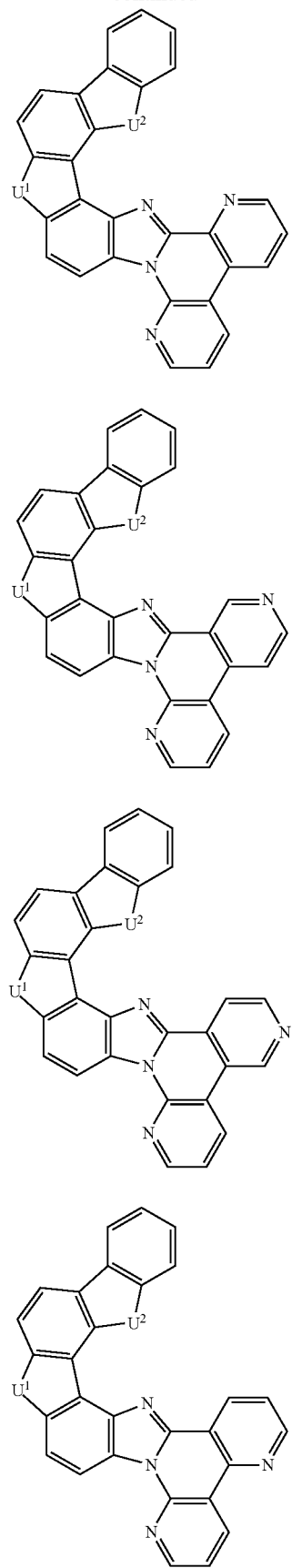

481
-continued
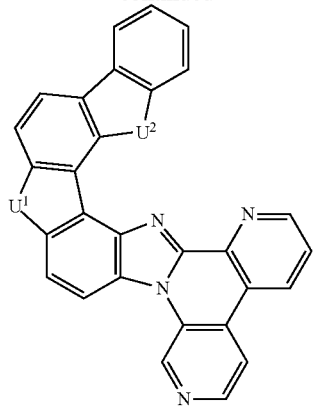
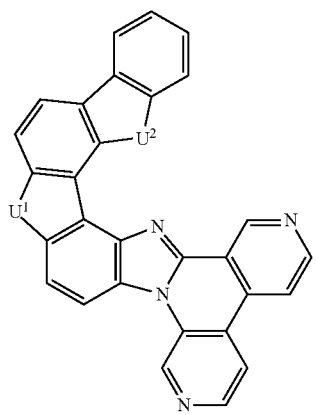
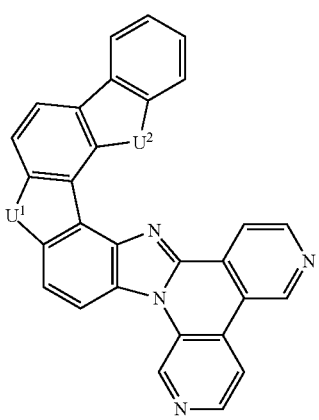
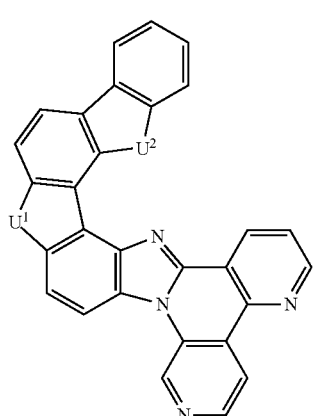
482
-continued
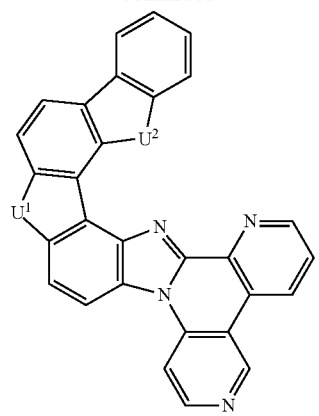
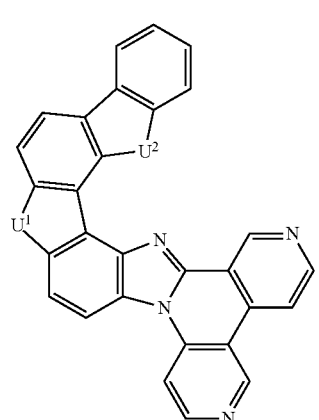
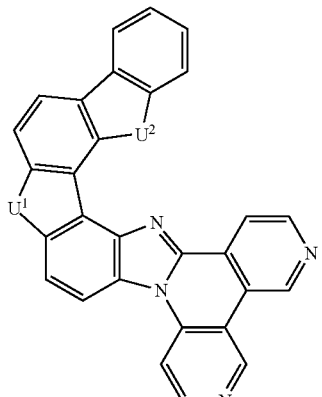
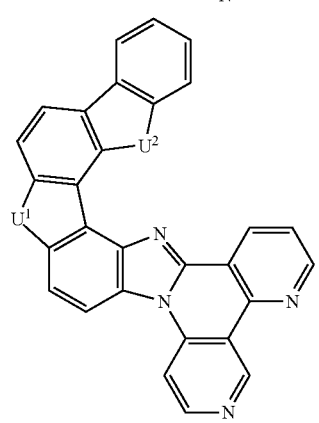

483
-continued
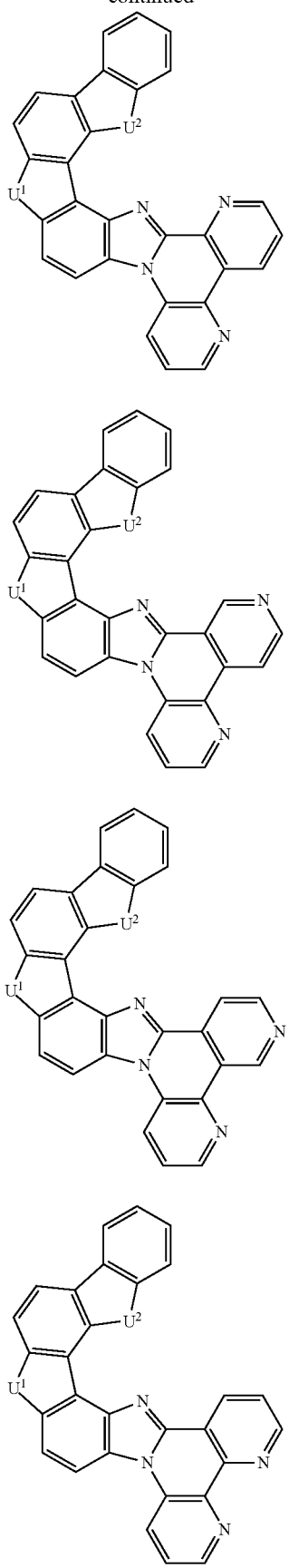
484
-continued
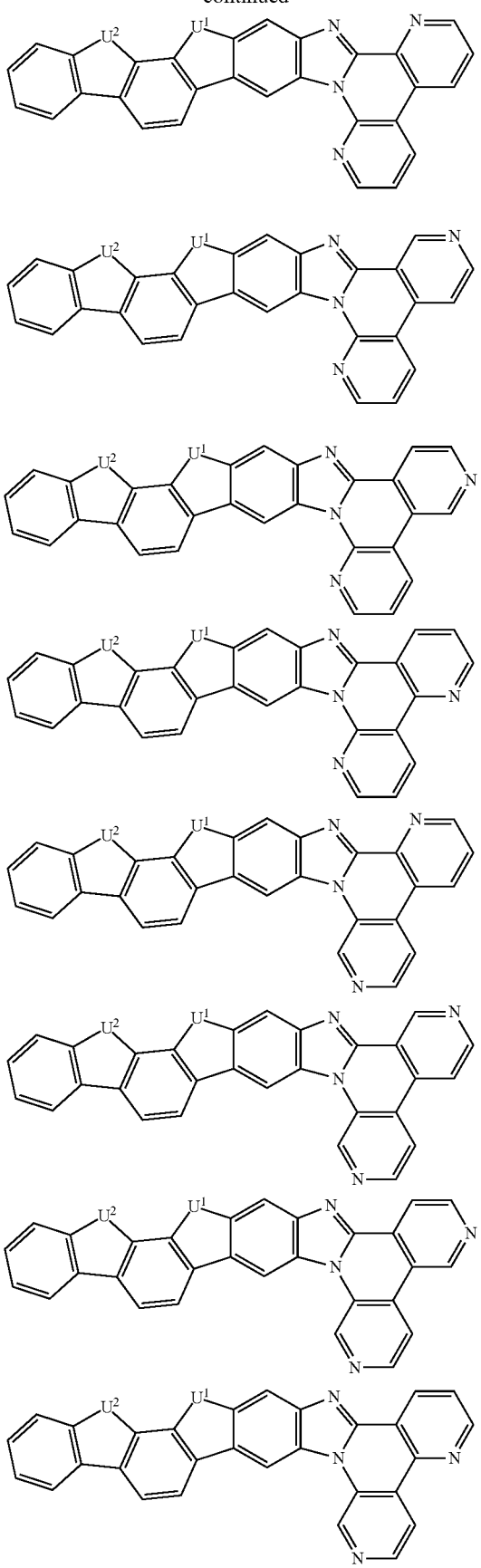

485
-continued
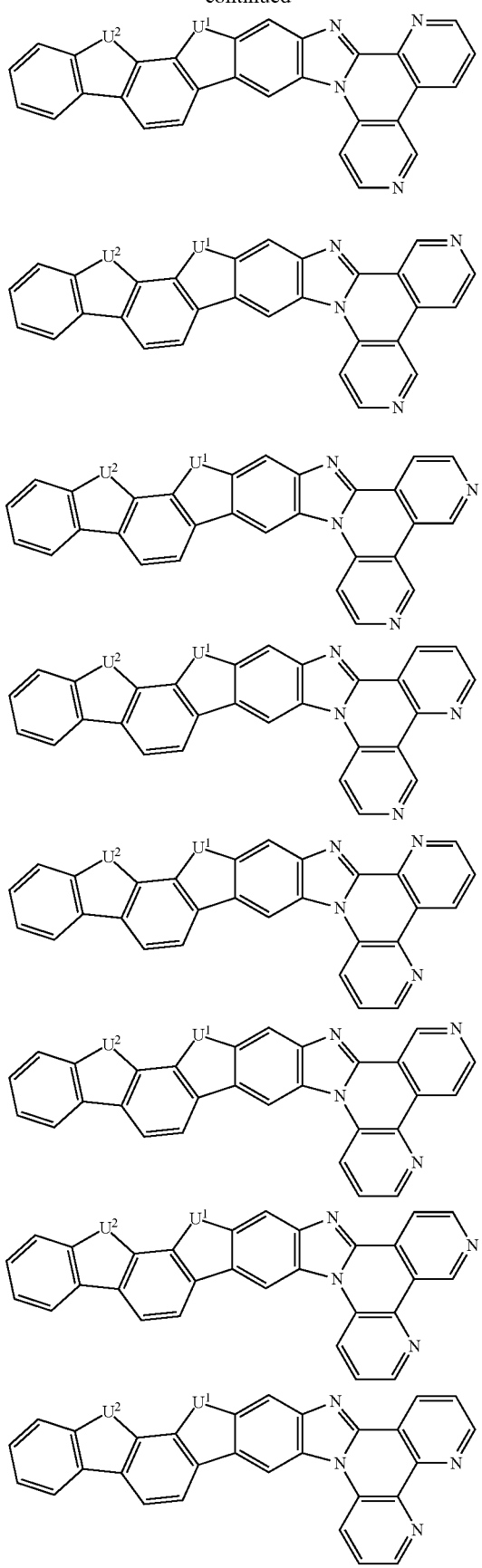
486
-continued
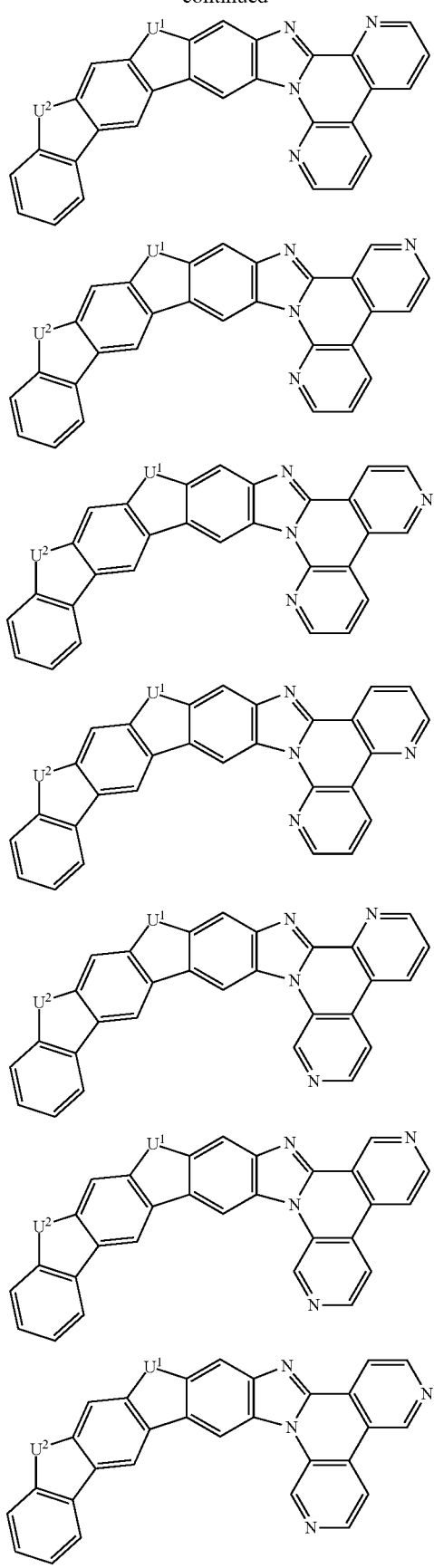

487
-continued
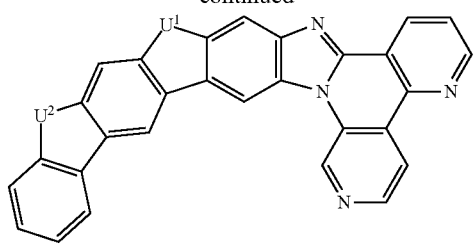
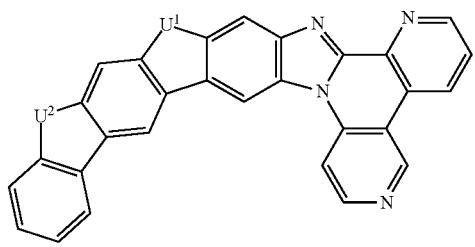
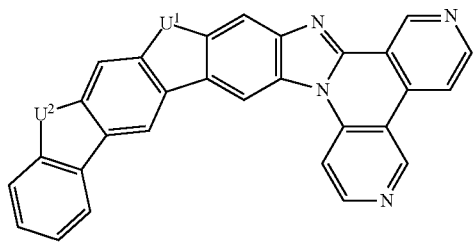
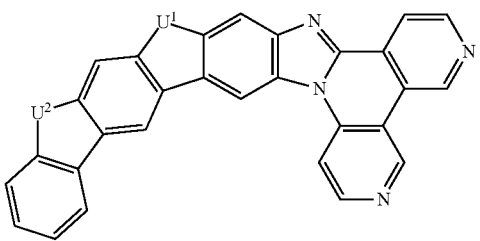
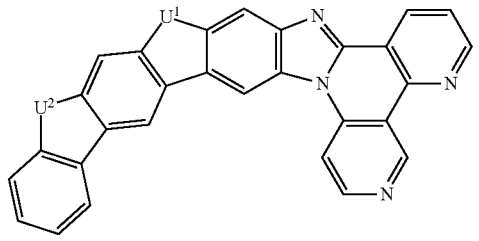
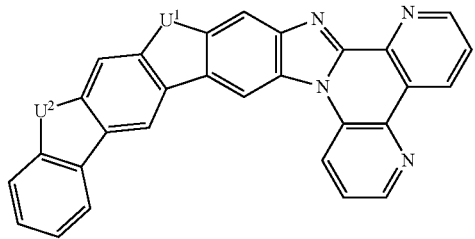
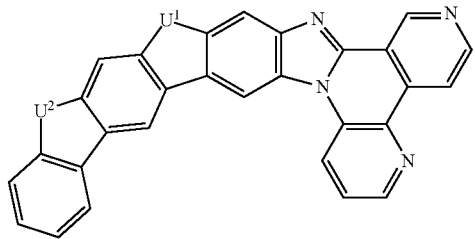
488
-continued
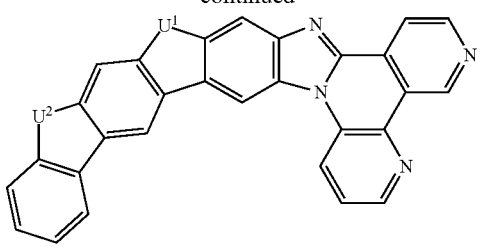
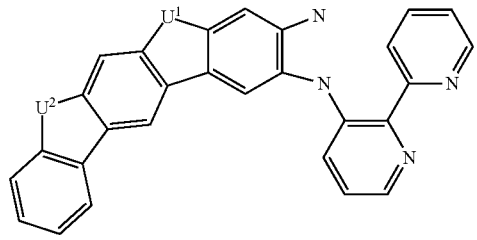
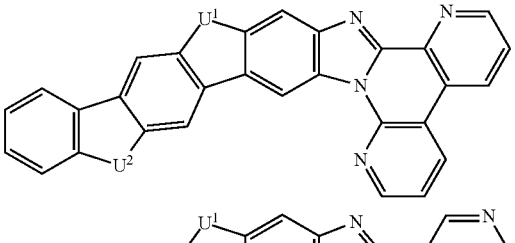
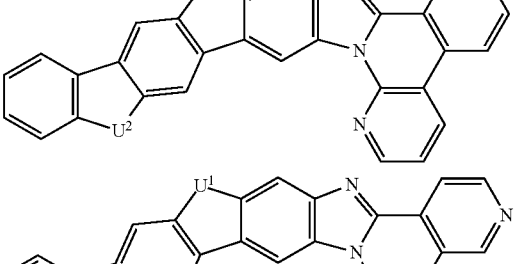

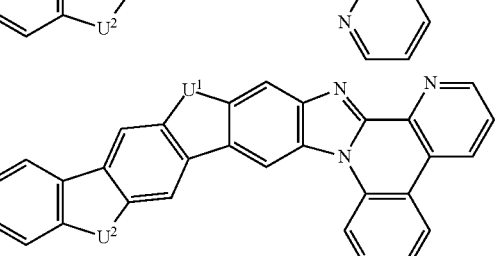
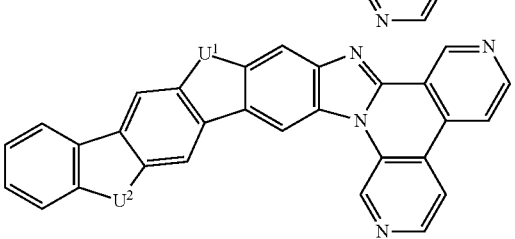

489
-continued
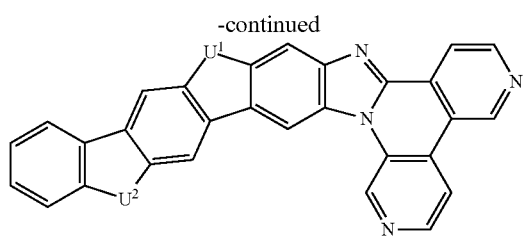
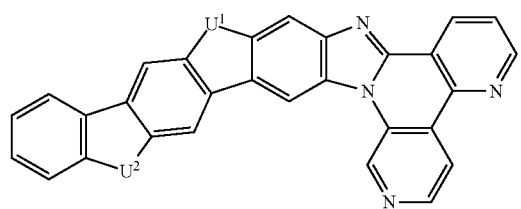
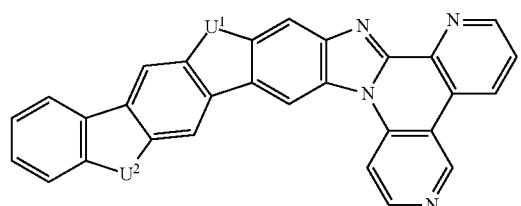
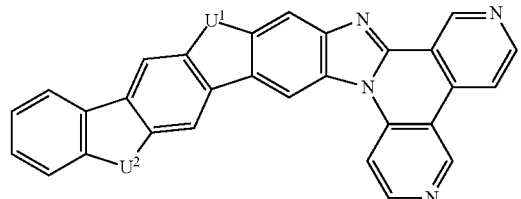
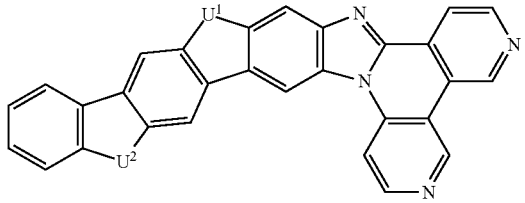
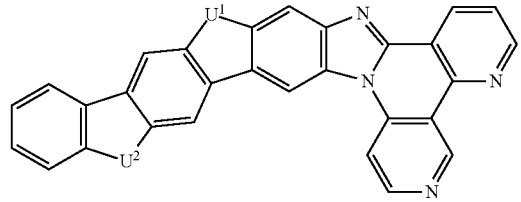
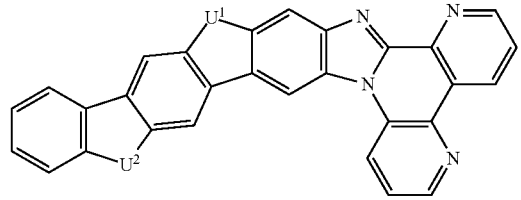
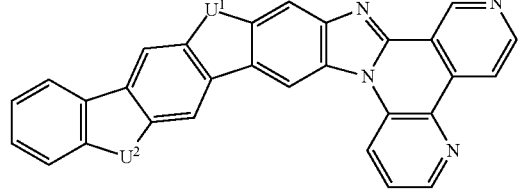
490
-continued
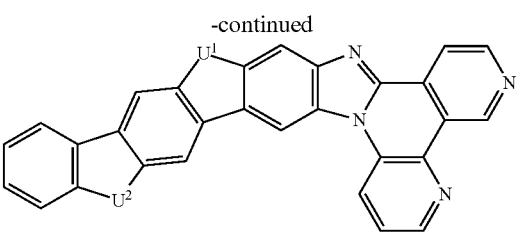
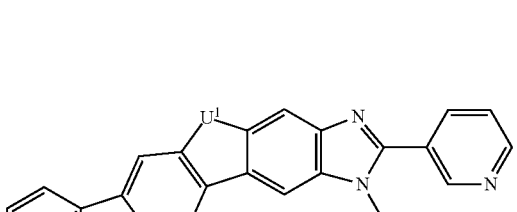
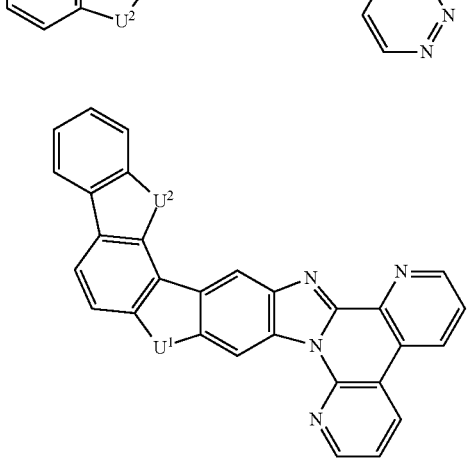
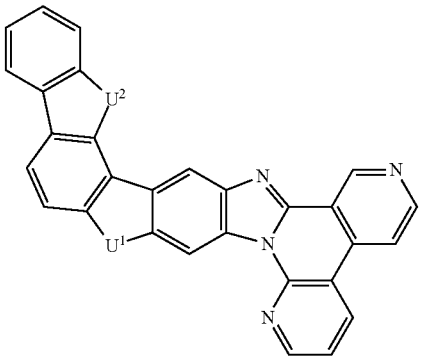
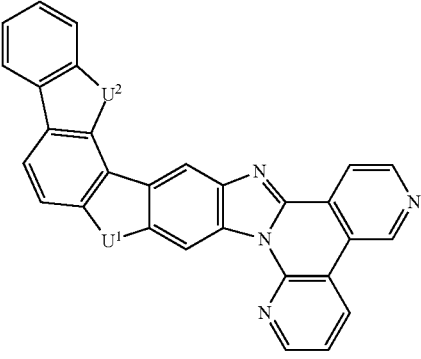

491
-continued
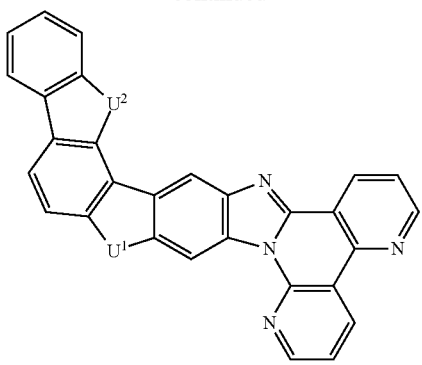
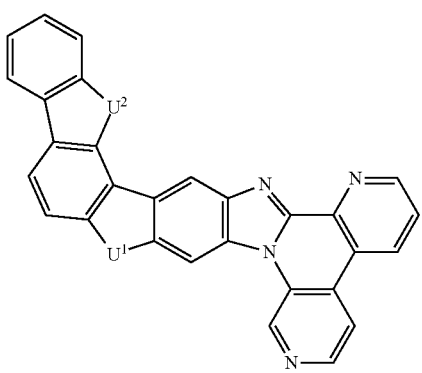
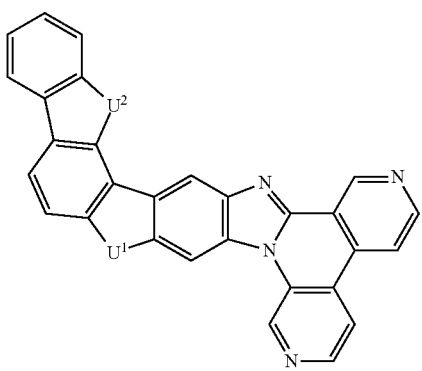
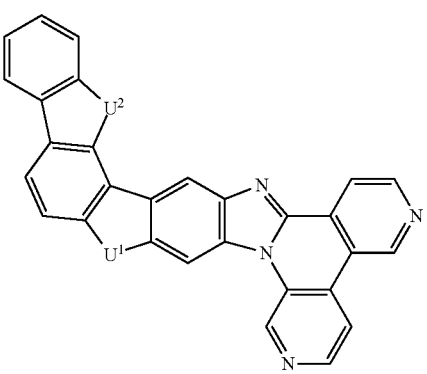
492
-continued
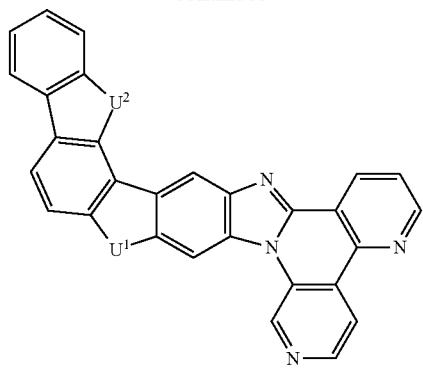
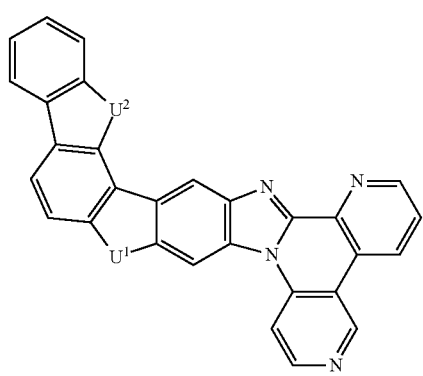
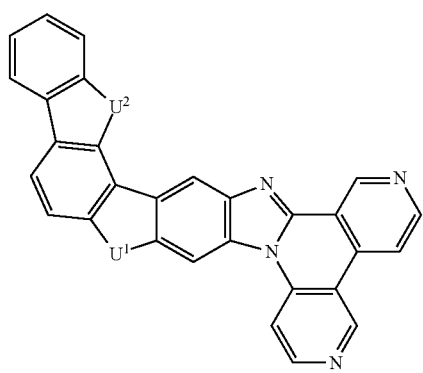
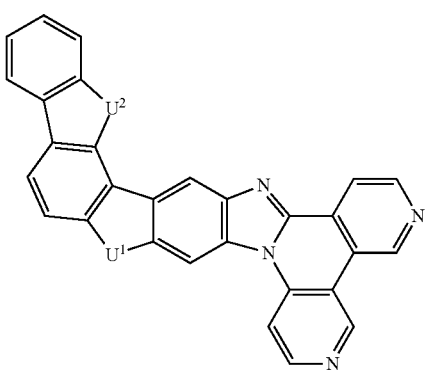

493
-continued
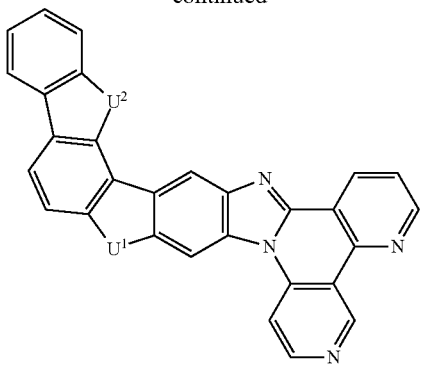
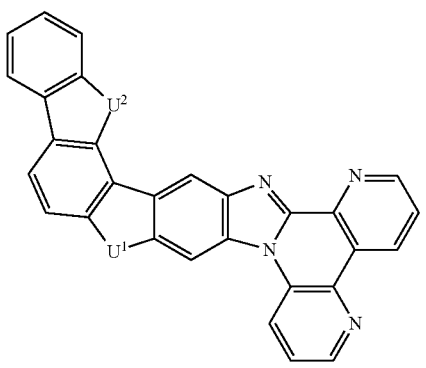
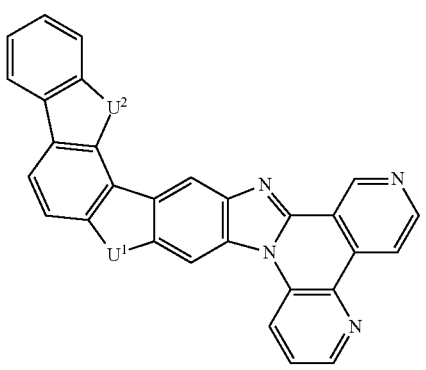
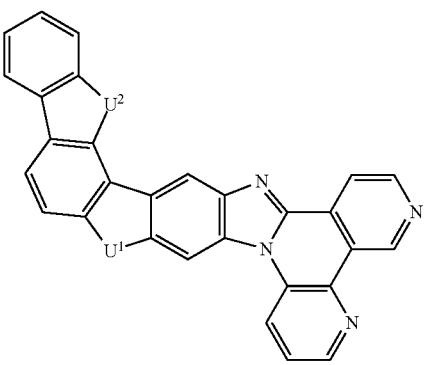
494
-continued
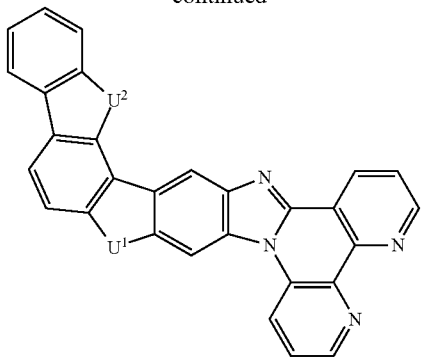
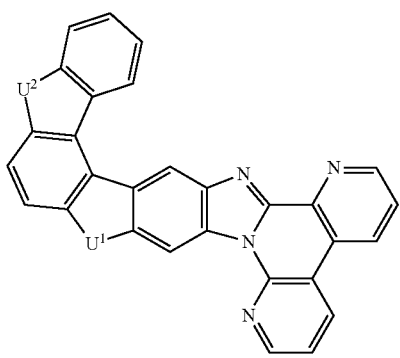
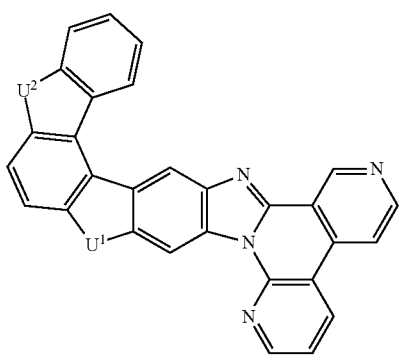
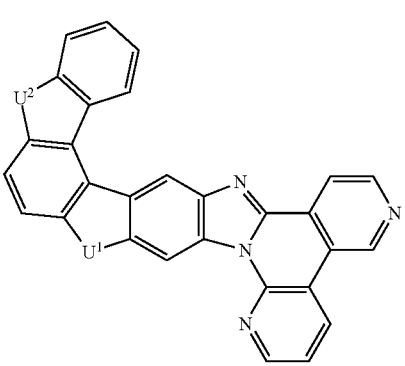

495
-continued
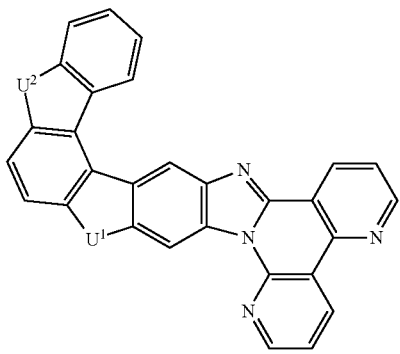
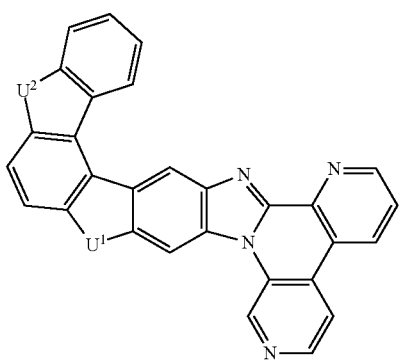
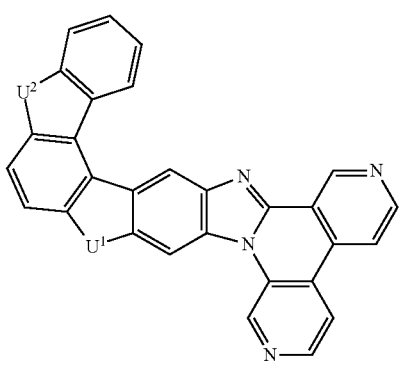
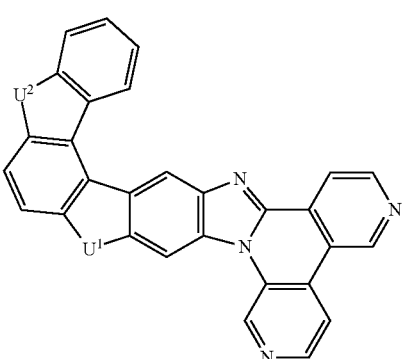
496
-continued
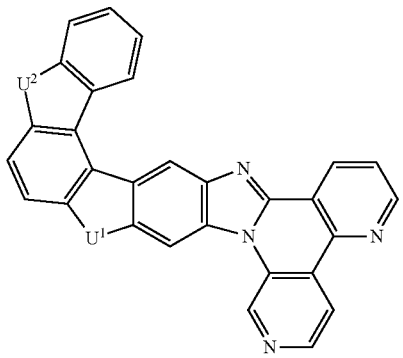
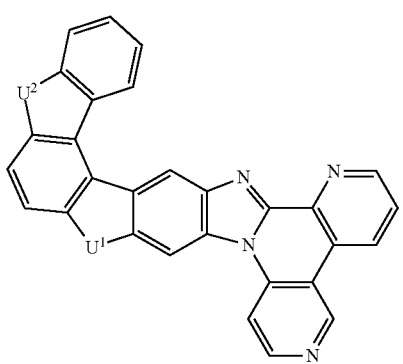
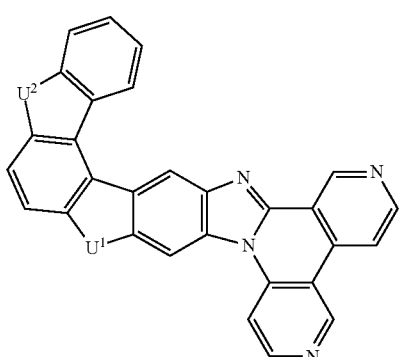
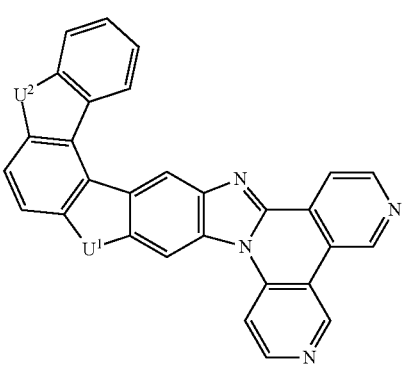

497
-continued
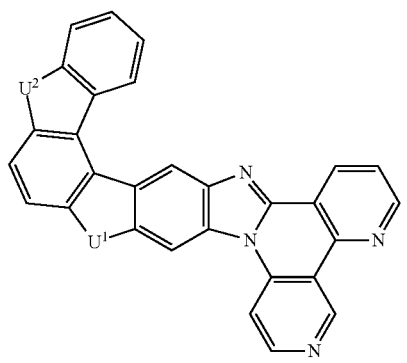
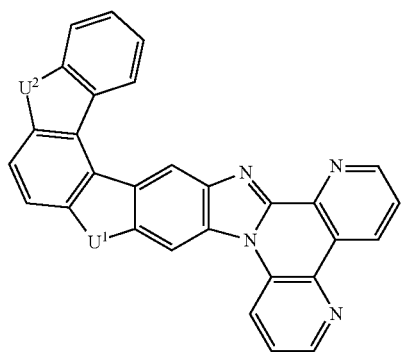
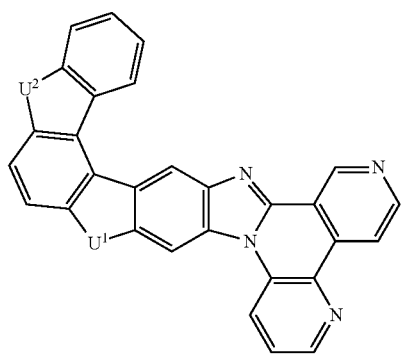
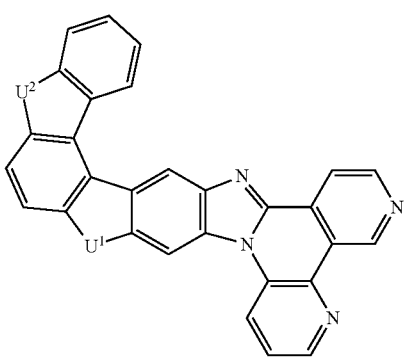
498
-continued
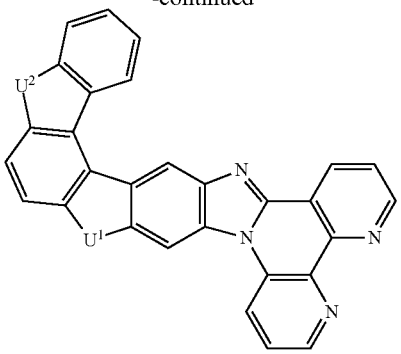
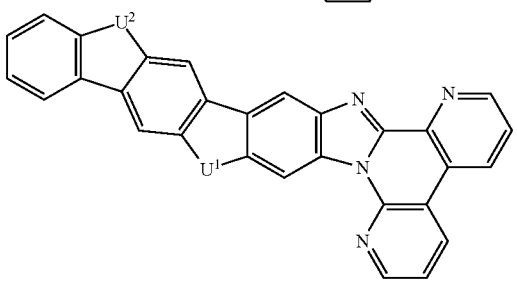
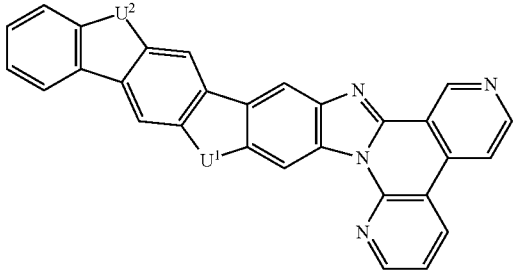
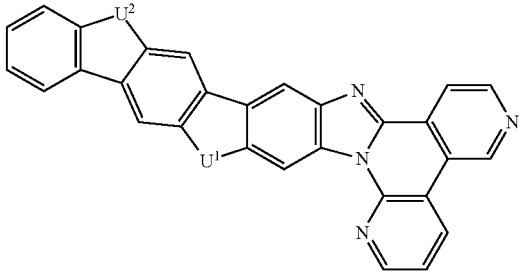
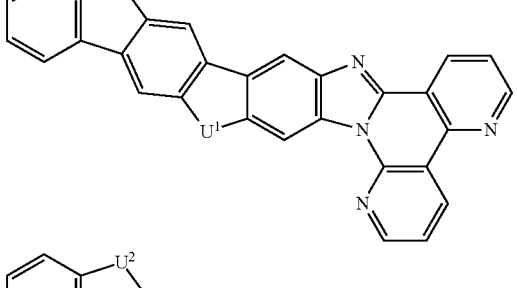
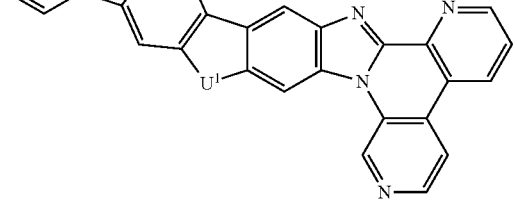

499
-continued
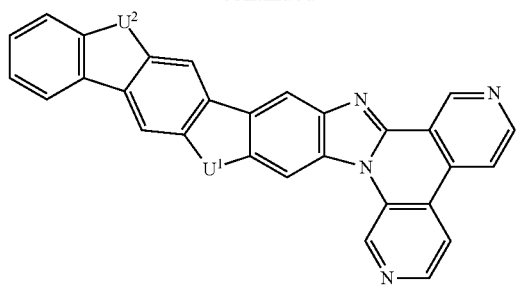
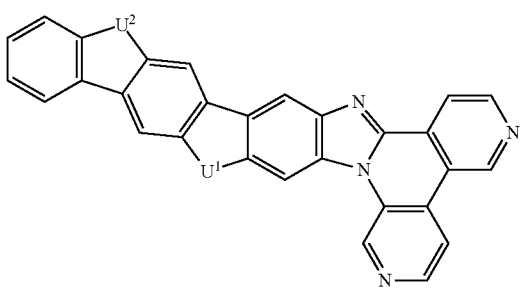
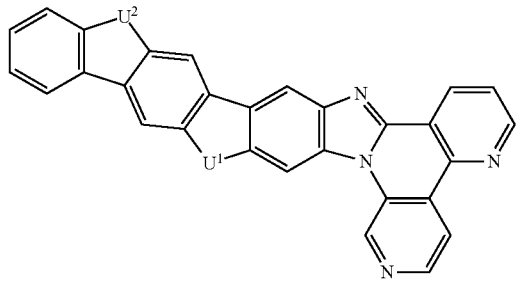
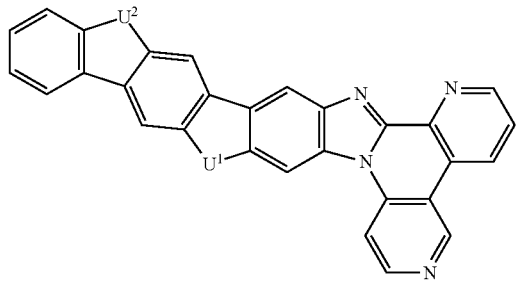
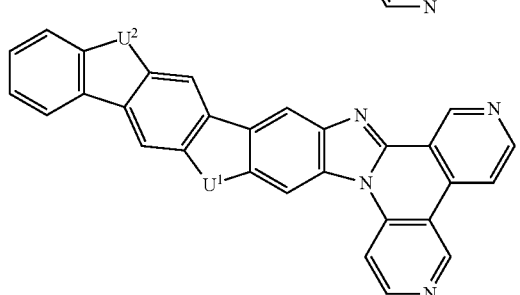
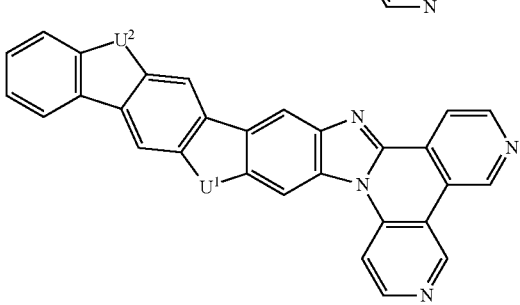
500
-continued
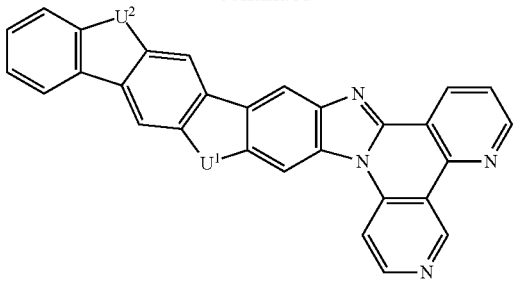
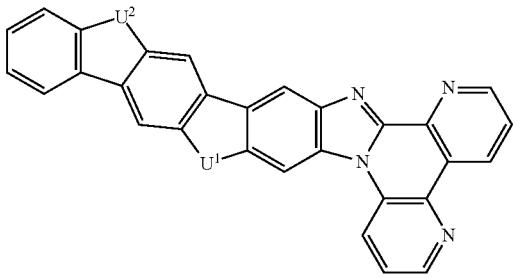
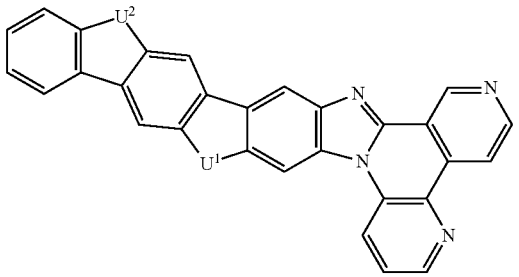
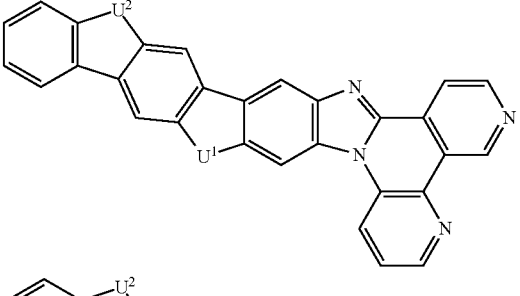
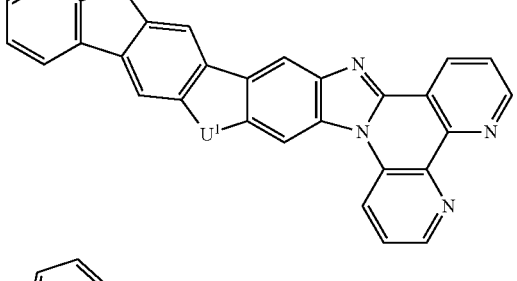
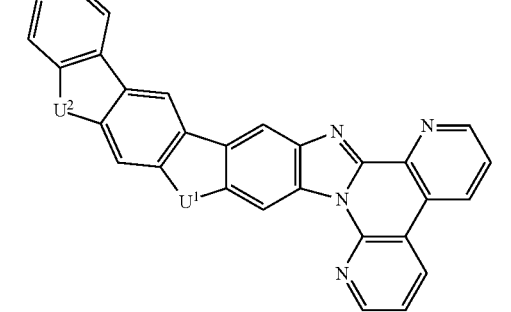

501
-continued
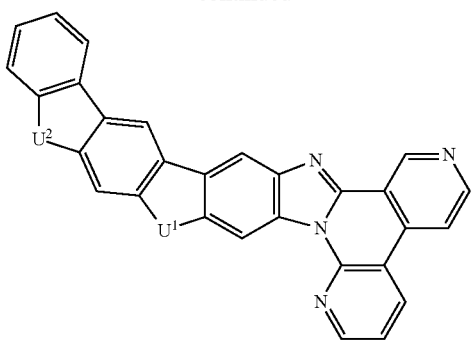
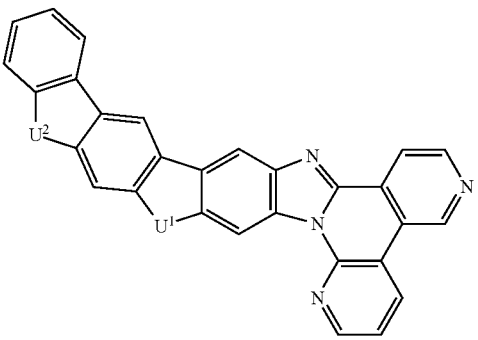
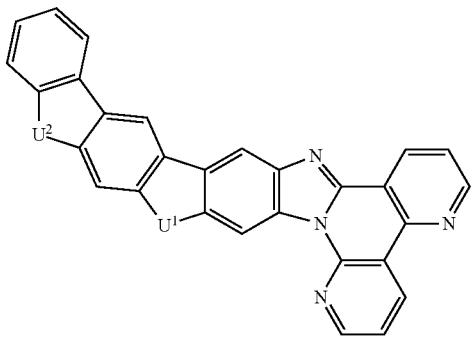
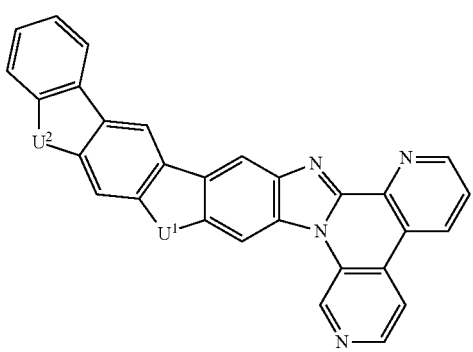
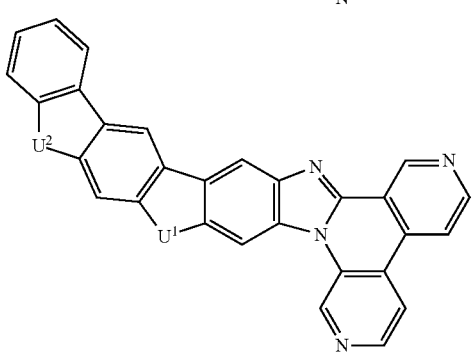
502
-continued
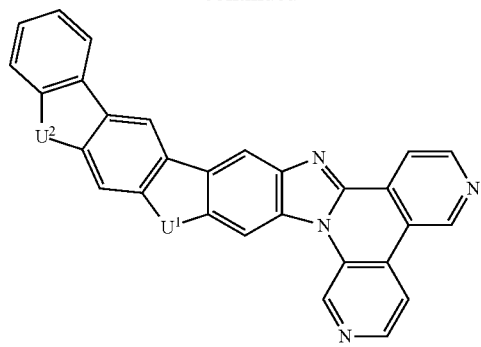
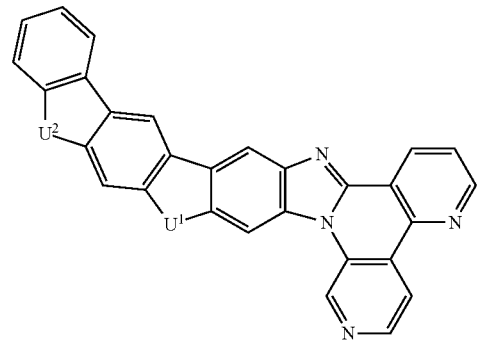
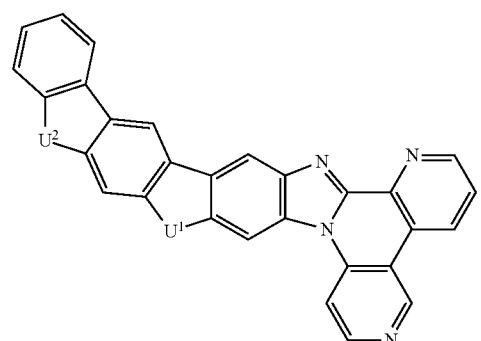
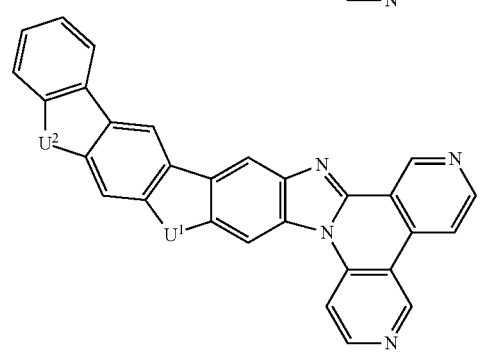
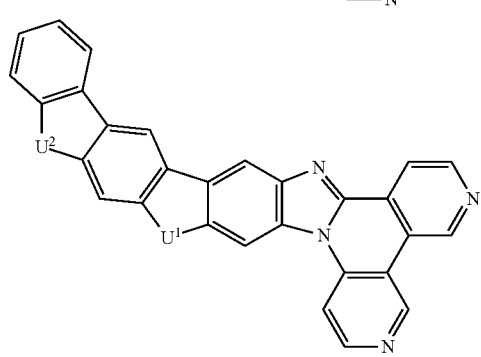

503
-continued
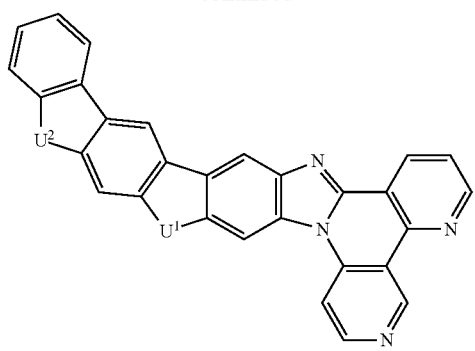
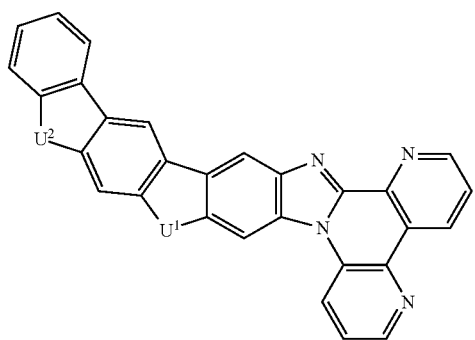
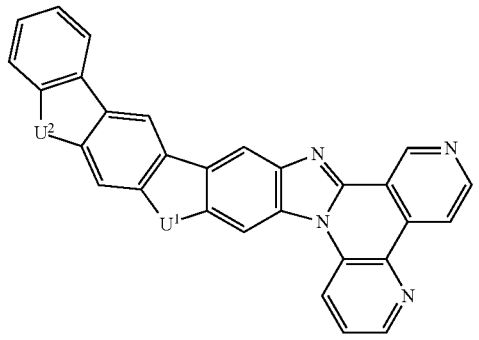
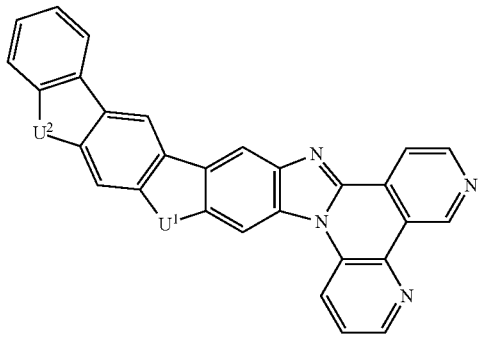
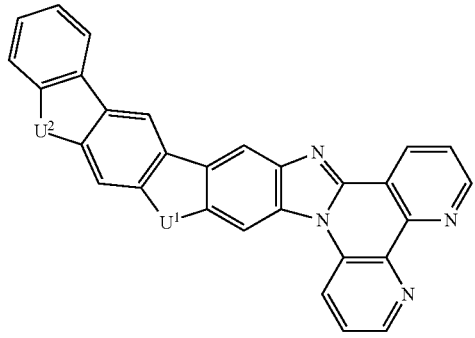
504
-continued
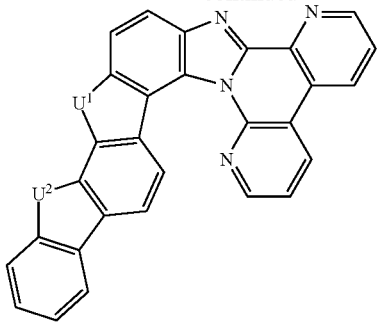
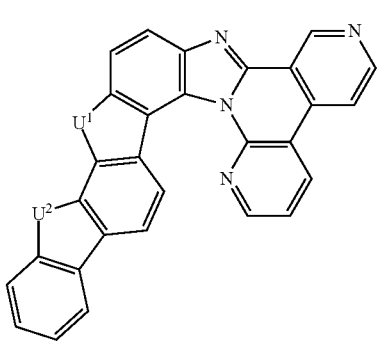
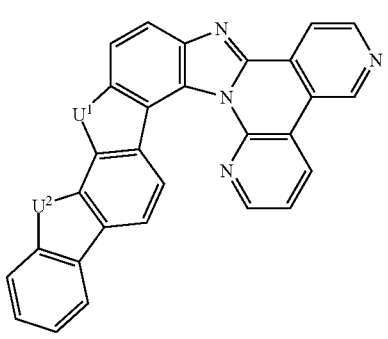
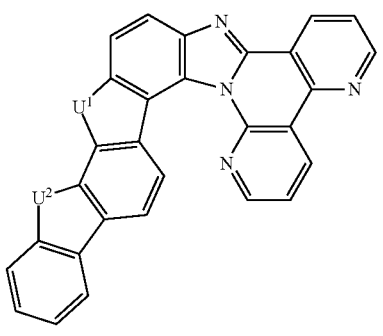
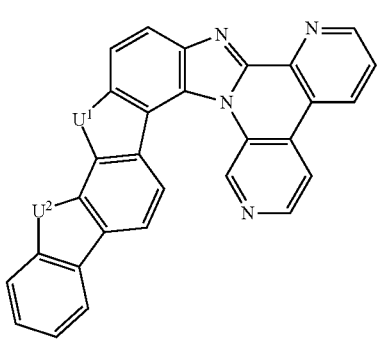

505
-continued
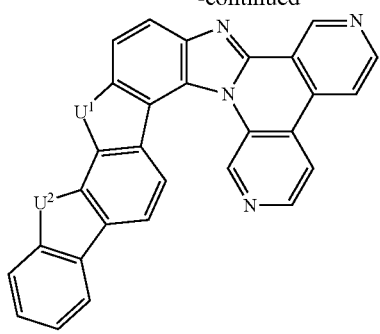
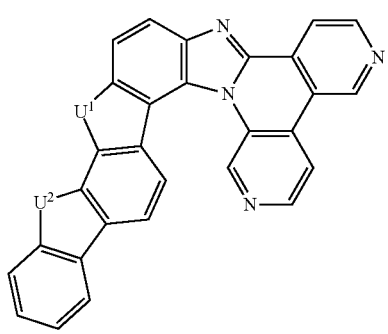
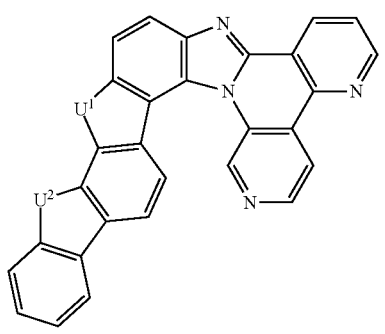
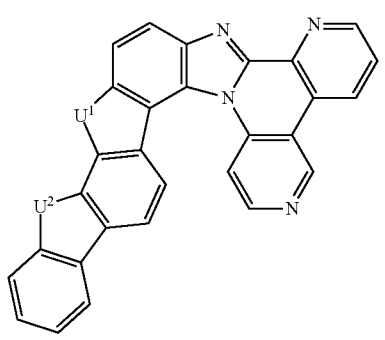
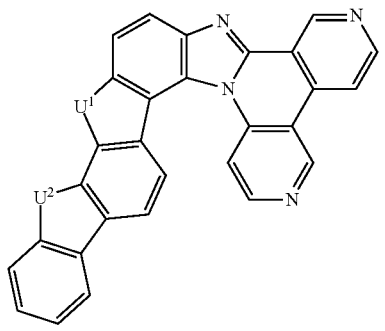
506
-continued
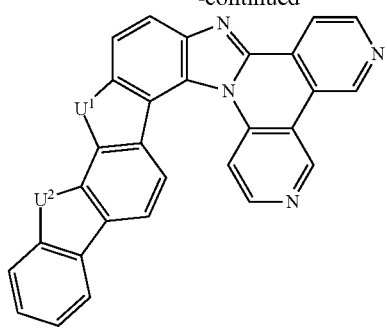
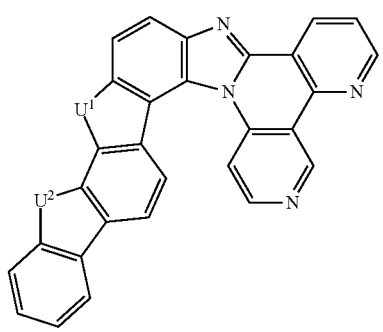
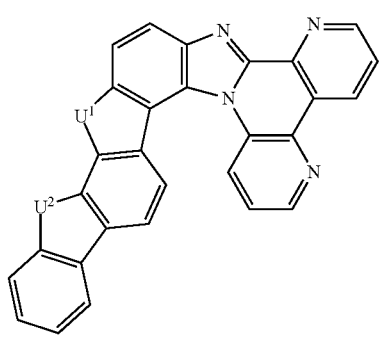
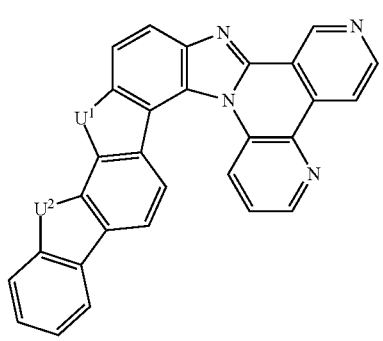
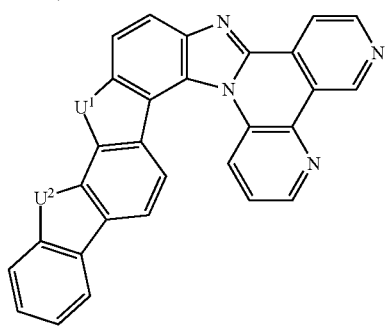

507
-continued
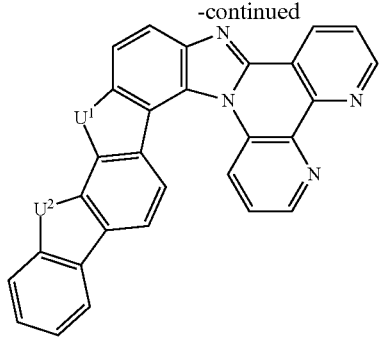
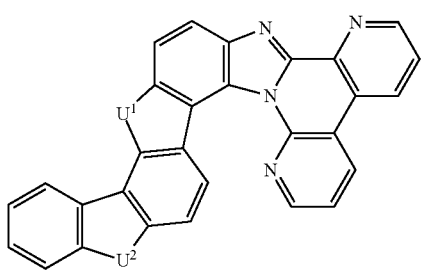
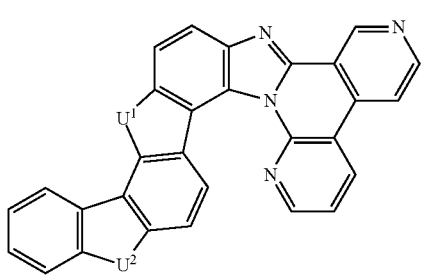
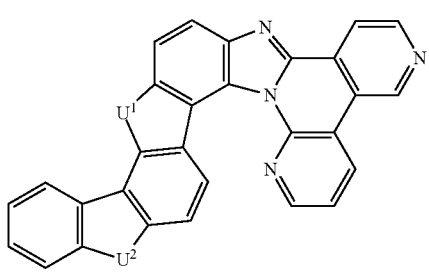
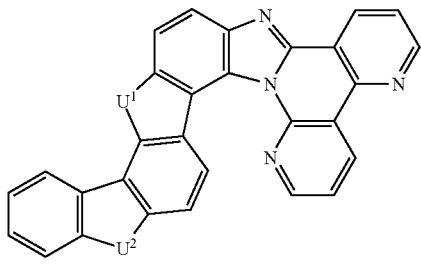
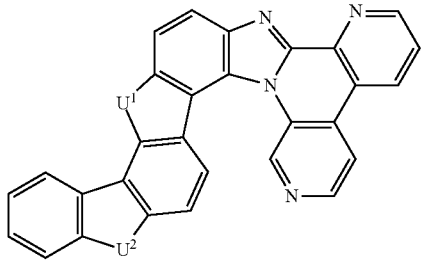
508
-continued
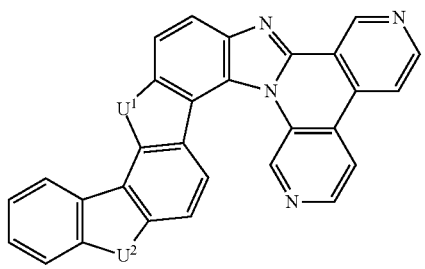
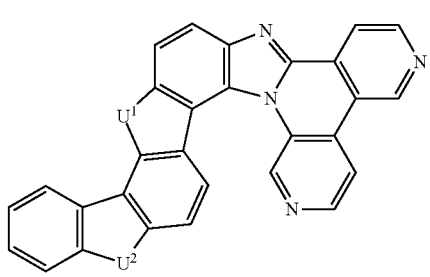
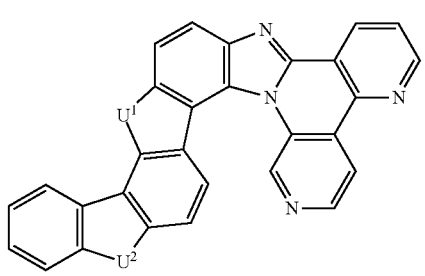
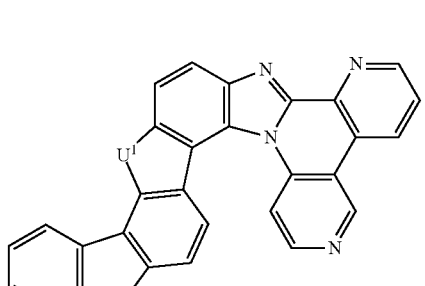
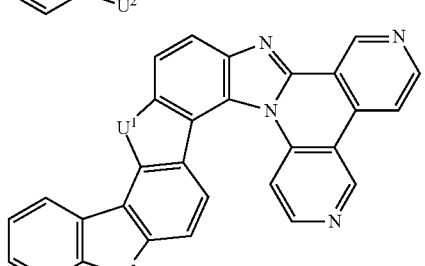
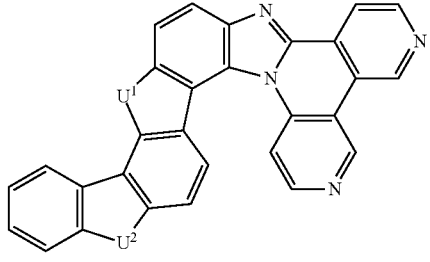

509
-continued
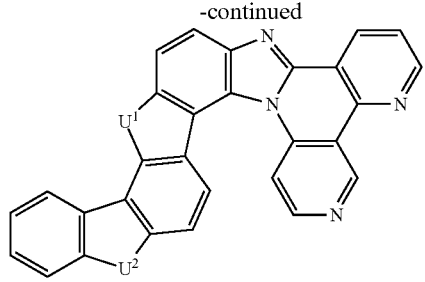
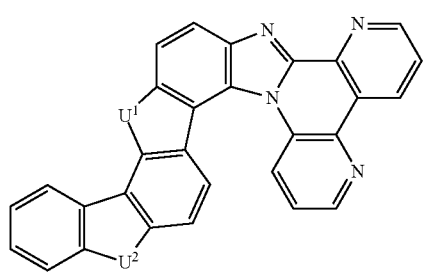
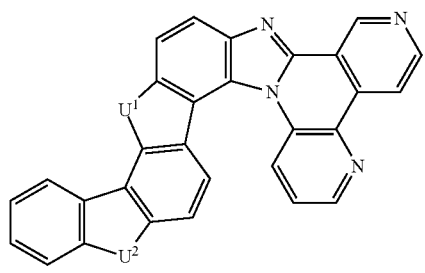
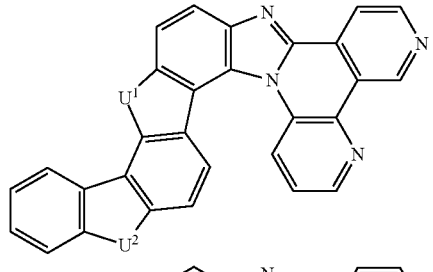
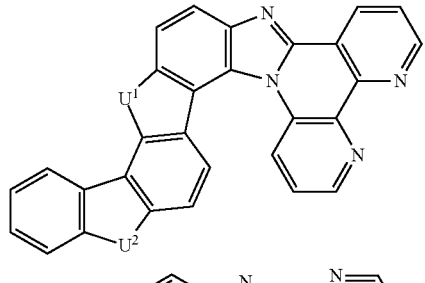
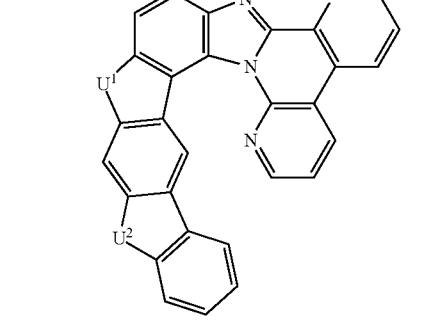
510
-continued
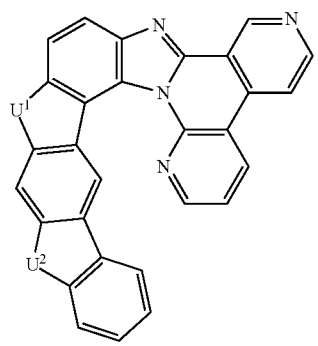
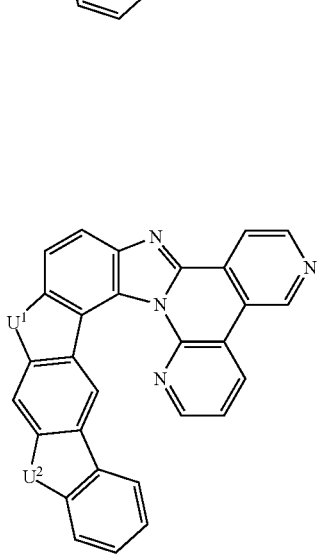
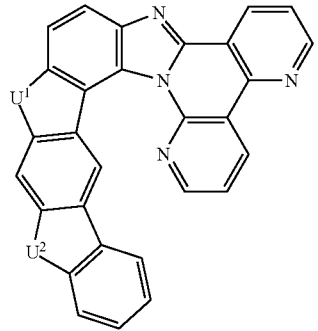
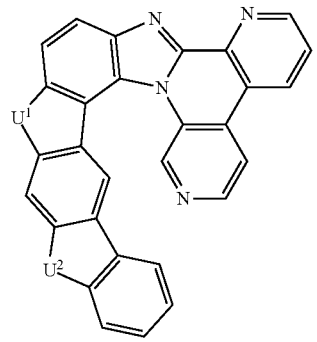

| 511 | 512 |
|---|---|
| -continued | -continued |
| 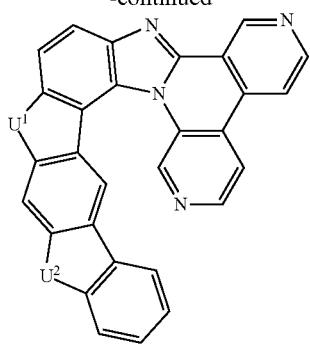 | 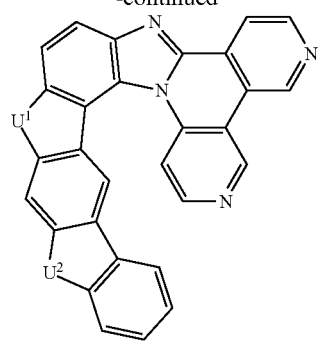 |
| 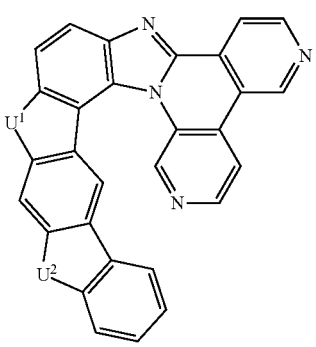 | 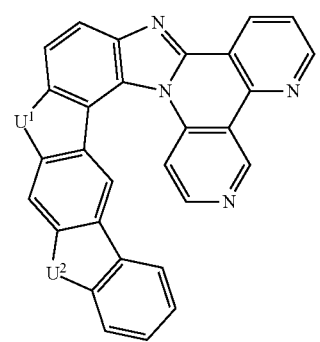 |
| 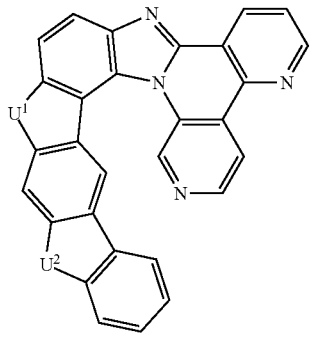 | 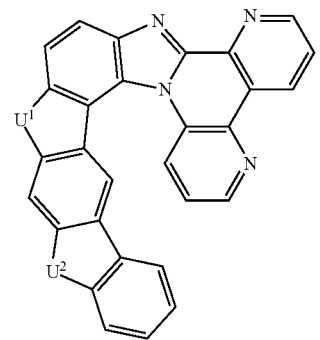 |
| 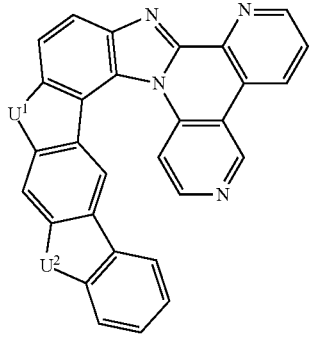 | 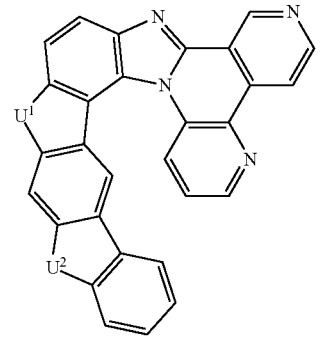 |
| 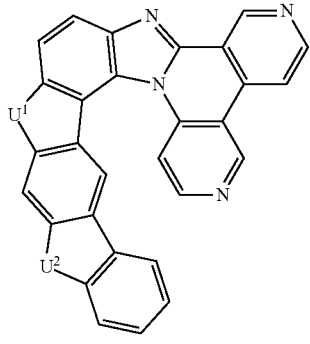 | 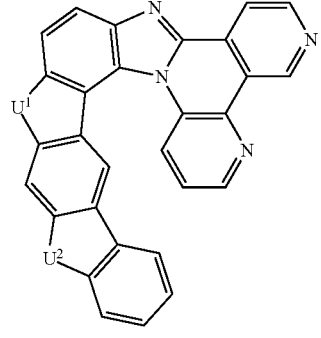 |

513
-continued
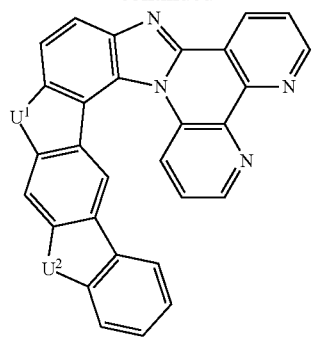
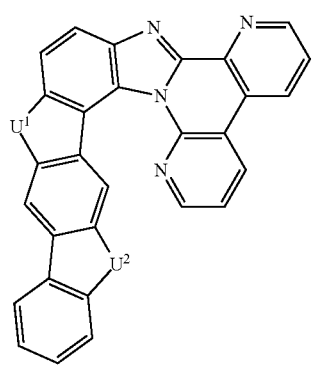
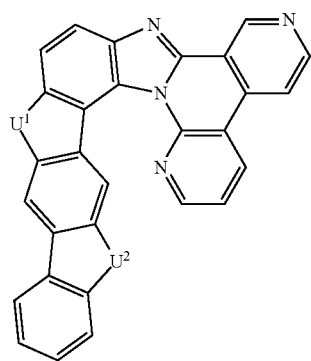
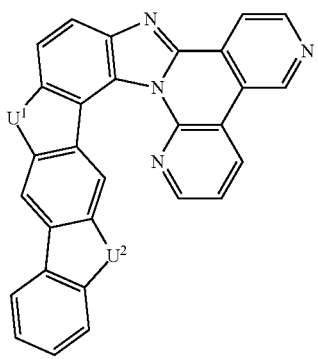
514
-continued
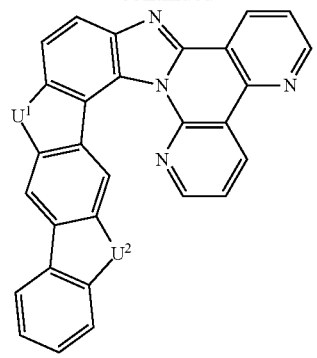
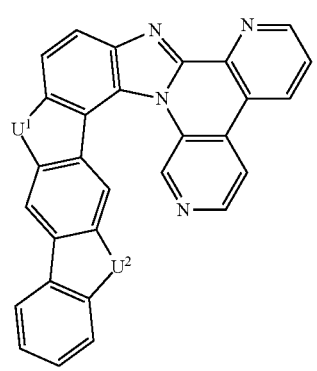
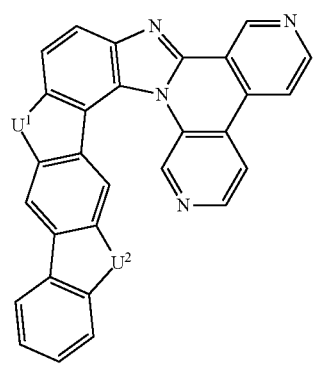
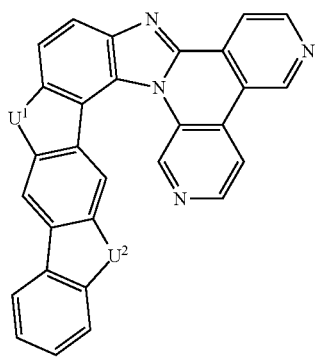

| 515 -continued | 516 -continued |
|---|---|
| 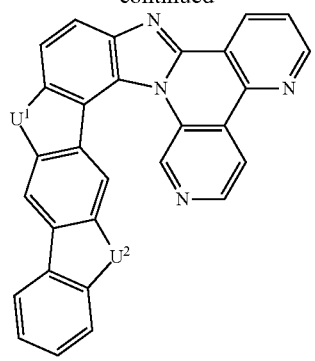 | 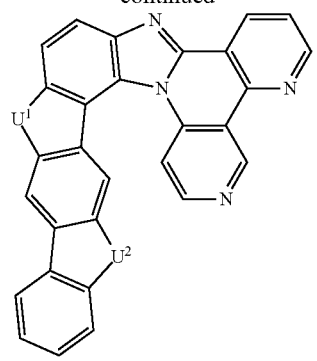 |
| 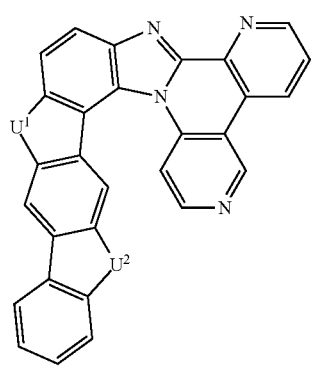 | 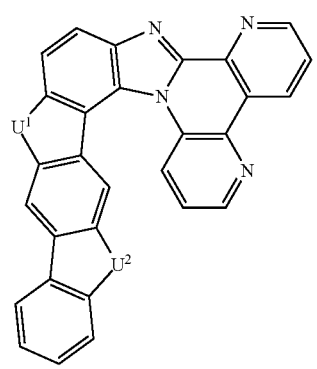 |
| 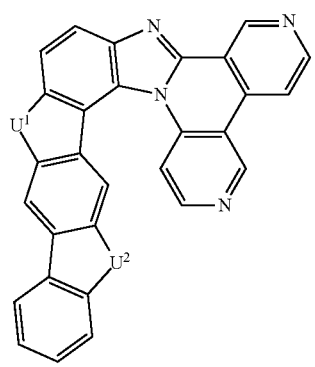 | 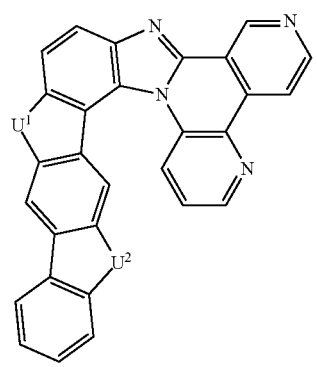 |
| 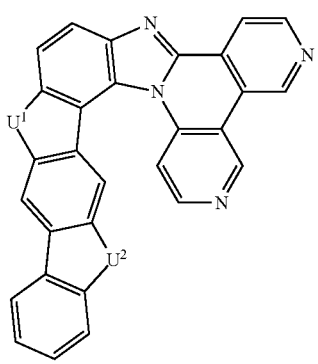 | 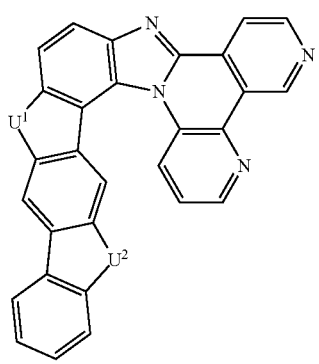 |

517
-continued
518
-continued
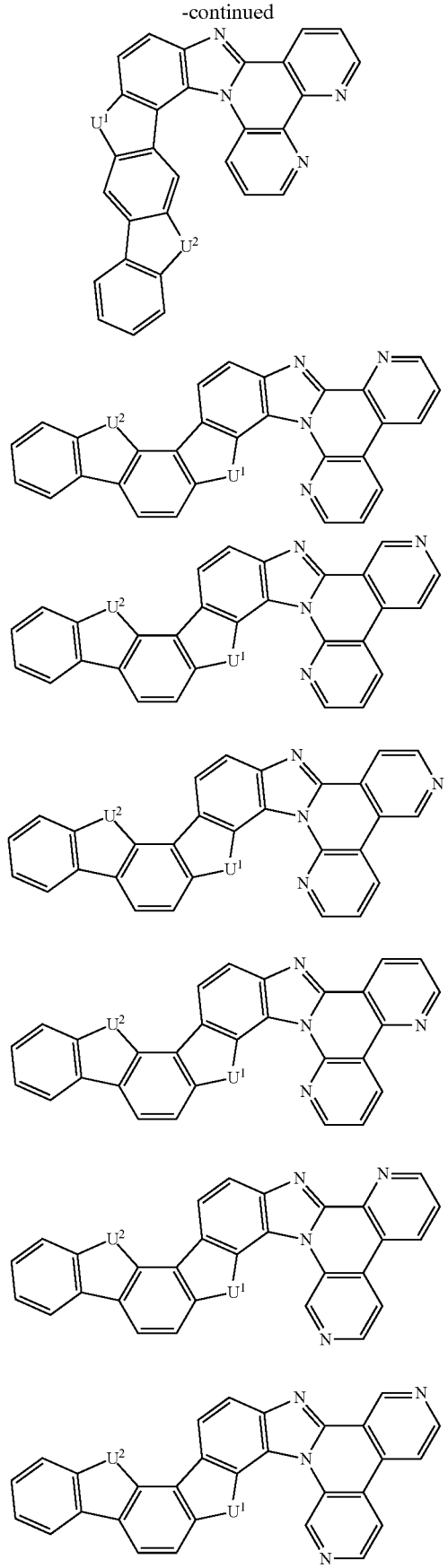
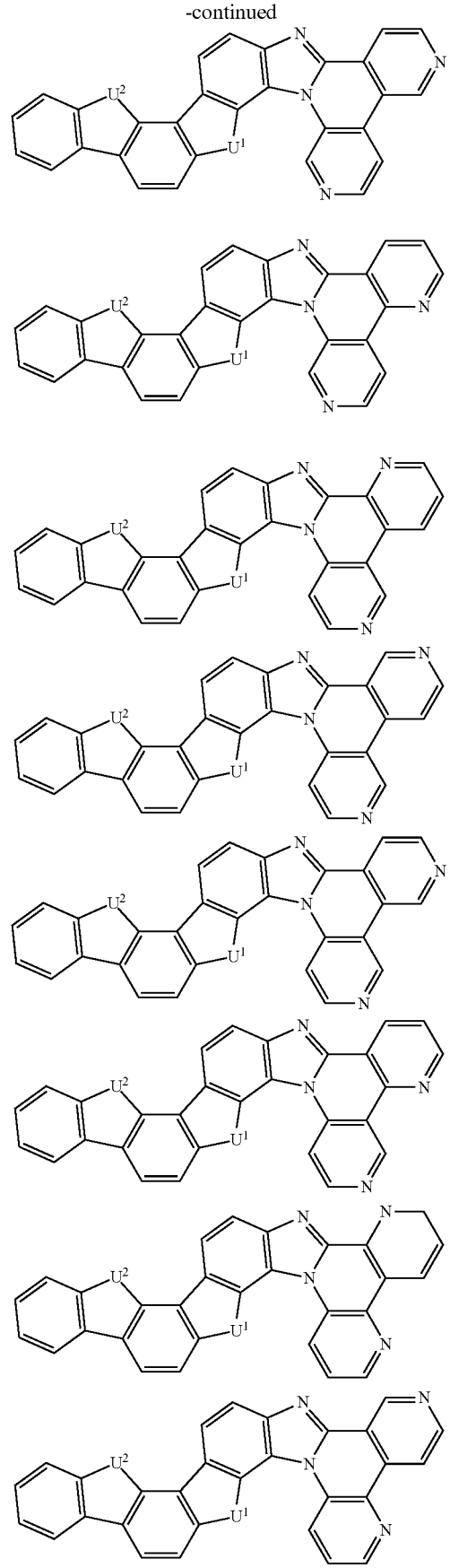

519
-continued
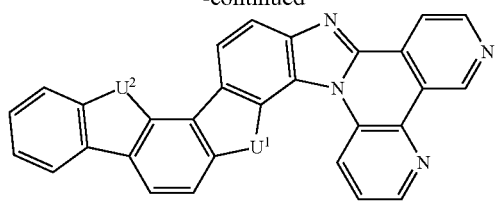
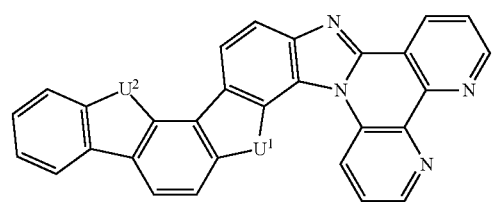
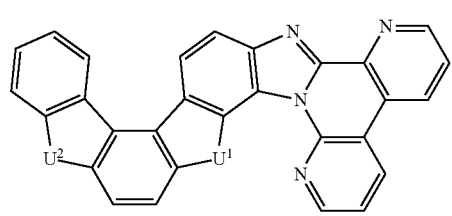
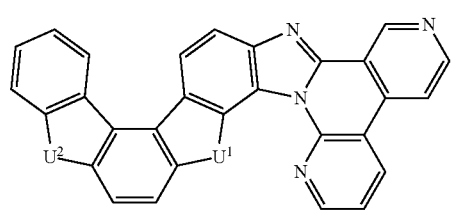
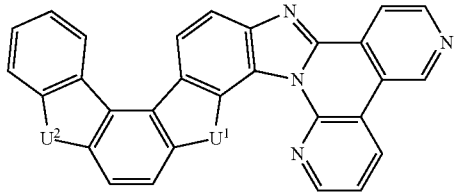
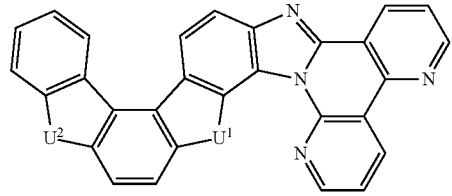
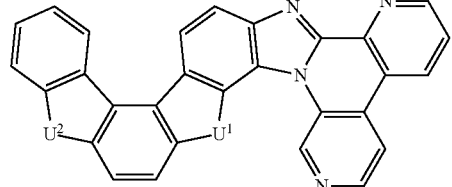
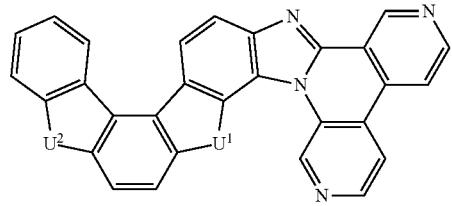
520
-continued
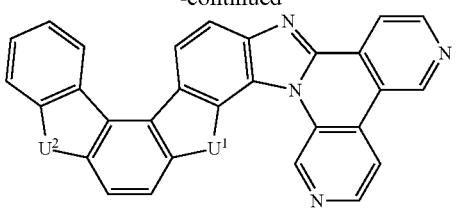
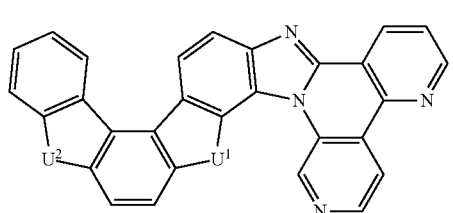
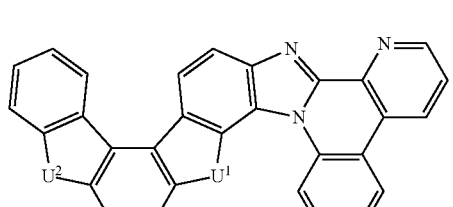
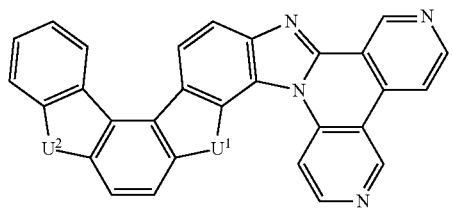
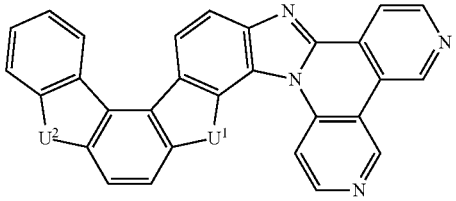
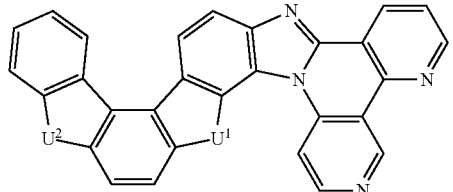
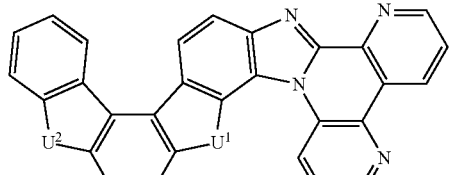
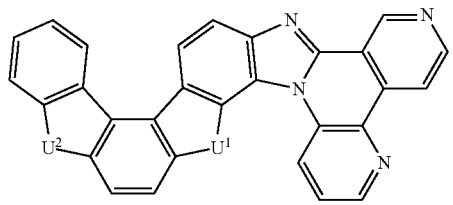

521
-continued
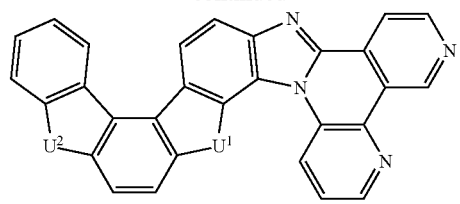
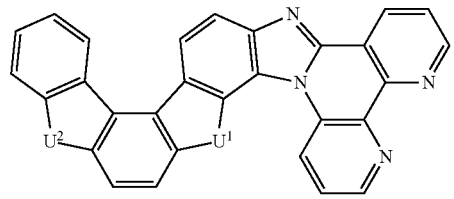
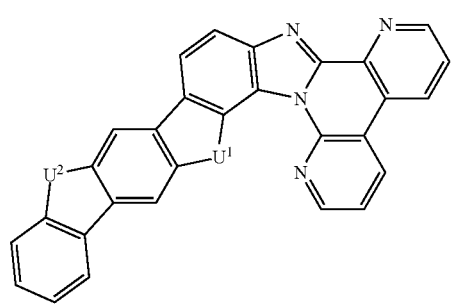
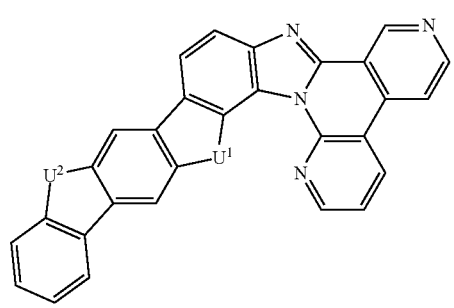
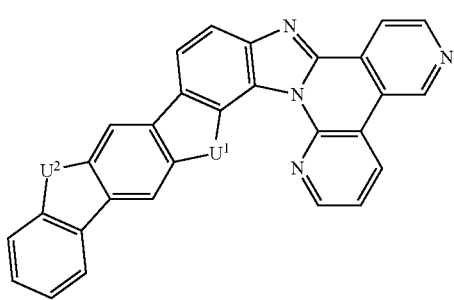
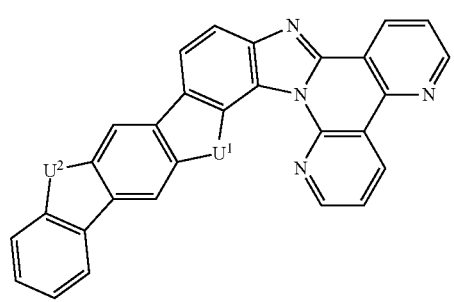
522
-continued
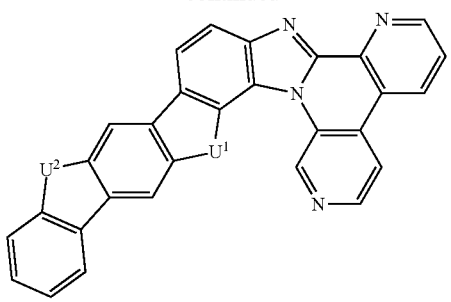
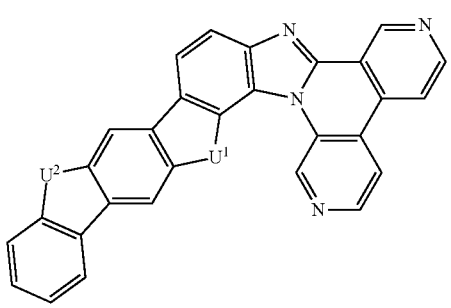
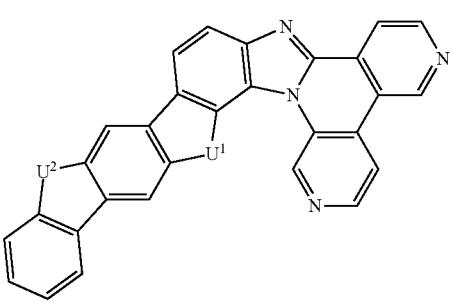
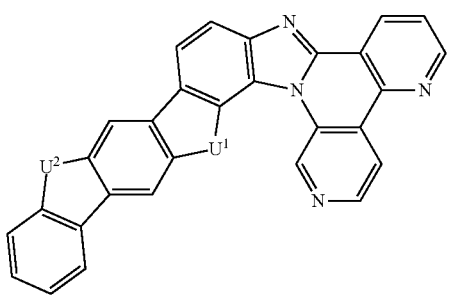
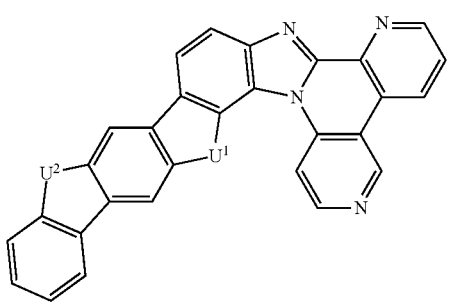

523
-continued
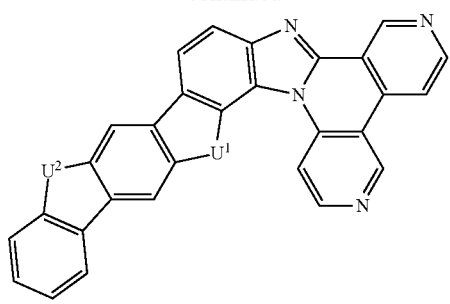
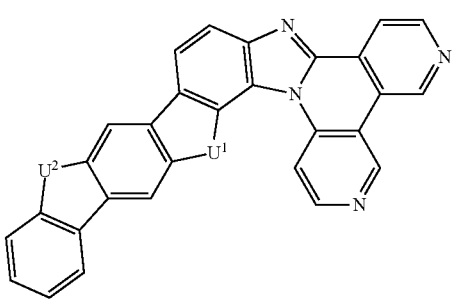
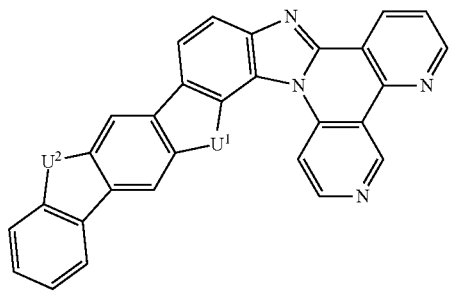
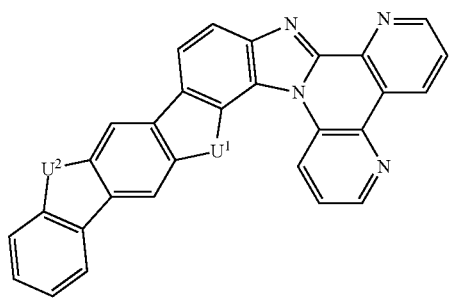
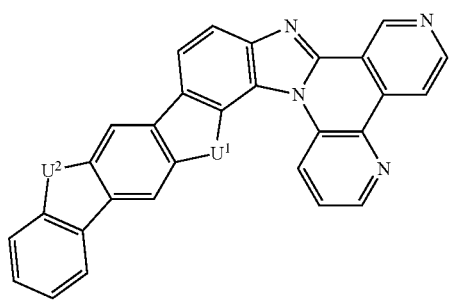
524
-continued
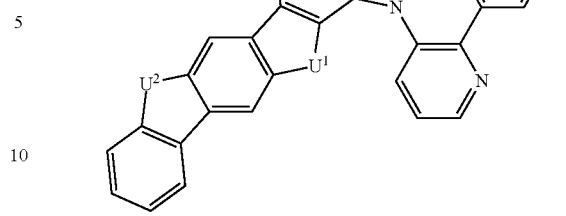
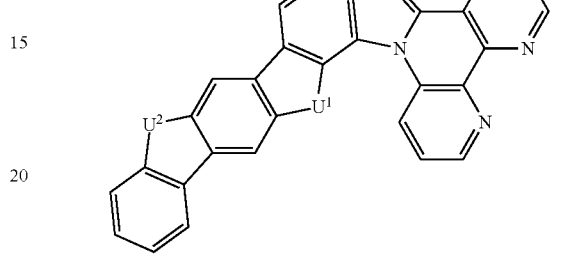
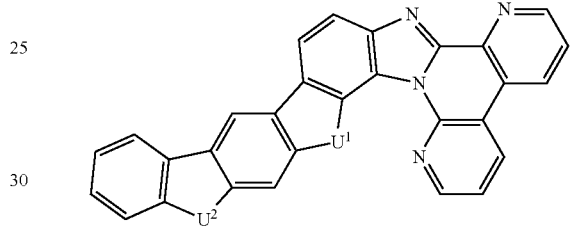
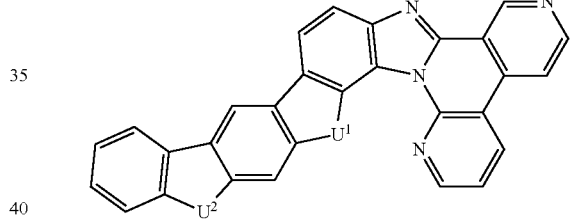
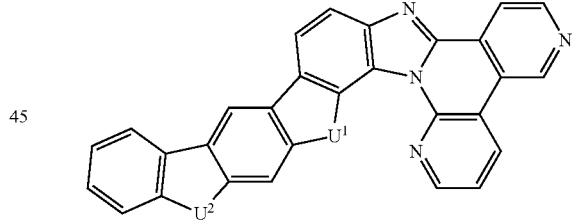
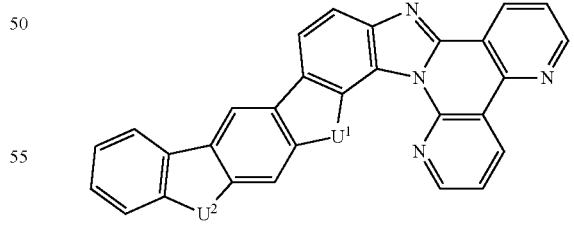
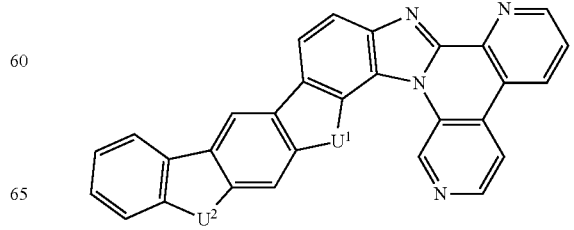

525
-continued
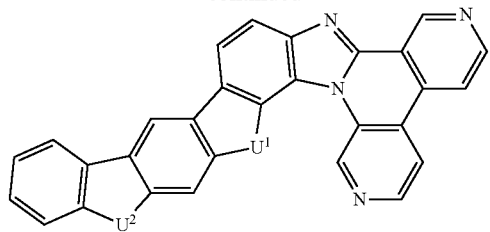
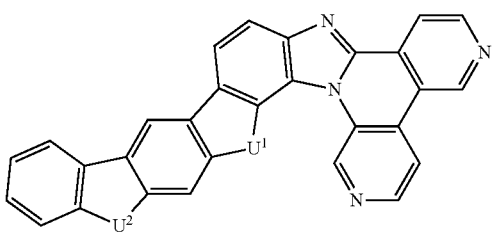
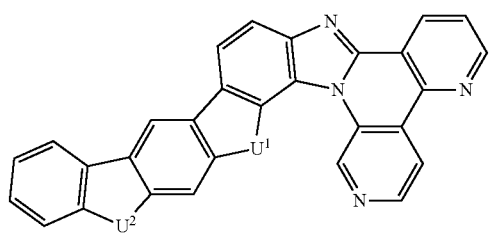
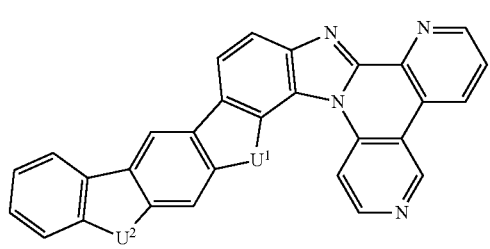
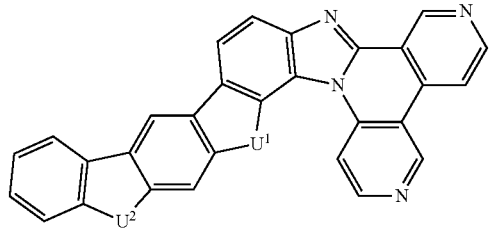
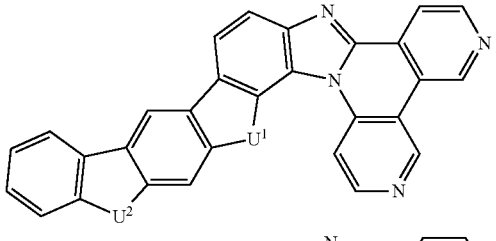
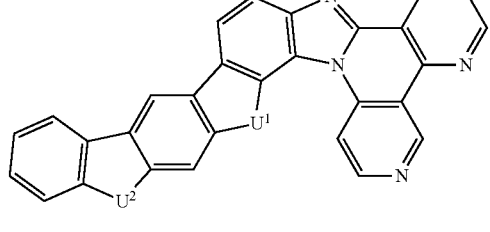
526
-continued
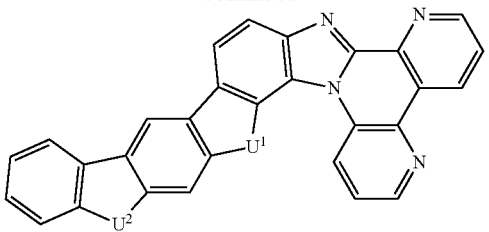
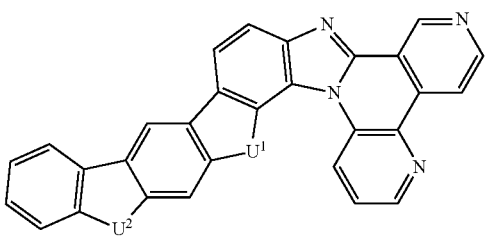
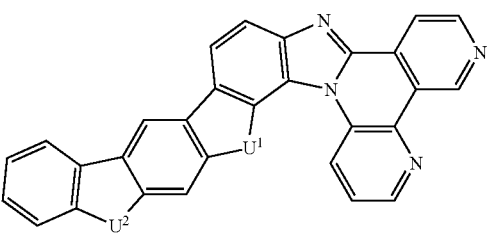
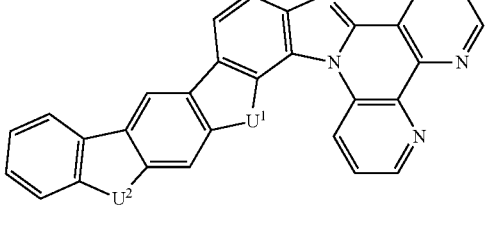
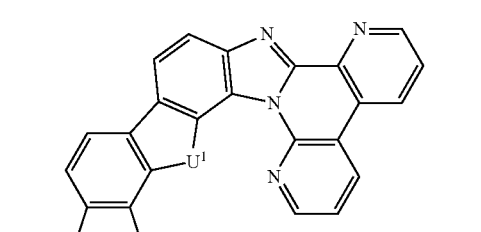
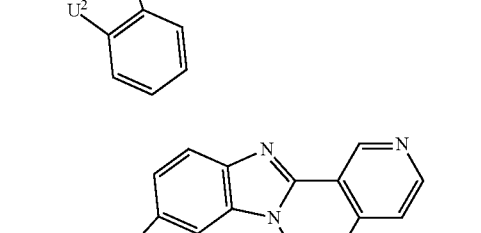
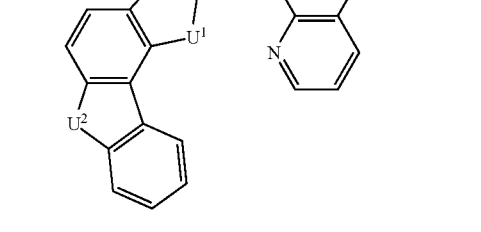

527
-continued
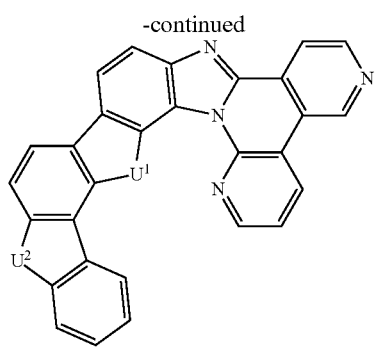
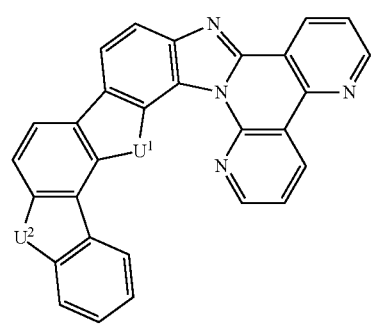
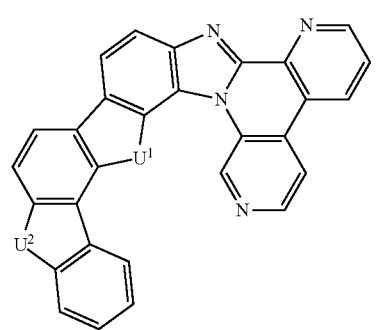
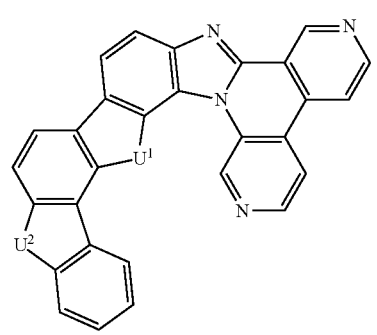
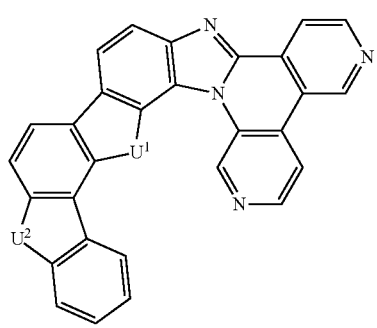
528
-continued
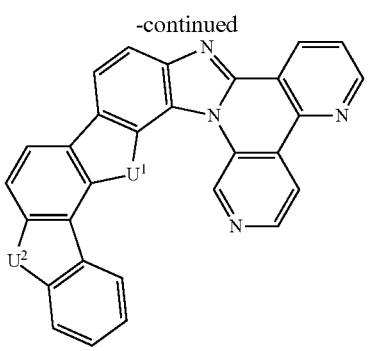
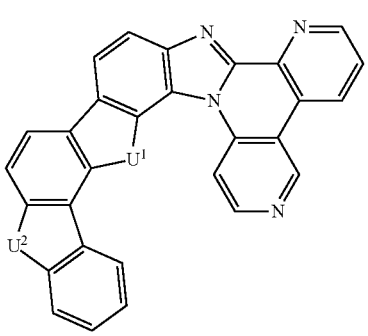
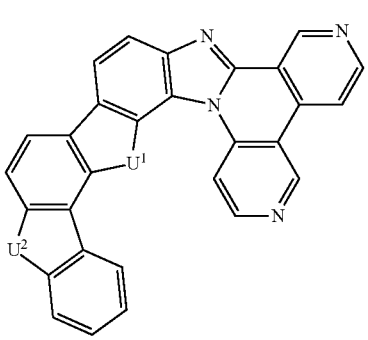
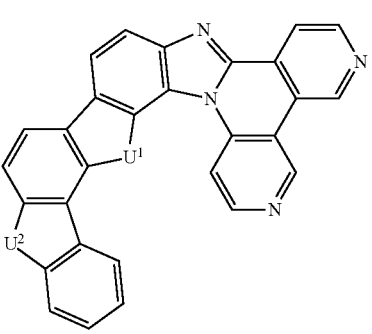
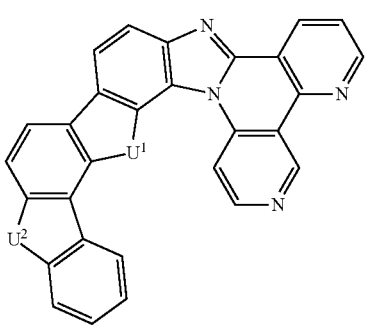

529
-continued
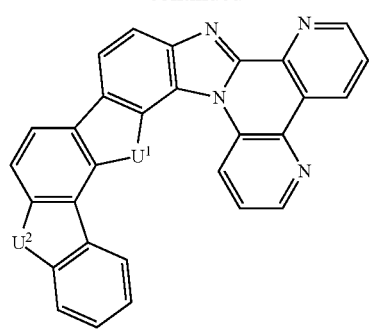
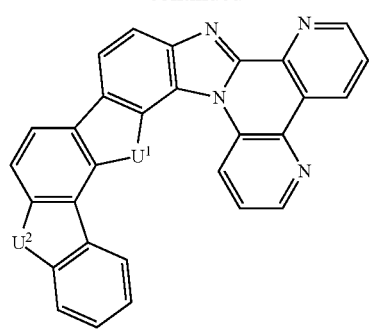
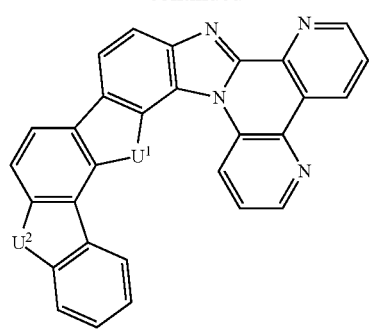
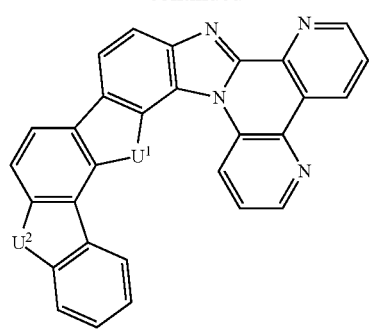
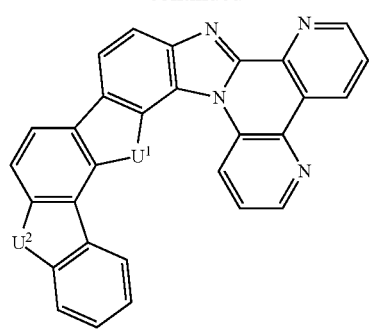
530
-continued
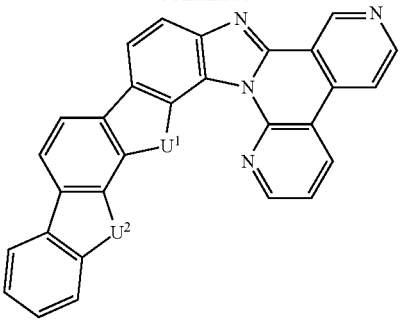
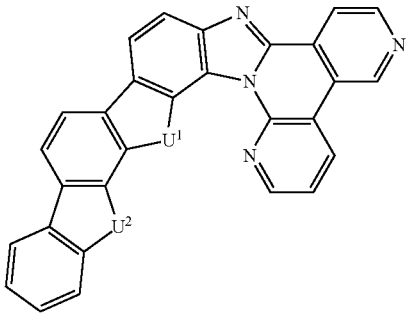
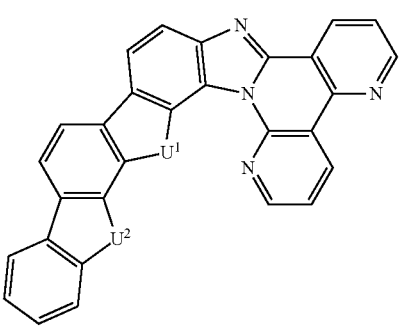
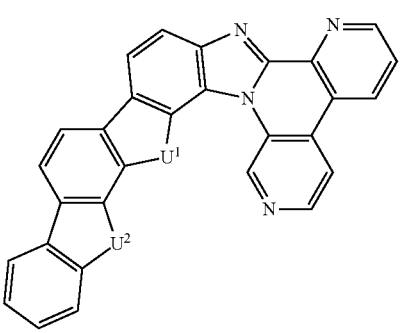
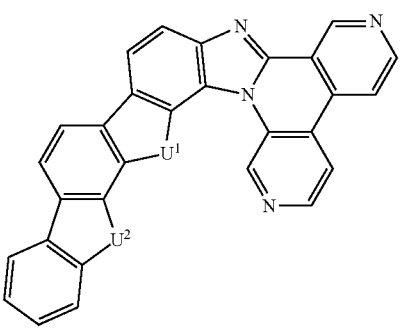

| 531 | 532 |
|---|---|
| -continued | -continued |
| 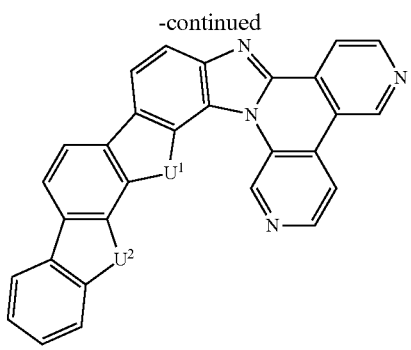 | 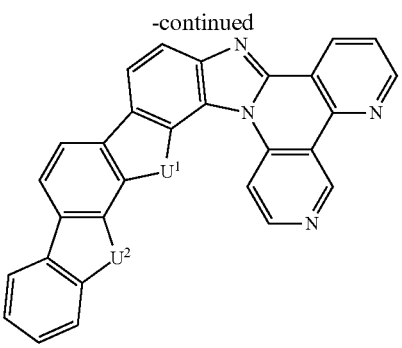 |
| 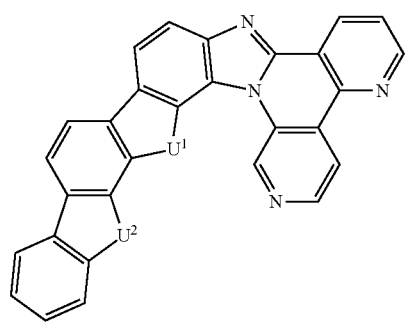 | 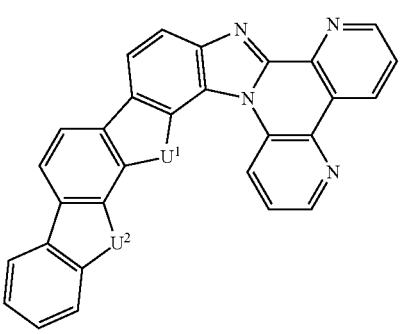 |
| 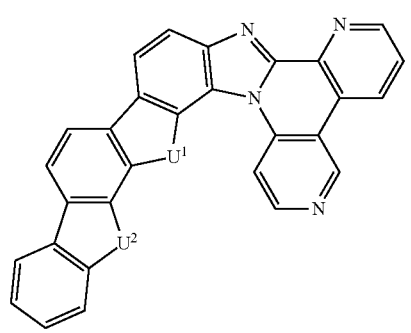 | 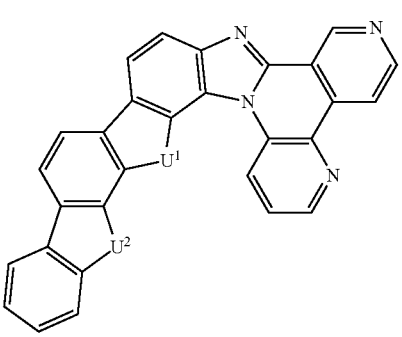 |
| 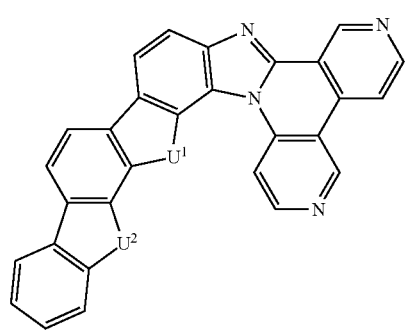 | 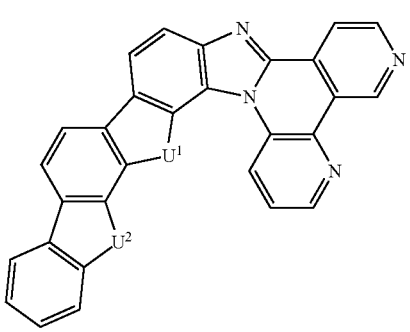 |
| 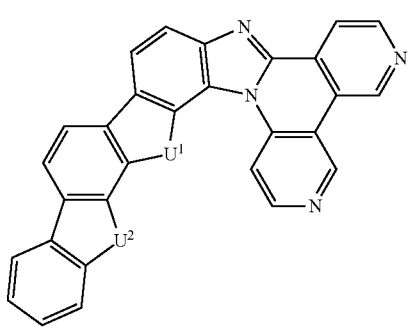 | 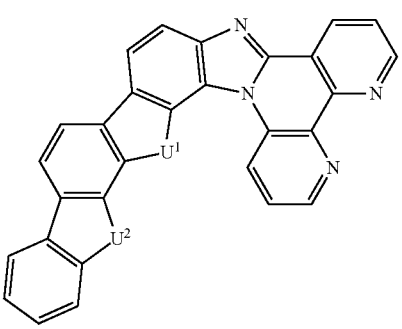 |

533
-continued
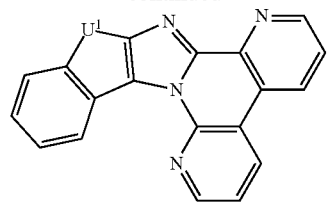
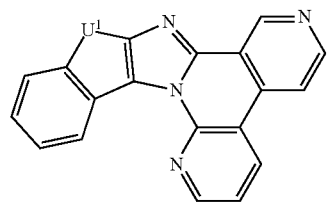
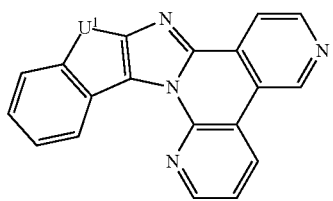
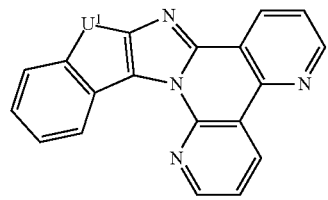
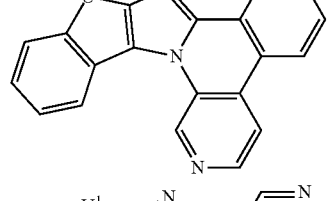
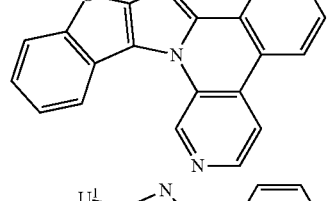
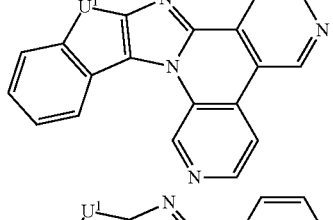
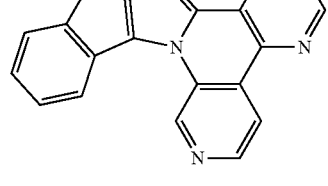
534
-continued
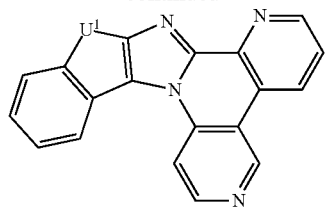
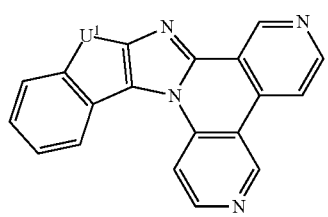
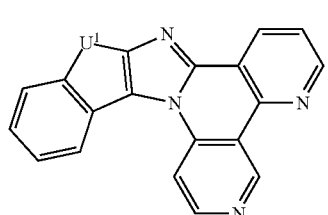
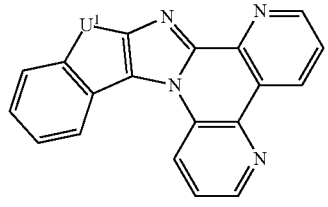
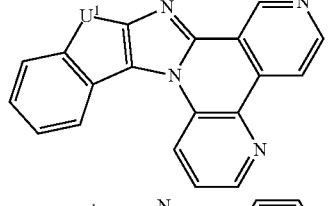
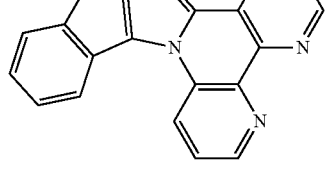

| 535 -continued | 536 -continued |
|---|---|
| 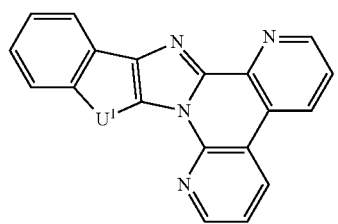 | 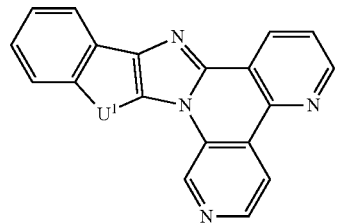 |
| 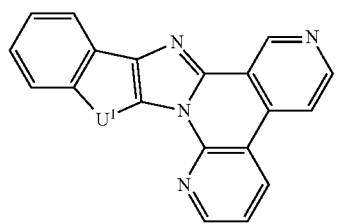 | 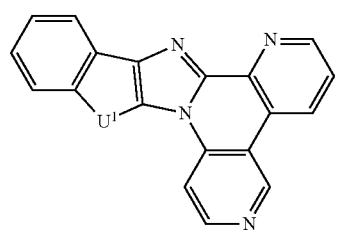 |
| 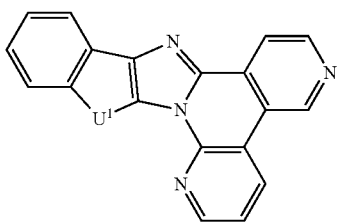 | 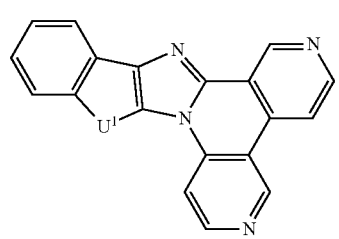 |
| 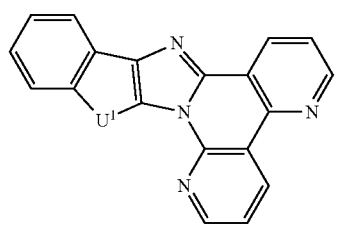 | 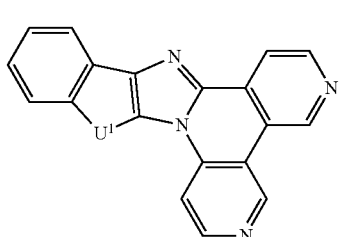 |
| 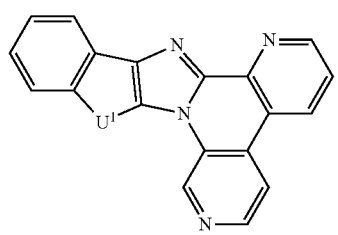 | 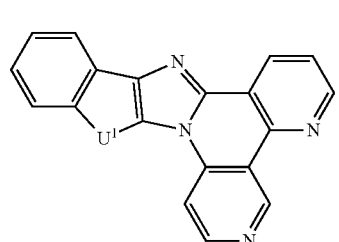 |
| 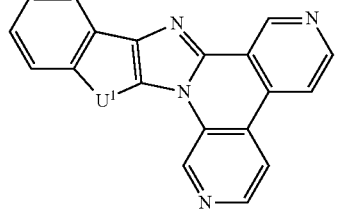 | 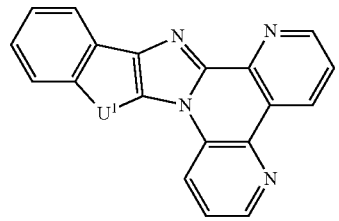 |
| 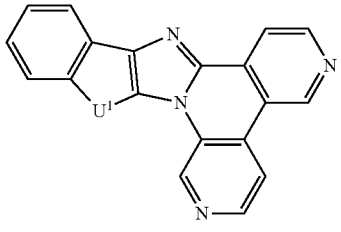 | 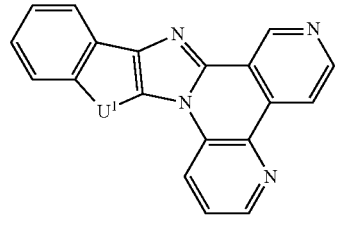 |

537
-continued
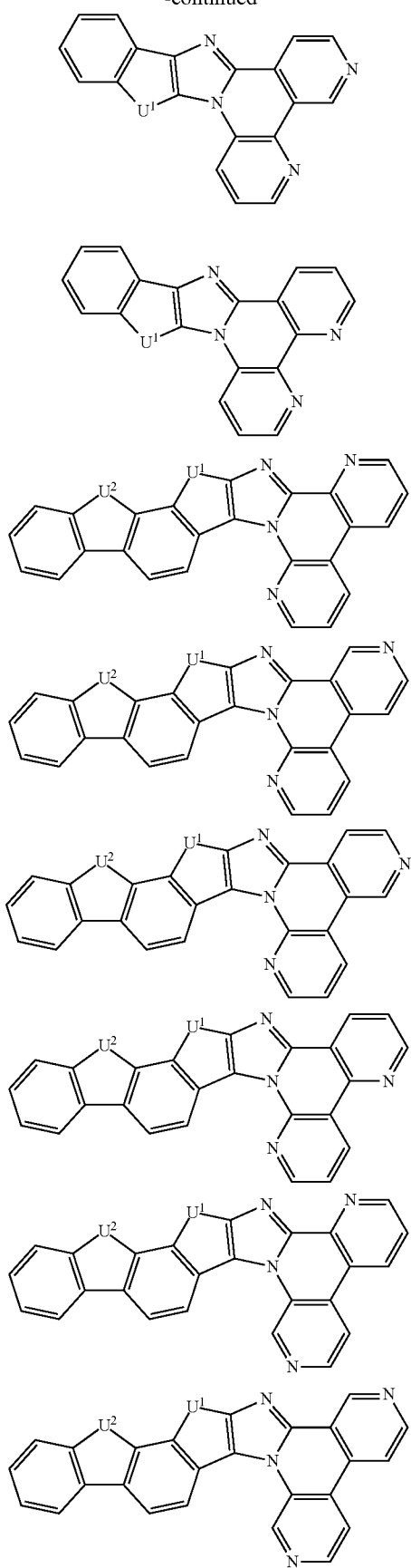
538
-continued
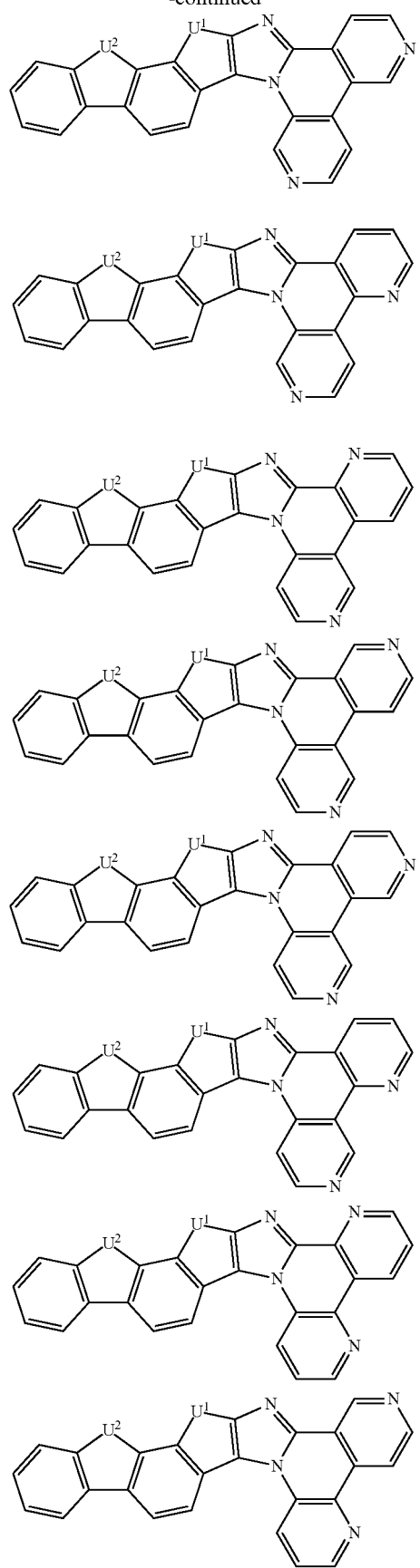

539
-continued
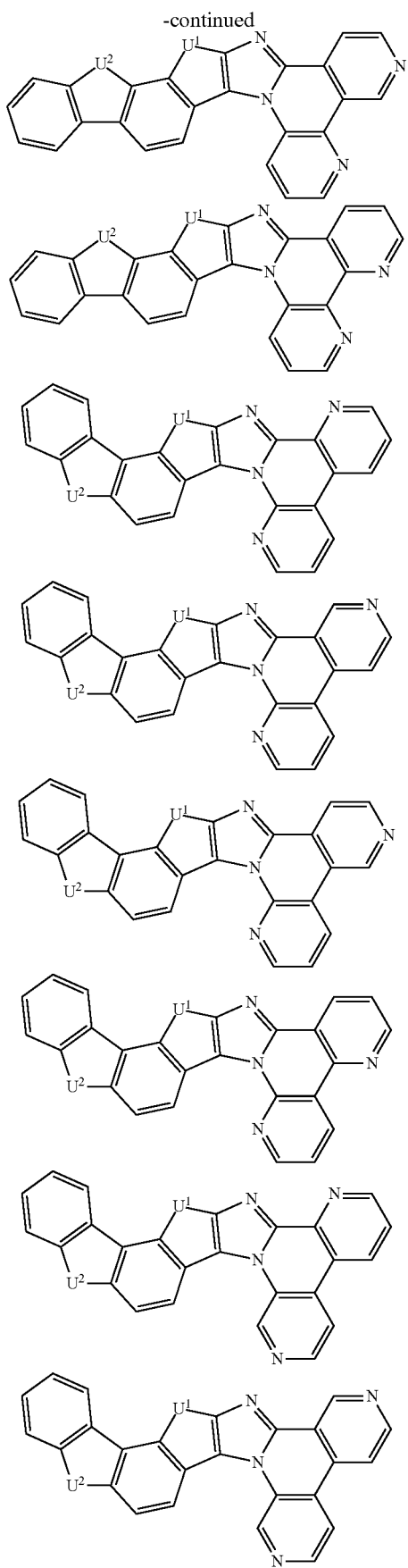
540
-continued
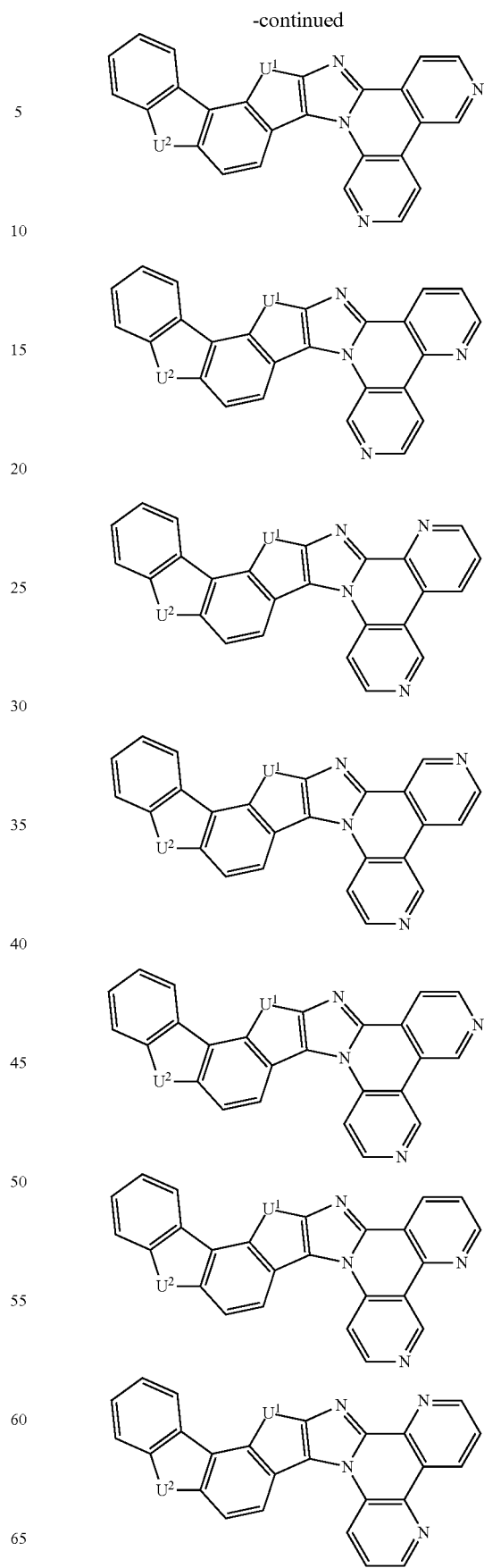

541
-continued
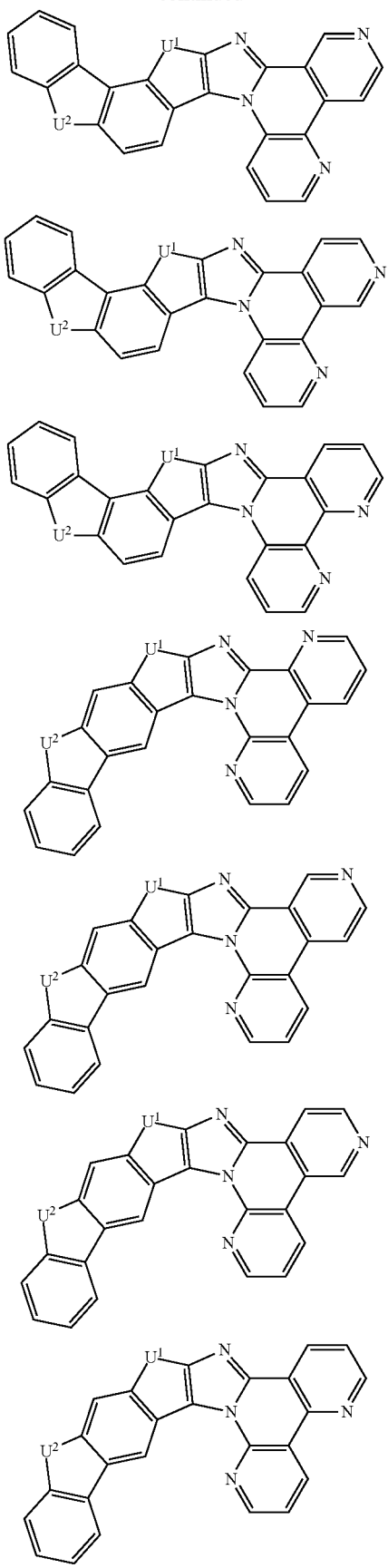
542
-continued
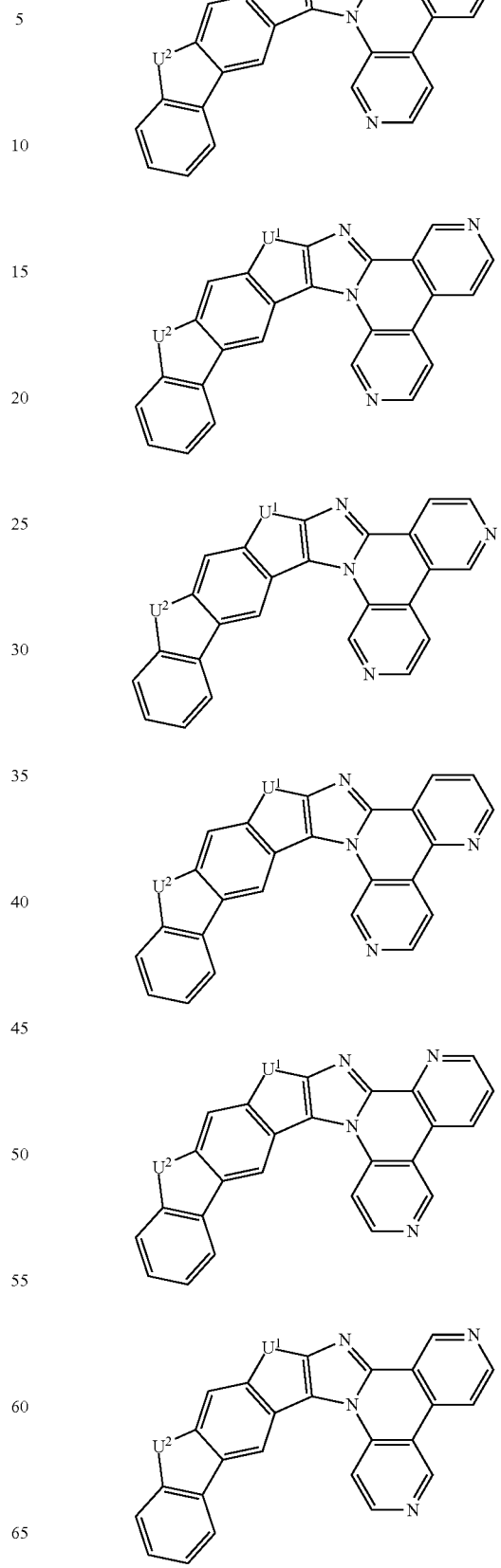

543
-continued
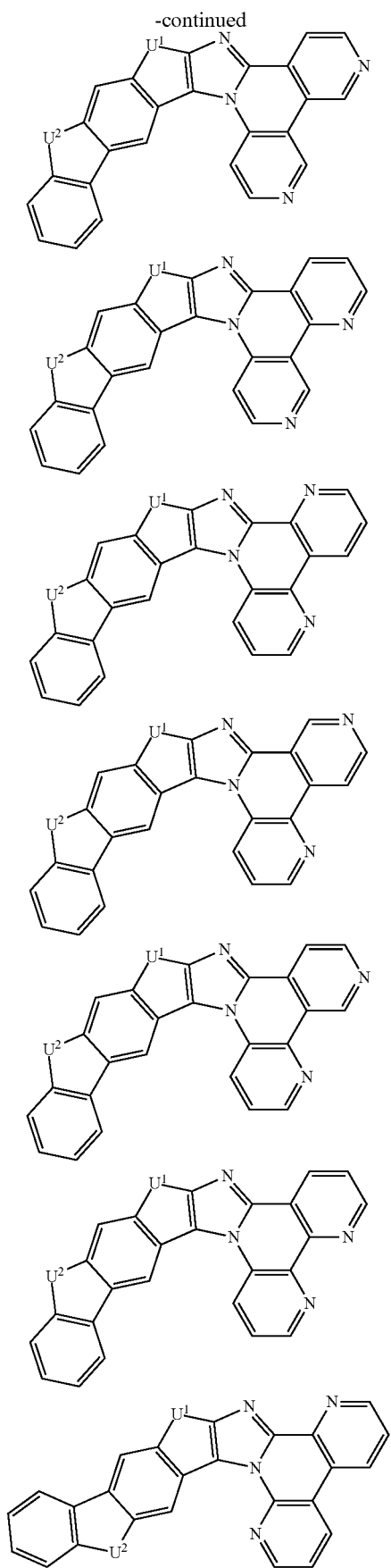
544
-continued
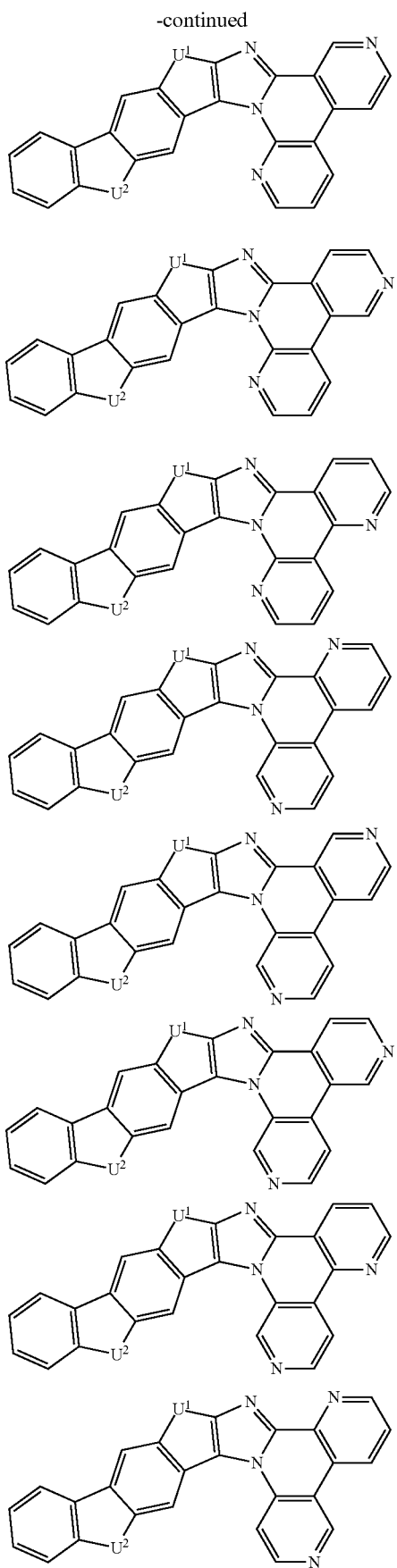

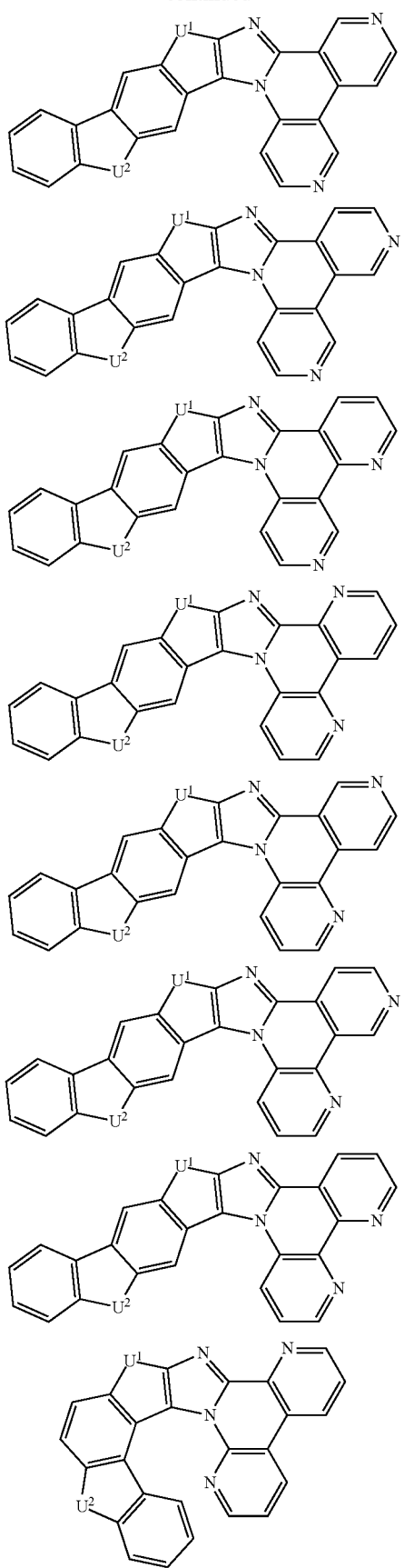
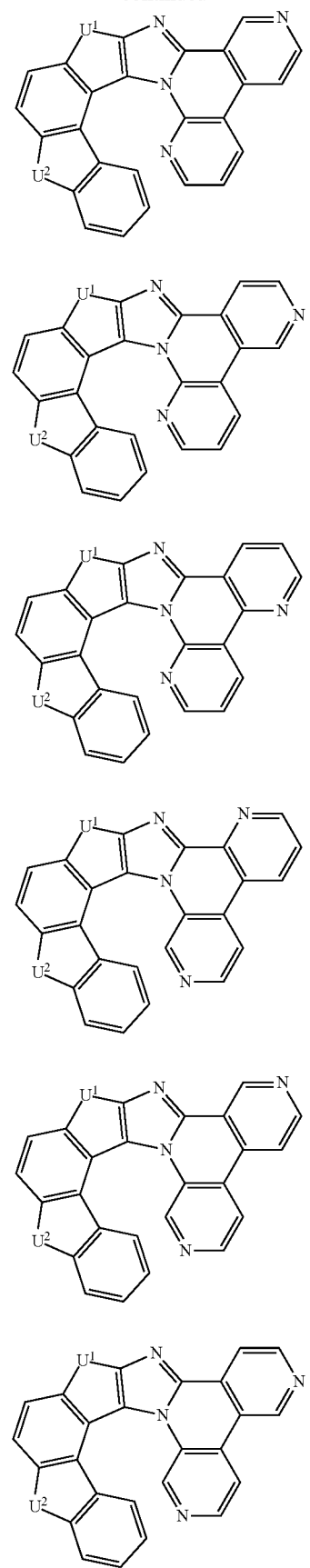

547
-continued
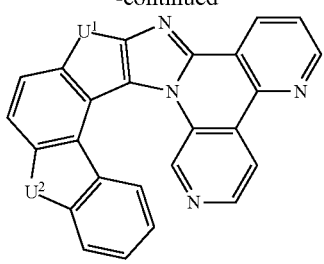
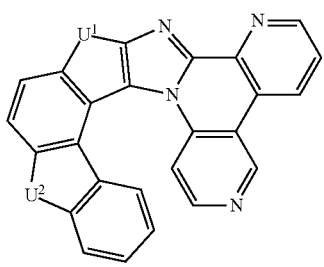
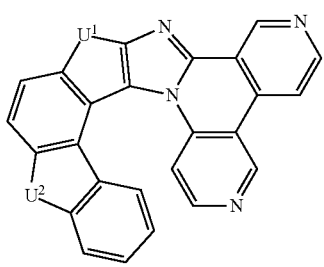
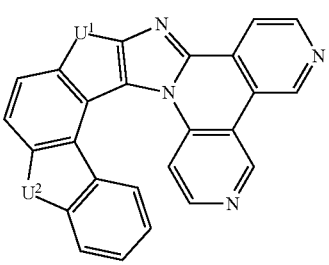
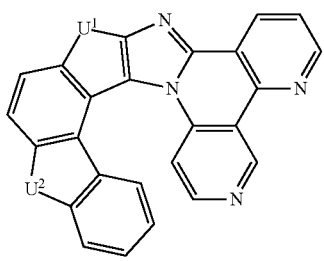
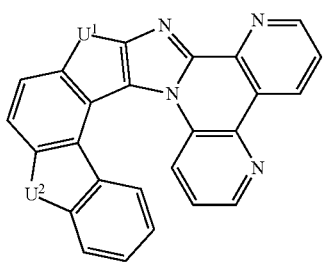
548
-continued
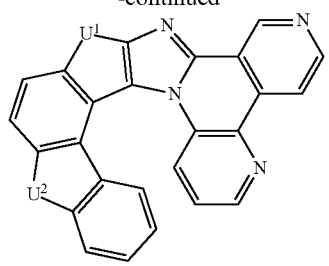
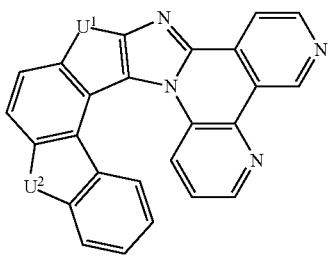
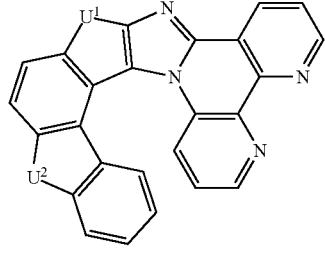
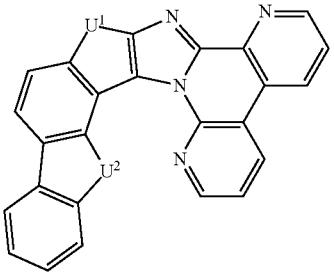
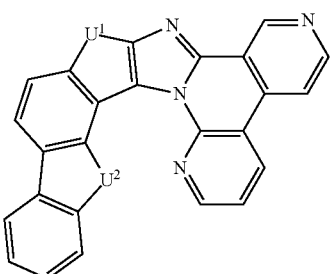
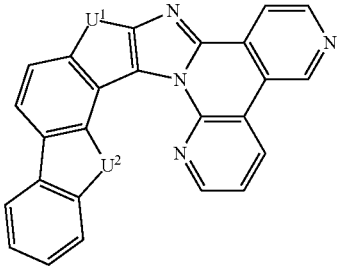

549
-continued
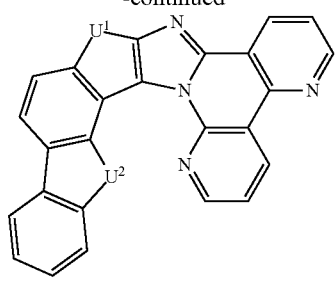
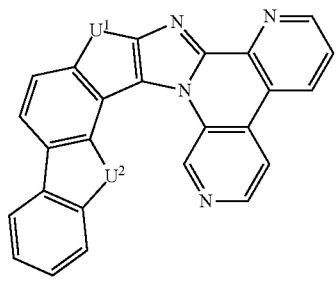
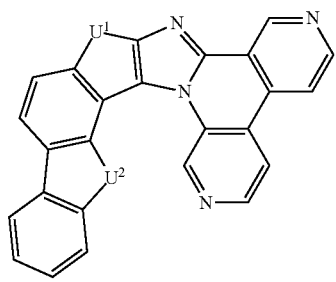
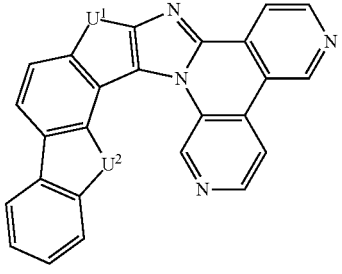
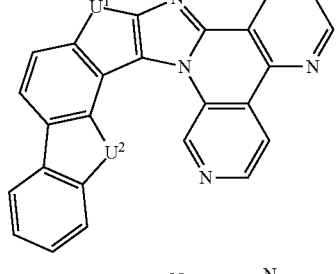
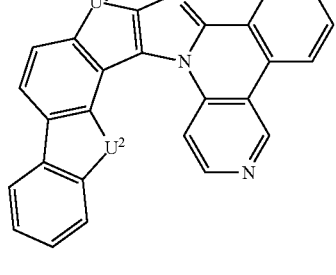
550
-continued
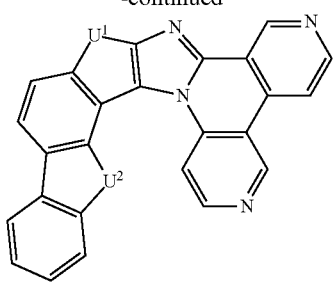
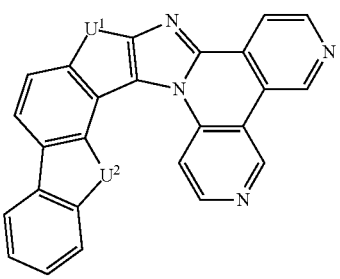
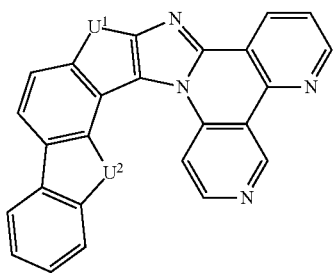
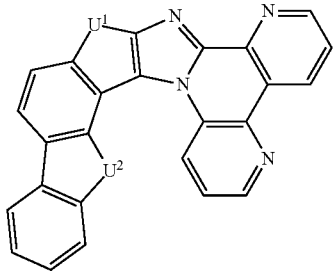
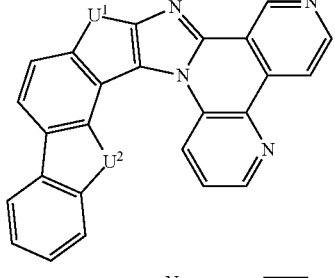
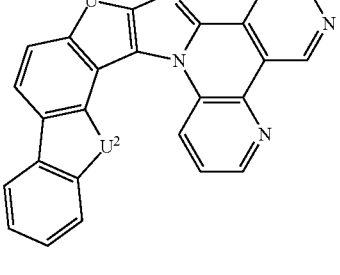

551
-continued
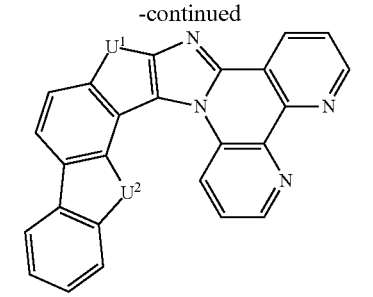
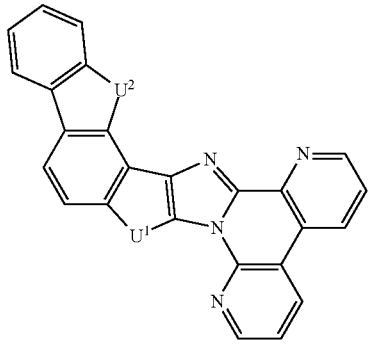
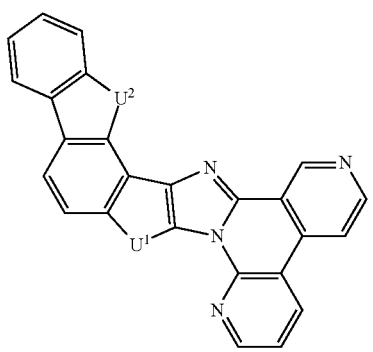
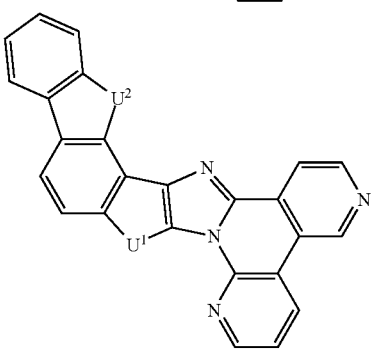
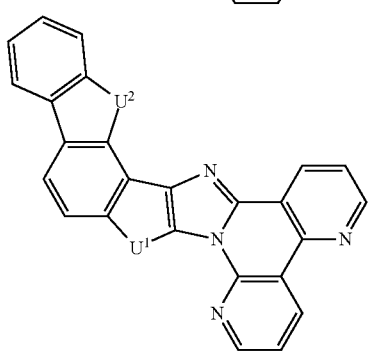
552
-continued
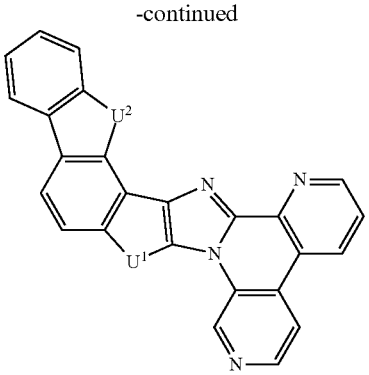
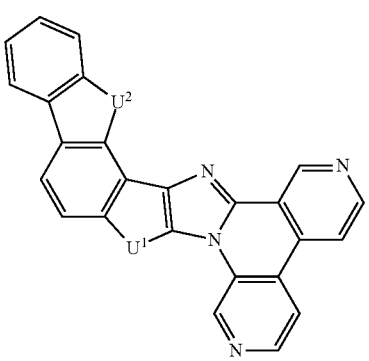
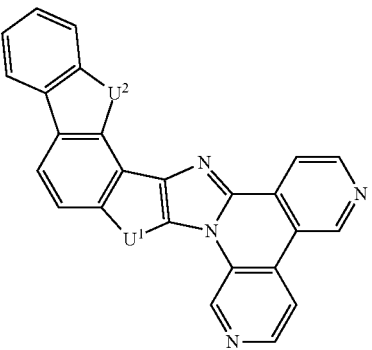
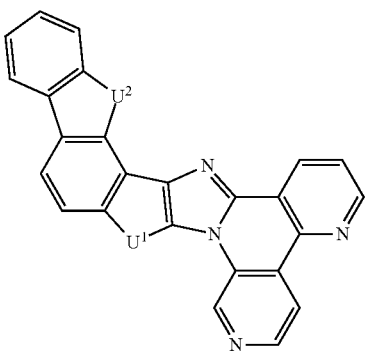

553
-continued
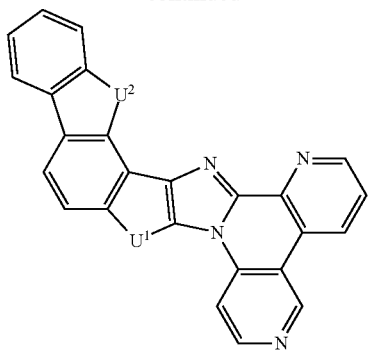
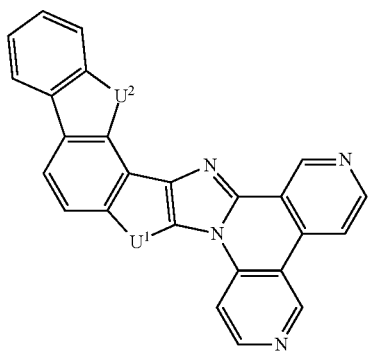
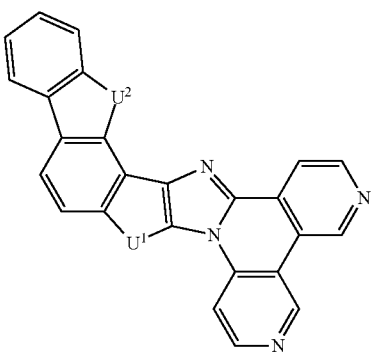
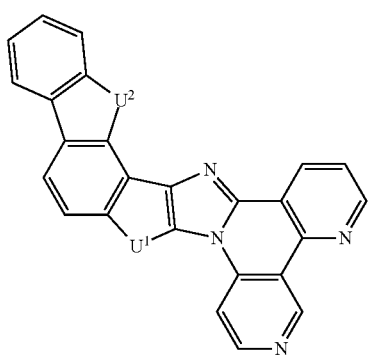
554
-continued
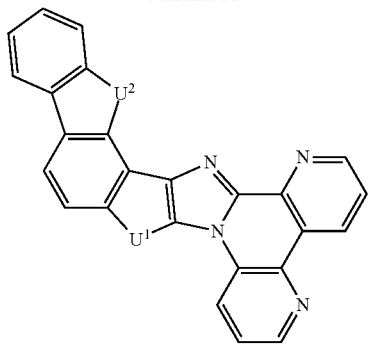
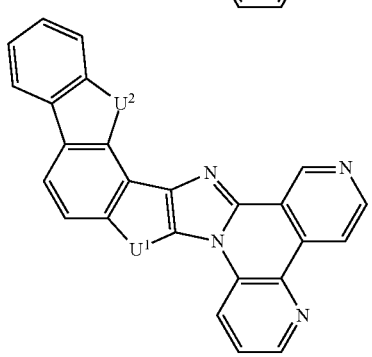
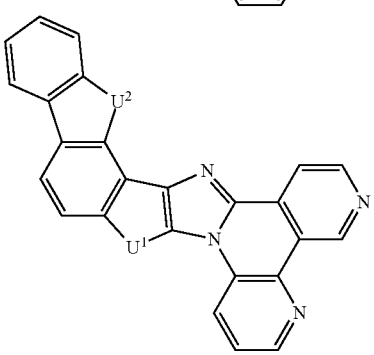
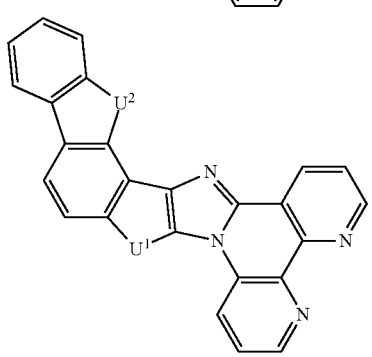
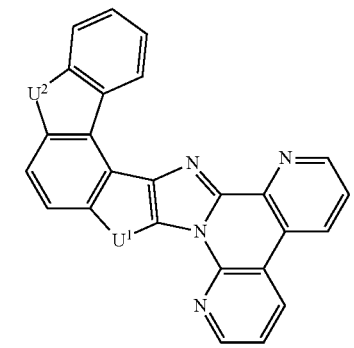

555
-continued
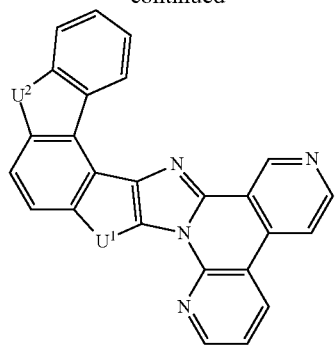
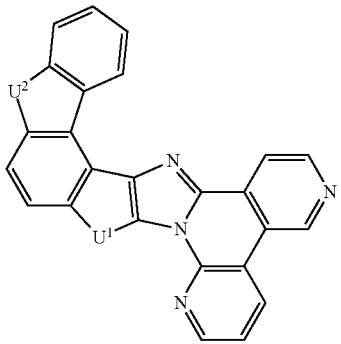
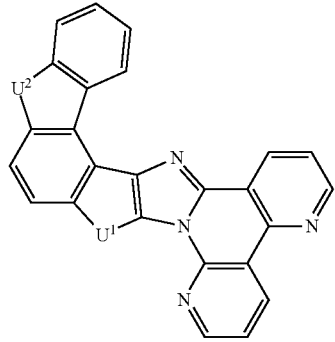
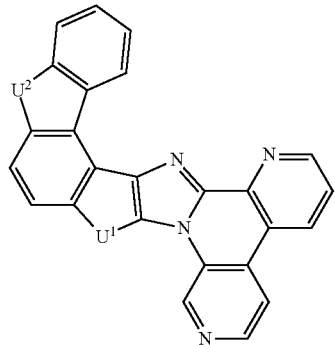
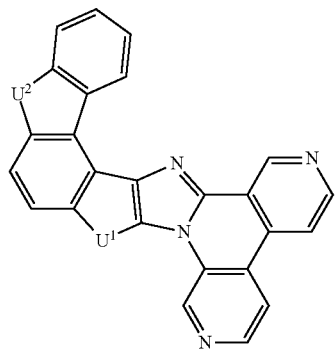
556
-continued
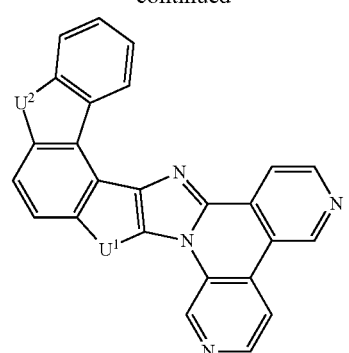
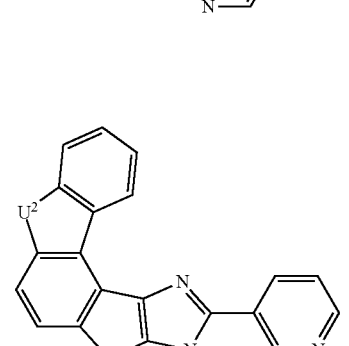
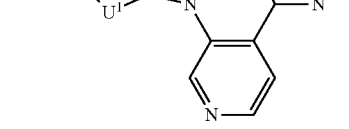
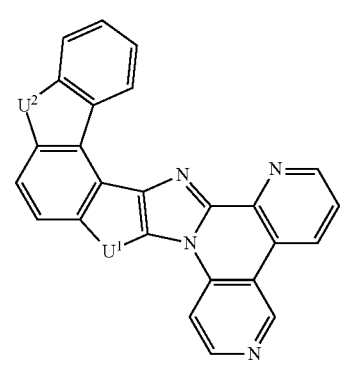
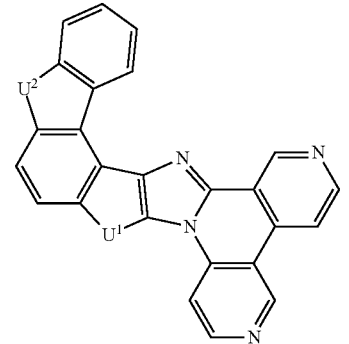

557
-continued
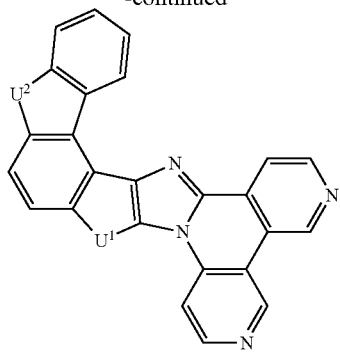
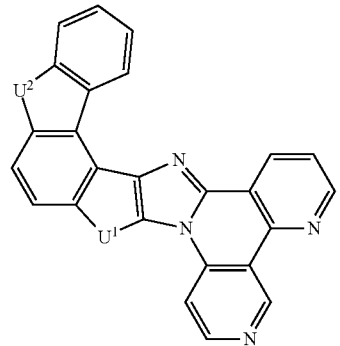
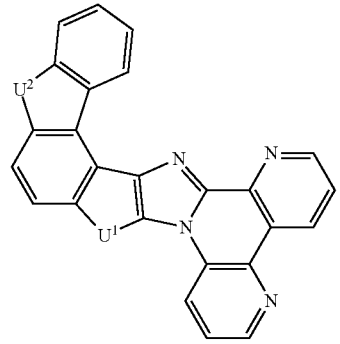
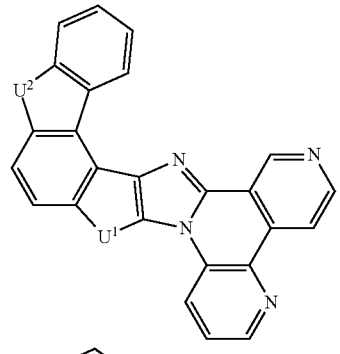
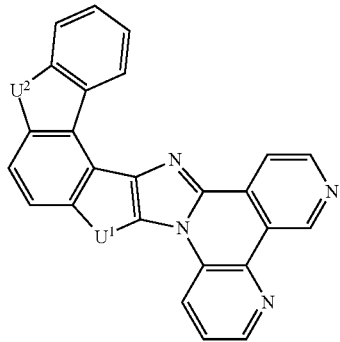
558
-continued
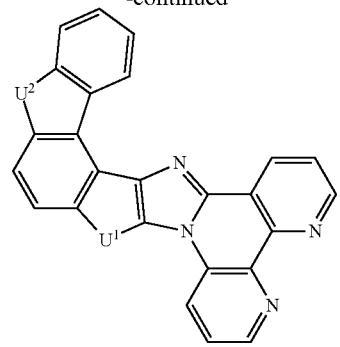
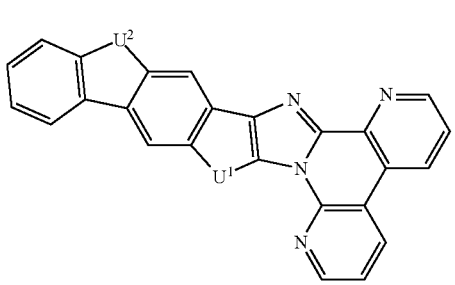
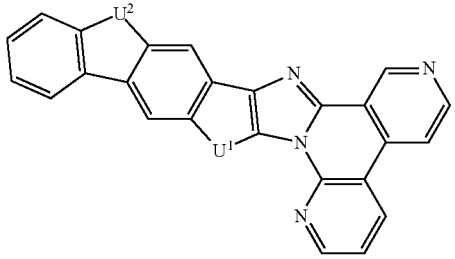
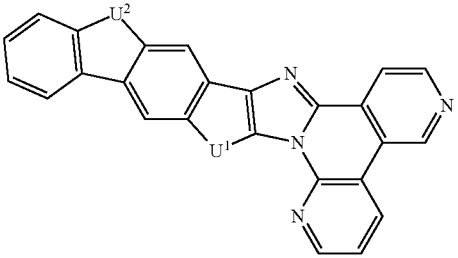
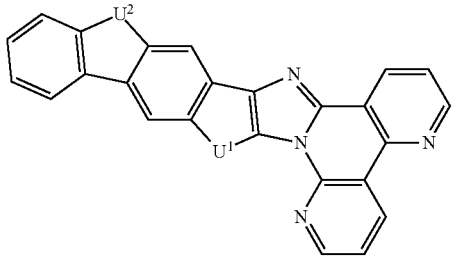
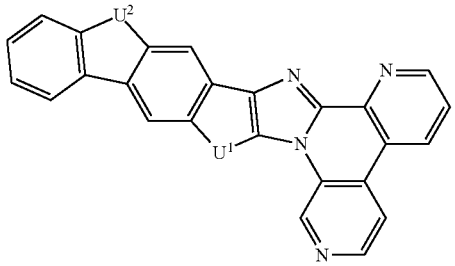

559
-continued
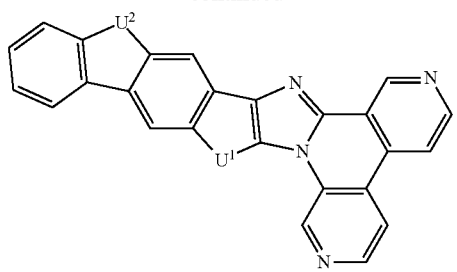
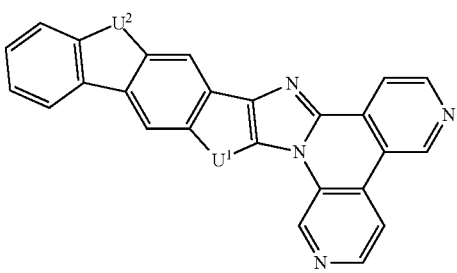
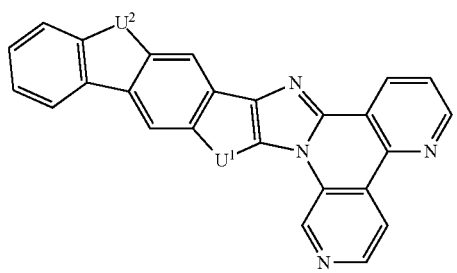
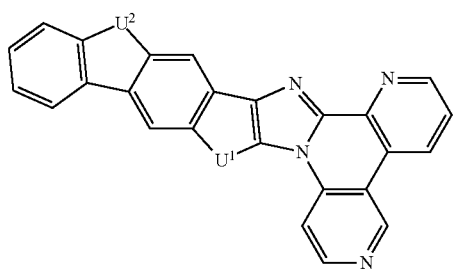
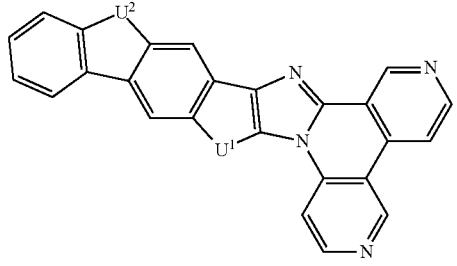
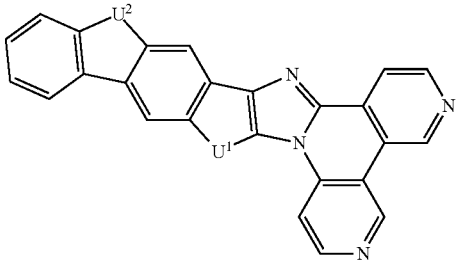
560
-continued
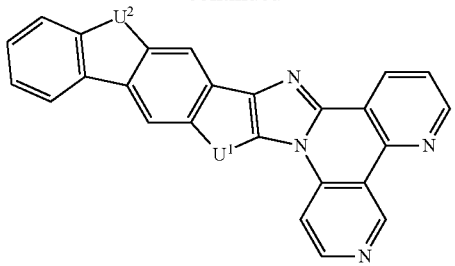
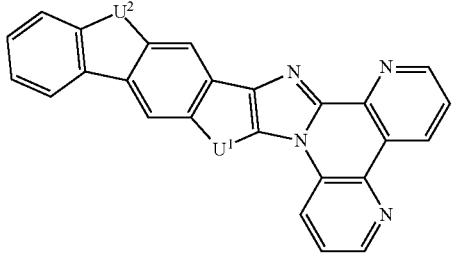
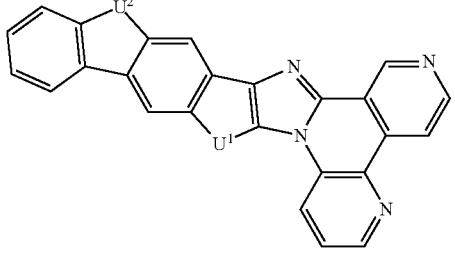
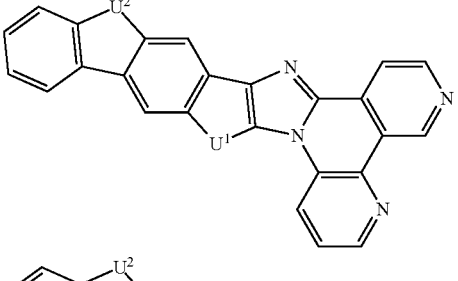
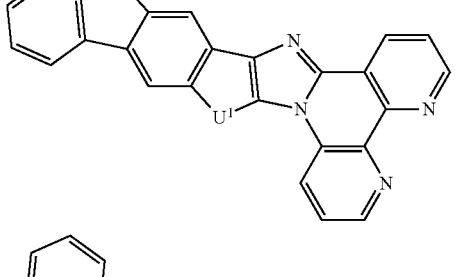
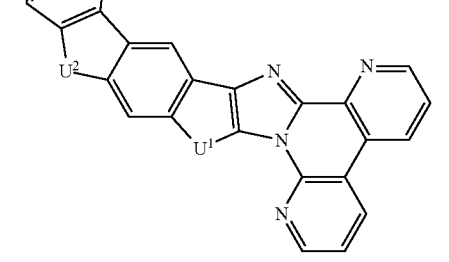

561
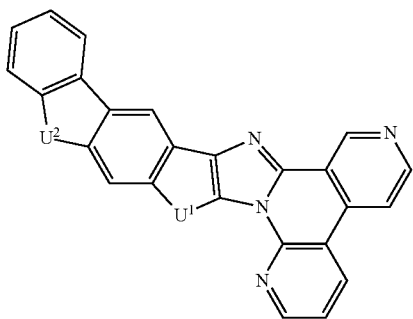
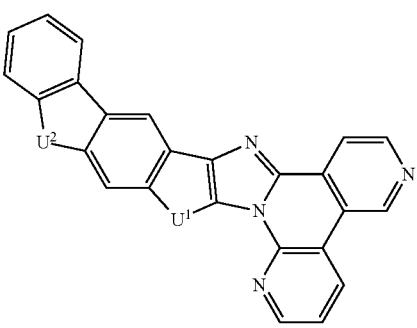
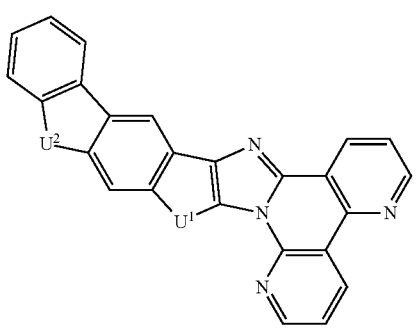
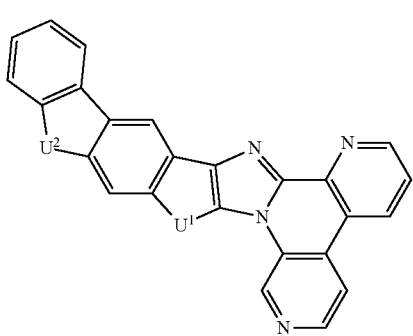
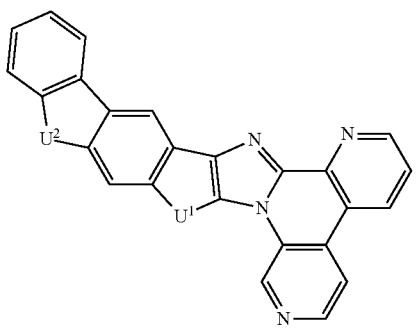
562
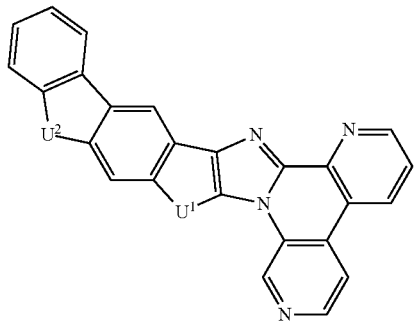
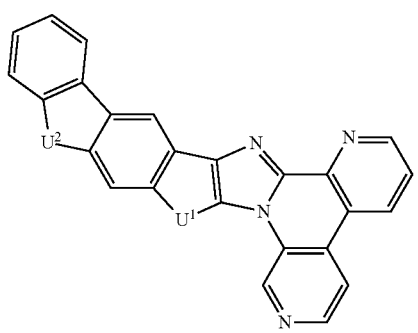
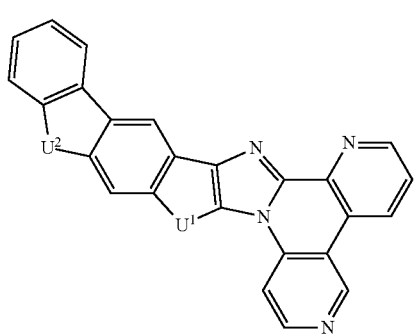
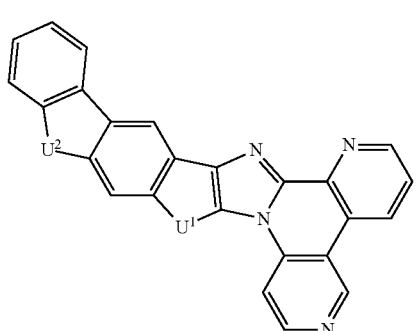
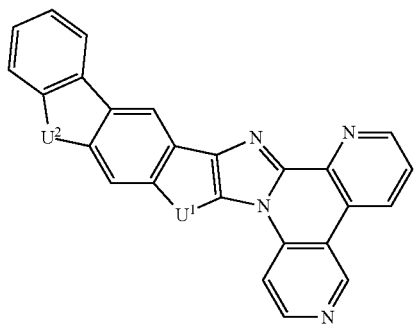

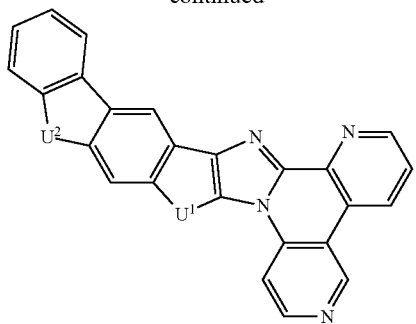
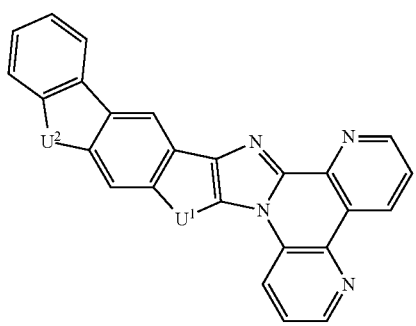
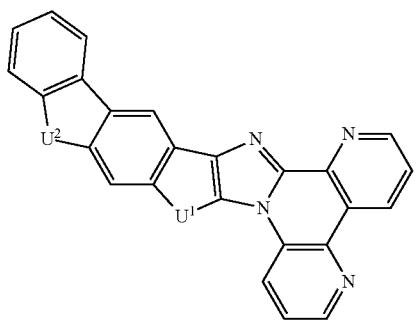
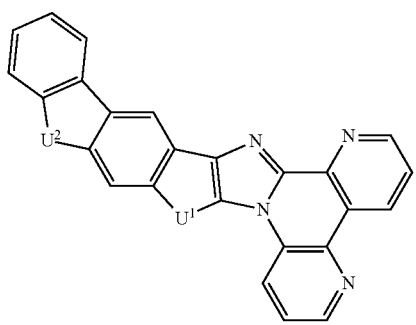
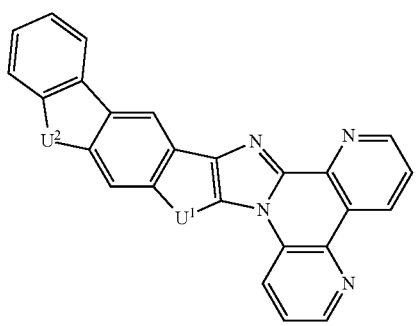
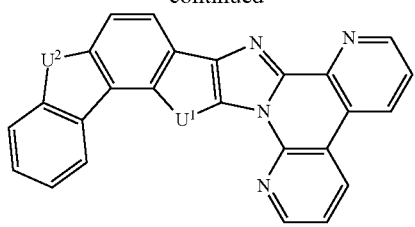
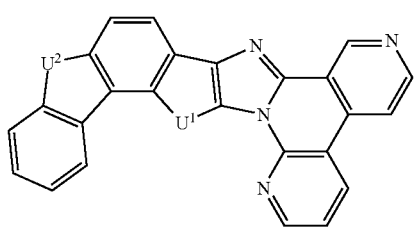
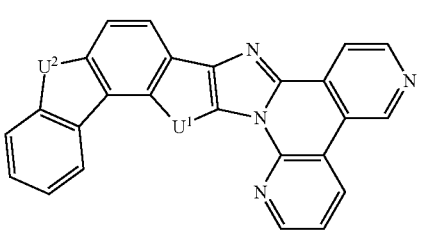
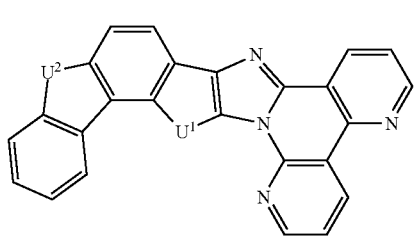
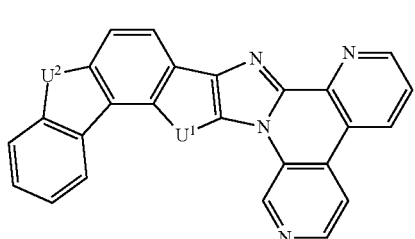
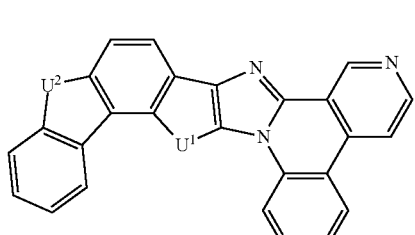
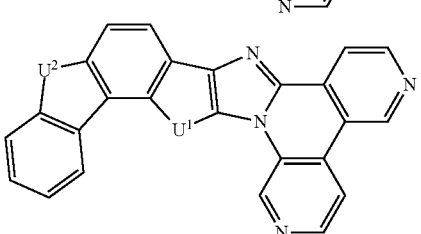

565
-continued
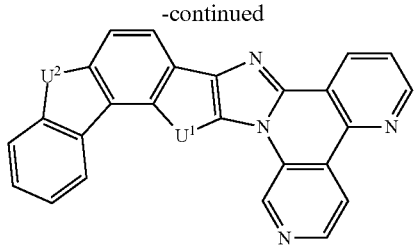
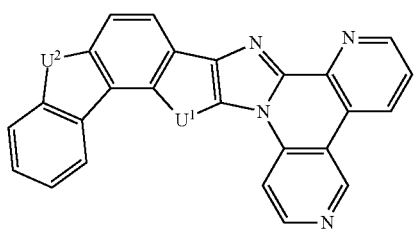
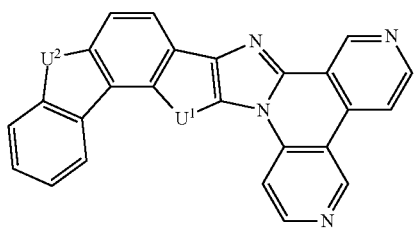
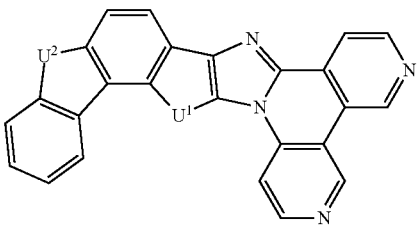
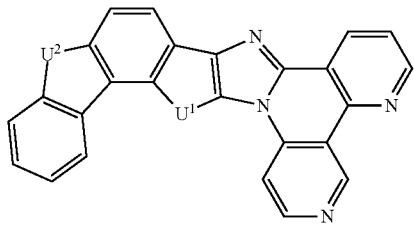
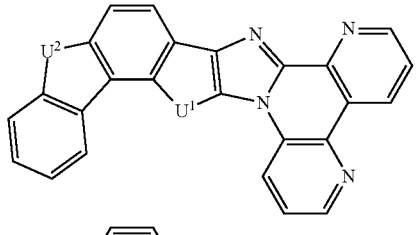
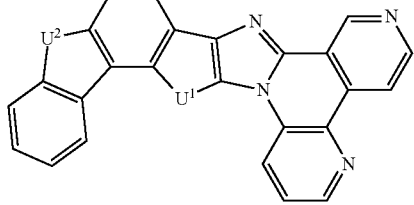
566
-continued
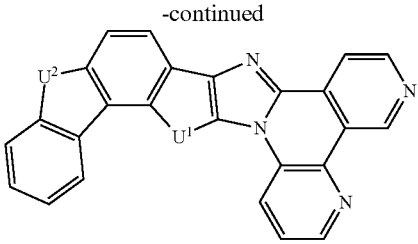
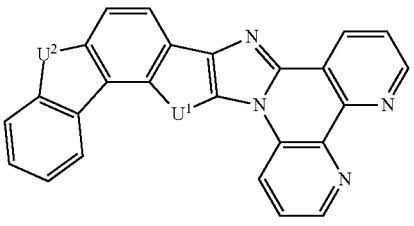
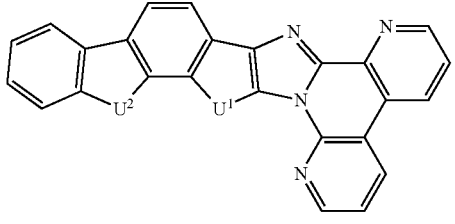
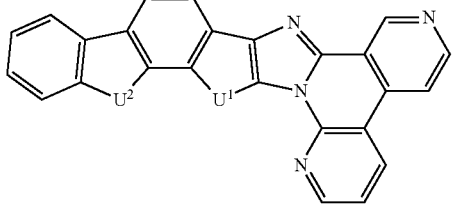
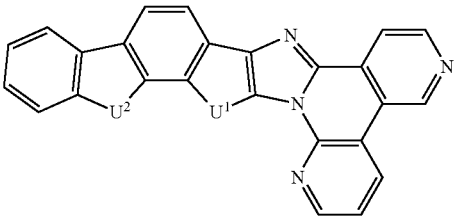
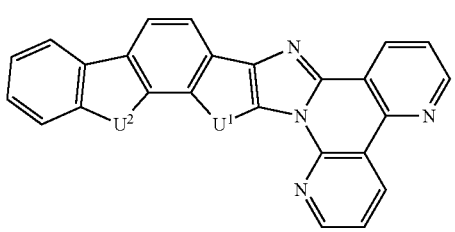
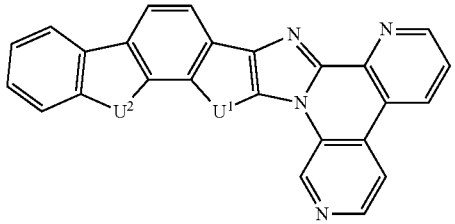

567
-continued
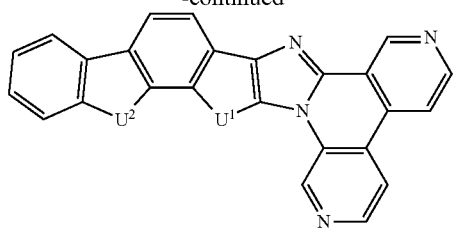
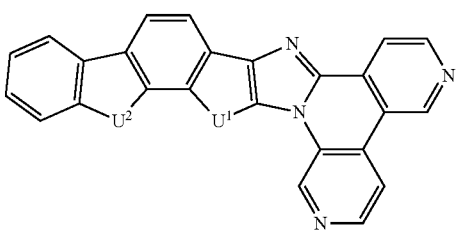
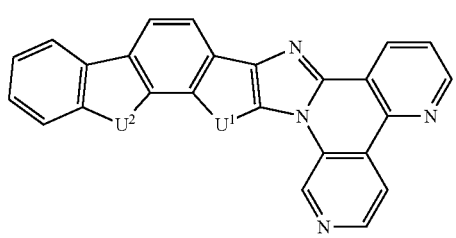
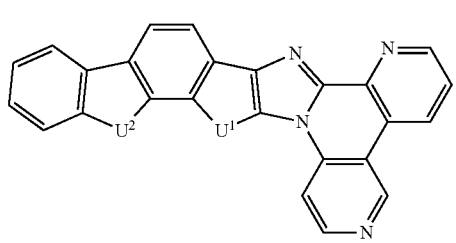
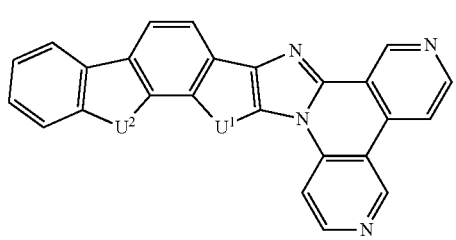
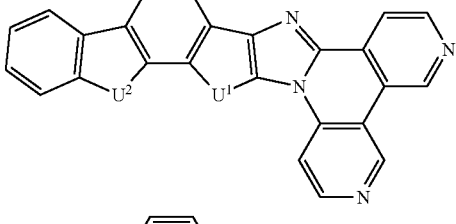
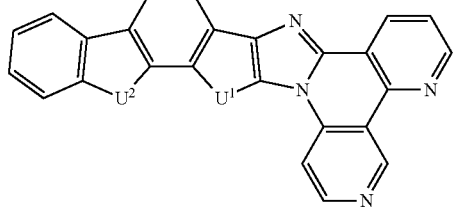
568
-continued
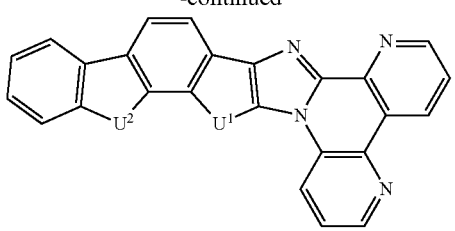
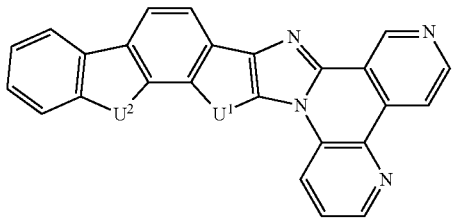
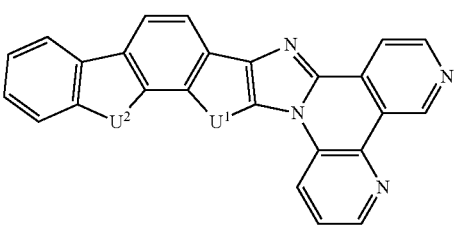
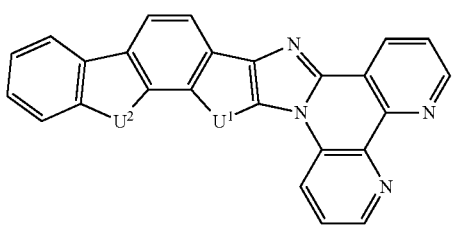
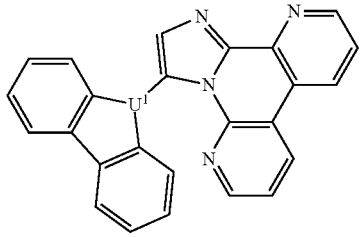
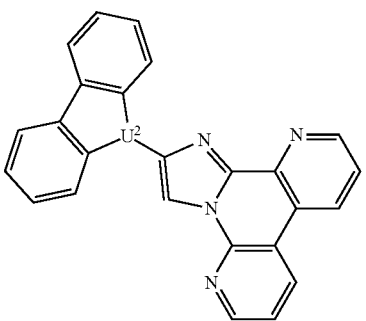

-continued

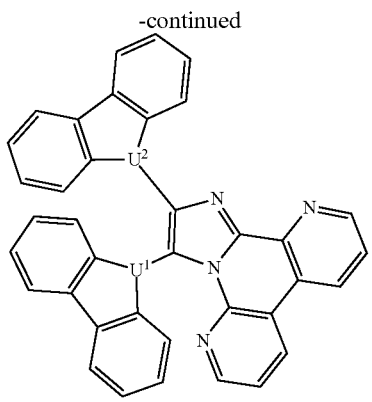

wherein each $U^1$ and $U^2$ independently represents, valency permitting, N, NPh, S, O, S=O, SO$_2$, P=O, Se=O, CPh$_2$, or CMe$_2$, where Me is methyl and Ph is phenyl.

Compositions and Devices of the Invention

Also disclosed herein are organic emitting diodes or light emitting devices comprising one or more compound and/or compositions disclosed herein.

In one aspect, the device is an electro-optical device. Electro-optical devices include, but are not limited to, photo-absorbing devices such as solar- and photo-sensitive devices, organic light emitting devices, photo-emitting devices, or devices capable of both photo-absorption and emission and as markers for bio-applications. For example, the device can be an OLED.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art. Such devices are disclosed herein which comprise one or more of the compounds or compositions disclosed herein.

OLEDs can be produced by methods known to those skilled in the art. In general, the OLED is produced by successive vapor deposition of the individual layers onto a suitable substrate. Suitable substrates include, for example, glass, inorganic materials such as ITO or IZO or polymer films. For the vapor deposition, customary techniques may be used, such as thermal evaporation, chemical vapor deposition (CVD), physical vapor deposition (PVD) and others.

In an alternative process, the organic layers may be coated from solutions or dispersions in suitable solvents, in which case coating techniques known to those skilled in the art are employed. Suitable coating techniques are, for example, spin-coating, the casting method, the Langmuir-Blodgett ("LB") method, the inkjet printing method, dip-coating, letterpress printing, screen printing, doctor blade printing, slit-coating, roller printing, reverse roller printing, offset lithography printing, flexographic printing, web printing, spray coating, coating by a brush or pad printing, and the like. Among the processes mentioned, in addition to the aforementioned vapor deposition, preference is given to spin-coating, the inkjet printing method and the casting method since they are particularly simple and inexpensive to perform. In the case that layers of the OLED are obtained by the spin-coating method, the casting method or the inkjet printing method, the coating can be obtained using a solution prepared by dissolving the composition in a concentration of 0.0001 to 90% by weight in a suitable organic solvent such as benzene, toluene, xylene, tetrahydrofuran, methyltetrahydrofuran, N,N-dimethylformamide, acetone, acetonitrile, anisole, dichloromethane, dimethyl sulfoxide, water and mixtures thereof.

Compounds described herein can be used in a light emitting device such as an OLED. The FIGURE depicts a cross-sectional view of an OLED 100. OLED 100 includes substrate 102, anode 104, hole-transporting material(s) (HTL) 106, light processing material 108, electron-transporting material(s) (ETL) 110, and a metal cathode layer 112. Anode 104 is typically a transparent material, such as indium tin oxide. Light processing material 108 may be an emissive material (EML) including an emitter and a host.

In various aspects, any of the one or more layers depicted in the FIGURE may include indium tin oxide (ITO), poly (3,4-ethylenedioxythiophene) (PEDOT), polystyrene sulfonate (PSS), N,N'-di-1-naphthyl-N,N-diphenyl-1,1'-biphenyl-4,4' diamine (NPD), 1,1-bis((di-4-tolylamino)phenyl)cyclohexane (TAPC), 2,6-Bis(N-carbazolyl)pyridine (mCpy), 2,8-bis(diphenylphosphoryl)dibenzothiophene (PO15), LiF, Al, or a combination thereof.

Light processing material 108 may include one or more compounds of the present disclosure optionally together with a host material. The host material can be any suitable host material known in the art. The emission color of an OLED is determined by the emission energy (optical energy gap) of the light processing material 108, which can be tuned by tuning the electronic structure of the emitting compounds, the host material, or both. Both the hole-transporting material in the HTL layer 106 and the electron-transporting material(s) in the ETL layer 110 may include any suitable hole-transporter known in the art.

Compounds described herein may exhibit phosphorescence. Phosphorescent OLEDs (i.e., OLEDs with phosphorescent emitters) typically have higher device efficiencies than other OLEDs, such as fluorescent OLEDs. Light emitting devices based on electrophosphorescent emitters are described in more detail in WO2000/070655 to Baldo et al., which is incorporated herein by this reference for its teaching of OLEDs, and in particular phosphorescent OLEDs.

As contemplated herein, an OLED of the present invention may include an anode, a cathode, and an organic layer disposed between the anode and the cathode. The organic layer may include a host and a phosphorescent dopant. The organic layer can include a compound of the invention and its variations as described herein.

In some embodiments, the OLED has one or more characteristics selected from the group consisting of being flexible, being rollable, being foldable, being stretchable, and being curved. In some embodiments, the OLED is transparent or semi-transparent. In some embodiments, the OLED further comprises a layer comprising carbon nanotubes.

In some embodiments, the OLED further comprises a layer comprising a delayed fluorescent emitter. In some embodiments, the OLED comprises a RGB pixel arrangement or white plus color filter pixel arrangement. In some embodiments, the OLED is a mobile device, a hand held device, or a wearable device. In some embodiments, the OLED is a display panel having less than 10 inch diagonal or 50 square inch area. In some embodiments, the OLED is a display panel having at least 10 inch diagonal or 50 square inch area. In some embodiments, the OLED is a lighting panel.

In one embodiment, the consumer product is selected from the group consisting of a flat panel display, a computer monitor, a medical monitor, a television, a billboard, a light for interior or exterior illumination and/or signaling, a heads-up display, a fully or partially transparent display, a flexible display, a laser printer, a telephone, a cell phone, tablet, a phablet, a personal digital assistant (PDA), a wearable device, a laptop computer, a digital camera, a camcorder, a viewfinder, a micro-display that is less than 2 inches diagonal, a 3-D display, a virtual reality or augmented reality display, a vehicle, a video wall comprising multiple displays tiled together, a theater or stadium screen, and a sign.

In some embodiments of the emissive region, the emissive region further comprises a host, wherein the host comprises at least one selected from the group consisting of metal complex, triphenylene, carbazole, dibenzothiophene, dibenzofuran, dibenzoselenophene, aza-triphenylene, aza-carbazole, aza-dibenzothiophene, aza-dibenzofuran, and aza-dibenzoselenophene.

The organic layer can also include a host. In some embodiments, two or more hosts are preferred. In some embodiments, the hosts used maybe a) bipolar, b) electron transporting, c) hole transporting or d) wide band gap materials that play little role in charge transport. In some embodiments, the host can include a metal complex. The host can be a triphenylene containing benzo-fused thiophene or benzo-fused furan. Any substituent in the host can be an unfused substituent independently selected from the group consisting of $CnH2n+1$, $OCnH2n+1$, $OAr1$, $N(CnH2n+1)2$, $N(Ar1)(Ar2)$, $CH=CH-CnH2n+1$, $C\equiv C-CnH2n+1$, $Ar1$, $Ar1-Ar2$, and $CnH2n-Ar1$, or the host has no substitutions.

In the preceding substituents n can range from 1 to 10; and Ar1 and Ar2 can be independently selected from the group consisting of benzene, biphenyl, naphthalene, triphenylene, carbazole, and heteroaromatic analogs thereof. The host can be an inorganic compound. For example, a Zn containing inorganic material e.g. ZnS.

Suitable hosts may include, but are not limited to, mCP (1,3-bis(carbazol-9-yl)benzene), mCPy (2,6-bis(N-carbazolyl)pyridine), TCP (1,3,5-tris(carbazol-9-yl)benzene), TCTA (4,4',4"-tris(carbazol-9-yl)triphenylamine), TPBi (1,3,5-tris(1-phenyl-1-H-benzimidazol-2-yl)benzene), mCBP (3,3-di(9H-carbazol-9-yl)biphenyl), pCBP (4,4'-bis(carbazol-9-yl)biphenyl), CDBP (4,4'-bis(9-carbazolyl)-2,2'-dimethylbiphenyl), DMFL-CBP (4,4'-bis(carbazol-9-yl)-9,9-dimethylfluorene), FL-4CBP (4,4'-bis(carbazol-9-yl)-9,9-bis(9-phenyl-9H-carbazole)fluorene), FL-2CBP (9,9-bis(4-carbazol-9-yl)phenyl)fluorene, also abbreviated as CPF), DPFL-CBP (4,4'-bis(carbazol-9-yl)-9,9-ditolylfluorene), FL-2CBP (9,9-bis(9-phenyl-9H-carbazole)fluorene), Spiro-CBP (2,2',7,7'-tetrakis(carbazol-9-yl)-9,9'-spirobifluorene), ADN (9,10-di(naphth-2-yl)anthracene), TBADN (3-tert-butyl-9,10-di(naphth-2-yl)anthracene), DPVBi (4,4'-bis(2,2-diphenylethen-1-yl)-4,4'-dimethylphenyl), p-DMDPVBi (4,4'-bis(2,2-diphenylethen-1-yl)-4,4'-dimethylphenyl), TDAF (tert(9,9-diarylfluorene)), BSBF (2-(9,9'-spirobifluoren-2-yl)-9,9'-spirobifluorene), TSBF (2,7-bis(9,9'-spirobifluoren-2-yl)-9,9'-spirobifluorene), BDAF (bis(9,9-diarylfluorene)), p-TDPVBi (4,4'-bis(2,2-diphenylethen-1-yl)-4,4'-di-(tert-butyl)phenyl), TPB3 (1,3,5-tri(pyren-1-yl)benzene, PBD (2-(4-biphenylyl)-5-(4-tert-butylphenyl)-1,3,4-oxadiazole), BCP (2,9-dimethyl-4,7-diphenyl-1,10-phenanthroline), BP-OXD-Bpy (6,6'-bis[5-(biphenyl-4-yl)-1,3,4-oxadiazo-2-yl]-2,2'-bipyridyl), NTAZ (4-(naphth-1-yl)-3,5-diphenyl-4H-1,2,4-triazole), Bpy-OXD (1,3-bis[2-(2,2'-bipyrid-6-yl)-1,3,4oxadiazo-5-yl]benzene), BPhen (4,7-diphenyl-1,10-phenanthroline), TAZ (3-(4-biphenylyl)-4-phenyl-5-tert-butylphenyl-1,2,4-triazole), PADN (2-phenyl-9,10-di(naphth-2-yl)anthracene), Bpy-FOXD (2,7-bis [2-(2,2'-bipyrid-6-yl)-1,3,4-oxadiazol-5-yl]-9,9-dimethylfluorene), OXD-7 (1,3-bis[2-(4-tert-butylphenyl)-1,3,4-oxadiazol-5-yl]benzene), HNBphen (2-(naphth-2-yl)-4,7-diphenyl-1,10-phenanthroline), NBphen (2,9-bis(naphth-2-yl)-4,7-diphenyl-1,10-phenanthroline), 3TPYMB (tris(2,4,6-trimethyl-3-(pyrid-3-yl)phenyl)borane), 2-NPIP (1-methyl-2-(4-(naphth-2-yl)phenyl)-1H-imidazo[4,5-f]-[1,10] phenanthroline), Liq (8-hydroxyquinolinolatolithium), and Alq (bis(2-methyl-8-quinolinolate)-4-(phenylphenolato)aluminum), and also of mixtures of the aforesaid substances.

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved.

Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804, US20150123047, and US2012146012.

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as MoOx; a p-type semiconducting organic compound, such as 1,4,5, 8,9,12-Hexaazatriphenylenehexacarbonitrile; a metal complex, and a cross-linkable compounds.

An electron blocking layer (EBL) may be used to reduce the number of electrons and/or excitons that leave the emissive layer. The presence of such a blocking layer in a device may result in substantially higher efficiencies, and/or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and/or higher triplet energy than one or more of the hosts closest to the EBL interface. In one aspect, the compound used in EBL contains the same molecule or the same functional groups used as one of the hosts described below.

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

One or more additional emitter dopants may be used in conjunction with the compound of the present disclosure. Examples of the additional emitter dopants are not particularly limited, and any compounds may be used as long as the compounds are typically used as emitter materials. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and/or higher triplet energy than the emitter closest to the HBL interface. In some embodiments, the HBL material has a lower HOMO (further from the vacuum level) and/or higher triplet energy than one or more of the hosts closest to the HBL interface.

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. may be undeuterated, partially deuterated, and fully deuterated versions thereof. Similarly, classes of substituents such as, without limitation, alkyl, aryl, cycloalkyl, heteroaryl, etc. also may be undeuterated, partially deuterated, and fully deuterated versions thereof.

In yet another aspect of the present disclosure, a formulation that comprises the novel compound disclosed herein is described. The formulation can include one or more components selected from the group consisting of a solvent, a host, a hole injection material, hole transport material, and an electron transport layer material, disclosed herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the composite materials of the present invention and practice the claimed methods. The following working examples therefore, specifically point out the preferred embodiments of the present invention, and are not to be construed as limiting in any way the remainder of the disclosure.

Example 1: Metal Assisted Delayed Fluorescence

In this invention, a series of novel donor-acceptor type potential functional materials is designed based on stable chemical structures. The materials can be used as TADF materials and can be used as hole and electron/hole blocking materials, etc. These materials could have good operational stability.

In one embodiment, exemplary compounds may be prepared according to the following scheme:
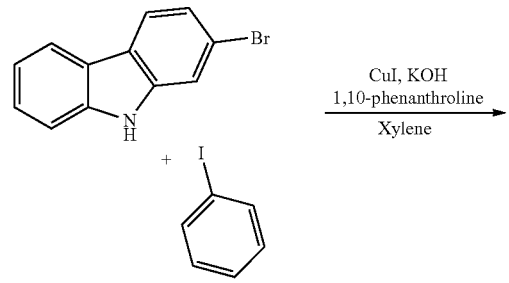 CuI, KOH
1,10-phenanthroline
———————————→
Xylene
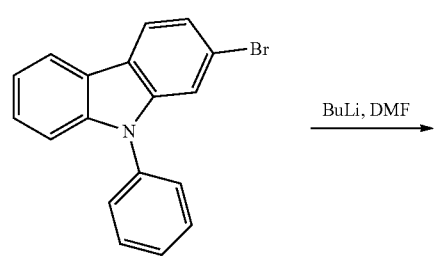 BuLi, DMF
———————→
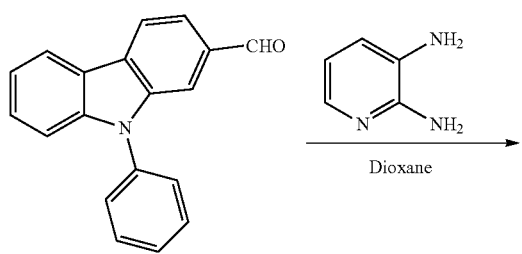 Dioxane
————→
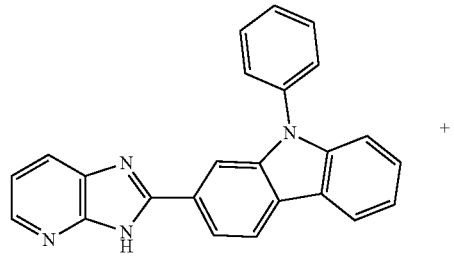
A
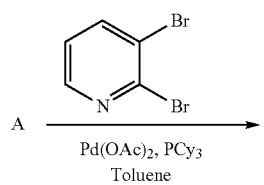 Pd(OAc)$_2$, PCy$_3$
————————→
Toluene
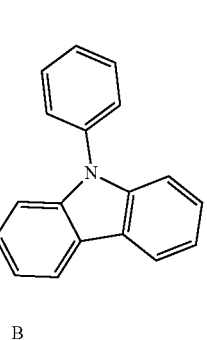
B
 Pd(OAc)$_2$, PCy$_3$
————————→
Toluene
-continued
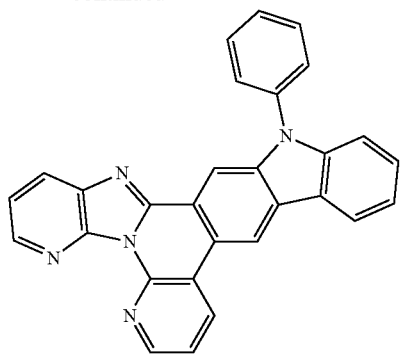
A 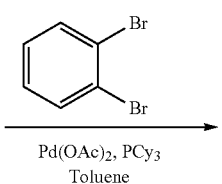 Pd(OAc)$_2$, PCy$_3$
————————→
Toluene
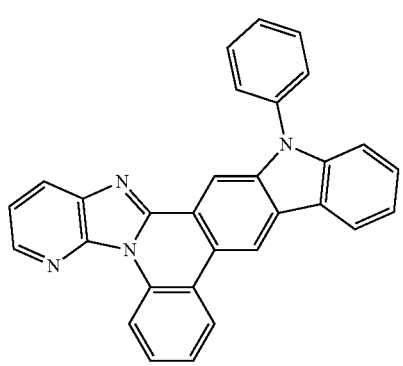
B 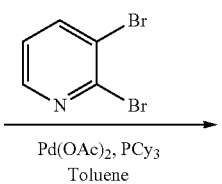 Pd(OAc)$_2$, PCy$_3$
————————→
Toluene
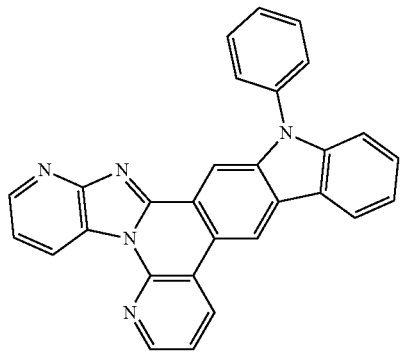
B 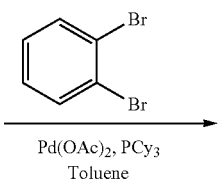 Pd(OAc)$_2$, PCy$_3$
————————→
Toluene 577
-continued
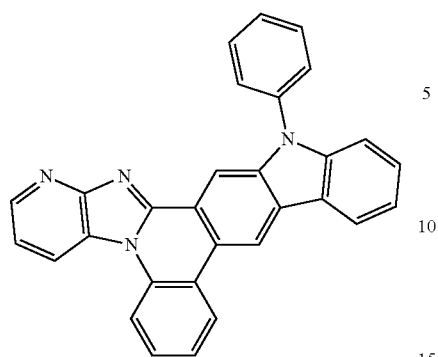
In one embodiment, exemplary compounds may be prepared according to the following scheme:
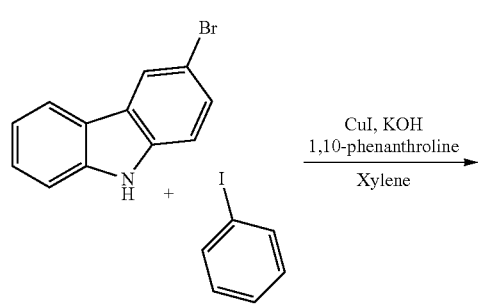
CuI, KOH
1,10-phenanthroline
——————————→
Xylene
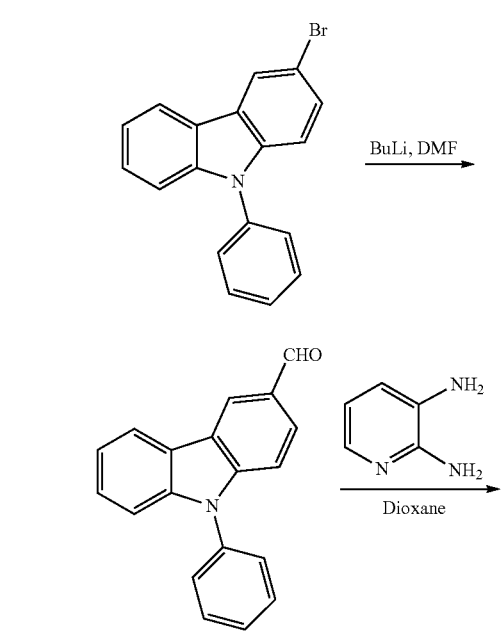
BuLi, DMF
——————→
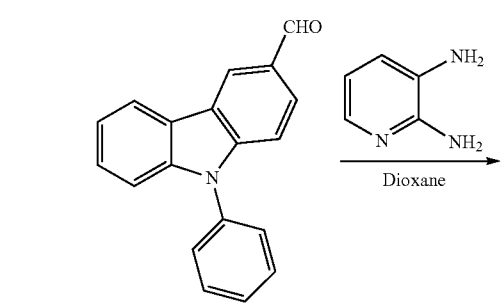
Dioxane
——————→
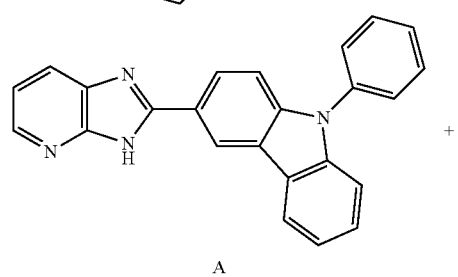
A
+
578
-continued
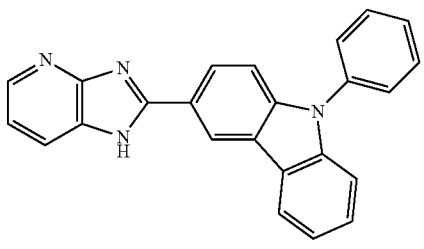
B
A
Pd(OAc)$_2$, PCy$_3$
——————————→
Toluene
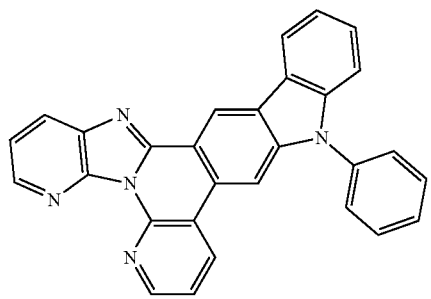
A
Pd(OAc)$_2$, PCy$_3$
——————————→
Toluene
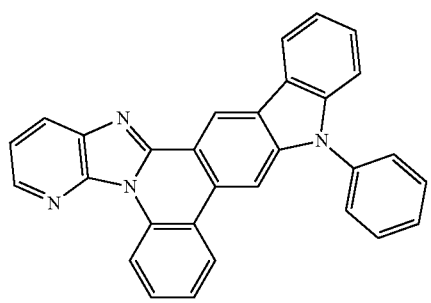
B
Pd(OAc)$_2$, PCy$_3$
——————————→
Toluene
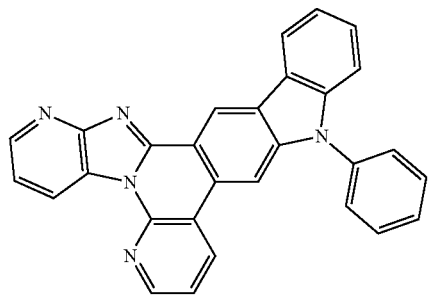

579
-continued
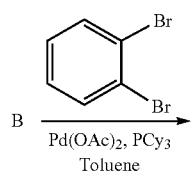
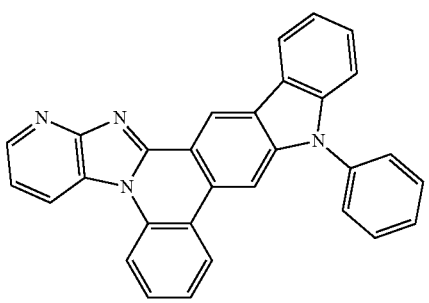
In one embodiment, exemplary compounds may be prepared according to the following scheme:
+
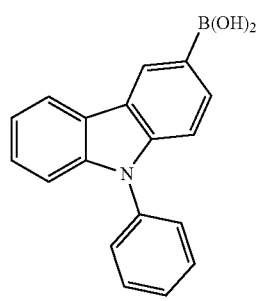
580
-continued
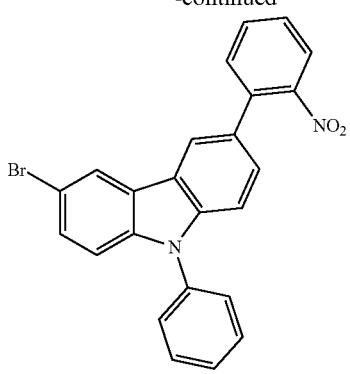
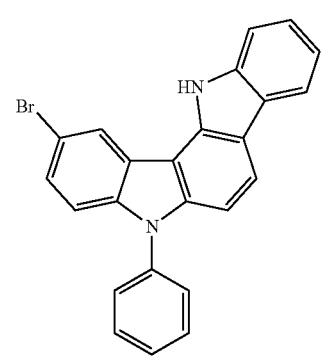
A
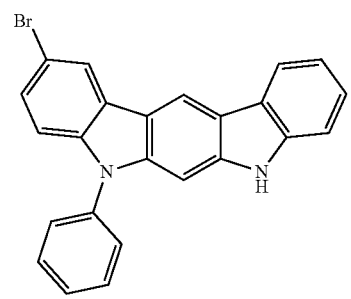
B
A + 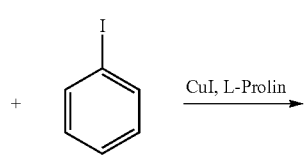
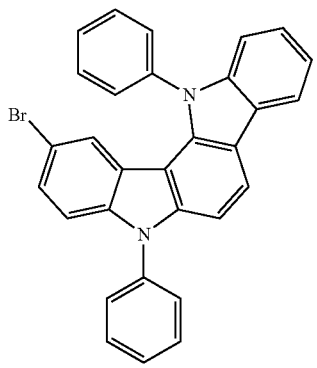
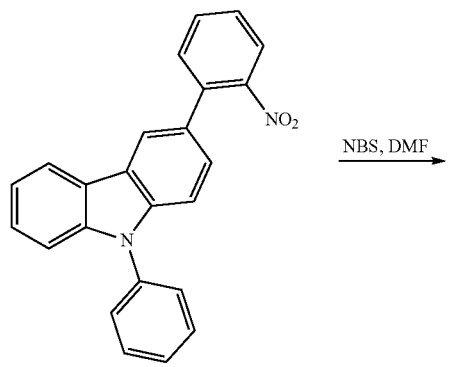

581
-continued
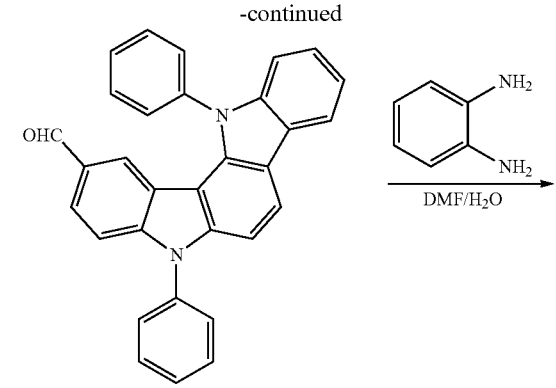
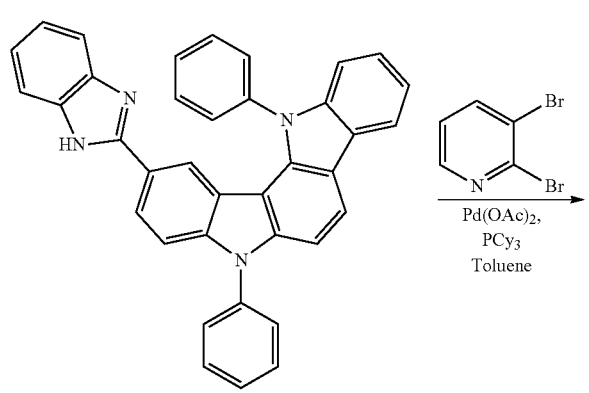
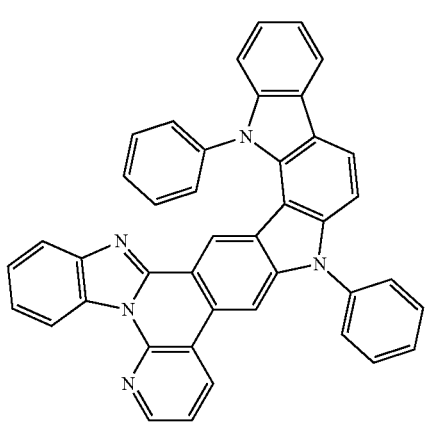
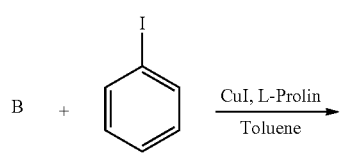
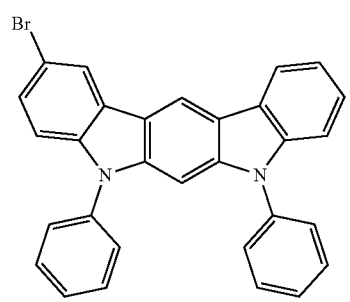
582
-continued
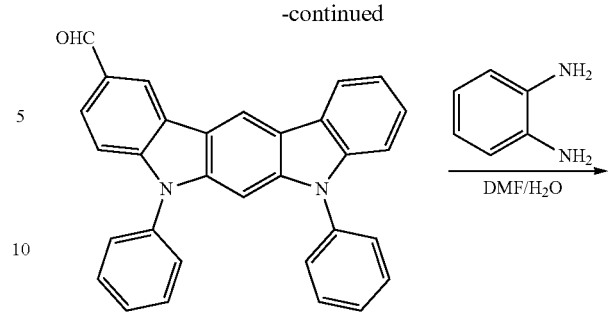
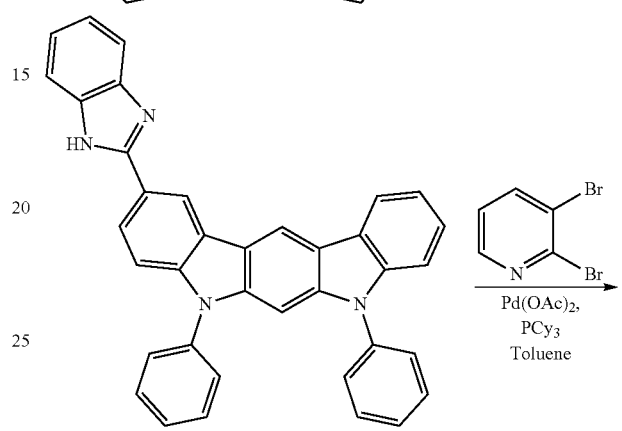
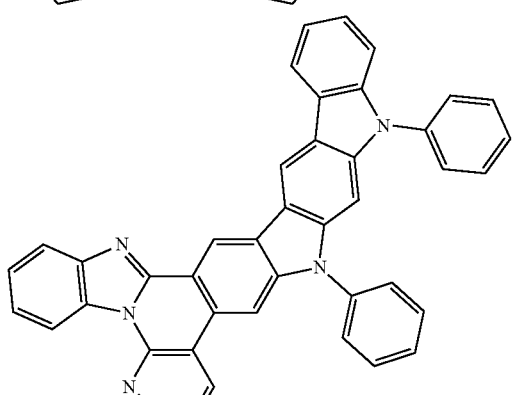
In one embodiment, exemplary compounds may be prepared according to the following scheme:
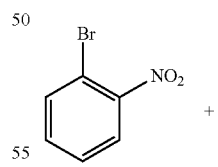
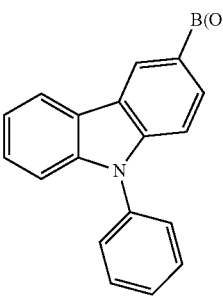

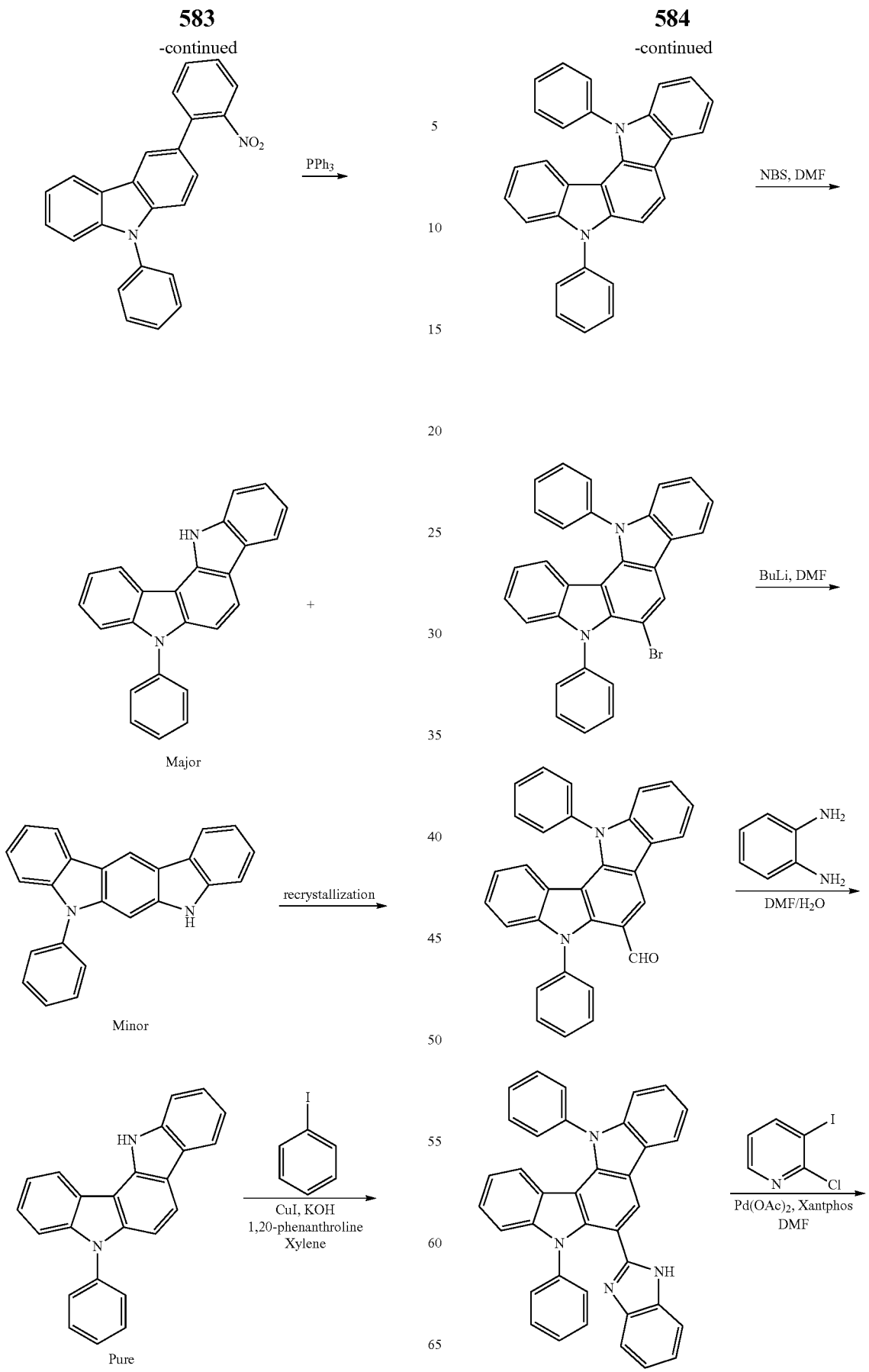

585
-continued
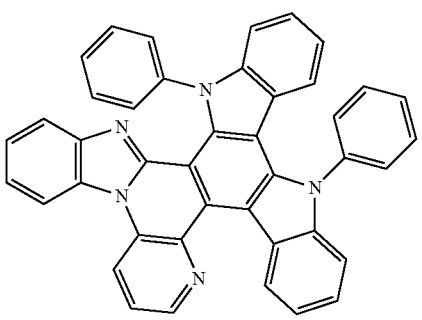
In one embodiment, exemplary compounds may be prepared according to the following scheme:
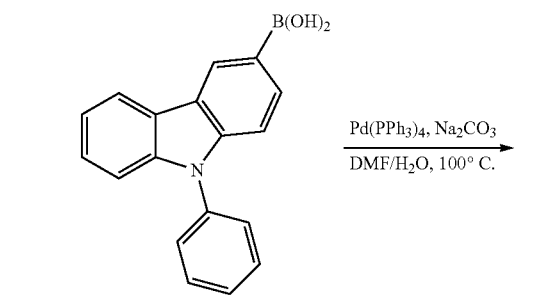
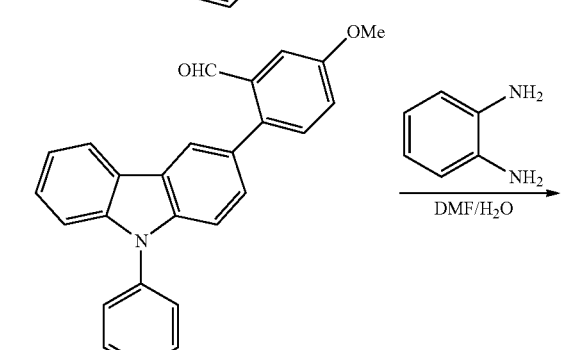
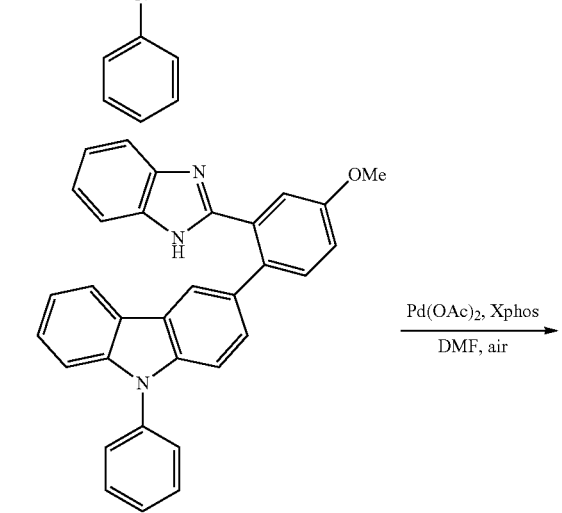
586
-continued
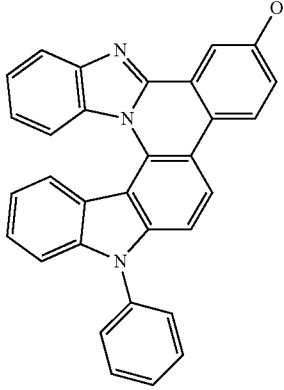
1, HBr
2, Tf₂O, pyridine
→
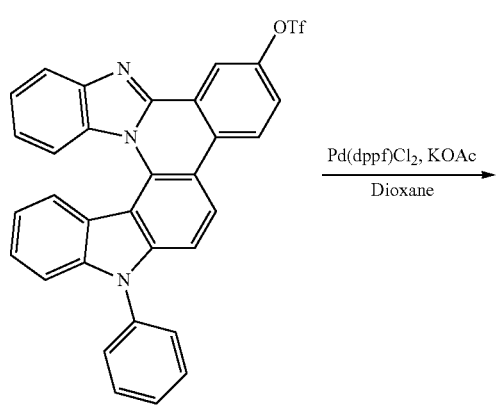
Pd(dppf)Cl₂, KOAc
Dioxane
→
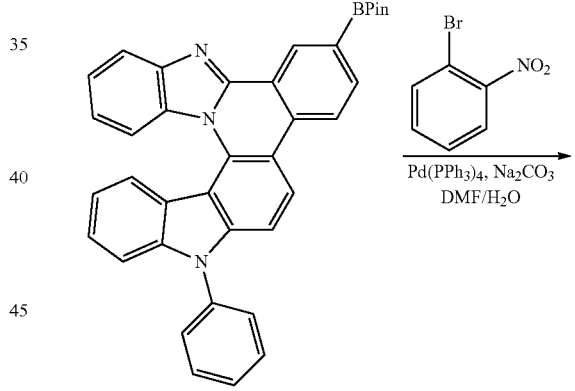
Pd(PPh₃)₄, Na₂CO₃
DMF/H₂O
→
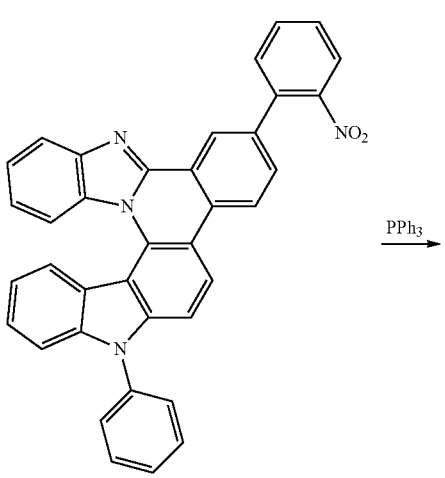
PPh₃
→

587
-continued
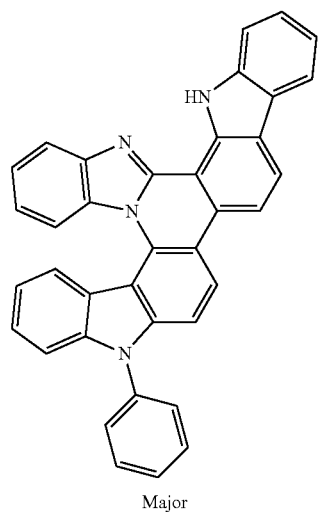
Major
+
588
-continued
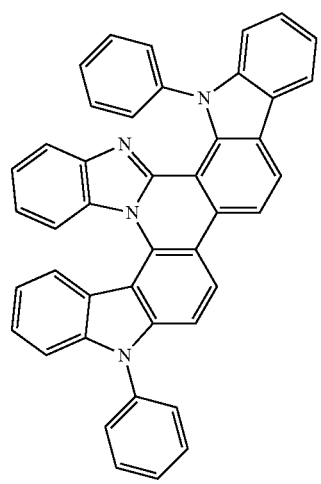
In one embodiment, exemplary compounds may be prepared according to the following scheme:
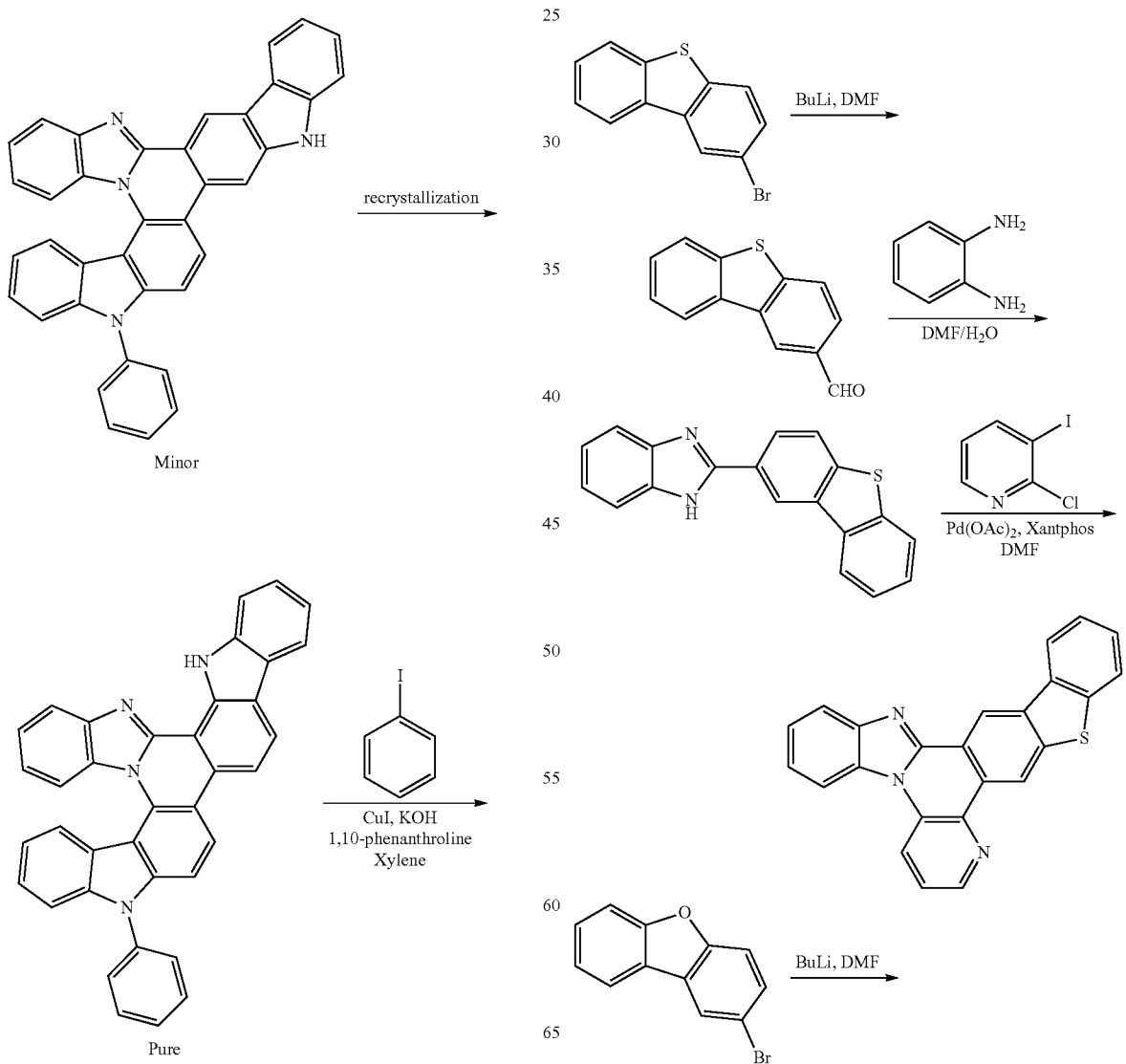

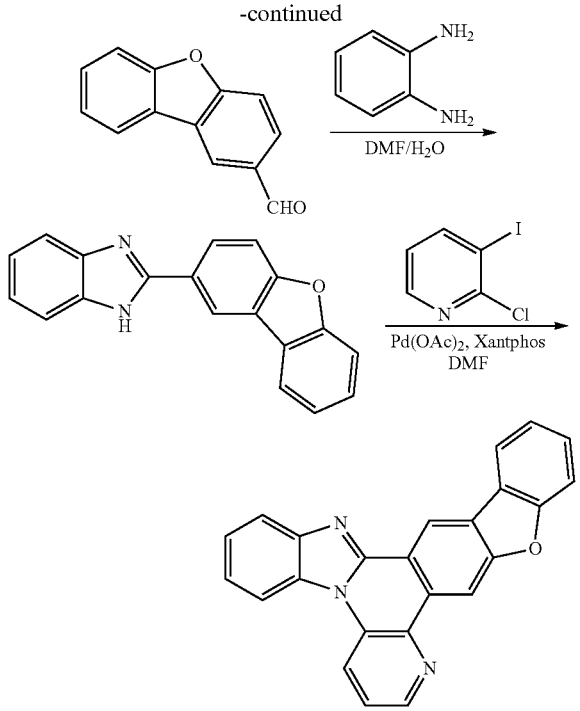
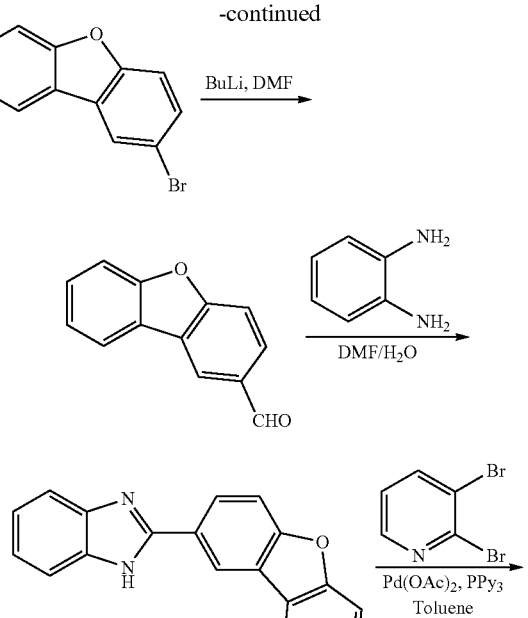
In one embodiment, exemplary compounds may be prepared according to the following scheme:
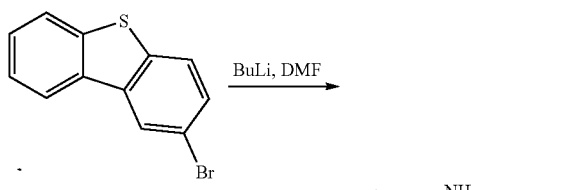
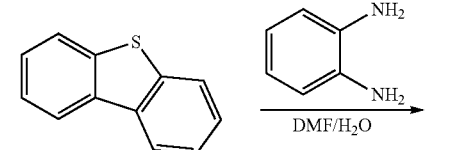
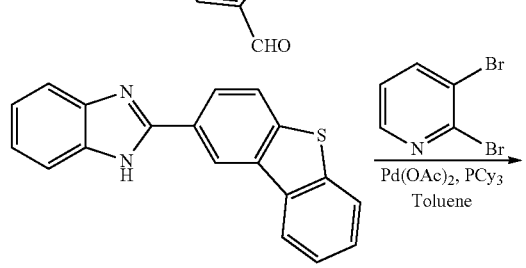
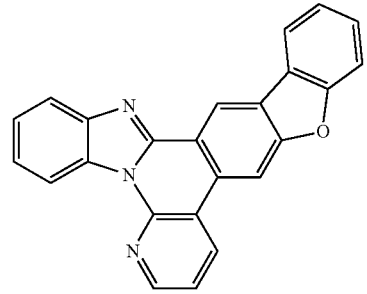 [SMILES: c1ccc2c(c1)nc1c3cc4c(cc3c3cccnc3n21)oc1ccccc14]
In one embodiment, an exemplary compound may be prepared according to the following scheme:
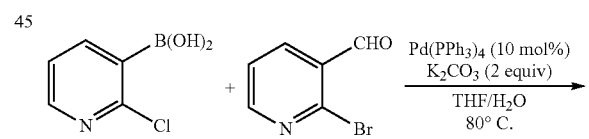
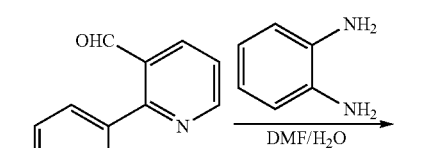
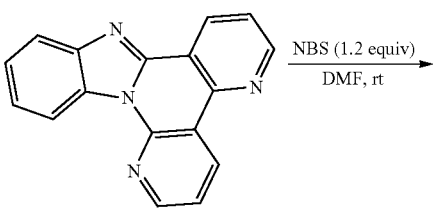
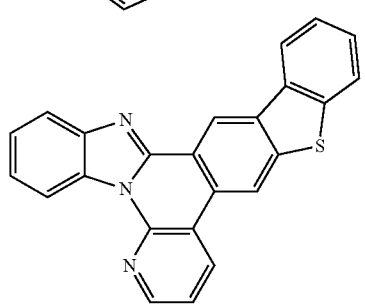

-continued
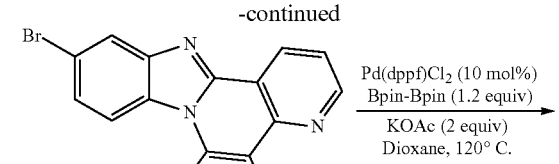
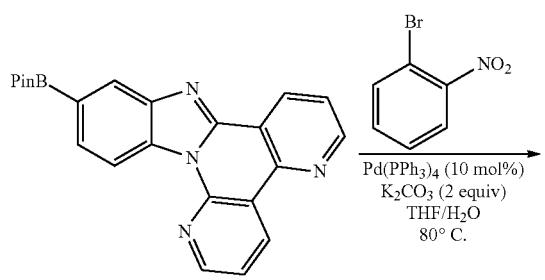
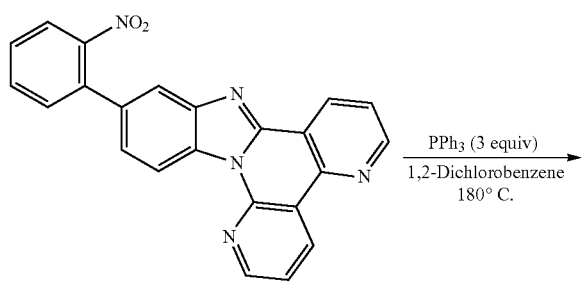
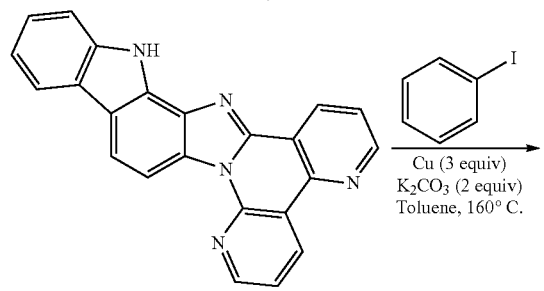
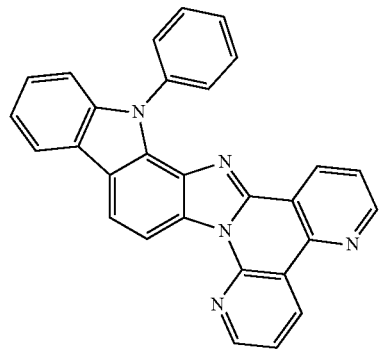
In one embodiment, an exemplary compound may be prepared according to the following scheme:
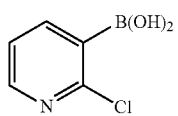
+
-continued
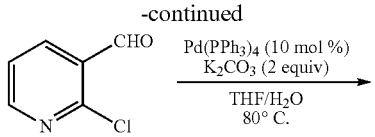
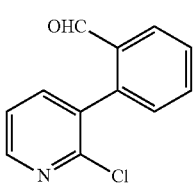
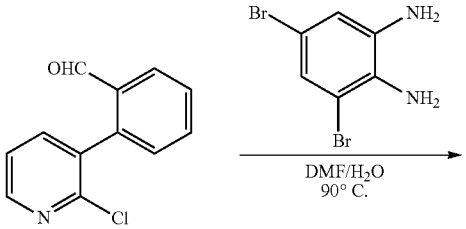
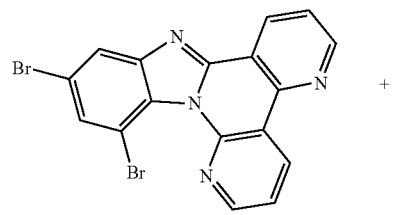
A
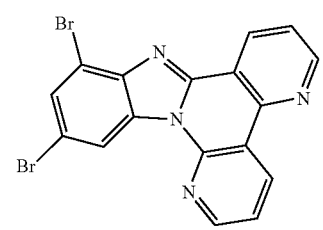
B
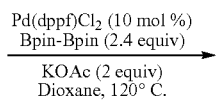
A
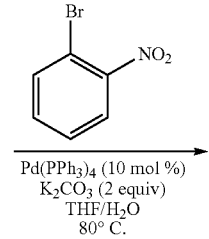
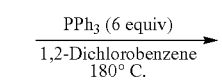

593
-continued
594
-continued
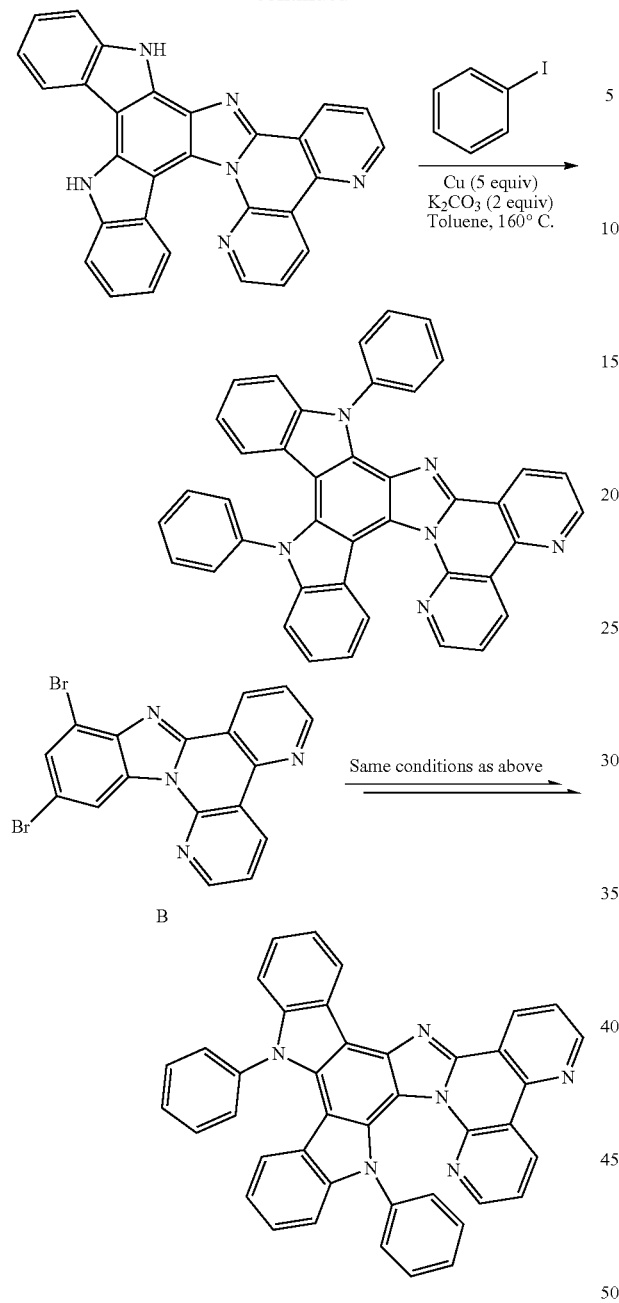
In one embodiment, an exemplary compound may be prepared according to the following scheme:
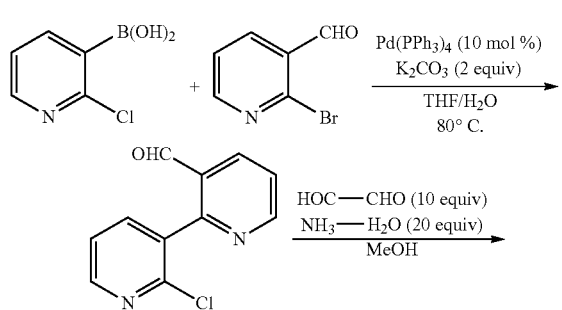
In one embodiment, an exemplary compound may be prepared according to the following scheme:
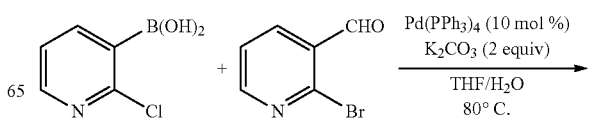

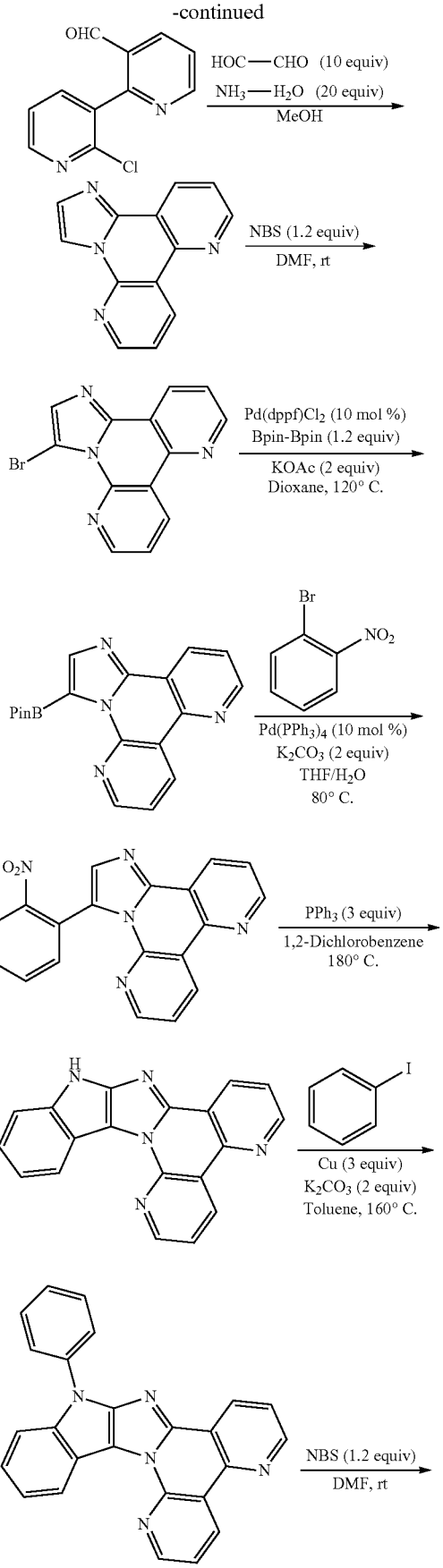
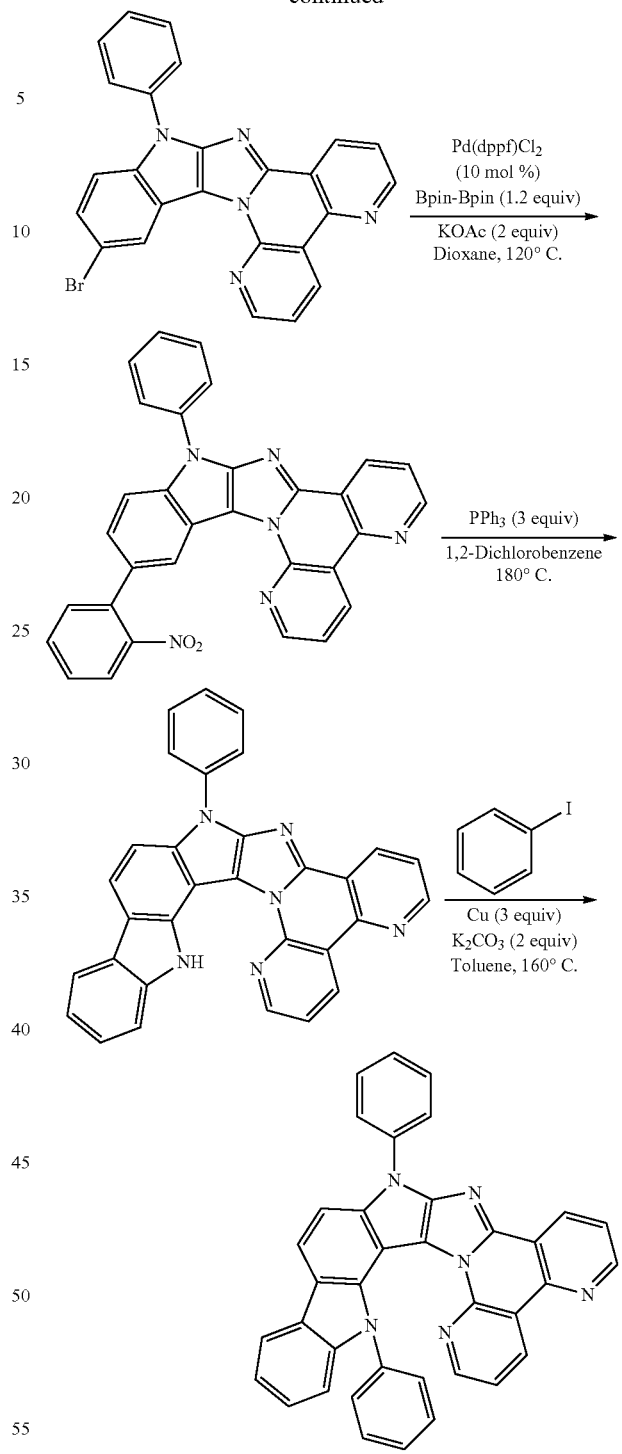
In one embodiment, an exemplary compound may be prepared according to the following scheme:
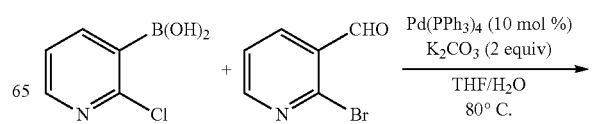

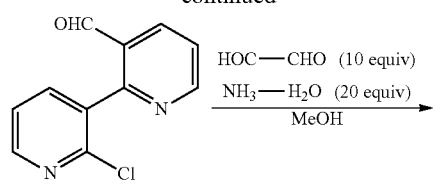
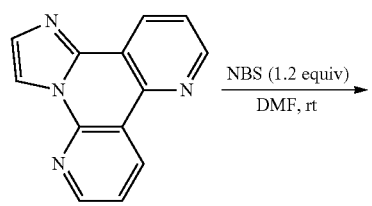
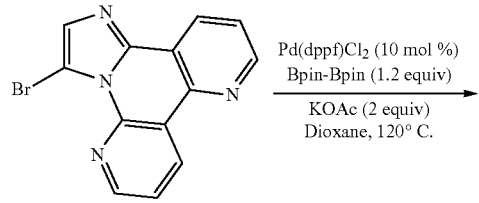
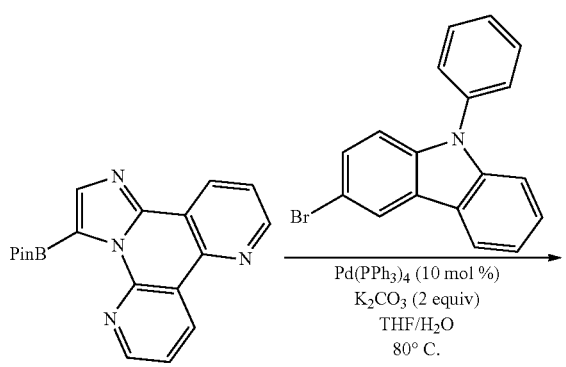
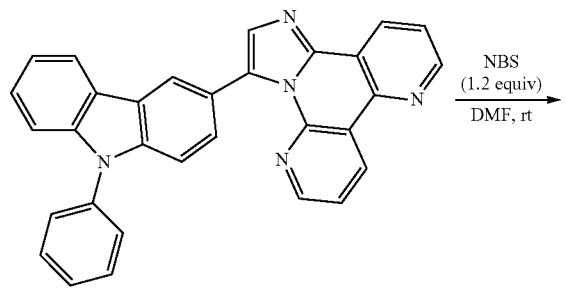
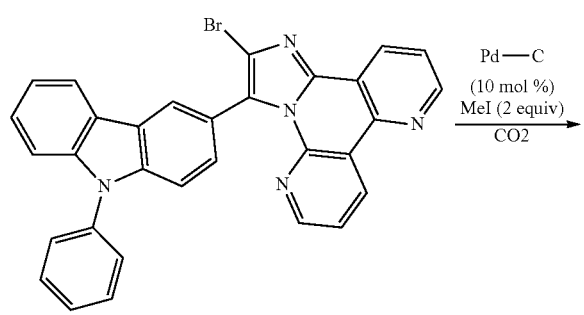
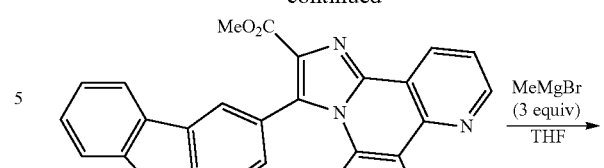
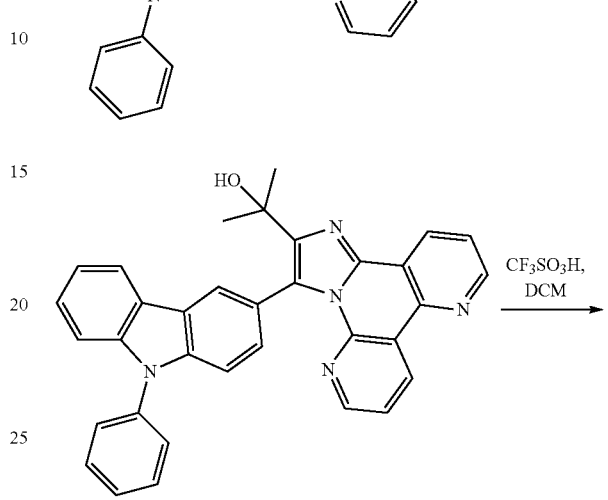
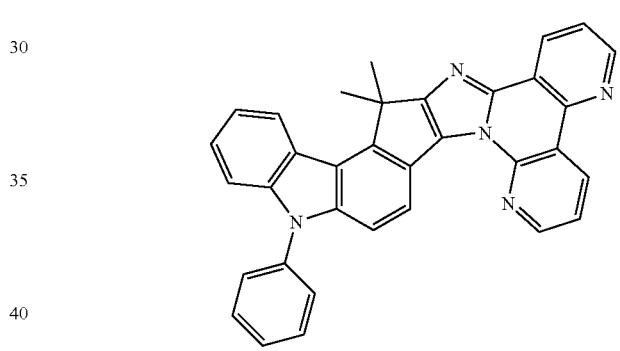
In one embodiment, an exemplary compound may be prepared according to the following scheme:
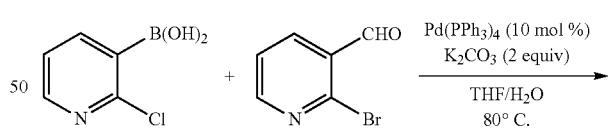
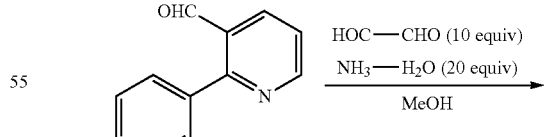
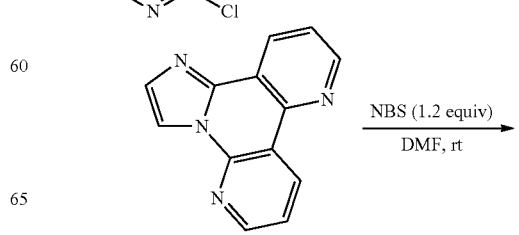

-continued
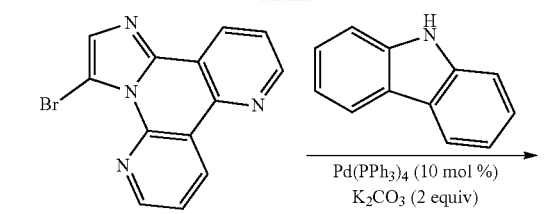
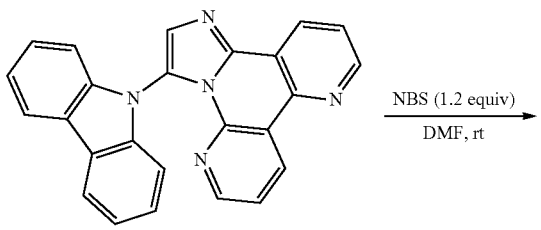
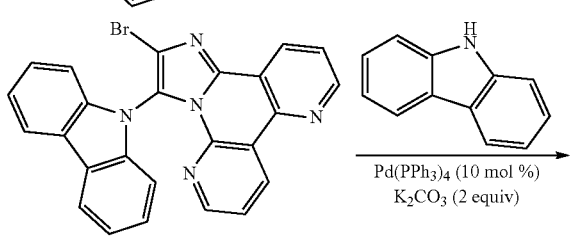
In one embodiment, an exemplary compound may be prepared according to the following scheme:
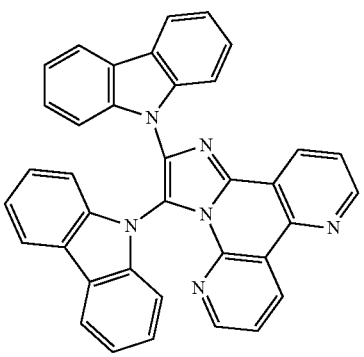
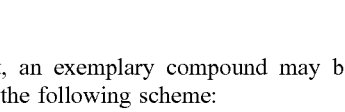
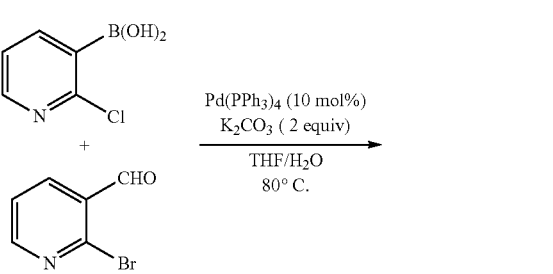
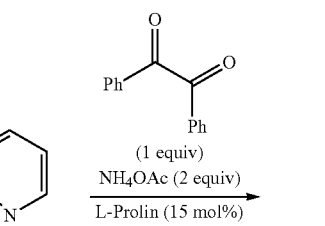
-continued
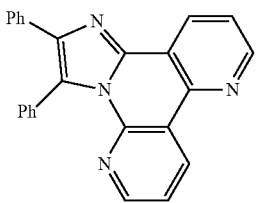
In one embodiment, an exemplary compound may be prepared according to the following scheme:
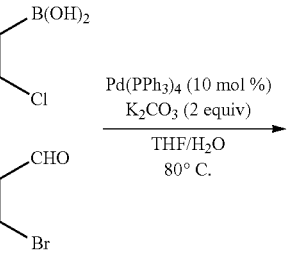
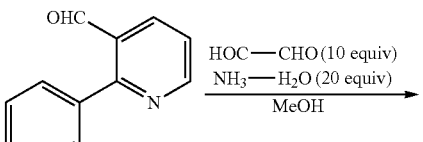
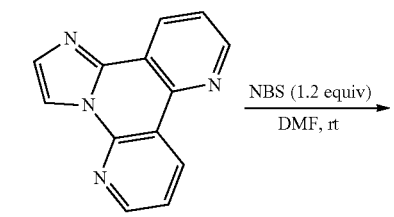
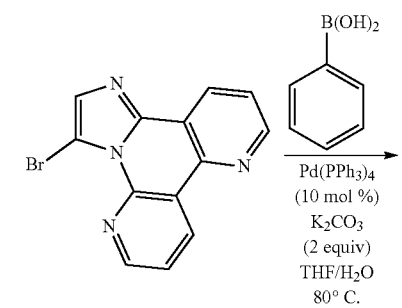
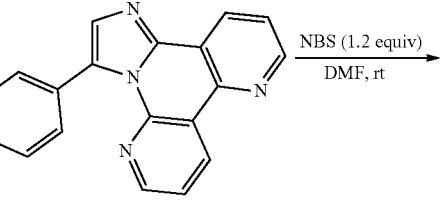

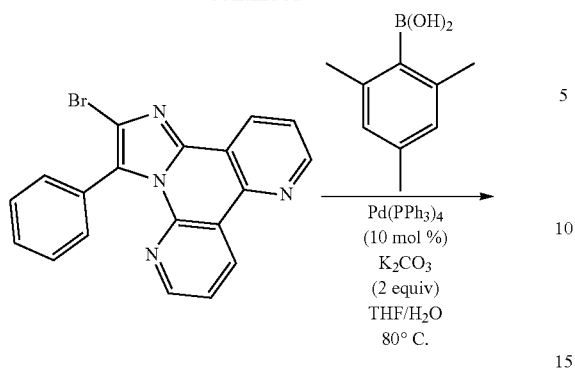
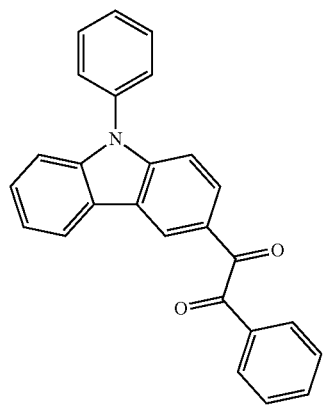
In one embodiment, an exemplary compound may be prepared according to the following scheme:
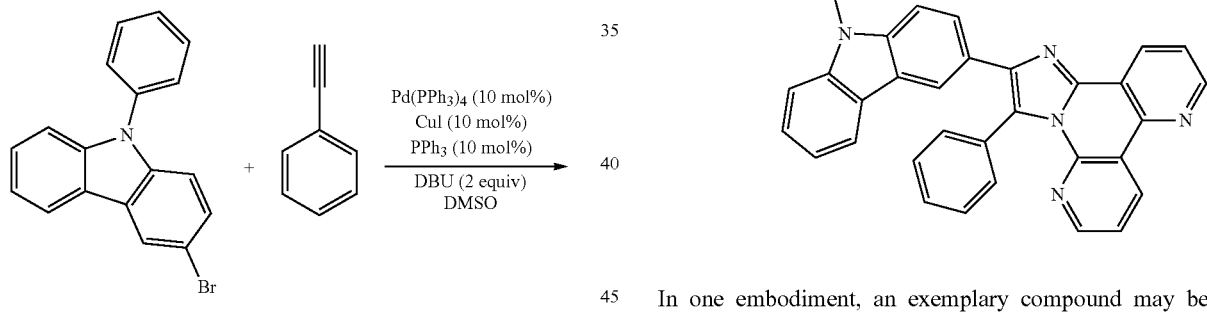
In one embodiment, an exemplary compound may be prepared according to the following scheme:
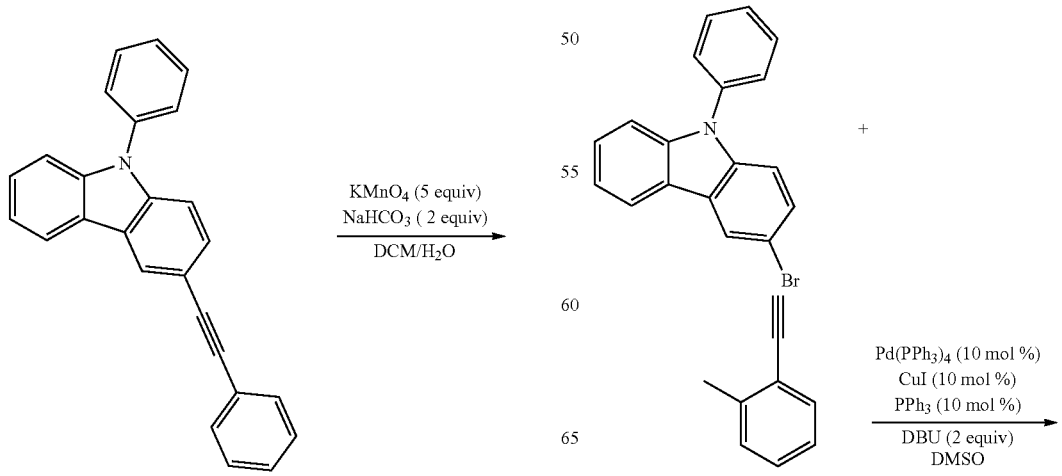

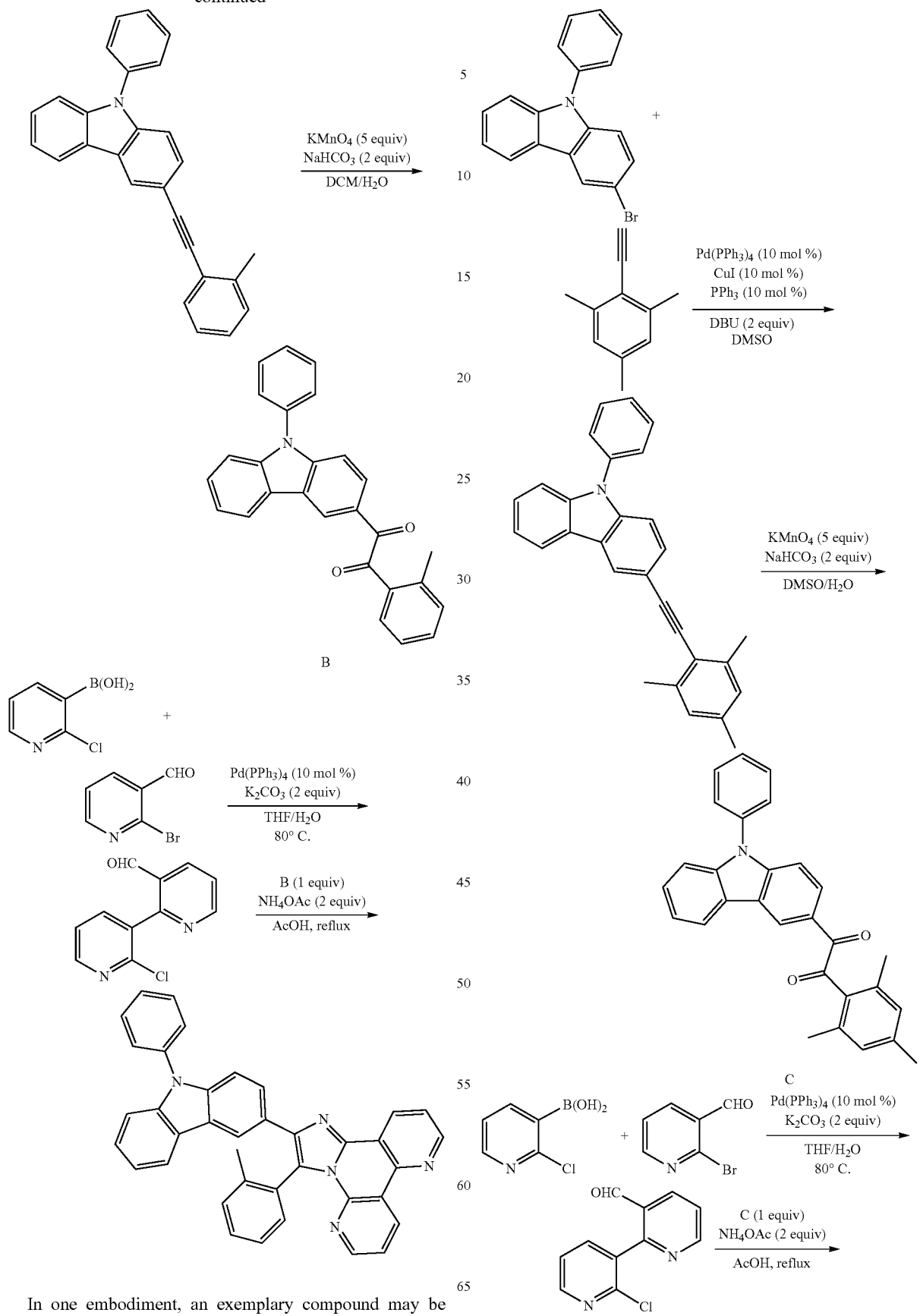
In one embodiment, an exemplary compound may be prepared according to the following scheme:

-continued
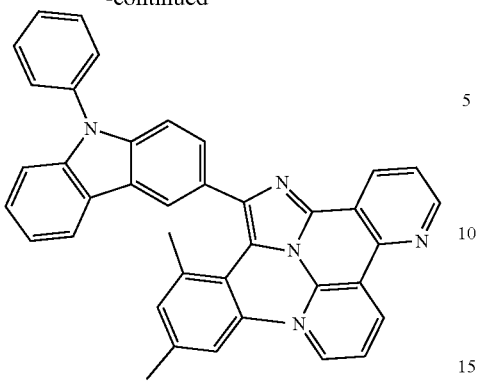
In one embodiment, an exemplary compound may be prepared according to the following scheme:
-continued
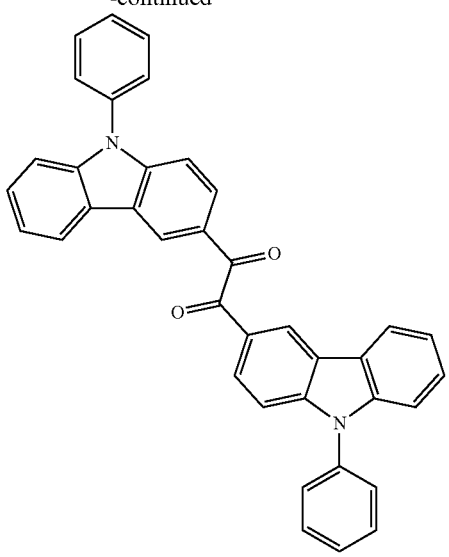
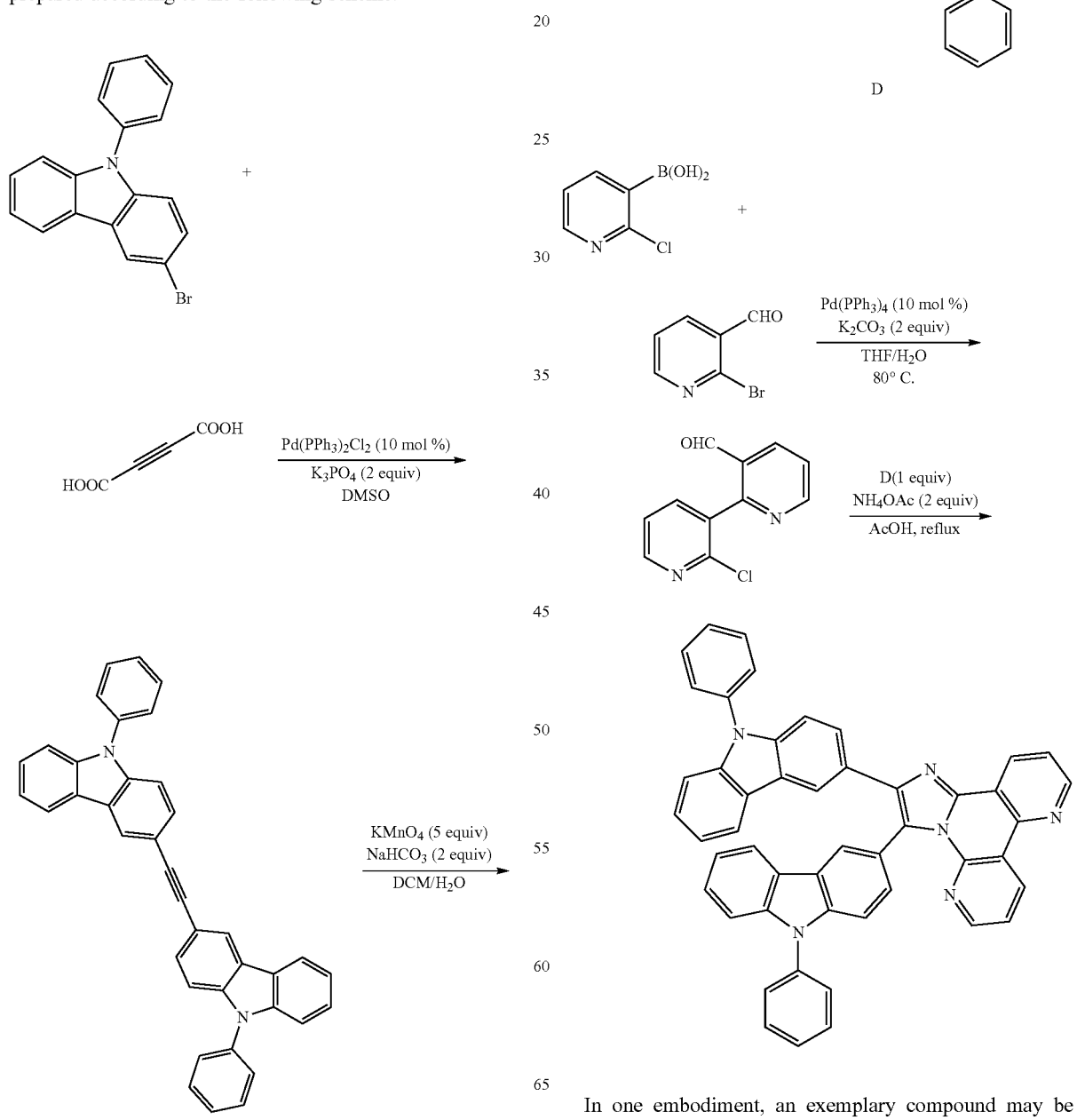
In one embodiment, an exemplary compound may be prepared according to the following scheme:

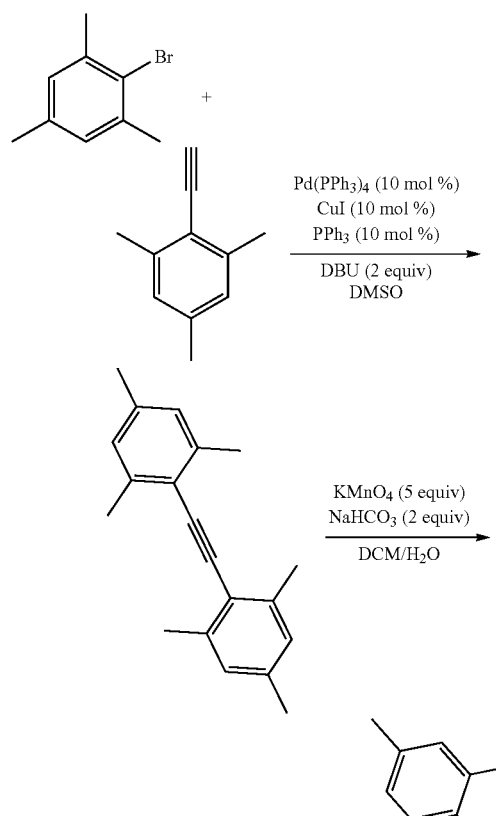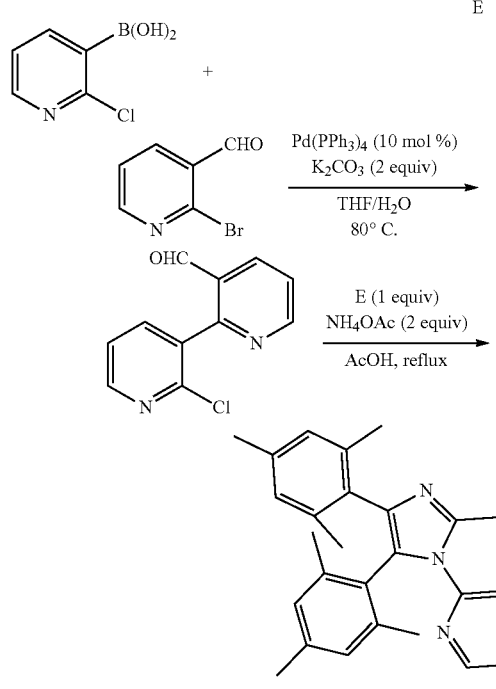
In one embodiment, an exemplary compound may be prepared according to the following scheme:
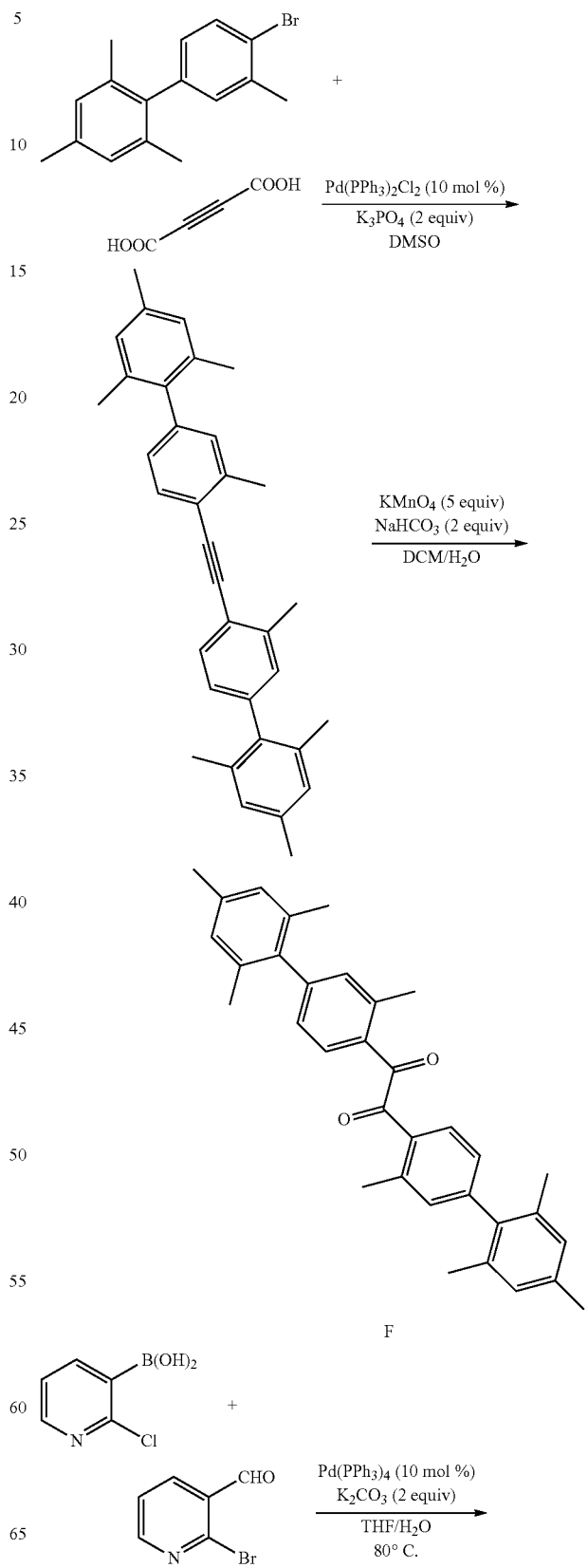

-continued

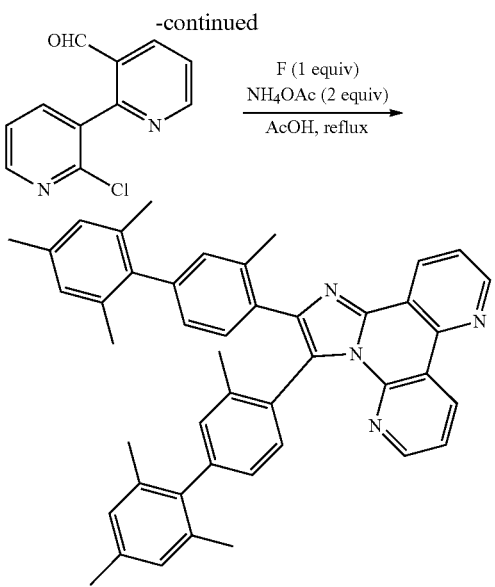

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

We claim:
1. A compound of General Formula I:

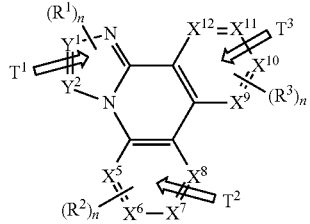

General Formula I wherein:
T² and T³ represent a Donor or an Acceptor; T¹ optionally represents a Donor;
$Y^1$ and $Y^2$ each independently represent C, N, Si, B, or P;
wherein when $Y^1$ and $Y^2$ both represent C, then two groups $R^1$ may optionally together form a fused aryl or heteroaryl ring having the following structure:

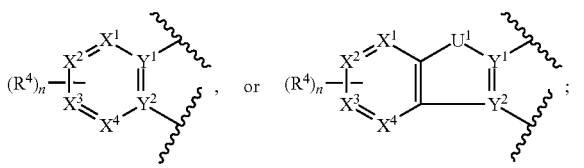

wherein for any two adjacent $X^a$ and $X^b$ representing $X^5$-$X^8$ where a and b are integers from 5-8, then two groups $R^2$ may optionally together form a fused aryl or heteroaryl ring having the following structure:

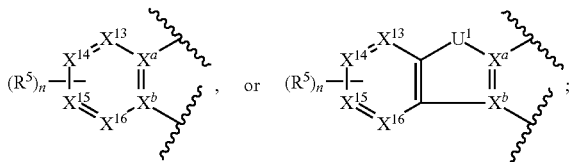

wherein for any two adjacent $X^c$ and $X^d$ representing $X^9$-$X^{12}$ where c and d are integers from 9-12, then two groups $R^3$ may optionally together form a fused aryl or heteroaryl ring having the following structure:

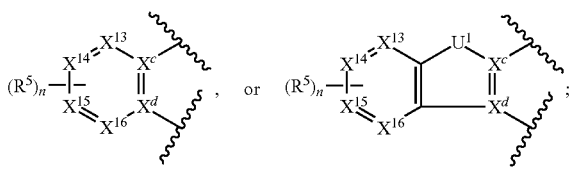

wherein:
$X^1, X^2, X^3, X^4, X^5, X^6, X^7, X^8, X^9, X^{10}, X^{11}, X^{12}, X^{13}, X^{14}, X^{15}$, and $X^{16}$ each independently represents C, N, Si, B, or P;
$U^1$ represents O, S, Se, $NR^{21}$, P=O, As=O, Bi=O, $CR^{21}R^{22}$, C=O, $SiR^{21}R^{22}$, $GeR^{21}R^{22}$, $NR^{21}$, $PR^{21}$, $PR^{21}R^{22}$, $R^{21}$P=O, $AsR^{21}$, $R^{21}$As=O, S=O, $SeO_2$, Se=O, $SeO_2$, $BR^{21}$, $BR^{21}R^{22}$, $AlR^{21}$, $AlR^{21}R^{22}$, $R^{21}$Bi=O, or $BiR^{21}$;
each n is independently an integer, valency permitting; and
each of $R^1$, $R^2$, $R^3$, $R^4$, $R^5$, $R^{21}$ and $R^{22}$ independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof;
wherein two adjacent groups $R^1$, $R^2$, $R^3$, $R^4$, $R^5$, $R^{21}$, $R^{22}$, or a combination thereof may optionally together form a fused ring; and
wherein at least one of the following conditions (i)-(iii) is satisfied:
(i) two groups $R^1$ together form a fused heteroaryl structure having the structure

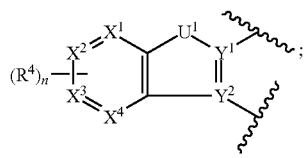

or (ii) $X^9$ and $X^{10}$ each represent C substituted by $R^3$, wherein the two groups $R^3$ are represented by the following structure:

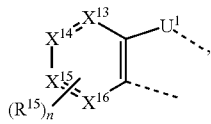

wherein the dashed lines indicate bonds to $X^9$ and $X^{10}$, and $X^{11}$ and $X^{12}$ each represent C substituted by $R^3$, wherein the two groups $R^3$ are represented by the following structure:

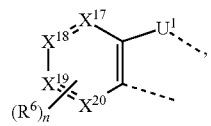

wherein the dashed lines indicate bonds to $X^{11}$ and $X^{12}$, or (iii) at least one of $Y^1$ and $Y^2$ represents C, and at least one $R^1$ is represented by the following structure:

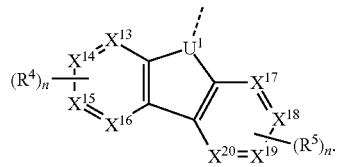

2. The compound of claim 1, wherein one or more of the following conditions is true:

(i) $Y^1$ and $Y^2$ are each C, and two groups $R^1$ are represented by one of the following structures, where dashed lines indicate bonds to $Y^1$ and $Y^2$ in General Formula I:

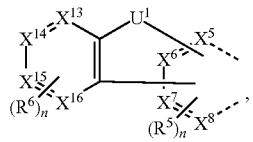

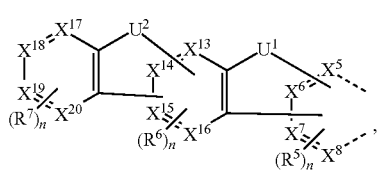

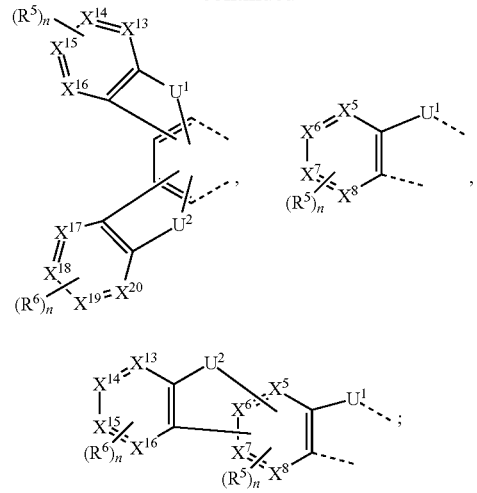

(ii) for two adjacent $X^a$ and $X^b$, two groups $R^2$ are represented by one of the following structures, where dashed lines indicate bonds to $X^a$ and $X^b$ in General Formula I:

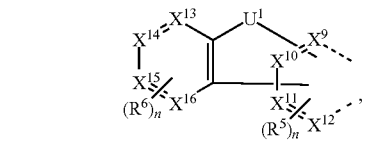

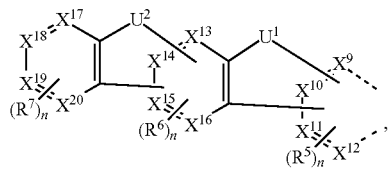

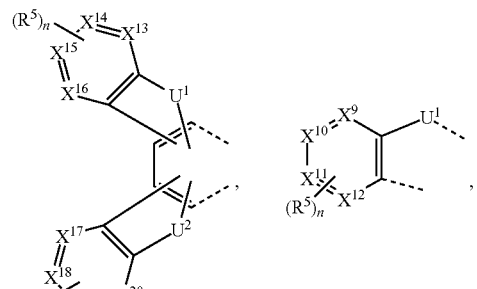

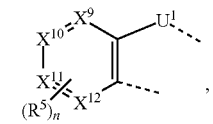

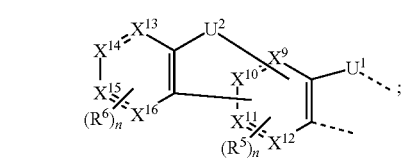

(iii) for two adjacent $X^c$ and $X^d$, two groups $R^3$ are represented by one of the following structures, where dashed lines indicate bonds to $X^c$ and $X^d$ in General Formula I:

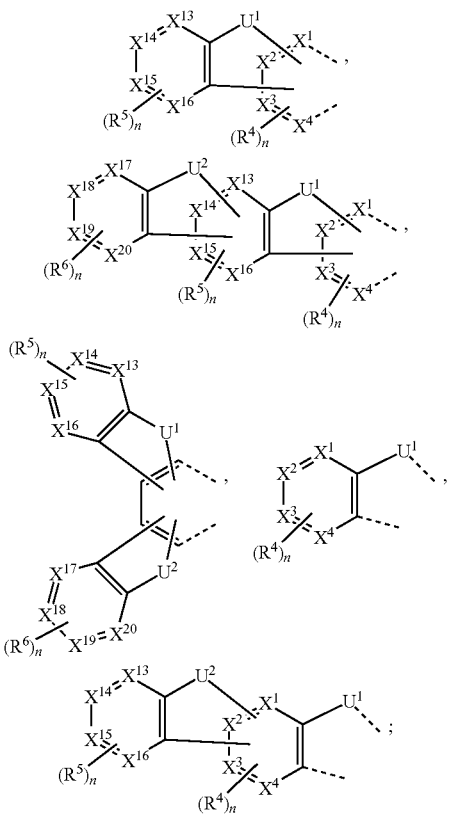

wherein:

$X^{13}$, $X^{14}$, $X^{15}$, $X^{16}$, $X^{17}$, $X^{18}$, $X^{19}$, and $X^{20}$ each independently represents C, N, Si, B, or P;

each $U^1$ and $U^2$ represents O, S, Se, P=O, As=O, Bi=O, $CR^{21}R^{22}$, C=O, $SiR^{21}R^{22}$, $GeR^{21}R^{22}$, $NR^{21}$, $PR^{21}$, $PR^{21}R^{22}$, $R^{21}P$=O, $AsR^{21}$, $R^{21}As$=O, S=O, $SeO^2$, Se=O, $SeO_2$, $BR^{21}$, $BR^{21}R^{22}$, $AlR^{21}$, $AlR^{21}R^{22}$, $R^{21}Bi$=O, or $BiR^{21}$;

each $R^4$, $R^5$, $R^6$, and $R^7$ is independently absent or present as a single substituent or multiple substituents, valency permitting, and each occurrence of $R^4$, $R^5$, $R^6$, $R^{21}$ and $R^{22}$ independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof;

any two adjacent $R^4$, $R^5$, $R^6$, $R^7$, or a combination thereof may optionally together form a fused ring; and each occurrence of n is independently an integer, valency permitting.

3. The compound of claim 1, wherein one or more of the following conditions are true:

(i) at least one of $Y^1$ and $Y^2$ represents C, and at least one $R^1$ is represented by the following structure:

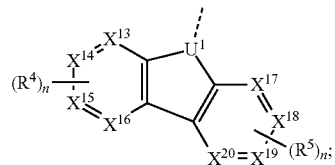

(ii) at least one $R^2$ is represented by the following structure:

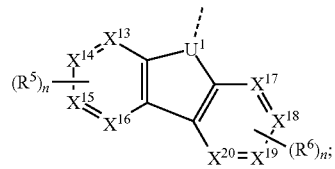

(iii) at least one $R^3$ is represented by the following structure:

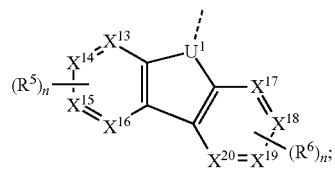

wherein
dashed lines indicate the bond to General Formula I;
$X^{13}$, $X^{14}$, $X^{15}$, $X^{16}$, $X^{17}$, $X^{18}$, $X^{19}$, and $X^{20}$, each independently represents C, N, Si, B, or P;
$U^1$ represents N, P, As, B, Al, or Bi, $CR^{21}$, $SiR^{21}$, $GeR^{21}$, P=O, As=O, B, Bi=O, $PR^{21}R^{22}$, $R^{21}P$=O, $AsR^{21}$, $R^{21}As$=O, S=O, $SeO^2$, S=O, $SeO_2$, $R^{21}Bi$=O, or $BiR^{21}$;
each $R^4$, $R^5$ and $R^6$ is independently absent or present as a single substituent or multiple substituents, valency permitting, and each occurrence of $R^4$, $R^5$, $R^6$, $R^{21}$ and $R^{22}$ independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof;
any two adjacent $R^4$, $R^5$, $R^6$, or a combination thereof may optionally join to form a fused ring; and
each occurrence of n is independently an integer, valency permitting.

4. The compound of claim 1, wherein at least one of $X^5$, $X^6$, $X^7$, $X^8$, $X^9$, $X^{10}$, $X^{11}$, and $X^{12}$ represents N.

5. The compound of claim 1, wherein at least two of $X^5$, $X^6$, $X^7$, $X^8$, $X^9$, $X^{10}$, $X^{11}$, and $X^{12}$ represents N.

6. The compound of claim 1, wherein at least one of $X^5$, $X^6$, $X^7$, and $X^8$ represents N, and at least one of $X^9$, $X^{10}$, $X^{11}$, and $X^{12}$ represents N.

7. The compound of claim 1, wherein the compound is represented by General Formula IV, General Formula V, or General Formula VI:

General Formula II

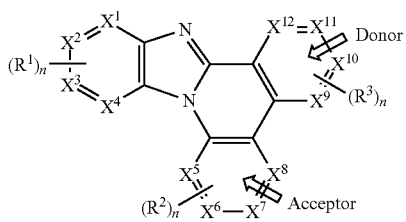

General Formula III

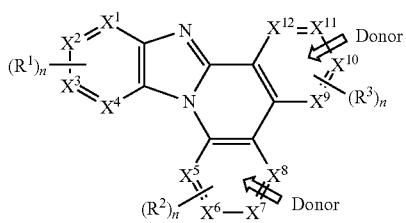

General Formula IV

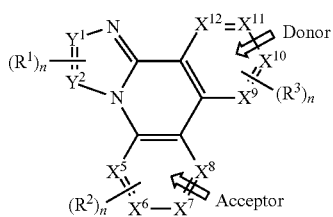

General Formula V

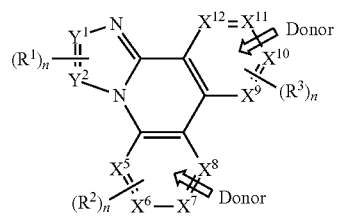

General Formula VI

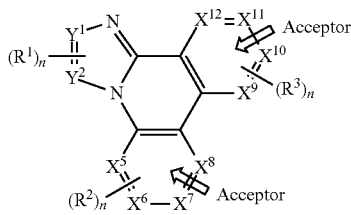

wherein $X^5$, $X^6$, $X^7$, $X^8$, $X^9$, $X^{10}$, $X^{11}$, and $X^{12}$ each independently represents C, N, Si, B, or P;
$Y^1$ and $Y^2$ each independently represent C, N, Si, B, or P;
each occurrence of n is independently an integer, valency permitting; and
each occurrence of $R^1$, $R^2$, and $R^3$ independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof; and any two adjacent $R^1$, $R^2$, $R^3$, or a combination thereof may optionally together form a fused ring.

8. The compound of claim 1, wherein the compound is represented by one of the following structures:

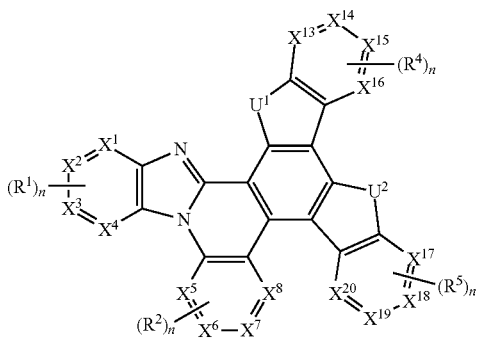

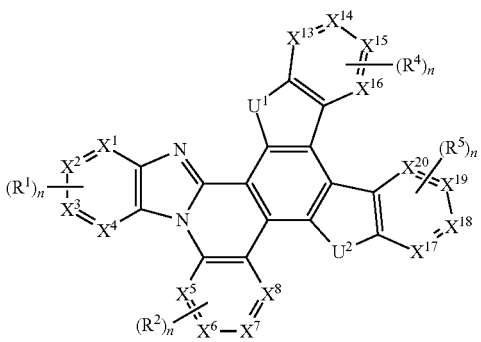

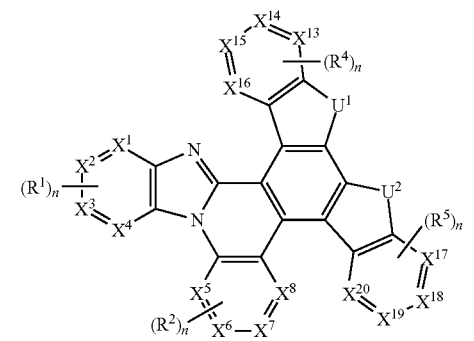

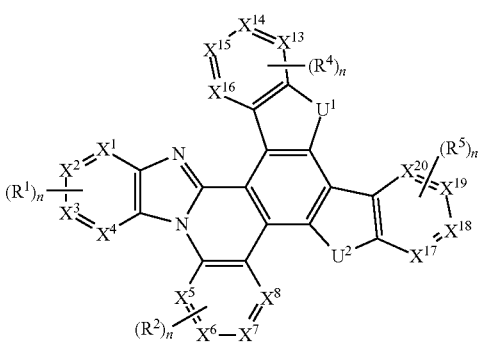

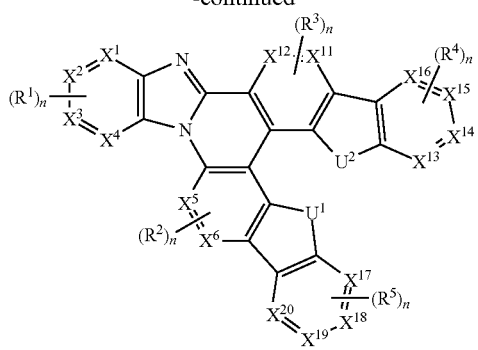
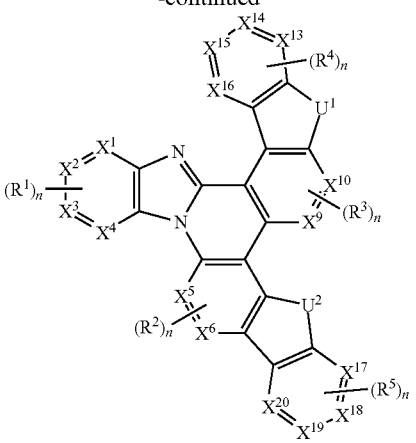
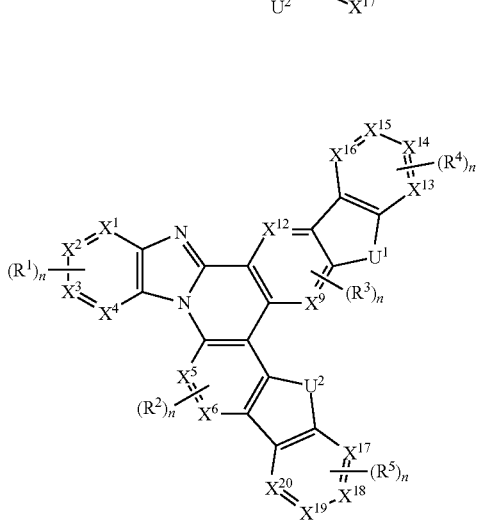
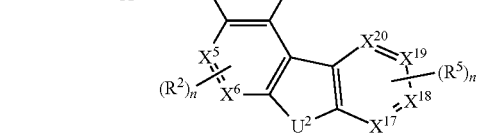
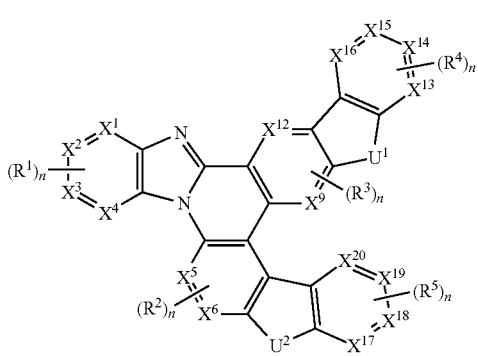
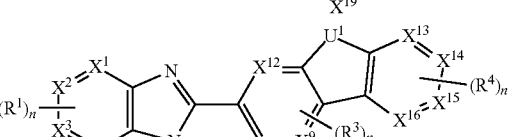
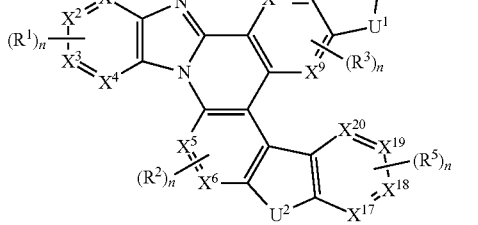
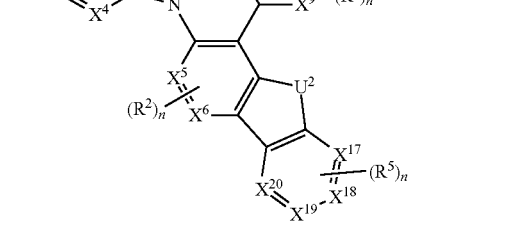

619
-continued
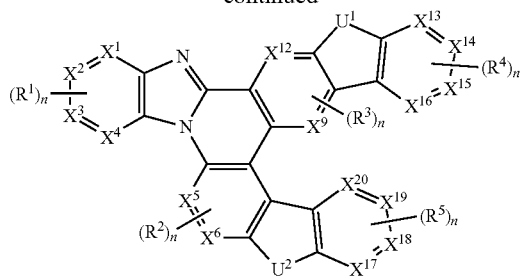
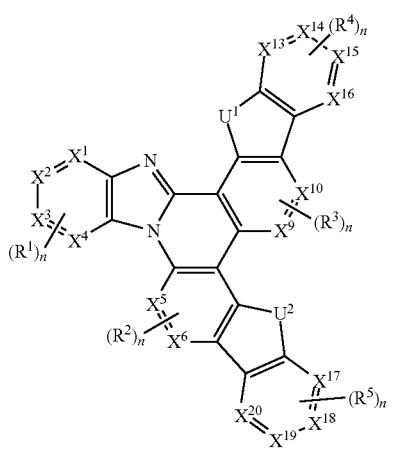
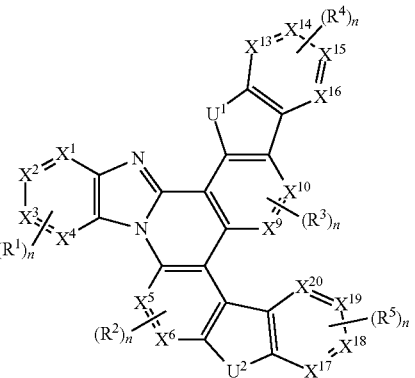
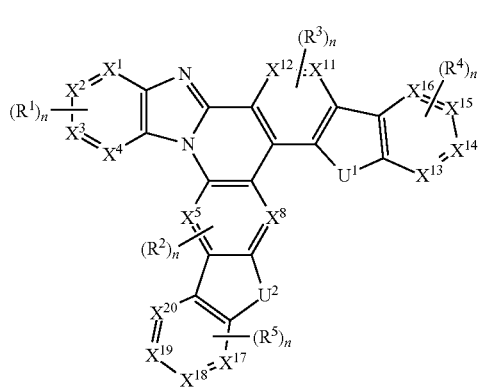
620
-continued
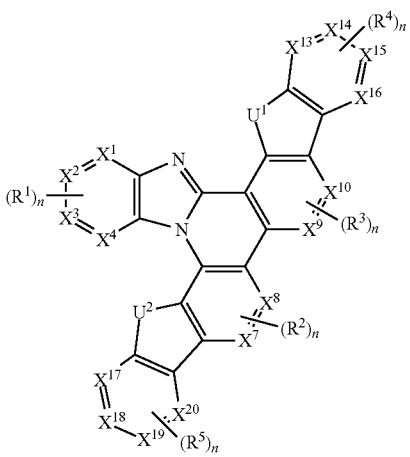
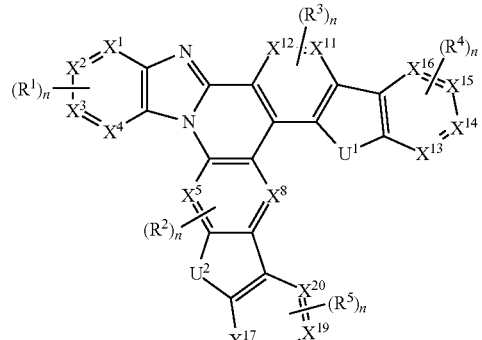
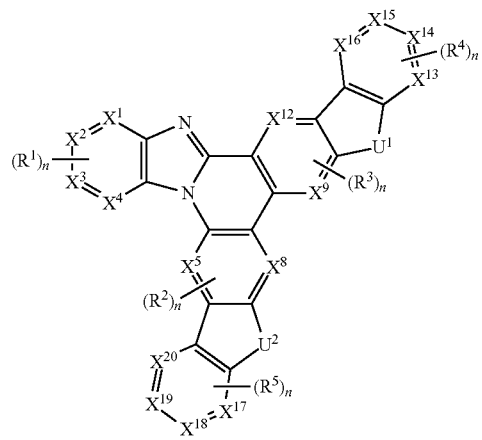
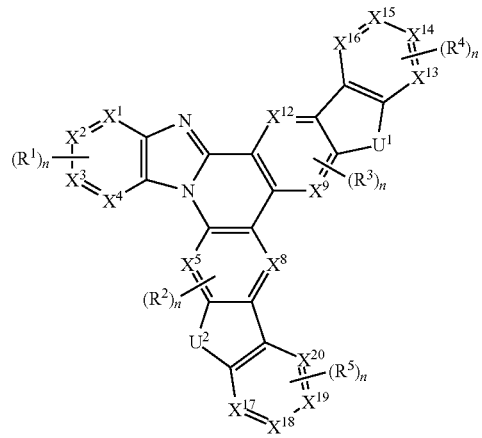

-continued
621
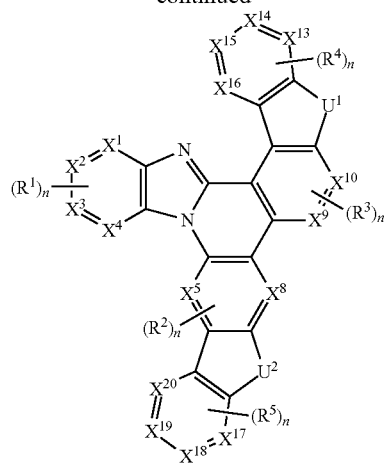
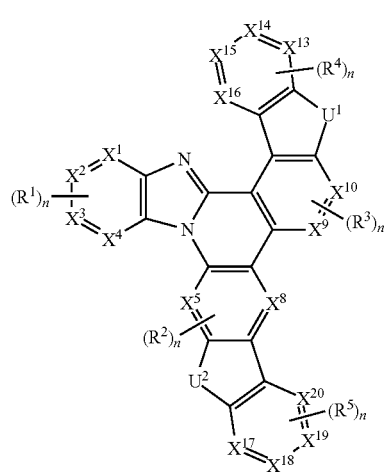
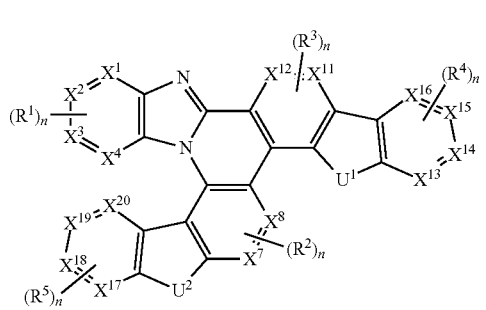
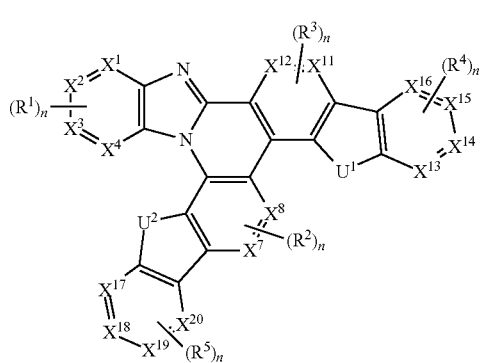
622
-continued
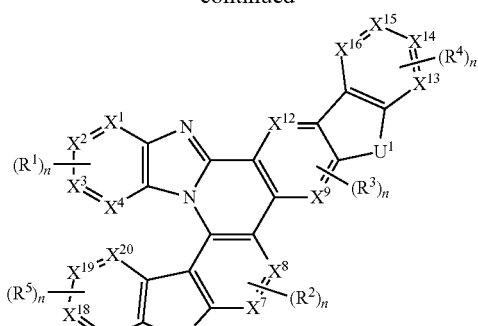
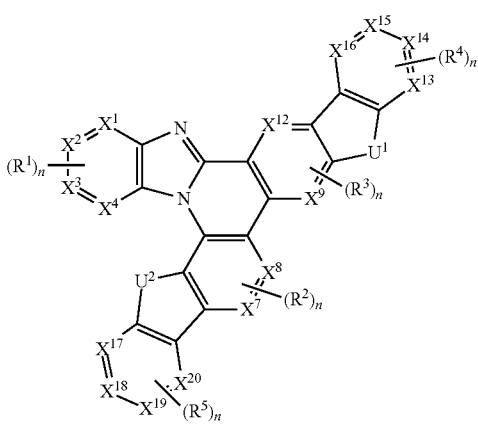
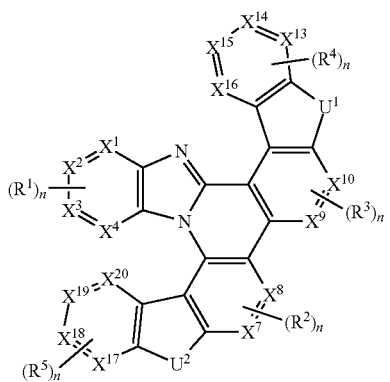
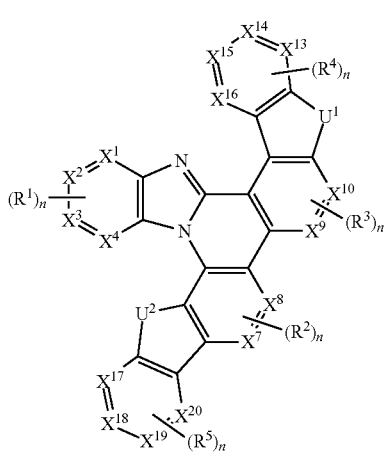

623
-continued
624
-continued
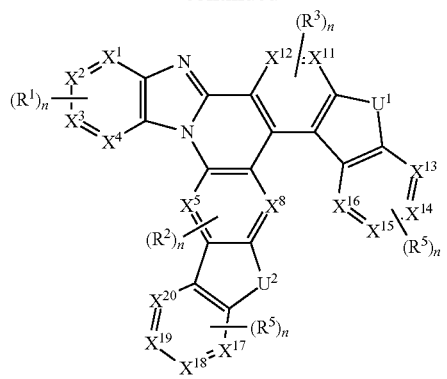
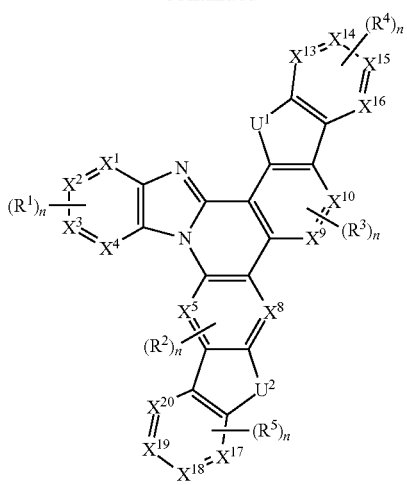
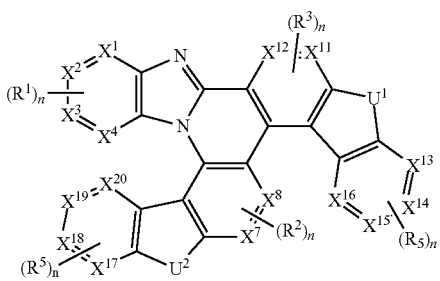
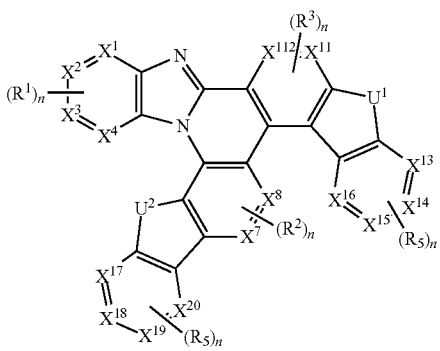

625
-continued
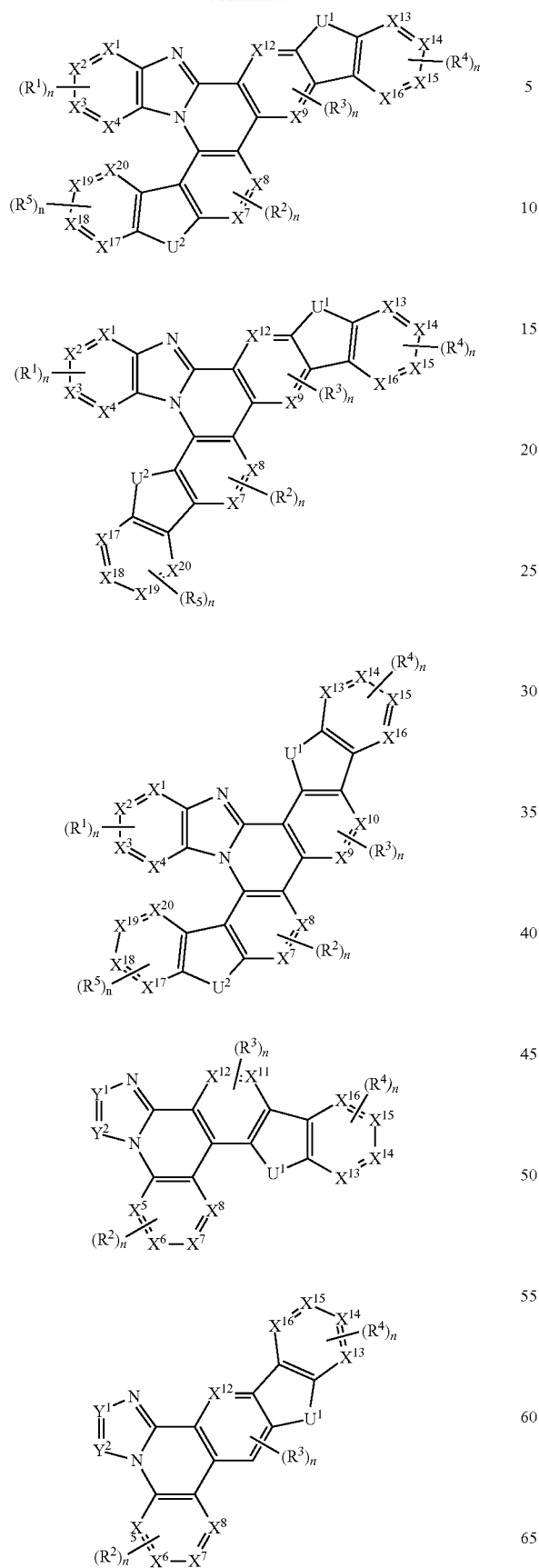
626
-continued
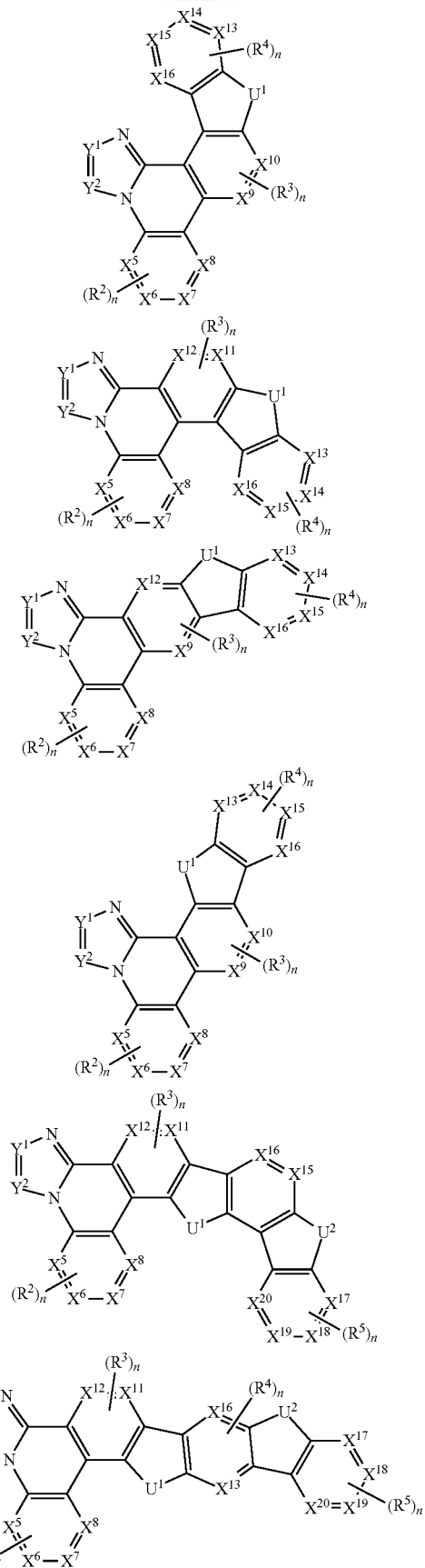

627
-continued
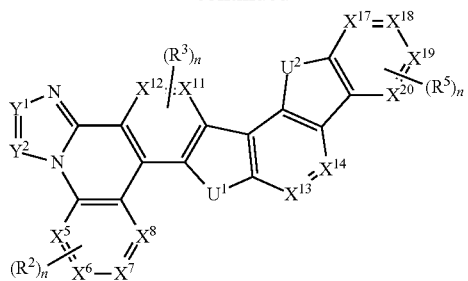
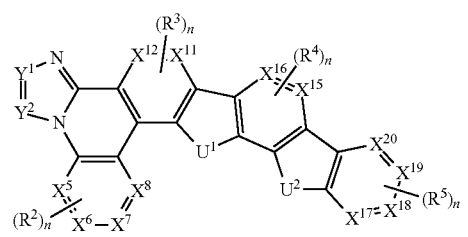
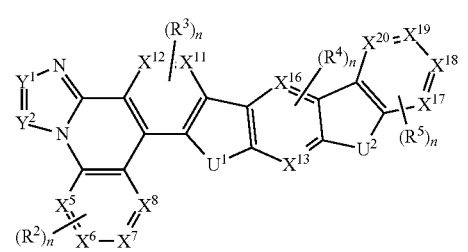
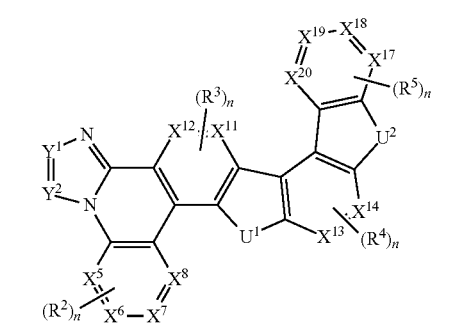
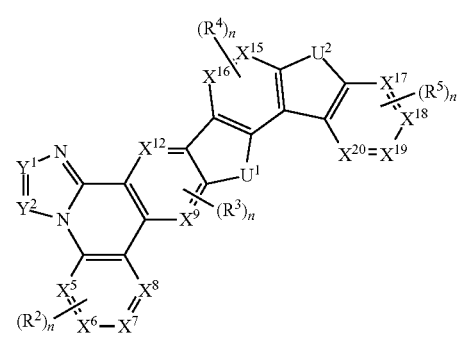
628
-continued
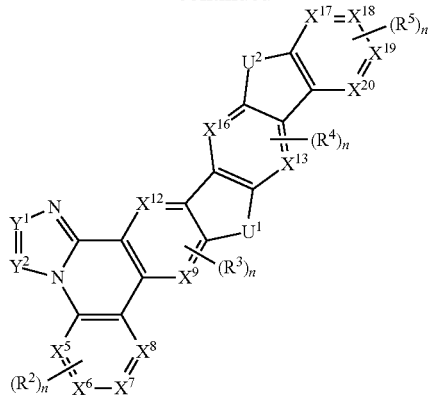
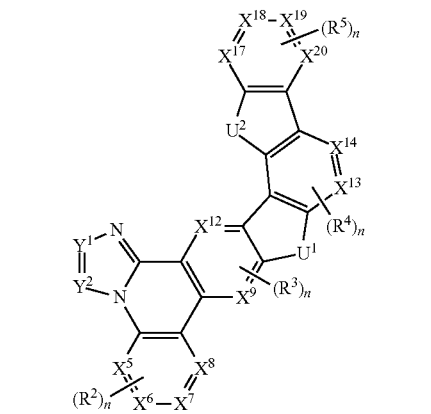
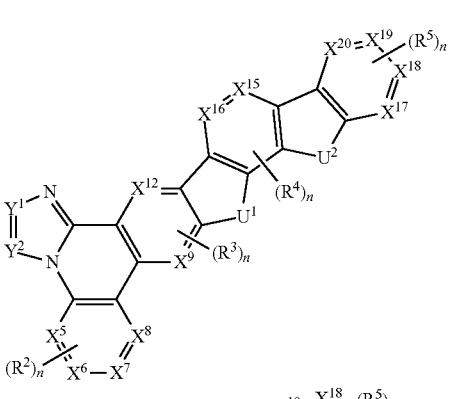
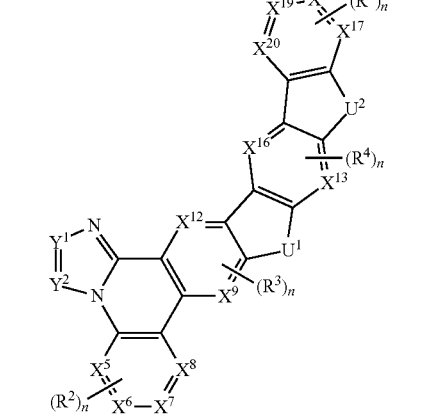

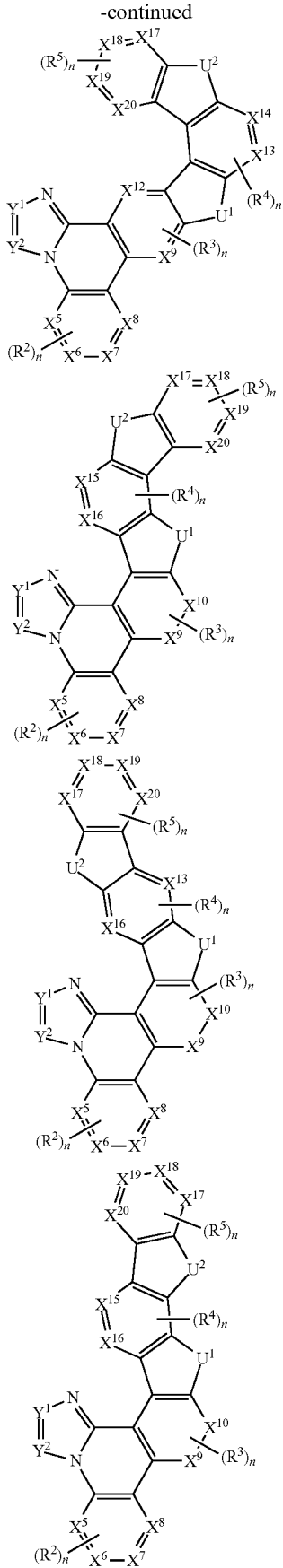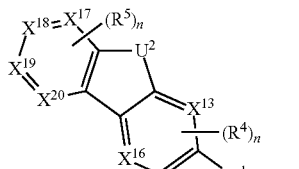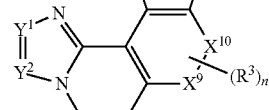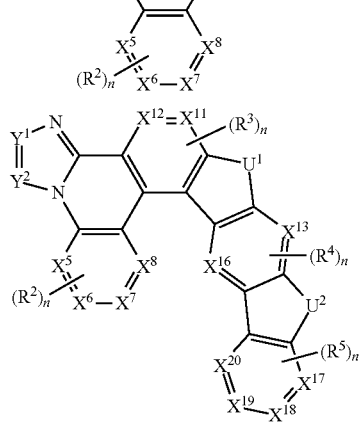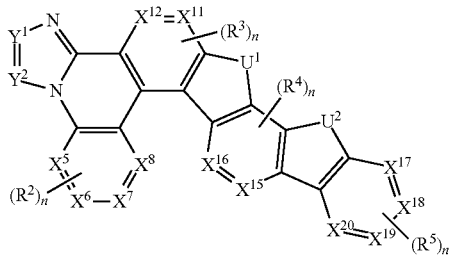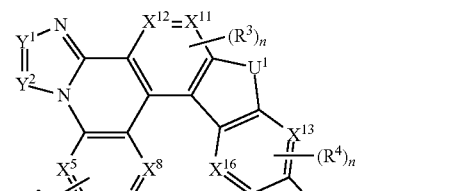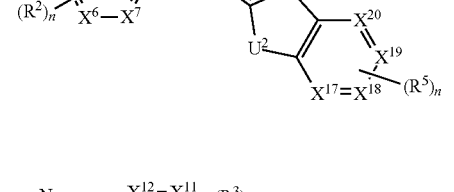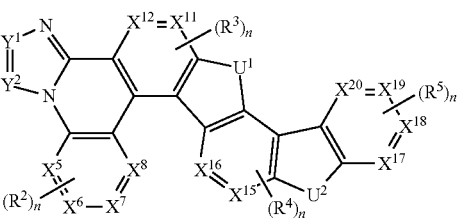

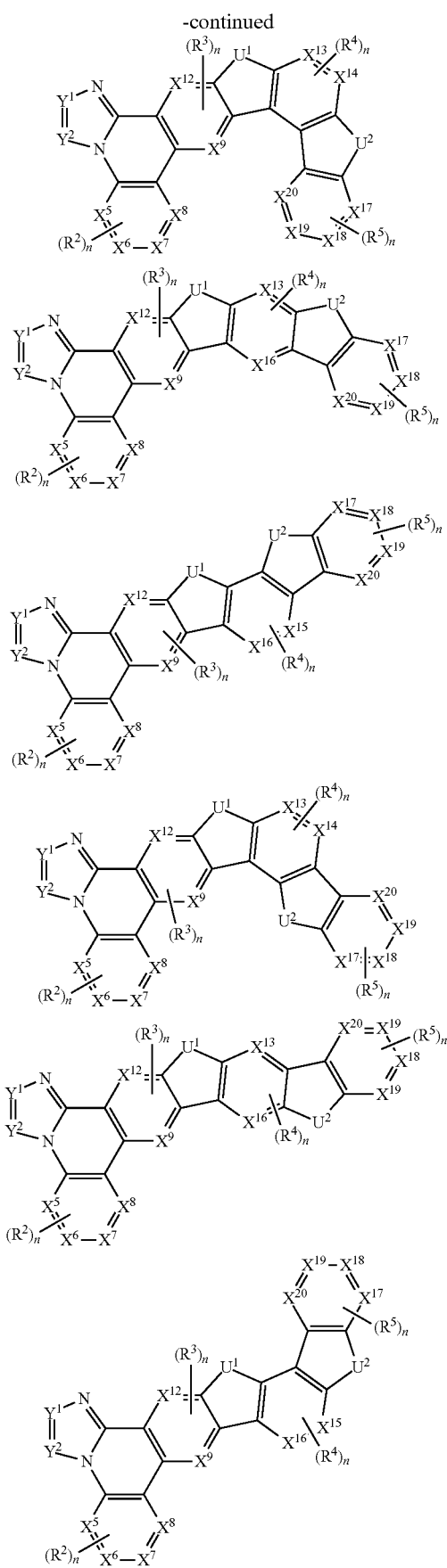
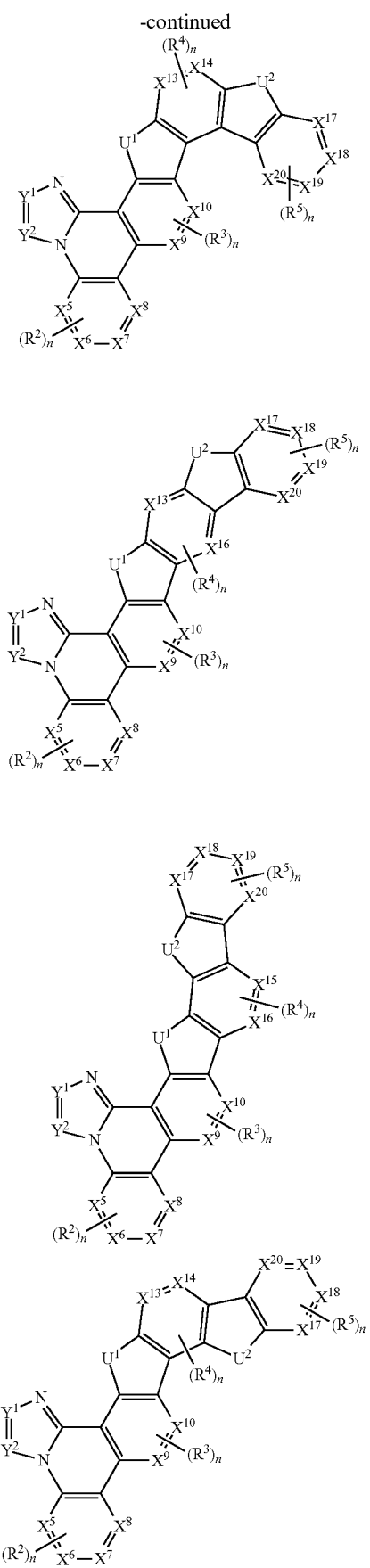

633
-continued
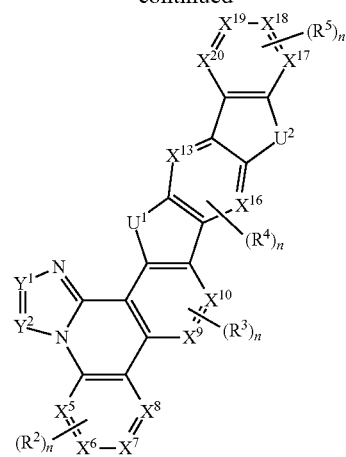
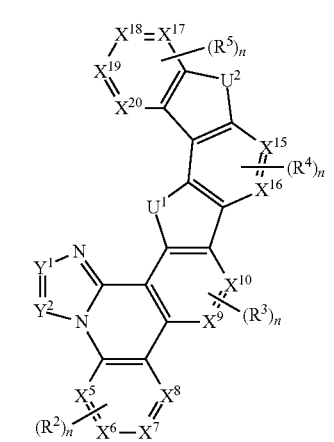
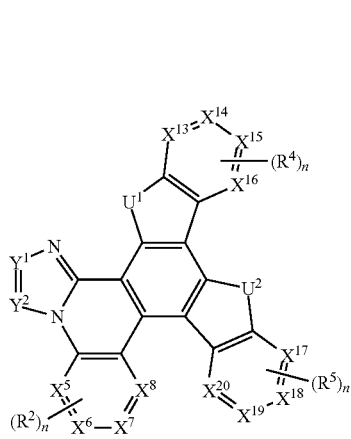
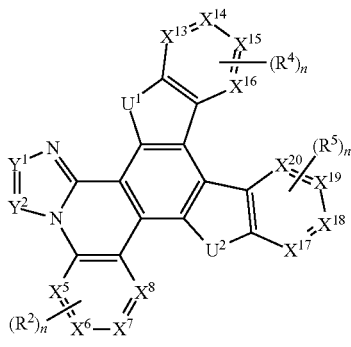
634
-continued
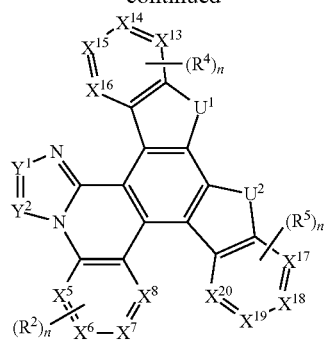
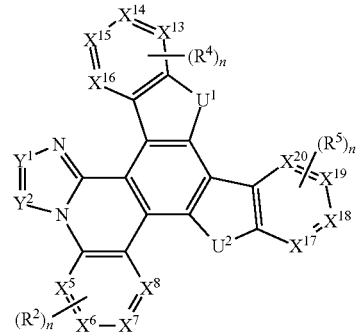
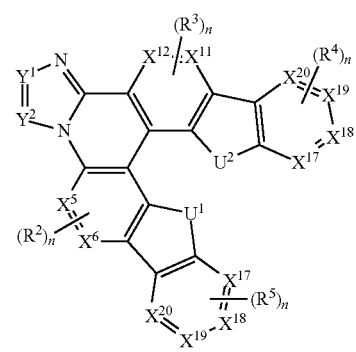
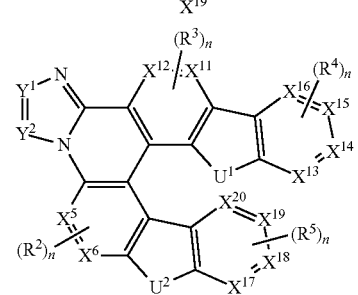
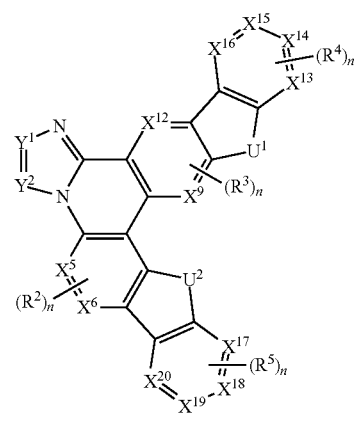

635
-continued
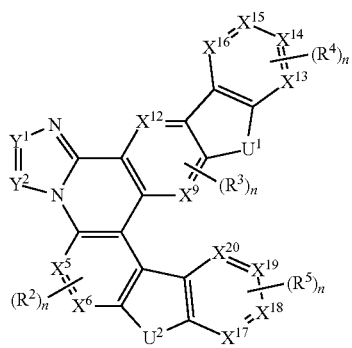
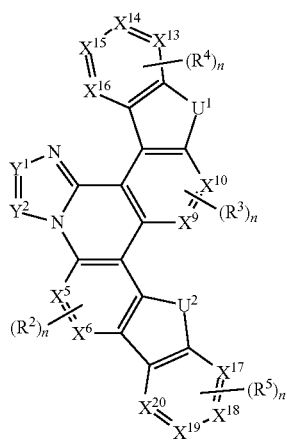
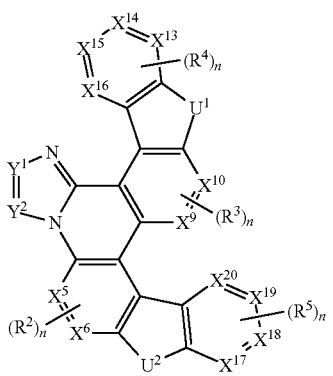
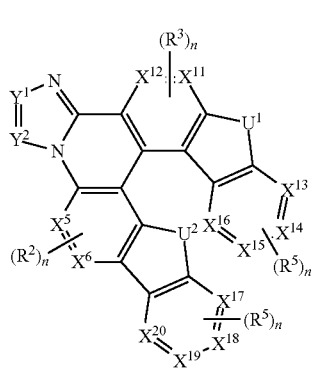
636
-continued
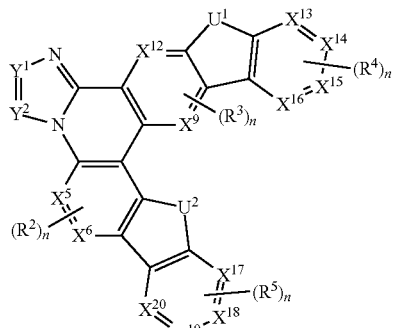
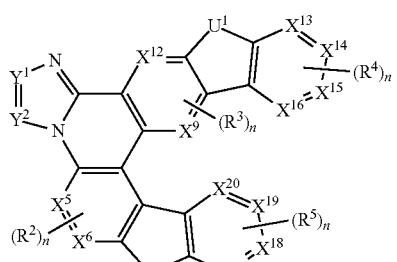
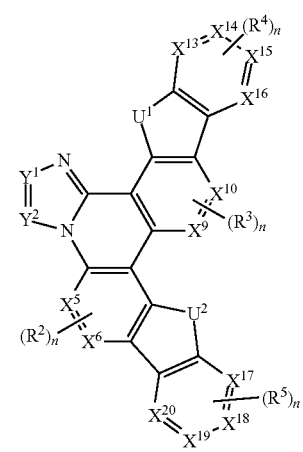
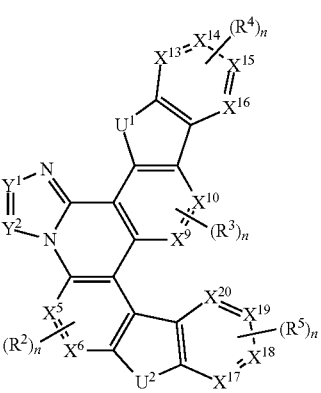

-continued
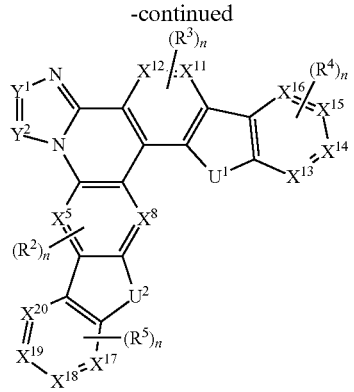
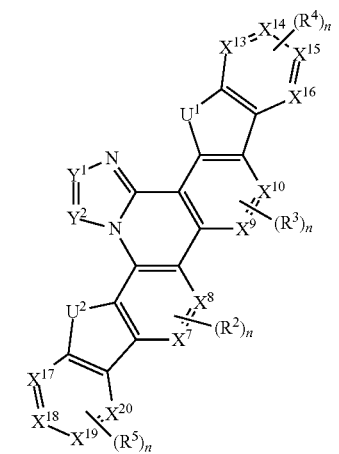
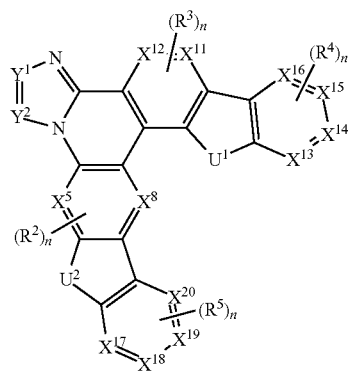
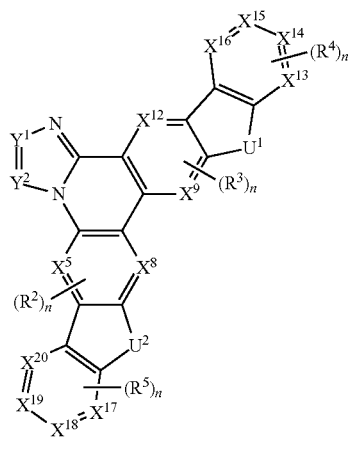
-continued
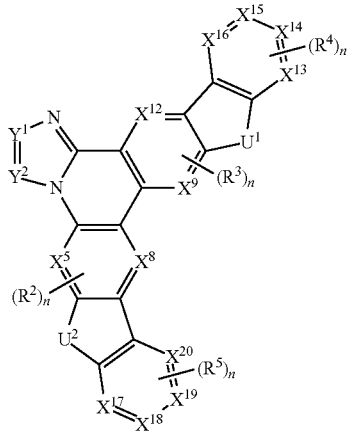
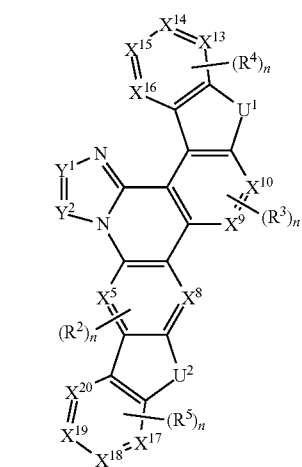
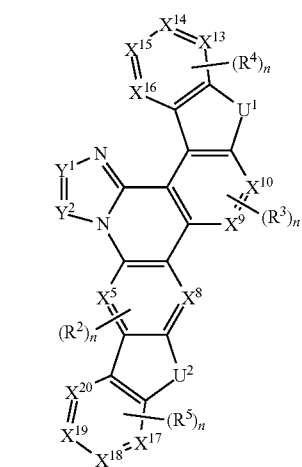
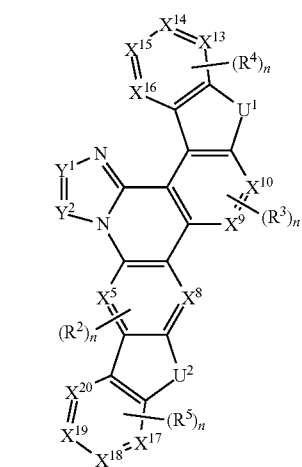

-continued
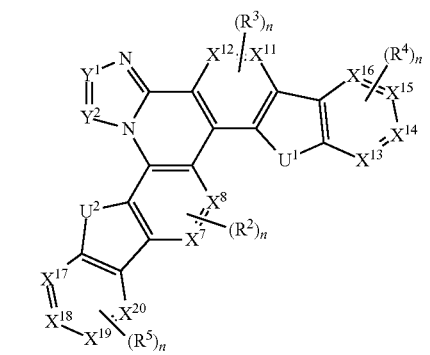
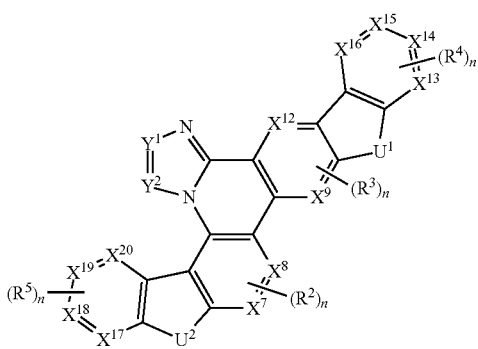
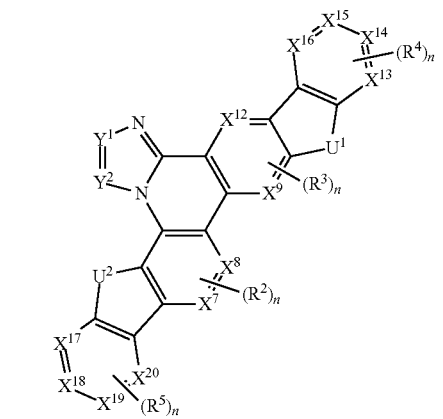
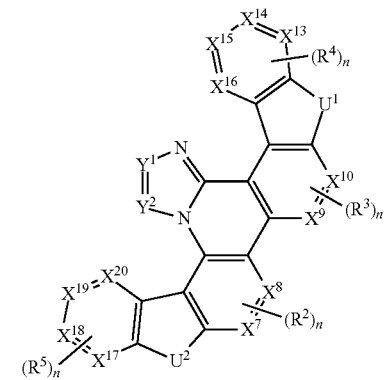
-continued
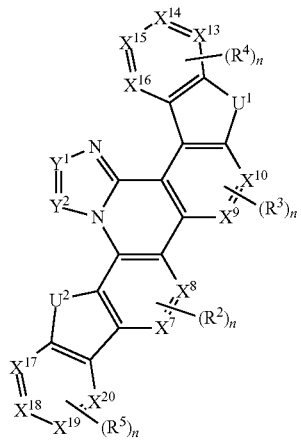
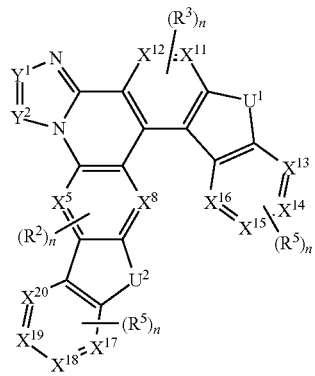
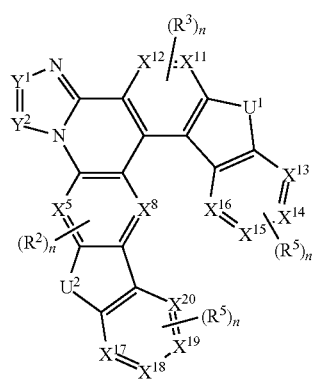
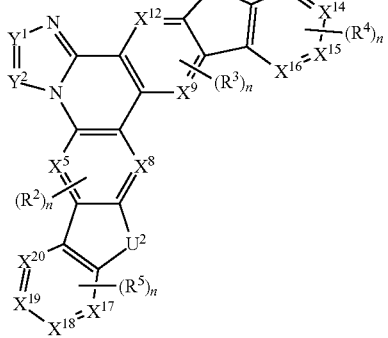

-continued
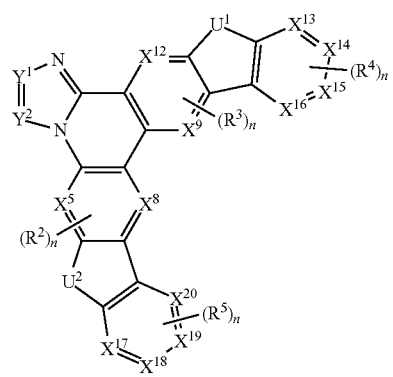
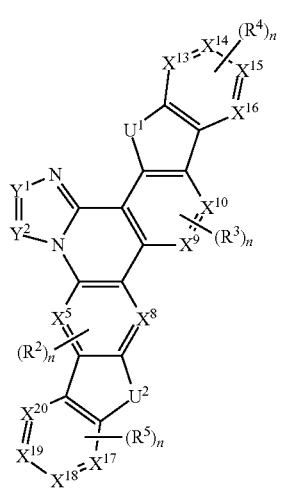
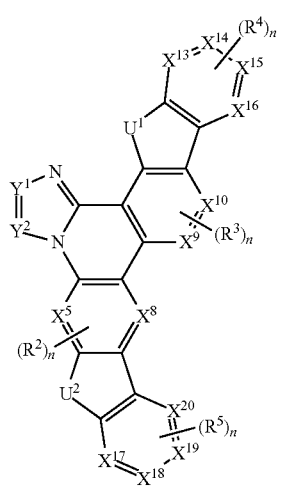
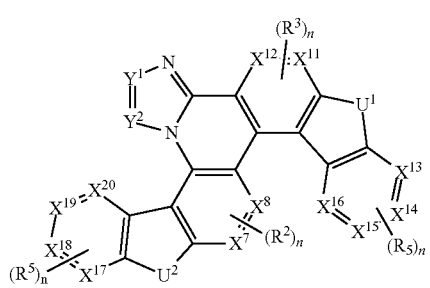
-continued
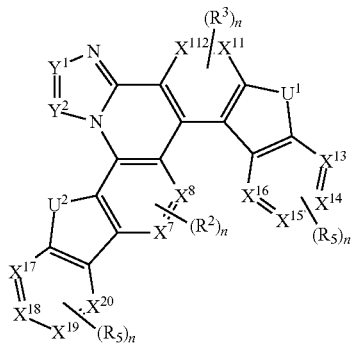
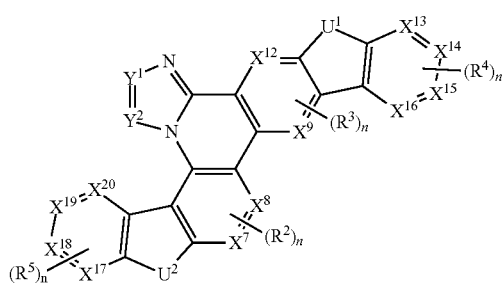
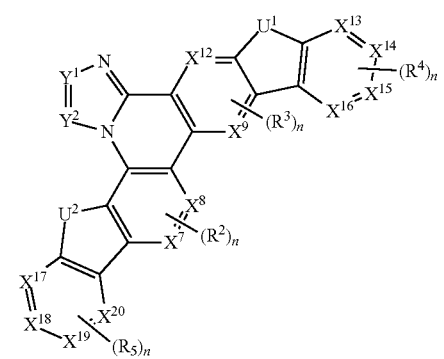
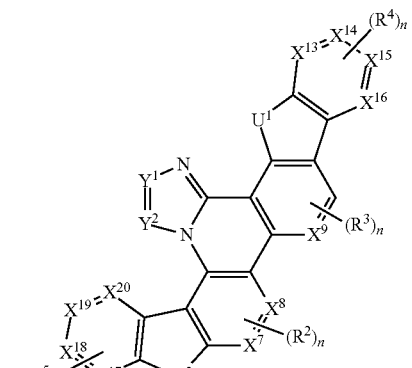
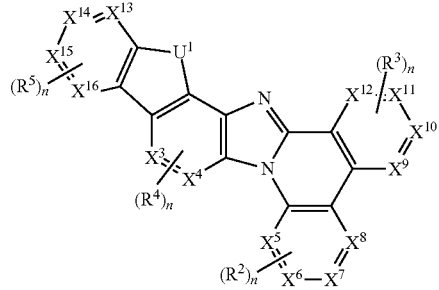

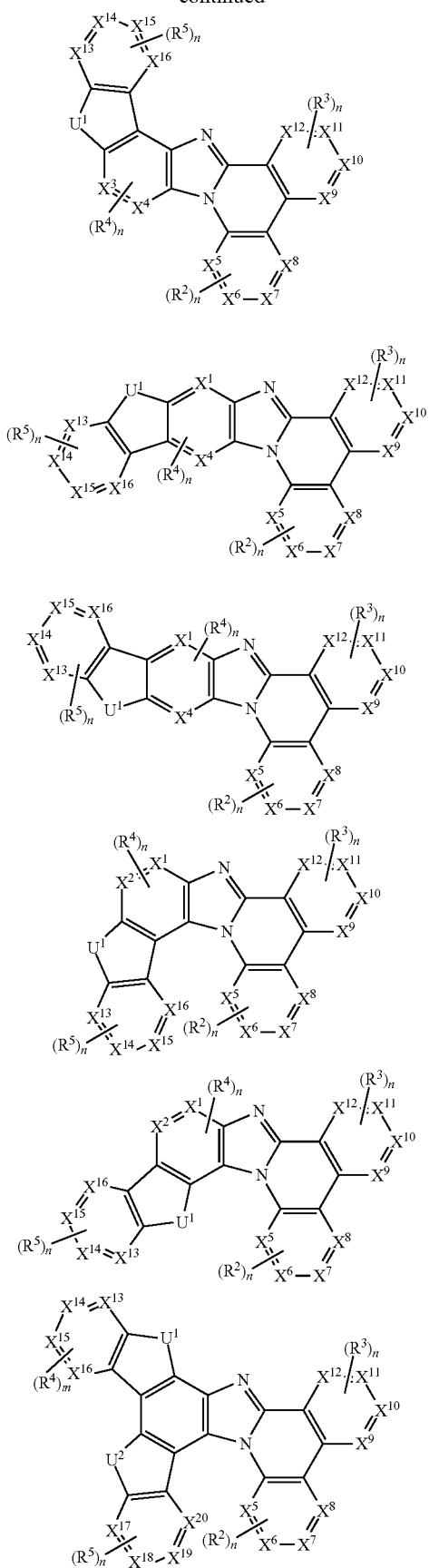
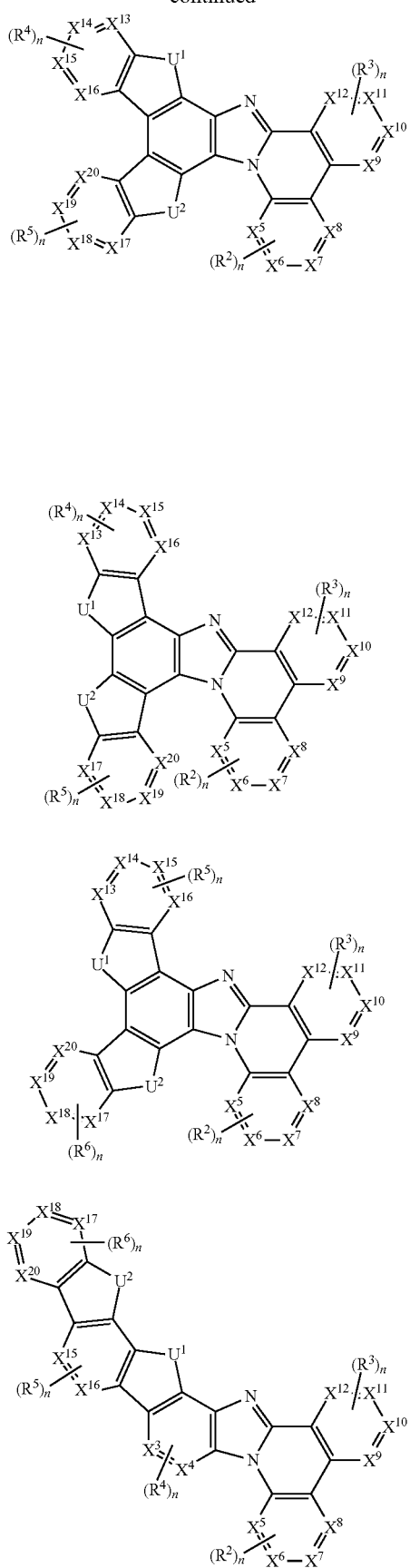

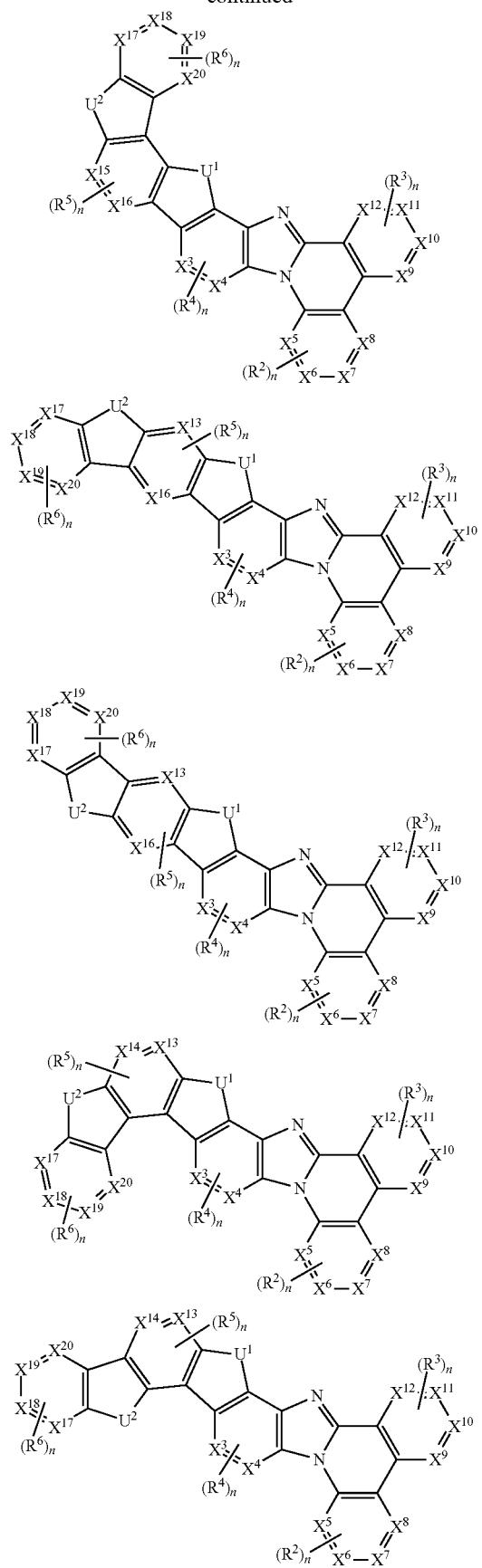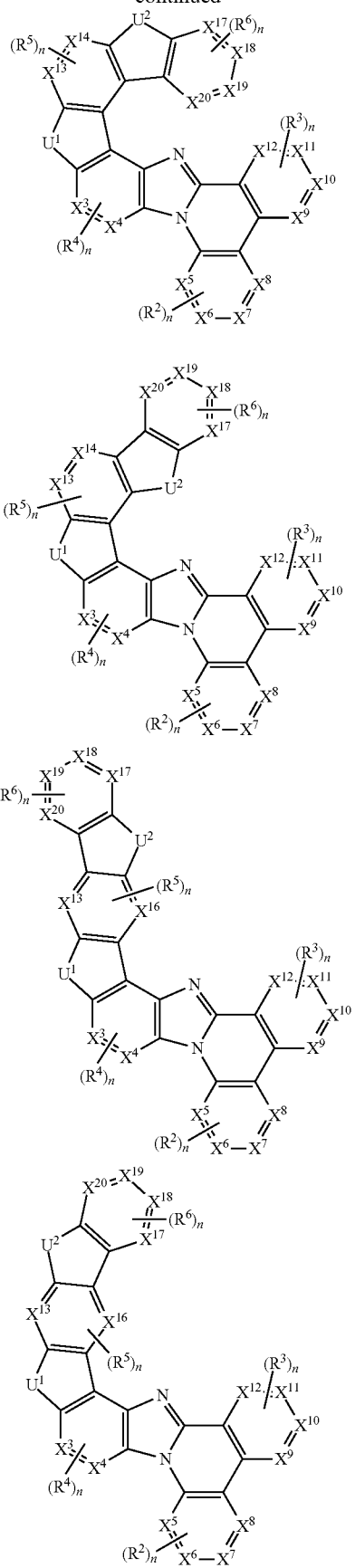

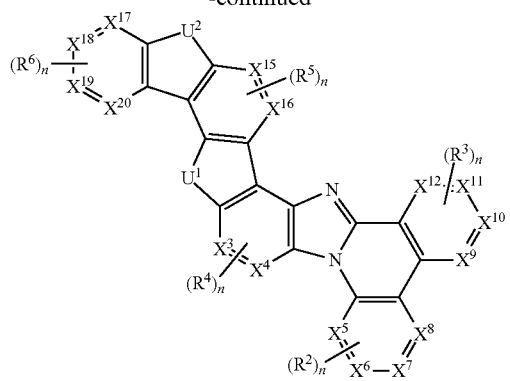
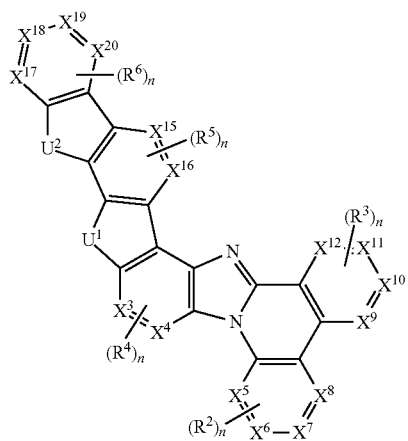
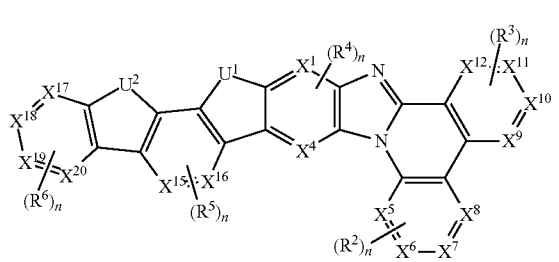
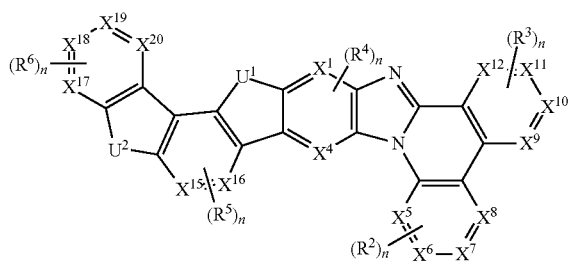
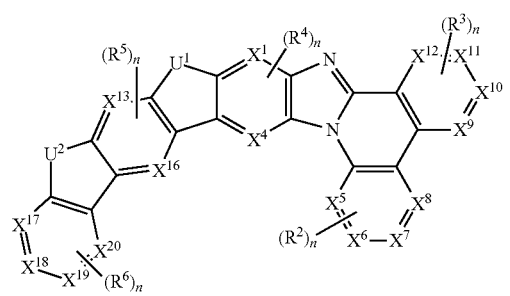
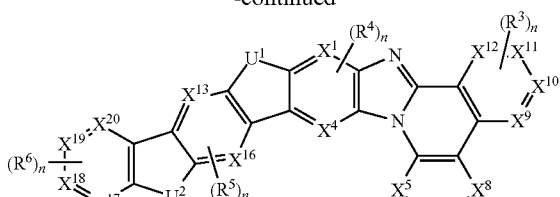
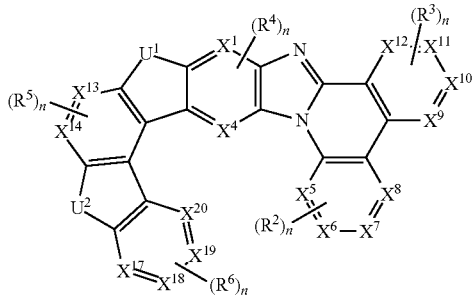
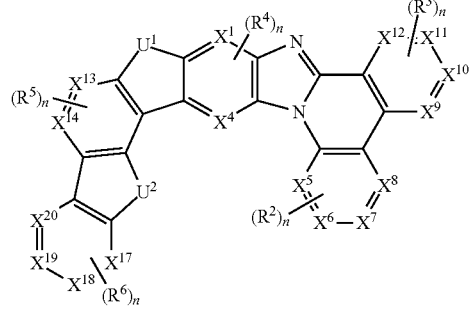
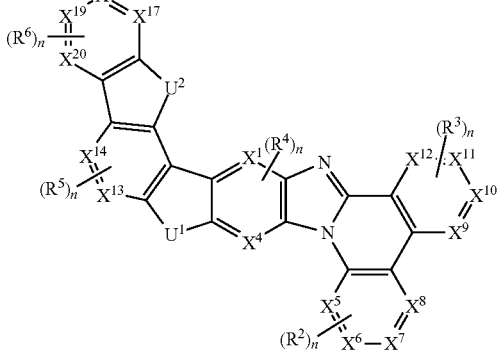
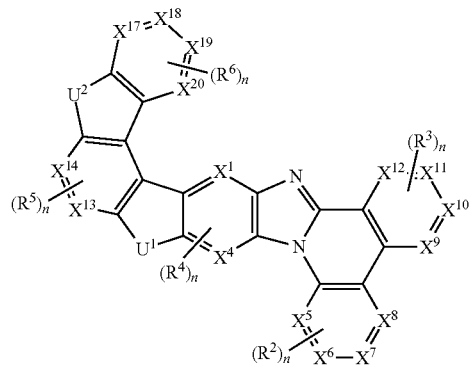

-continued
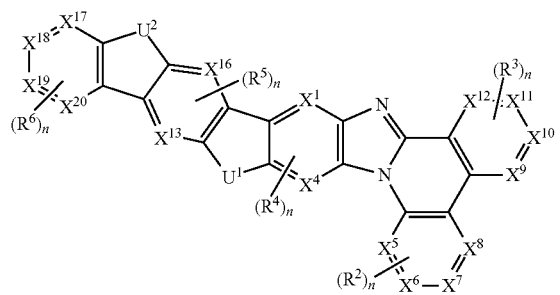
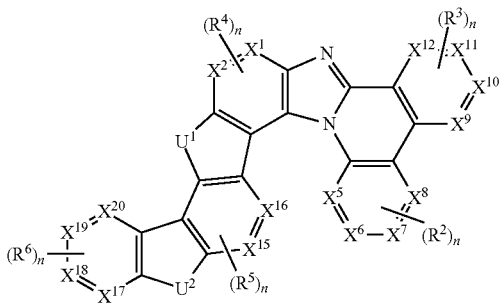
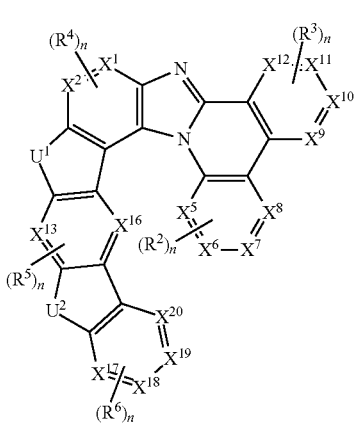
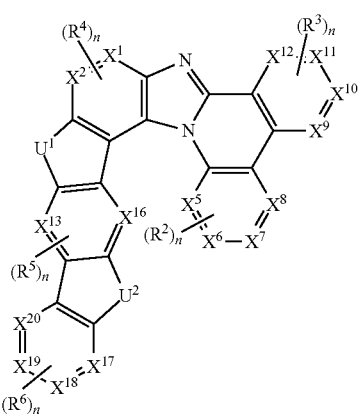
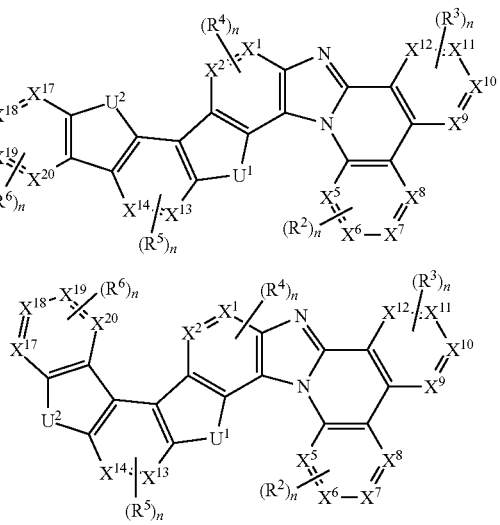

-continued
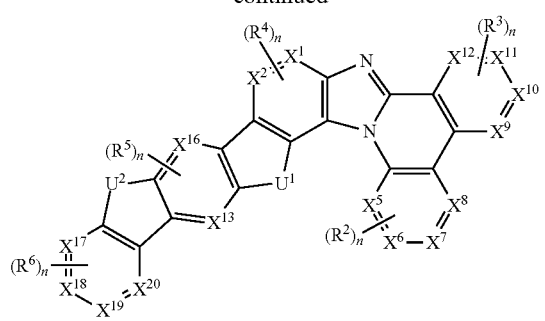
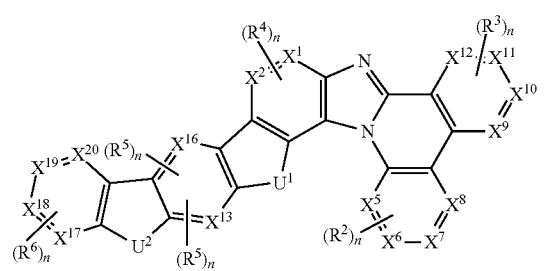
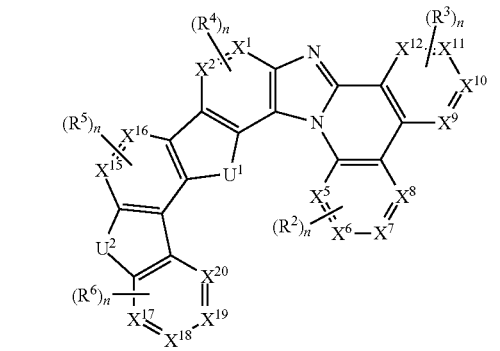
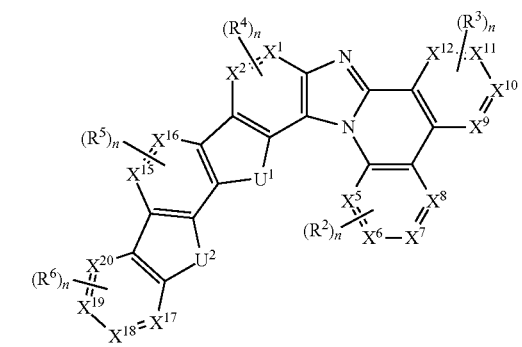
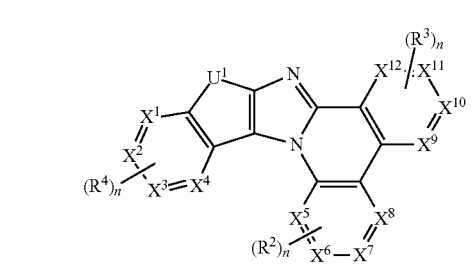
-continued
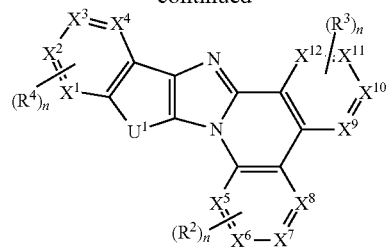
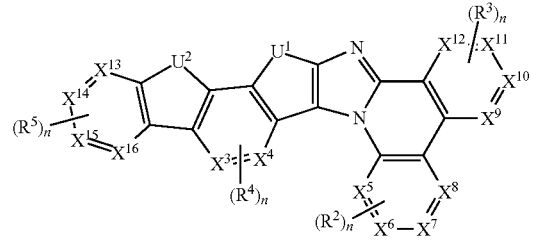
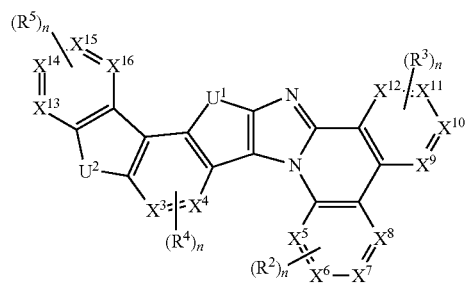
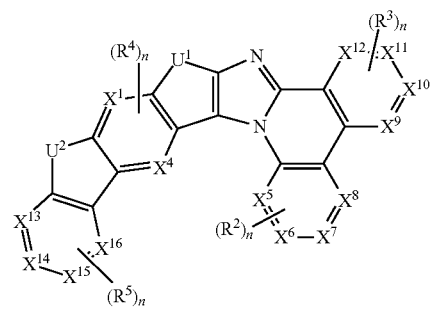
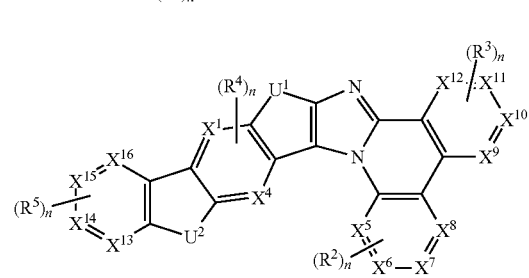
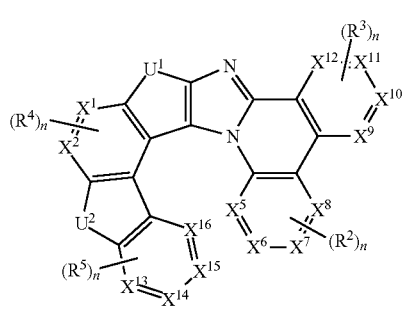

653
-continued
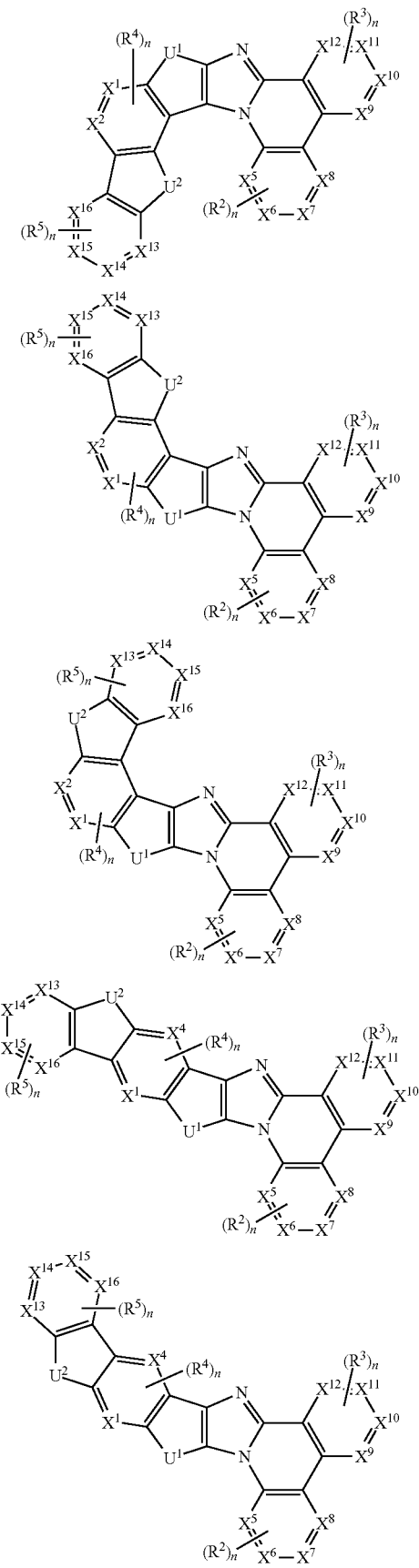
654
-continued
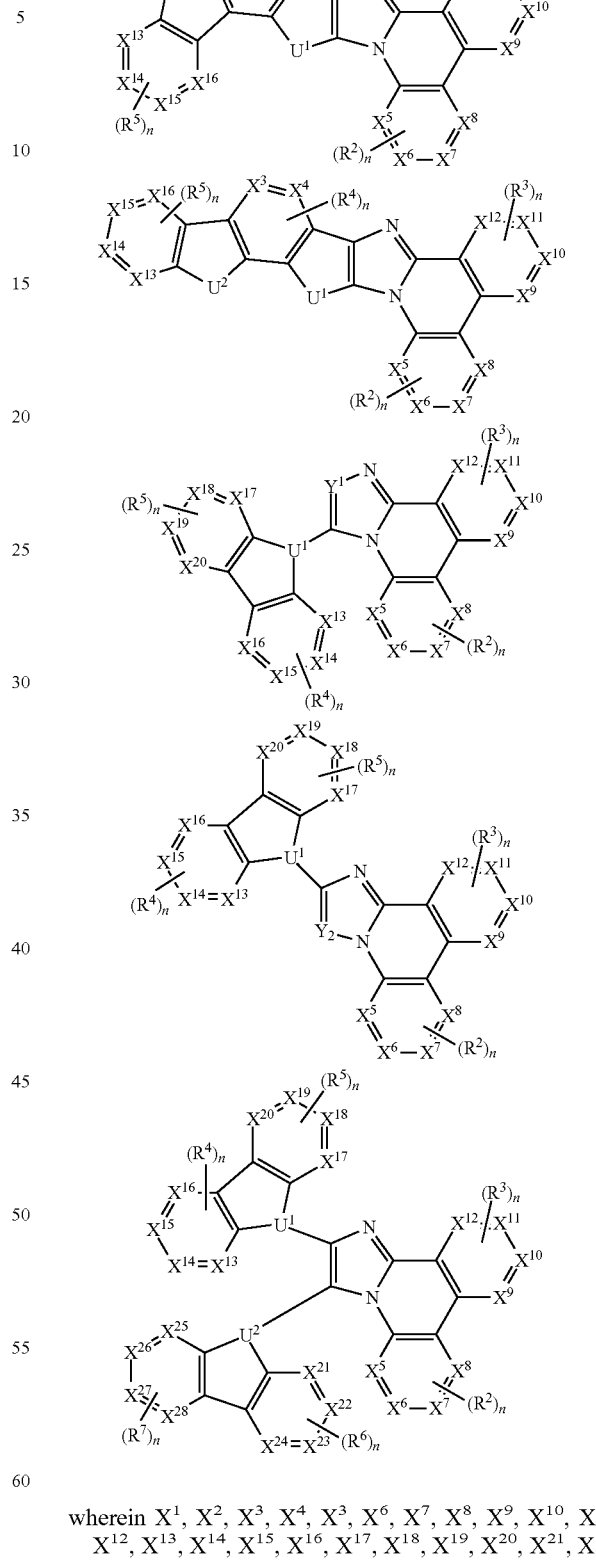
wherein $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$, $X^{25}$, $X^{26}$, $X^{27}$, and $X^{28}$ each independently represents C, N, Si, B, or P;
$Y^1$ and $Y^2$ each independently represents C, N, Si, B, or P each occurrence of n is independently an integer, valency permitting;

each $U^1$ and $U^2$ represents, valency permitting, O, S, Se, N, P, As, B, Al, Bi, P=O, As=O, Bi=O, $CR^{21}$, $CR^{21}R^{22}$, C=O, $SiR^{21}$, $SiR^{21}R^{22}$, $GeR^{21}$, $GeR^{21}R^{22}$, $NR^{21}$, $PR^{21}$, $PR^{21}R^{22}$, $R^{21}$P=O, $AsR^{21}$, $R^{21}$As=O, S=O, $SeO_2$, S=O, $SeO_2$, $BR^{21}$, $BR^{21}R^{22}$, $AlR^{21}$, $AlR^{21}R^{22}$, $R^{21}$Bi=O, or $BiR^{21}$, each occurrence of $R^1$, $R^2$, $R^3$, $R^4$, $R^5$, $R^6$, $R^7$, $R^8$, $R^{21}$ and $R^{22}$ independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

9. The compound of claim 1, wherein the compound is represented by one of the following structures:

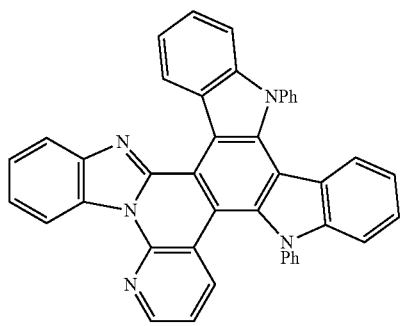

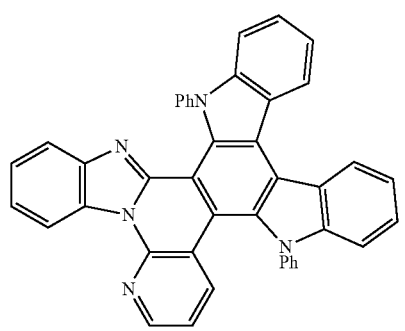

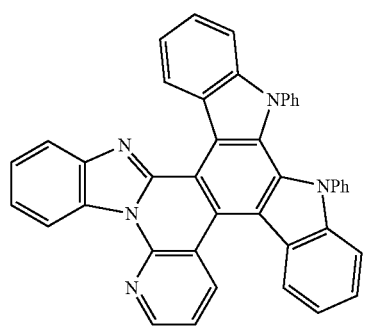

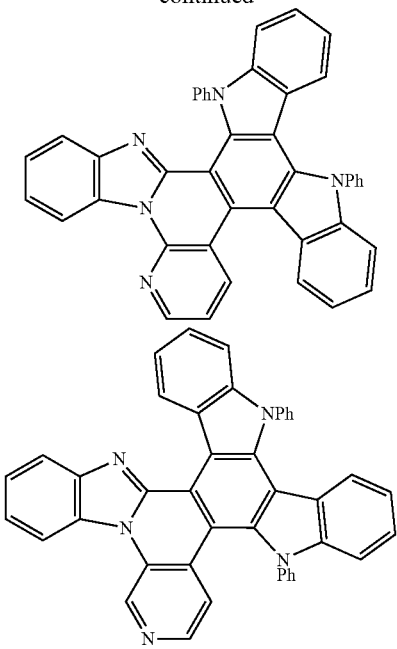

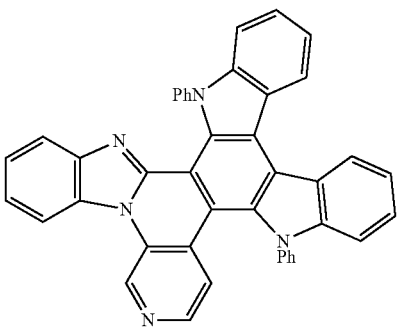

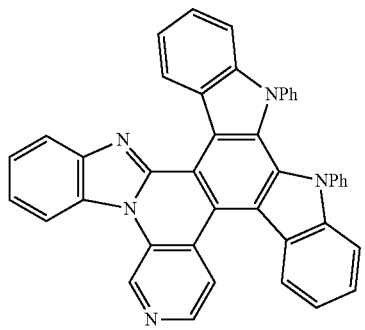

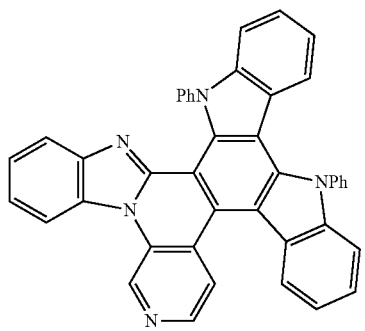

657
-continued
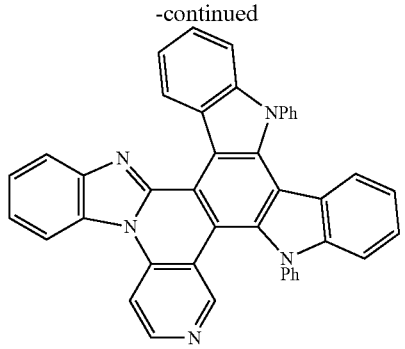
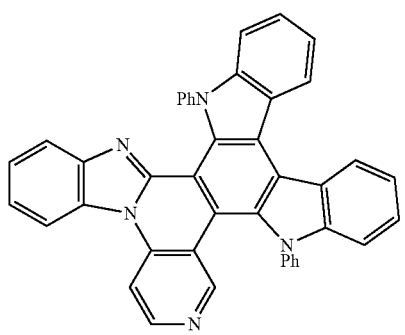
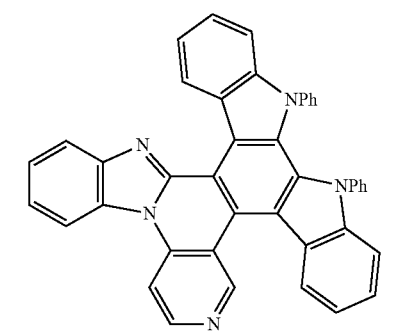
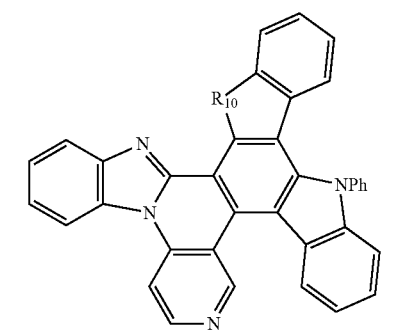
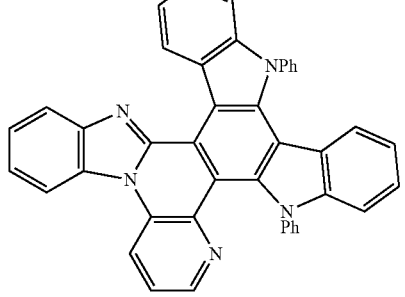
658
-continued
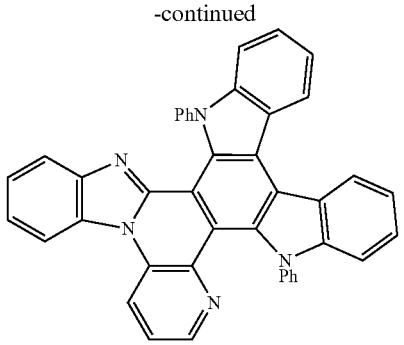
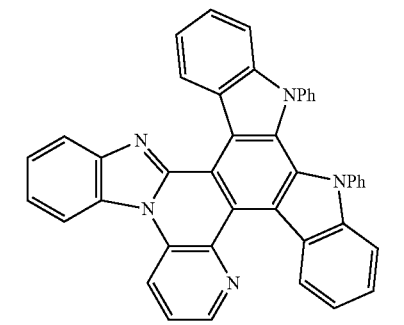
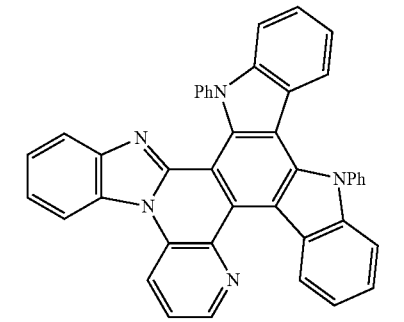
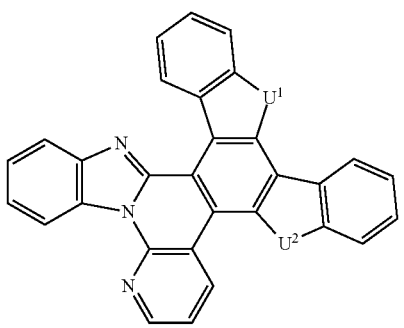
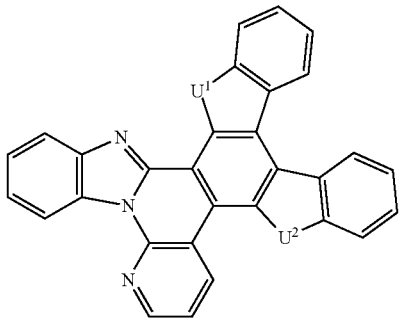

659
-continued
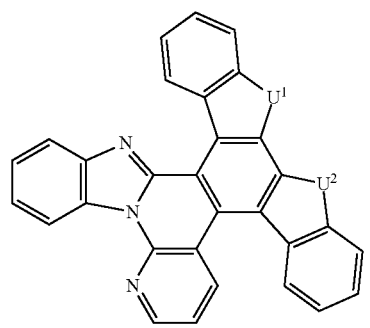
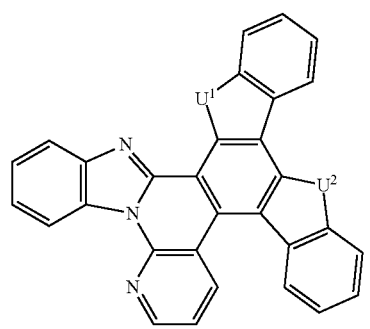
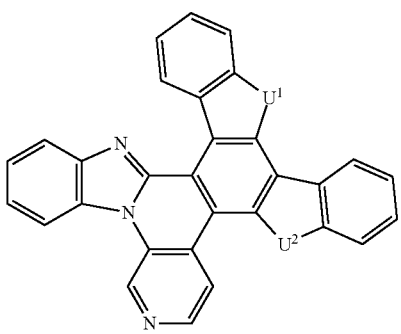
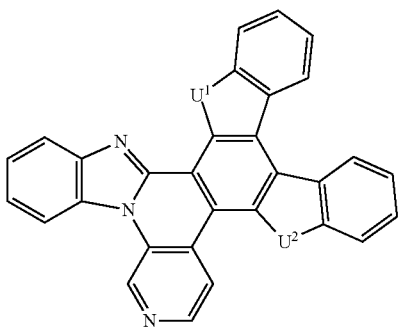
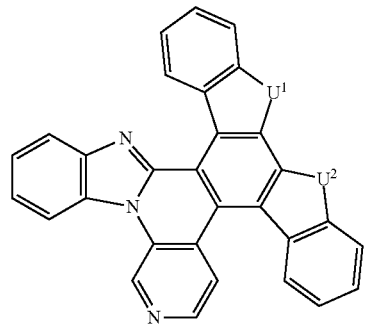
660
-continued
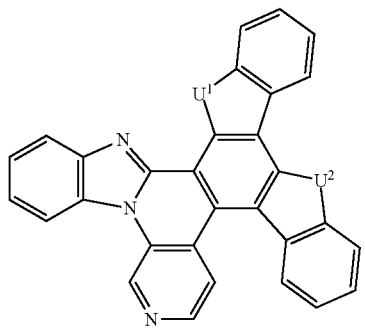
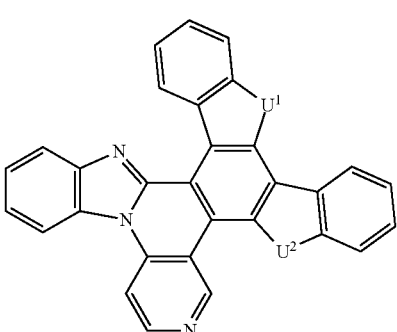
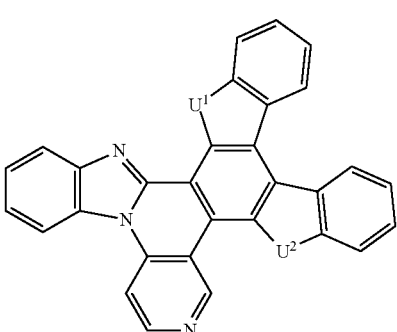
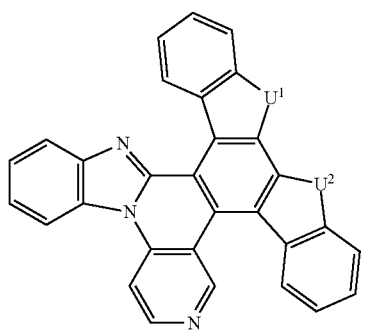
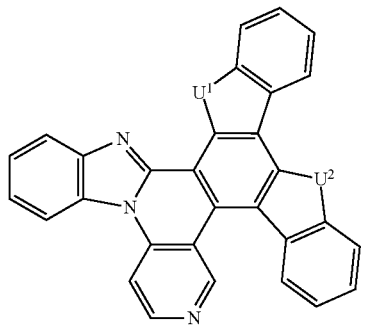

661
-continued
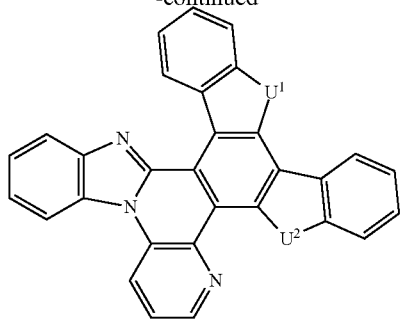
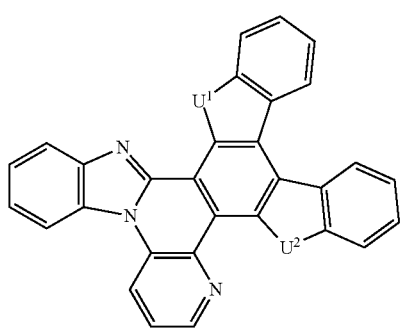
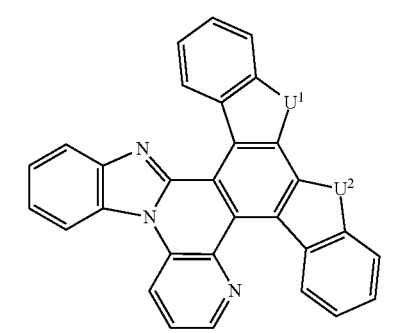
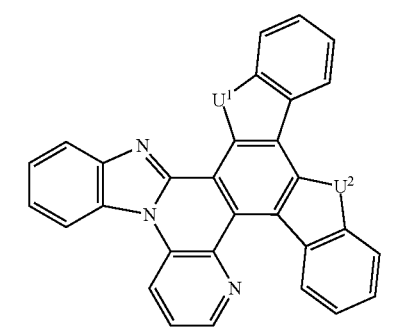
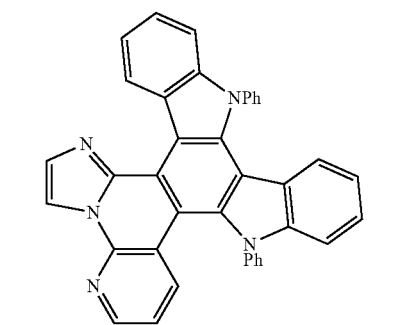
662
-continued
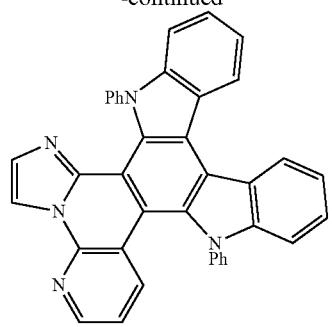
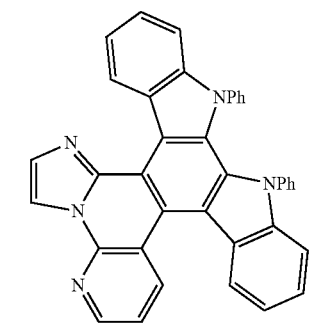
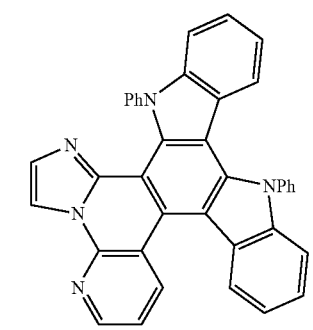
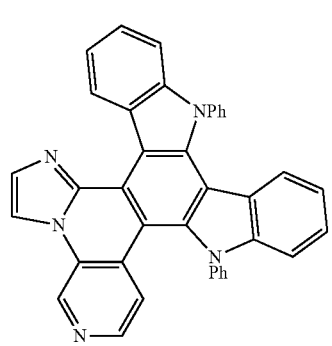
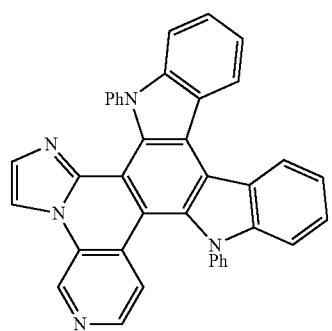

663
-continued
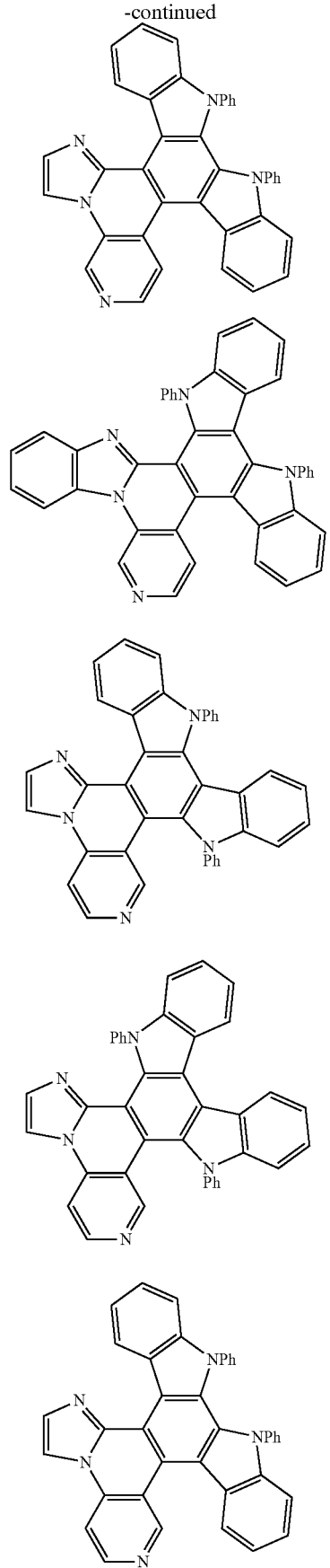
664
-continued
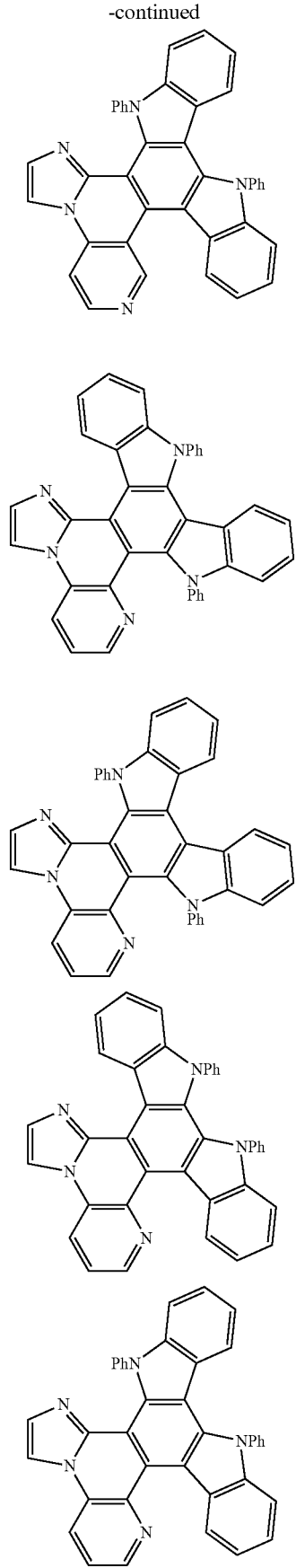

665
-continued
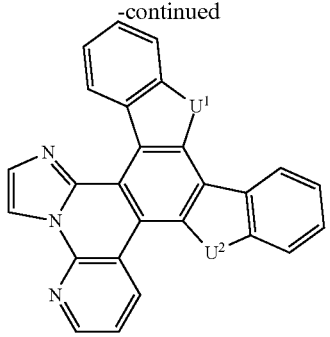
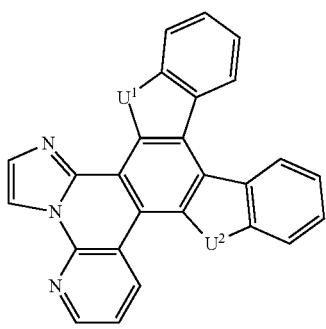
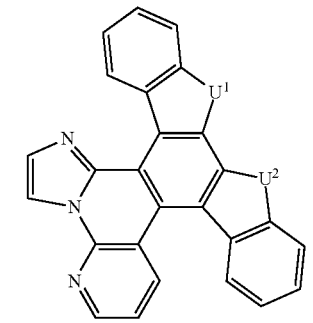
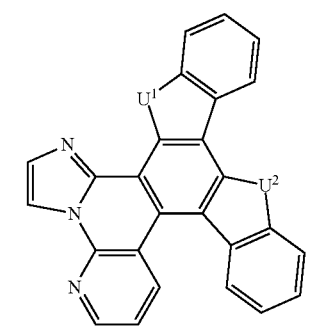
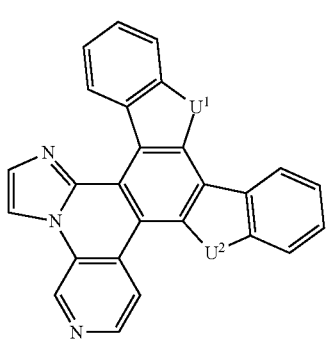
666
-continued
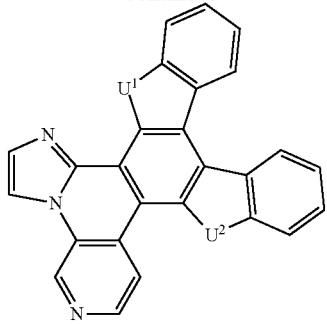
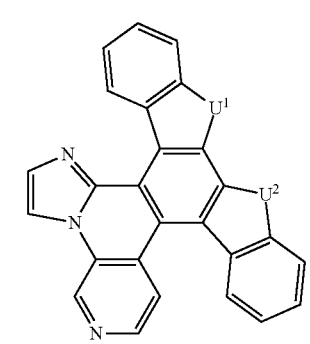
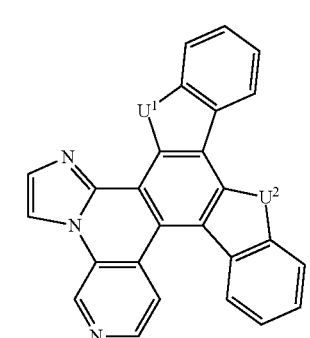
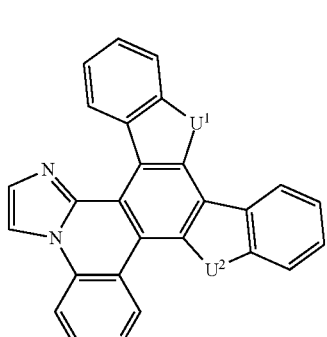
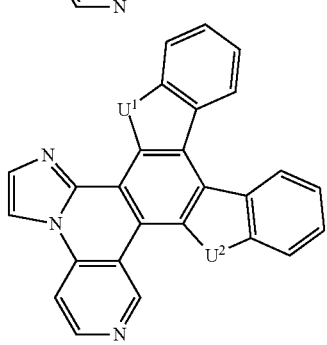

667
-continued
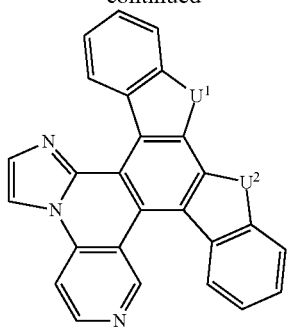
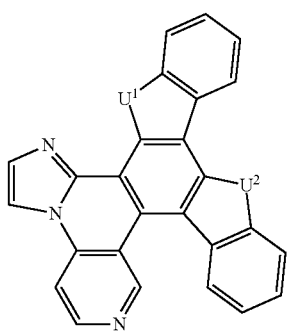
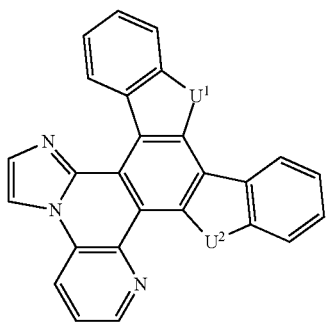
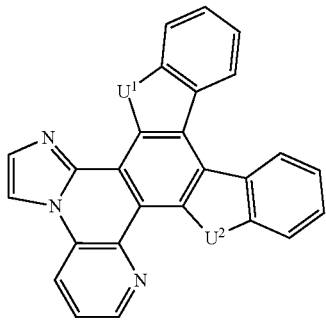
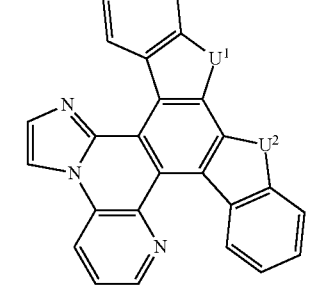
668
-continued
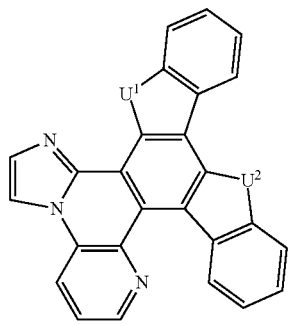
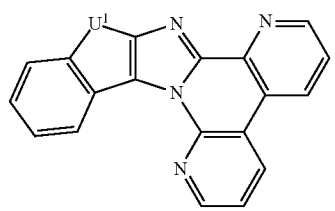
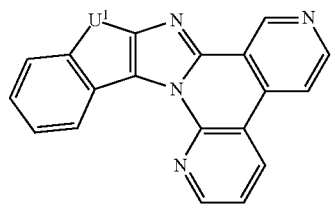
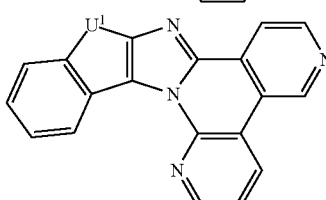
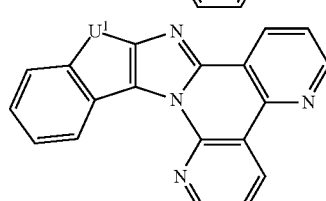
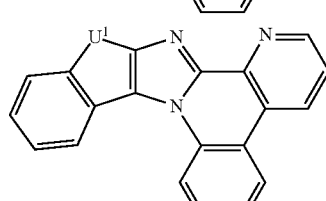
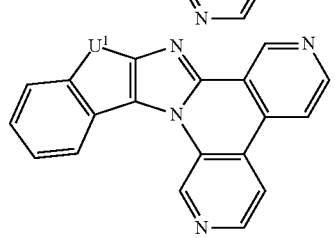

669
-continued
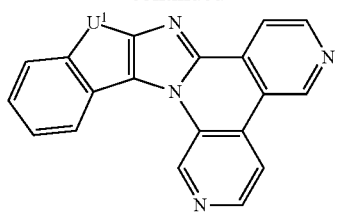
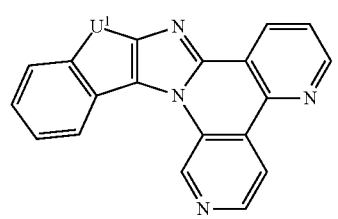
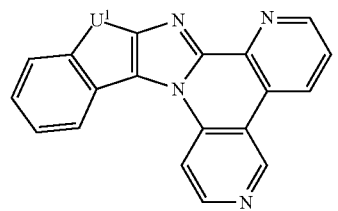
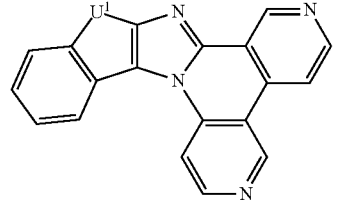
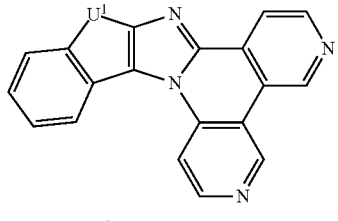
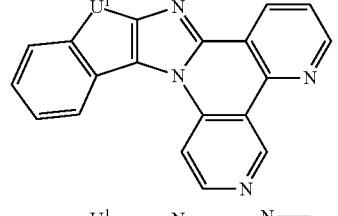
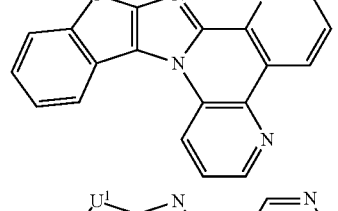
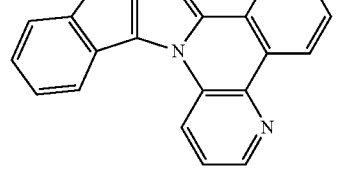
670
-continued
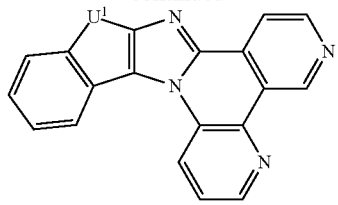
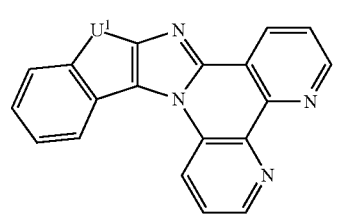
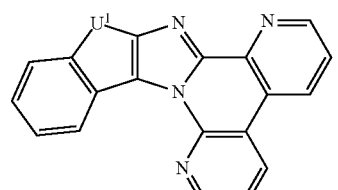
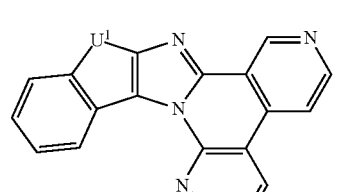
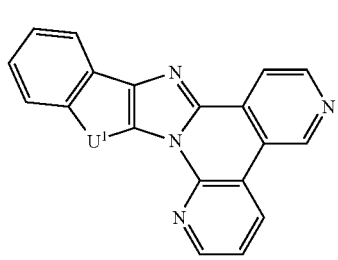
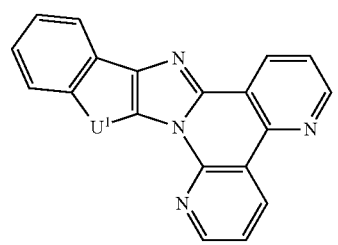
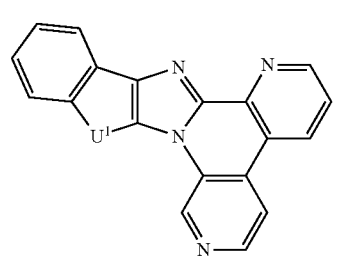

671
-continued
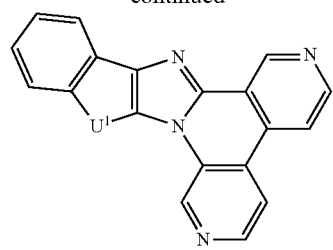
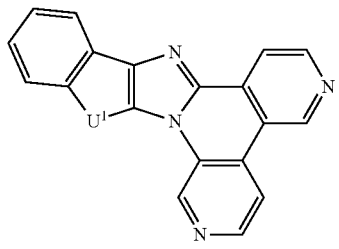
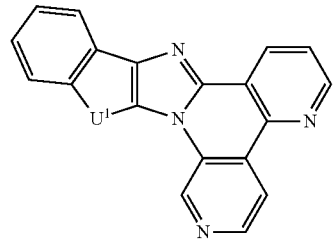
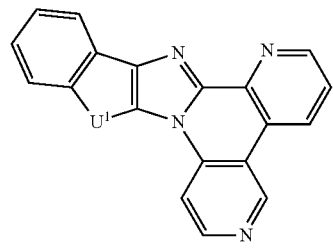
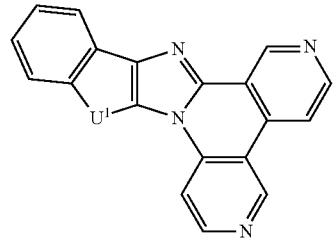
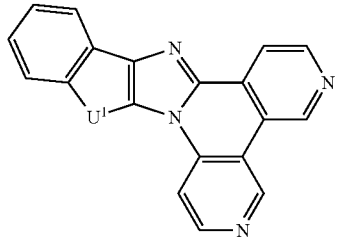
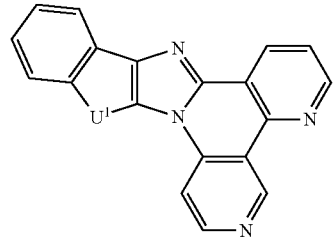
672
-continued
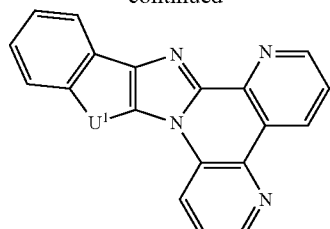
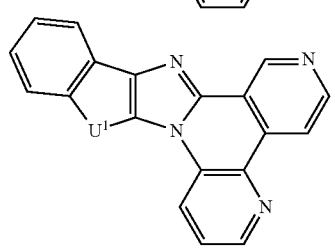
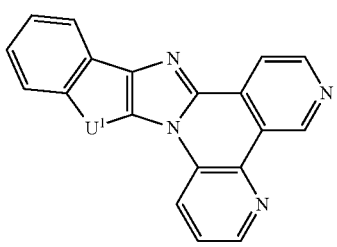
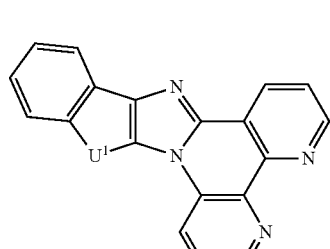
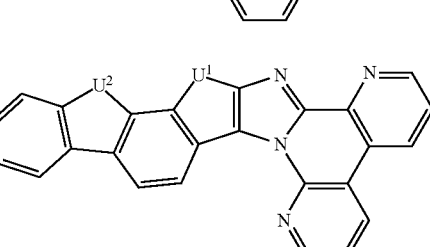
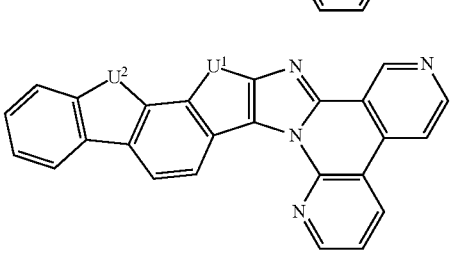
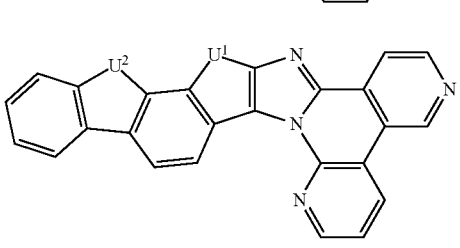

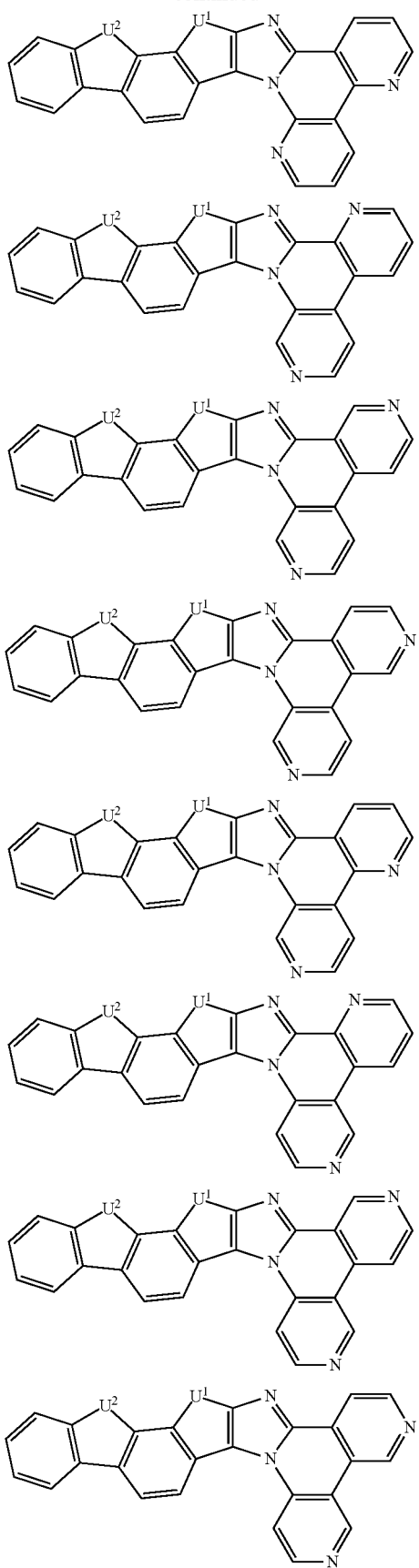
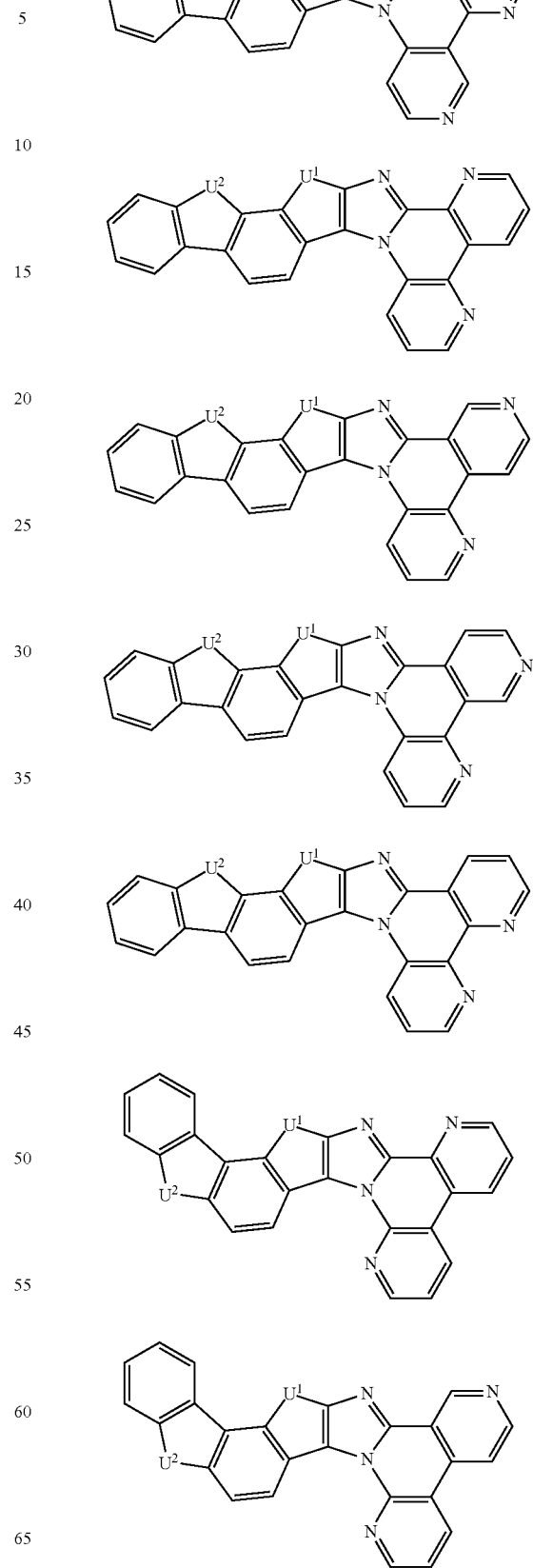

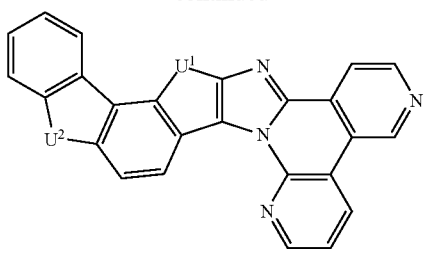
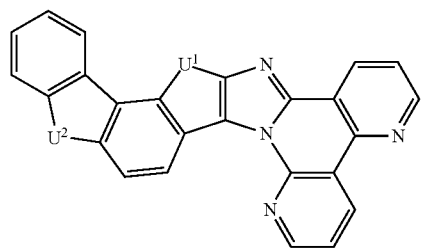
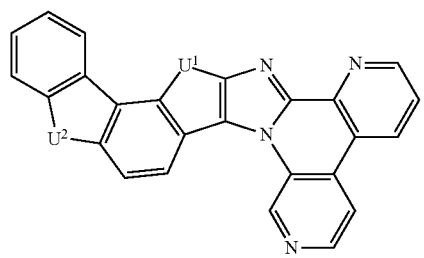
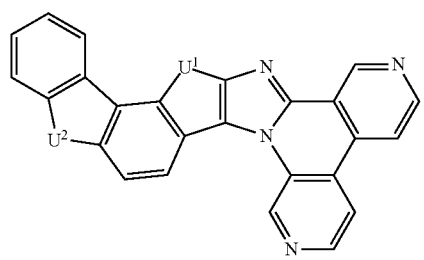
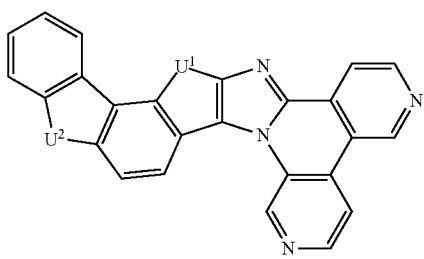
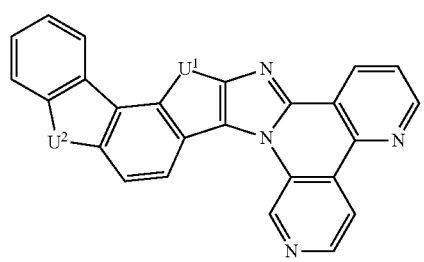
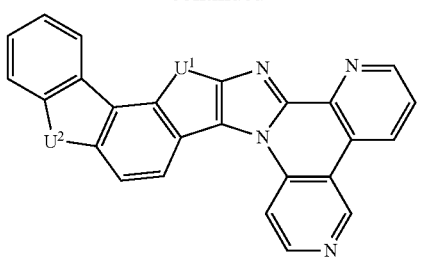
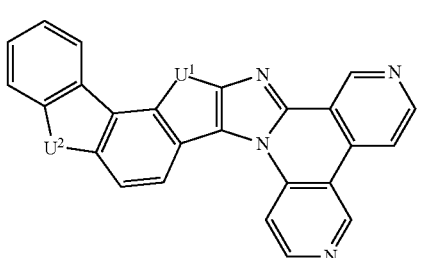
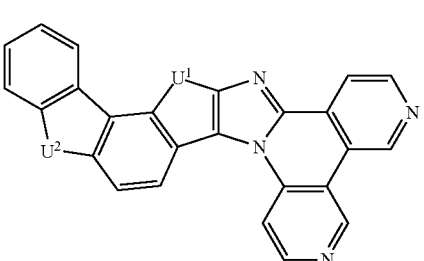
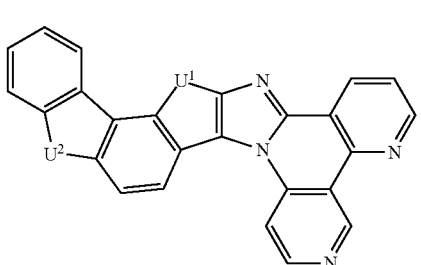
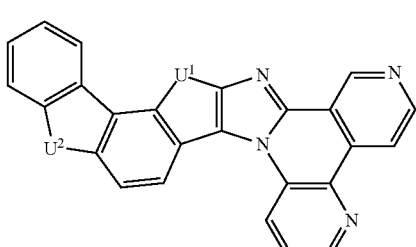
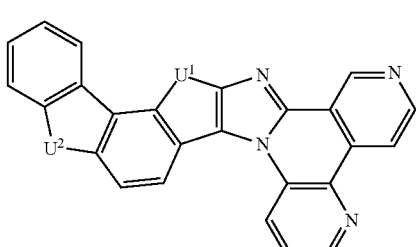

677
-continued
678
-continued
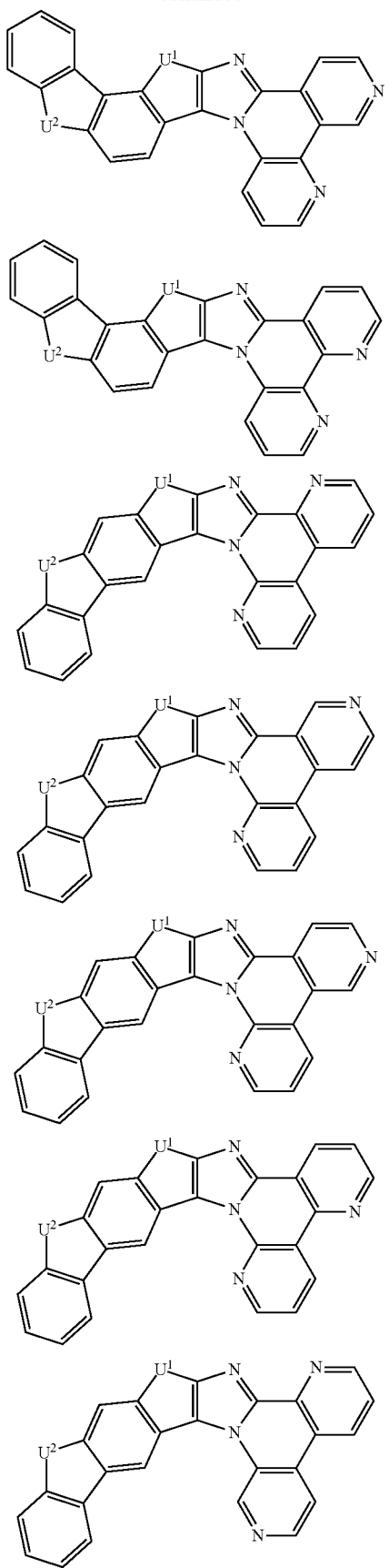
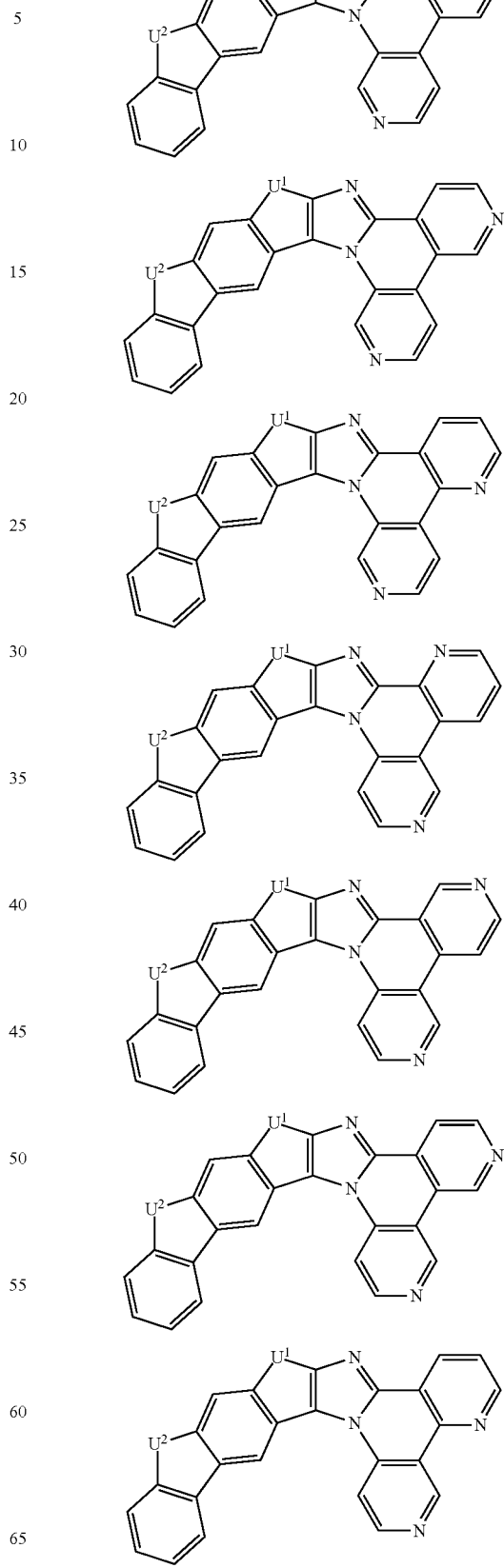

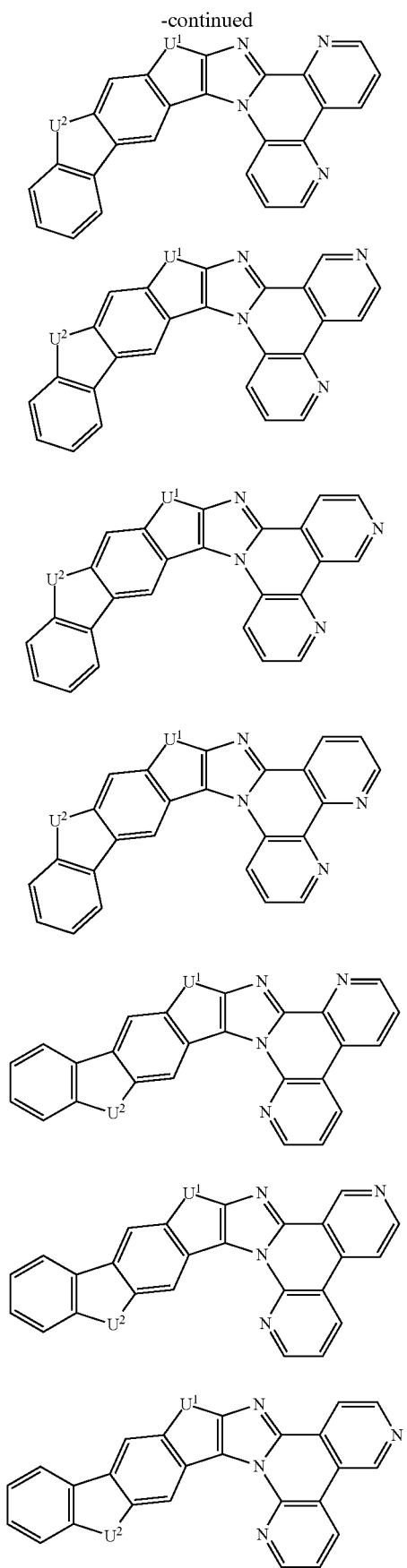
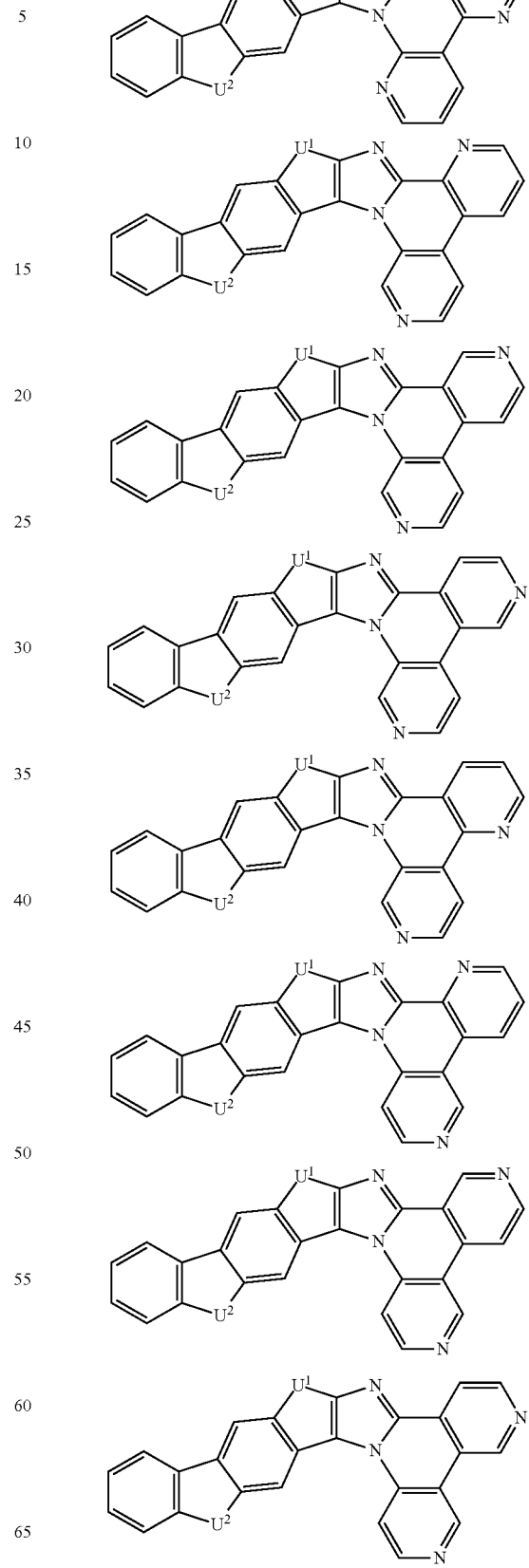

681
-continued
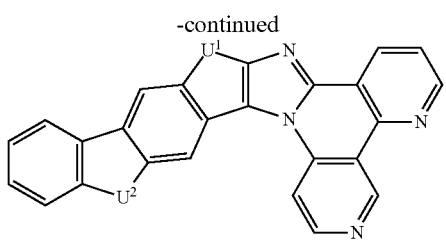
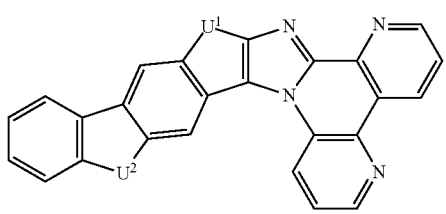
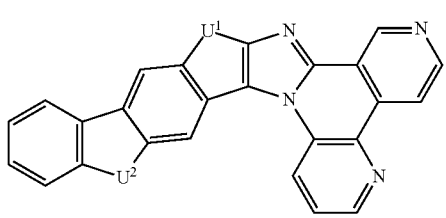
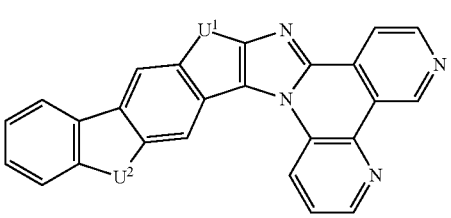
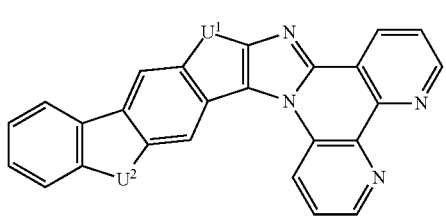
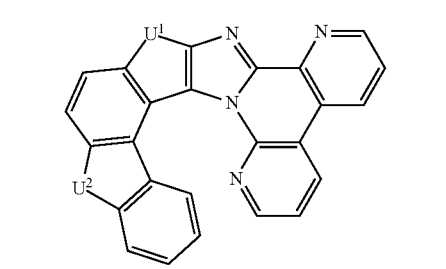
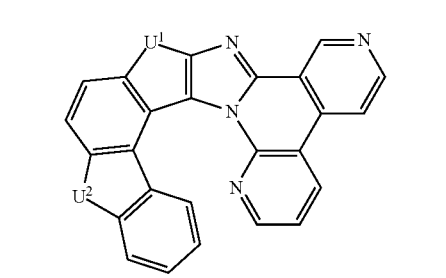
682
-continued
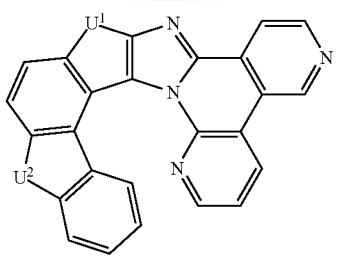
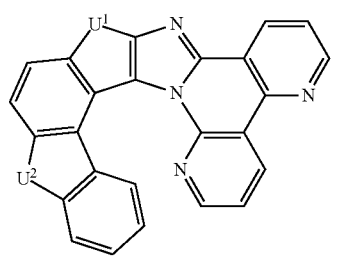
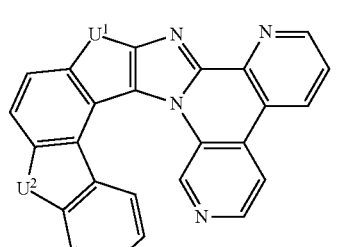
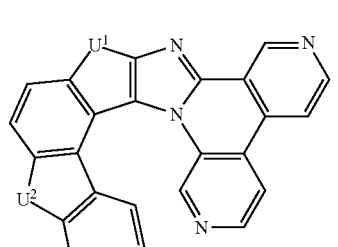
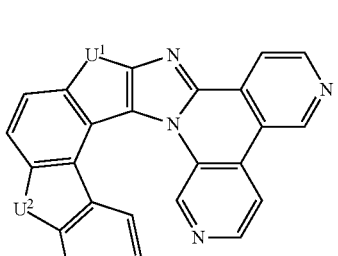
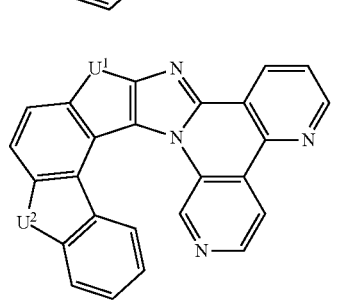

683
-continued
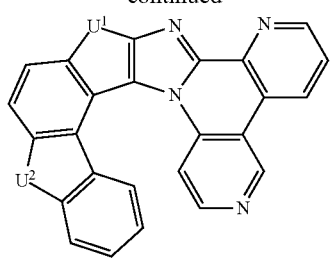
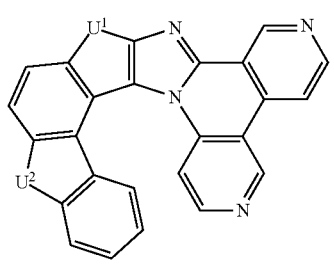
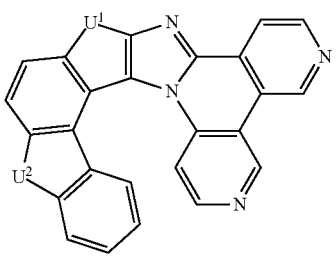
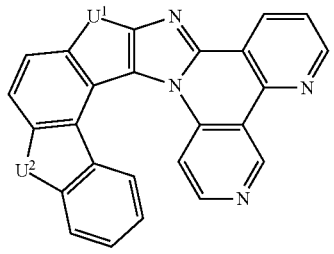
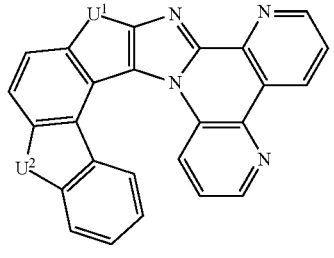
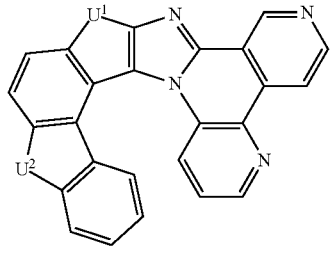
684
-continued
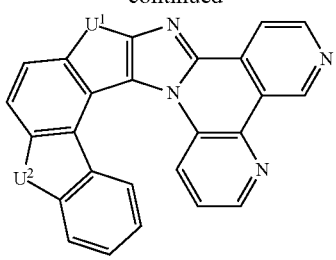
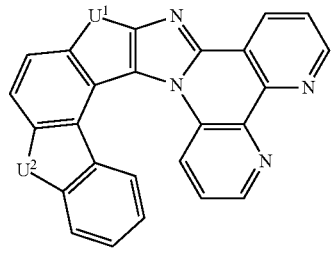
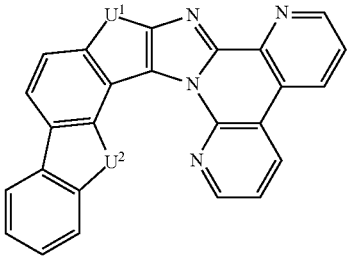
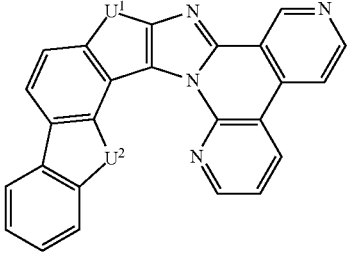
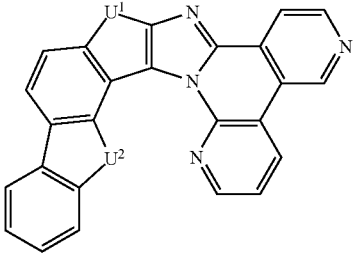
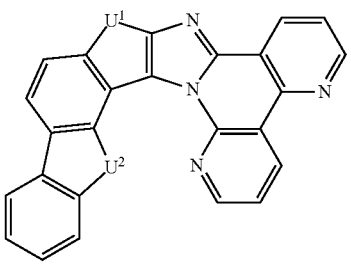

685
-continued
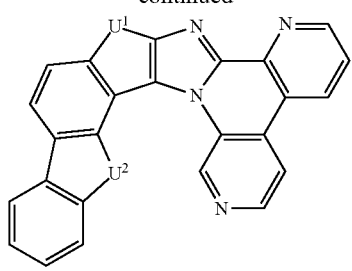
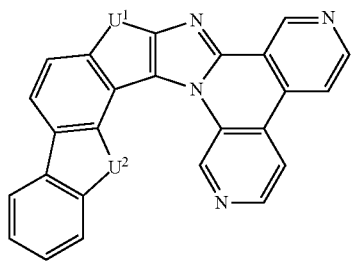
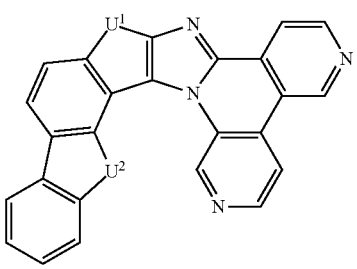
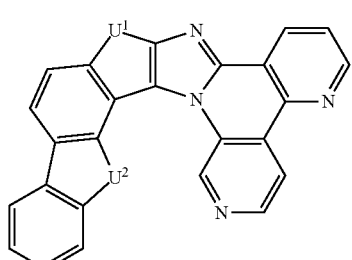
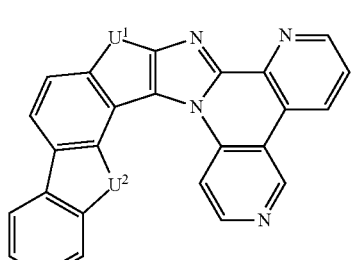
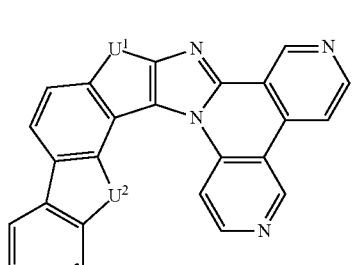
686
-continued
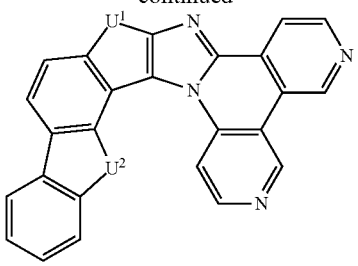
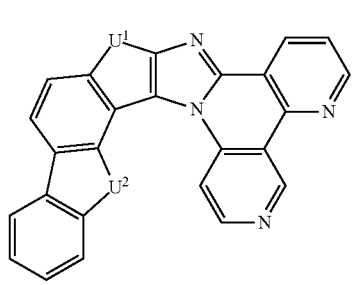
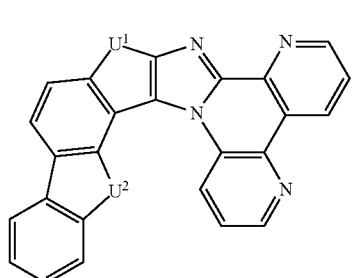
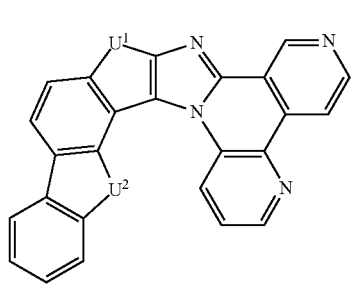
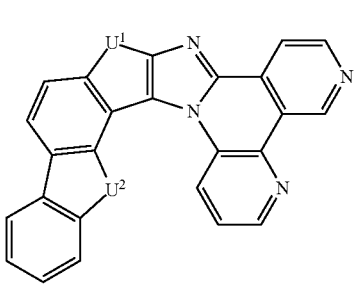
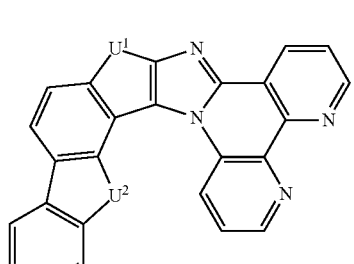

687
-continued
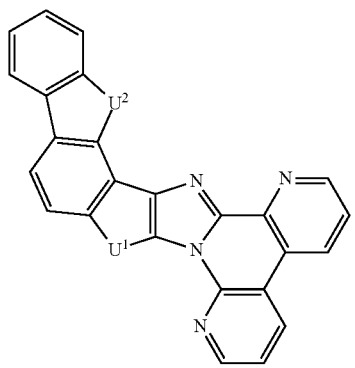
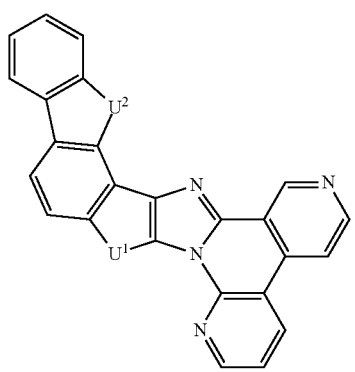
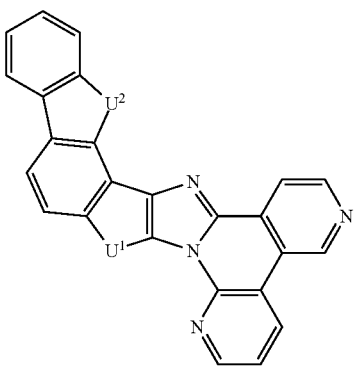
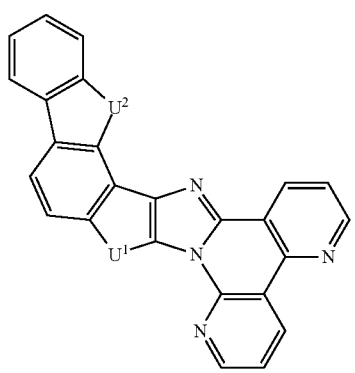
688
-continued
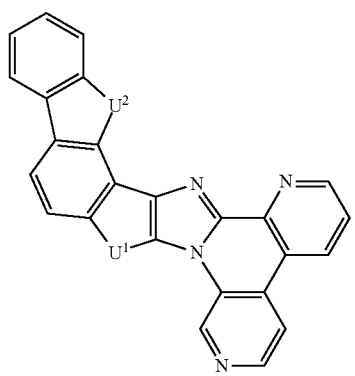
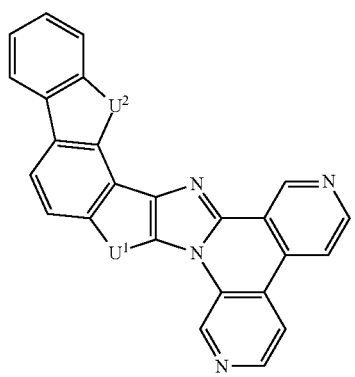
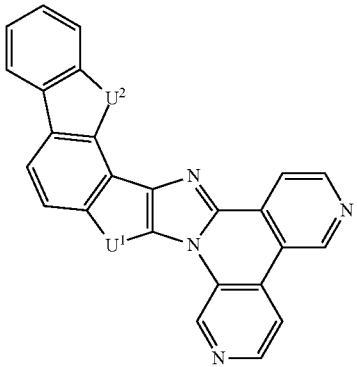
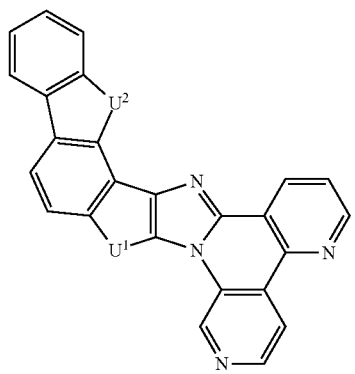

689
-continued
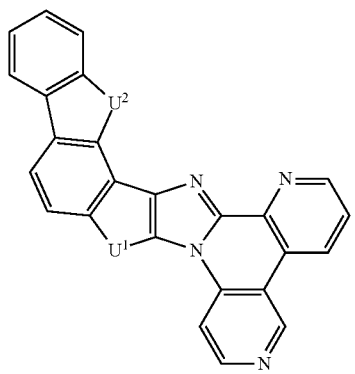
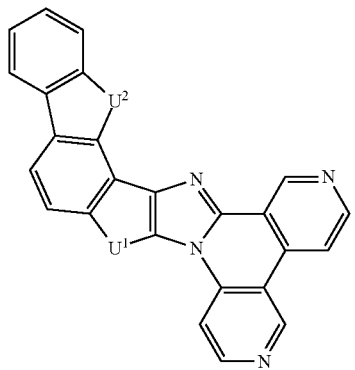
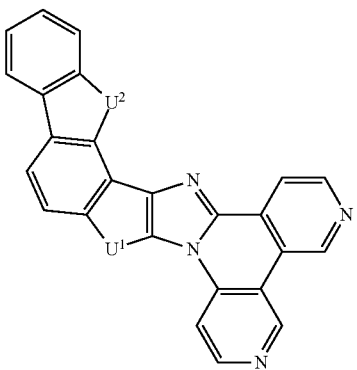
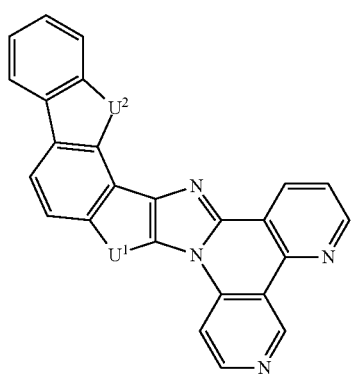
690
-continued
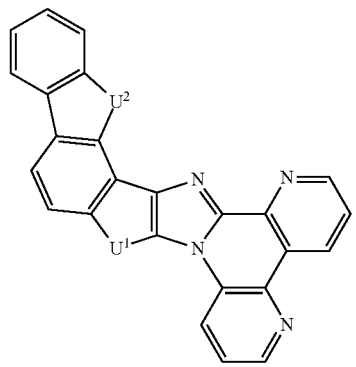
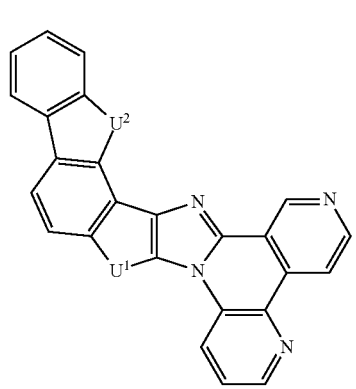
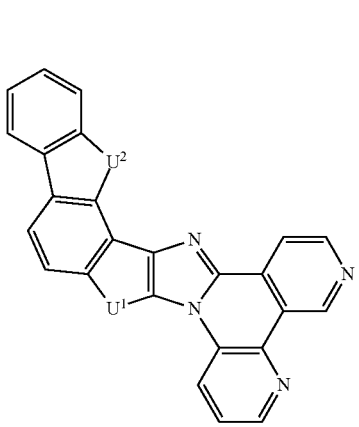
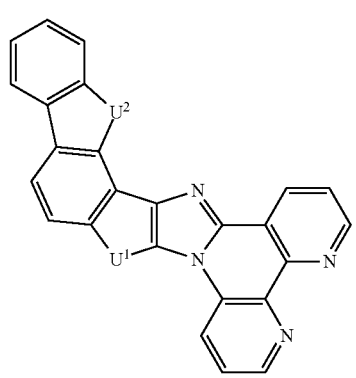

691
-continued
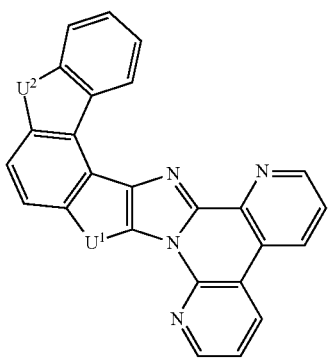
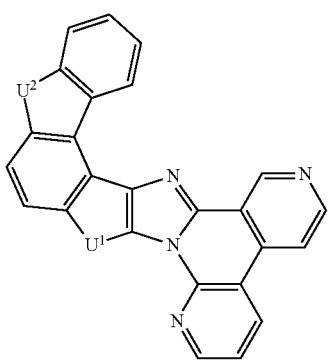
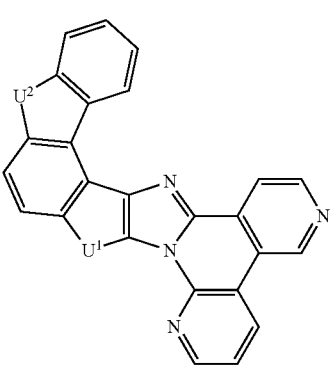
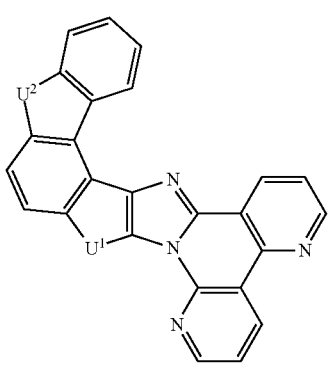
692
-continued
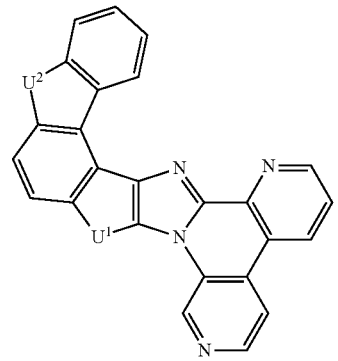
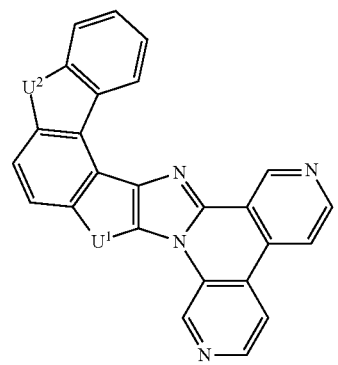
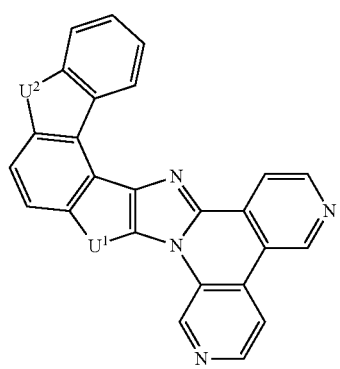
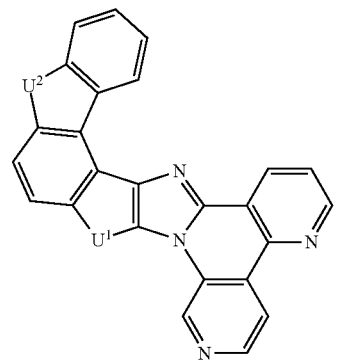

693
-continued
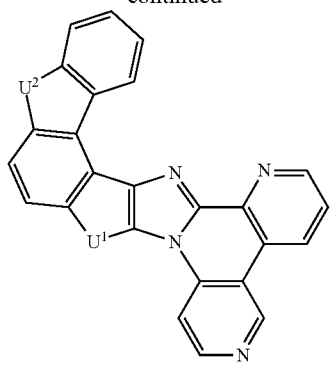
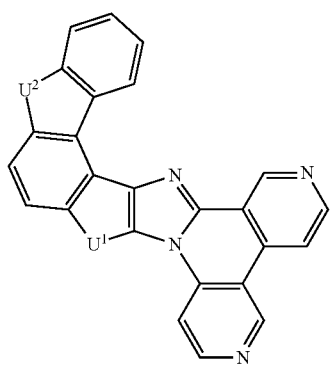
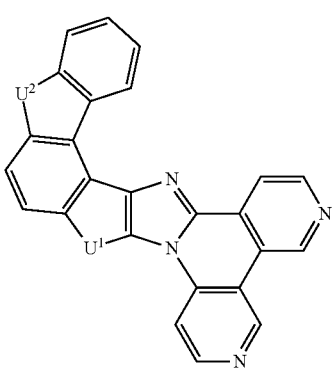
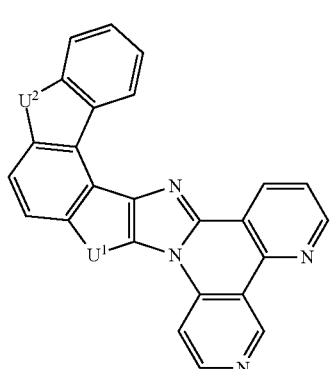
694
-continued
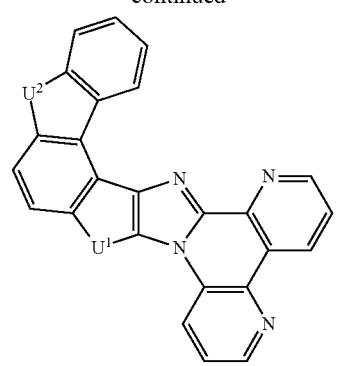
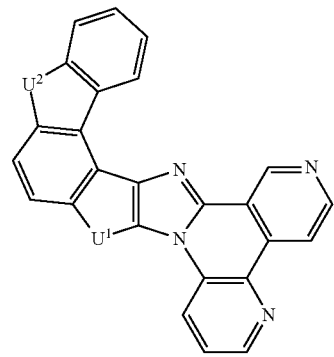
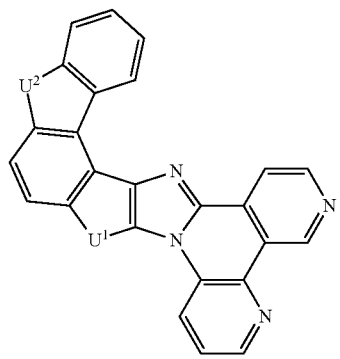
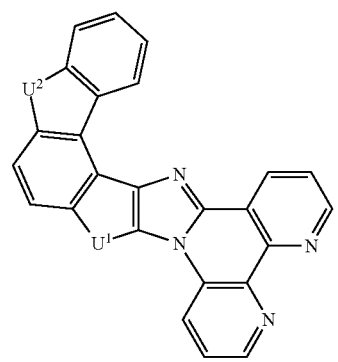
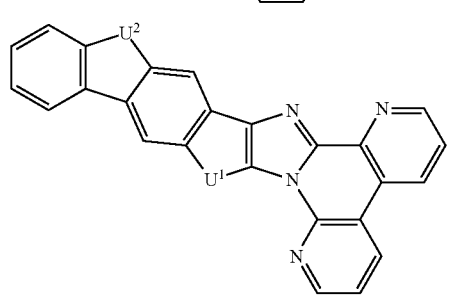

695
-continued
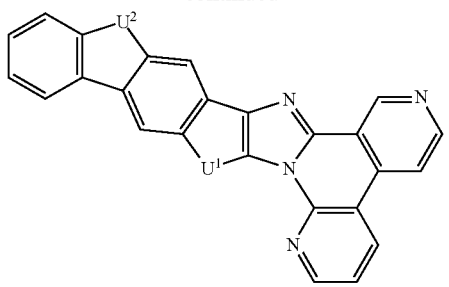
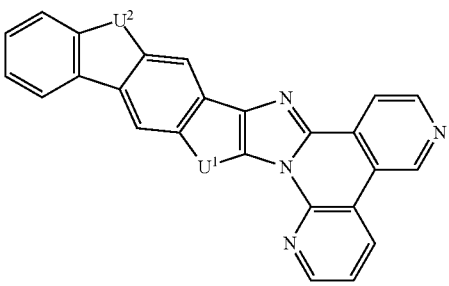
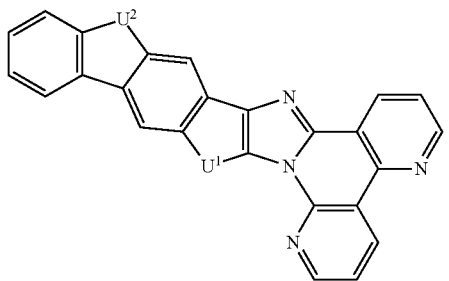
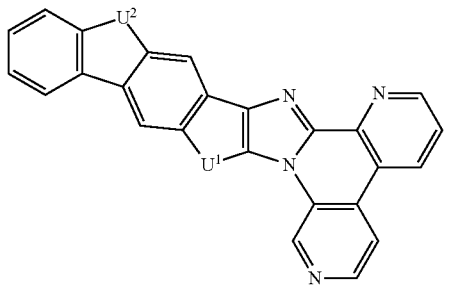
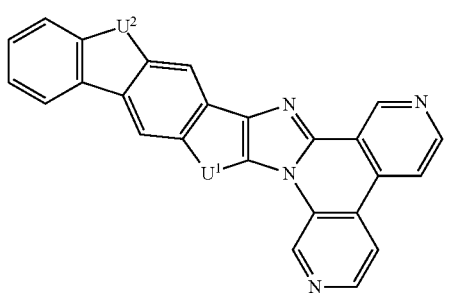
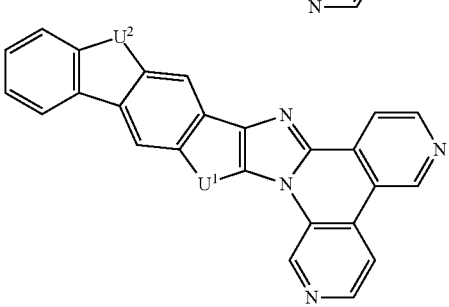
696
-continued
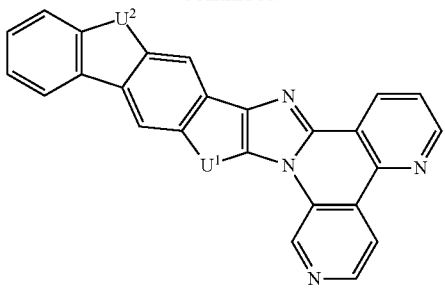
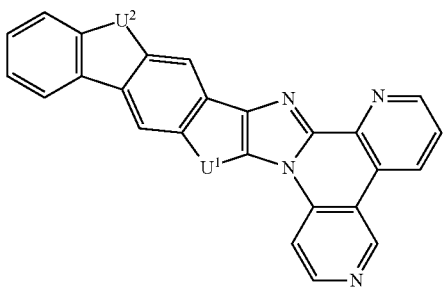
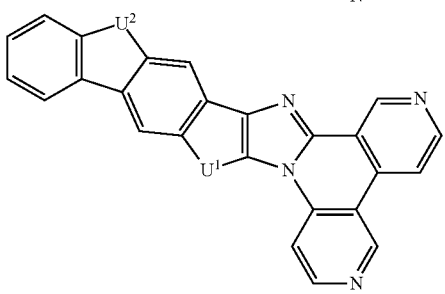
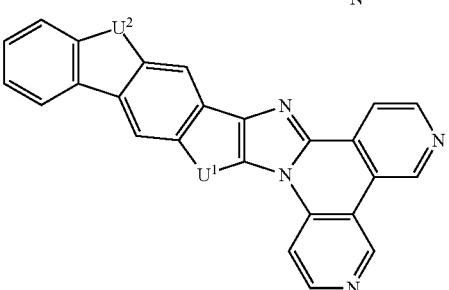
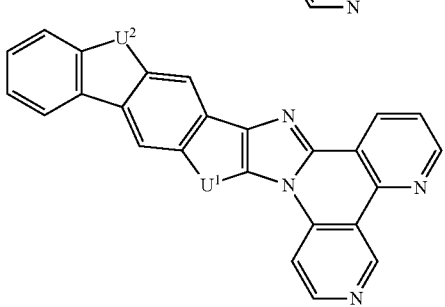
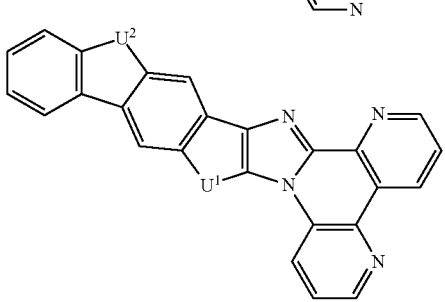

697
-continued
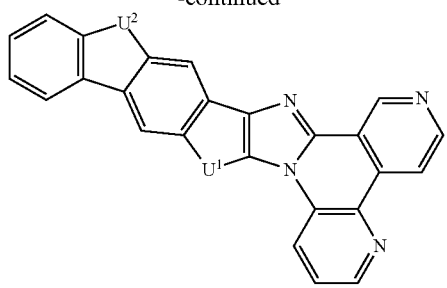
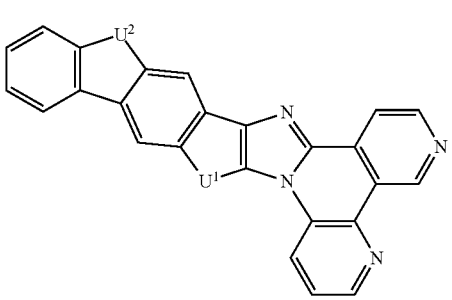
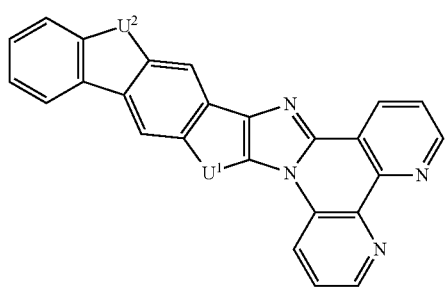
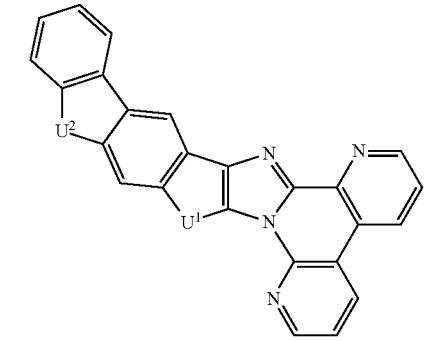
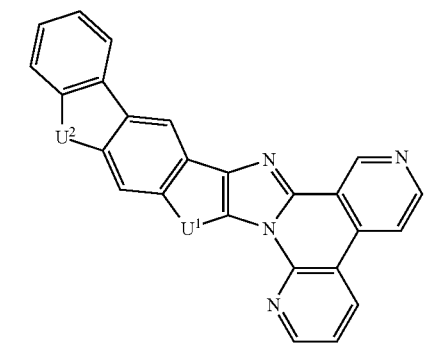
698
-continued
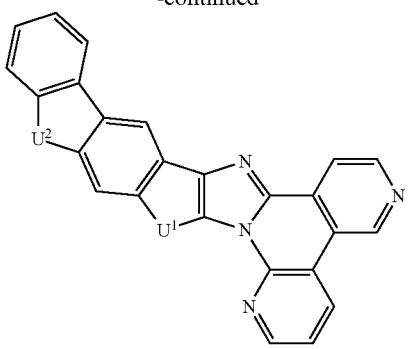
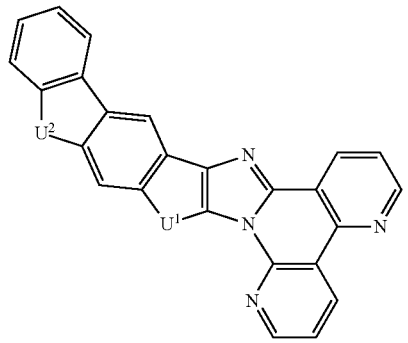
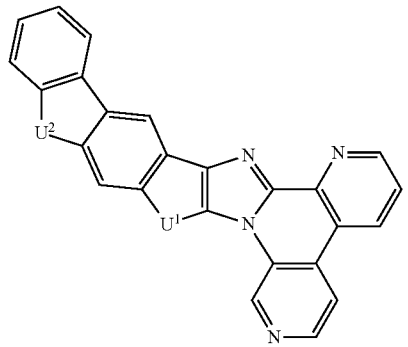
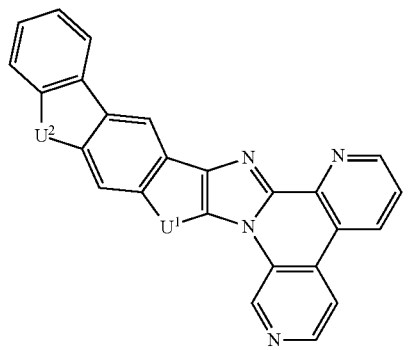
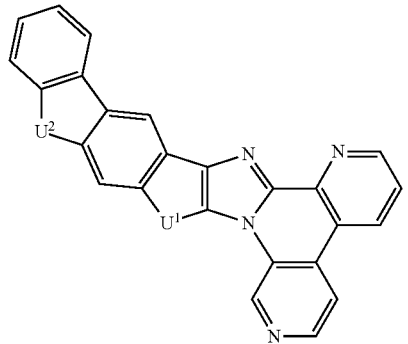

699
-continued
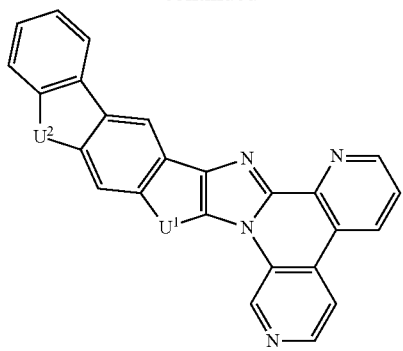
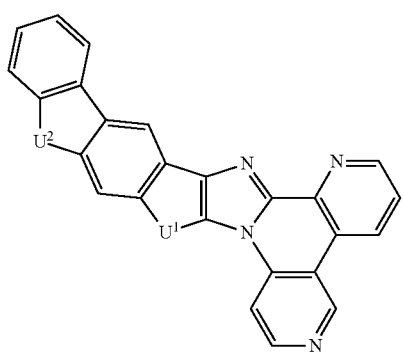
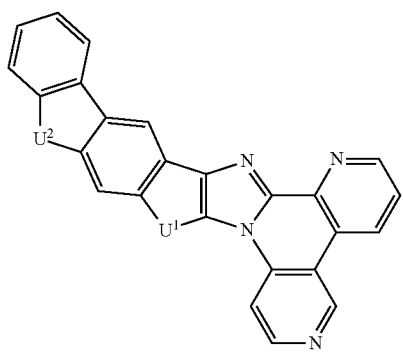
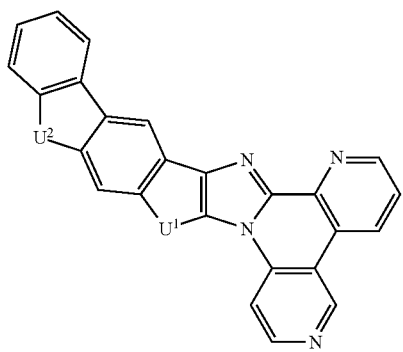
700
-continued
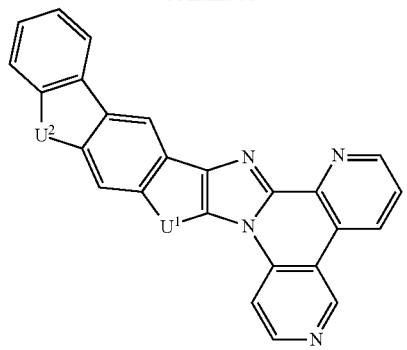
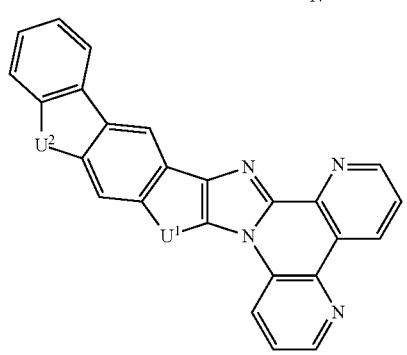
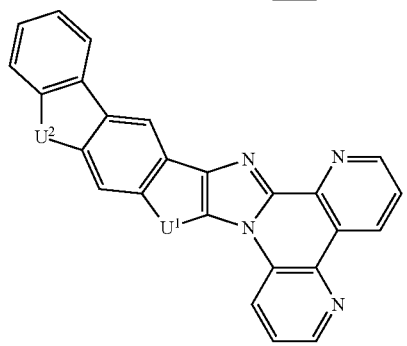
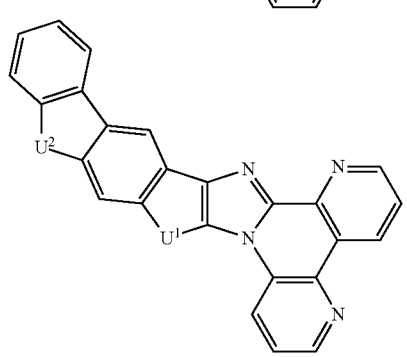
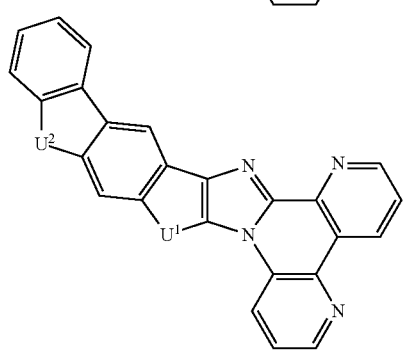

701
-continued
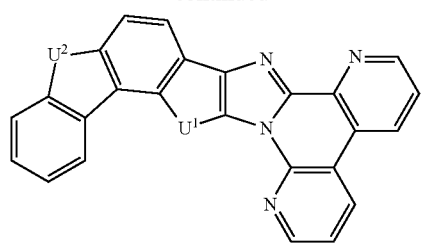
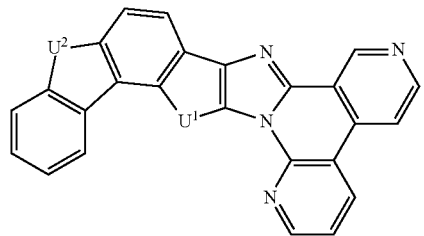
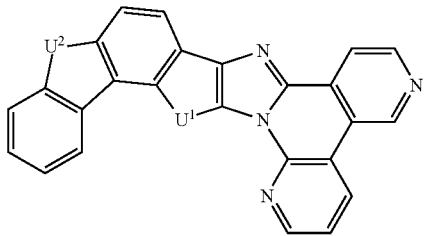
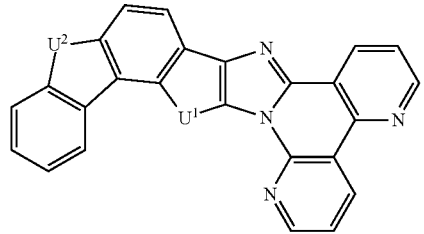
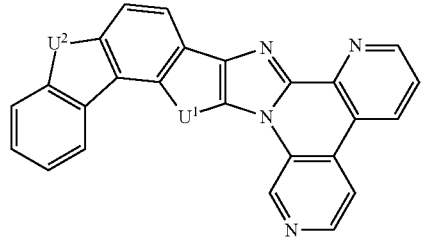
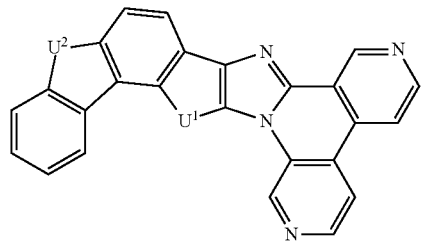
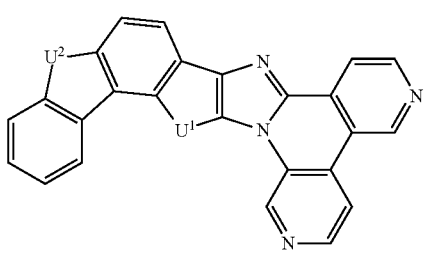
702
-continued
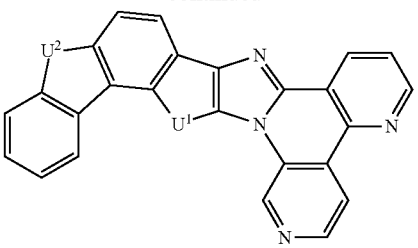
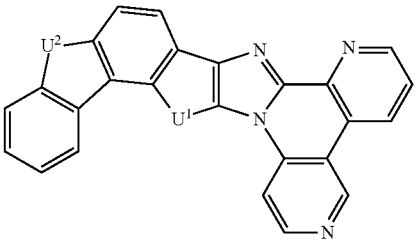
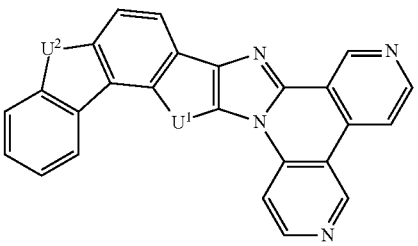
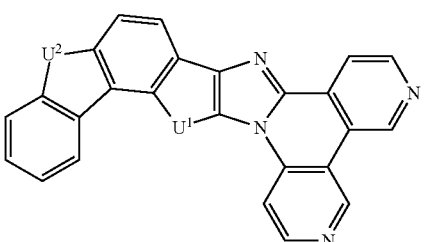
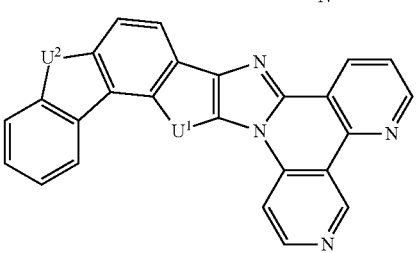
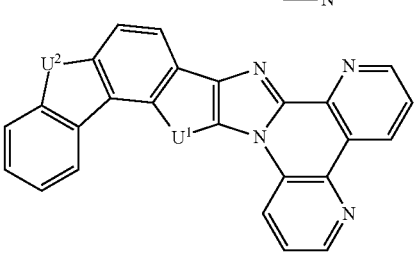
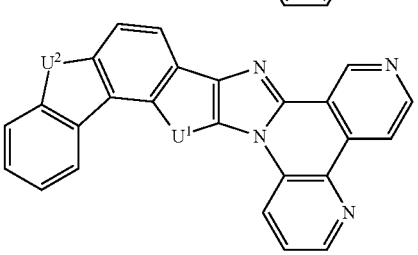

703
-continued
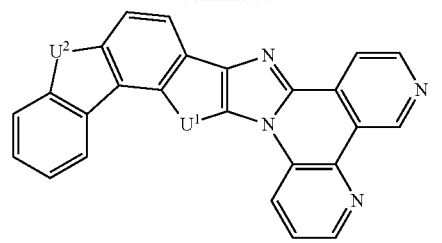
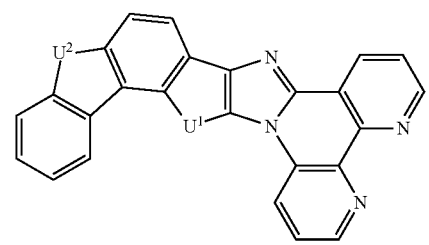
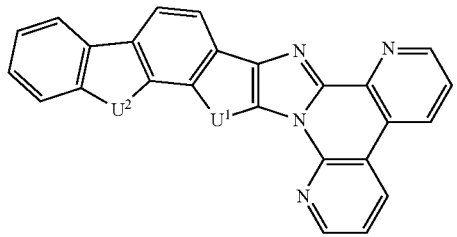
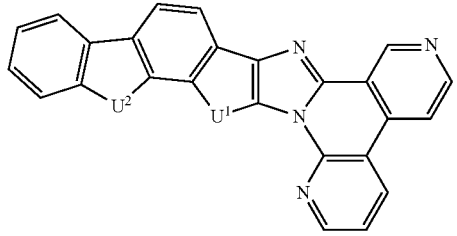
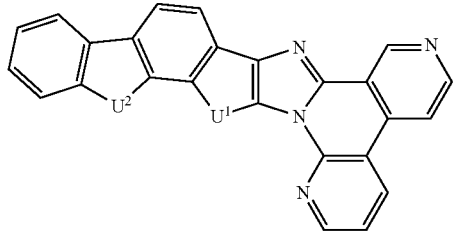
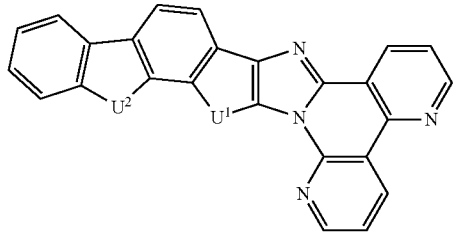
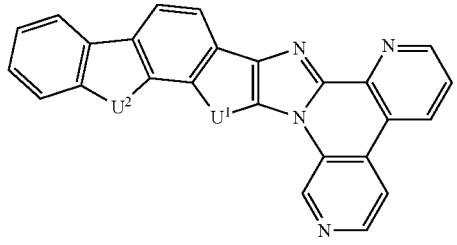
704
-continued
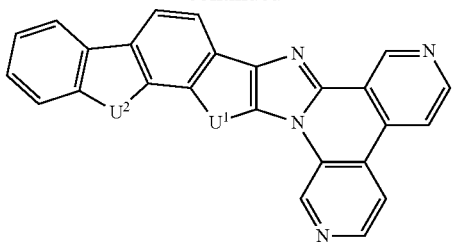
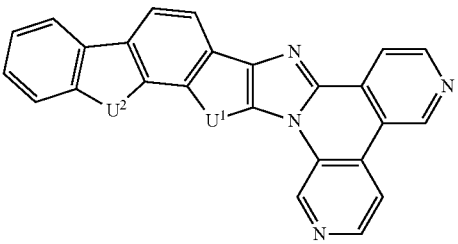
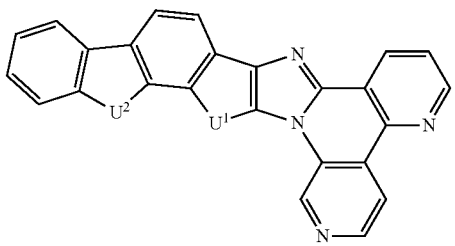
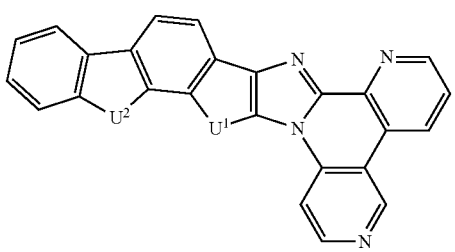
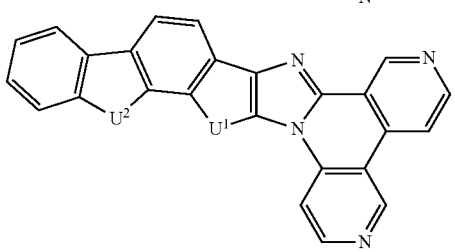
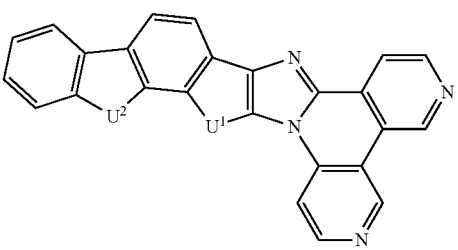
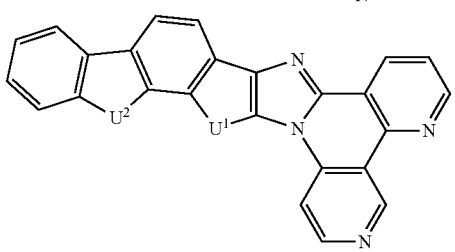

-continued

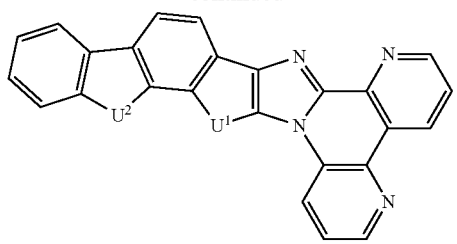

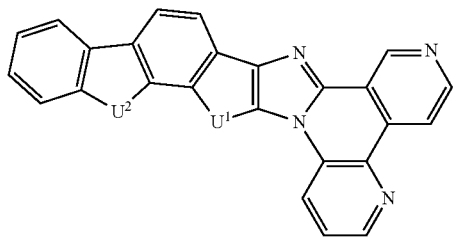

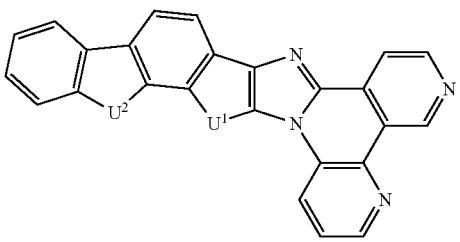

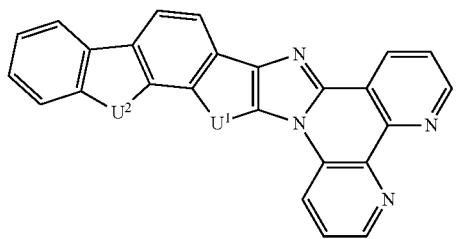

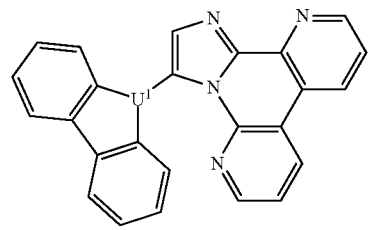

-continued

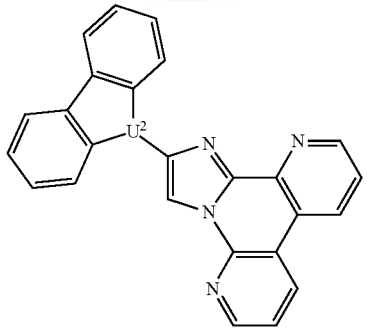

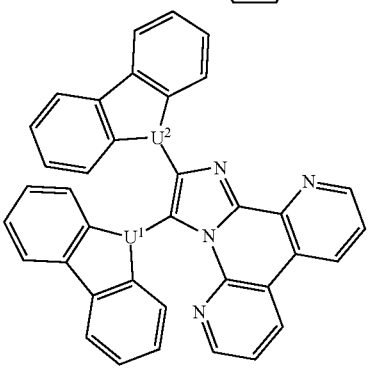

wherein each $U^1$ and $U^2$ independently represents, valency permitting, N, NPh, S, O, S=O, SO$_2$, P=O, Se=O, CPh$_2$, or CMe$_2$, where Me is methyl and Ph is phenyl.

10. An organic light emitting diode comprising the compound of claim 1.

11. A light emitting device comprising the organic light emitting diode of claim 10.

12. An organic light emitting diode comprising the compound of claim 2.

13. A light emitting device comprising the organic light emitting diode of claim 12.

14. An organic light emitting diode comprising the compound of claim 3.

15. An organic light emitting diode comprising the compound of claim 7.

16. A light emitting device comprising the organic light emitting diode of claim 15.

17. An organic light emitting diode comprising the compound of claim 8.

18. A light emitting device comprising the organic light emitting diode of claim 17.

19. An organic light emitting diode comprising the compound of claim 9.

20. A light emitting device comprising the organic light emitting diode of claim 19.

* * * * *